(12) United States Patent
Lee et al.

(10) Patent No.: US 10,608,185 B2
(45) Date of Patent: Mar. 31, 2020

(54) ORGANIC ELECTROLUMINESCENT MATERIALS AND DEVICES

(71) Applicant: Universal Display Corporation, Ewing, NJ (US)

(72) Inventors: Chi Hang Lee, Chaiwan (HK); Raymond Kwong, Fo Tan (HK)

(73) Assignee: UNIVERAL DISPLAY CORPORATION, Ewing, NJ (US)

( * ) Notice: Subject to any disclaimer, the term of this patent is extended or adjusted under 35 U.S.C. 154(b) by 410 days.

(21) Appl. No.: 15/483,032

(22) Filed: Apr. 10, 2017

(65) Prior Publication Data

US 2018/0108844 A1 Apr. 19, 2018

Related U.S. Application Data

(60) Provisional application No. 62/409,112, filed on Oct. 17, 2016, provisional application No. 62/449,915, (Continued)

(51) Int. Cl.
*H01L 51/00* (2006.01)
*H01L 51/50* (2006.01)
(Continued)

(52) U.S. Cl.
CPC .......... *H01L 51/0056* (2013.01); *C07C 13/62* (2013.01); *C07D 209/86* (2013.01); *C07D 221/18* (2013.01); *C07D 241/38* (2013.01); *C07D 265/34* (2013.01); *C07D 307/91* (2013.01); *C07D 311/78* (2013.01); *C07D 327/06* (2013.01); *C07D 401/04* (2013.01); *C07D 401/14* (2013.01); *C07D 403/04* (2013.01); *C07D 403/10* (2013.01); *C07D 403/14* (2013.01); *C07D 405/04* (2013.01); *C07D 405/14* (2013.01); *C07D 407/10* (2013.01); *C07D 409/04* (2013.01); *C07D 409/10* (2013.01); *C07D 409/14* (2013.01); *C07D 411/04* (2013.01); *C07D 411/14* (2013.01); *C07D 413/04* (2013.01); *C07D 413/14* (2013.01); *C07D 471/04* (2013.01); (Continued)

(58) Field of Classification Search
CPC .................................................. H01L 51/0057
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

CN 103524518 1/2014
EP 650955 5/1995
(Continued)

OTHER PUBLICATIONS https://www.ledsmagazine.com/leds-ssl-design/oleds/article/16696501/oled-update-market-growth-lighting-rd-and-partnerships (Year: 2005).*
(Continued)

*Primary Examiner* — Vu A Nguyen
(74) *Attorney, Agent, or Firm* — Riverside Law LLP

(57) ABSTRACT

The present invention includes fused tetraphenylene compounds that may be used as charge transporters, hosts or emitters in OLEDs.

20 Claims, 2 Drawing Sheets

Related U.S. Application Data filed on Jan. 24, 2017, provisional application No. 62/449,921, filed on Jan. 24, 2017.

(51) Int. Cl.

| | | |
|---|---|---|
| C09K 11/06 | (2006.01) | |
| C09K 11/02 | (2006.01) | |
| C07C 13/62 | (2006.01) | |
| C07D 409/14 | (2006.01) | |
| C07D 403/04 | (2006.01) | |
| C07D 409/10 | (2006.01) | |
| C07D 493/04 | (2006.01) | |
| C07D 491/147 | (2006.01) | |
| C07D 407/10 | (2006.01) | |
| C07D 497/04 | (2006.01) | |
| C07D 221/18 | (2006.01) | |
| C07D 411/14 | (2006.01) | |
| C07D 401/04 | (2006.01) | |
| C07D 403/14 | (2006.01) | |
| C07D 241/38 | (2006.01) | |
| C07D 471/04 | (2006.01) | |
| C07D 403/10 | (2006.01) | |
| C07D 498/04 | (2006.01) | |
| C07D 411/04 | (2006.01) | |
| C07D 471/14 | (2006.01) | |
| C07D 209/86 | (2006.01) | |
| C07D 413/04 | (2006.01) | |
| C07D 409/04 | (2006.01) | |
| C07D 401/14 | (2006.01) | |
| C07D 405/04 | (2006.01) | |
| C07D 405/14 | (2006.01) | |
| C07D 497/14 | (2006.01) | |
| C07D 311/78 | (2006.01) | |
| C07D 265/34 | (2006.01) | |
| C07D 307/91 | (2006.01) | |
| C07D 413/14 | (2006.01) | |
| C07D 491/052 | (2006.01) | |
| C07D 498/14 | (2006.01) | |
| C07D 327/06 | (2006.01) | |
| C07D 491/048 | (2006.01) | |

(52) U.S. Cl.
CPC ....... *C07D 471/14* (2013.01); *C07D 491/048* (2013.01); *C07D 491/052* (2013.01); *C07D 491/147* (2013.01); *C07D 493/04* (2013.01); *C07D 497/04* (2013.01); *C07D 497/14* (2013.01); *C07D 498/04* (2013.01); *C07D 498/14* (2013.01); *C09K 11/025* (2013.01); *C09K 11/06* (2013.01); *H01L 51/0057* (2013.01); *C07C 2603/54* (2017.05); *C09K 2211/1011* (2013.01); *H01L 51/0085* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baido et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,968,146 B2 | 6/2011 | Wanger et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1* | 5/2005 | Ogasawara ............ C07C 15/20 428/690 |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0240285 A1* | 10/2006 | Uchida ............... C09K 11/06 428/690 |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2013/0026452 A1 | 1/2013 | Kottas et al. |
| 2013/0119354 A1 | 5/2013 | Ma et al. |
| 2016/0013422 A1 | 1/2016 | Kwong et al. |

FOREIGN PATENT DOCUMENTS

| | | |
|---|---|---|
| EP | 1238981 | 9/2002 |
| EP | 1725079 | 11/2006 |

(56) References Cited

FOREIGN PATENT DOCUMENTS

| | | |
|---|---|---|
| EP | 2034538 | 3/2009 |
| JP | 2000077186 | 3/2000 |
| JP | 200511610 | 1/2005 |
| JP | 2007123392 | 5/2007 |
| JP | 2007254297 | 10/2007 |
| JP | 2008074939 | 10/2009 |
| JP | 2010/135467 | 6/2010 |
| WO | 2001039234 | 5/2001 |
| WO | 2002002714 | 1/2002 |
| WO | 0215645 | 2/2002 |
| WO | 2003040257 | 5/2003 |
| WO | 2003060956 | 7/2003 |
| WO | 2004093207 | 10/2004 |
| WO | 2004/111066 | 12/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006/072002 | 7/2006 |
| WO | 2006130598 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007/002683 | 1/2007 |
| WO | 2007004380 | 1/2007 |
| WO | 2007063754 | 6/2007 |
| WO | 2007063796 | 6/2007 |
| WO | 2008/044723 | 4/2008 |
| WO | 2008057394 | 5/2008 |
| WO | 2008101842 | 8/2008 |
| WO | 2008132085 | 11/2008 |
| WO | 2009000673 | 12/2008 |
| WO | 2009/003898 | 1/2009 |
| WO | 2009/008311 | 1/2009 |
| WO | 2009/018009 | 2/2009 |
| WO | 2009050290 | 4/2009 |
| WO | 2008/056746 | 5/2009 |
| WO | 2009/021126 | 5/2009 |
| WO | 2009/062578 | 5/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 2009100991 | 8/2009 |
| WO | 2010011390 | 1/2010 |
| WO | 2010/111175 | 9/2010 |

OTHER PUBLICATIONS

SciFinder Searches.*
SciFinder Search (Oct. 31, 2019).*
Yang et al., 1999, "Synthesis, structure and inclusion properties of 1,4,15,18-tetrahydro-1,4,15,18-tetraoxodibenzo[b,h] tetraphenylene," Chem. Comm. 1607-1608.
Gugel and Meier, 1980, "Die Bildung von 9,10-Didehydrotribenzo[a, c, e]cyclooctene," Chem. Ber. 113:1431-1443.
Hogberg, 1972, "Cyclo-oligomerization of Quinones," Acta Chem. Scand. 26:2752-2758.
Erdtman and Hogberg, 1970, "Cyclooligomerization of Quinones," Tet. Lett. 38:3389-3392.
Baryshnikov et al., 2013, "Nucleus-independent chemical shift criterion for aromaticity in π-extended tetraoxa[8] circulenes," J. Mol. Model. 19:847-850.
Rathore and Abdelwahed, 2004, "Soluble cycloannulated tetroxa[8]circulane derivatives: synthesis, optical and electrochemical properties, and generation of their robust cation—radical salts," Tel Lett. 45:5267-5270.

Minaev et al., 2011, "Density functional theory study of electronic structure and spectra of tetraoxa[8]circulenes," Computational and Theoretical Chemistry 972:68-74.
Denis, 2014, "Design and characterization of two strong fullerene receptors based on ball—socket interactions," Chem. Phys. Lett. 591:323-327.
Josa et al., 2015, "Fullerene recognition with molecular tweezers made up of efficient buckybowls: a dispersion-corrected DFT study," Phys. Chem. Chem. Phys. 17, 13206-13214.
Denis, 2014, "A theoretical study on the interaction between well curved conjugated systems and fullerenes smaller than C60 or larger than C70," J. Phys. Org. Chem. 27:918-925.
Le et al., 2014, "Thermodynamics of Host—Guest Interactions between Fullerenes and a Buckycatcher," J. Phys. Chem. B 118:11956-11964.
Zabula et al., 2014, "An unsolvated buckycatcher and its first dianion," Chem. Comm. 50:2657-2659.
Denis, 2013, "Theoretical characterization of existing and new fullerene receptors," RSC Adv. 3:25296-25305.
Yang et al., 2012, "Probing the zero-field splitting in the ordered N@C60 in buckycatcher C60H28 studied by EPR spectroscopy," Physics Letters A 376:1748-1751.
Podeszwa et al., 2012, "Efficient Calculations of Dispersion Energies for Nanoscale Systems from Coupled Density Response Functions," J. Chem. Theory Comput. 8:1963-1969.
Muck-Lichtenfeld et al., 2010, "Inclusion complexes of buckycatcher with C60 and C70," Physical Chemistry Chemical Physics 12:7091-7097.
Waldvogel and Welschoff, 2010, "Product Class 26: Triphenylenes, Tetraphenylenes, and Related Compounds," Science of Synthesis 45b:1147-1191.
Chakrabarti and Ruud, 2009, "Intermolecular Interaction-Controlled Tuning of the Two-Photon Absorption of Fullerene Sound in a Buckycatcher," Journal of Physical Chemistry A Letters 113:5485-5488.
Zhao nd Truhlar, 2008, "Computational characterization and modeling of buckyball tweezers: density functional study of concave-convex π• ••π interactions," Physical Chemistry Chemical Physics 10:2813-2818.
Voityuk and Duran, 2008, "Buckycatcher. A New Opportunity for Charge-Transfer Mediation?" Journal of Physical Chemistry C 112:1672-1678.
Sygula et al., 2007, "A Double Concave Hydrocarbon Buckycatcher," Journal of the American Chemical Society 129:3842-3843.
Coluci et al., 2009, "A molecular dynamics study of the rotational dynamics and polymerization of C60 in C60-cubane crystals," Materials Research Society Symposium Proceedings vol. 1130.
Kosugi et al, 1992, "High-resolution and symmetry-resolved oxygen K-edge spectra of O2," Chemical Physics Letters 190:481-488.
Sharma et al., 1988, "Synthesis and spectroscopic studies on dibutyl-, tributyl- and triphenyltin esters of p-methoxy trans-cinnamic acid," J Organomet. Chem. 353:9-15.
Rajca et al., 2000, "D2-Symmetric Dimer of 1,1'-Binaphthyl and Its Chiral π-Conjugated Carbodianion," J. Am. Chem. Soc. 122:3351-3357.
Song et al., 2005, "Polyphenyl Macrocyclic Oligophenylenes," J. Am. Chem. Soc. 127:13732-13737.
Du et al., 2001, "Preparation and crystal structure of a 1:1 inclusion compound of 1,4,11,14-tetramethoxy-dibenzo[b,n] tetraphenylene with pyridine," J. Mol. Structure 560:23-28.
Rashidi-Ranjbar et al., "Enantiomer Resolution, Absolute Configuration, and Attempted Thermal Racemization of Two Tetrabenzocyclooctatetraene (o-Tetraphenylene) Derivatives. An Exceptionally High Barrier to Ring Inversion," J. Org. Chem. 54:4888-4892.
Man et al., 1990, "Synthesis of Benzo-Fused Tetraphenylenes and Crystal Structure of a 4:I Clathrate Inclusion Compound of Dibenzo[b,h]tetraphenylene with p-Xylene," J. Org. Chem. 55:3214-3221.
Iyoda et al., 1998, "Novel Synthesis of Biphenylene and Its Derivatives Using Intramolecular Coupling of Zincacyclopentadienes," Tet. Lett. 39:5393-5396.

(56) References Cited

OTHER PUBLICATIONS

Baldo et al., "Highly Efficient Phosphorescent Emission from Organic Electroluminescent Devices," Nature, vol. 395, 151-154, (1998).
Baldo et al., "Very high-efficiency green organic light-emitting devices based on electrophosphorescence," Appl. Phys. Lett., vol. 75, No. 1, 4-6 (1999).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Tung, Yung-Liang et al., "Organic Light-Emitting Diodes Based on Charge-Neutral $Ru^{II}$ PHosphorescent Emitters," Adv. Mater., 17(8):1059-1064 (2005).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Wong, Wai-Yeung, "Multifunctional Iridium Complexes Based on Carbazole Modules as Highly Efficient Electrophosphors," Angew. Chem. Int. Ed., 45:7800-7803 (2006).
Tang, C.W. and VanSlyke, S.A., "Organic Electroluminescent Diodes," Appl. Phys. Lett., 51(12):913-915 (1987).
Adachi, Chihaya et al., "Organic Electroluminescent Device Having a Hole Conductor as an Emitting Layer," Appl. Phys. Lett., 55(15):1489-1491 (1989).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Gao, Zhiqiang et al., "Bright-Blue Etectroluminescence From a Silyl-Substituted ter-(phenylene-vinylene) derivative," Appl. Phys. Lett., 74(6):865-867 (1999).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Hung, L.S. et al., "Anode Modification in Organic Light-Emitting Diodes by Low-Frequency Plasma Polymerization of $CHF_3$," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Wang, Y. et al., "Highly Efficient Electroluminescent Materials Based on Fluorinated Organometallic Iridium Compounds," Appl. Phys. Lett., 79(4):449-451 (2001).
Kwong, Raymond C. et al., "High Operational Stability of Electrophosphorescent Devices," Appl. Phys. Lett., 81(1):162-164 (2002).
Holmes, R.J. et al., "Blue Organic Electrophosphorescence Using Exothermic Host-Guest Energy Transfer," Appl. Phys. Lett., 82(15):2422-2424 (2003).
Sotoyama, Wataru et al., "Efficient Organic Light-Emitting Diodes with Phosphorescent Platinum Complexes Containing NCN—Coordinating Tridentate Ligand," Appl. Phys. Lett., 86:153505-1-153505-3 (2005).
Okumoto, Kenji et al., "Green Fluorescent Organic Light-Emitting Device with External Quantum Efficiency of Nearly 10%," Appl. Phys. Lett., 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Aonuma, Masaki et al., "Material Design of Hole Transport Materials Capable of Thick-Film Formation in Organic Light Emitting Diodes," Appl. Phys. Lett., 90:183503-1-183503-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
Adachi, Chihaya et al., "High-Efficiency Red Electrophosphorescence Devices," Appl. Phys. Lett., 78(11):1622-1624 (2001).
Wong, Keith Man-Chung et al., "A Novel Class of Phosphorescent Gold(III) Alkynyl-Based Organic Light-Emitting Devices with Tunable Colour," Chem. Commun., 2906-2908 (2005).
Hamada, Yuji et al., "High Luminance in Organic Electroluminescent Devices with Bis(10-hydroxybenzo[h]quinolinato)beryllium as an Emitter," Chem. Lett., 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4):592-593 (2005).
Mi, Bao-Xiu et al., "Thermally Stable Hole-Transporting Material for Organic Light-Emitting Diode: an isoindole Derivative," Chem. Mater., 15(16):3148-3151 (2003).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Niu, Yu-Hua et al., "Highly Efficient Electrophosphorescent Devices with Saturated Red Emission from a Neutral Osmium Complex," Chem. Mater., 17(13):3532-3538 (2005).
Lo, Shih-Chun et al., "Blue Phosphorescence from Iridium(III) Complexes at Room Temperature," Chem. Mater., 18(21):5119-5129 (2006).
Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," Inorg. Chem., 46(10):4308-4319 (2007).
Lamansky, Sergey et al., "Synthesis and Characterization of Phosphorescent Cyclometalated Iridium Complexes," Inorg. Chem., 40(7):1704-1711 (2001).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Noda, Tetsuya and Shirota,Yasuhiko, "5,5'-Bis(dimesitylboryl)-2,2'-bithiophene and 5,5'—Bis(dimesitylboryl)-2,2':5',2"—terthiophene as a Novel Family of Electron-Transporting Amorphous Molecular Materials," J. Am. Chem. Soc., 120 (37):9714-9715 (1998).
Sakamoto, Youichi et al., "Synthesis, Characterization, and Electron-Transport Property of Perfluorinated Phenylene Dendrimers," J. Am. Chem. Soc., 122(8):1832-1833 (2000).
Adachi, Chihaya et al., "Nearly 100% Internal Phosphorescence Efficiency in an Organic Light Emitting Device," J. Appl. Phys., 90(10):5048-5051 (2001).
Shirota, Yasuhiko et al., "Starburst Molecules Based on p-Electron Systems as Materials for Organic Electroluminescent Devices," Journal of Luminescence, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kido, Junji et al., 1,2,4-Triazole Derivative as an Electron Transport Layer in Organic Electroluminescent Devices, Jpn. J. Appl. Phys., 32:L917-L920 (1993).
Van Slyke, S. A. et al., "Organic Electroluminescent Devices with Improved Stability," Appl. Phys. Lett., 69(15):2160-2162 (1996).
Guo, Tzung-Fang et al., "Highly Efficient Electrophosphorescent Polymer Light-Emitting Devices," Organic Electronics, 1:15-20 (2000).
Palilis, Leonidas C., "High Efficiency Molecular Organic Light-Emitting Diodes Based on Silole Derivatives and Their Exciplexes," Organic Electronics, 4:113-121 (2003).
Ikeda, Hisao et al., "P-185: Low-Drive-Voltage OLEDs with a Buffer Layer Having Molybdenum Oxide," SID Symposium Digest, 37:923-926 (2006).
T. Östergård et al., "Langmuir-Blodgett Light-Emitting Diodes of Poly(3-Hexylthiophene): Electro-Optical Characteristics Related to Structure," Synthetic Metals, 87:171-177 (1997).

(56) References Cited

OTHER PUBLICATIONS

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

\* cited by examiner

ORGANIC ELECTROLUMINESCENT MATERIALS AND DEVICES

CROSS-REFERENCE TO RELATED APPLICATIONS

This application claims priority to U.S. Provisional Patent Application Ser. Nos. 62/409,112, filed Oct. 17, 2016, 62/449,915, filed Jan. 24, 2017, and 62/449,921, filed Jan. 24, 2017, the entire contents of all of which are incorporated herein by reference.

FIELD

The present invention relates to compounds for use as hosts and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

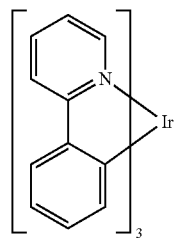

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

There is a need in the art for novel compounds that may be used as charge transporters, hosts or emitters in OLEDs. The present invention addresses this need in the art.

SUMMARY

According to an embodiment, a compound is provided that has the structure of Formula I shown below:

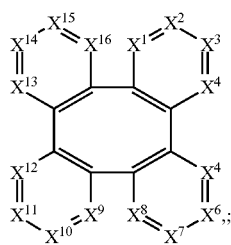

Formula I wherein $X^1$-$X^{16}$ are each independently selected from the group consisting of CR and N;
wherein at least two adjacent $X^1$-$X^{16}$ are CR;
wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one pair of adjacent Rs is

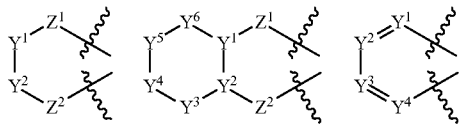

Attachment A, Attachment B, Attachment C, or is fused with two or more aromatic rings such that no scene unit of more than 3 fused rings is formed;
wherein in Attachments A and B, $Y^1$-$Y^2$, $Y^2$-$Y^3$, $Y^3$-$Y^4$, $Y^4$-$Y^5$ and $Y^5$-$Y^6$ are connected by single or double bonds;
wherein $Y^1$-$Y^6$ are each independently selected from the group consisting of C and N;

wherein any unsaturated C in $Y^1$-$Y^6$ is substituted by one or two $R^1$;
wherein in Attachment A, $Z^1$ and $Z^2$ are each independently selected from the group consisting of C=$CR^2R^3$, C=$NR^2$, $NR^2$, O, S, SO, $SO_2$, $BR^2$, $PR^2$, $SiR^2R^3$, and Se;
wherein in Attachment B, $Z^1$ and $Z^2$ are each independently selected from the group consisting of $CR^2R^3$, C=$CR^2R^3$, C=O, C=$NR^2$, $NR^2$, O, S, SO, $SO_2$, $BR^2$, P, $SiR^2R^3$, and Se;
wherein in Attachment C, at least one of $Y^1$-$Y^4$ is N;
wherein $R^1$-$R^3$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein

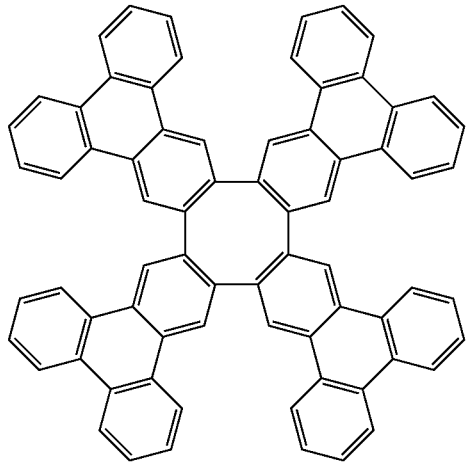 [SMILES: c1ccc2c(c1)c1ccccc1c1cc3c(cc21)-c1cc2c4ccccc4c4ccccc4c2cc1-c1cc2c4ccccc4c4ccccc4c2cc1-c1cc2c4ccccc4c4ccccc4c2cc1-3]

is excluded.

According to another embodiment, a device comprising one or more organic light emitting devices is also provided. At least one of the one or more organic light emitting devices can include an anode, a cathode, and an organic layer, disposed between the anode and the cathode, wherein the organic layer can include a compound of Formula I. The device can be a consumer product, an electronic component module, an organic light-emitting device, and/or a lighting panel.

According to another embodiment, a consumer product comprising one or more organic light emitting devices is also provided. At least one of the one or more organic light emitting devices can include an anode, a cathode, and an organic layer, disposed between the anode and the cathode, wherein the organic layer can include a compound of Formula I. The consumer product can be a flat panel display, computer monitor, medical monitors television, billboard, light for interior or exterior illumination and/or signaling, heads-up display, fully or partially transparent display, flexible display, laser printer, telephone, cell phone, tablet, phablet, personal digital assistant (PDA), wearable device, laptop computer, digital camera, camcorder, viewfinder, a micro-display that is less than 2 inches diagonal, a 3-D display, a virtual reality or augmented reality display, a vehicle, a video wall comprising multiple displays tiled together, a theater or stadium screen, and/or a sign.

According to yet another embodiment, a formulation containing a compound of Formula I is provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
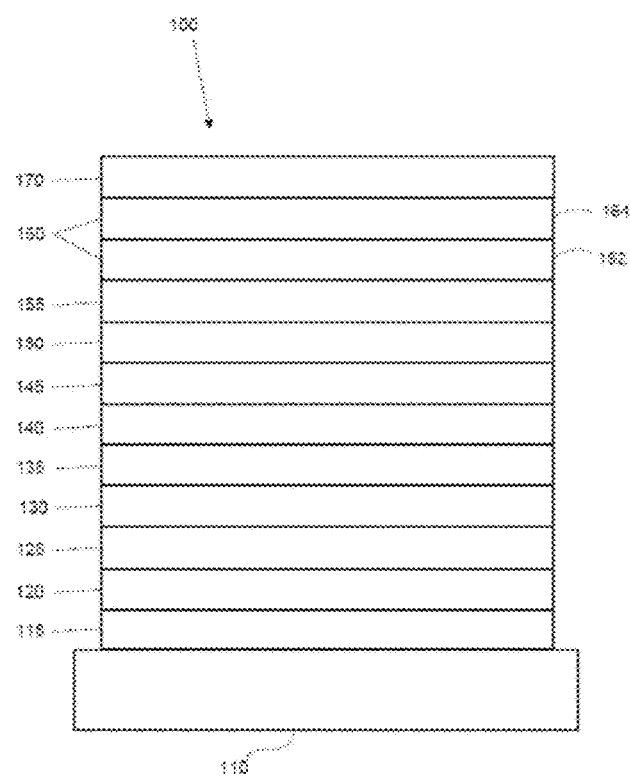
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
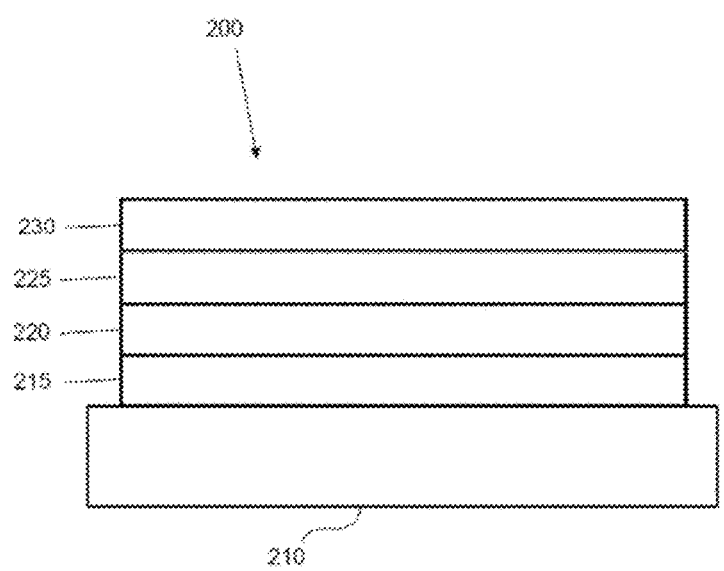
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays that are less than 2 inches diagonal, 3-D displays, virtual reality or augmented reality displays, vehicles, video walls comprising multiple displays tiled together, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The term "acene" as used herein contemplates a polycyclic aromatic hydrocarbon group having at least three fused benzene rings in a linear configuration. Non-limiting examples of acene groups include three to five fused benzene rings (i.e., anthracene, tetracene, and pentacene).

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In one aspect, the present invention includes novel tetraphenylene compounds with at least one ring fused to form a polyaromatic hydrocarbons (formed by ≥3 aromatic rings). In another aspect, the present invention includes novel fused ring tetraphenylene compounds. In another aspect, the present invention includes novel pyrido fused tetraphenylene compounds.

Compounds of the Invention

In one aspect, the present invention includes a compound having Formula I:

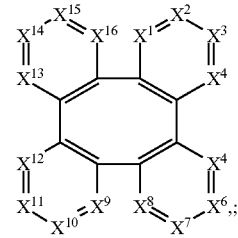

Formula I wherein $X^1$-$X^{16}$ are each independently selected from the group consisting of CR and N;

wherein at least two adjacent $X^1$-$X^{16}$ are CR;

wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein at least one pair of adjacent Rs is

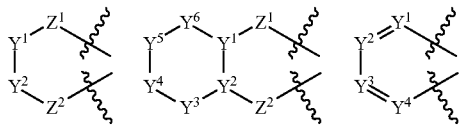

Attachment A, Attachment B, Attachment C, or is fused with two or more aromatic rings such that no acene unit of more than 3 fused rings is formed;

wherein in Attachments A and B, $Y^1$-$Y^2$, $Y^2$-$Y^3$, $Y^3$-$Y^4$, $Y^4$-$Y^5$ and $Y^5$-$Y^6$ are connected by single or double bonds;

wherein $Y^1$-$Y^6$ are each independently selected from the group consisting of C and N;

wherein any unsaturated C in $Y^1$-$Y^6$ is substituted by one or two $R^1$;

wherein in Attachment A, $Z^1$ and $Z^2$ are each independently selected from the group consisting of C=$CR^2R^3$, C=$NR^2$, $NR^2$, O, S, SO, $SO_2$, $BR^2$, $PR^2$, $SiR^2R^3$, and Se;

wherein in Attachment B, $Z^1$ and $Z^2$ are each independently selected from the group consisting of $CR^2R^3$, C=$CR^2R^3$, C=O, C=$NR^2$, $NR^2$, O, S, SO, $SO_2$, $BR^2$, P, $SiR^2R^3$, and Se;

wherein in Attachment C, at least one of $Y^1$-$Y^4$ is N;

wherein $R^1$-$R^3$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein

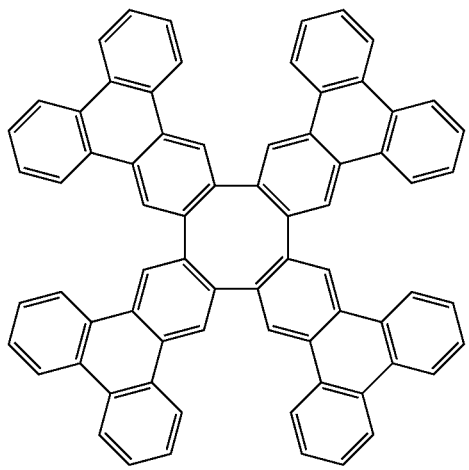 [SMILES: c1ccc2c(c1)c1ccccc1c1cc3c(cc21)-c1cc2c4ccccc4c4ccccc4c2cc1-c1cc2c4ccccc4c4ccccc4c2cc1-c1cc2c4ccccc4c4ccccc4c2cc1-3]

is excluded.

In one embodiment, $X^1$-$X^{16}$ are CR. In one embodiment, $X^1$-$X^{16}$ are CR and in Attachments A and B, $Y^1$-$Y^6$ are C.

In one embodiment, at least two pairs of adjacent Rs are attachment A, B, C, or are fused with two or more aromatic rings such that no acene unit of more than 3 fused rings is formed. In one embodiment, at least three pairs of adjacent Rs are attachment A, B, C, or are fused with two or more aromatic rings such that no acene unit of more than 3 fused rings is formed. In one embodiment, at least four pairs of adjacent Rs are attachment A, B, C, or are fused with two or more aromatic rings such that no acene unit of more than 3 fused rings is formed.

In one embodiment, the compound is selected from the group consisting of:

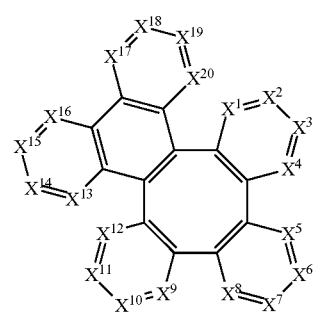

Formula 2

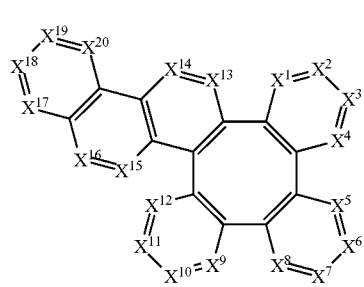

Formula 3

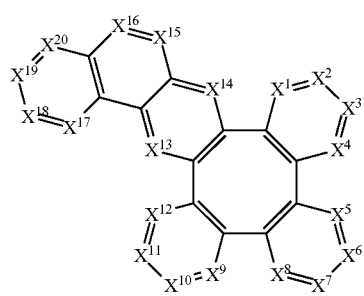

Formula 4

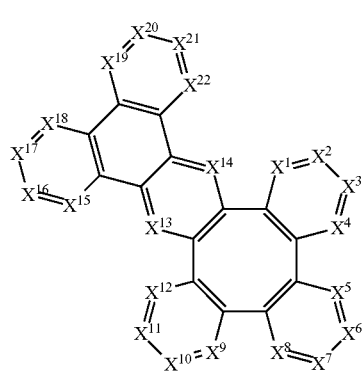

Formula 5

Formula 6
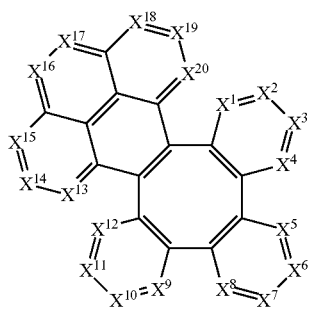
Formula 7
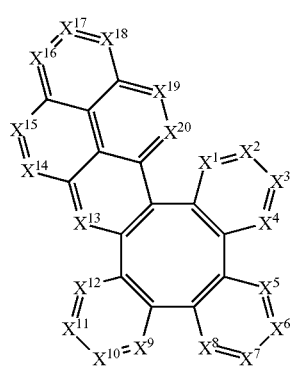
Formula 8
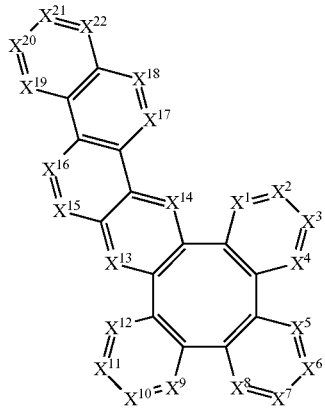
Formula 9
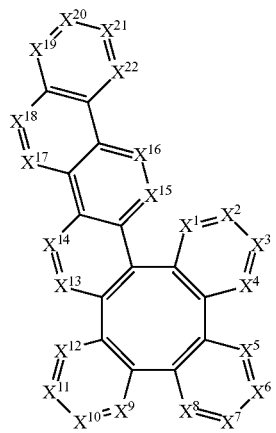
wherein $X^1$-$X^{22}$ are each independently selected from the group consisting of CR and N.
In one embodiment, the compound is selected from the group consisting of:
Compound A1
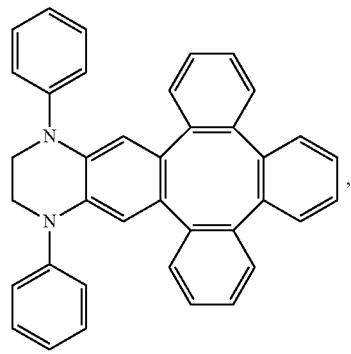
,
Compound A2
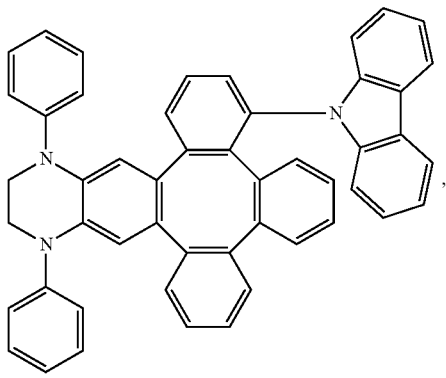
, -continued
Compound A3
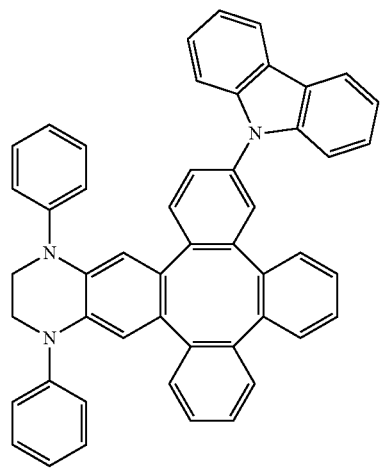
Compound A4
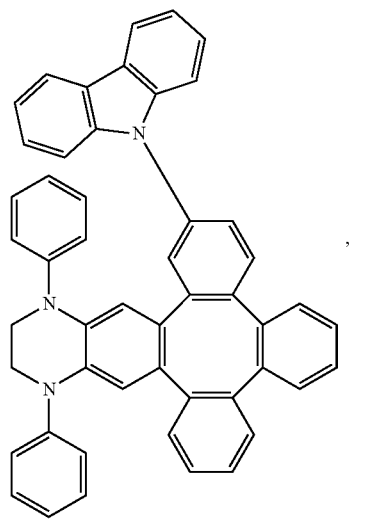
Compound A5
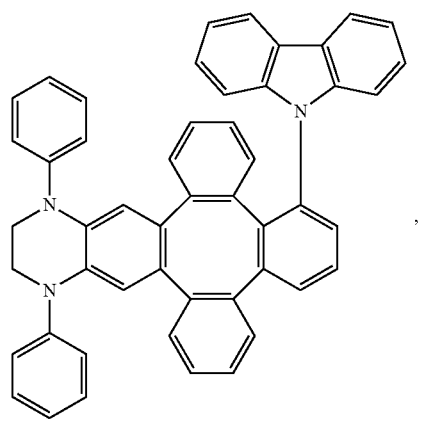
Compound A6
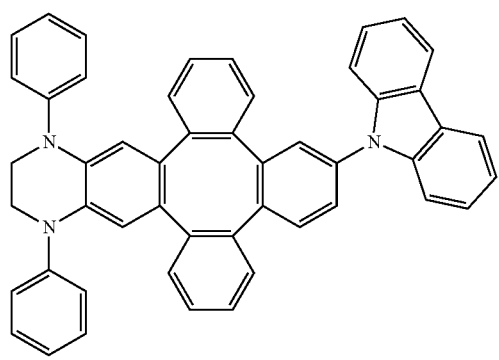
Compound A7
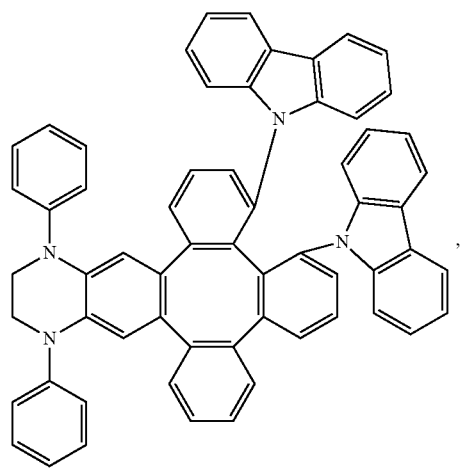
Compound A8
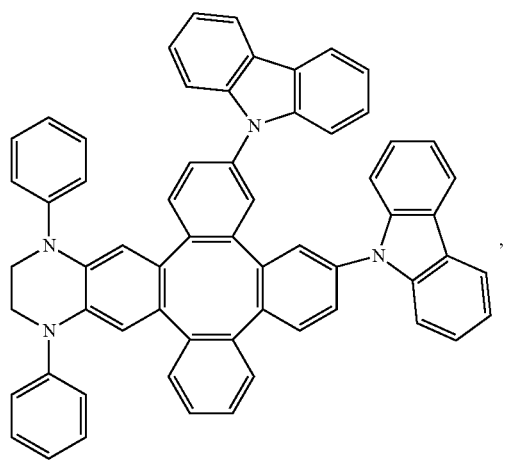

-continued
Compound A9
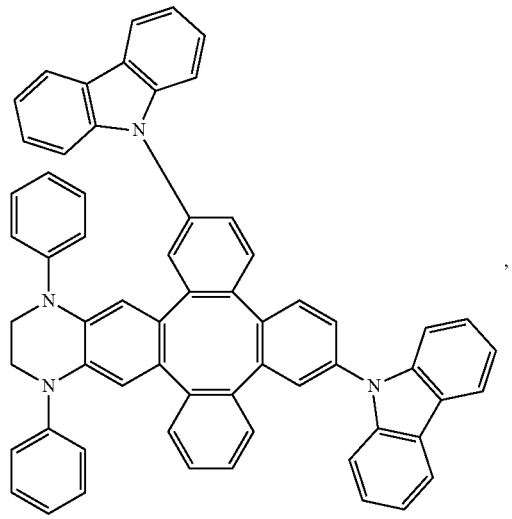
Compound A10
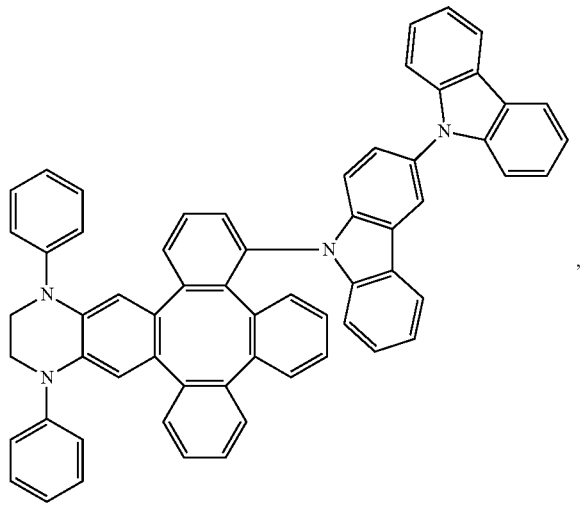
Compound A11
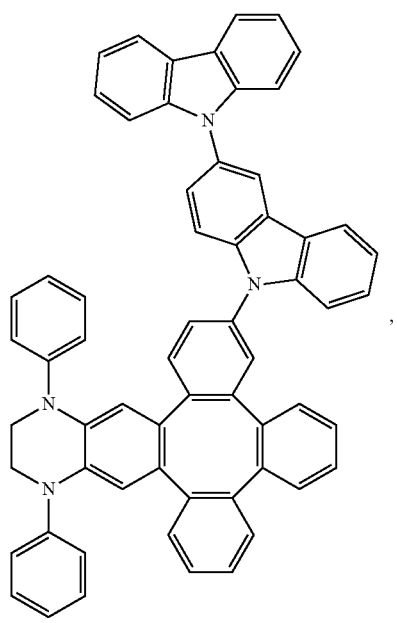
Compound A12
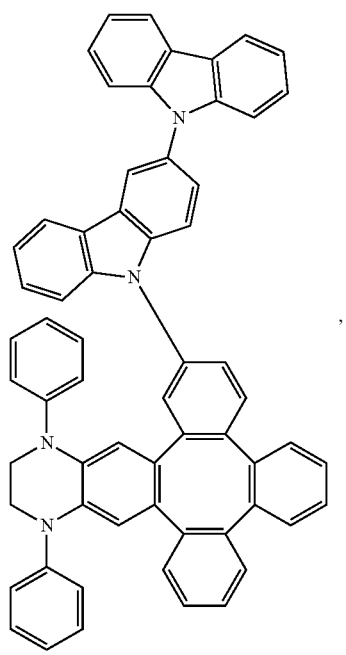

-continued
Compound A13
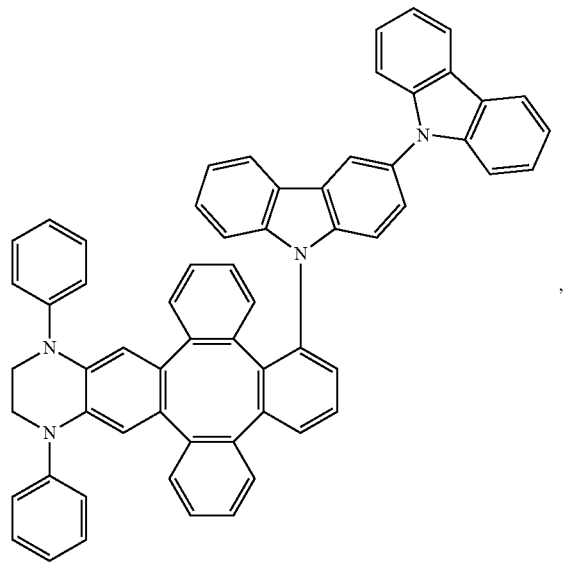
Compound A14
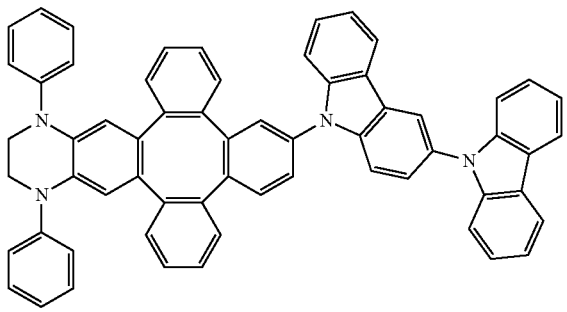
Compound A15
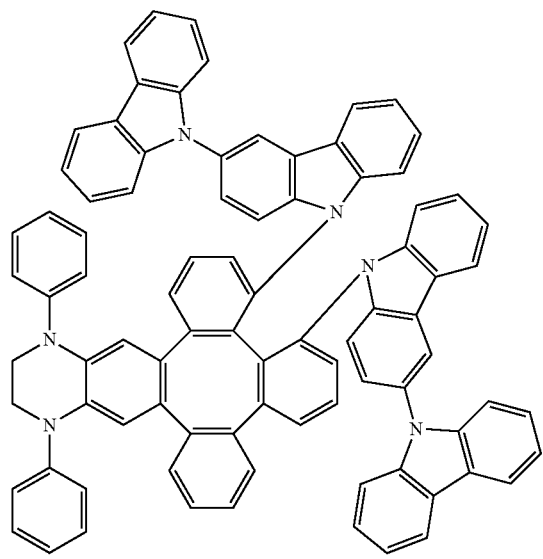
Compound A16
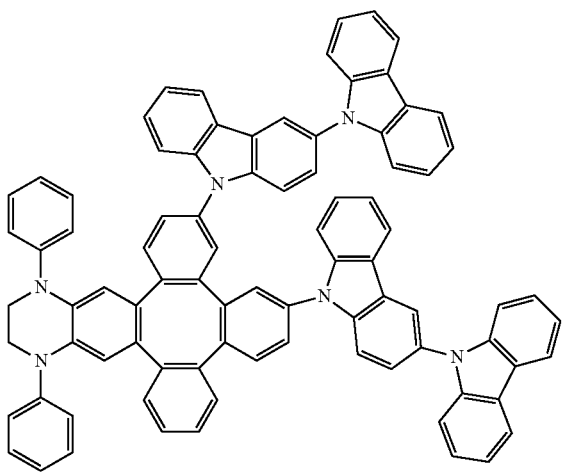

-continued
Compound A17
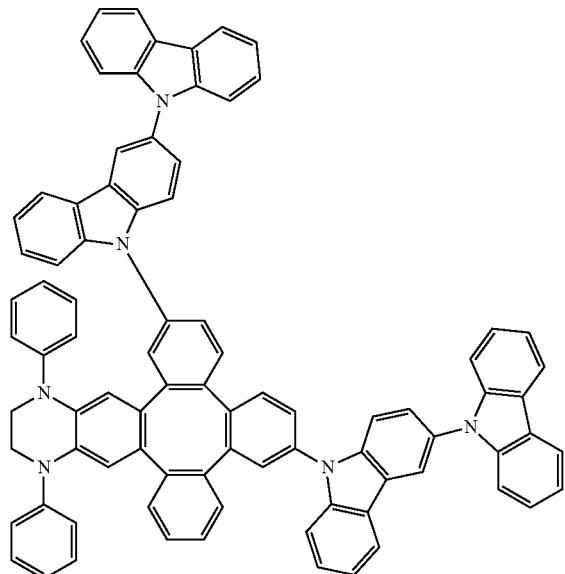
Compound A18
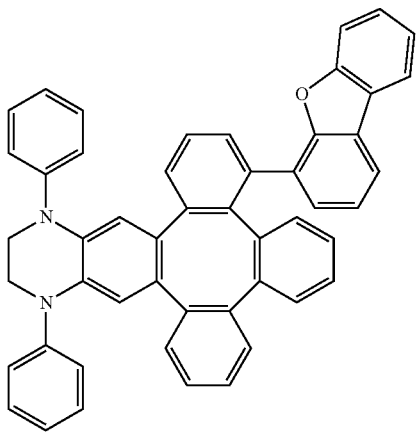
Compound A19
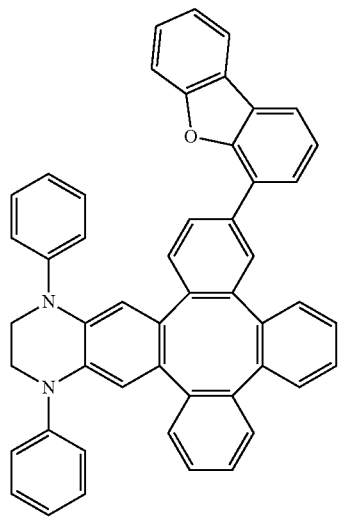
Compound A20
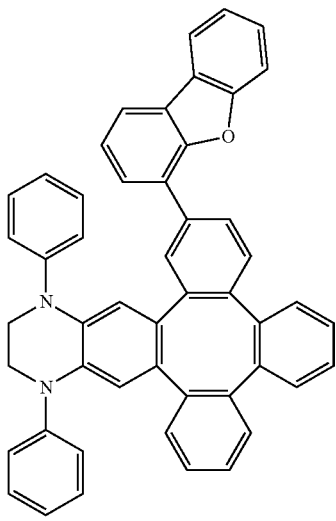
Compound A21
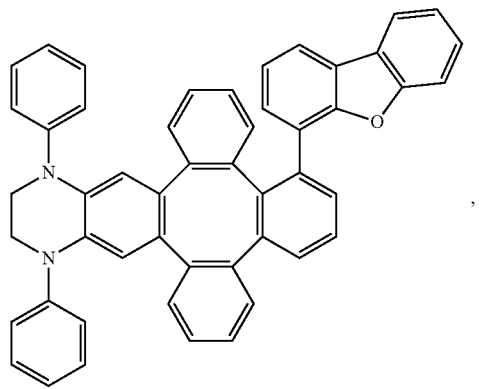
Compound A22
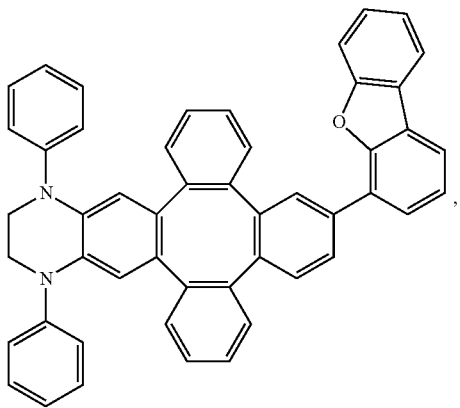

-continued
Compound A23
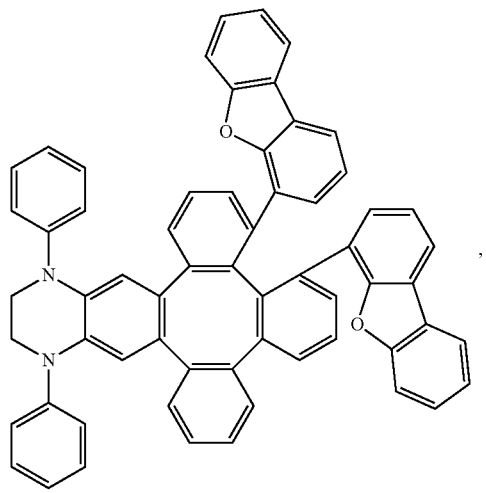
Compound A24
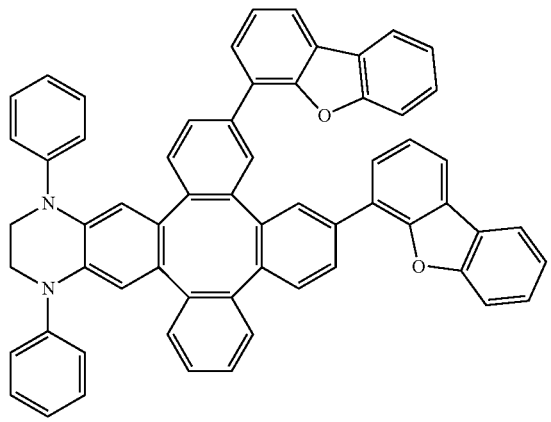
Compound A25
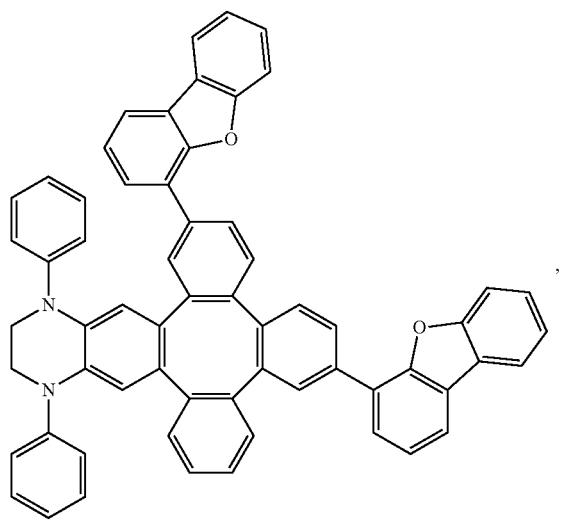
Compound A26
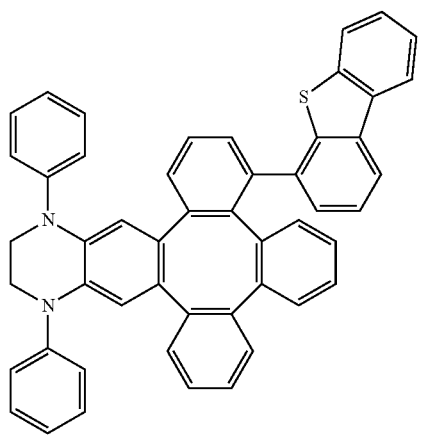
Compound A27
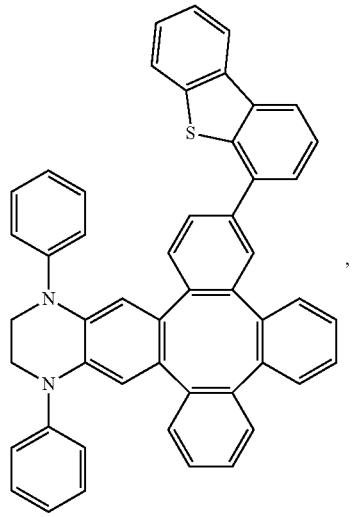
Compound A28
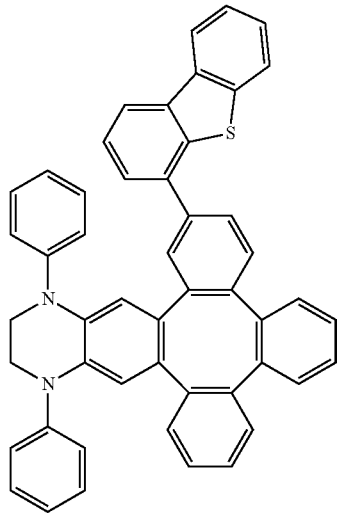

-continued
Compound A29
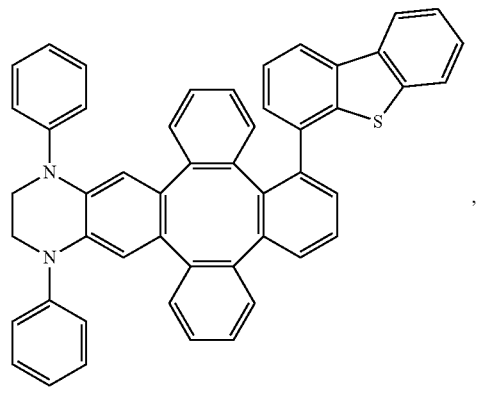
Compound A30
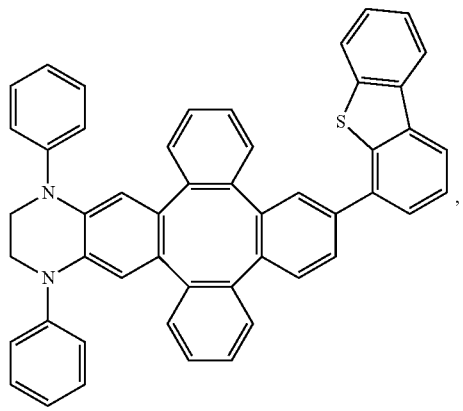
Compound A31
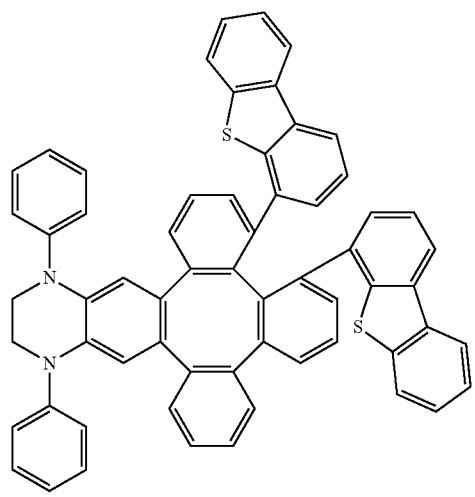
Compound A32
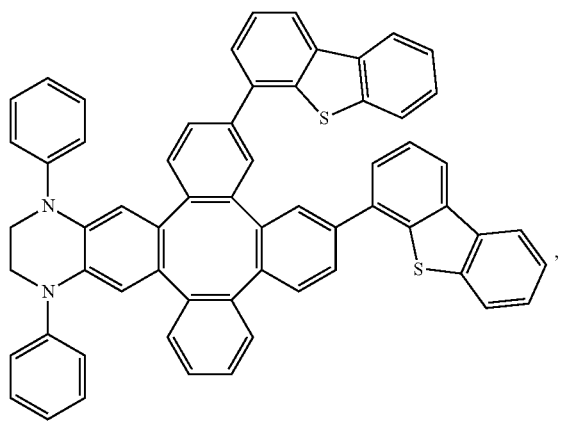
Compound A33
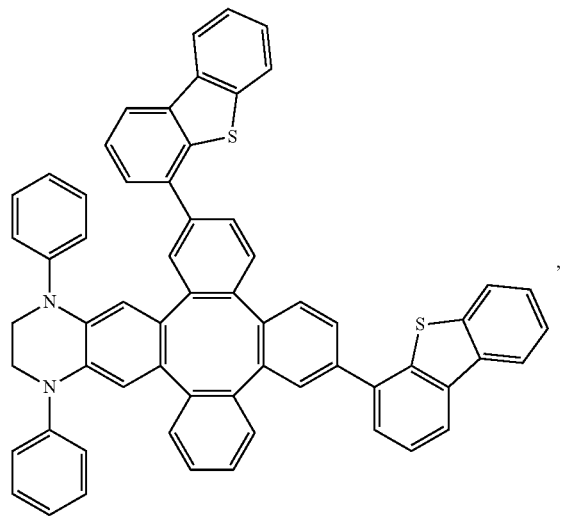
Compound C1
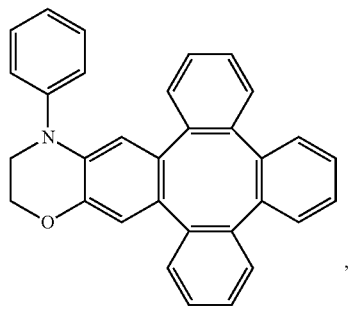

-continued
Compound C2
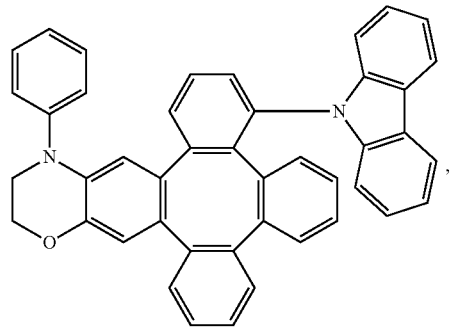
Compound C3
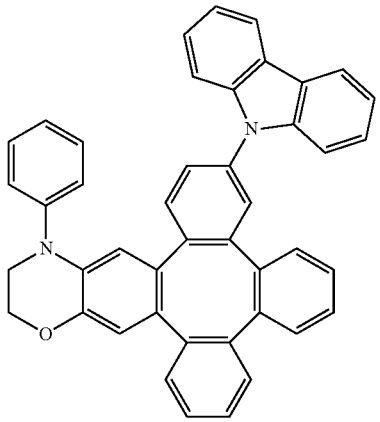
Compound C4
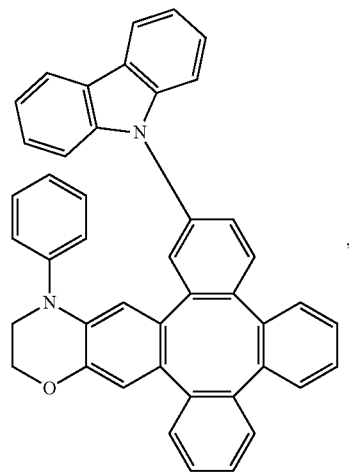
Compound C5
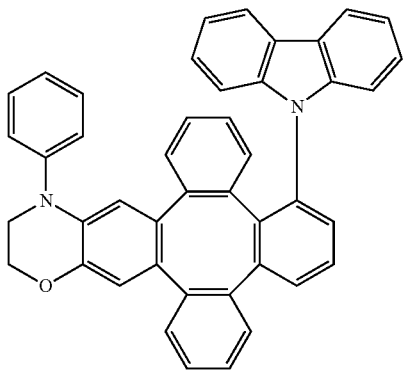
Compound C6
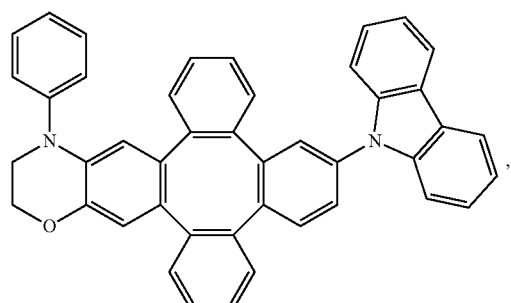
Compound C7
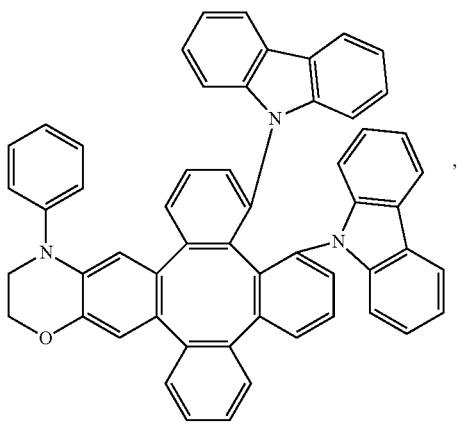

-continued
Compound C8
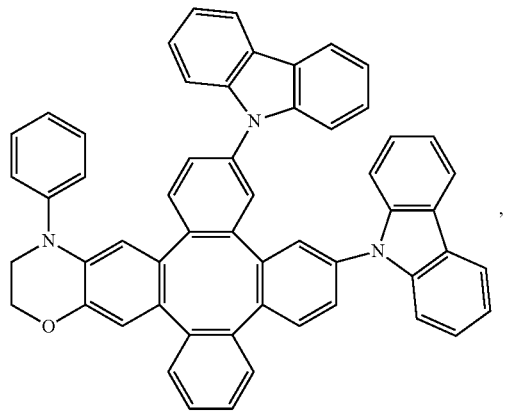
Compound C9
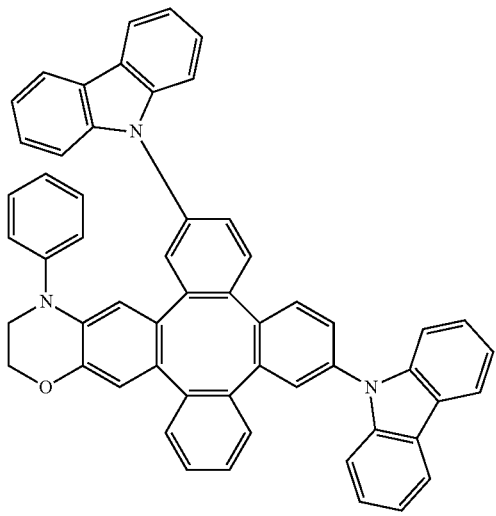
Compound C10
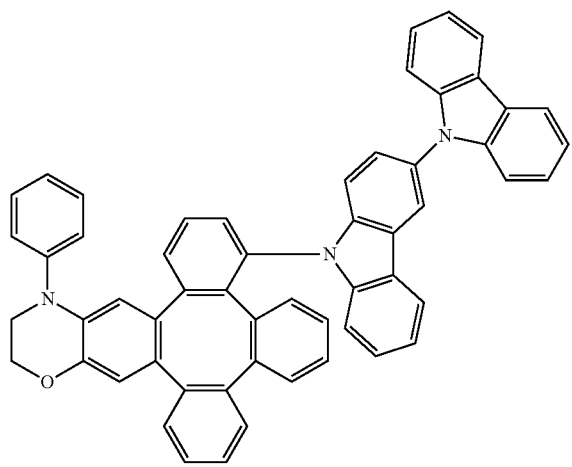
Compound D1
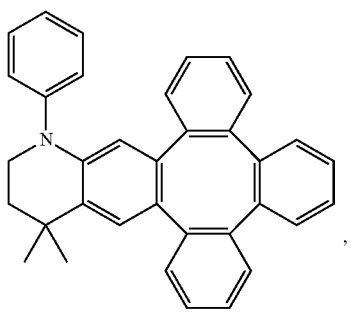
Compound D2
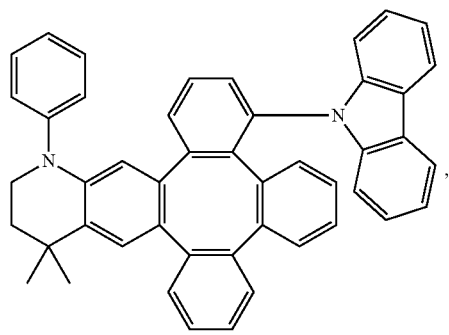
Compound D3
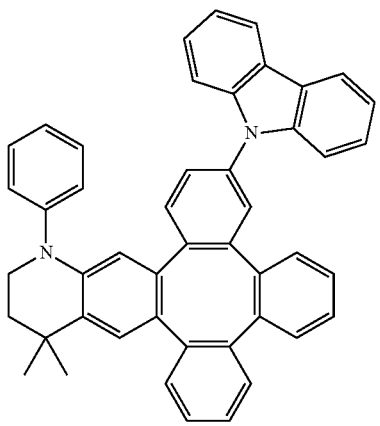

-continued
Compound D4
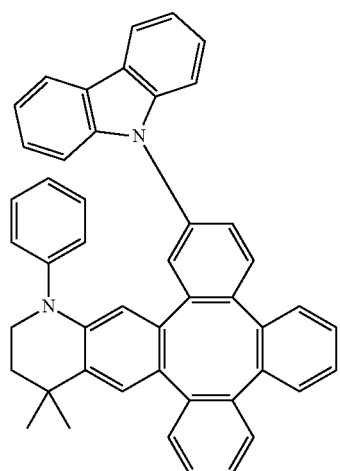
Compound D5
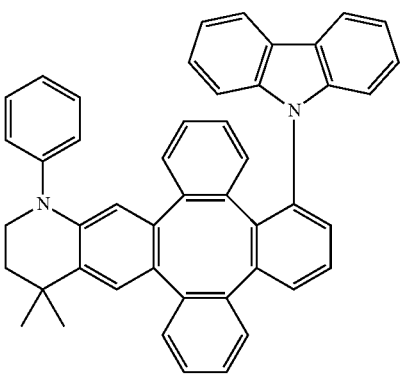
Compound D6
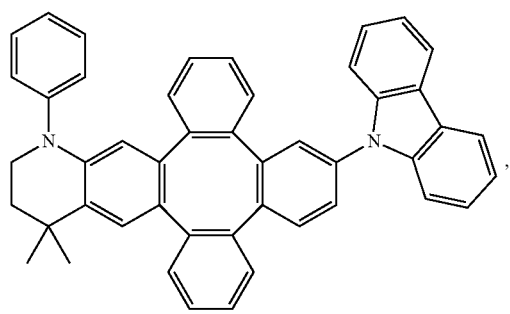
Compound D7
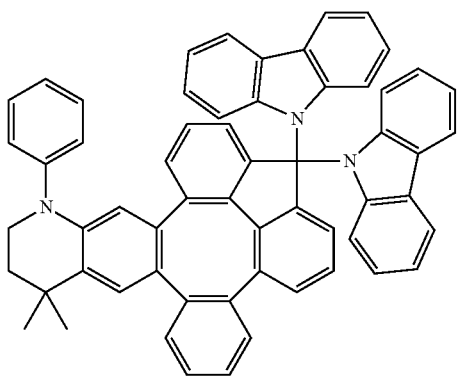
Compound D8
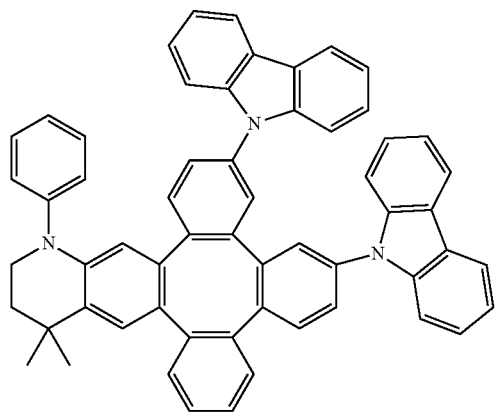
Compound D9
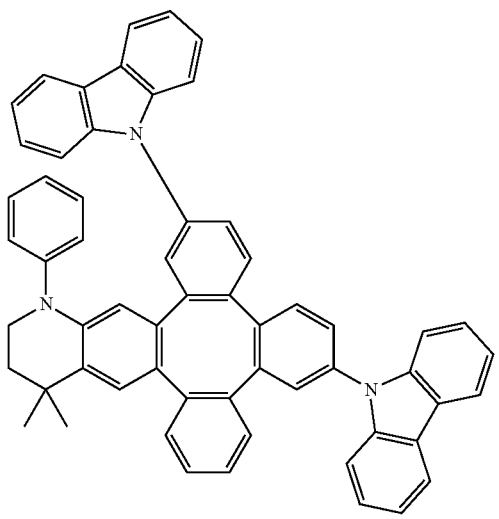

-continued
Compound D10
Compound B1
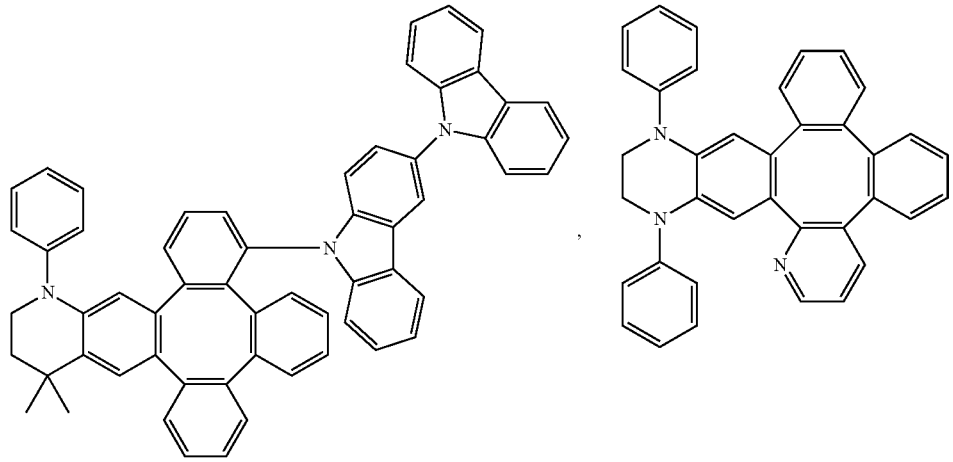
Compound B2
Compound B3
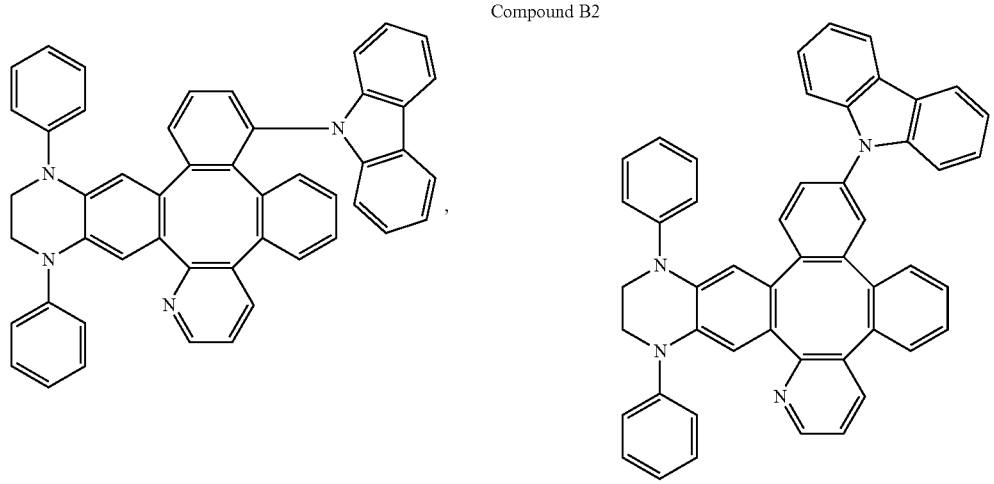
Compound B4
Compound B5
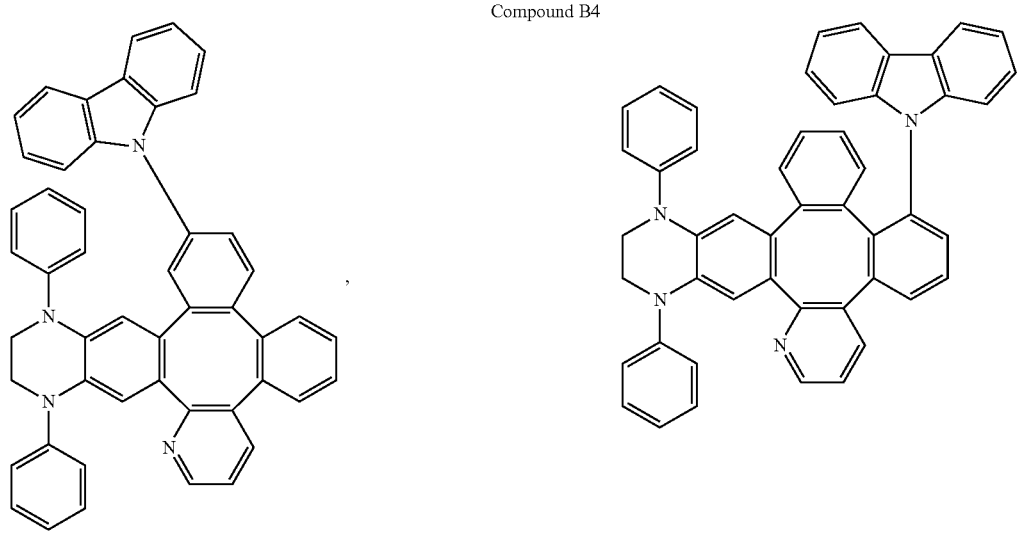

-continued
Compound B6
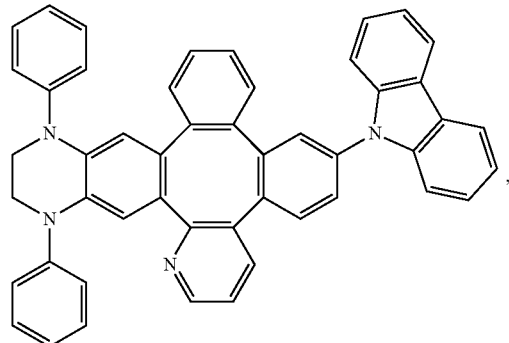
Compound B7
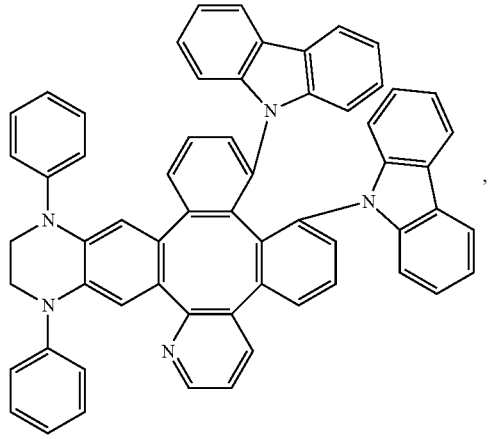
Compound B8
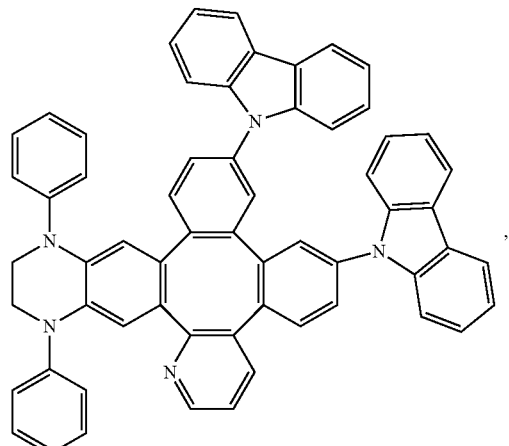
Compound B9
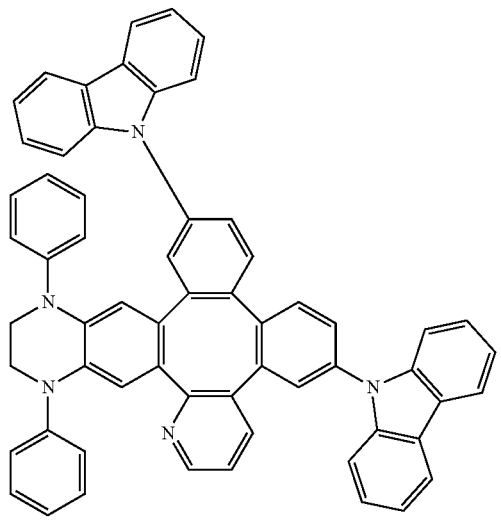
Compound B10
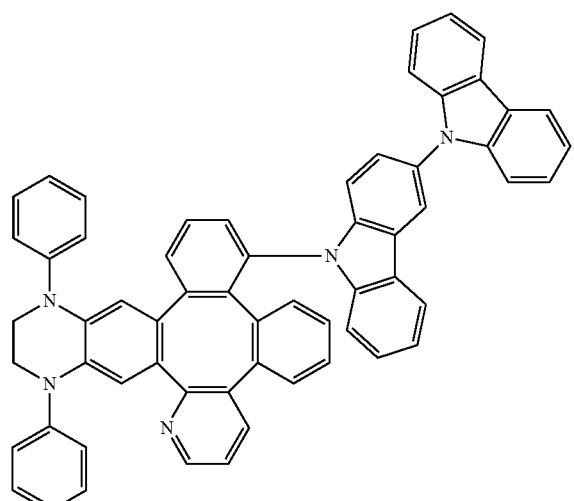
Compound B11
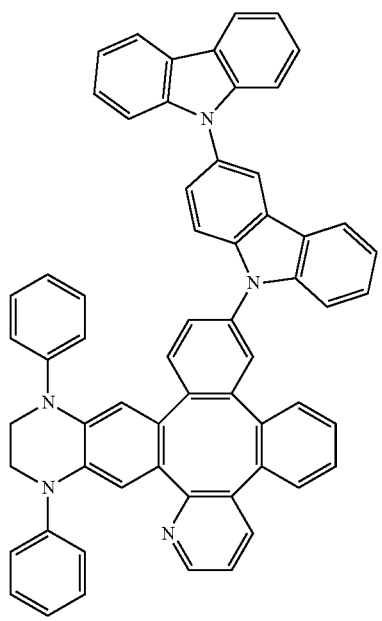

-continued
Compound B12
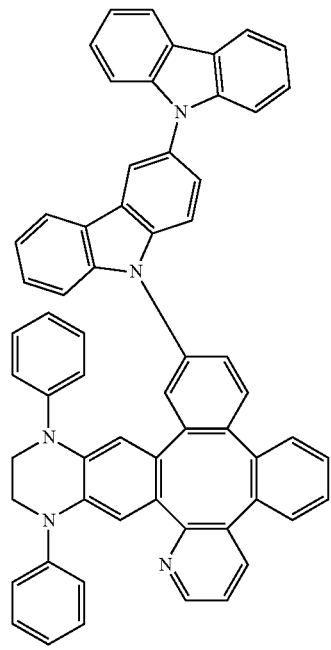
Compound B13
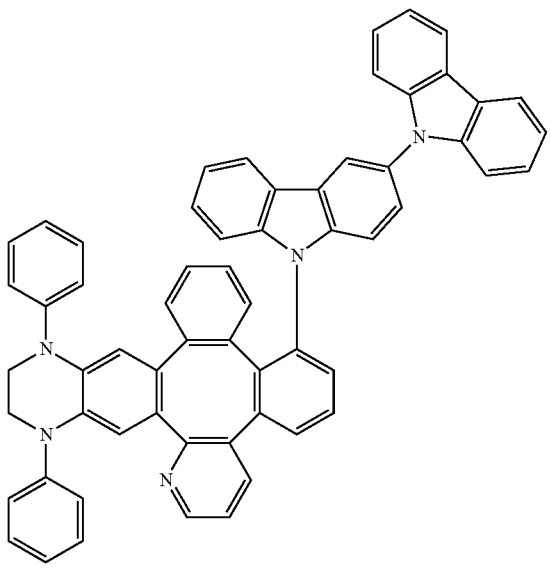
Compound B14
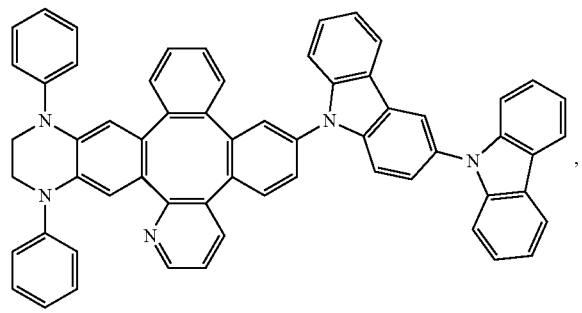
Compound B15
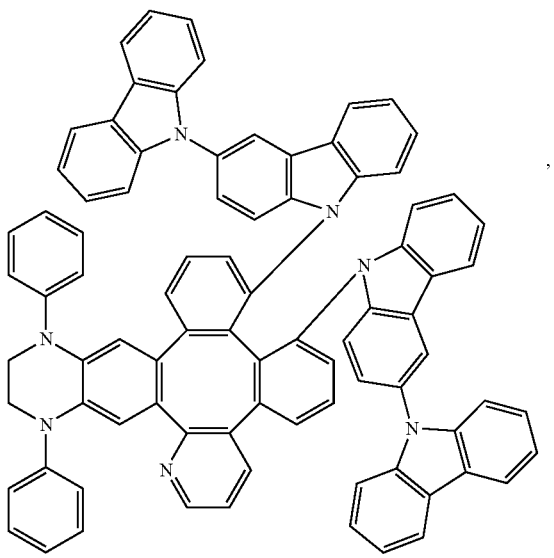

-continued
Compound B16
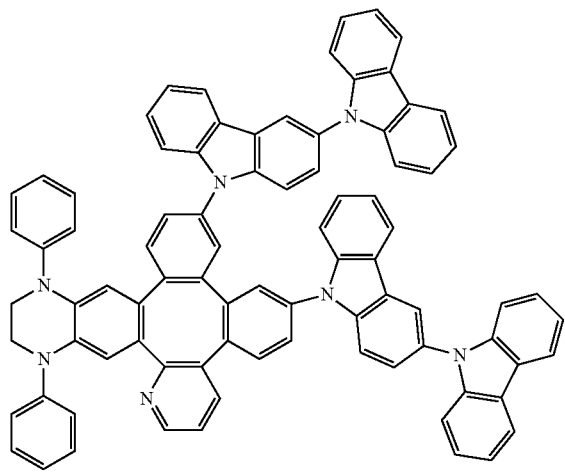
Compound B17
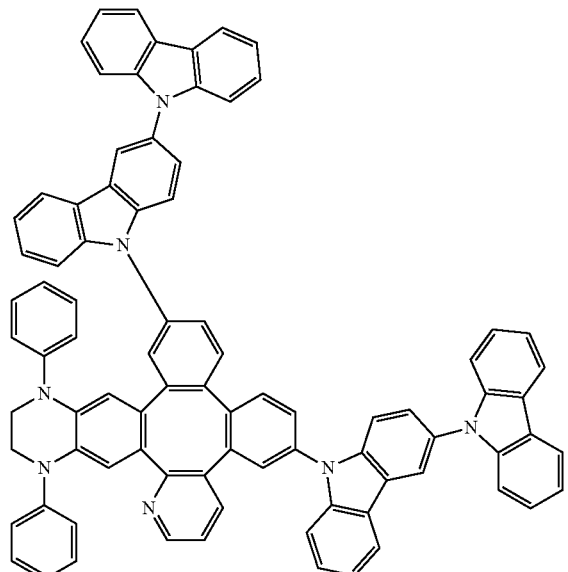
Compound B18
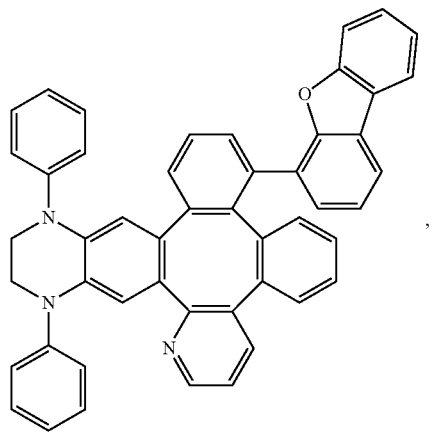
Compound B19
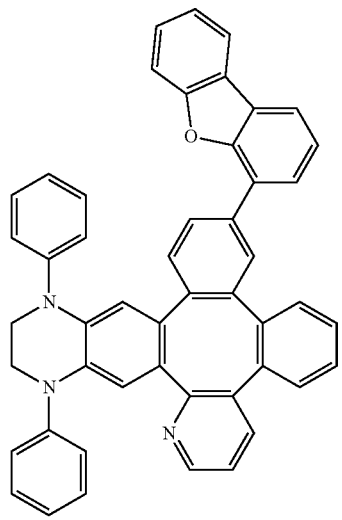
Compound B20
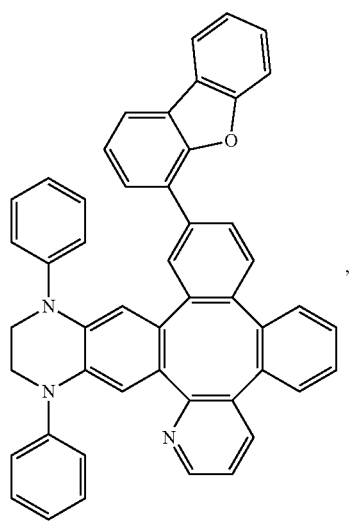
Compound B21
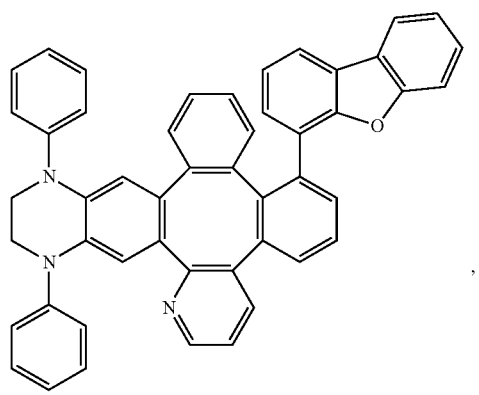

-continued
Compound B22
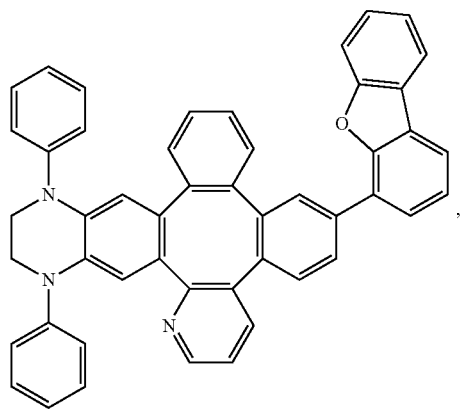
Compound B23
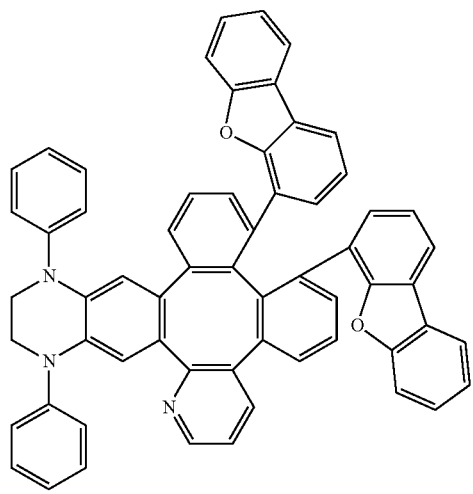
Compound B24
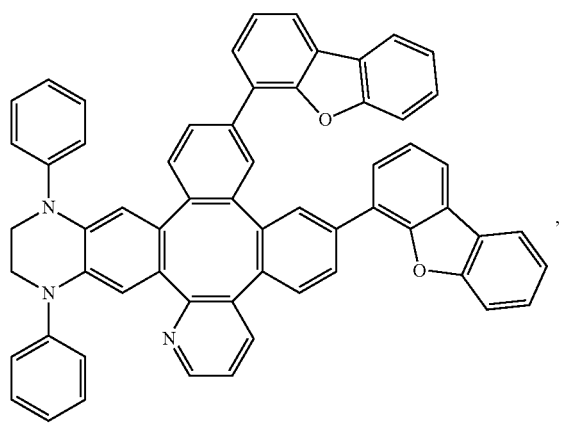
Compound B25
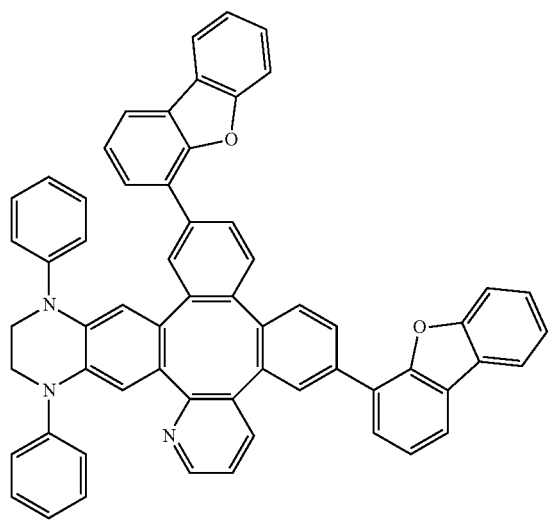
Compound B26
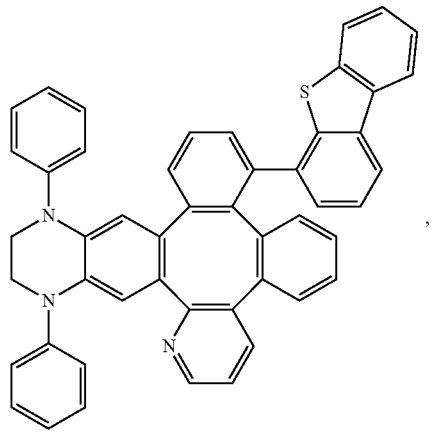
Compound B27
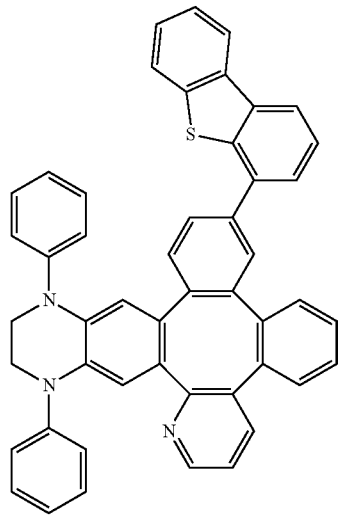

-continued
Compound B28
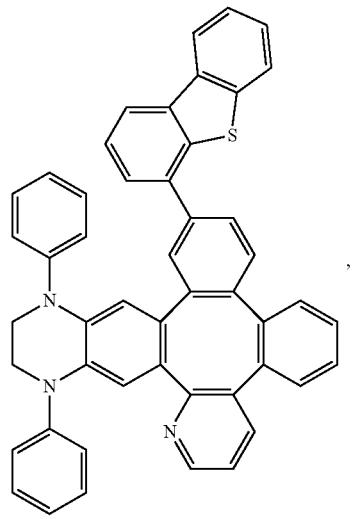
Compound B29
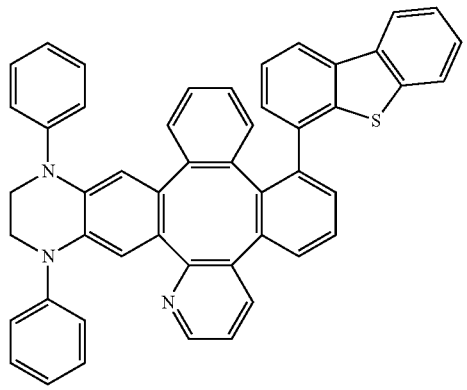
Compound B30
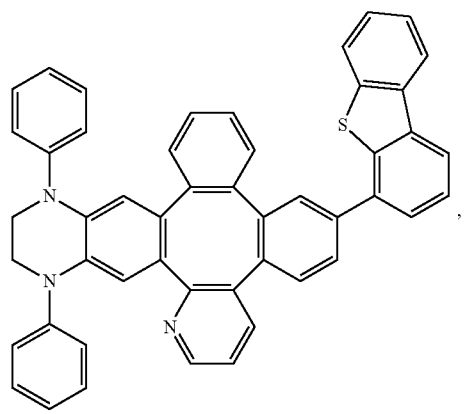
Compound B31
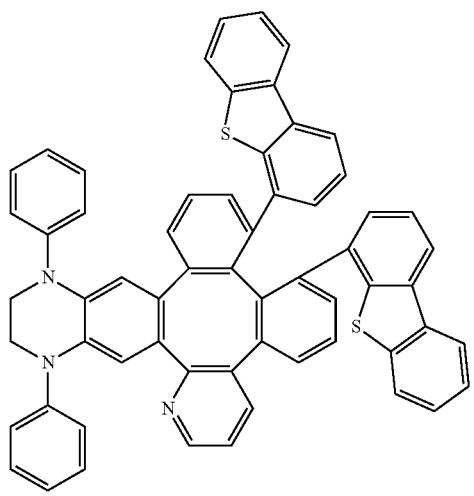
Compound B32
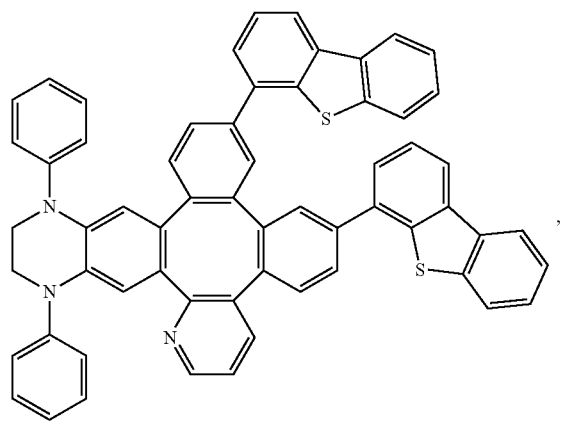
Compound B33
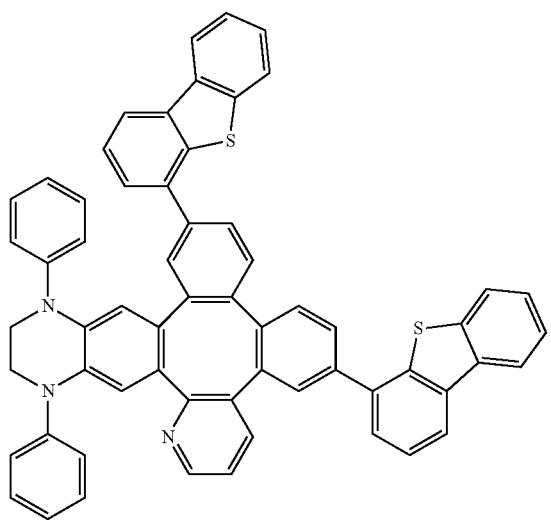

-continued
Compound CC1
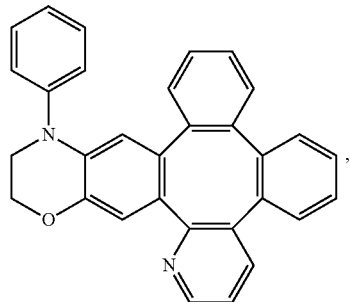
Compound CC2
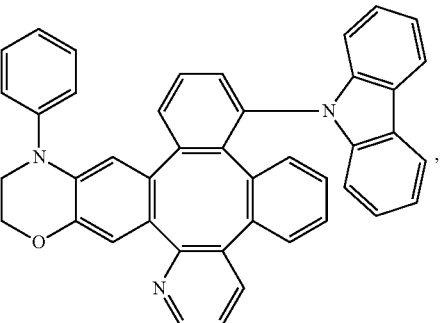
Compound CC3
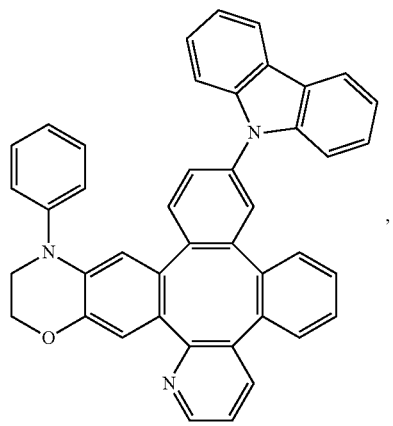
Compound CC4
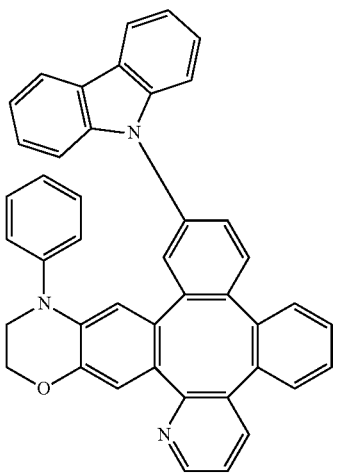
Compound CC5
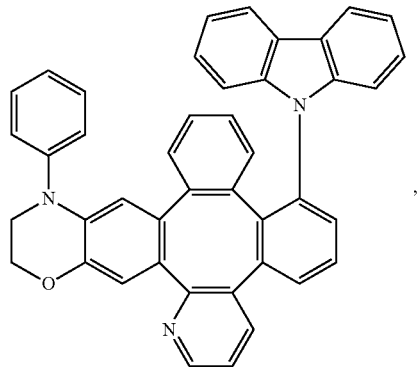
Compound CC6
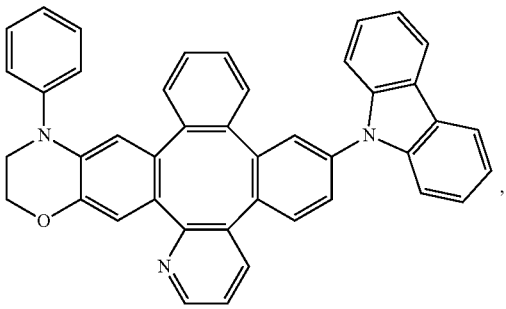
Compound CC7
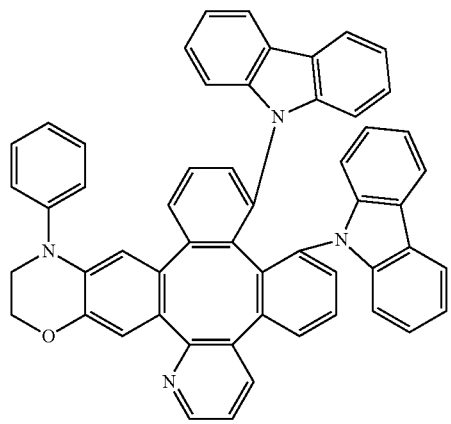
Compound CC8
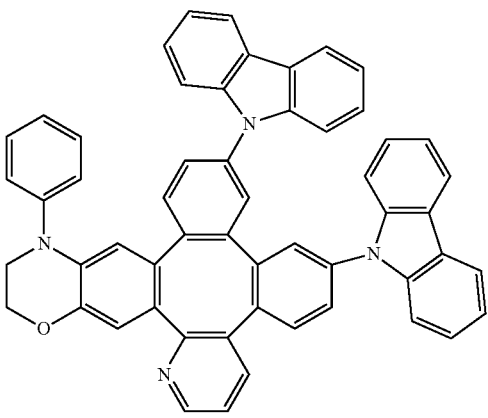

Compound CC9
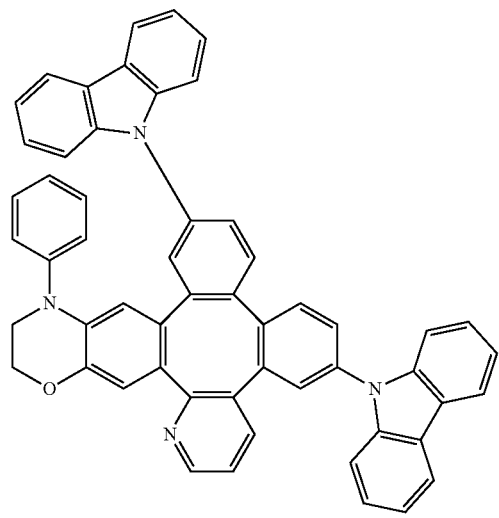
Compound CC10
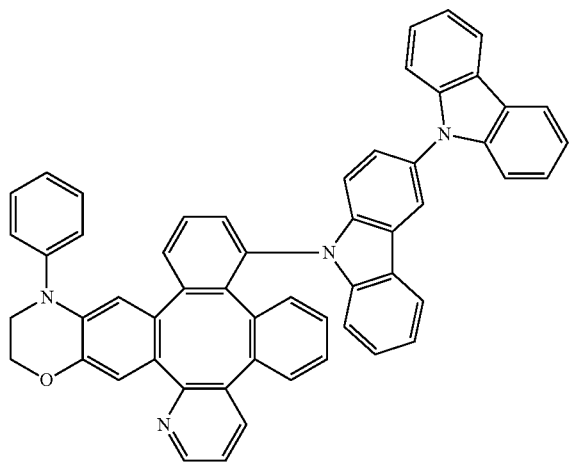
Compound DD1
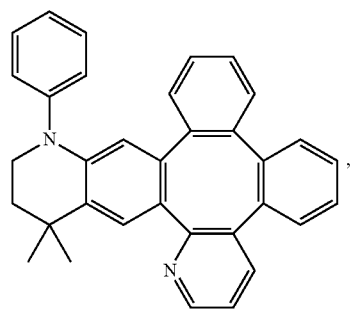
,
Compound DD2
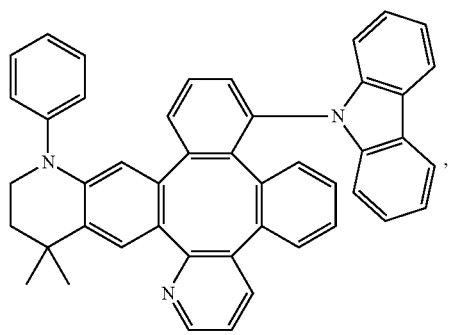
,
Compound DD3
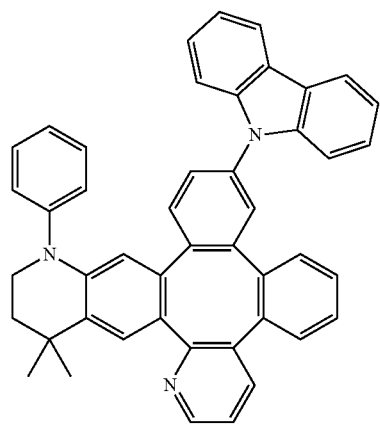
,
Compound DD4
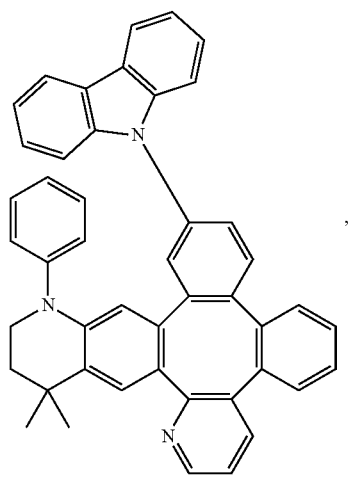
, -continued
Compound DD5
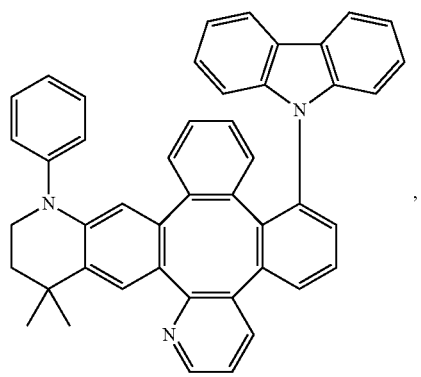
Compound DD6
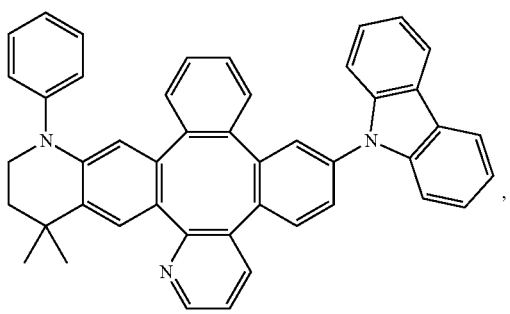
Compound DD7
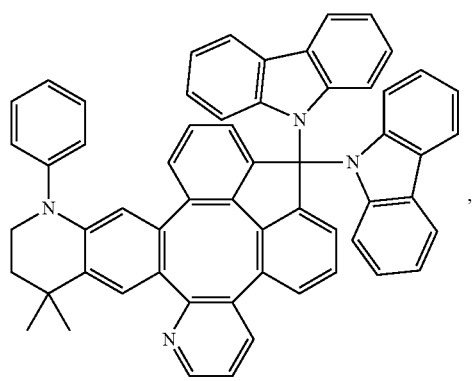
Compound DD8
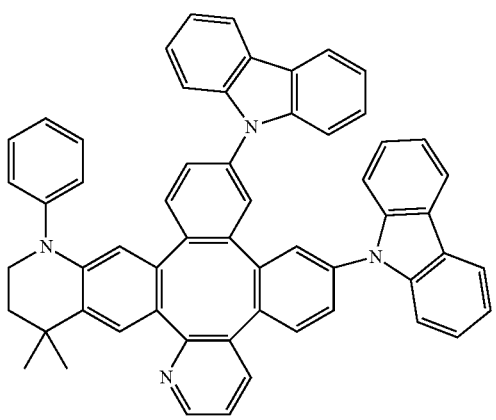
Compound DD9
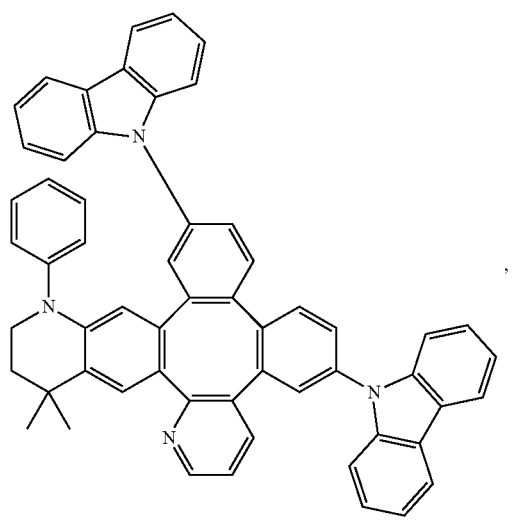
Compound DD10
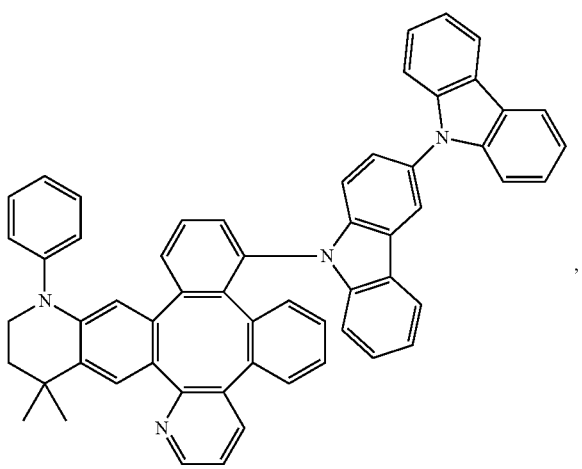

Compound A34
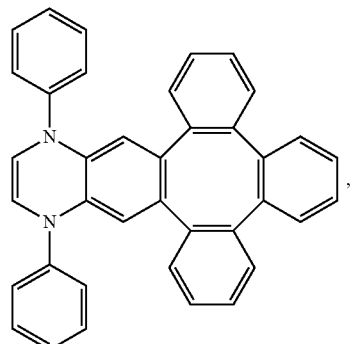
Compound A35
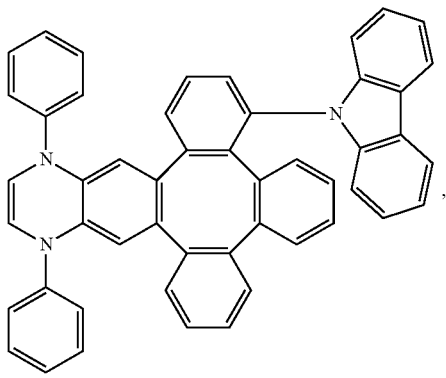
Compound A36
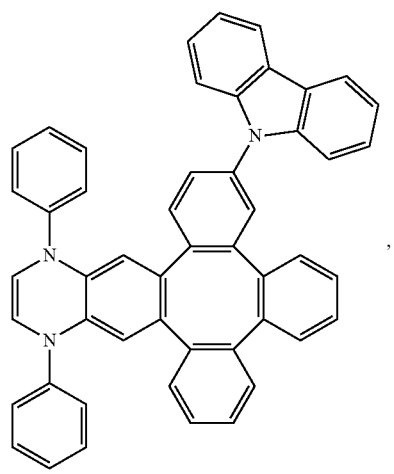
Compound A37
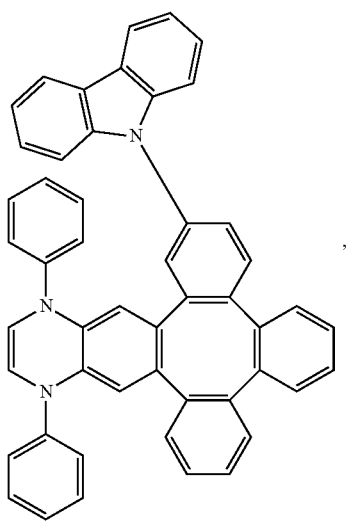
Compound A38
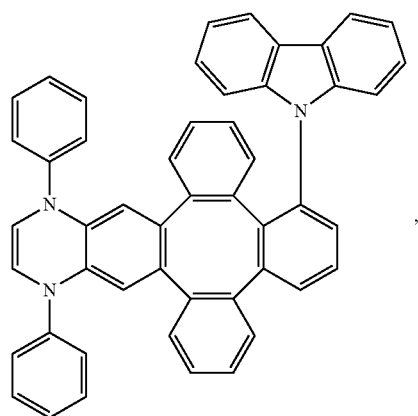
Compound A39
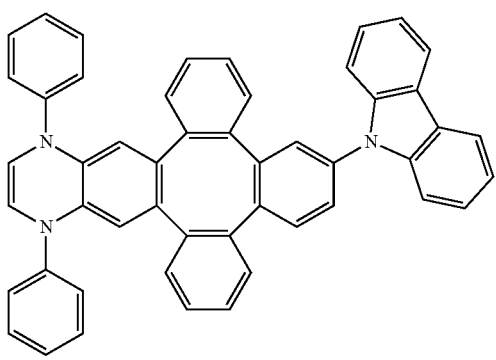

-continued
Compound A40
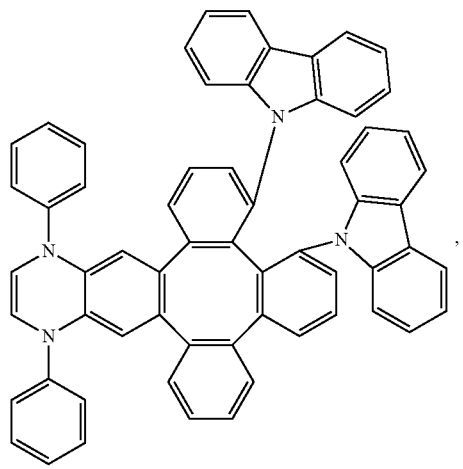
Compound A41
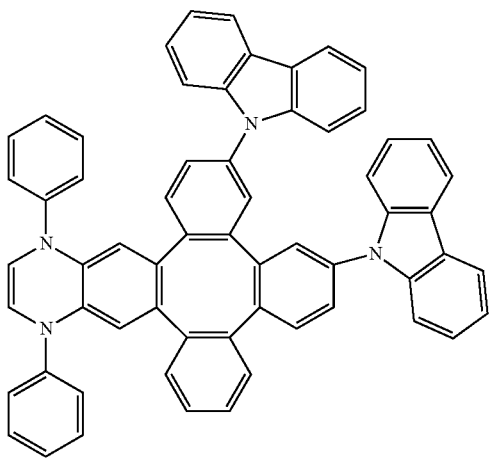
Compound A42
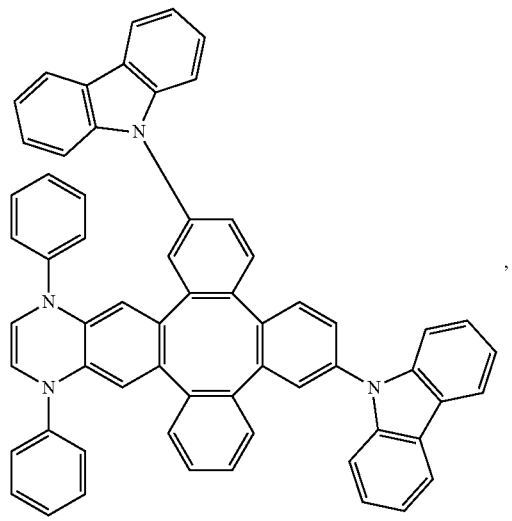
Compound A43
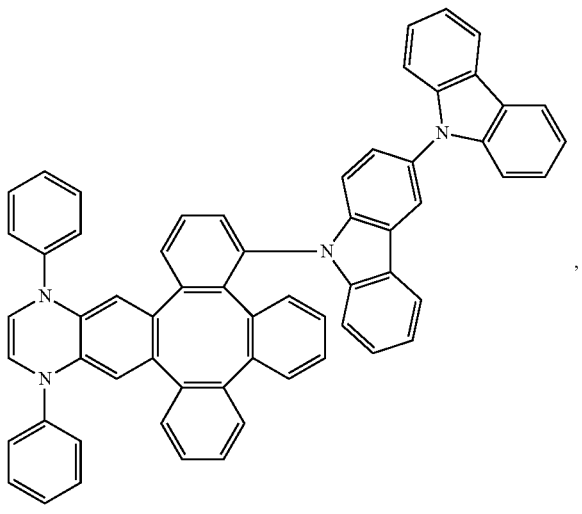
Compound A44
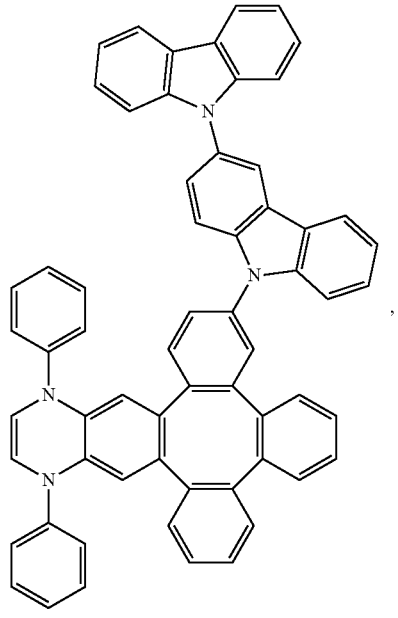
Compound A45
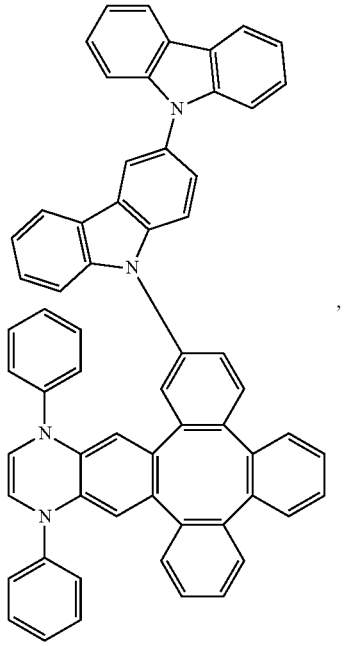

-continued
Compound A46
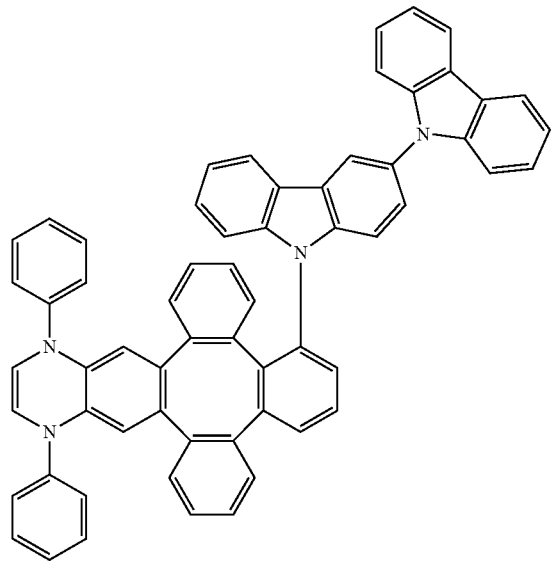
Compound A47
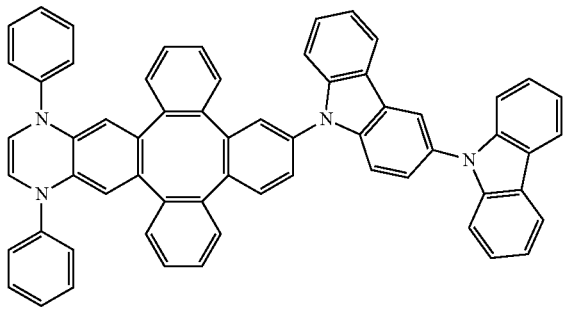
Compound A48
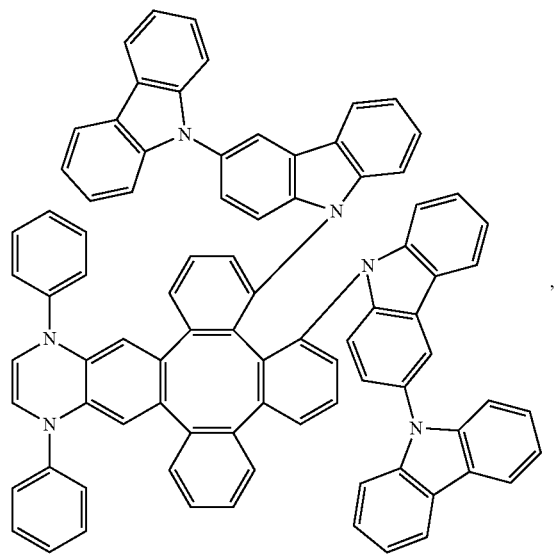
Compound A49
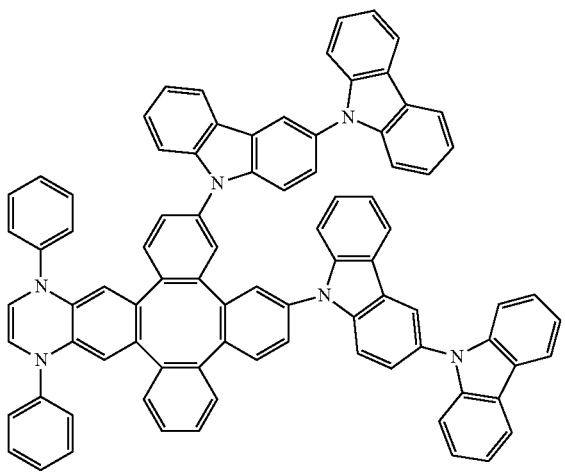

-continued
Compound A50
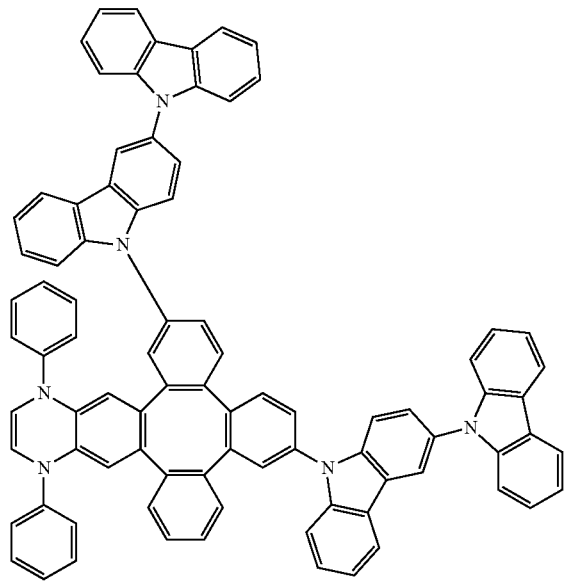
Compound A51
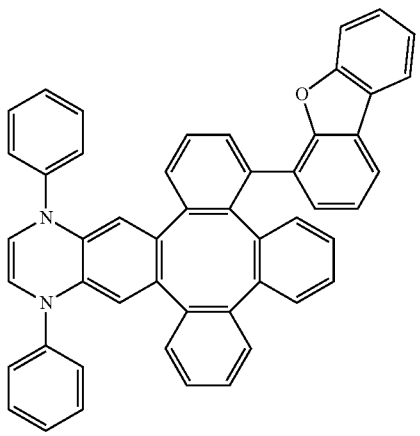
Compound A52
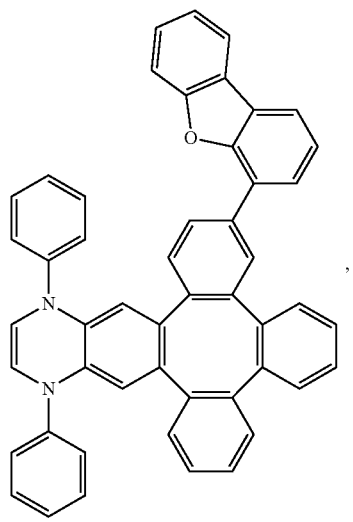
Compound A53
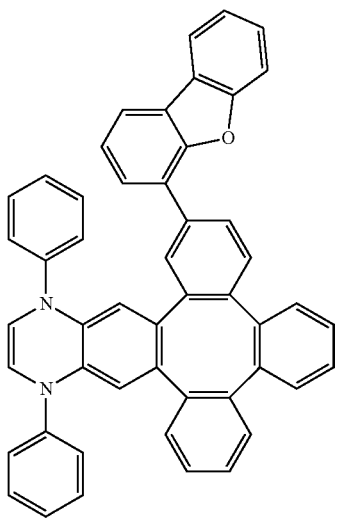
Compound A54
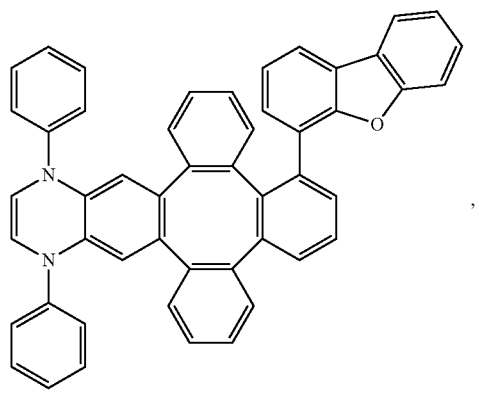
Compound A55
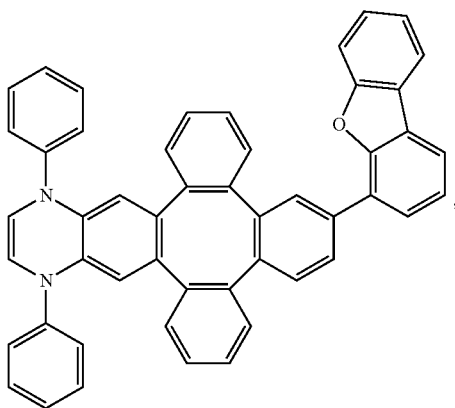

-continued
Compound A56
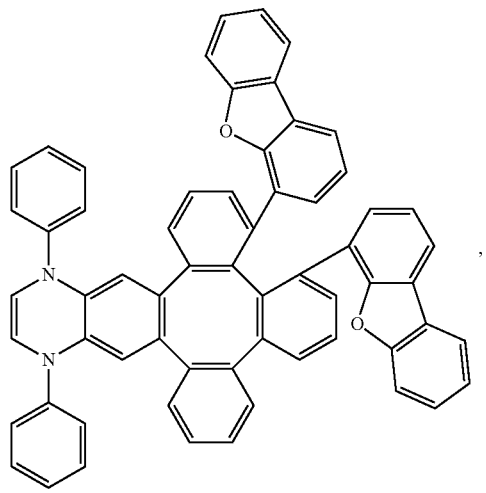
Compound A57
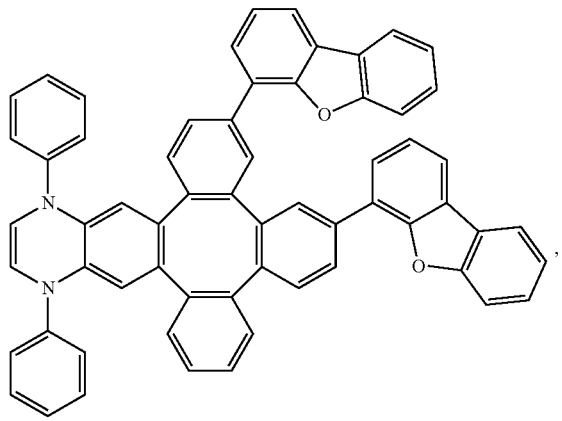
Compound A58
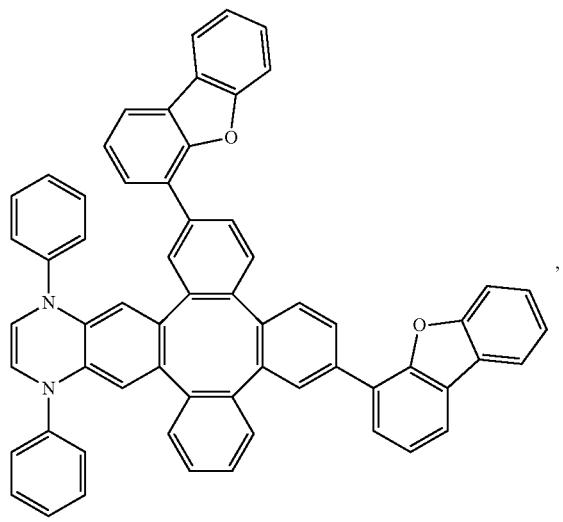
Compound A59
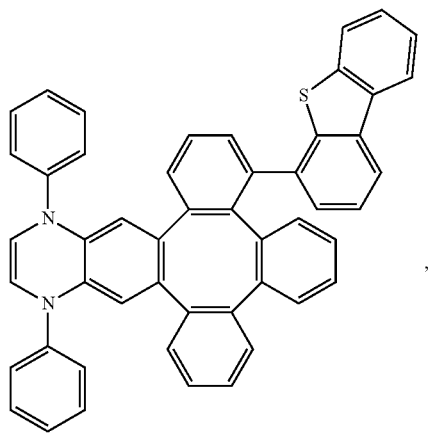
Compound A60
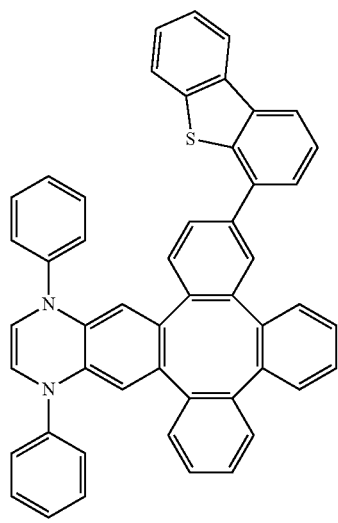
Compound A61
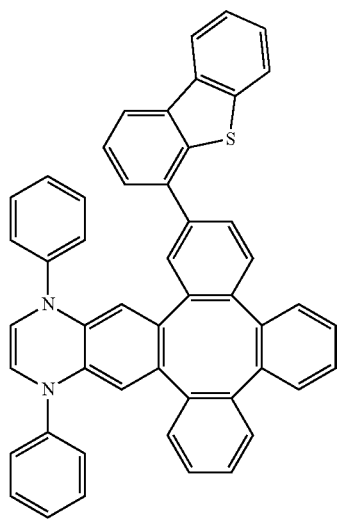

-continued
Compound A62
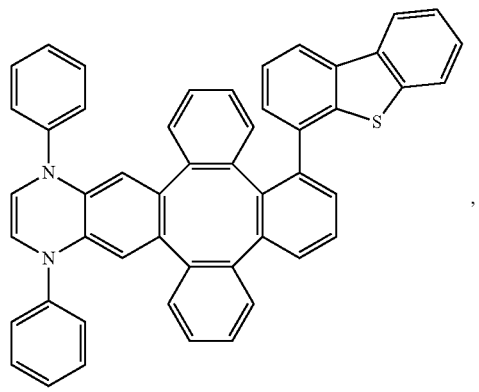
Compound A63
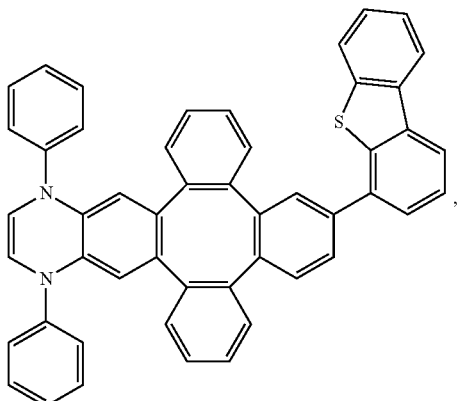
Compound A64
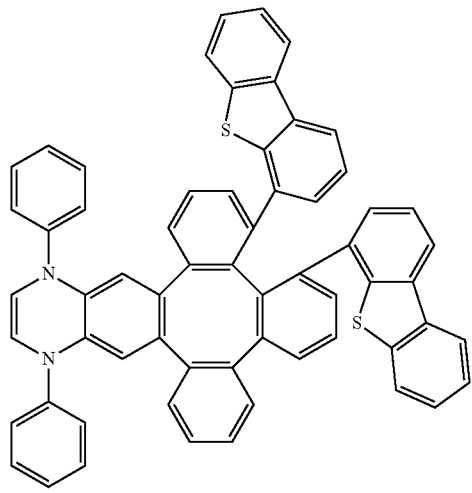
Compound A65
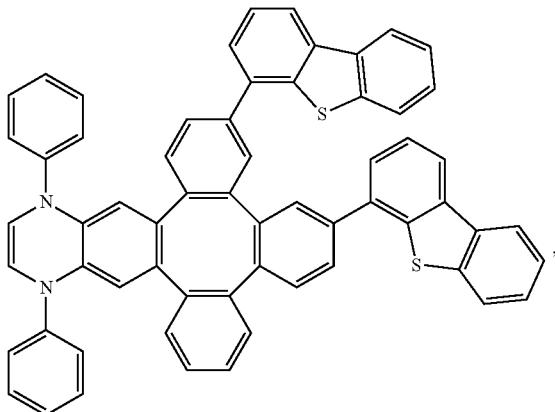
Compound A66
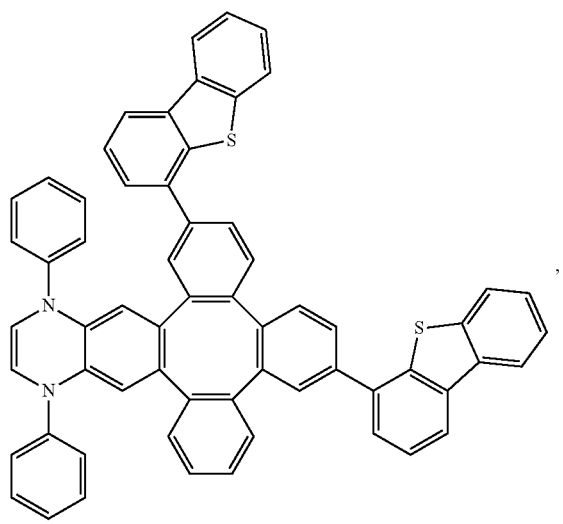
Compound C34
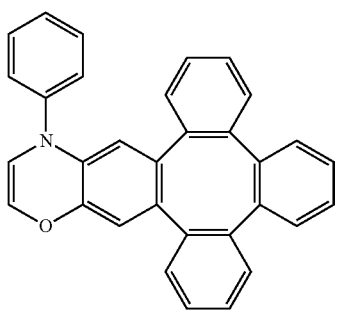

-continued
Compound C35
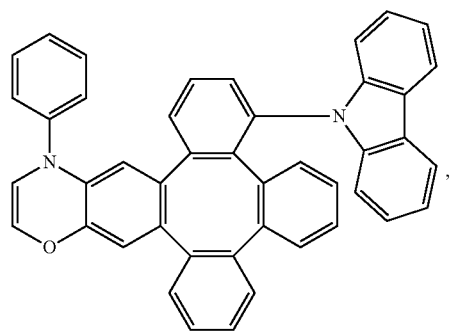
Compound C36
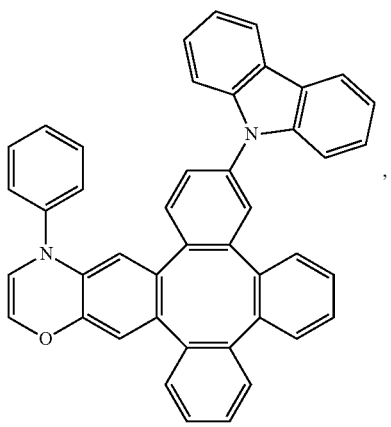
Compound C37
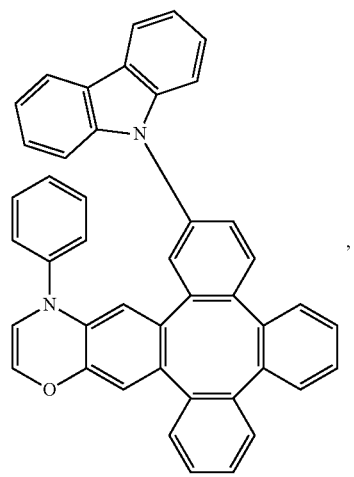
Compound C38
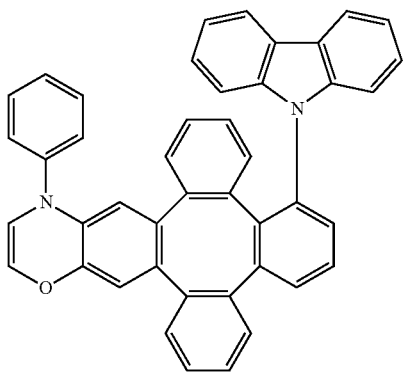
Compound C39
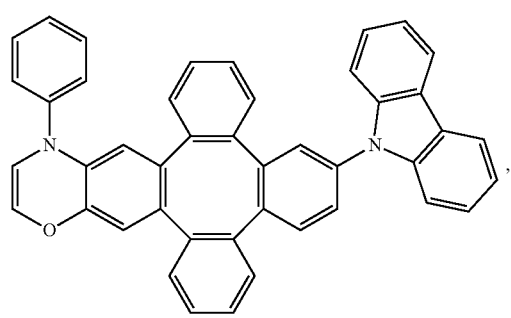
Compound C40
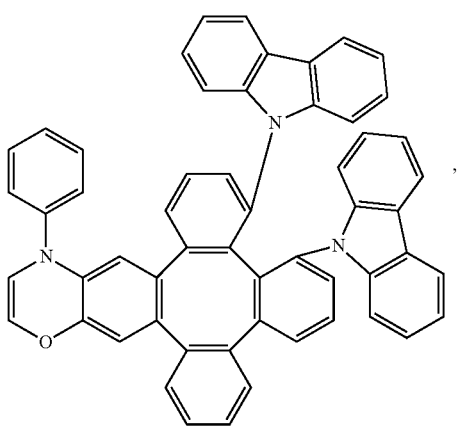

-continued
Compound C41
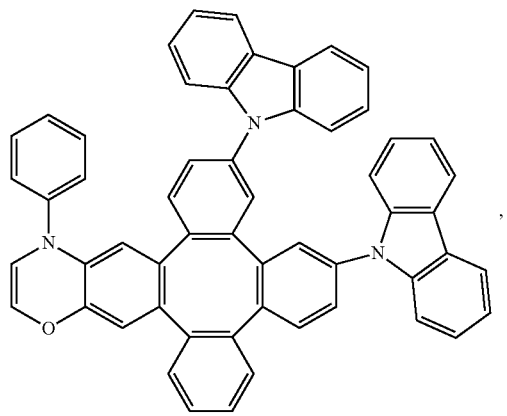
Compound C42
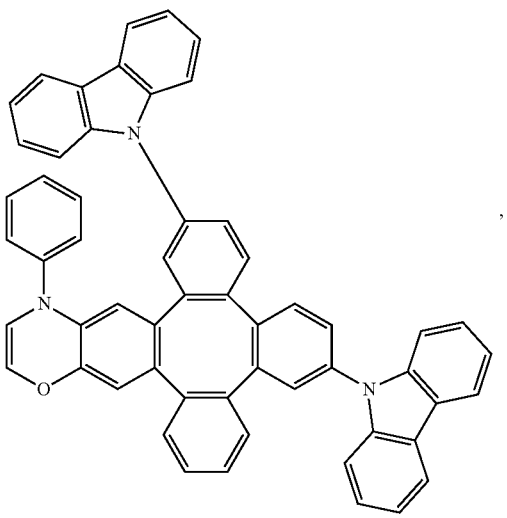
Compound C43
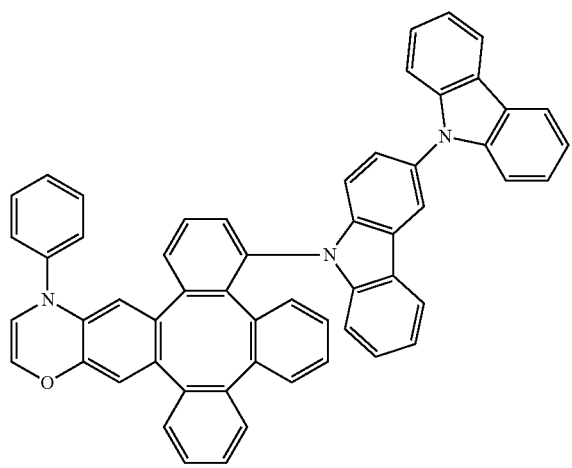
Compound D34
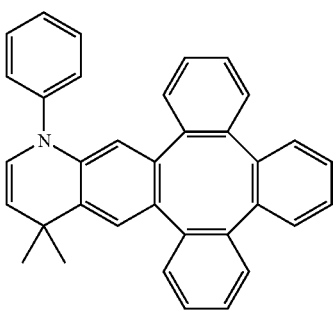
Compound D35
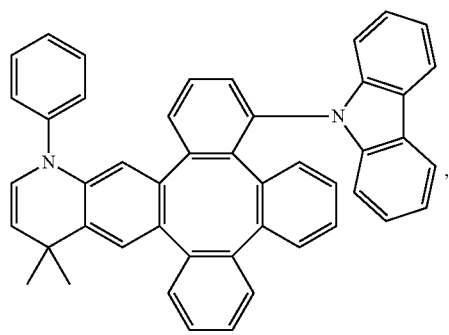
Compound D36
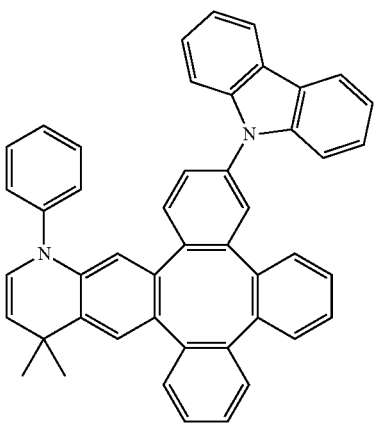

-continued
Compound D37
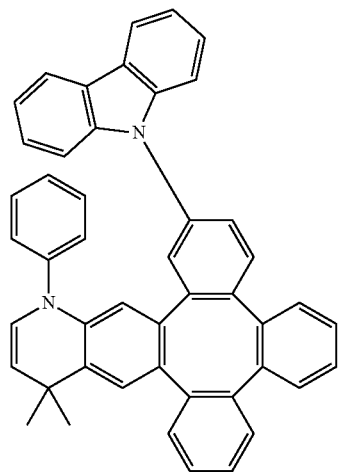
Compound D38
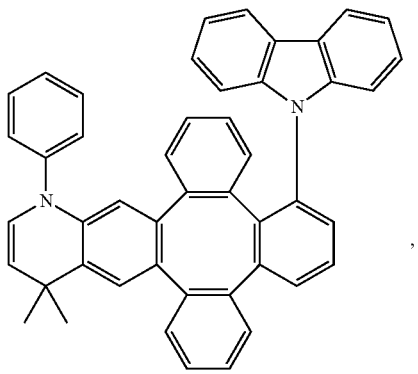
Compound D39
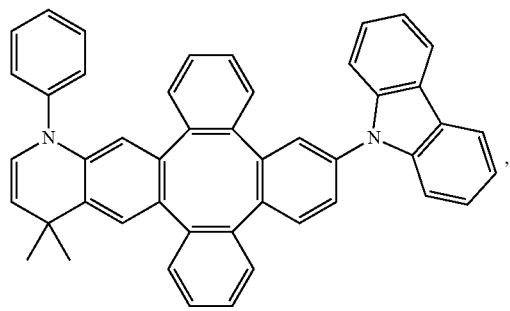
Compound D40
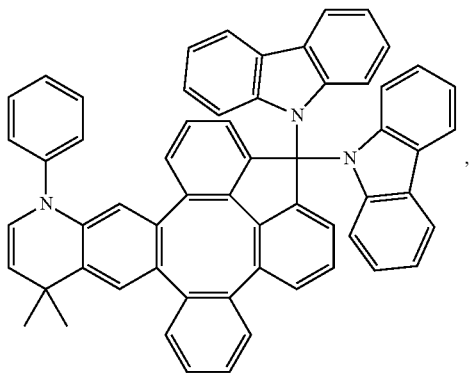
Compound D41
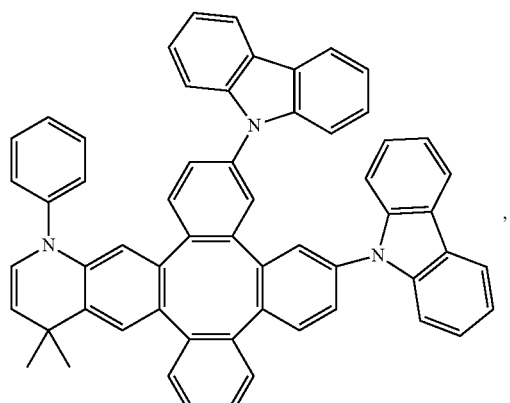
Compound D42
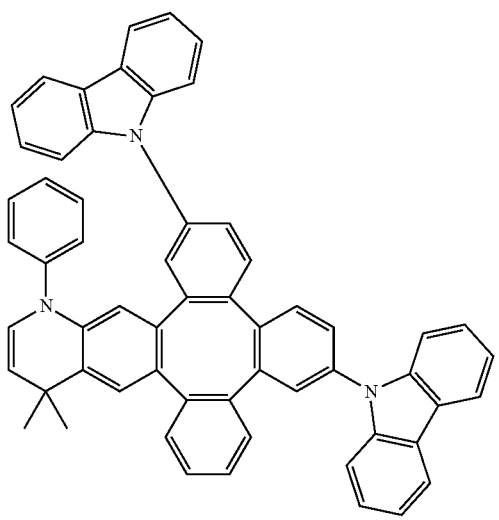

-continued
Compound D43
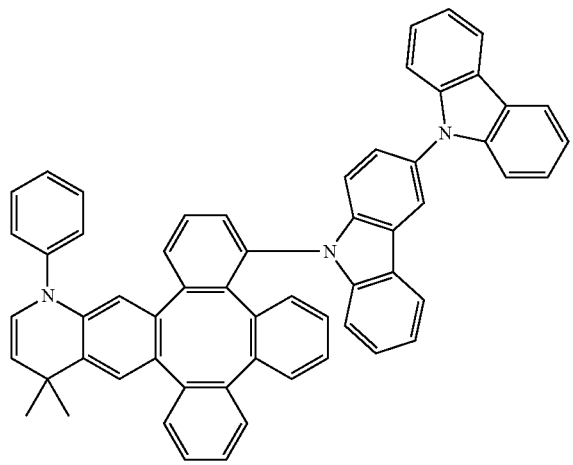
Compound B34
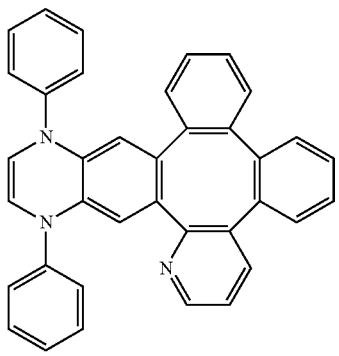
Compound B35
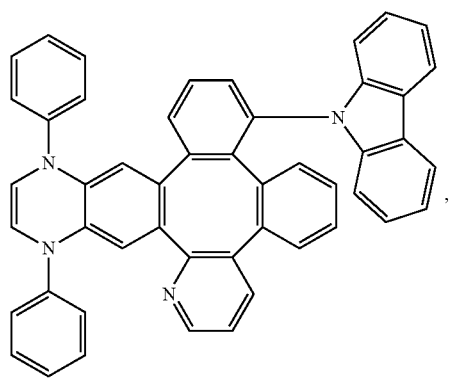
Compound B36
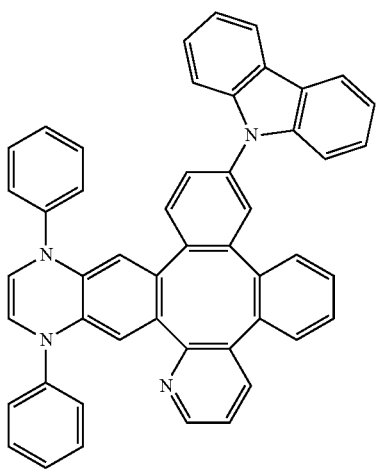
Compound B37
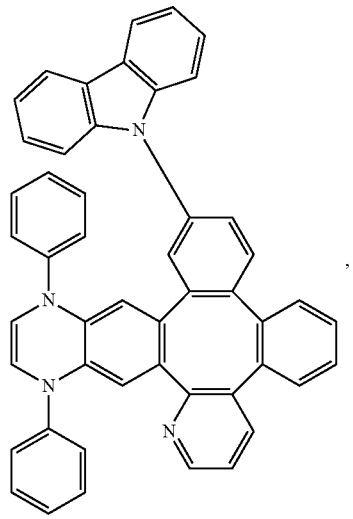
Compound B38
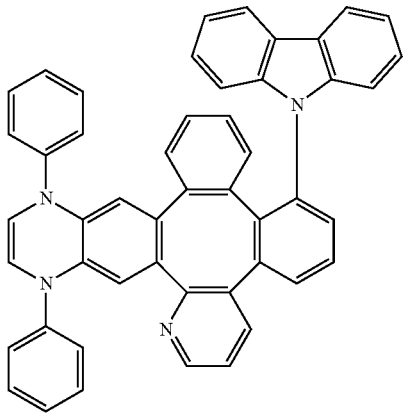

-continued
Compound B39
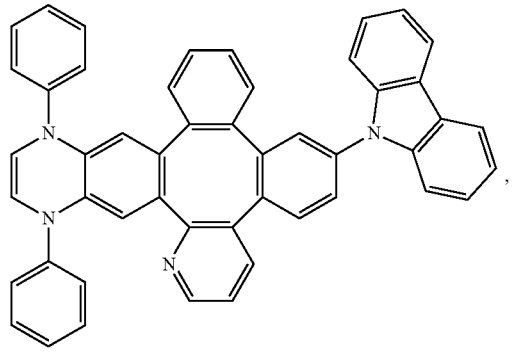
Compound B40
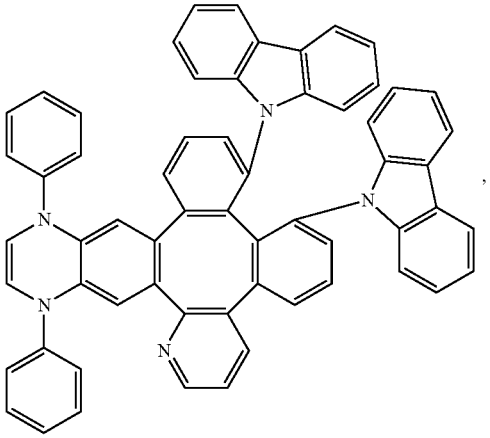
Compound B41
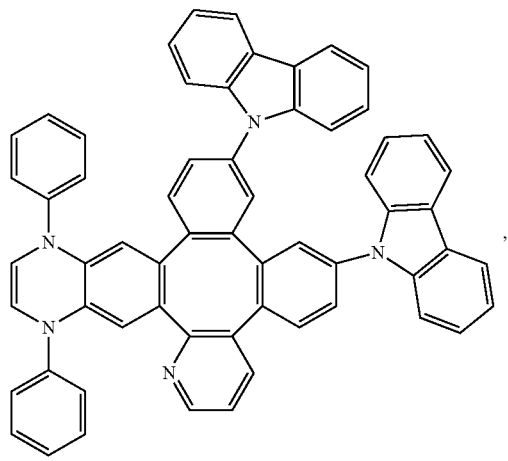
Compound B42
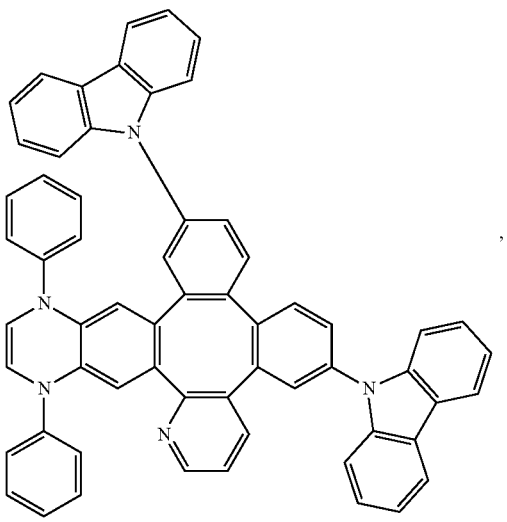
Compound B43
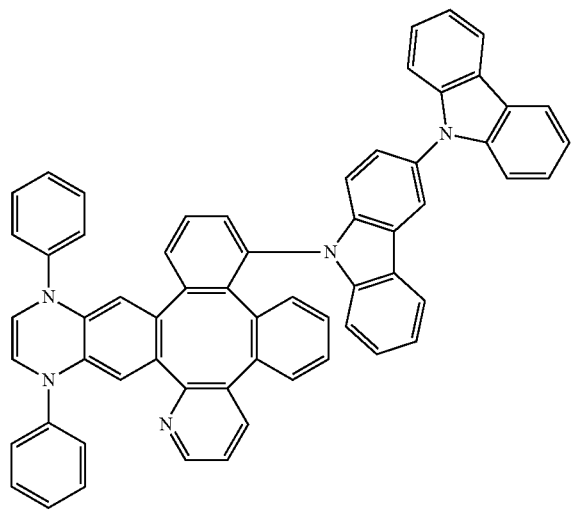
Compound B44
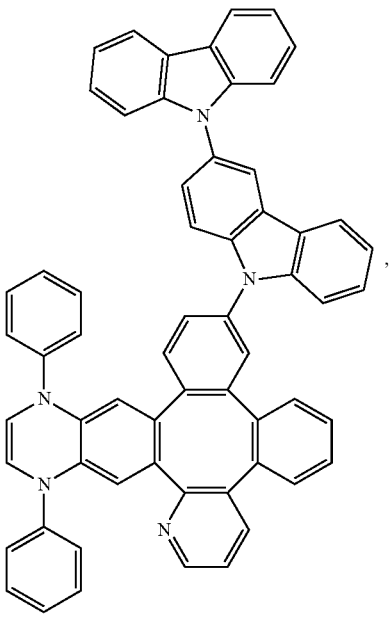

Compound B45
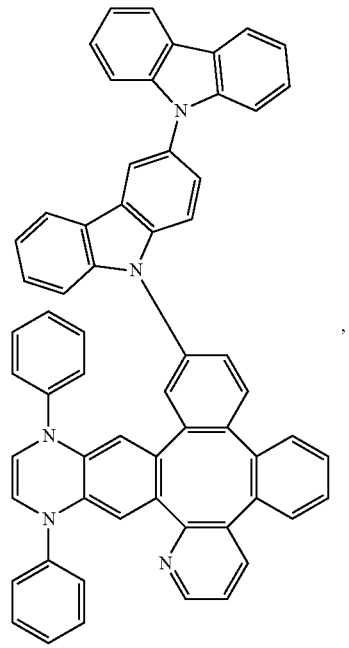
Compound B46
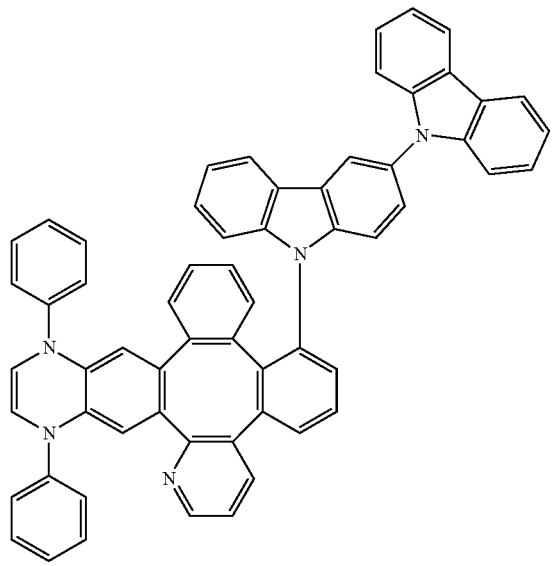
Compound B47
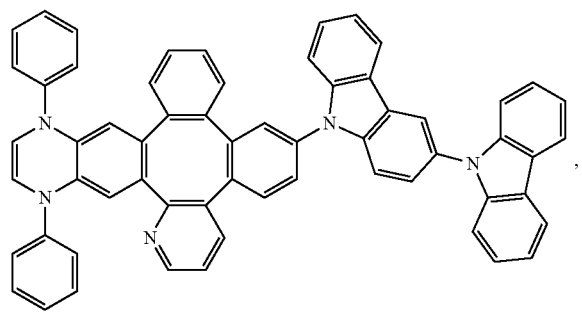
Compound B48
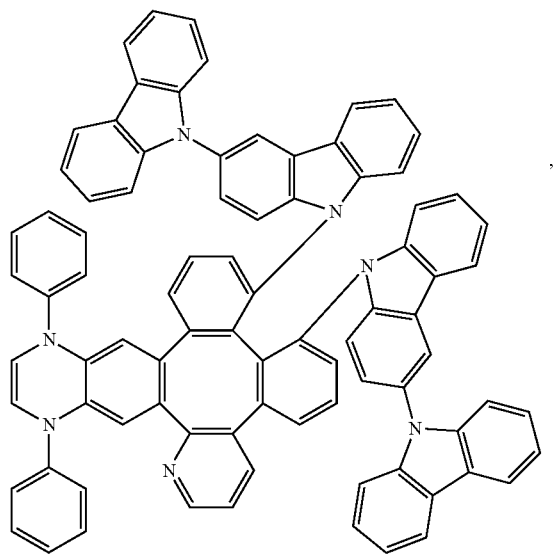

-continued
Compound B49
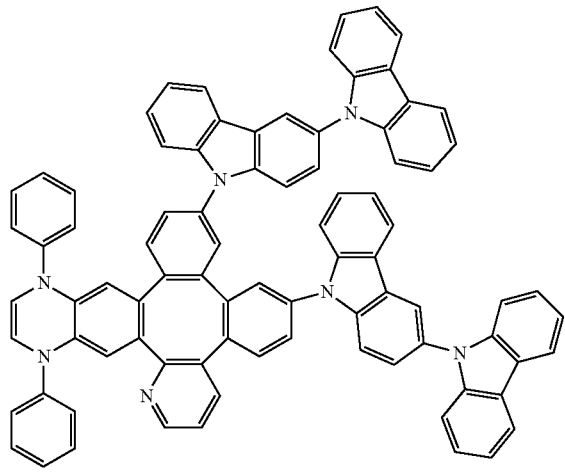
Compound B50
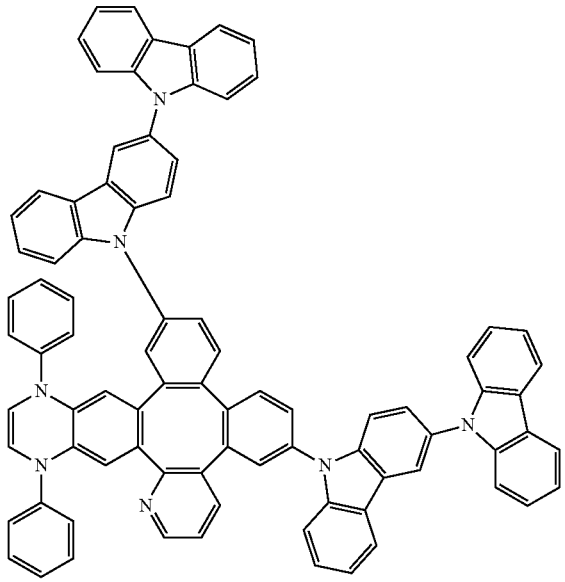
Compound B51
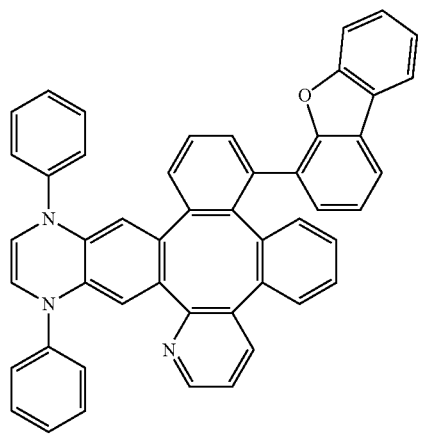
Compound B52
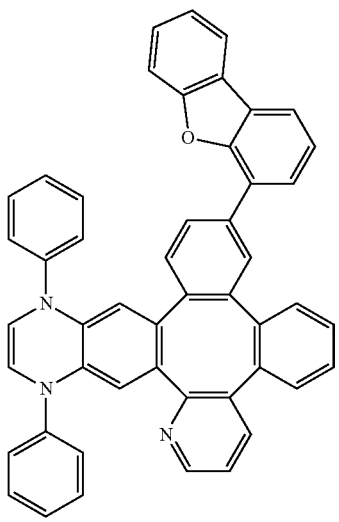
Compound B53
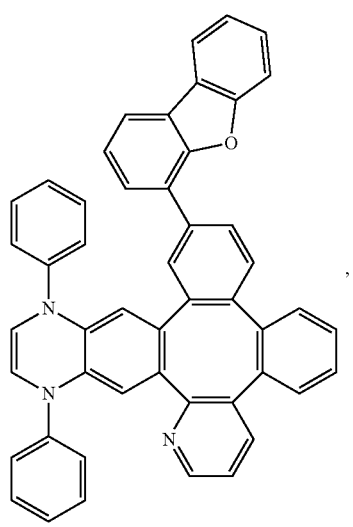
Compound B54
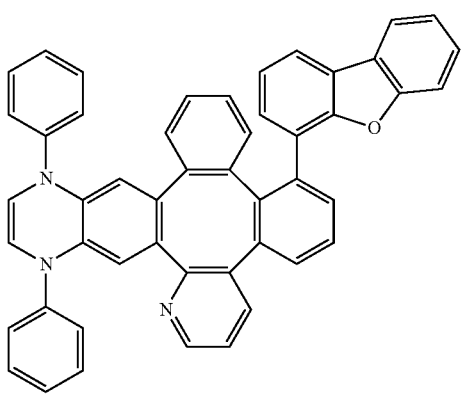

-continued
Compound B55
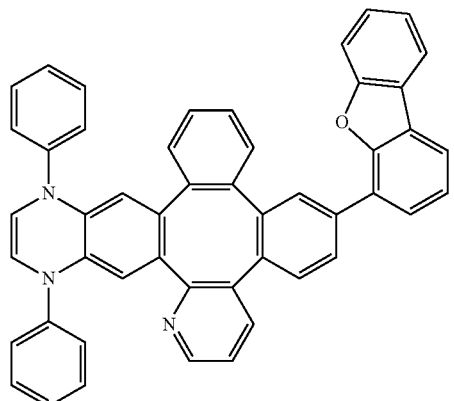
Compound B56
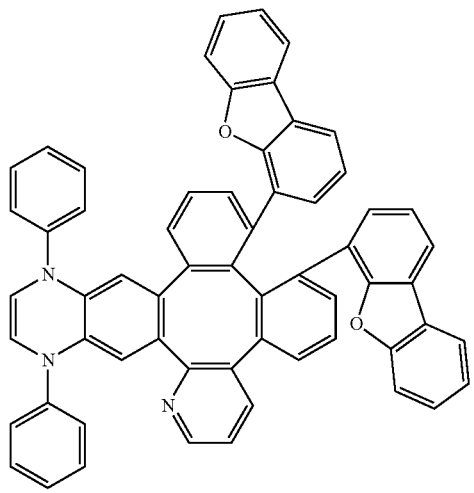
Compound B57
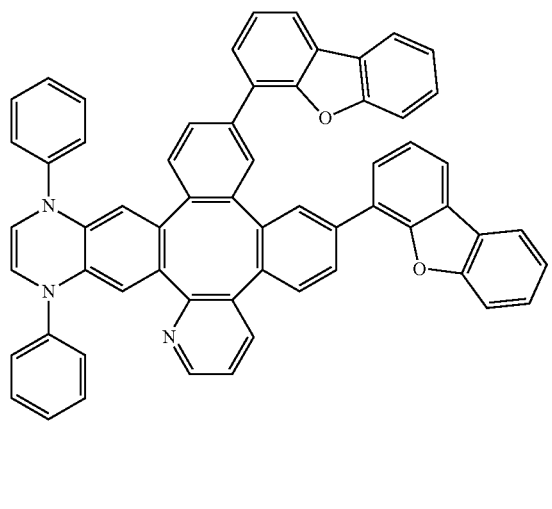
Compound B58
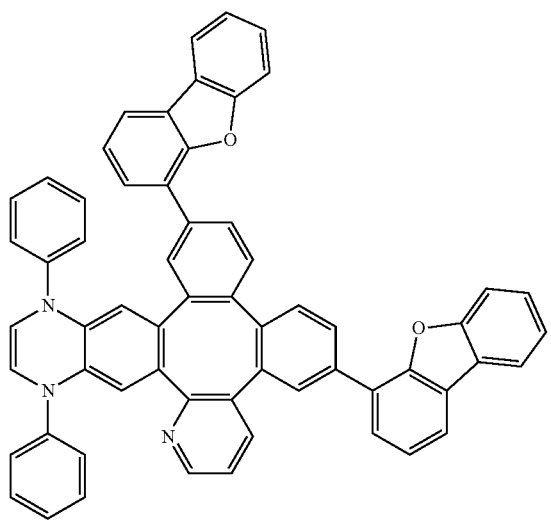
Compound B59
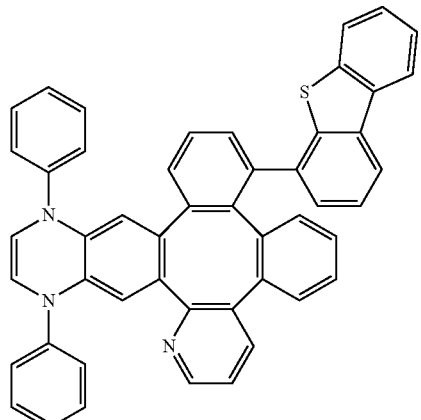
Compound B60
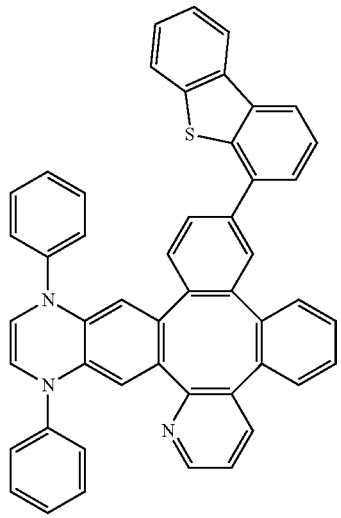

Compound B61
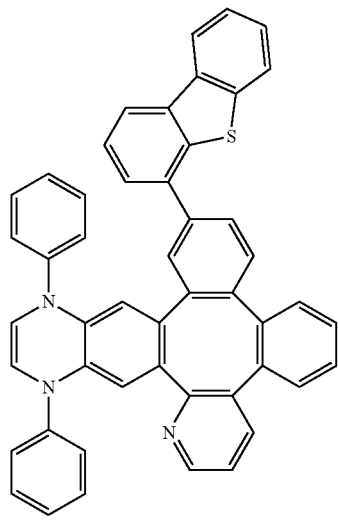
Compound B62
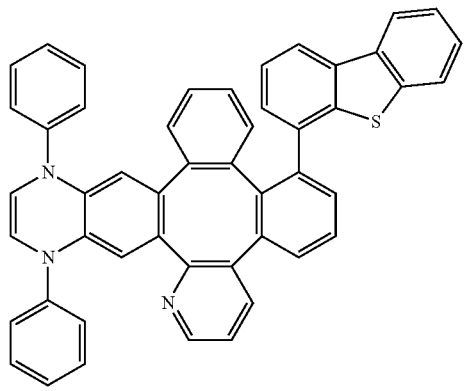
Compound B63
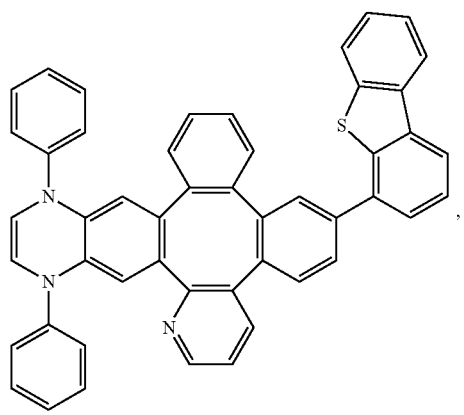
Compound B64
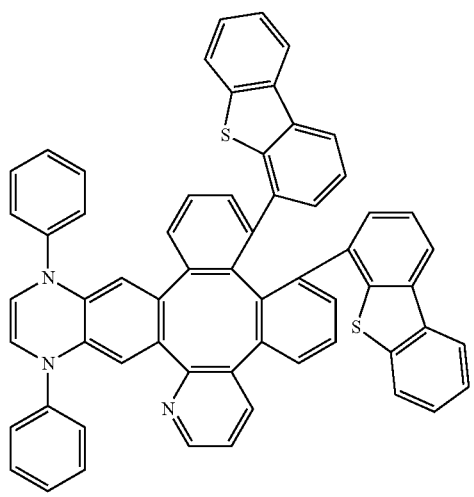
Compound B65
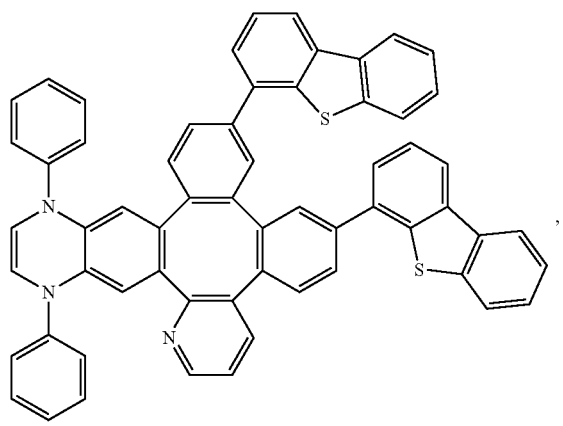
Compound B66
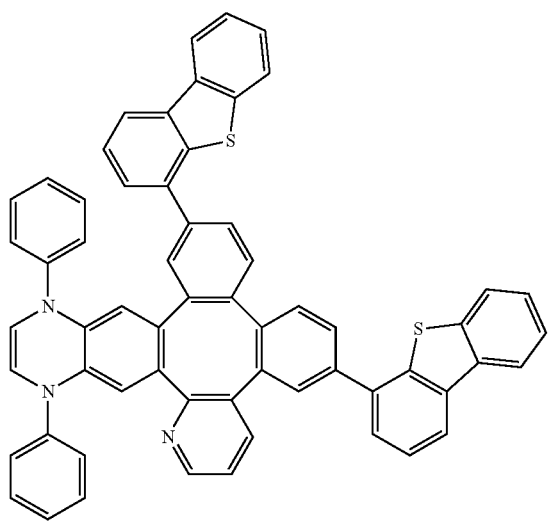

Compound CC34
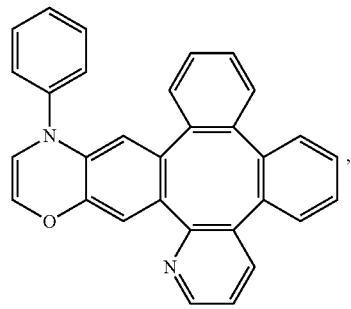
Compound CC35
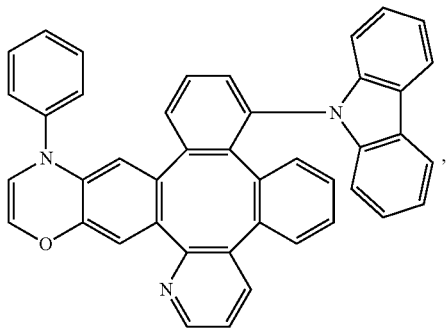
Compound CC36
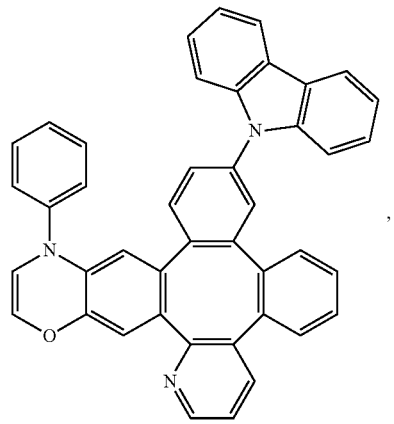
Compound CC37
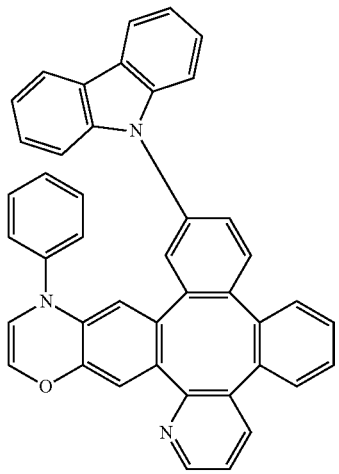
Compound CC38
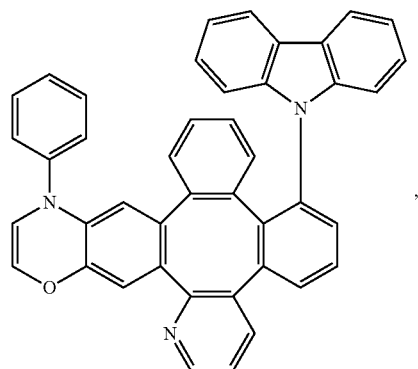
Compound CC39
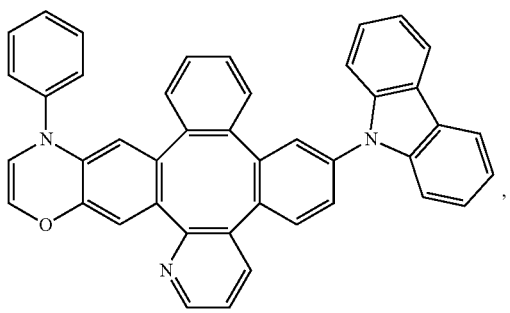
Compound CC40
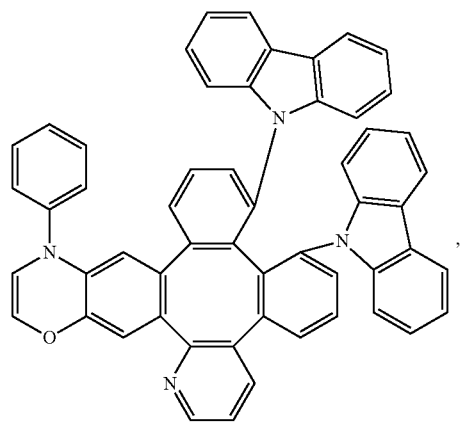
Compound CC41
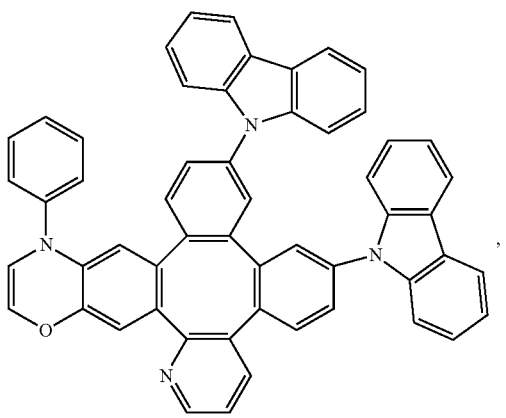

Compound CC42
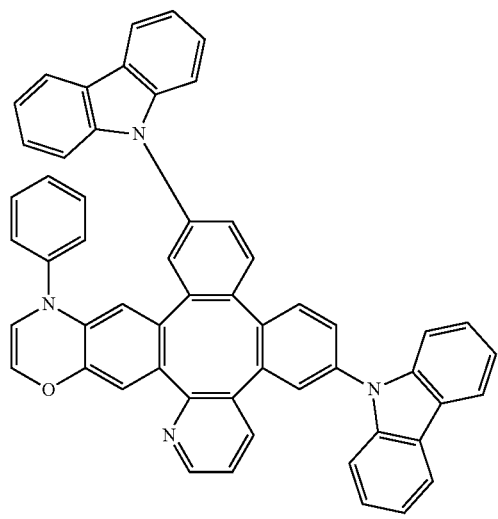
Compound CC43
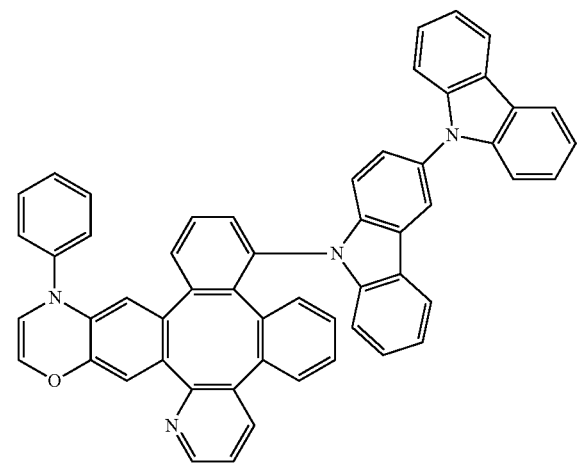
Compound DD34
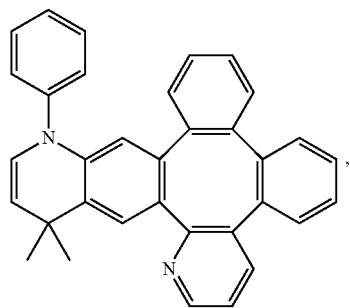
Compound DD35
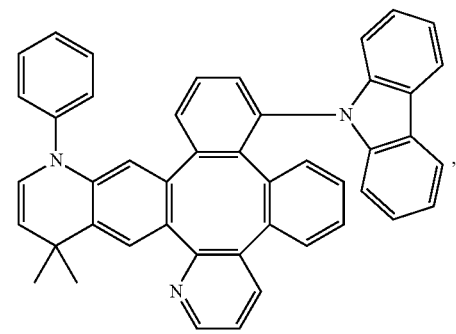
Compound DD36
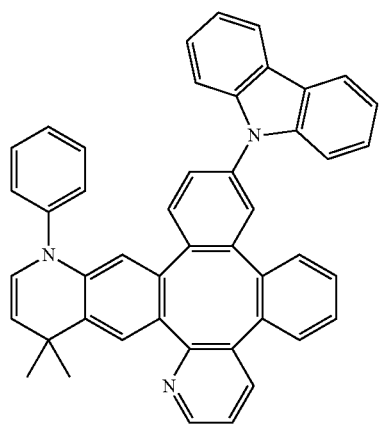
Compound DD37
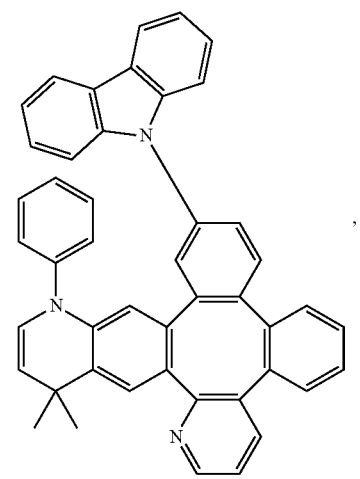

Compound DD38
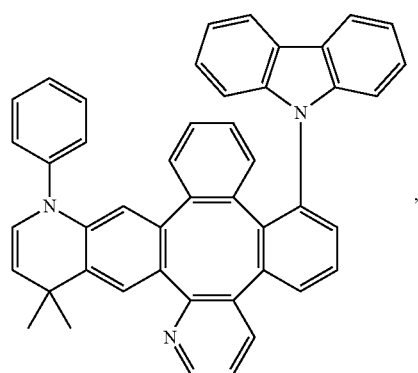
Compound DD39
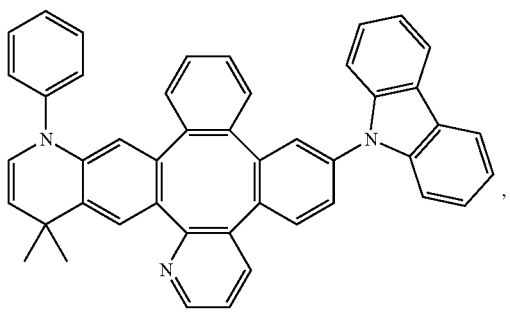
Compound DD40
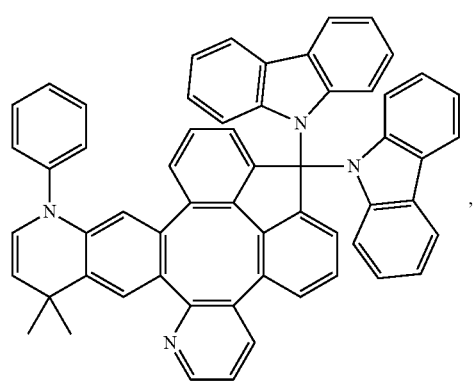
Compound DD41
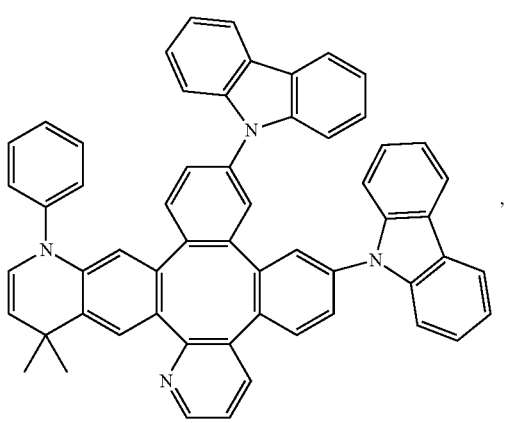
Compound DD42
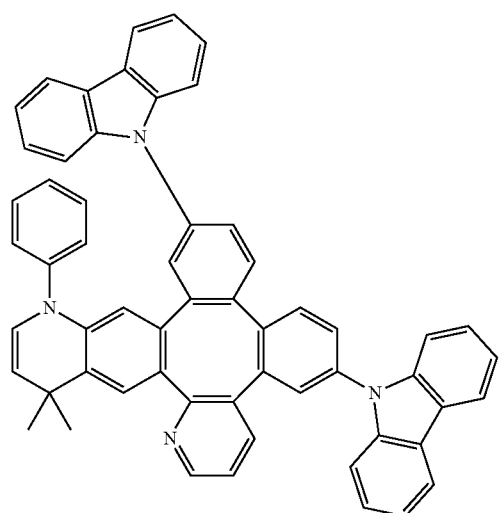
Compound DD43
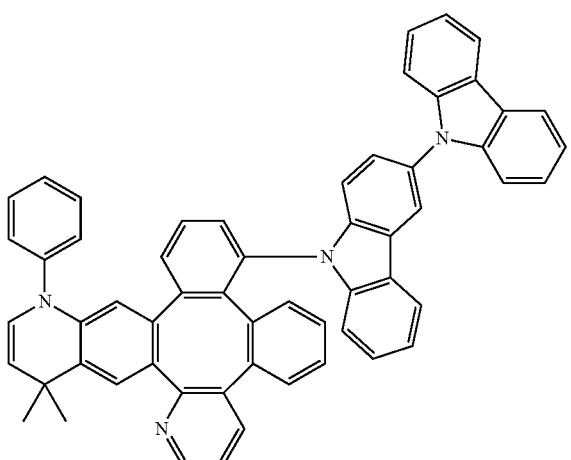

-continued
Compound A67
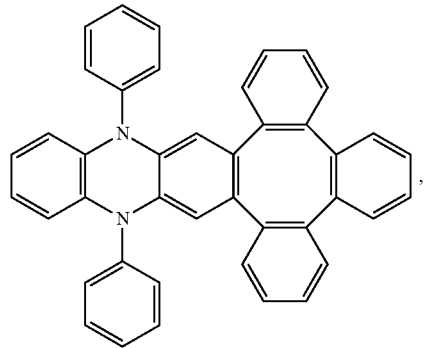
Compound A68
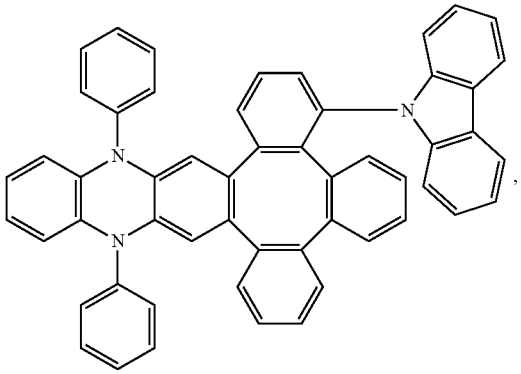
Compound A69
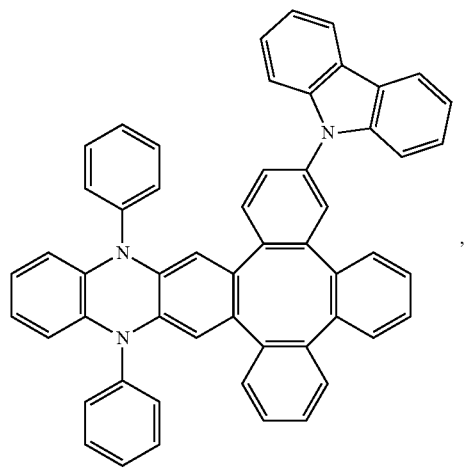
Compound A70
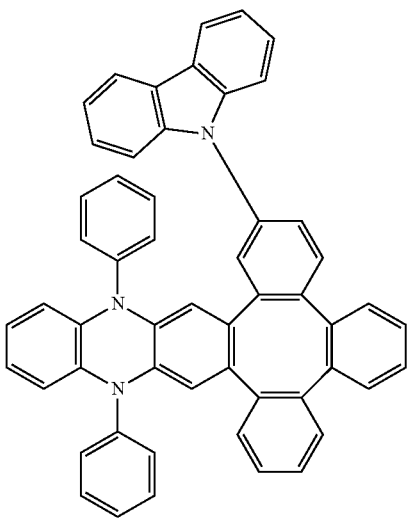
Compound A71
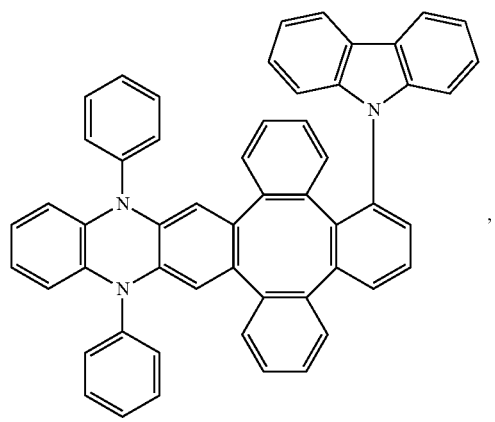
Compound A72
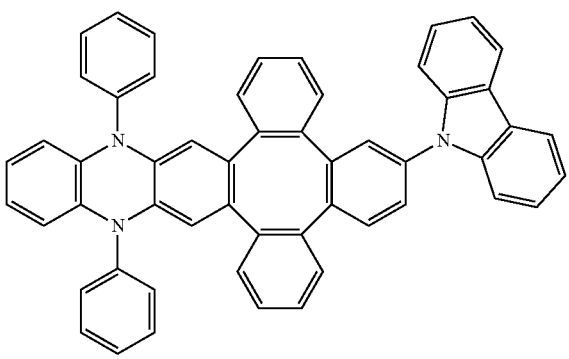

Compound A73
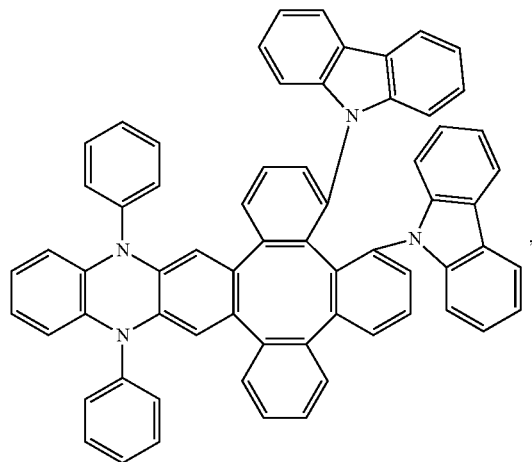
Compound A74
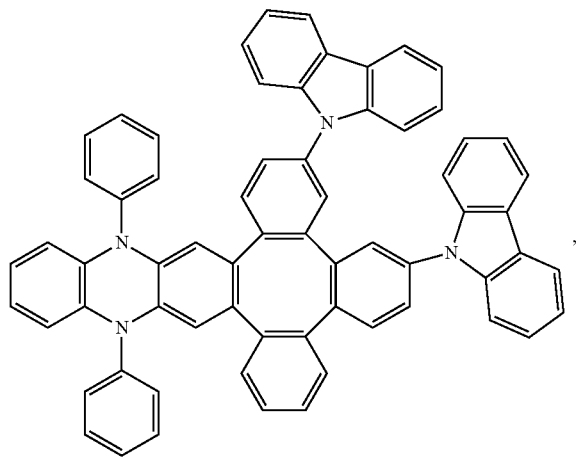
Compound A75
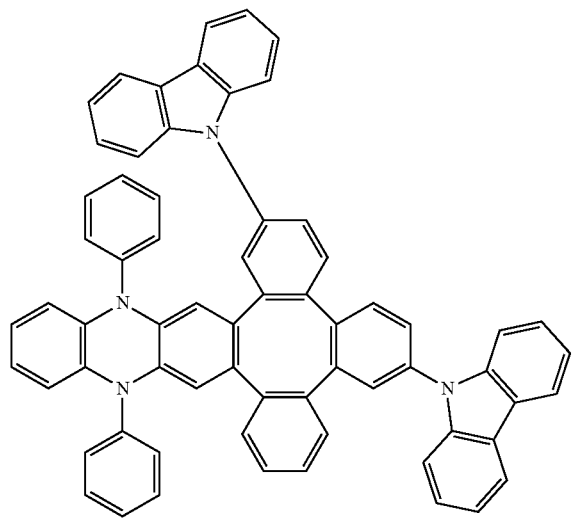
Compound A76
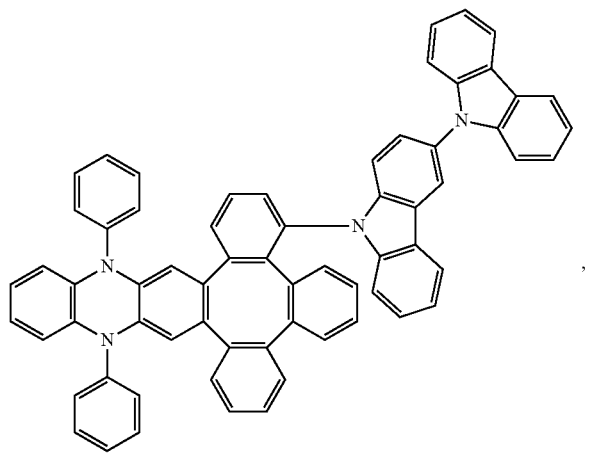

-continued
Compound A77
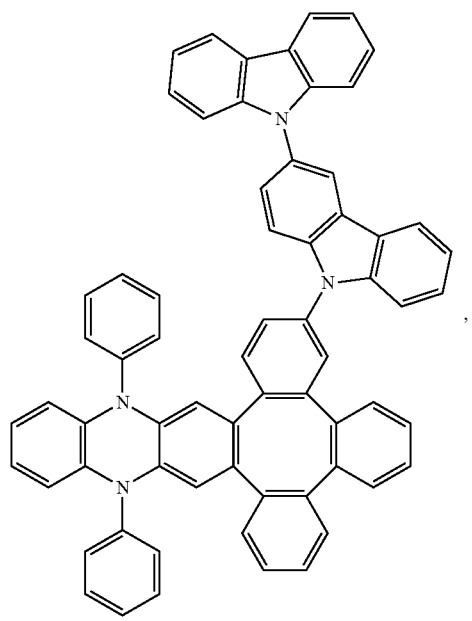
Compound A78
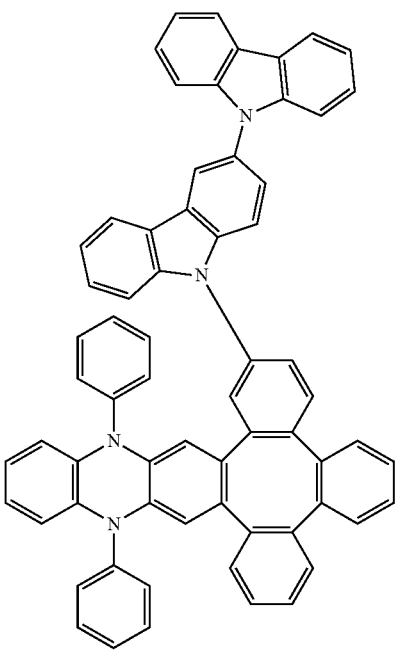
Compound A79
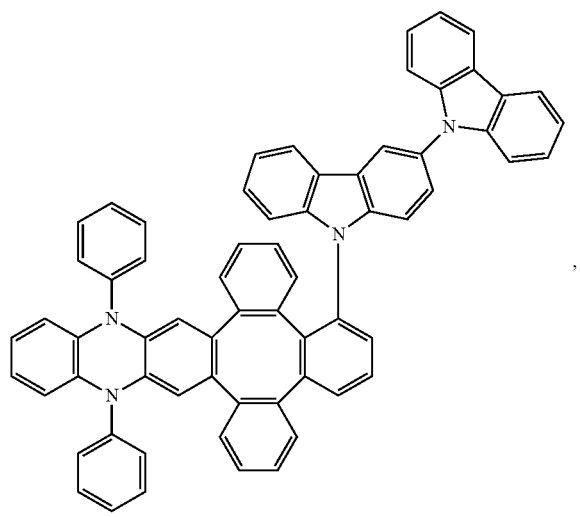
Compound A80
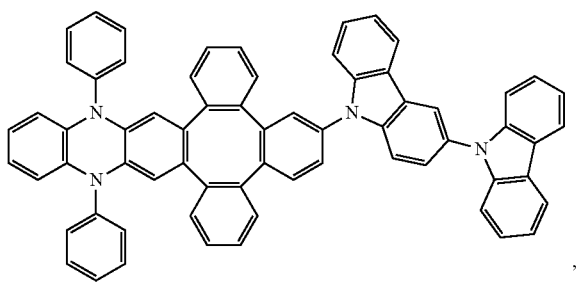

-continued
Compound A81
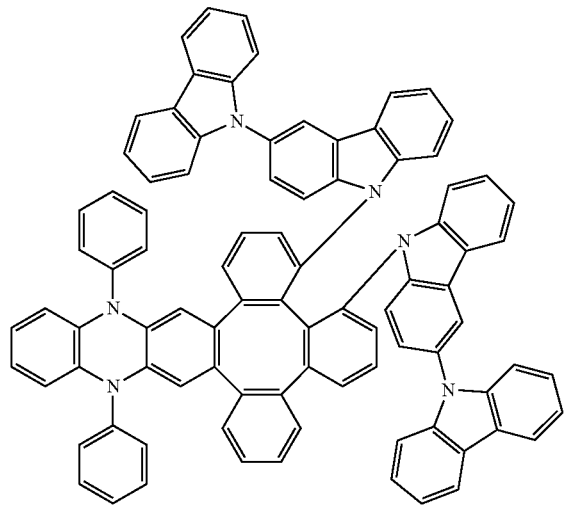
Compound A82
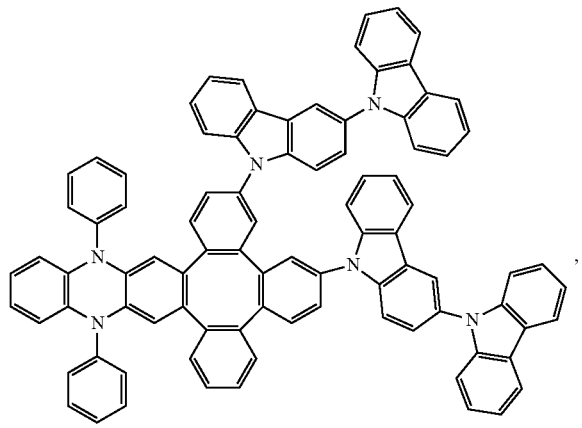
Compound A83
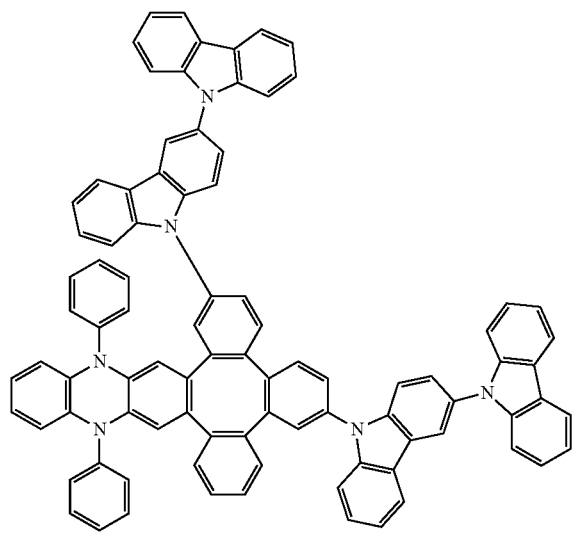
Compound A84
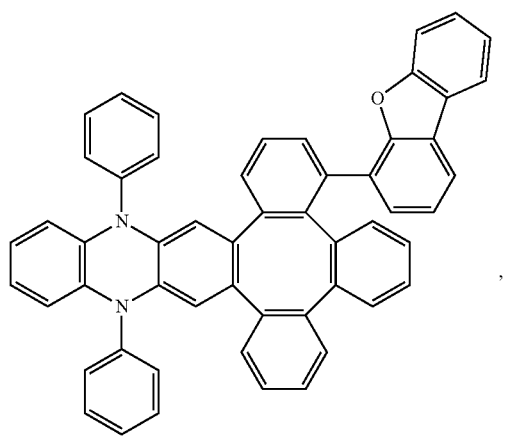
Compound A85
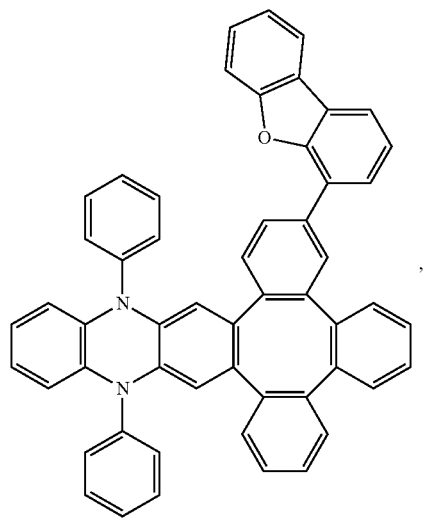
Compound A86
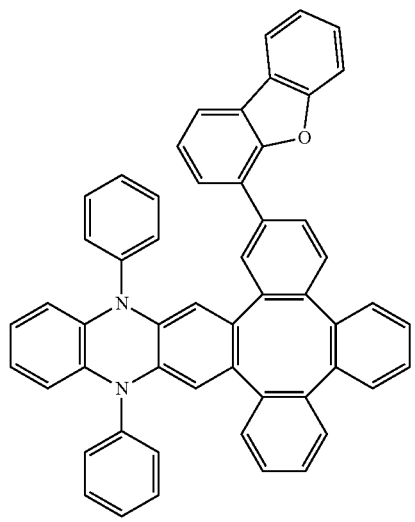

Compound A87
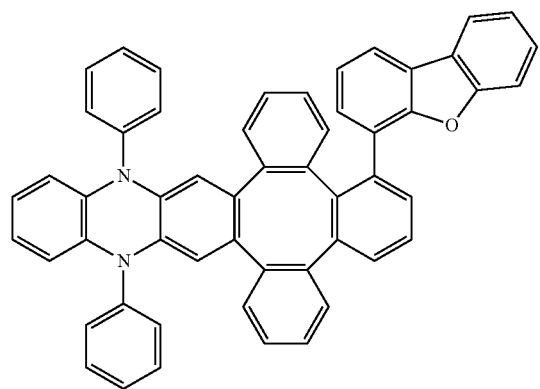
Compound A88
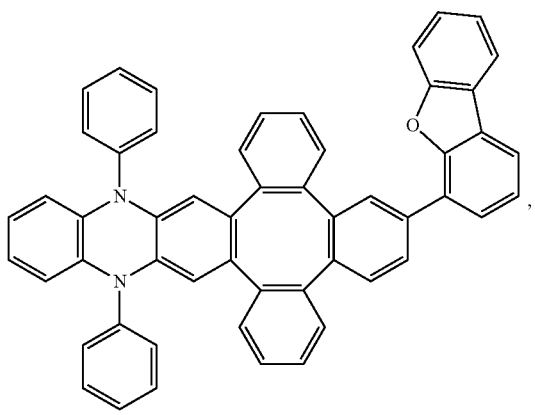
Compound A89
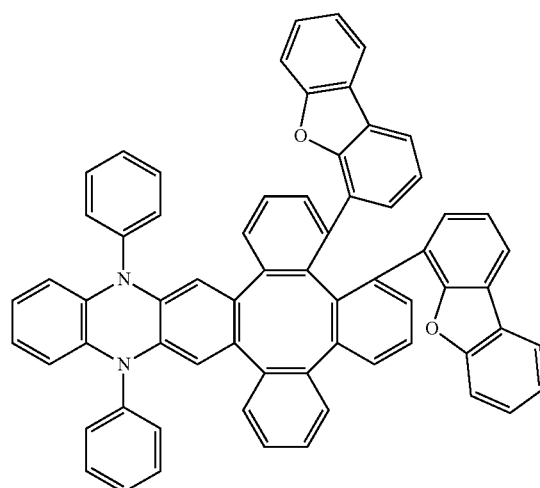
Compound A90
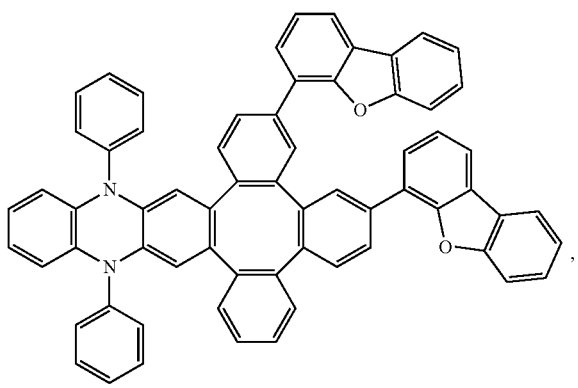
Compound A91
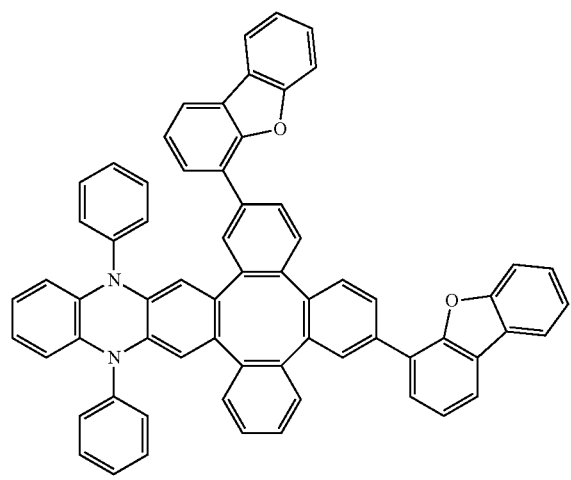
Compound A92
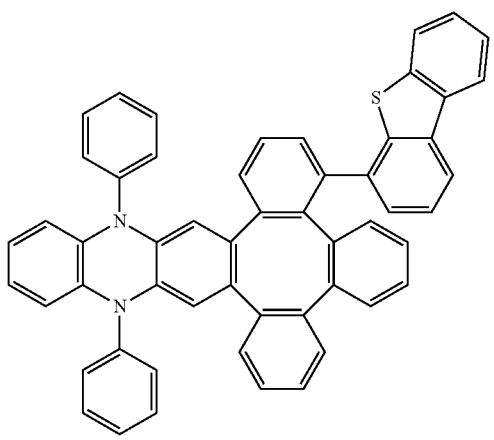

-continued
Compound A93
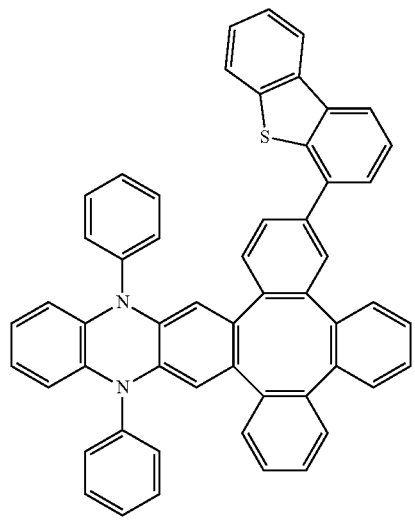
Compound A94
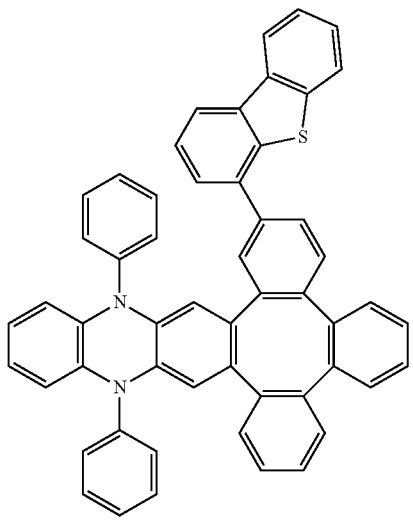
Compound A95
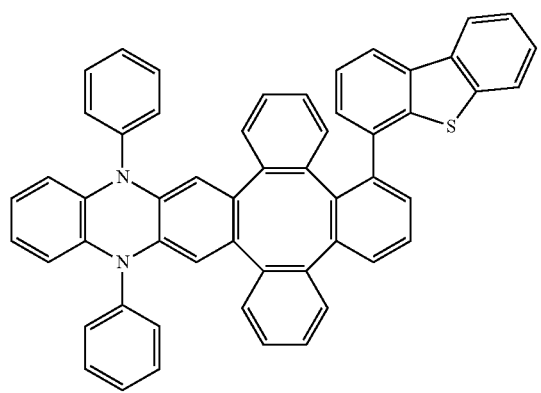
Compound A96
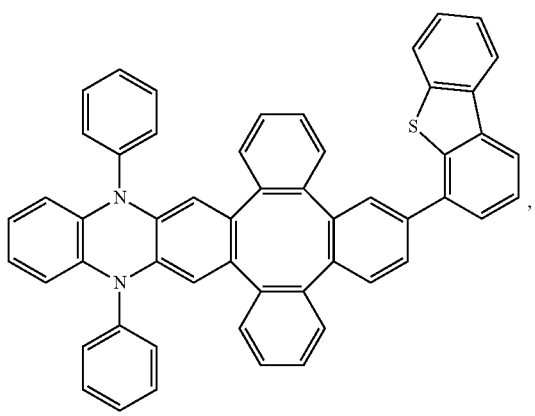
Compound A97
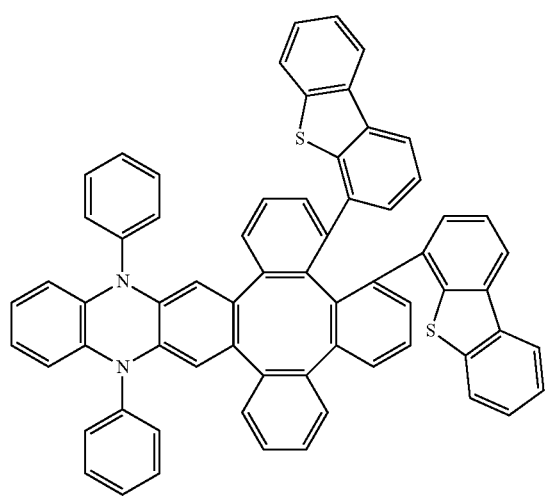
Compound A98
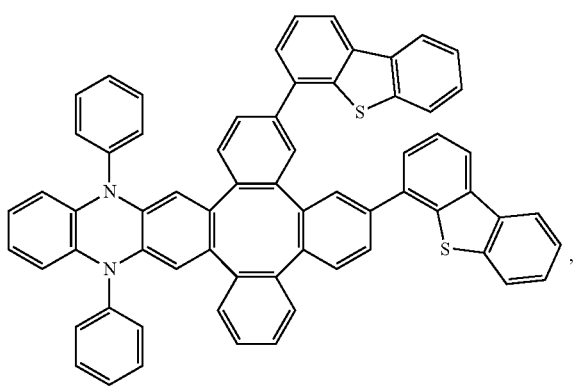

-continued
Compound A99
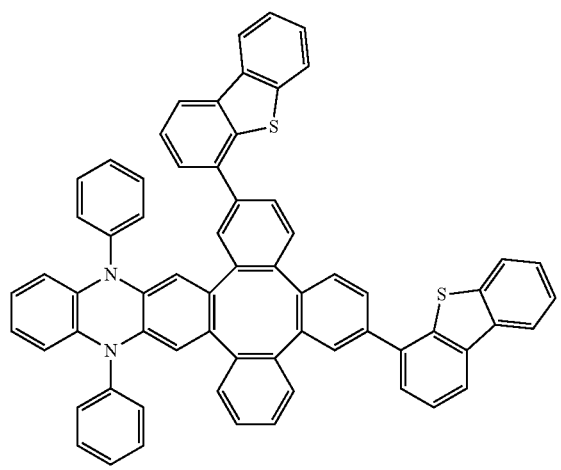
Compound C67
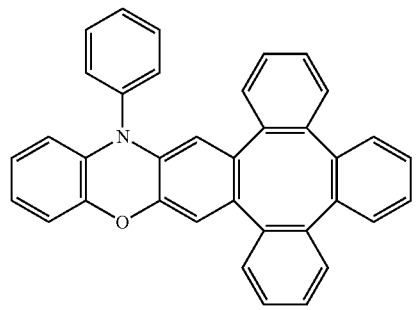
Compound C68
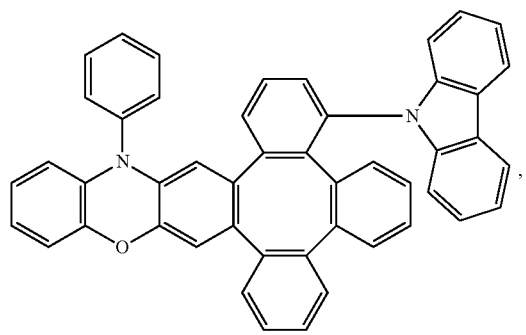
Compound C69
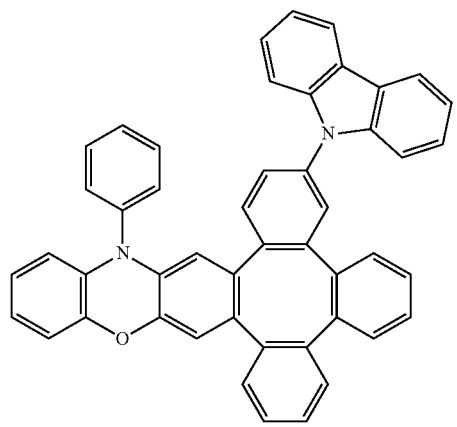
Compound C70
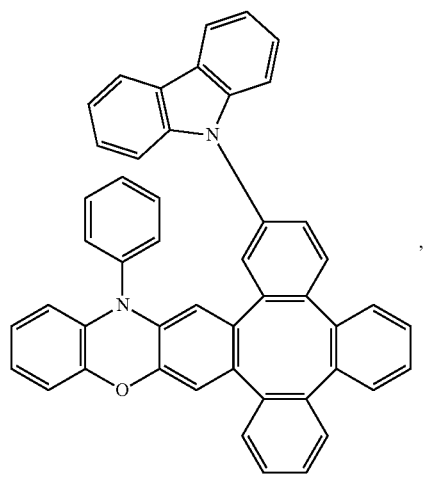
Compound C71
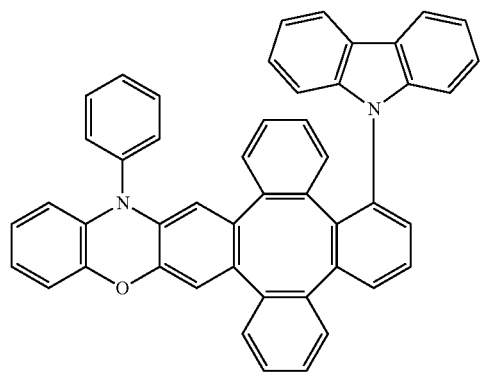

-continued
Compound C72
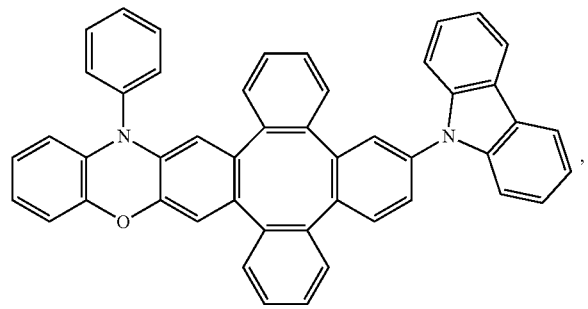
Compound C73
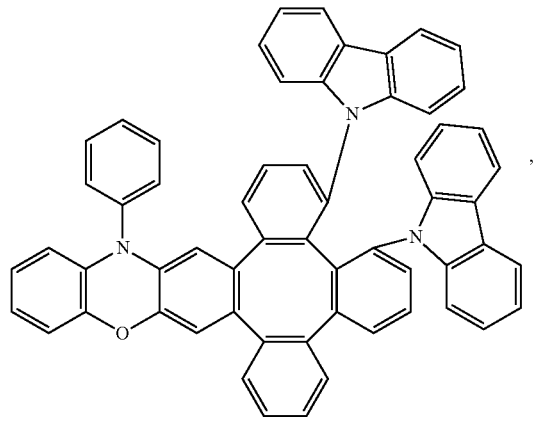
Compound C74
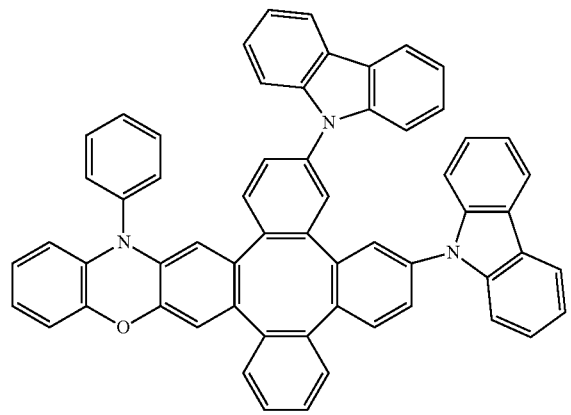
Compound C75
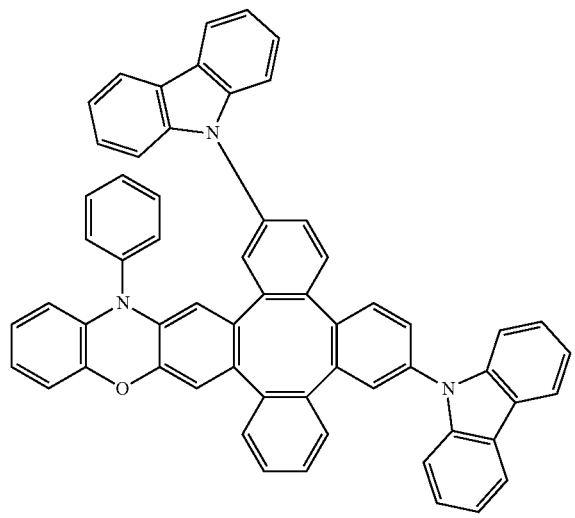
Compound C76
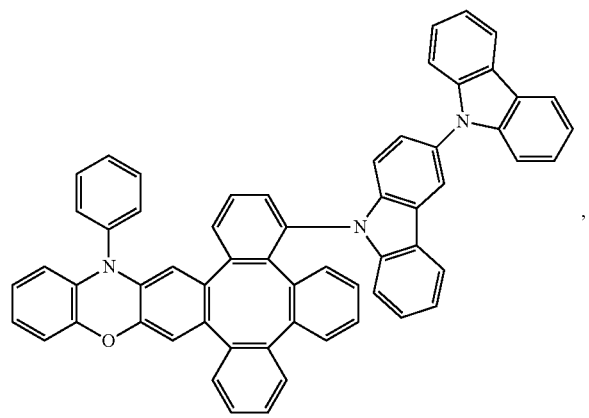
Compound D67
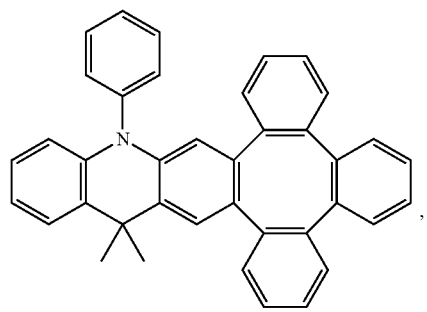

Compound D68
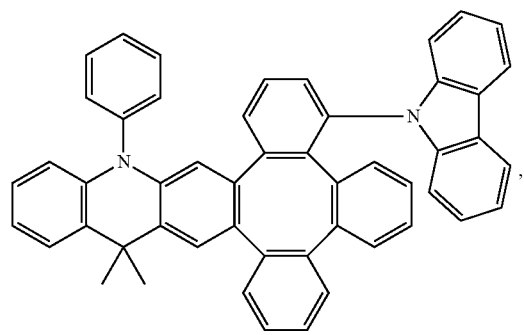
Compound D69
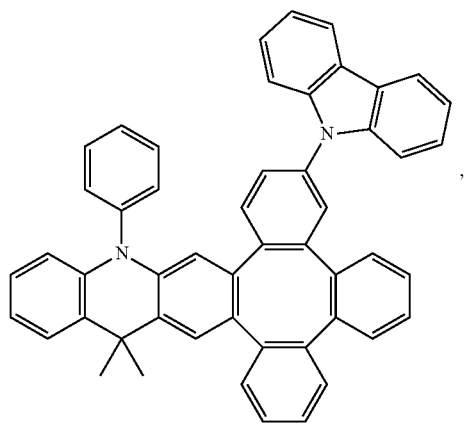
Compound D70
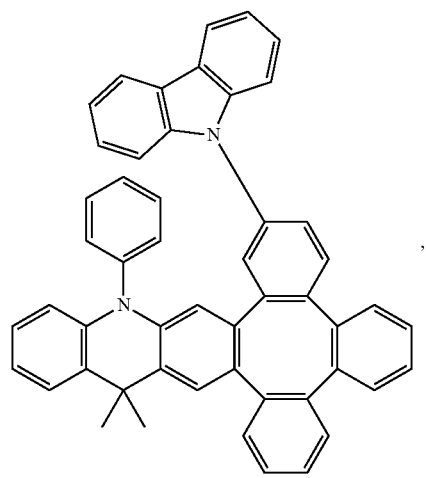
Compound D71
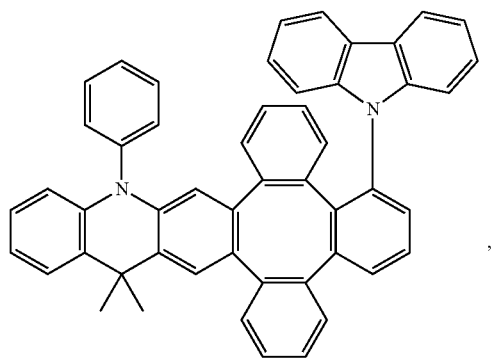
Compound D72
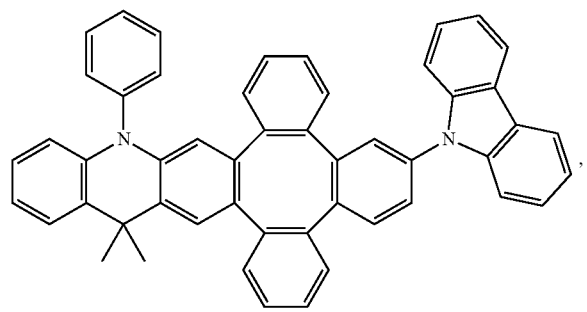
Compound D73
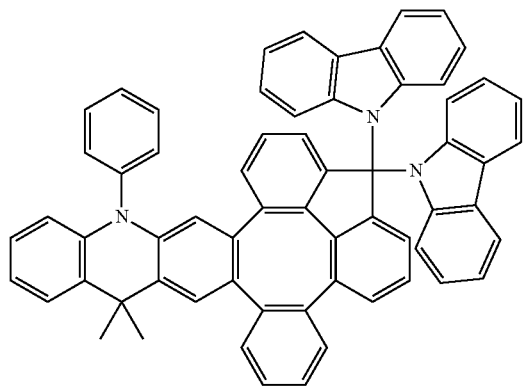

-continued
Compound D74
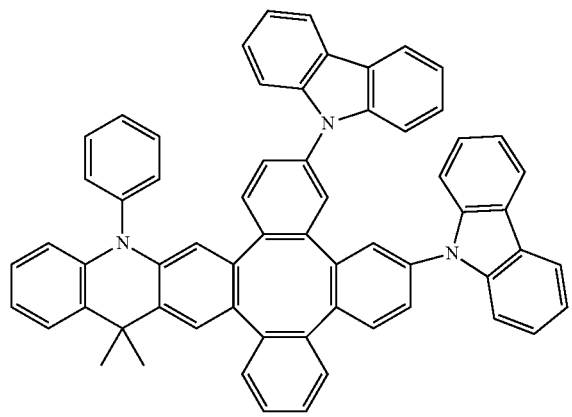
Compound D75
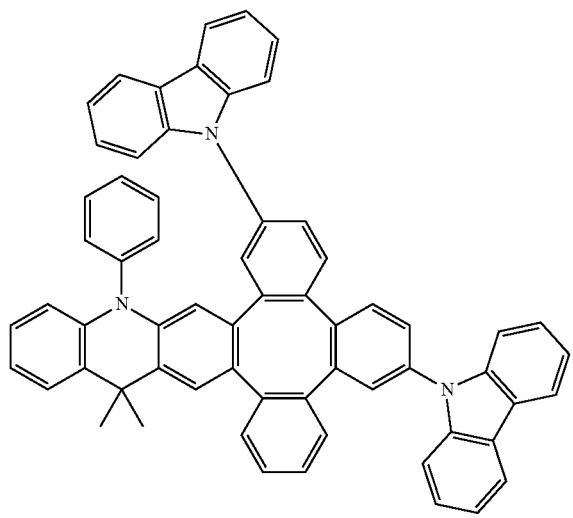
Compound D76
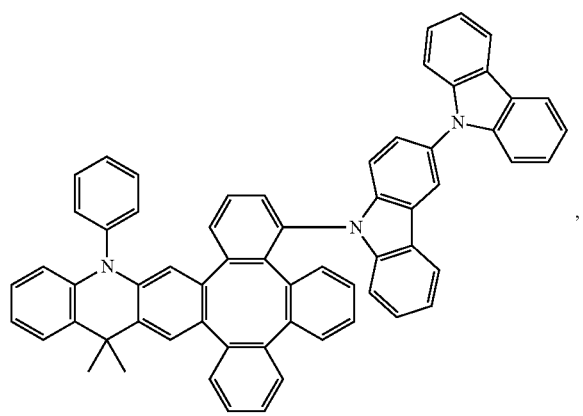
Compound E67
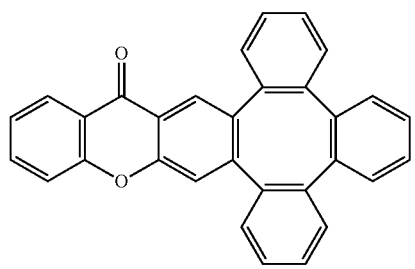
Compound E68
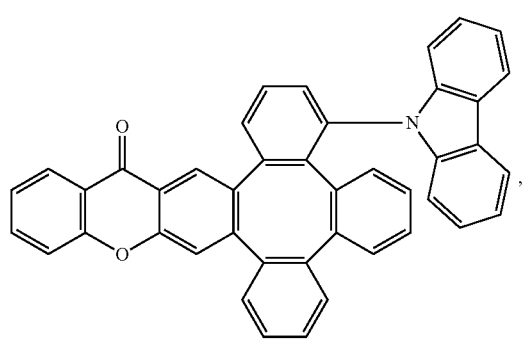
Compound E69
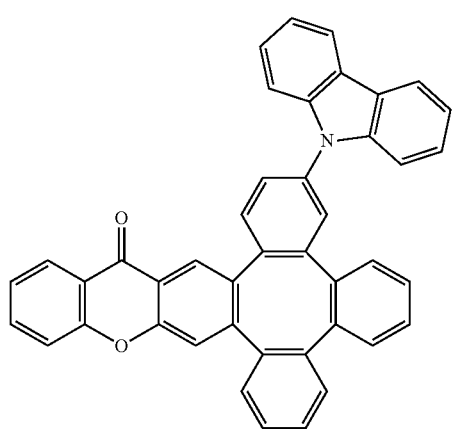

-continued
Compound E70
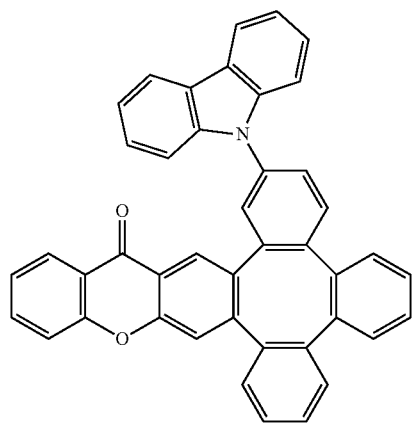
Compound E71
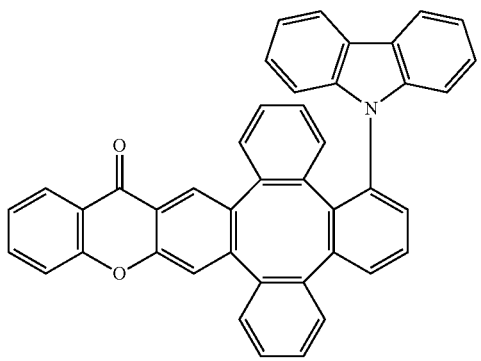
Compound E72
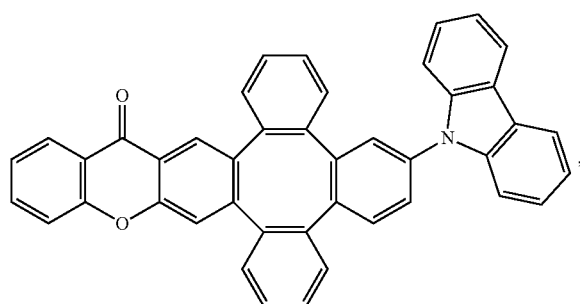
Compound E73
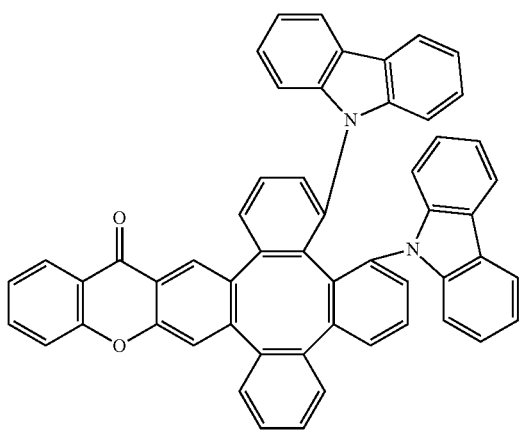
Compound E74
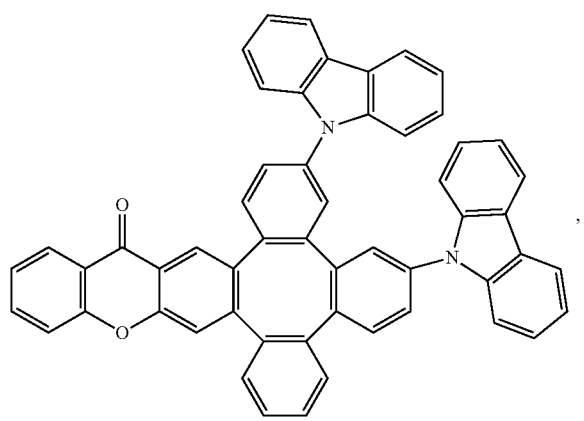
Compound E75
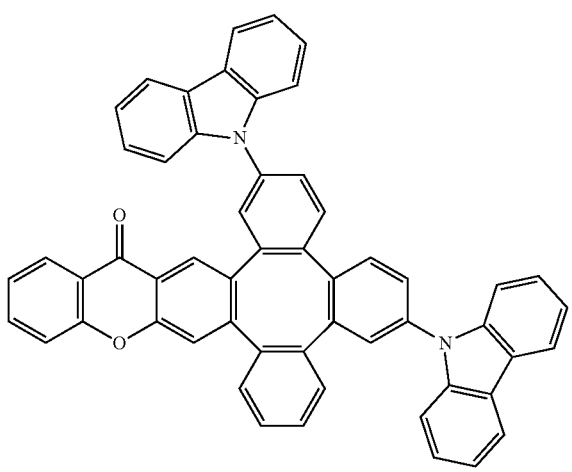

Compound E76
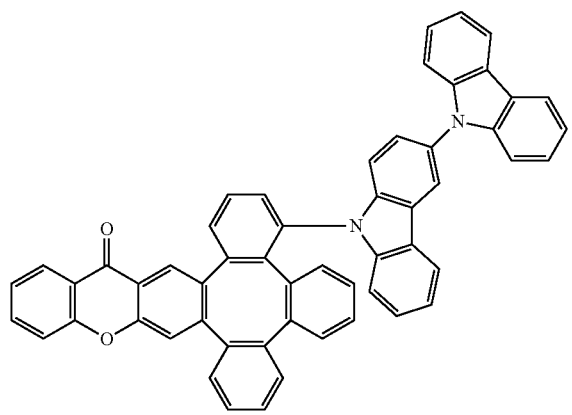
Compound F67
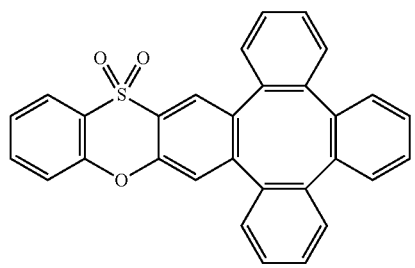
Compound F68
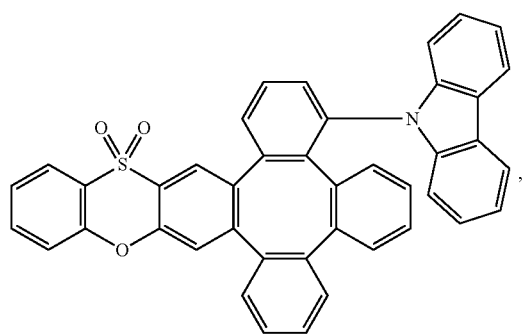
Compound F69
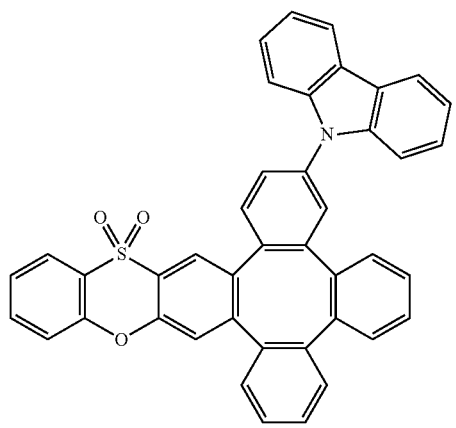
Compound F70
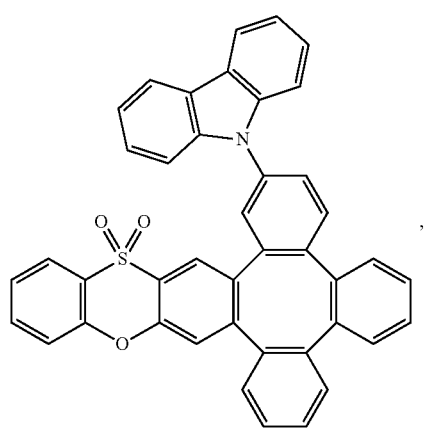
Compound F71
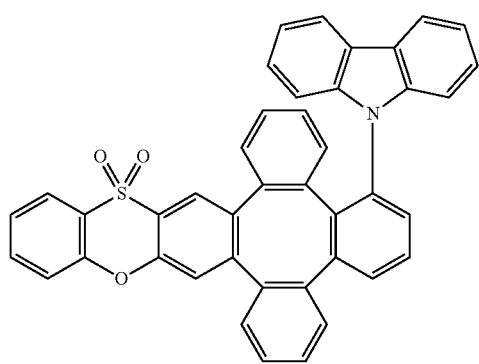

-continued
Compound F72
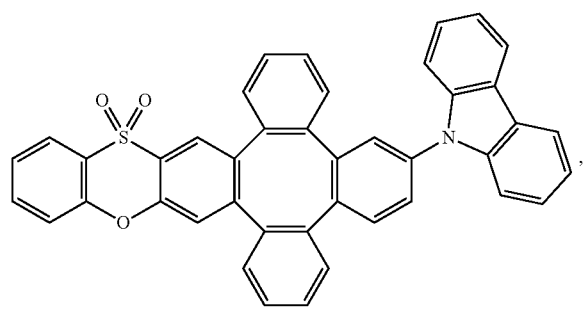
Compound F73
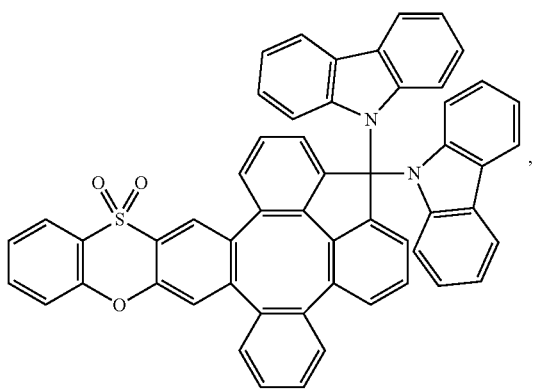
Compound F74
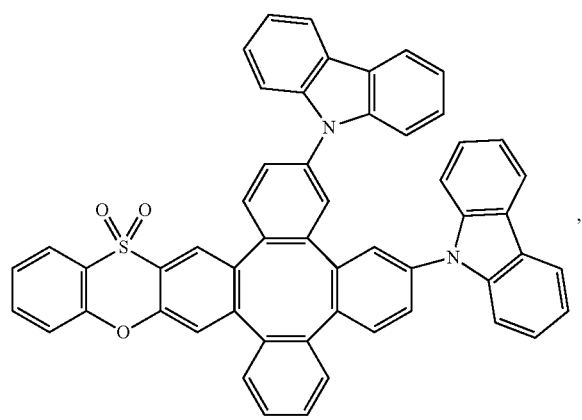
Compound F75
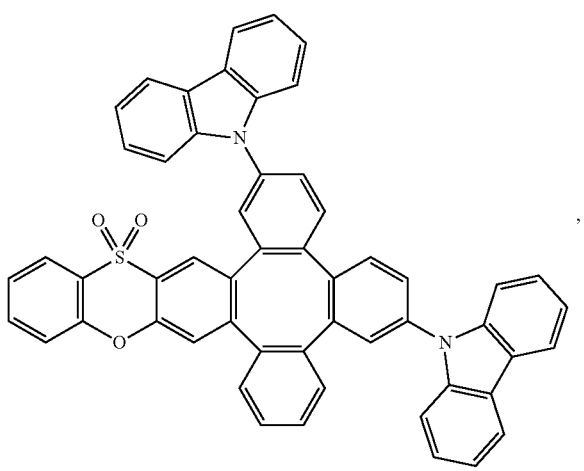
Compound F76
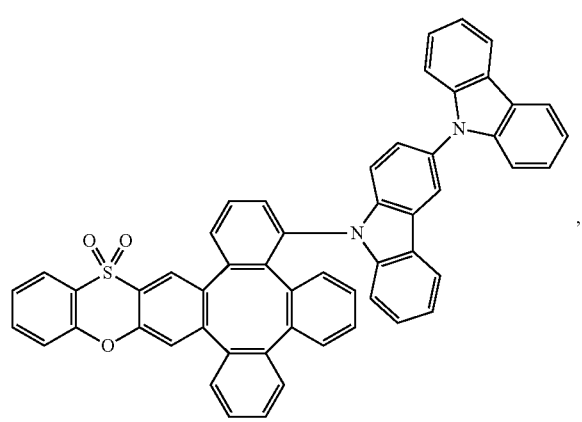
Compound B67
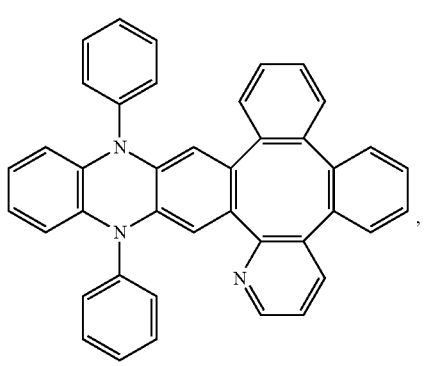

-continued
Compound B68
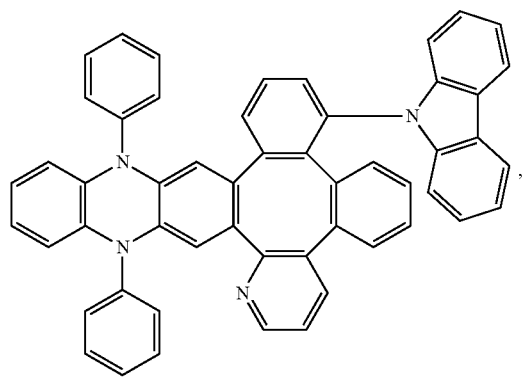
Compound B69
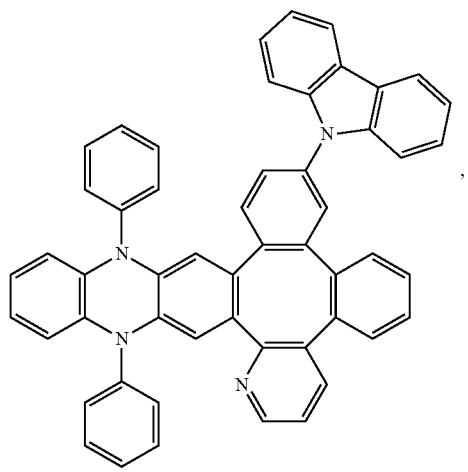
Compound B70
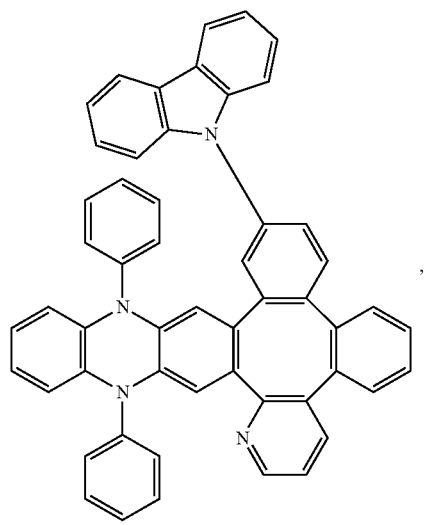
Compound B71
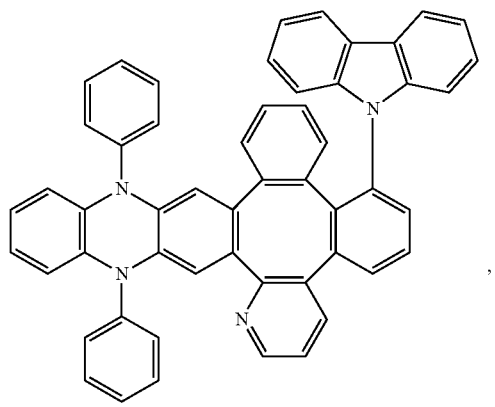
Compound B72
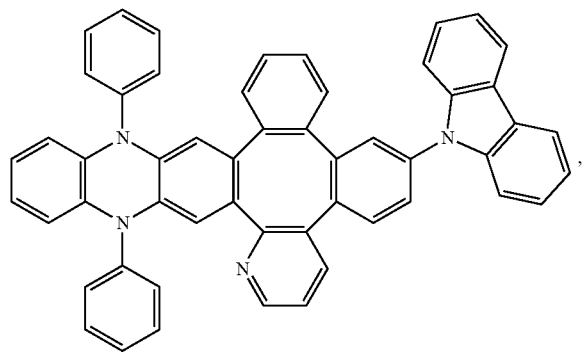
Compound B73
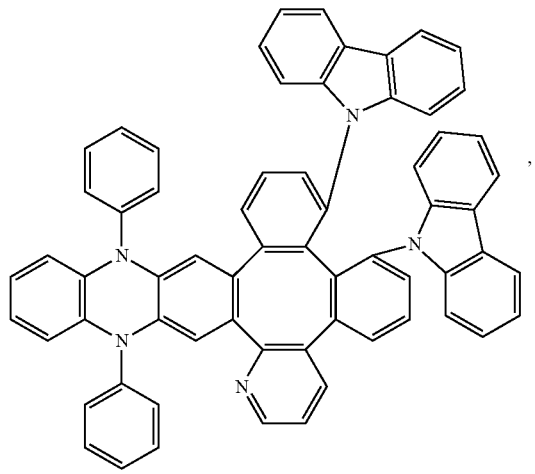

-continued
Compound B74
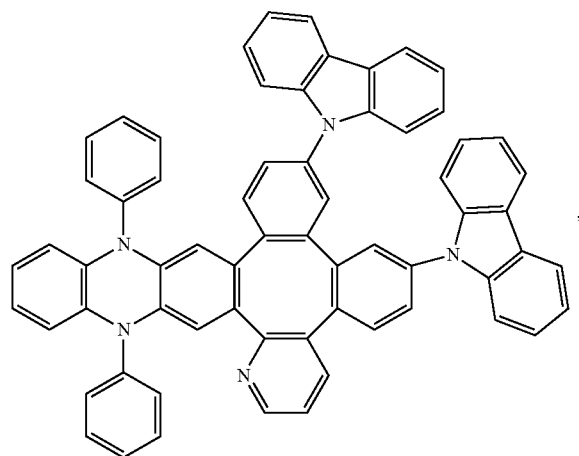
Compound B75
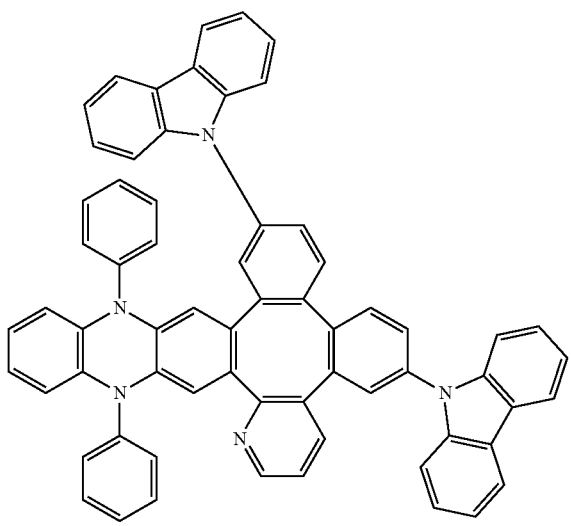
Compound B76
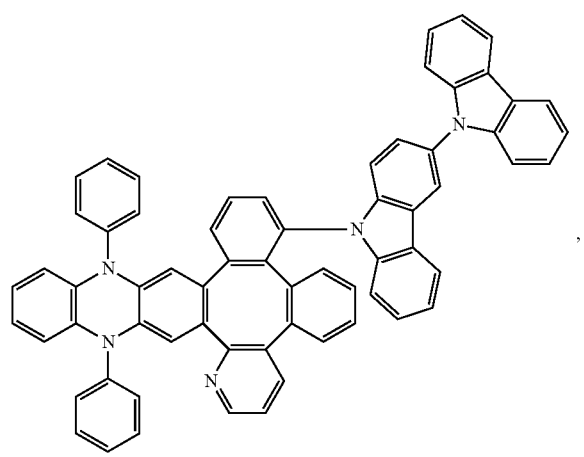
Compound B77
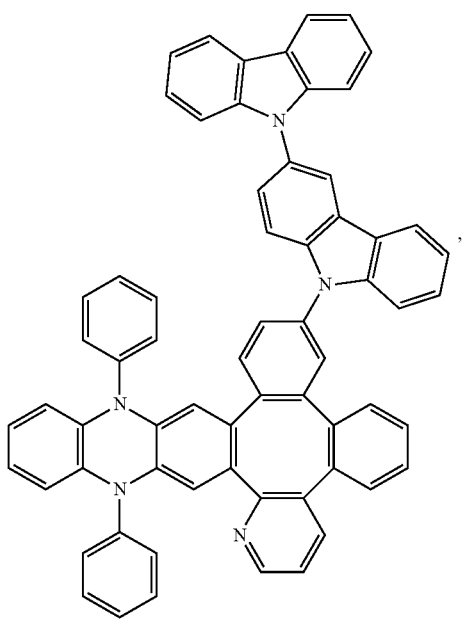

-continued
Compound B78
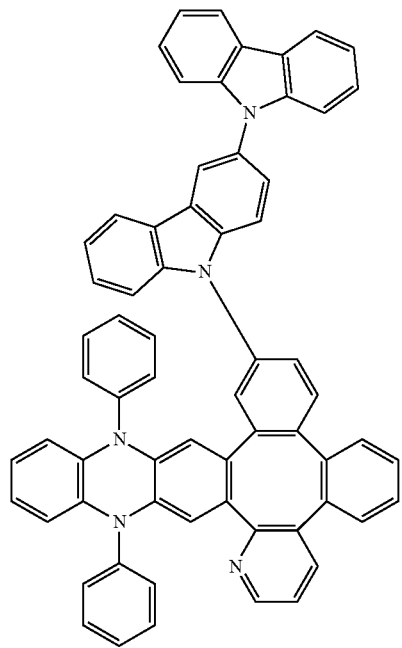
Compound B79
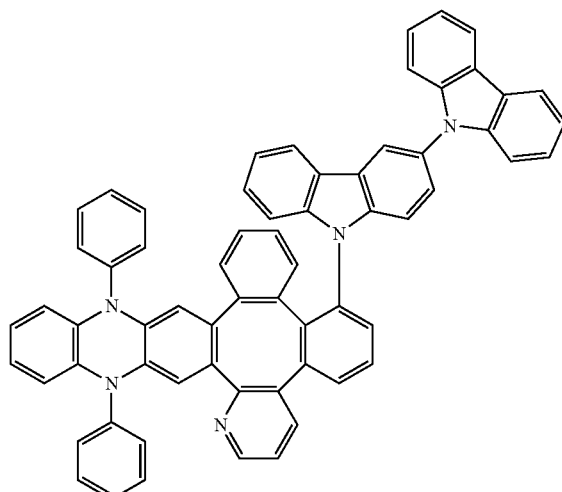
Compound B80
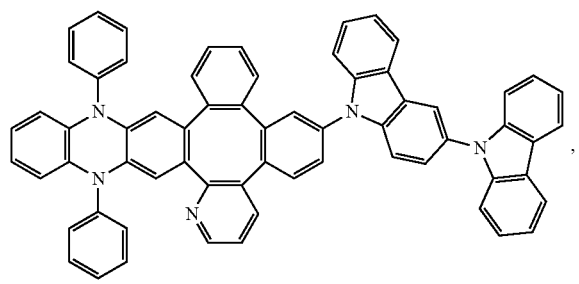
Compound B81
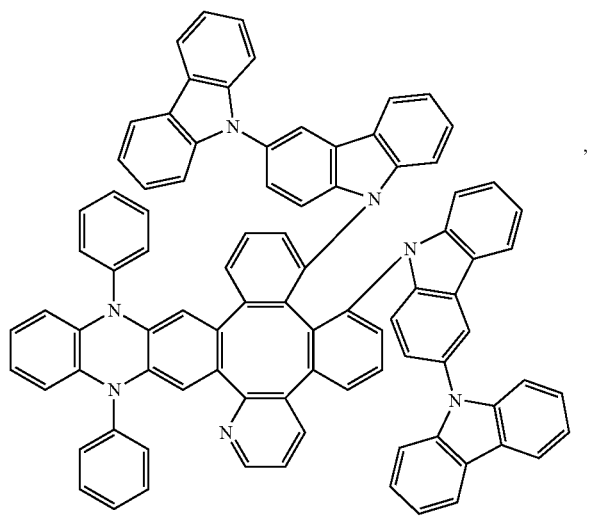

-continued
Compound B82
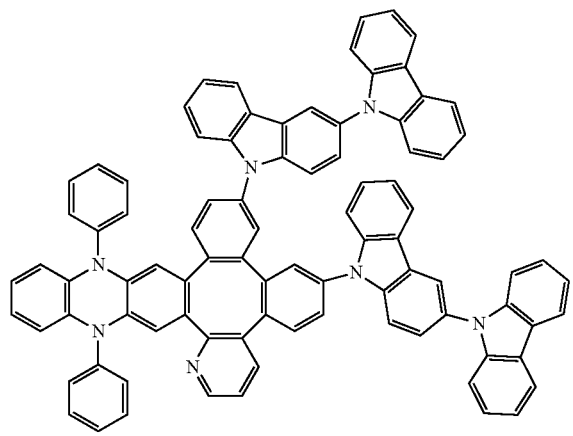
Compound B83
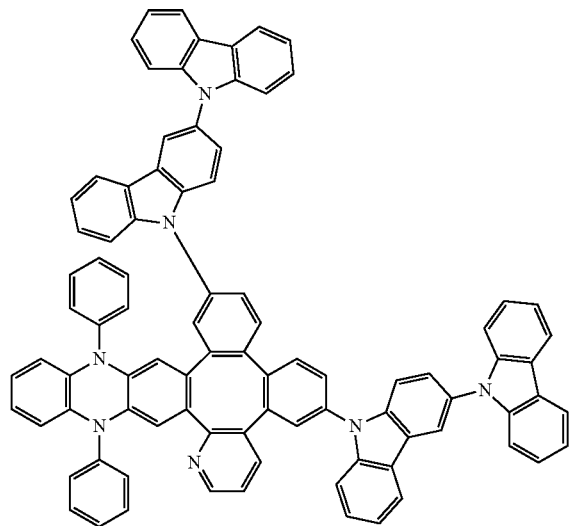
Compound B84
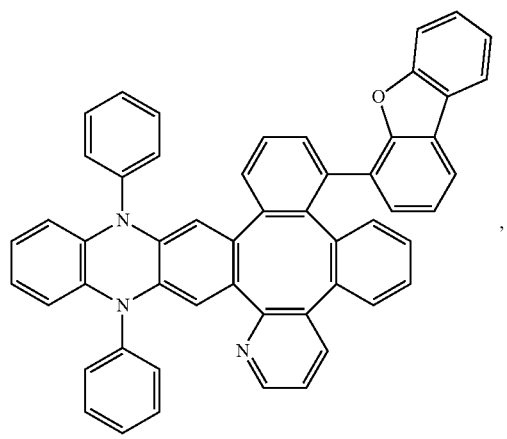
Compound B85
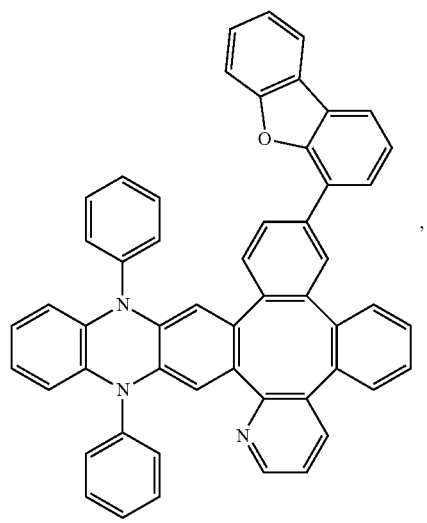
Compound B86
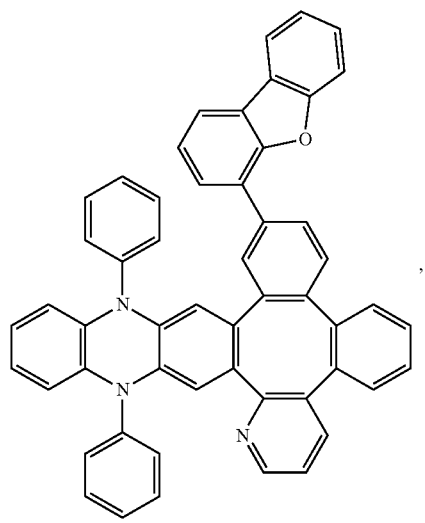
Compound B87
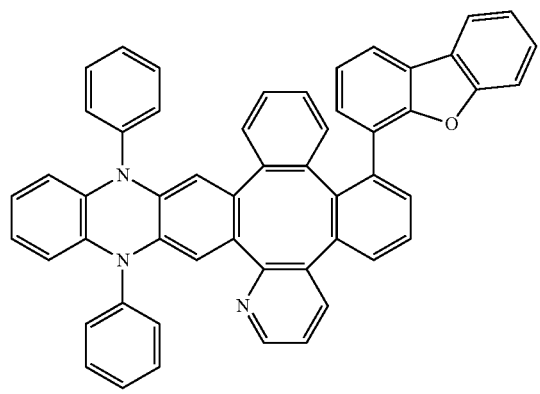

-continued
Compound B88
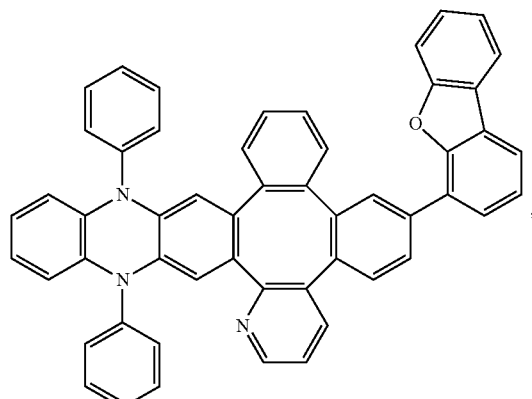
Compound B89
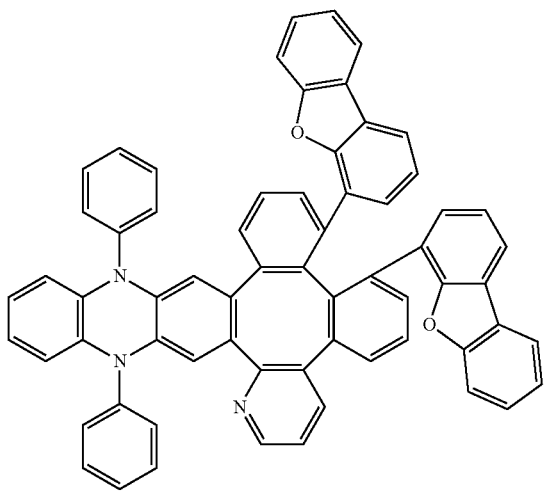
Compound B90
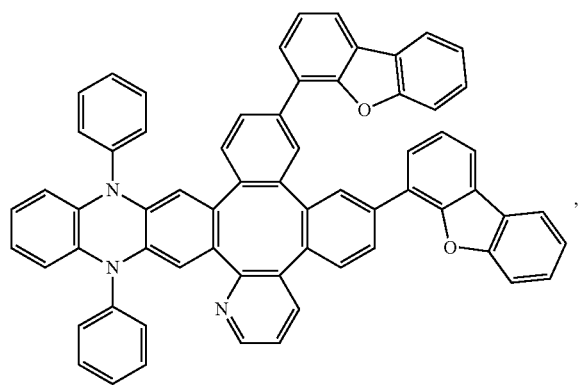
Compound B91
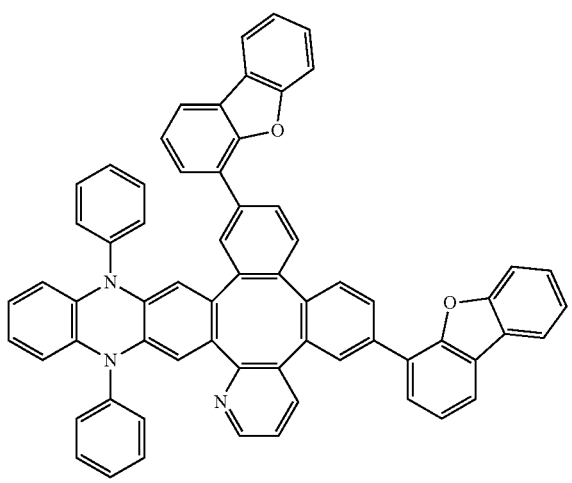
Compound B92
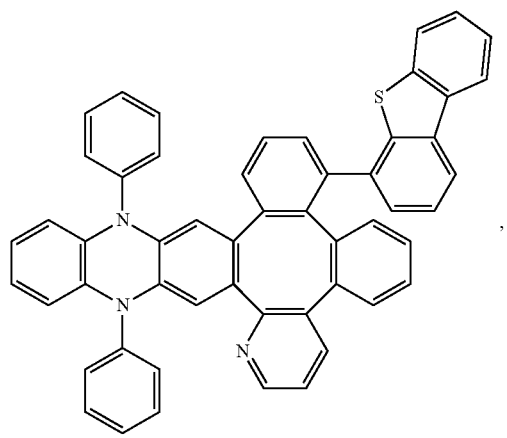
Compound B93
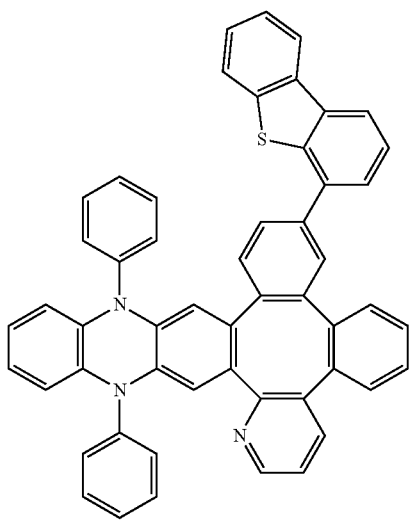

-continued
Compound B94
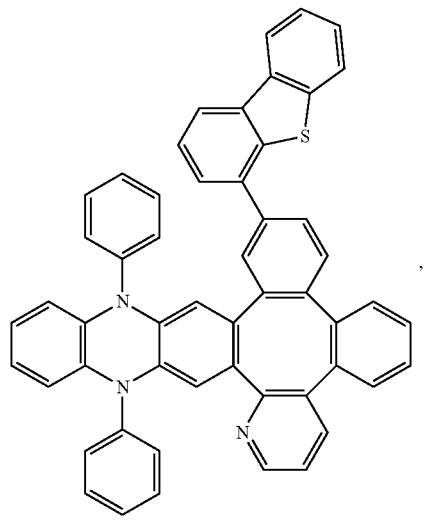
Compound B95
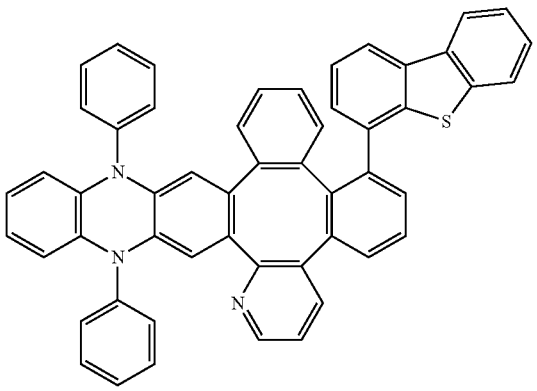
Compound B96
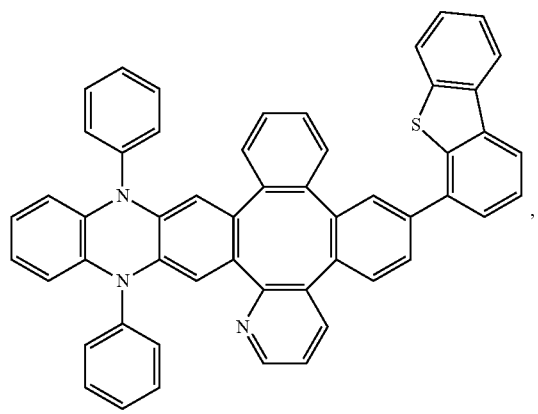
Compound CC67
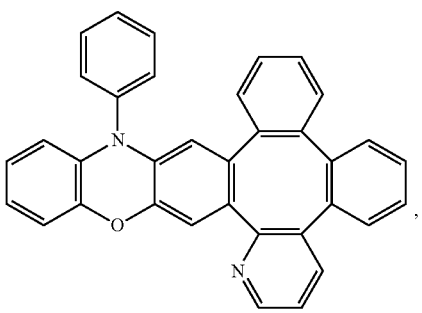
Compound CC68
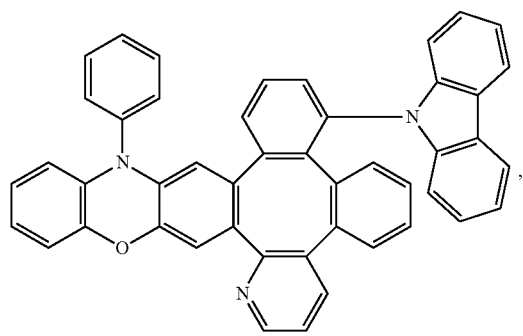
Compound CC69
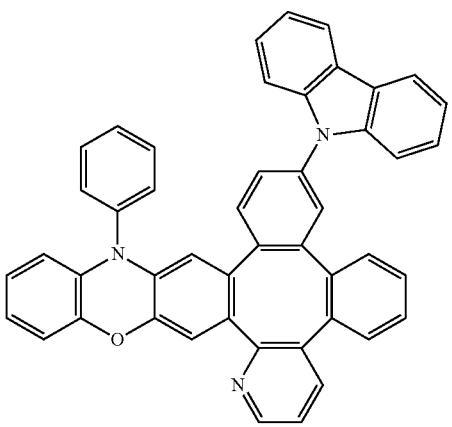

-continued
Compound CC70
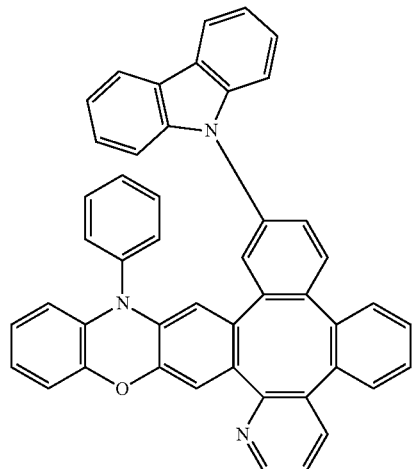
Compound CC71
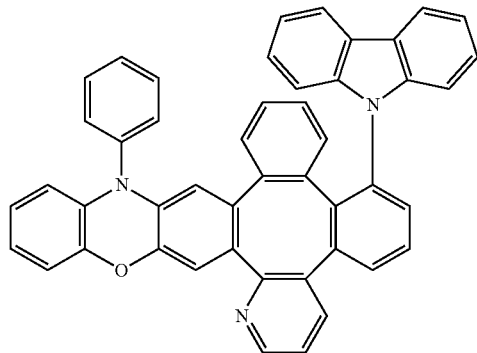
Compound CC72
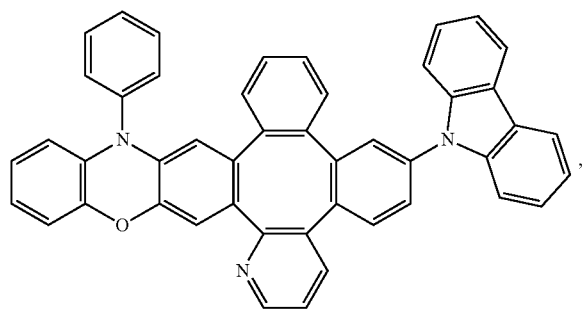
Compound CC73
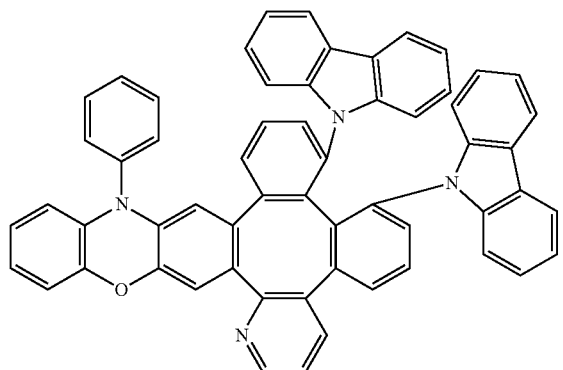
Compound CC74
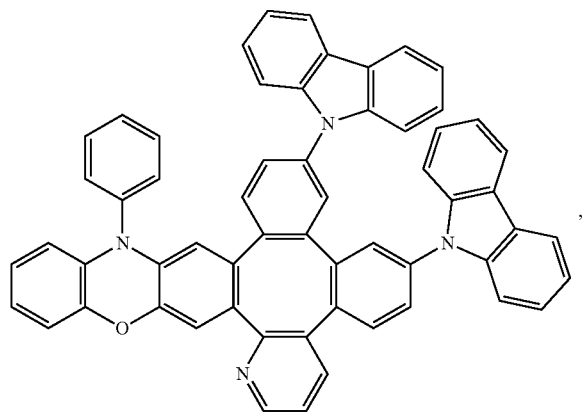
Compound CC75
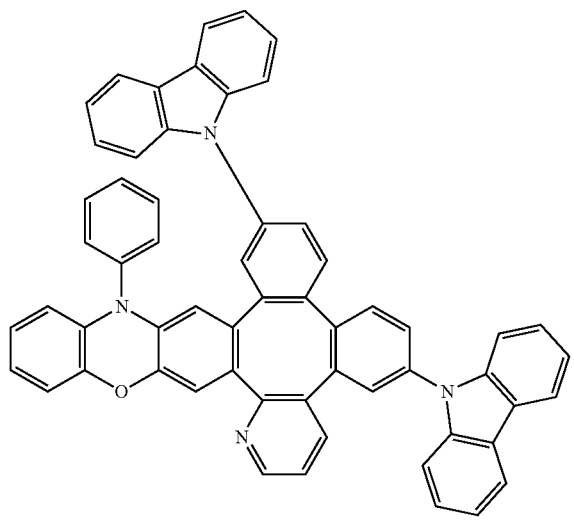

-continued
Compound CC76
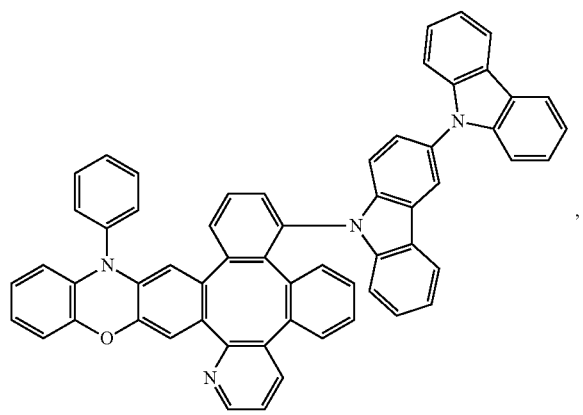
Compound DD67
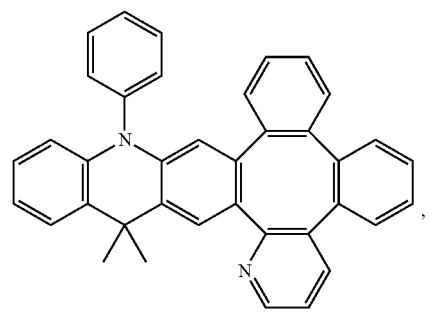
Compound DD68
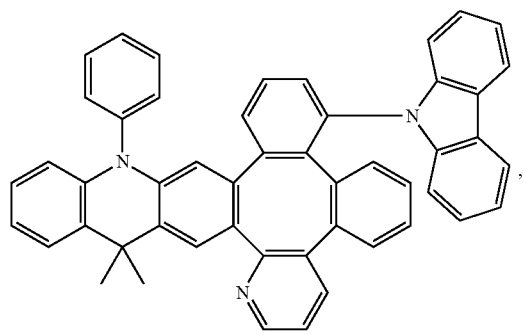
Compound DD69
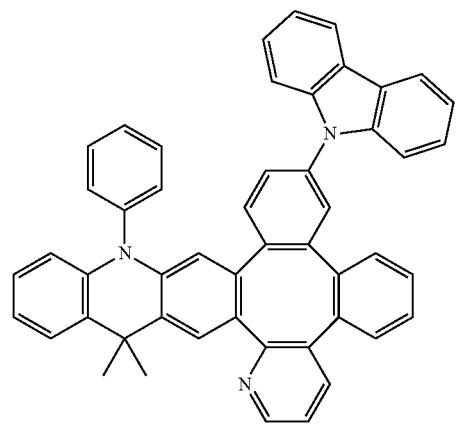
Compound DD70
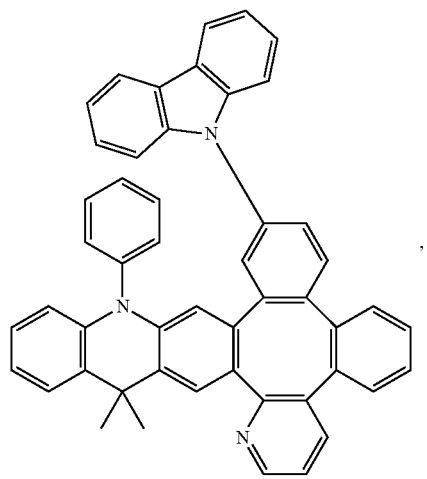
Compound DD71
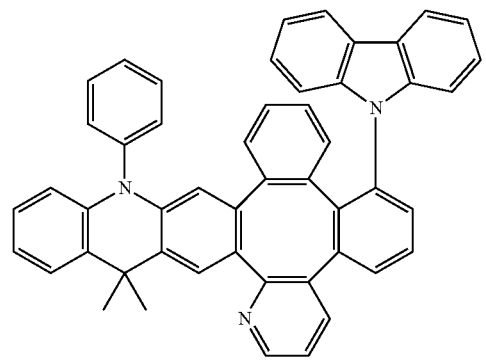

-continued
Compound DD72
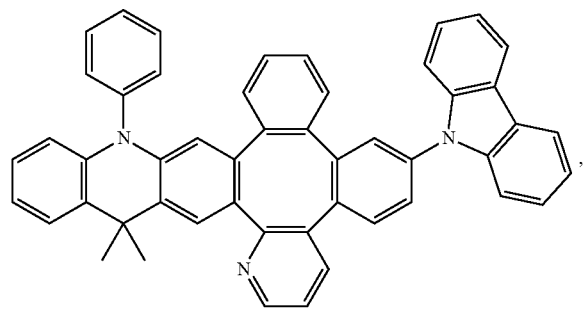
Compound DD73
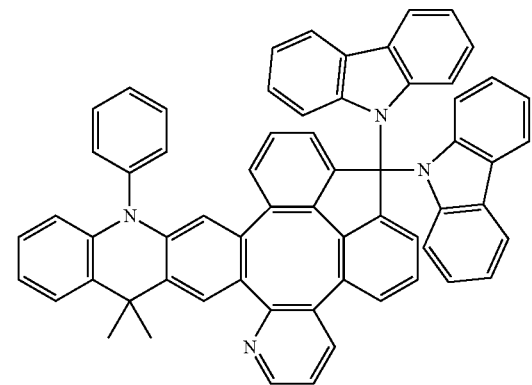
Compound DD74
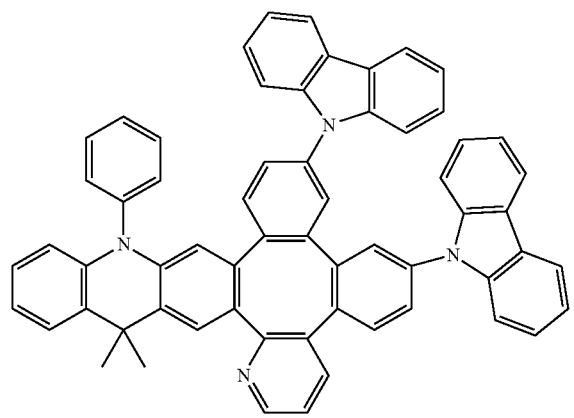
Compound DD75
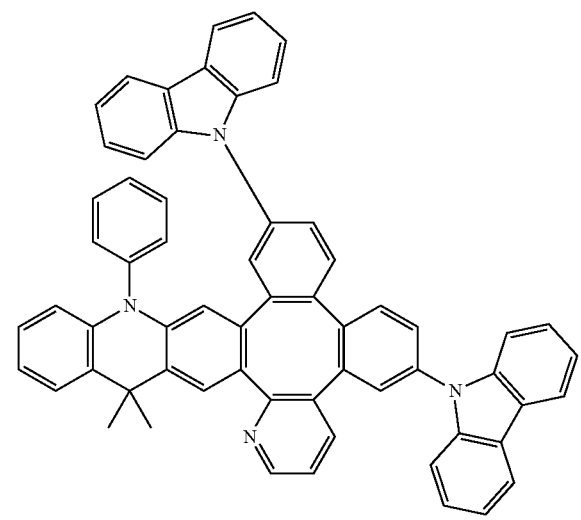
Compound DD76
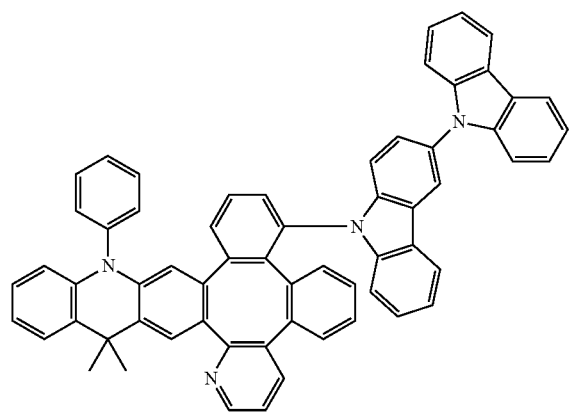
Compound EE67
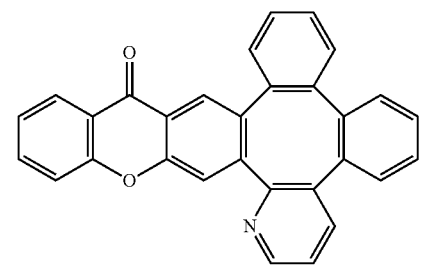

-continued
Compound EE68
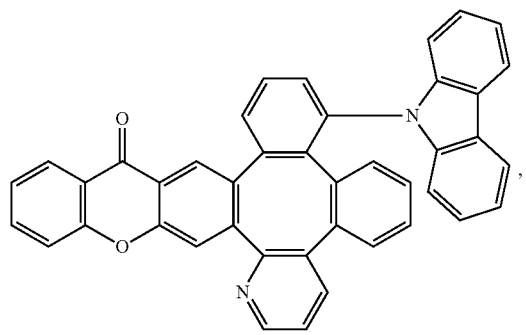
Compound EE69
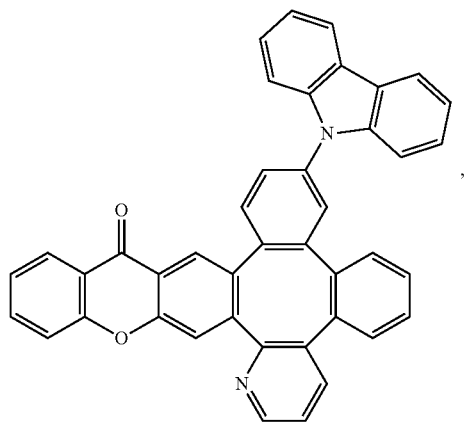
Compound EE70
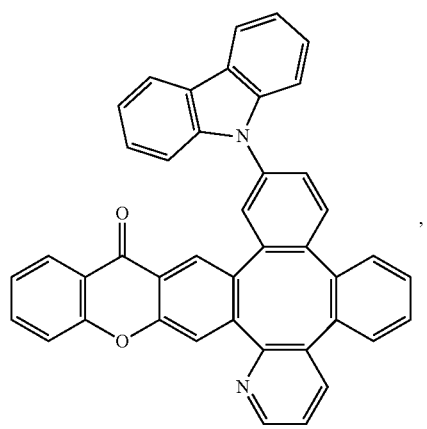
Compound EE71
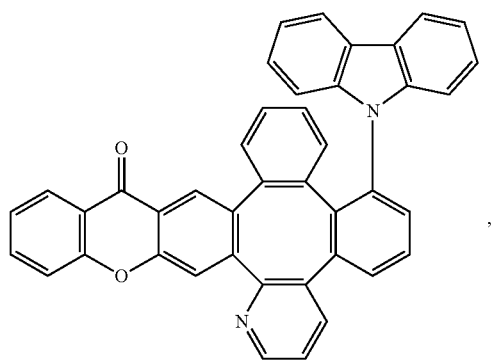
Compound EE72
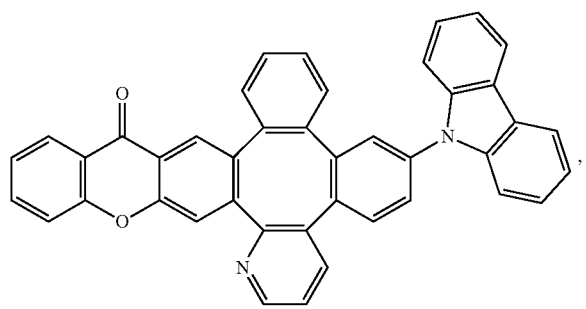
Compound EE73
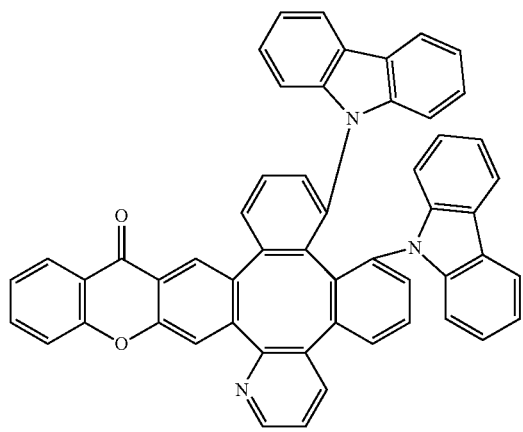

Compound EE74
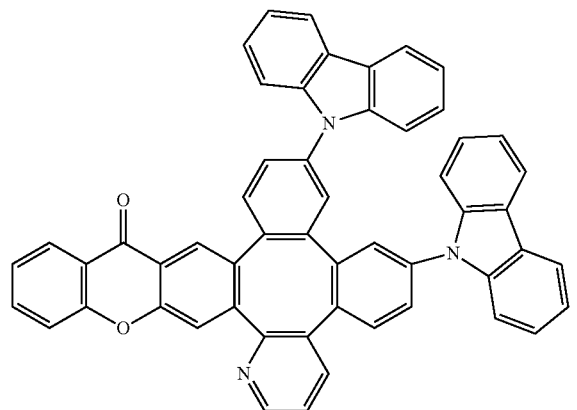
Compound EE75
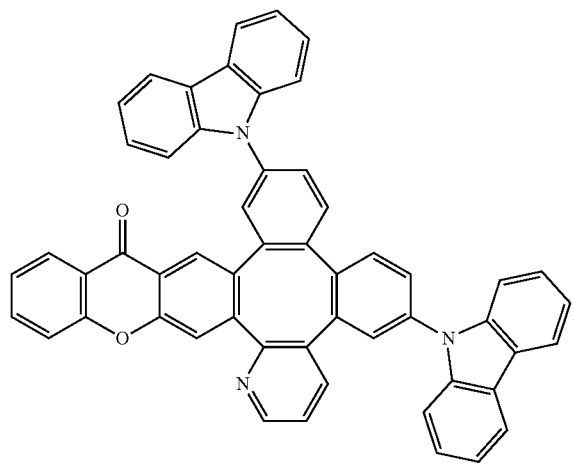
Compound EE76
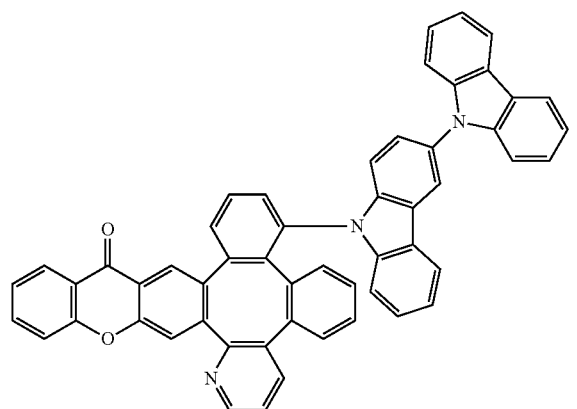
Compound FF67
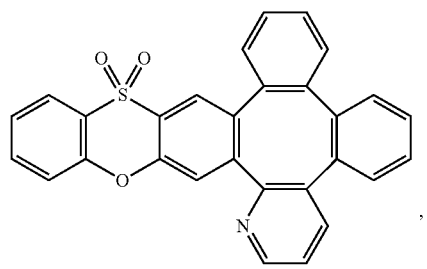
Compound FF68
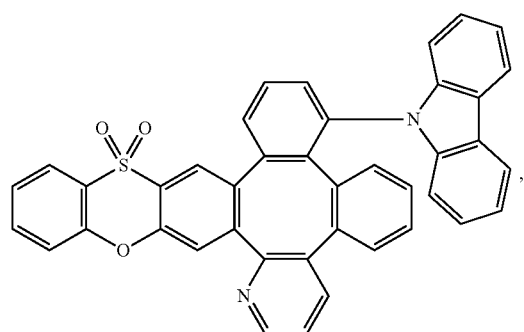
Compound FF69
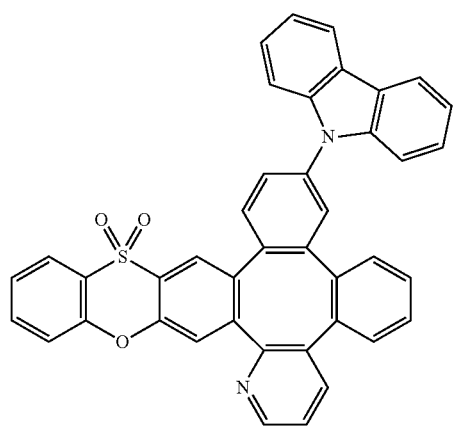

Compound FF70
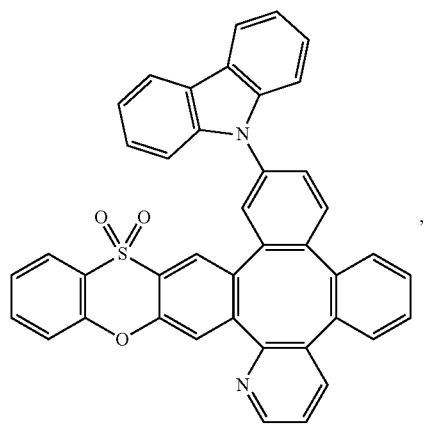
Compound FF71
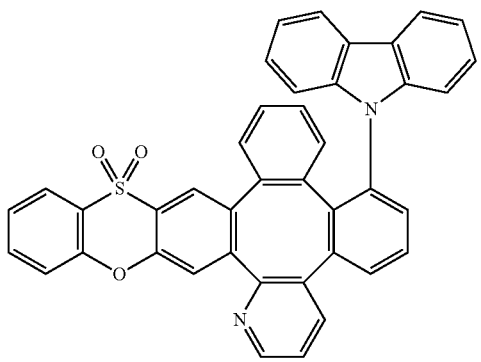
,
Compound FF72
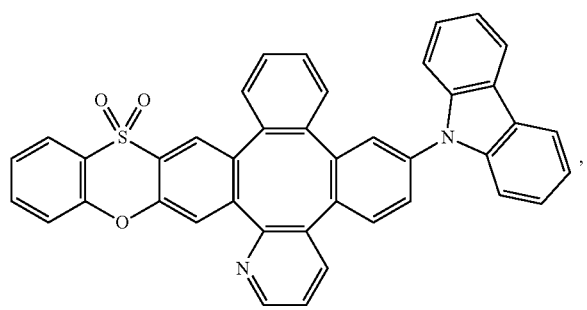
,
Compound FF73
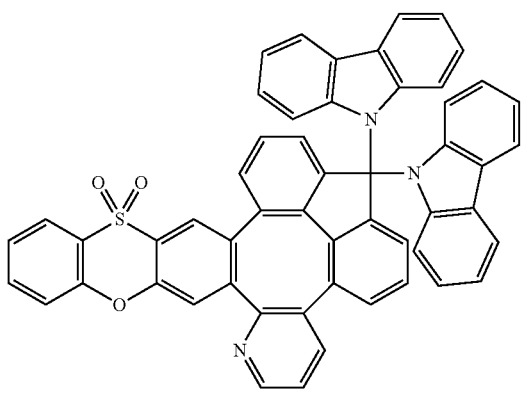
,
Compound FF74
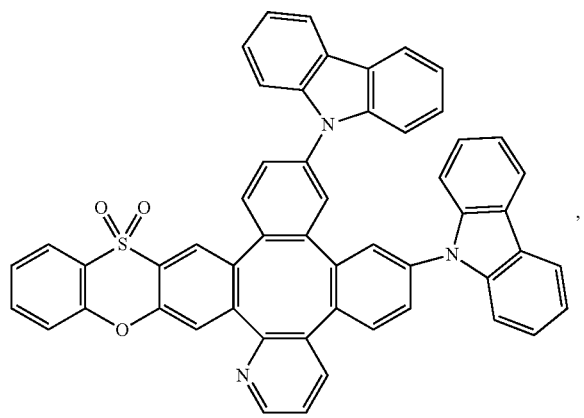
,
Compound FF75
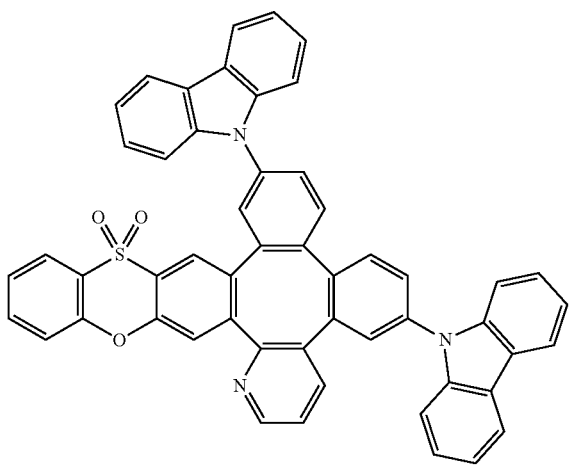
, -continued
Compound FF76
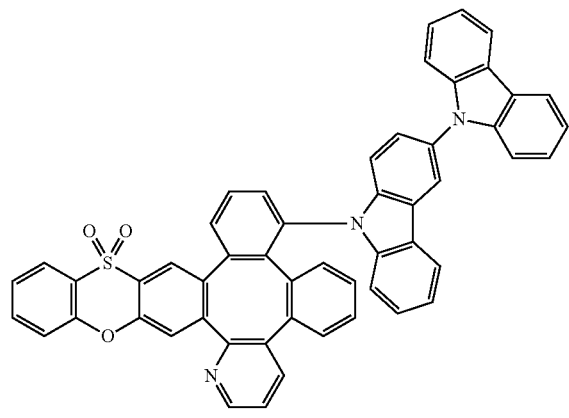
Compound A97
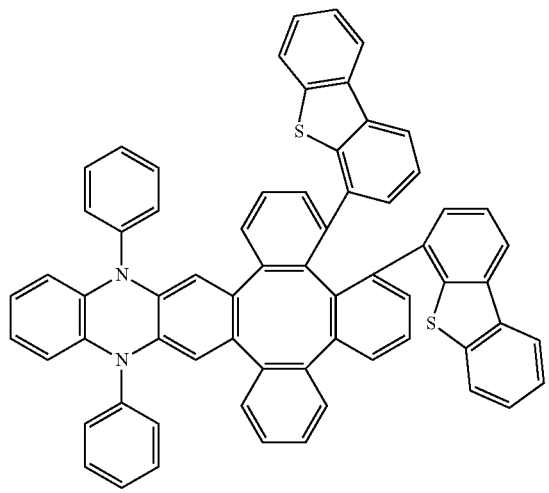
Compound A98
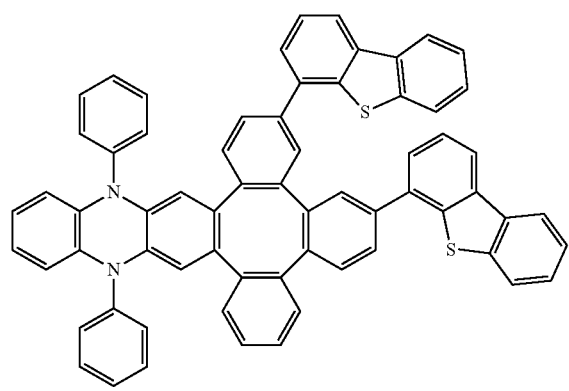
Compound A99
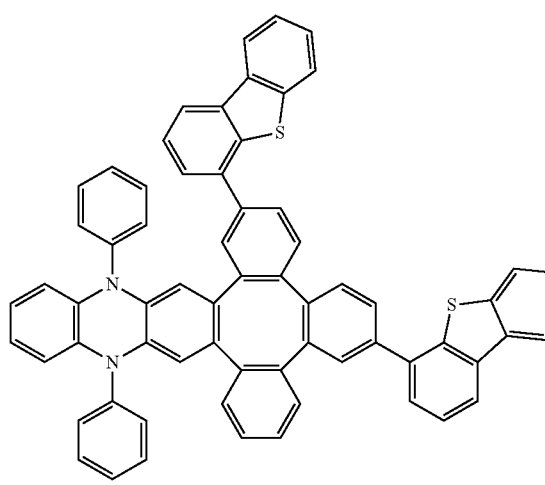
Compound A100
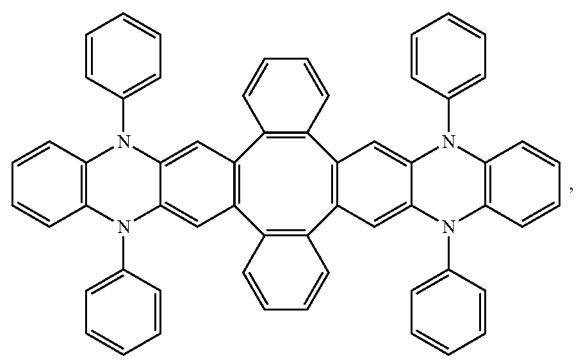
Compound A101
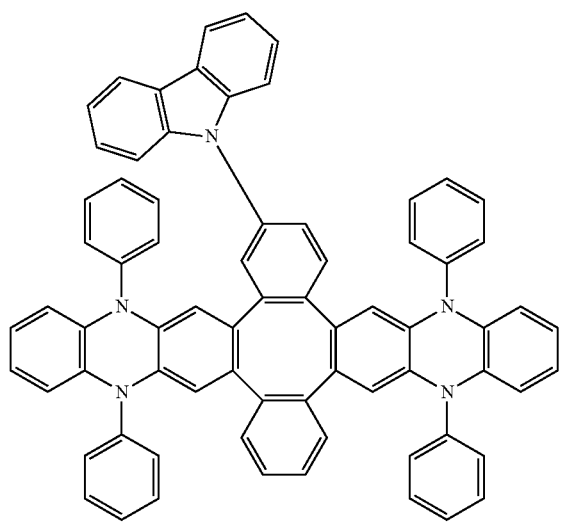

-continued
Compound A102
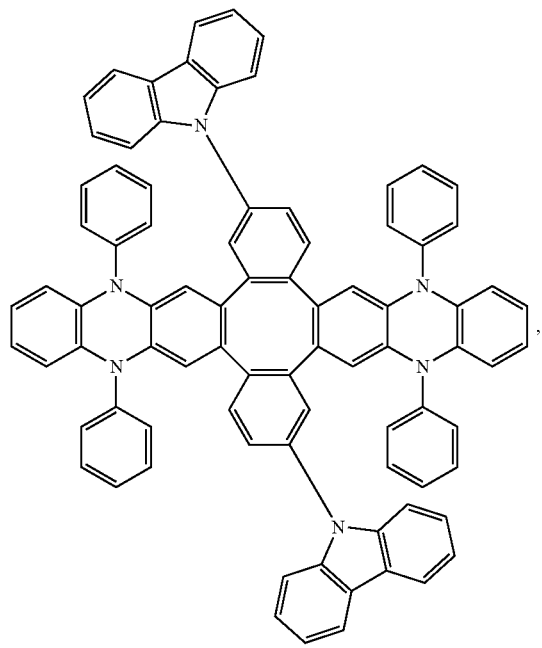
Compound A103
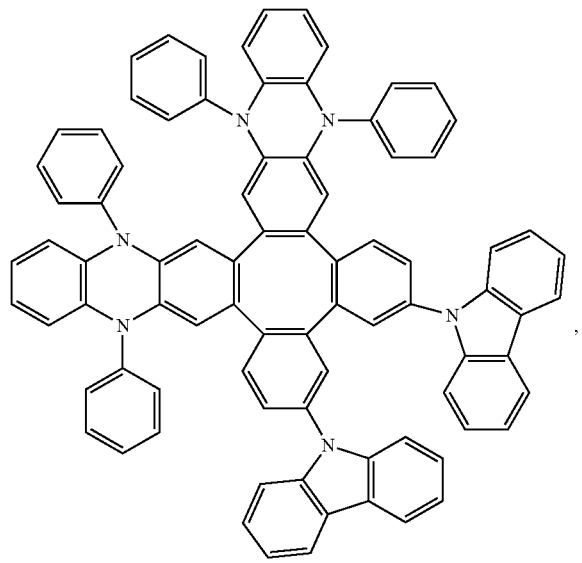
Compound A104
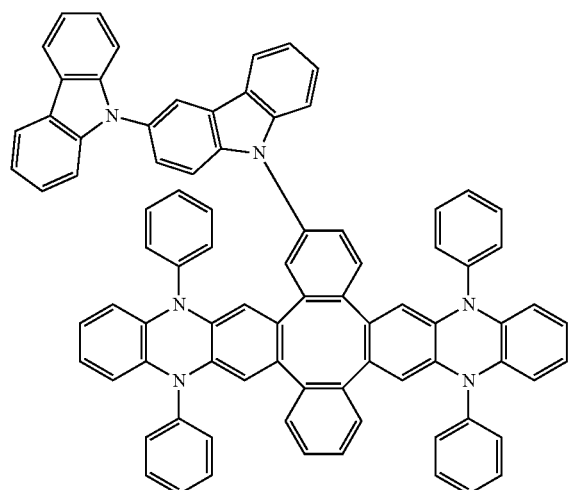
Compound A105
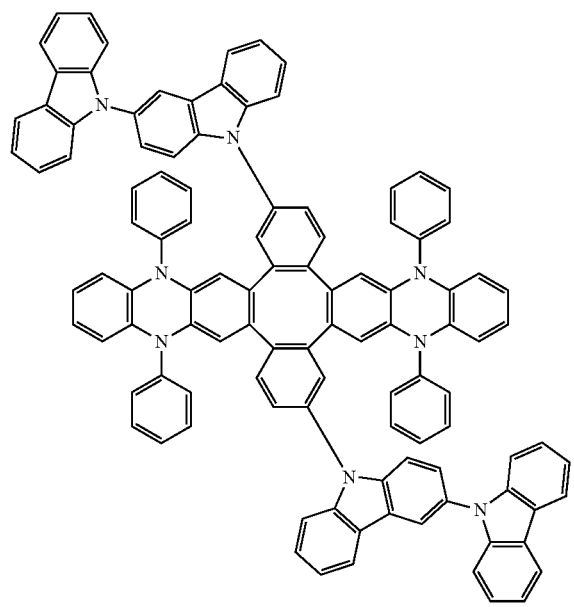

-continued
Compound A106
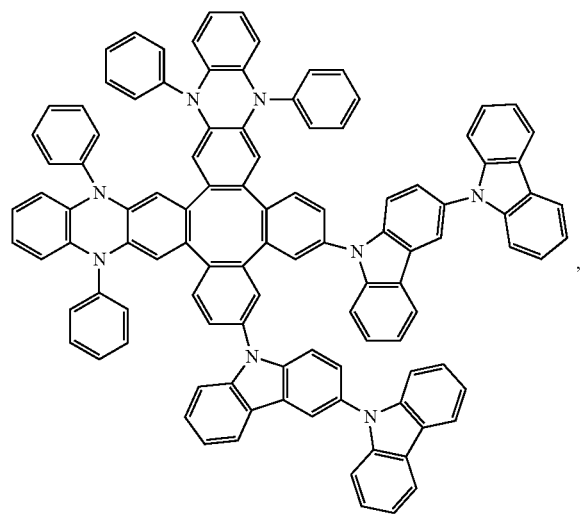
Compound A107
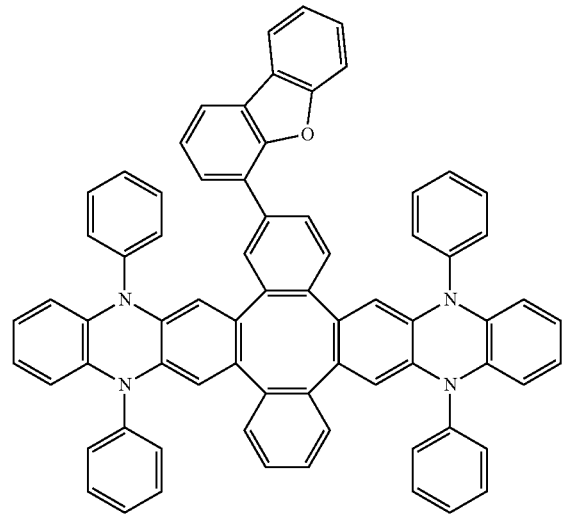
Compound A108
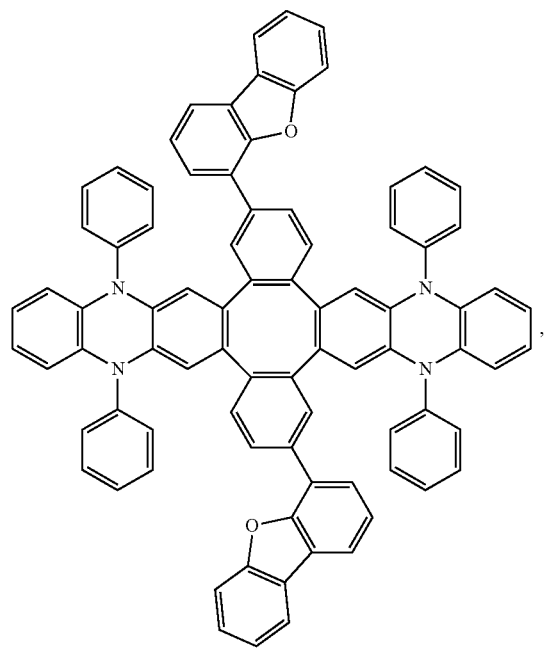
Compound A109
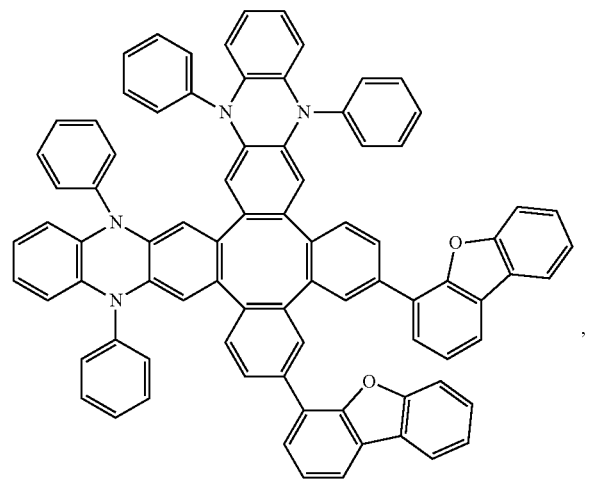

-continued
Compound A110
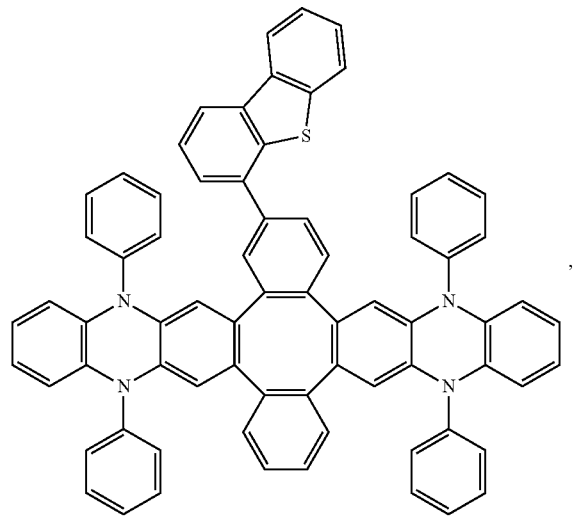
Compound A111
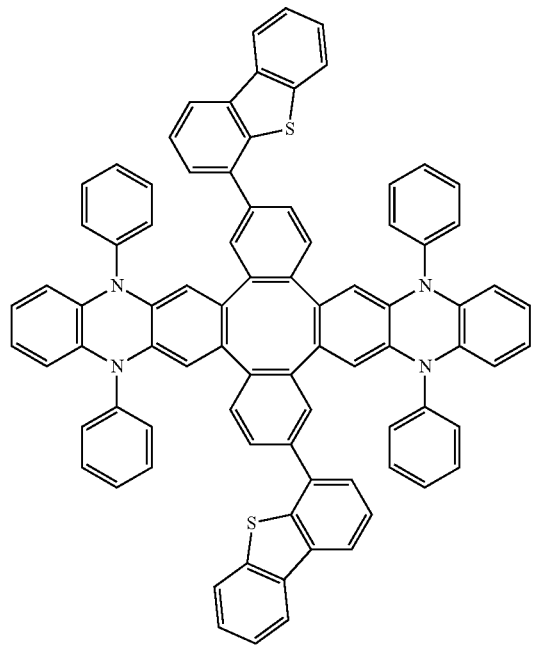
Compound A112
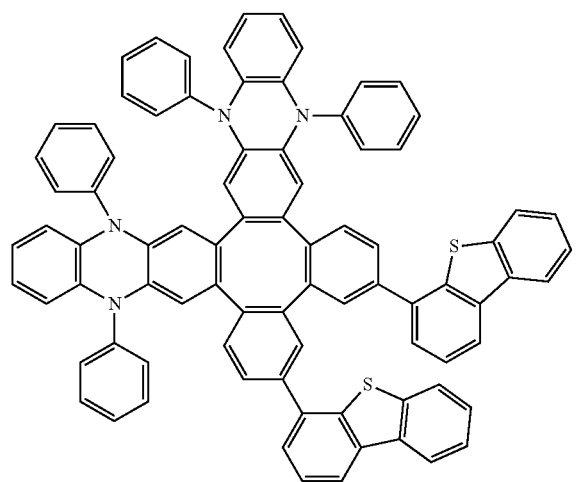
Compound C100
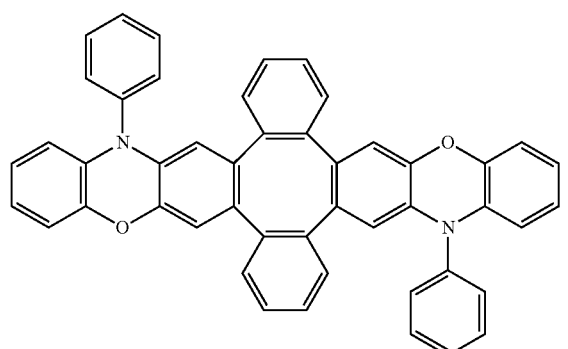

-continued
Compound C101
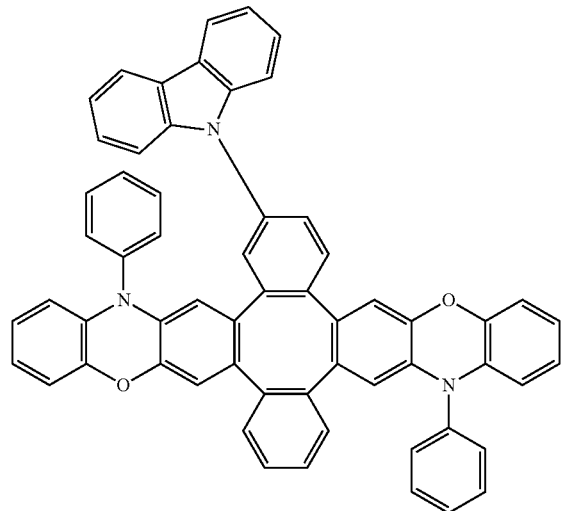
Compound C102
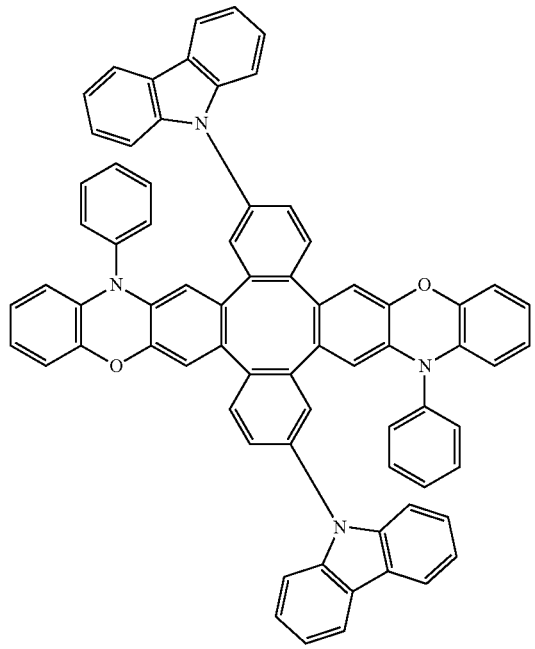
Compound C103
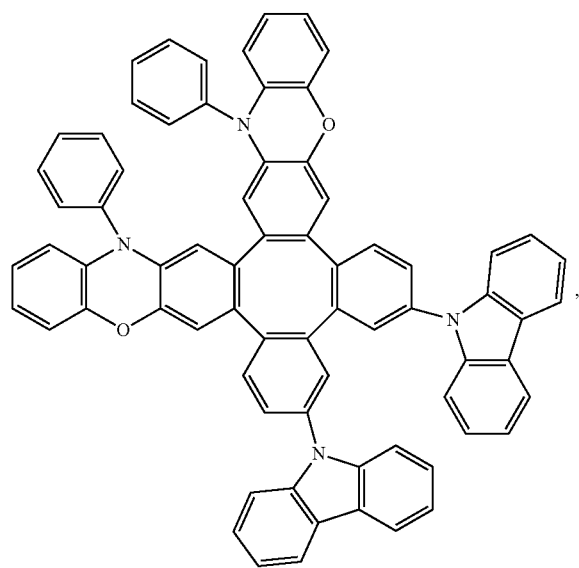
Compound C104
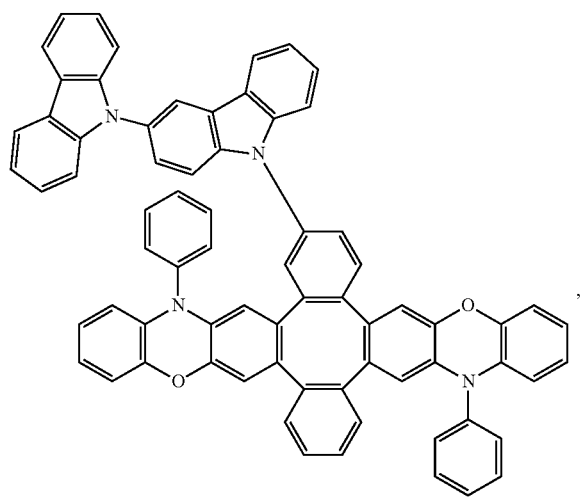

-continued
Compound C105
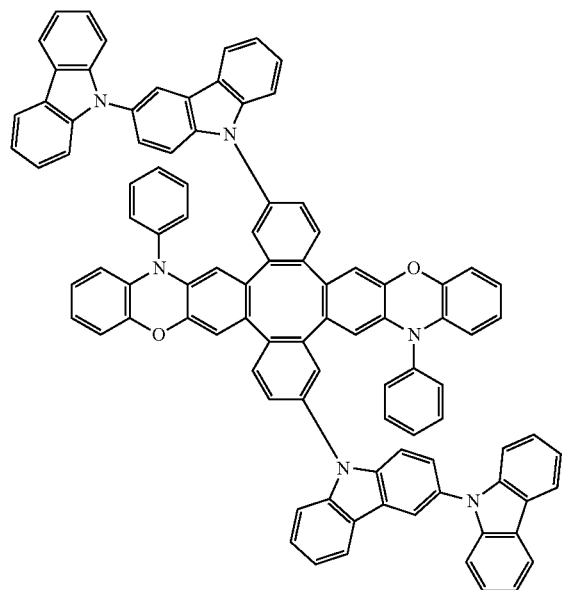
Compound C106
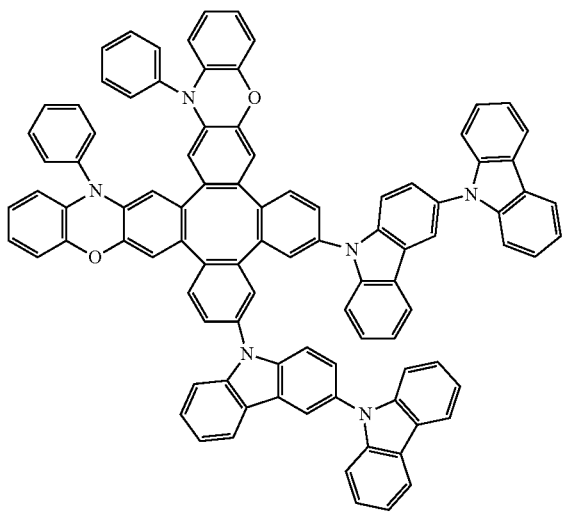
Compound C107
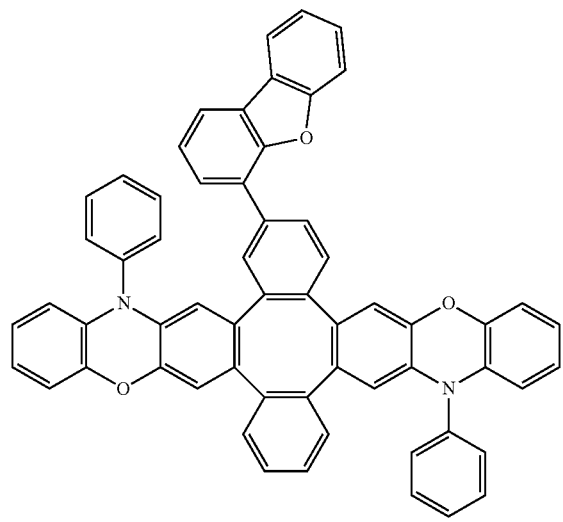
Compound C108
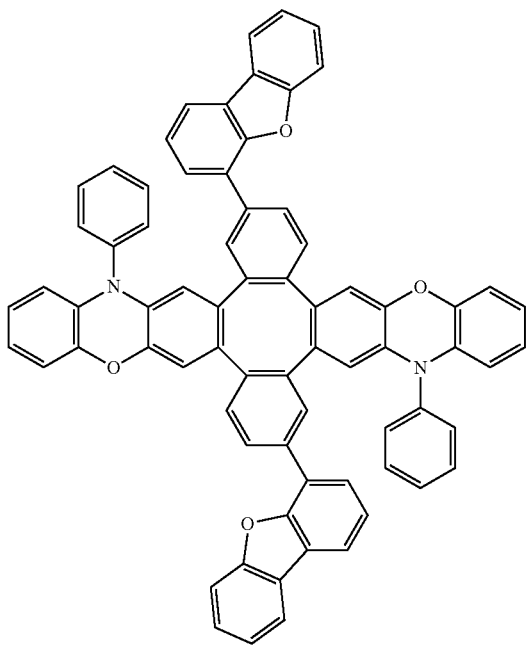

-continued
Compound D100
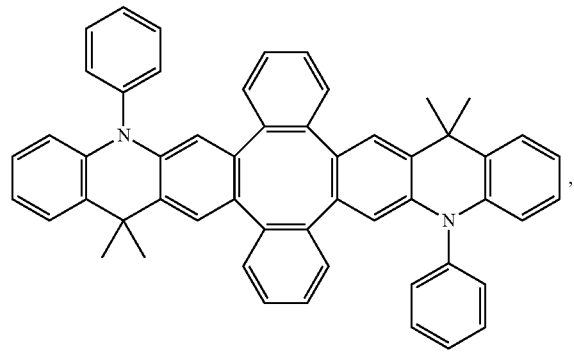
Compound D101
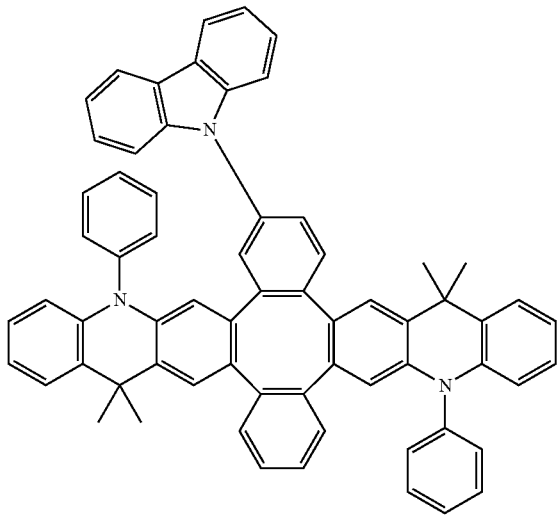
Compound D102
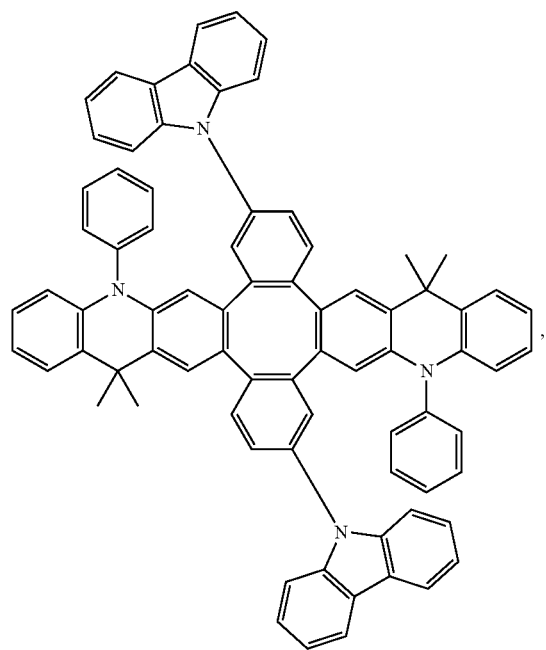
Compound D103
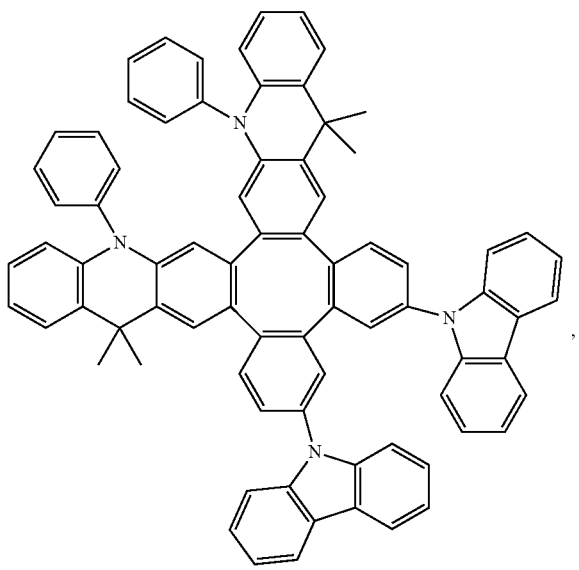

Compound D104
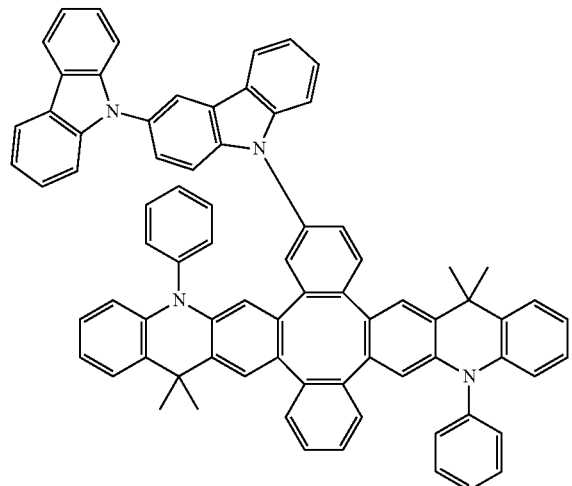
Compound D105
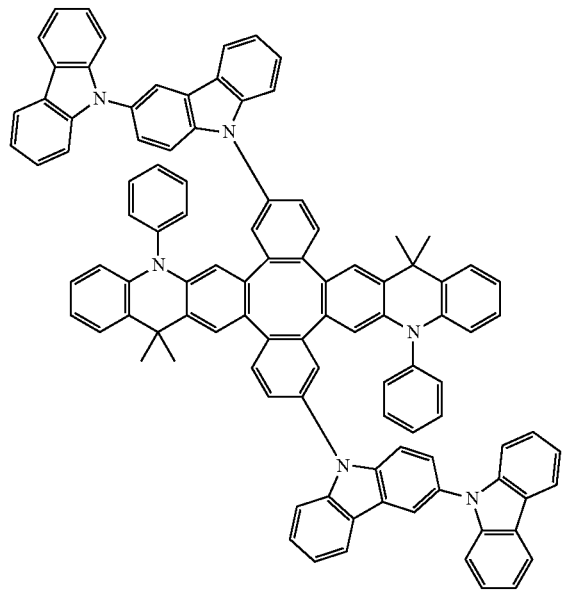
Compound D106
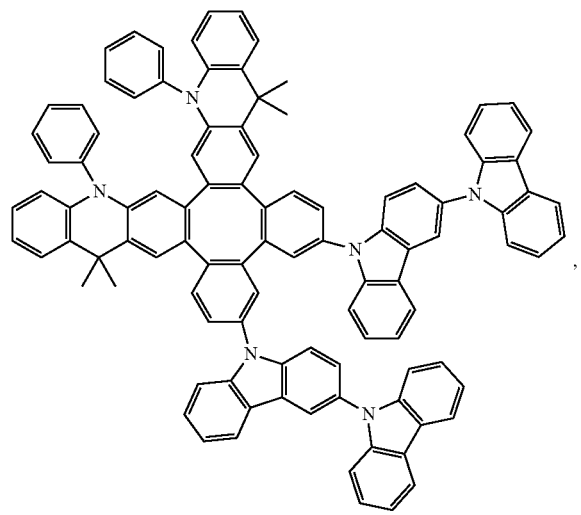
Compound D107
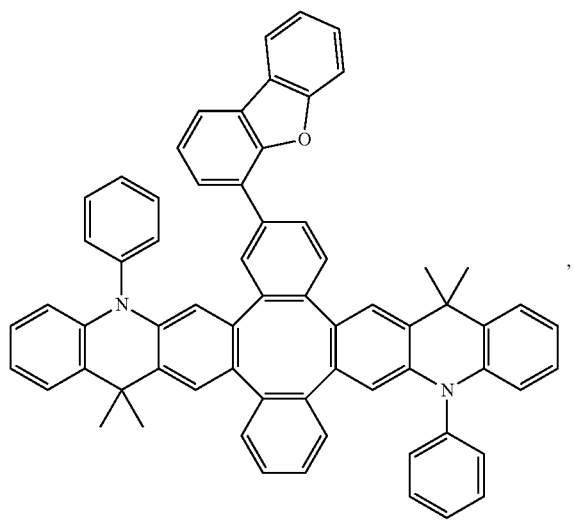

Compound D108
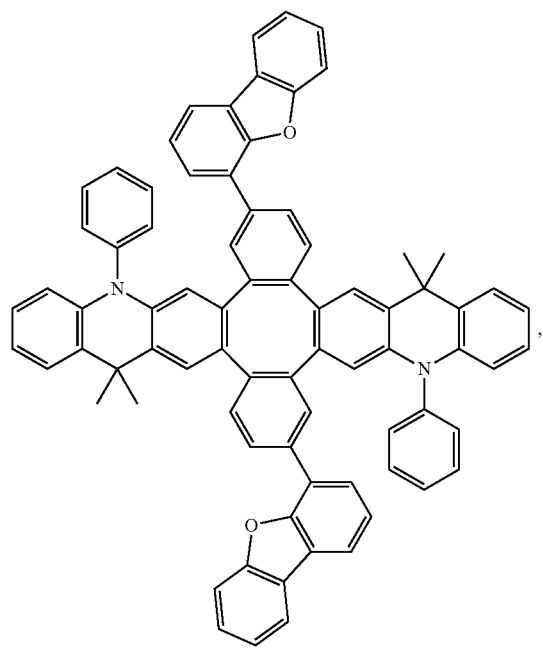
Compound E100
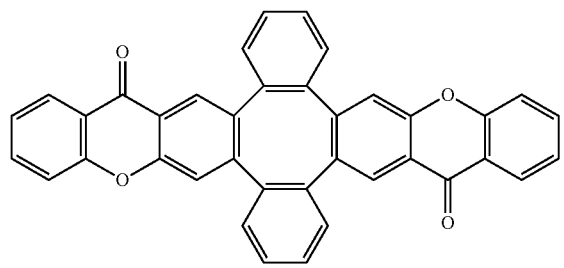
Compound E101
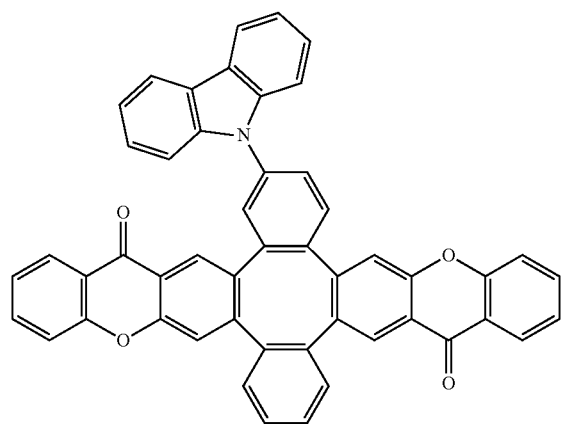
Compound E102
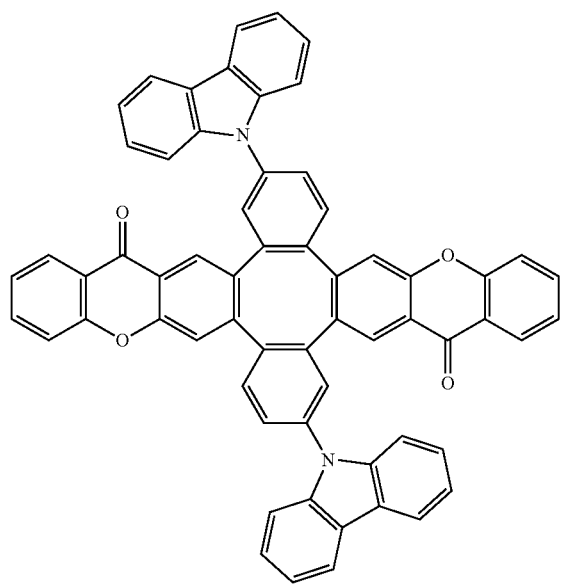

-continued
Compound E103
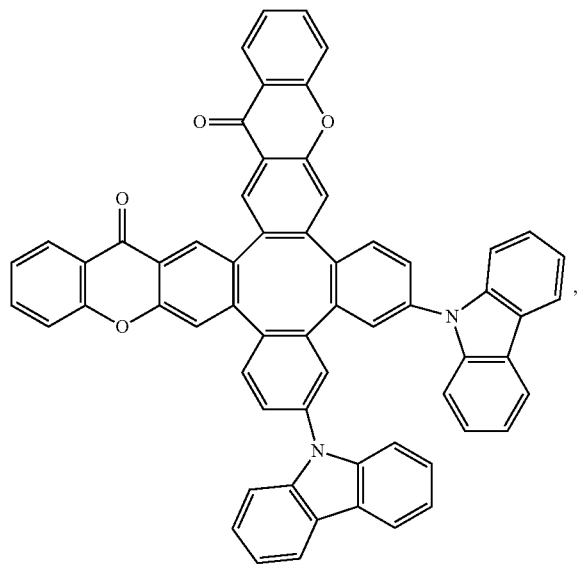
Compound E104
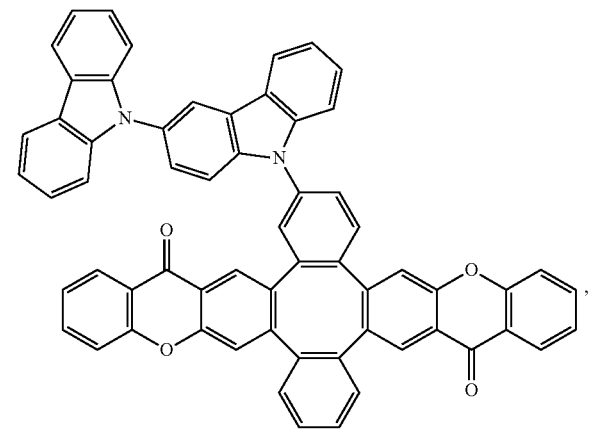
Compound E105
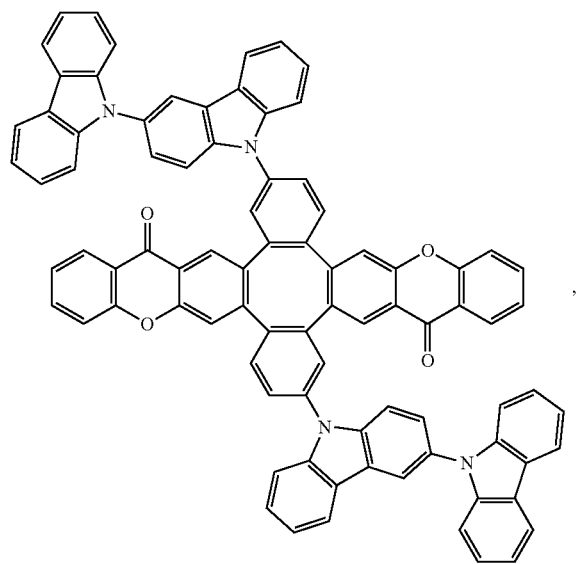
Compound E106
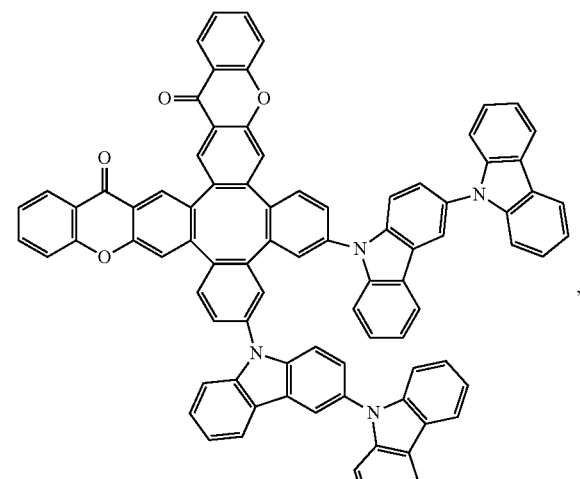

-continued
Compound E107
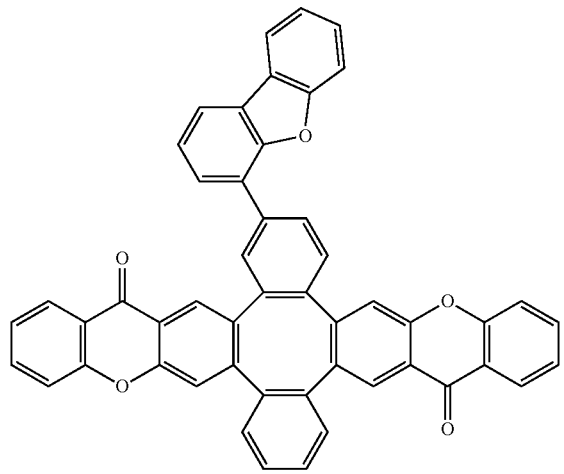
Compound E108
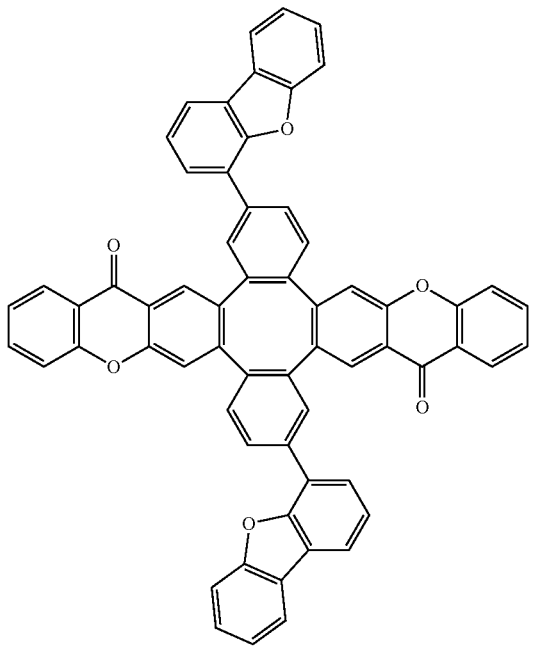
Compound F100
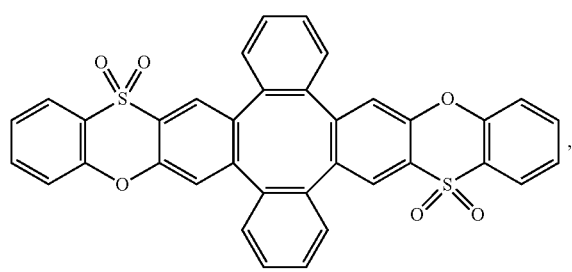
Compound F101
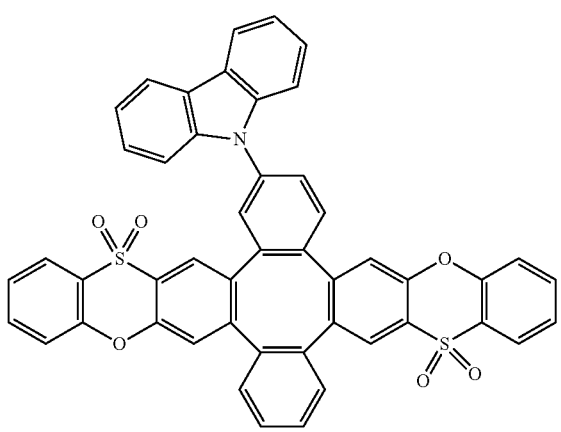

-continued
Compound F102
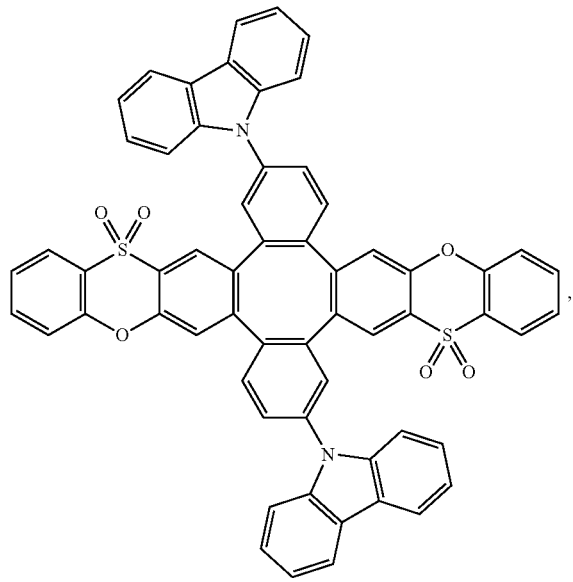
Compound F103
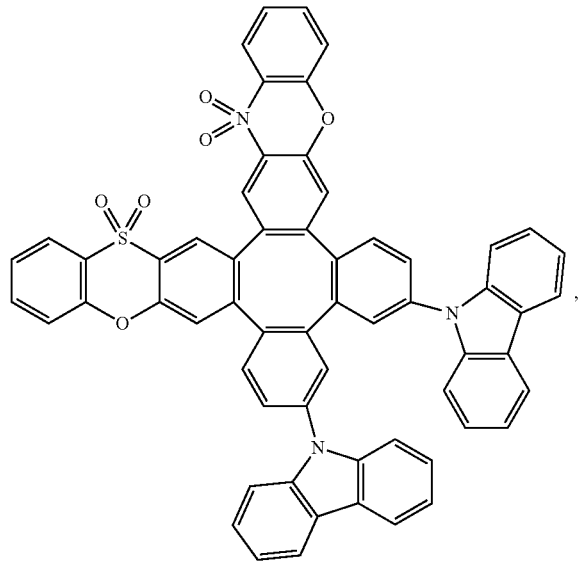
Compound F104
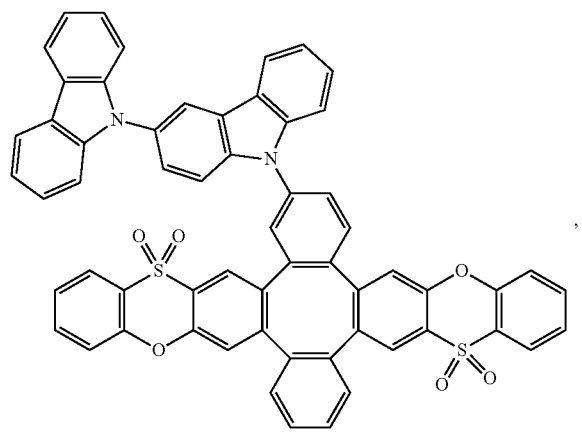
Compound F105
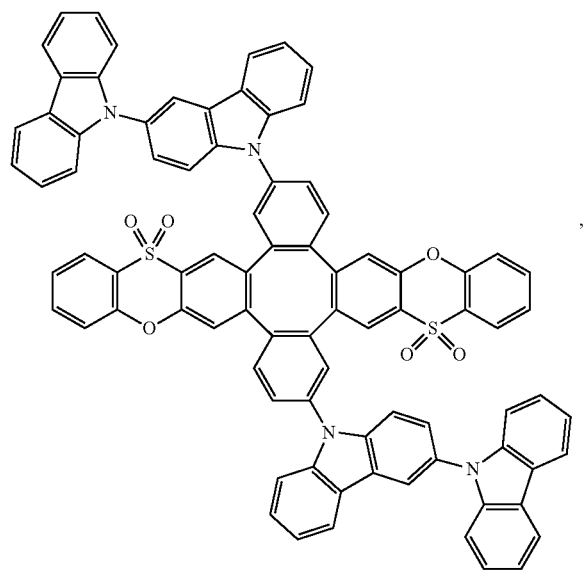

-continued
Compound F106
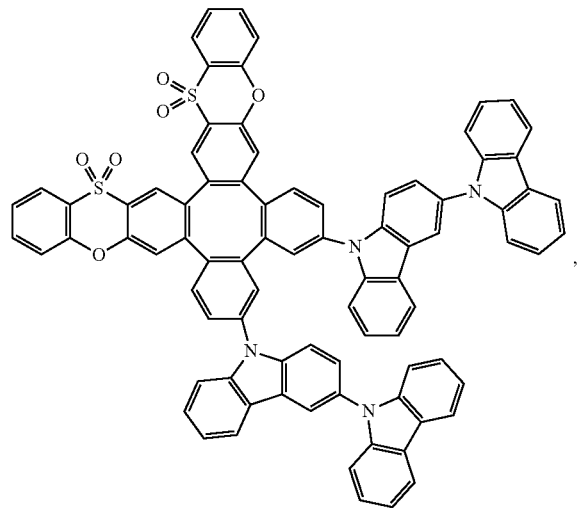
Compound F107
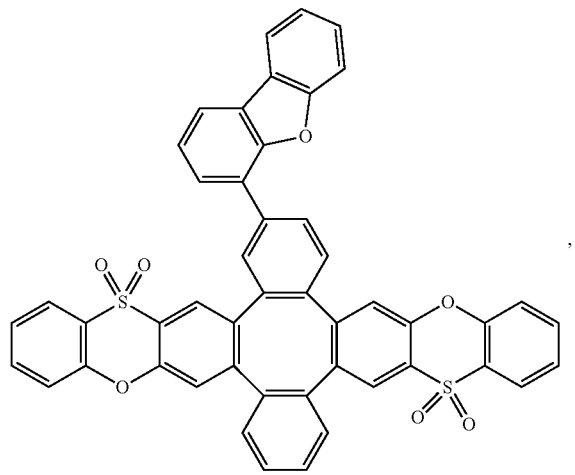
Compound F108
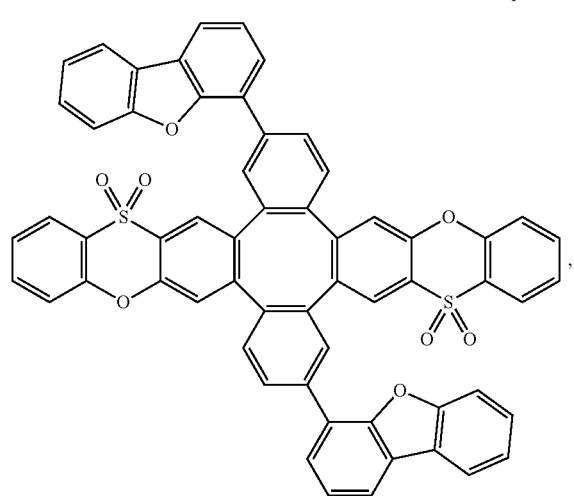
Compound B100
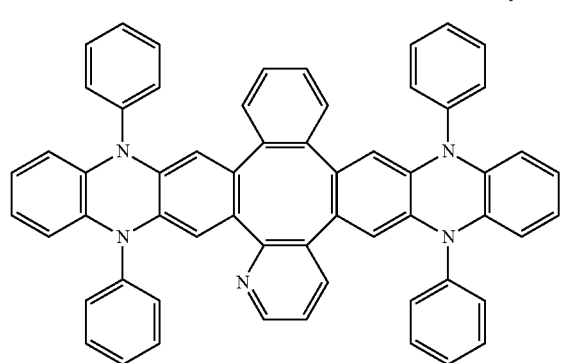

-continued
Compound B101
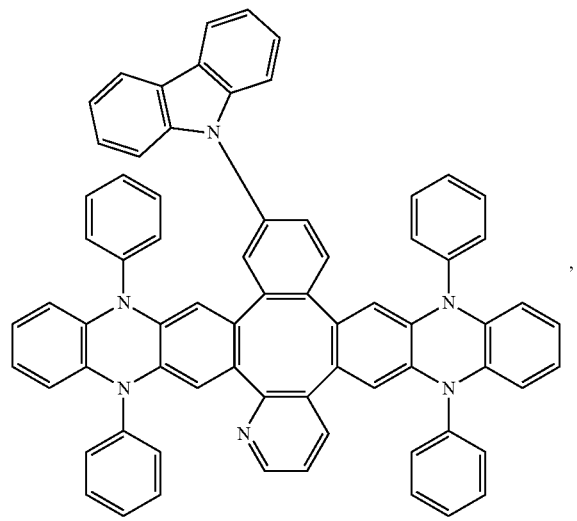
Compound B102
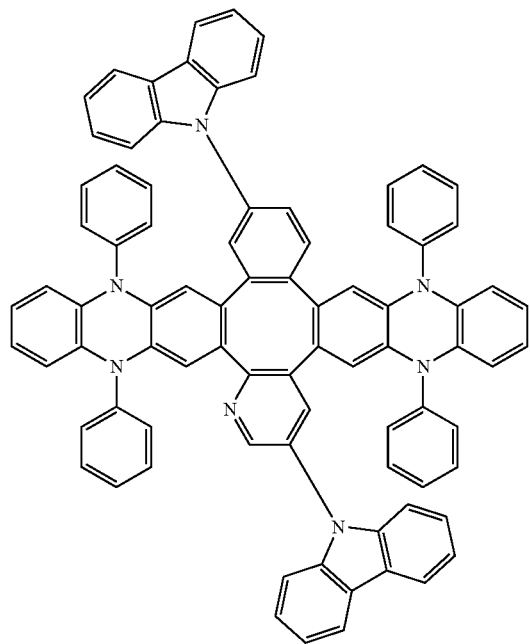
Compound B103
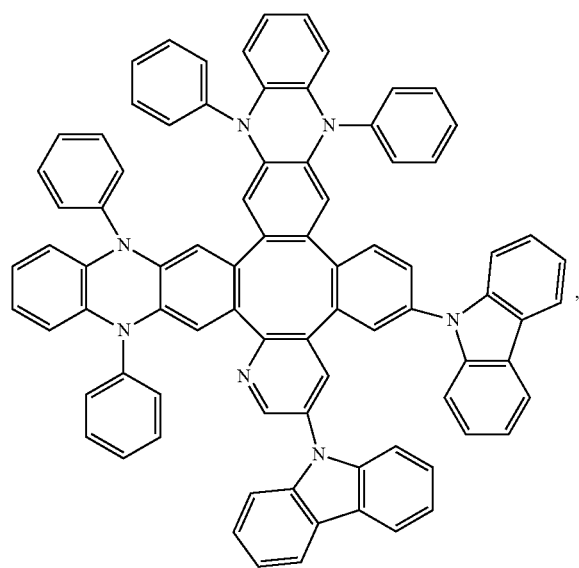
Compound B104
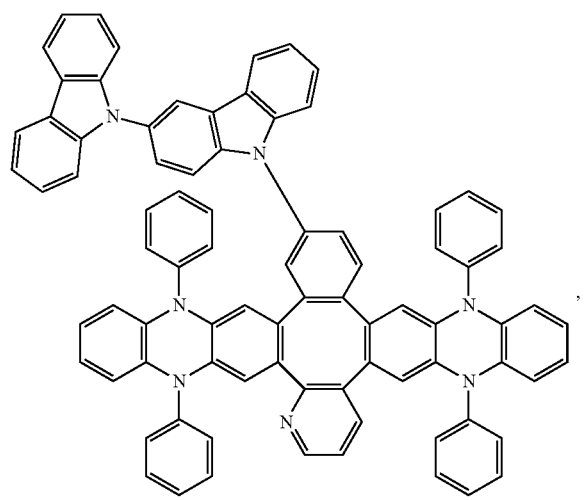

-continued
Compound B105
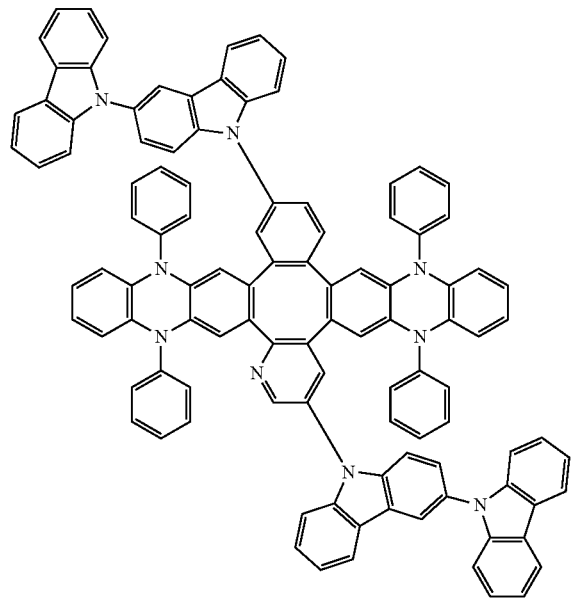
Compound B106
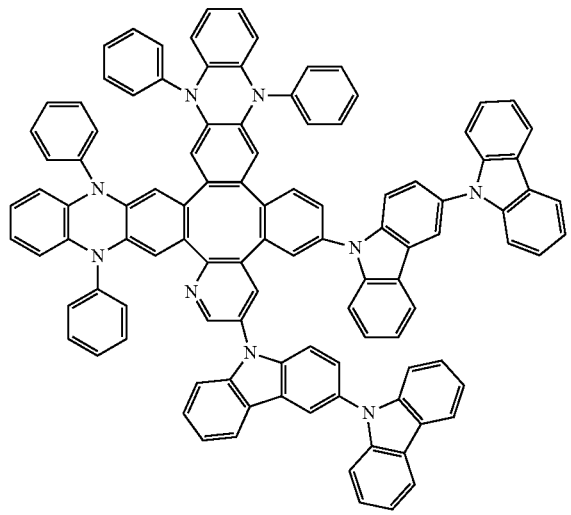
Compound B107
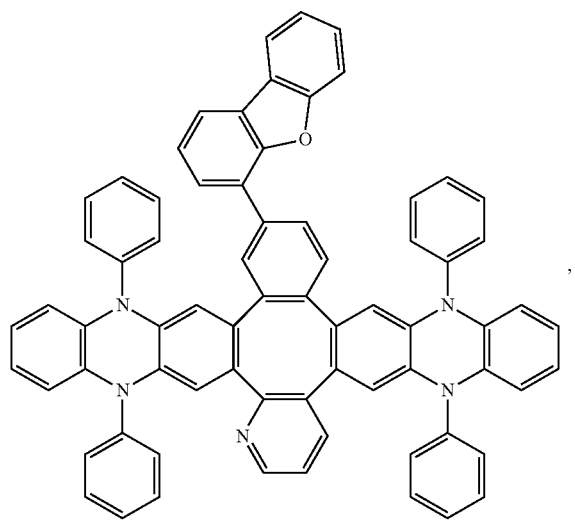
Compound B108
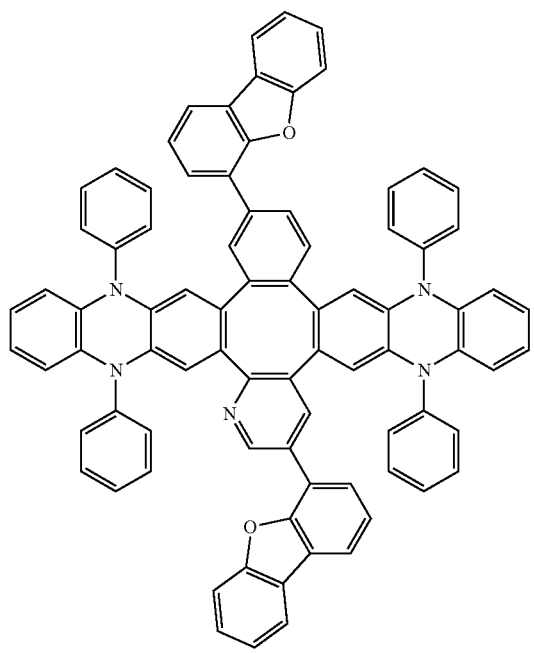

-continued
Compound B109
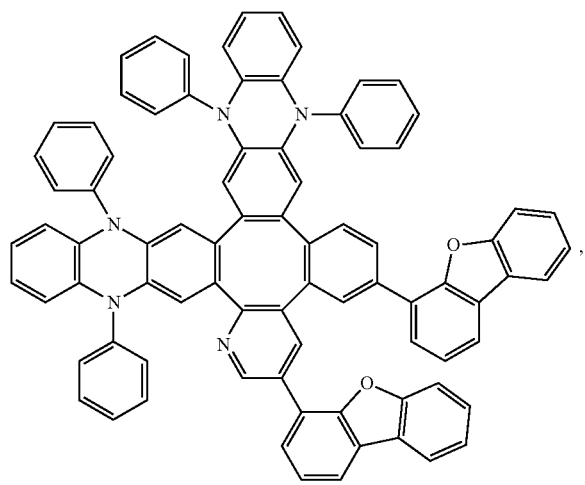
Compound B110
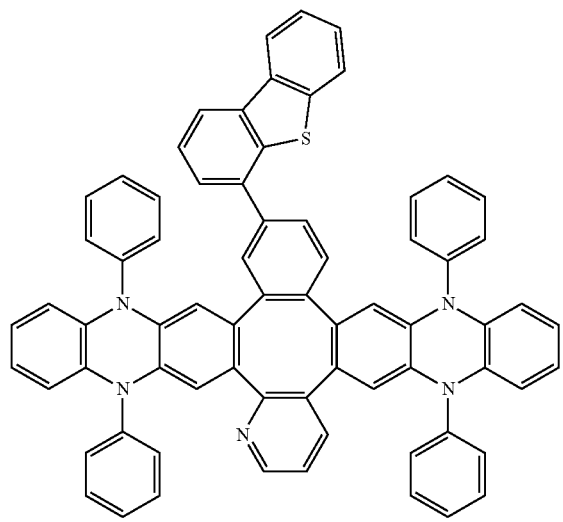
Compound B111
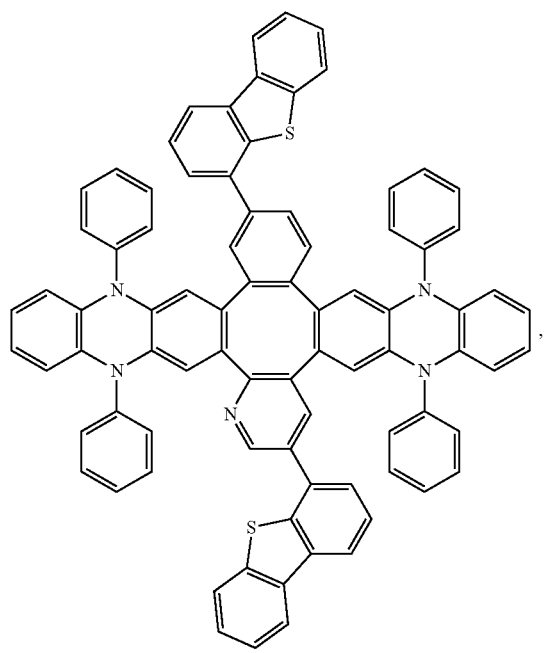
Compound B112
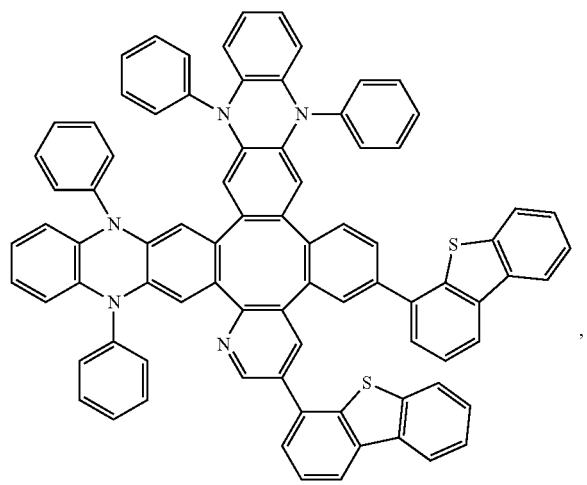
Compound B113
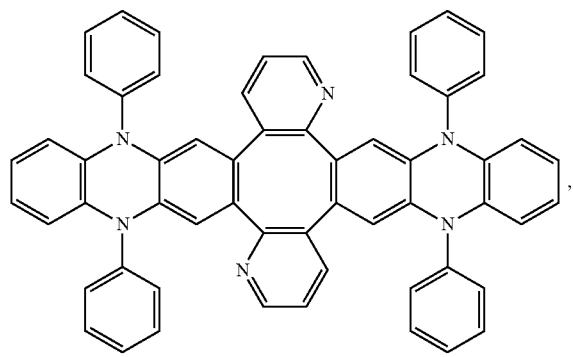
Compound CC100
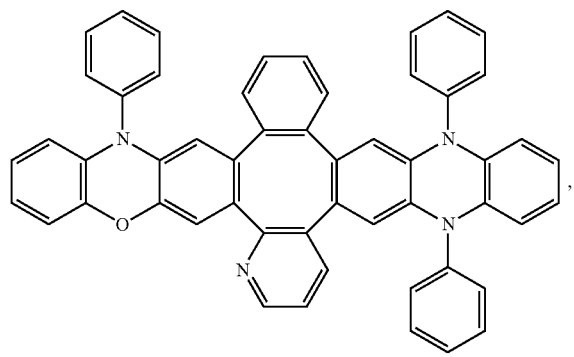

-continued
Compound CC101
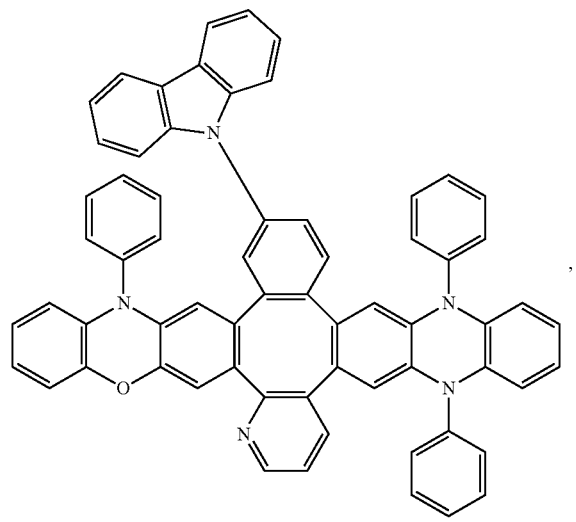
Compound CC102
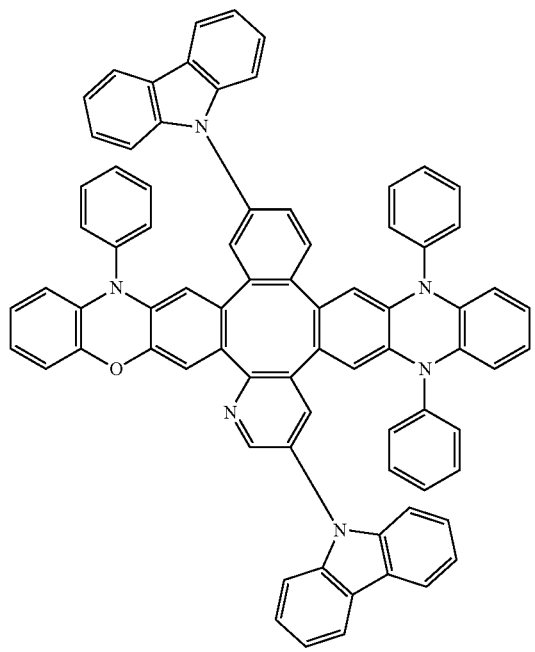
Compound CC103
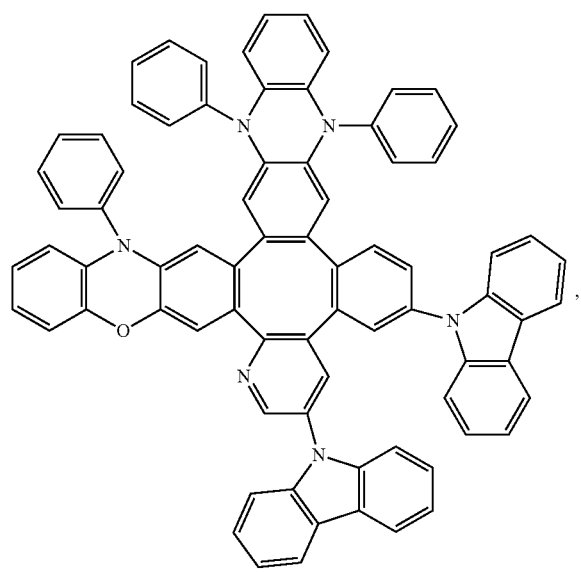
Compound CC104
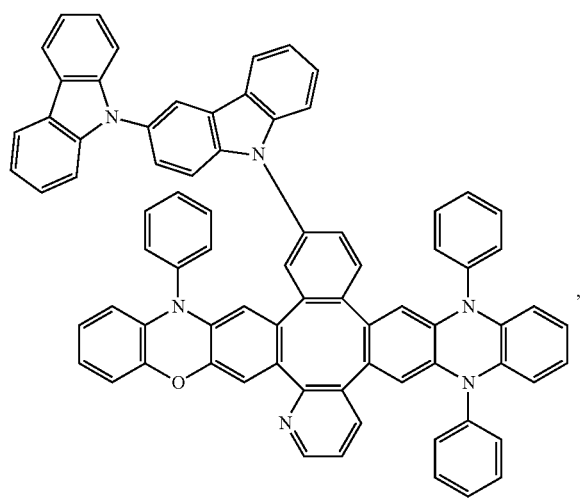

Compound CC105
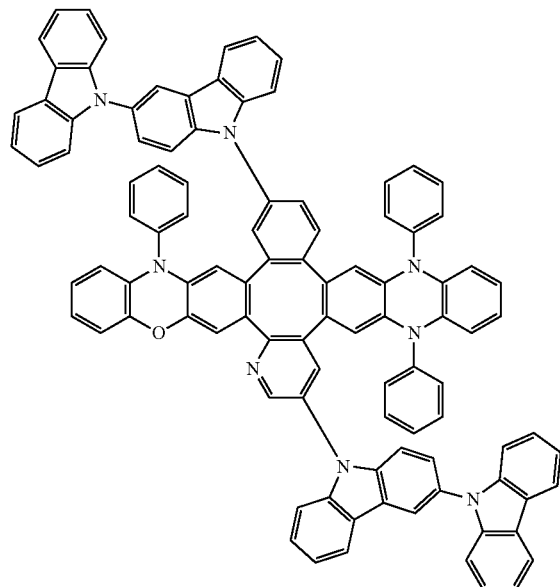
Compound CC106
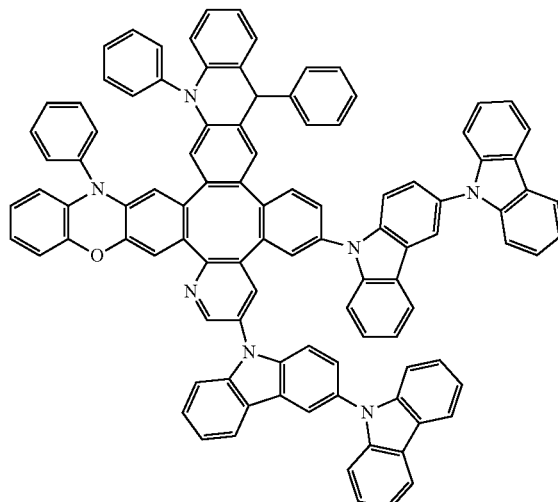
Compound CC107
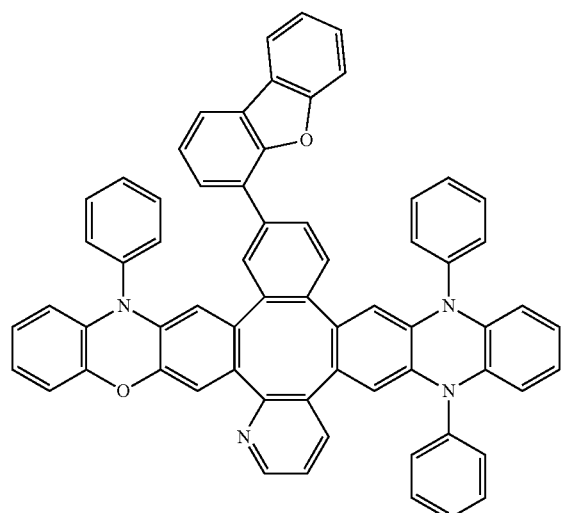
Compound CC108
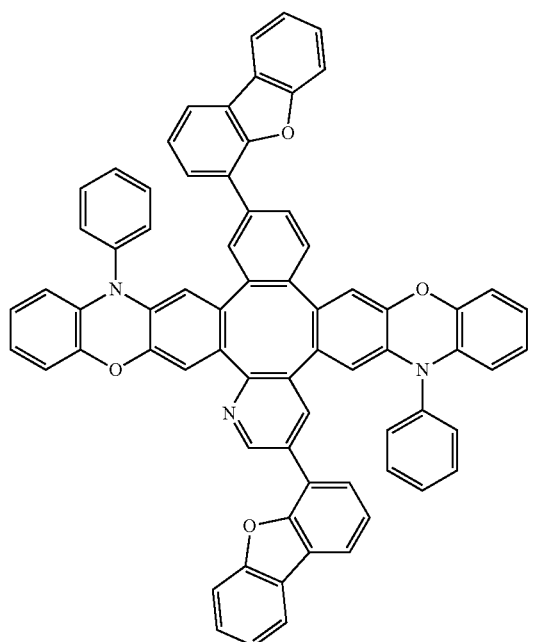

-continued
Compound DD100
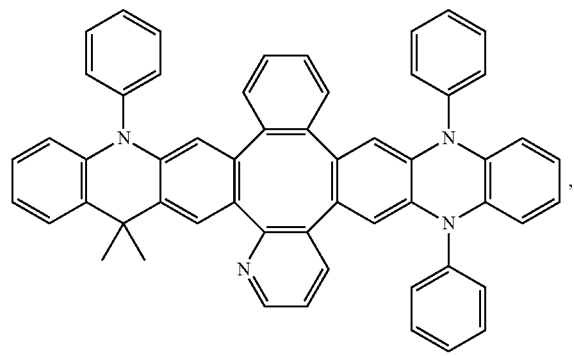
Compound DD101
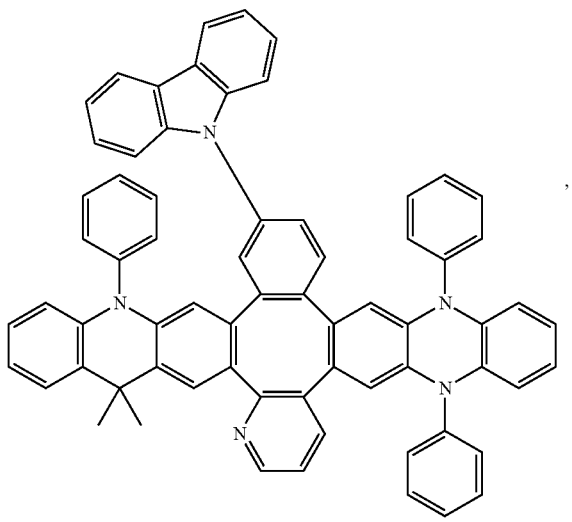
Compound DD102
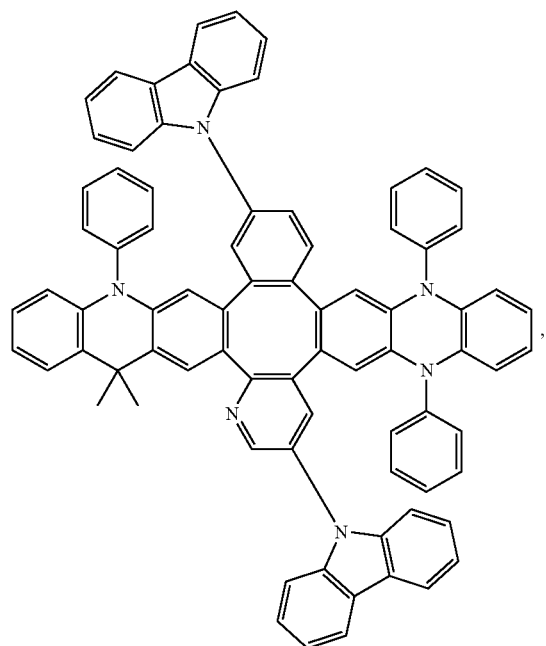
Compound DD103
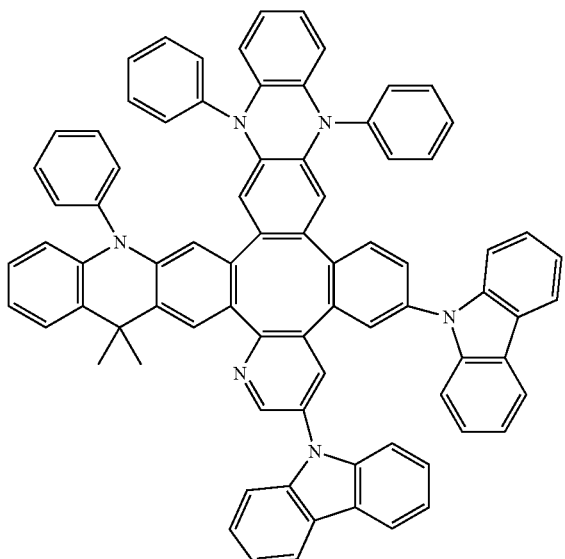

Compound DD104
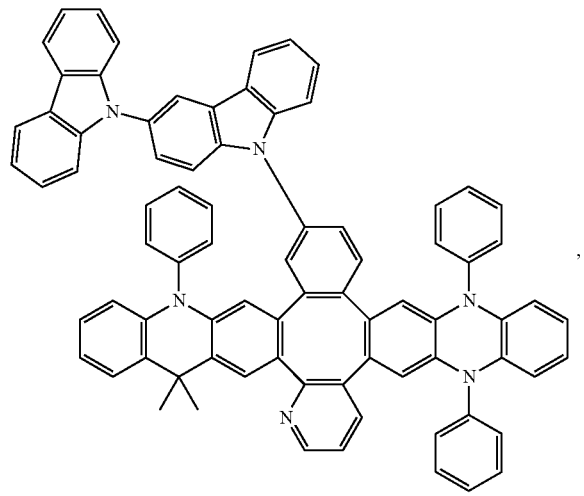
Compound DD105
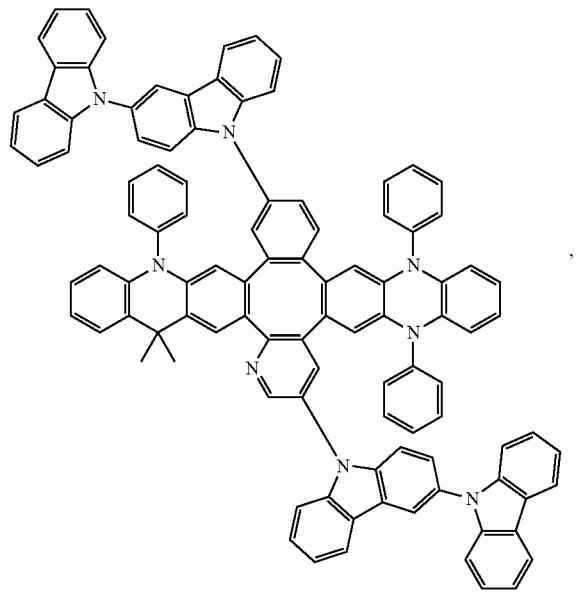
Compound DD106
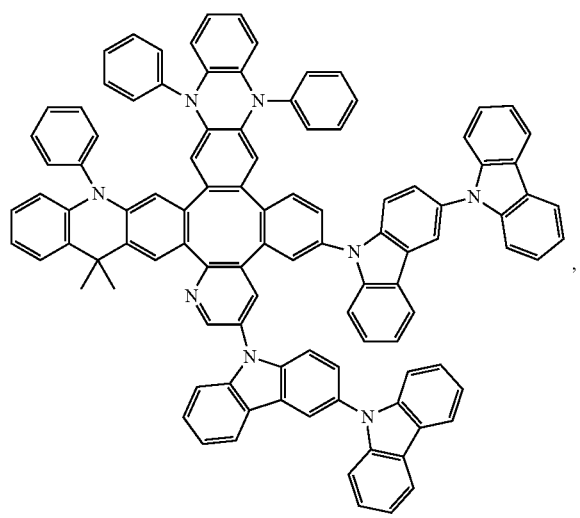
Compound DD107
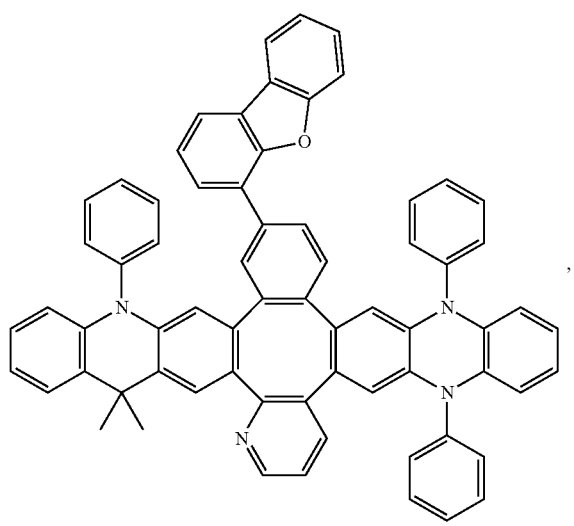

Compound DD108
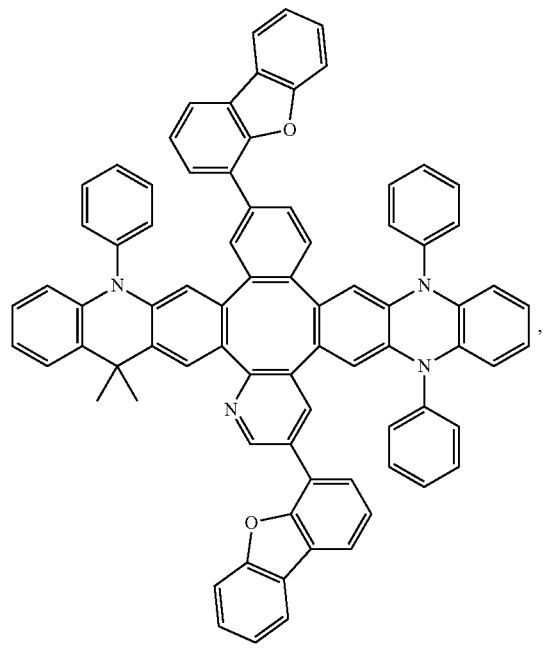
Compound EE100
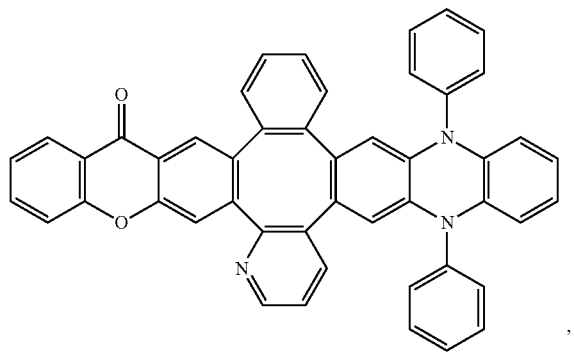
Compound EE101
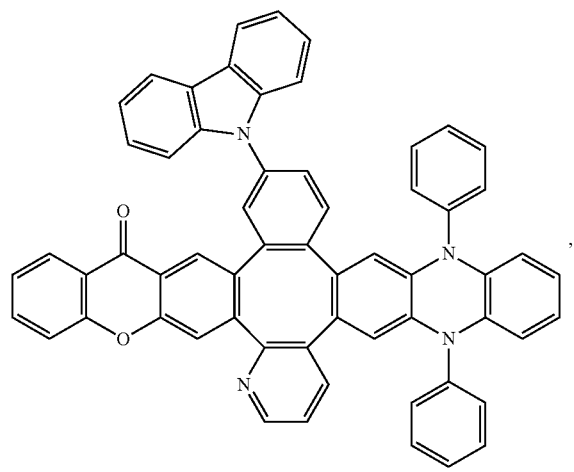
Compound EE102
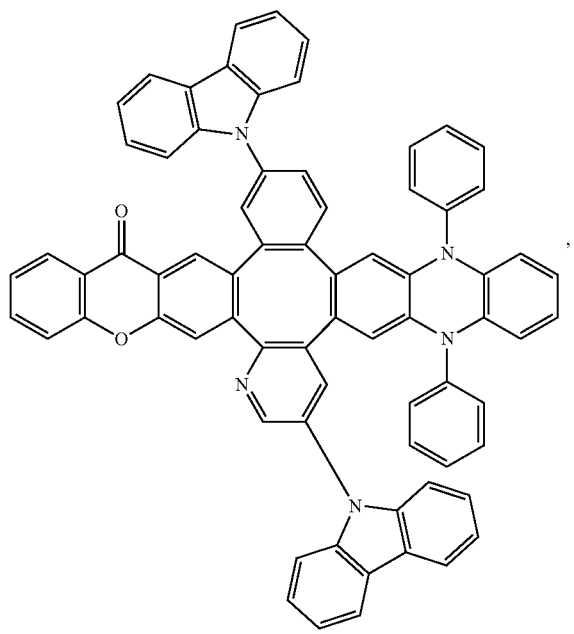

-continued
Compound EE103
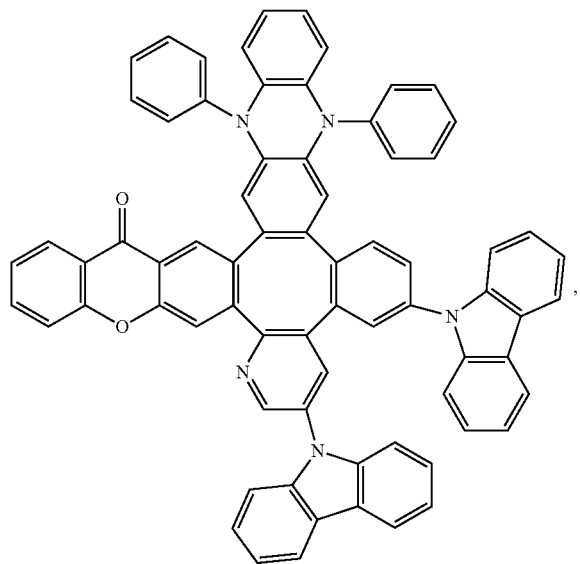
Compound EE104
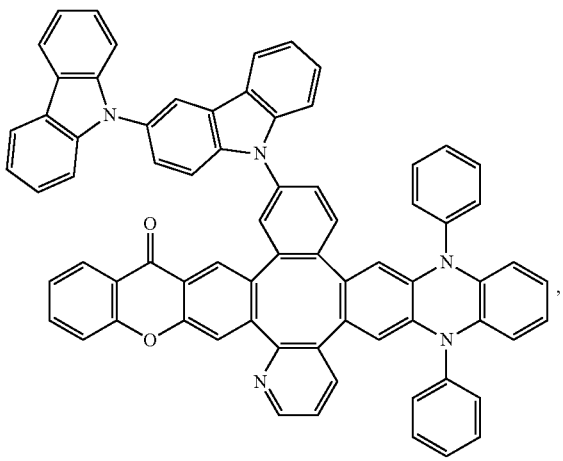
Compound EE105
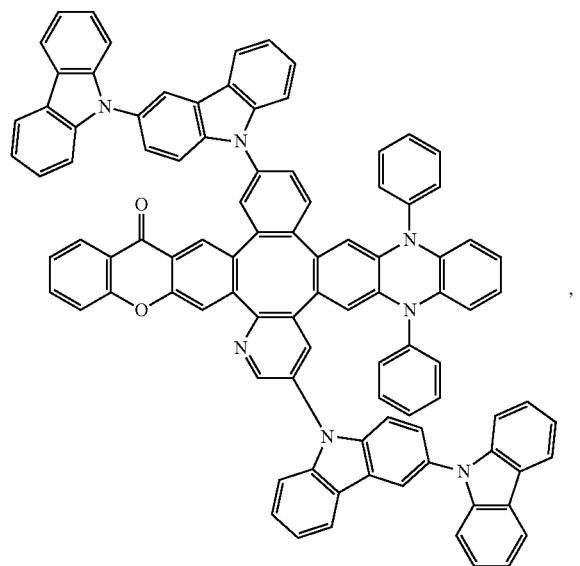
Compound EE106
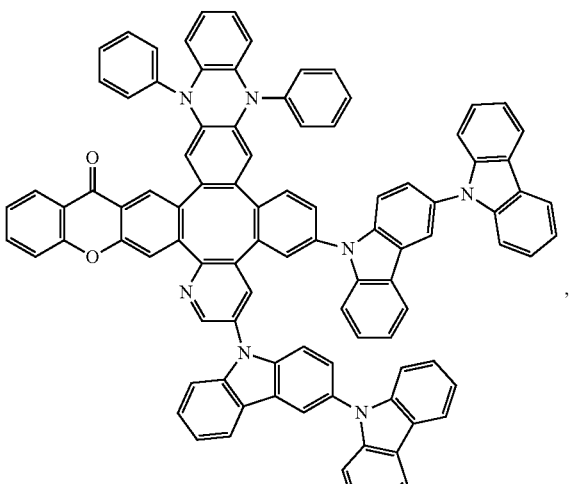

-continued
Compound EE107
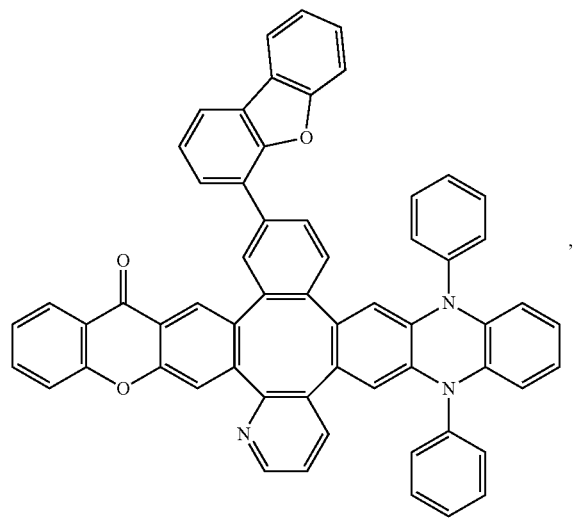
Compound EE108
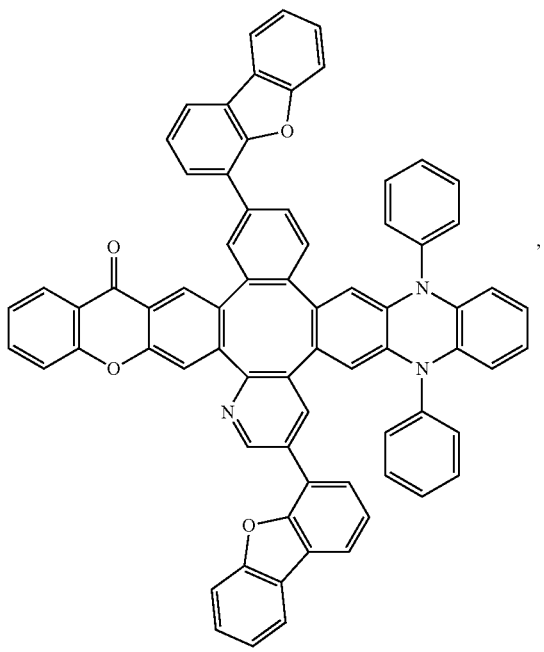
Compound FF100
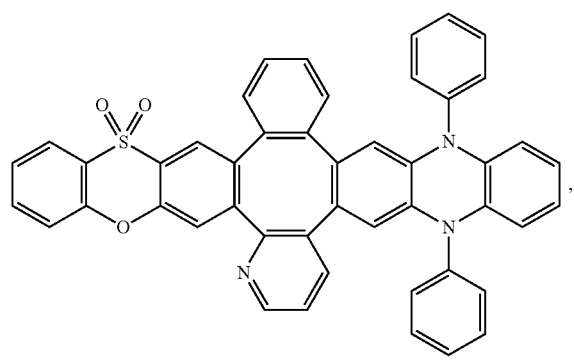
Compound FF101
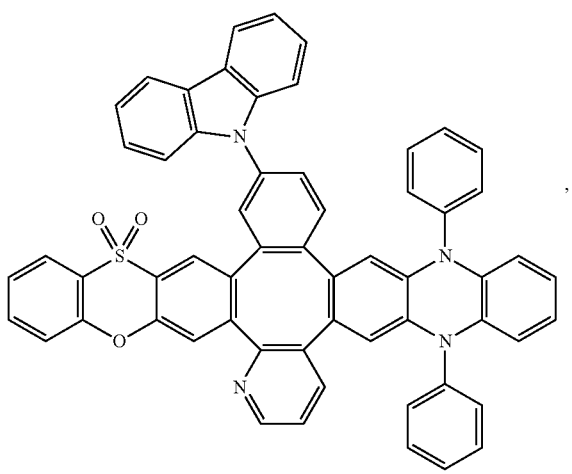

Compound FF102
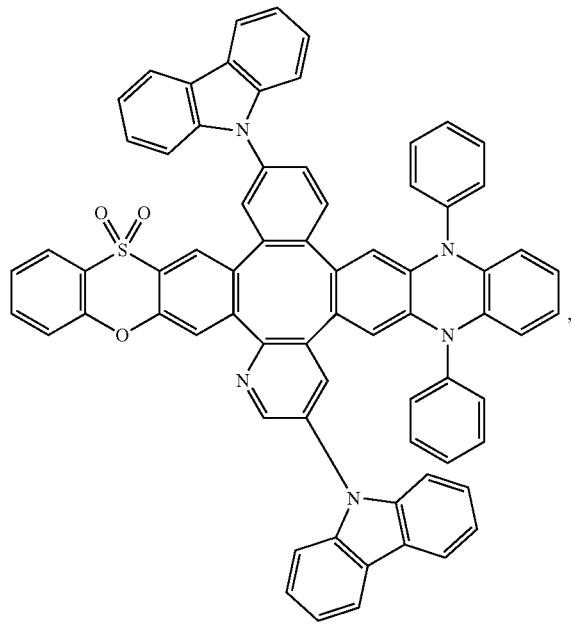
Compound FF103
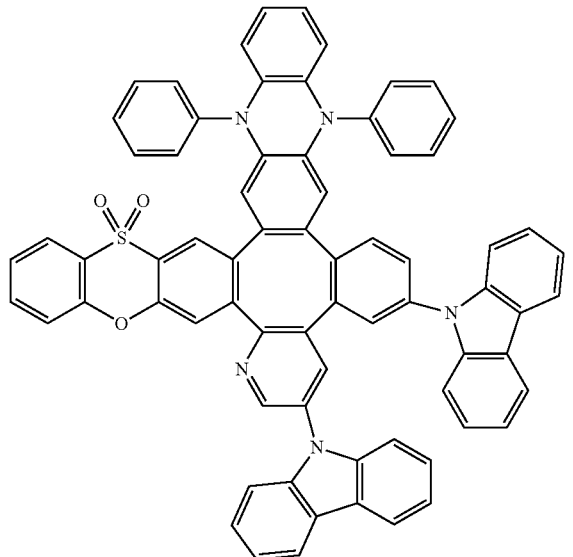
Compound FF104
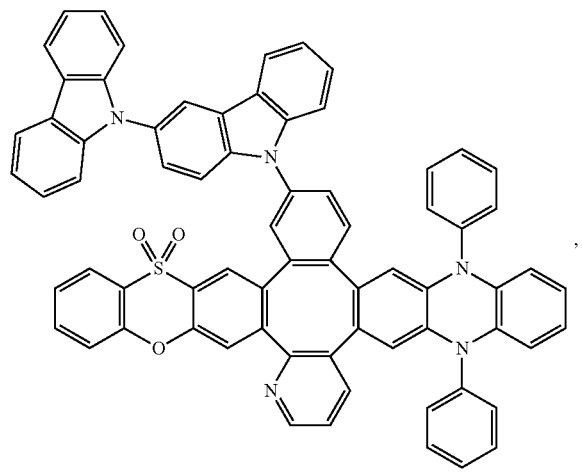
Compound FF105
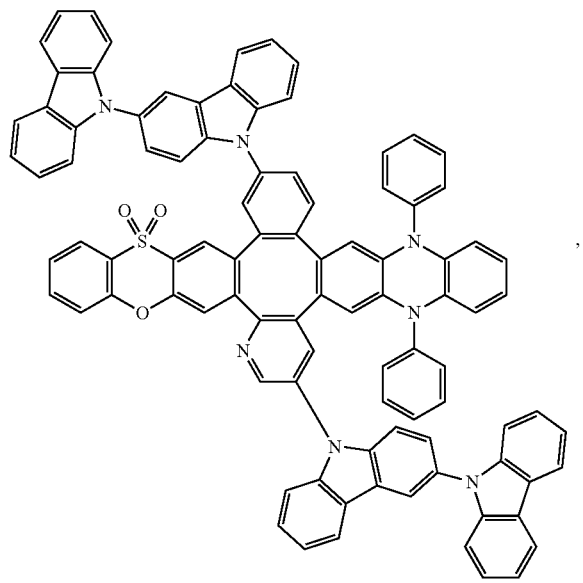

-continued
Compound FF106
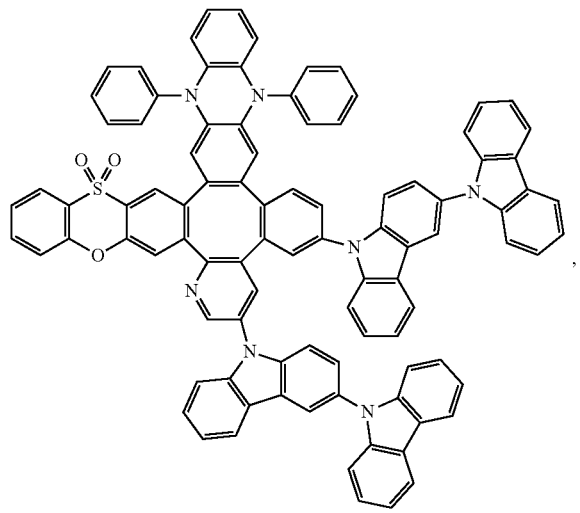
Compound FF107
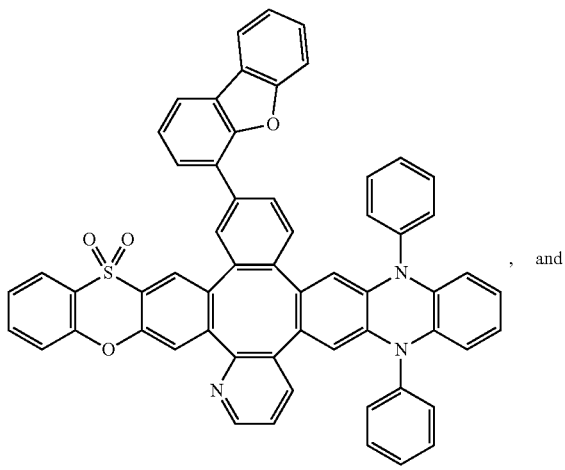
, and
Compound FF108
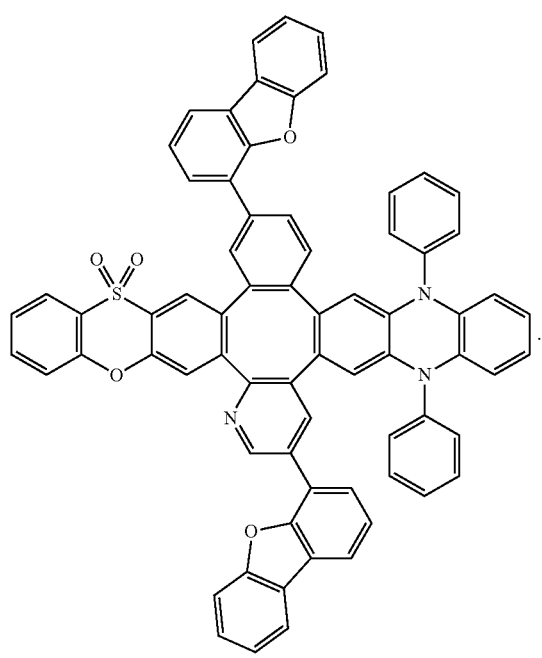
.

In one embodiment, the compound is selected from the group consisting of:
Compound M1
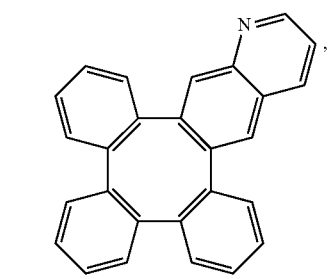
Compound M2
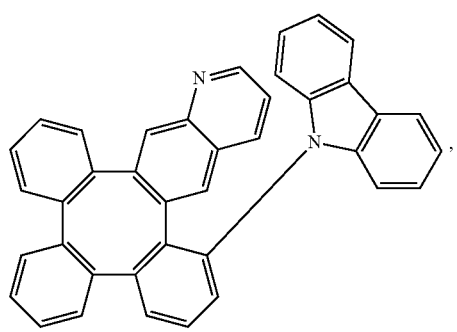
Compound M3
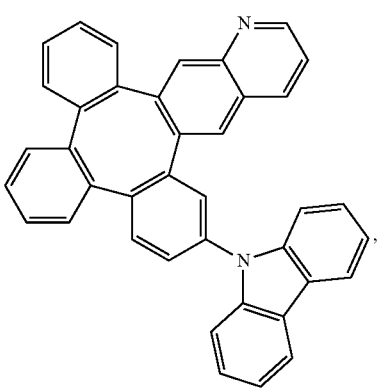
Compound M4
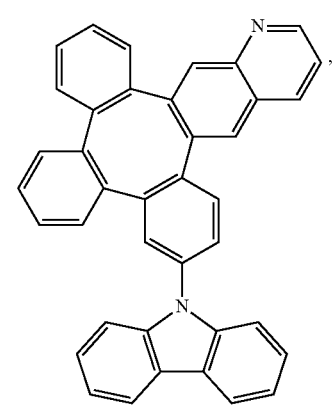
Compound M5
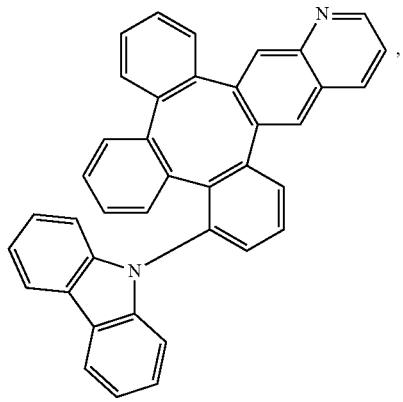
Compound M6
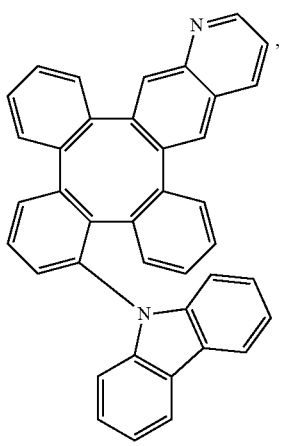
Compound M7
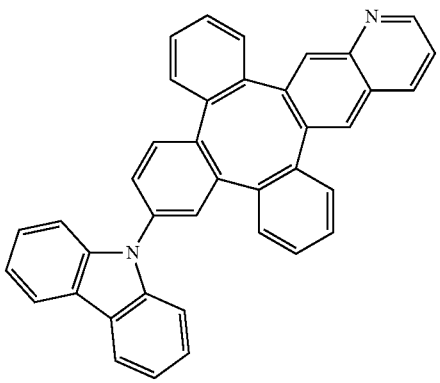
Compound M8
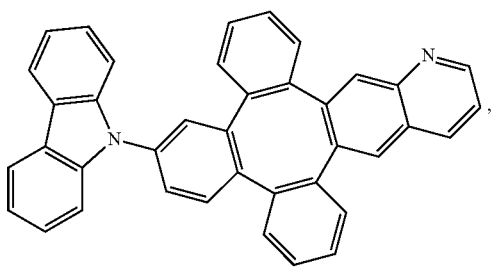

Compound M9
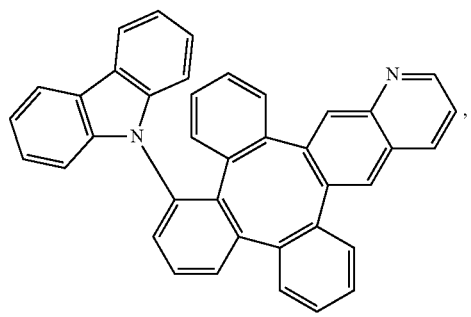
Compound M10
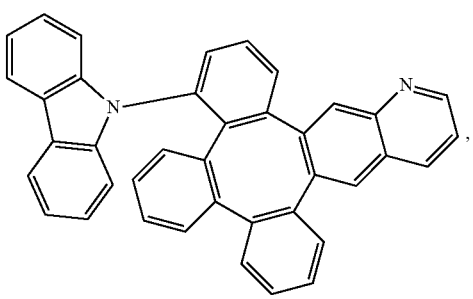
Compound M11
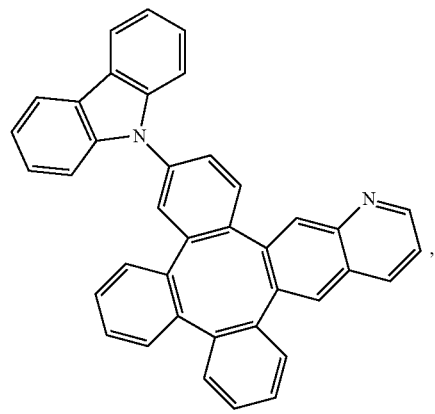
Compound M12
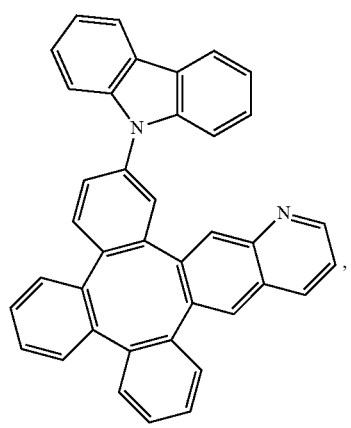
Compound 13
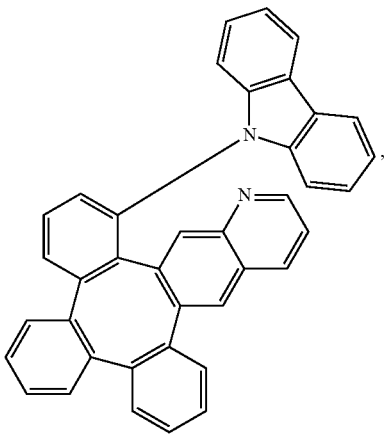
Compound 14
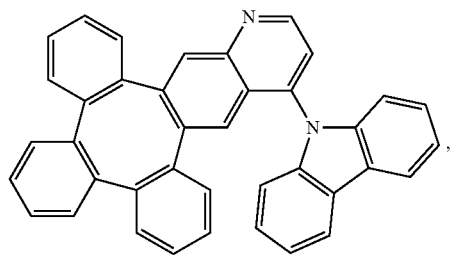
Compound M15
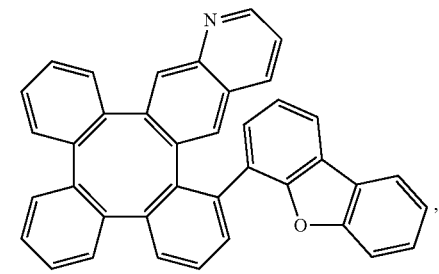
Compound M16
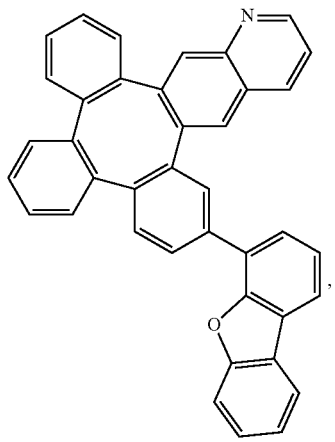

Compound M17

Compound M18

Compound M19

Compound M20

Compound M21

Compound M22

Compound M23

Compound M24

Compound M25
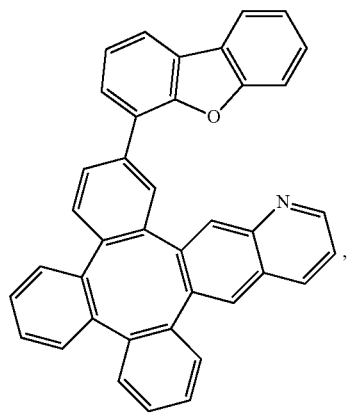
Compound M26
Compound M27
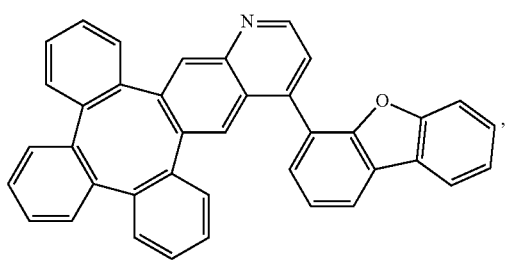
Compound M28
Compound M29
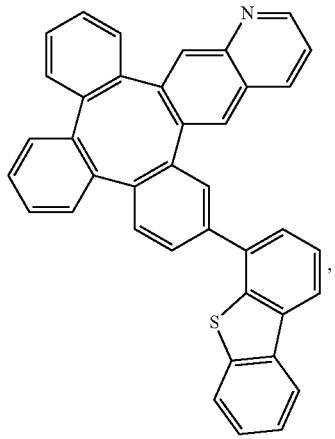
Compound M30
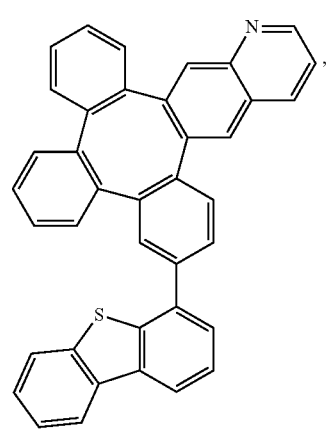
Compound M31
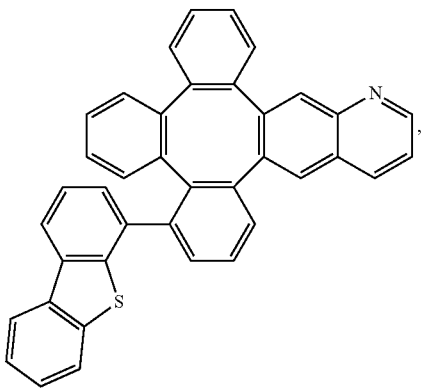

Compound M32
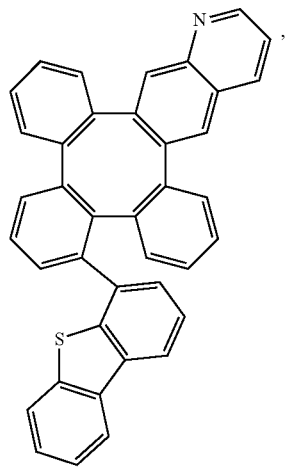
Compound M36
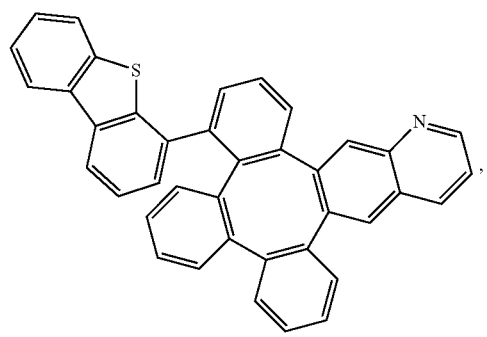
Compound M33
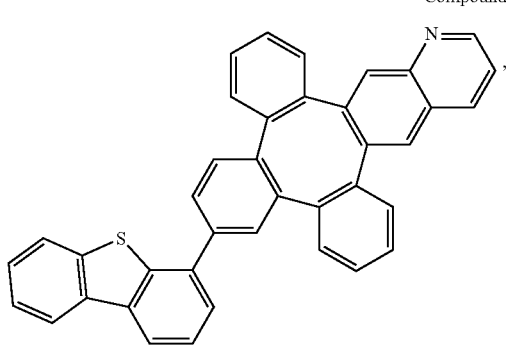
Compound M37
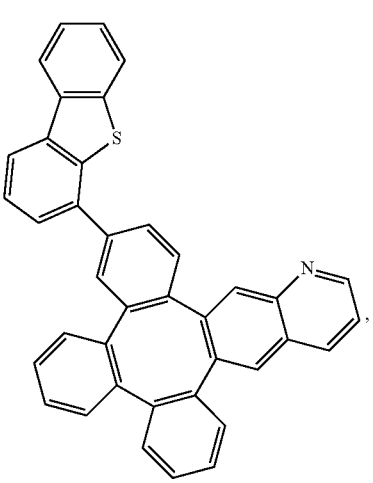
Compound M34
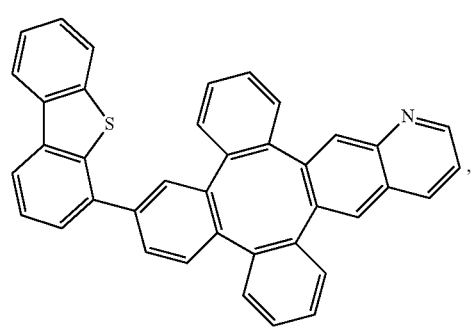
Compound M35
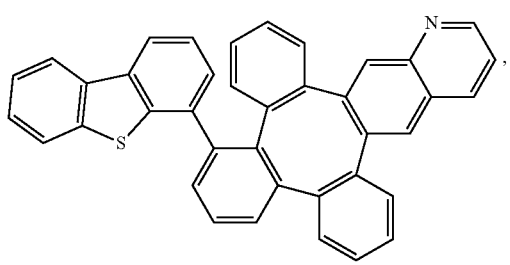
Compound M38
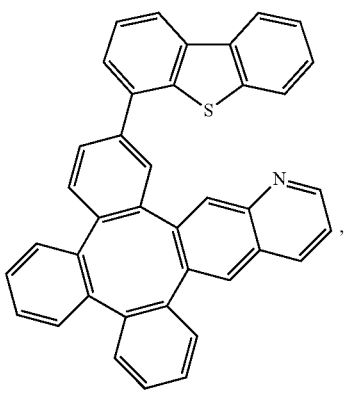

Compound M39
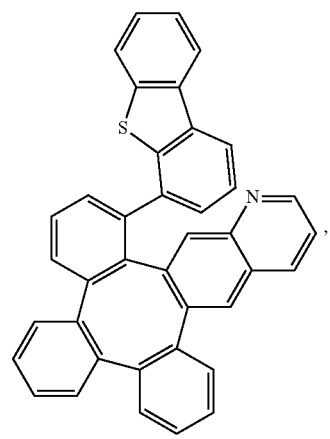
Compound M40
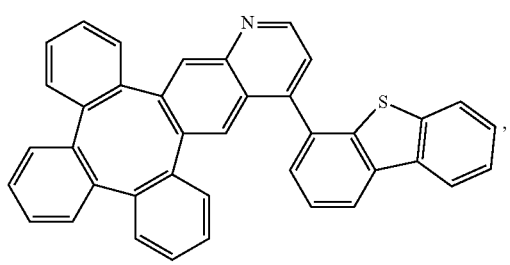
Compound N1
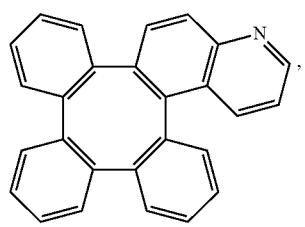
Compound N2
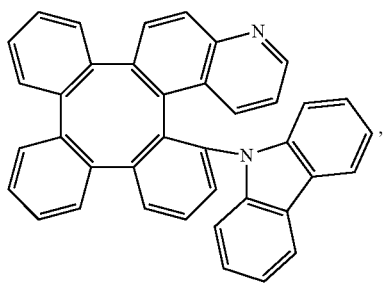
Compound N3
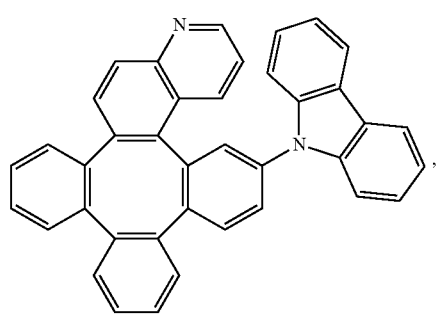
Compound N4
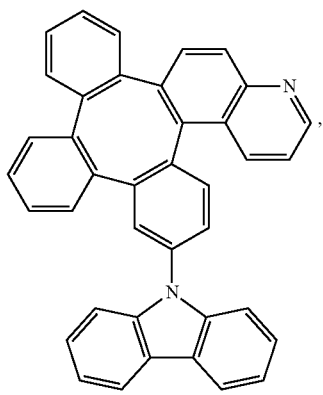
Compound N5
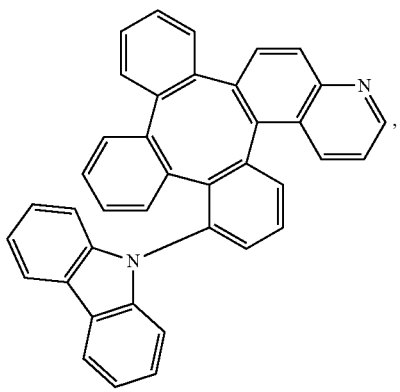
Compound N6
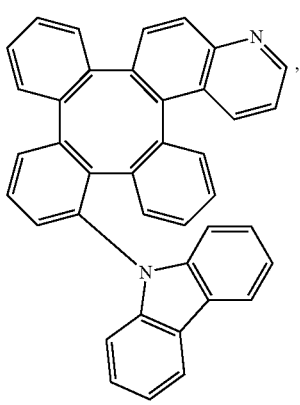

Compound N7
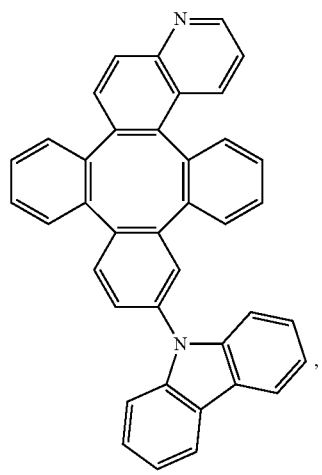
Compound N8
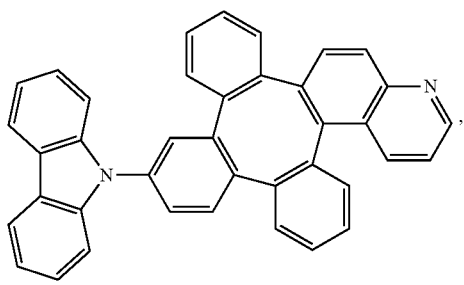
Compound N9
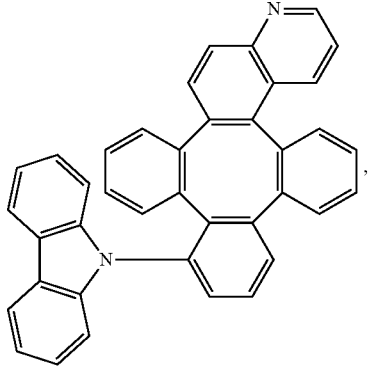
Compound N10
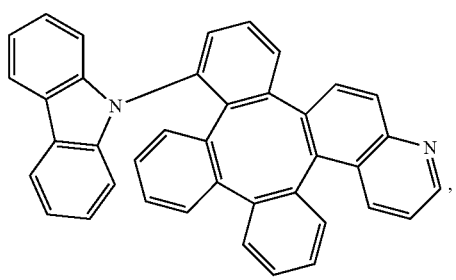
Compound N11
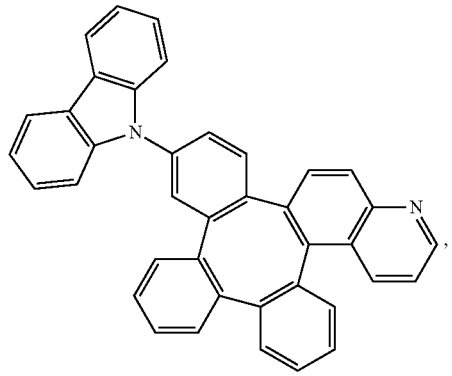
Compound N12
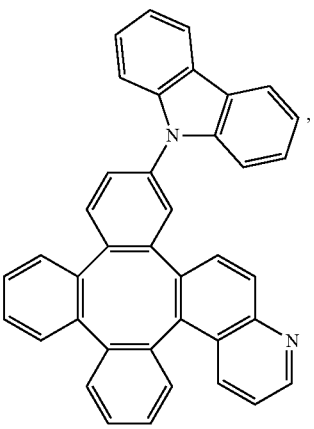
Compound N13
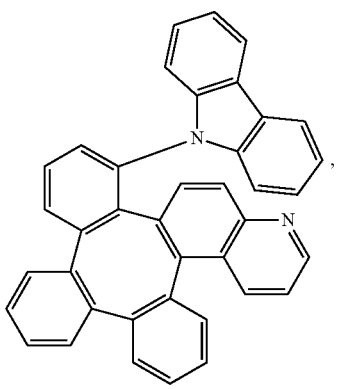
Compound N14
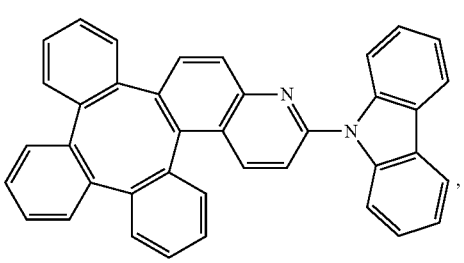

Compound N15
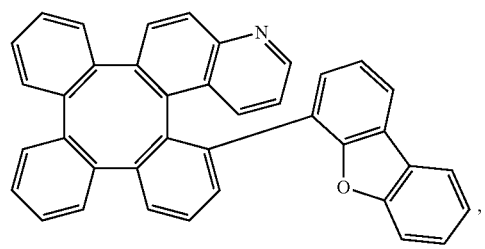
Compound N16
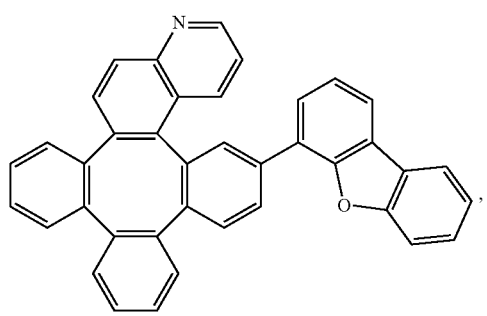
Compound N17
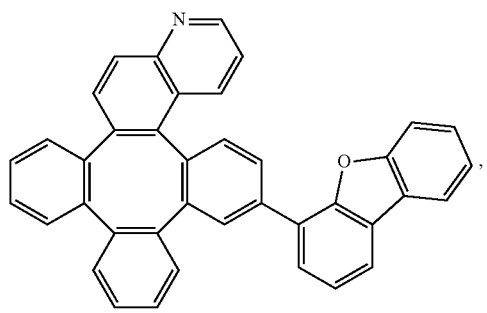
Compound N18
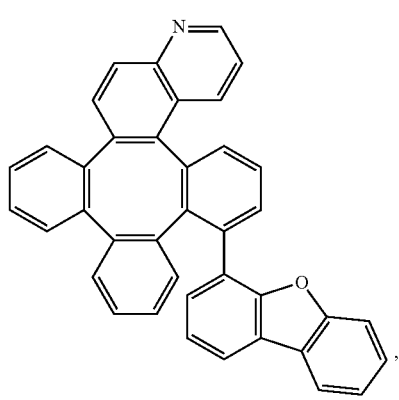
Compound N19
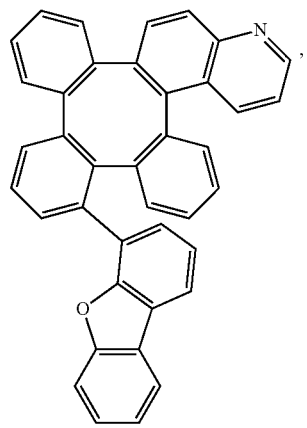
Compound N20
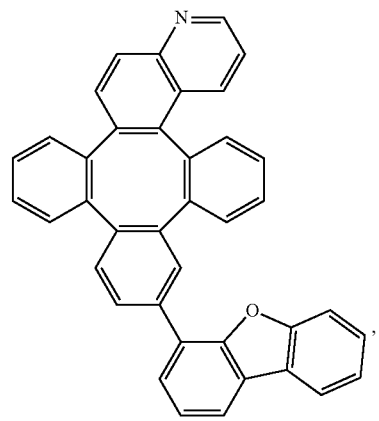
Compound N21
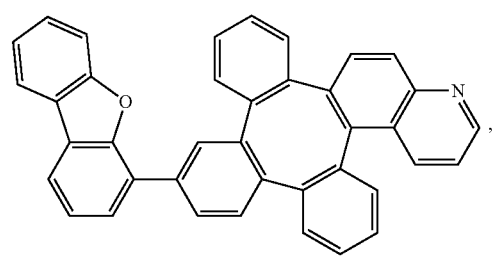
Compound N22
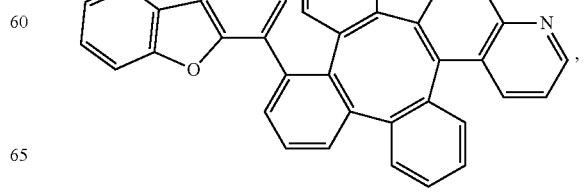

Compound N23
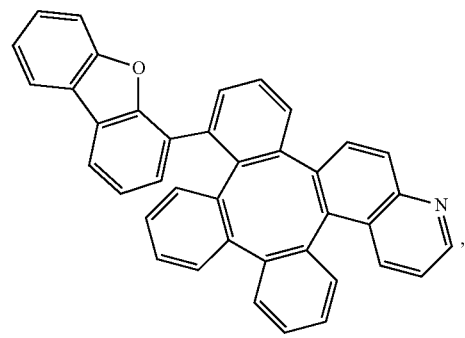
Compound N24
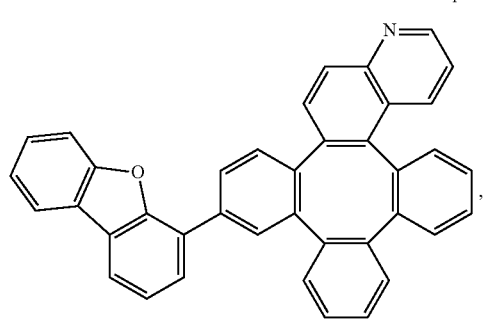
Compound N25
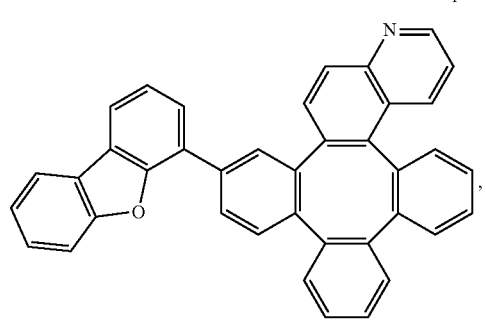
Compound N26
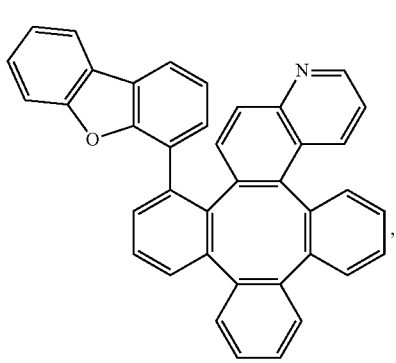
Compound N27
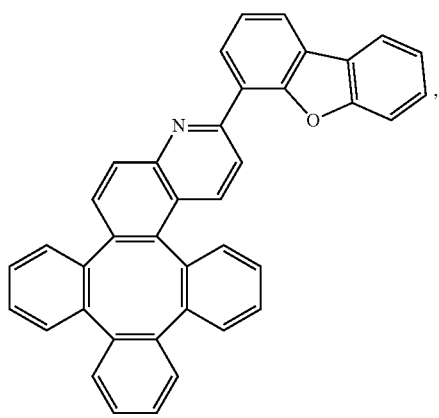
Compound N28
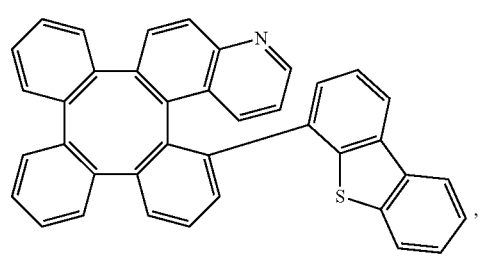
Compound N29
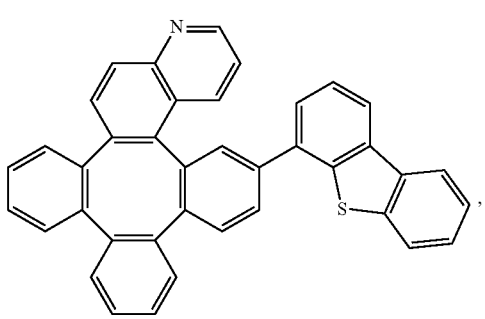
Compound N30
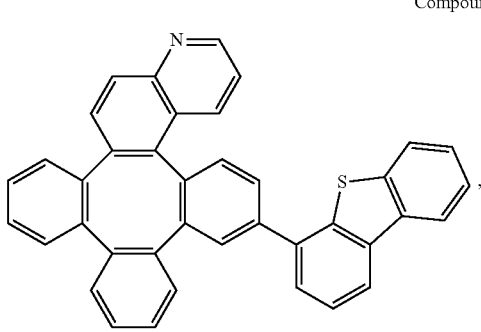

Compound N31
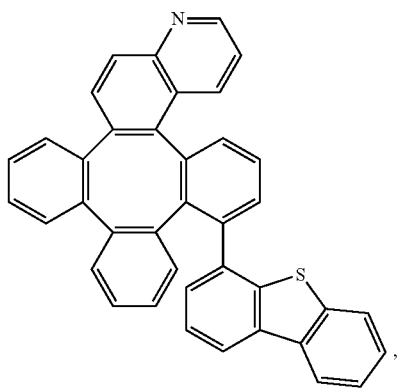
Compound N32
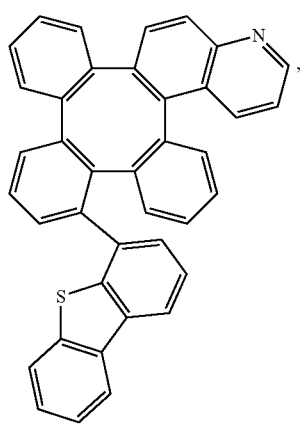
Compound N33
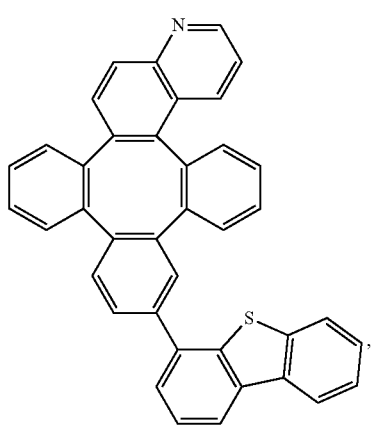
Compound N34
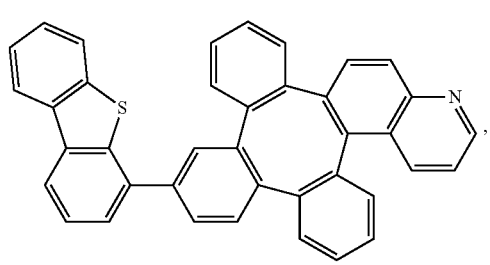
Compound N35
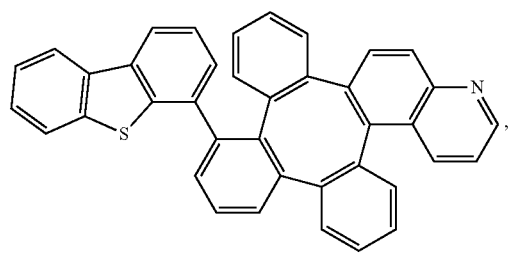
Compound N36
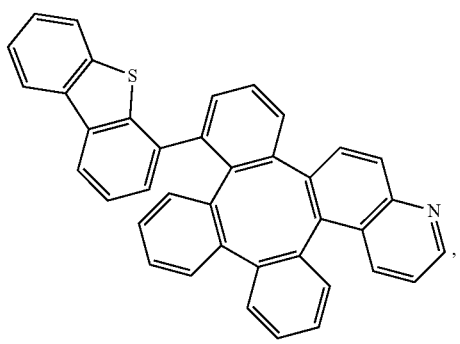
Compound N37
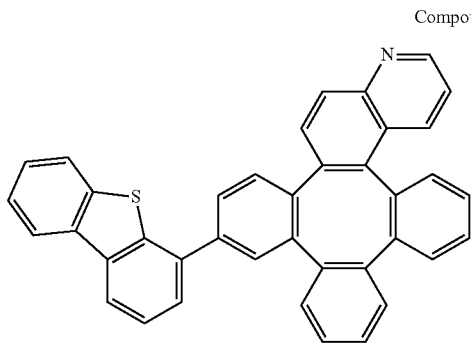
Compound N38
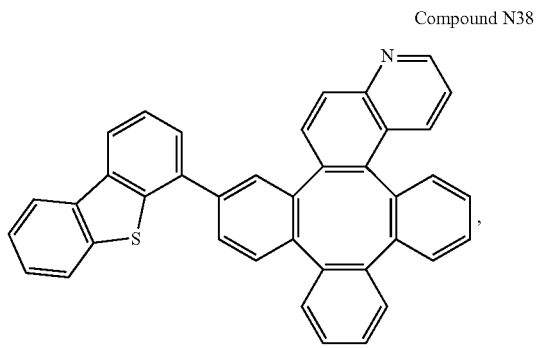

-continued
Compound N39
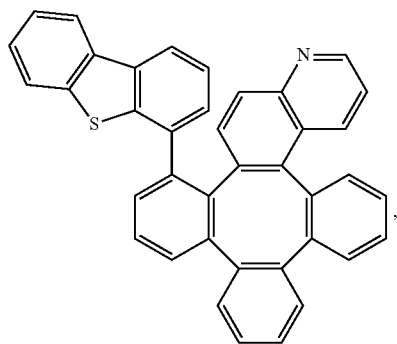
Compound N40
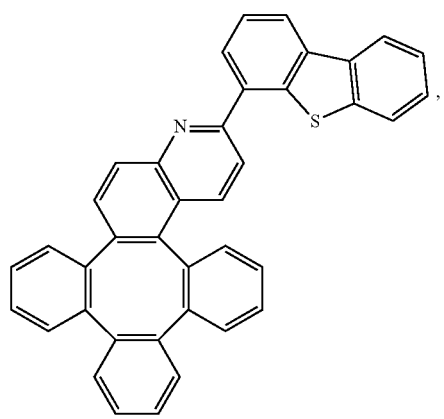
Compound P1
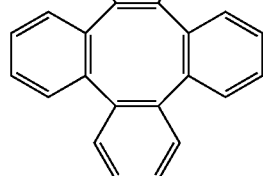
Compound P2
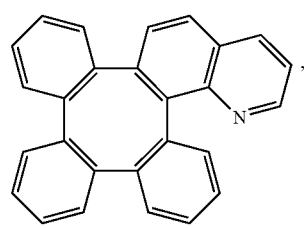
Compound P3
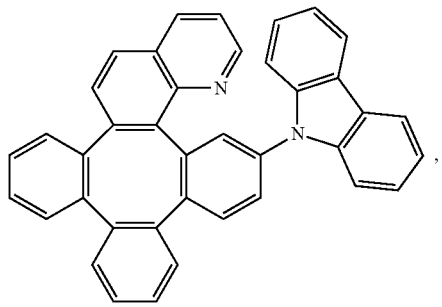
Compound P4
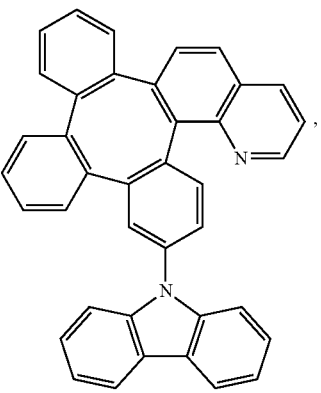
Compound P5
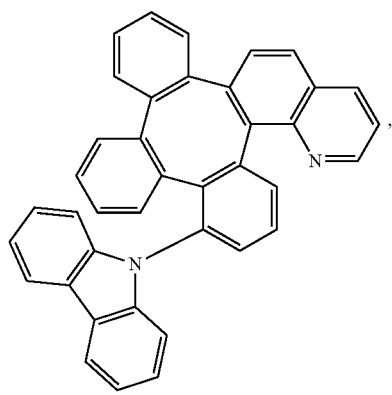
Compound P6
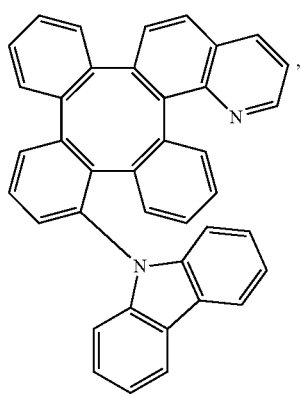
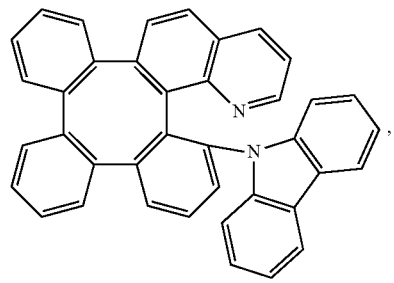

Compound P7
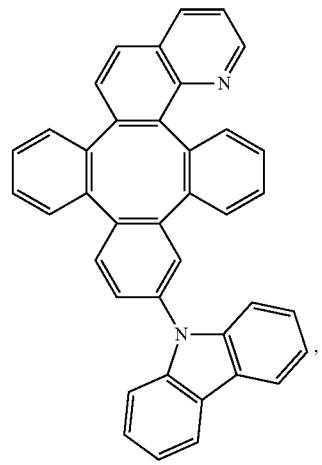
Compound P8
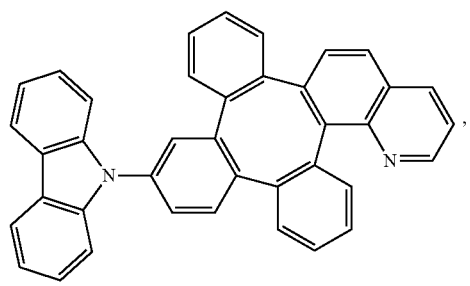
Compound P9
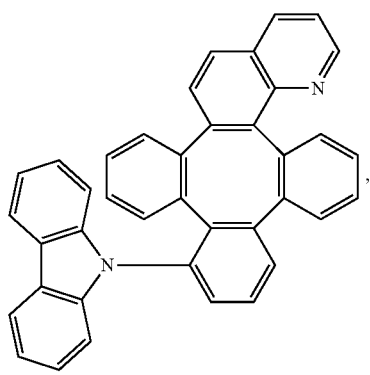
Compound P10
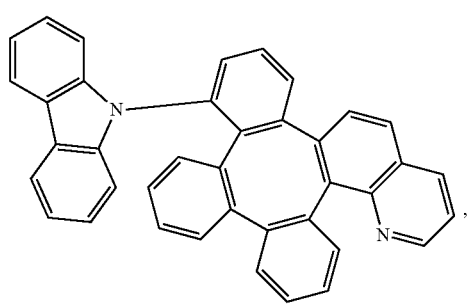
Compound P11
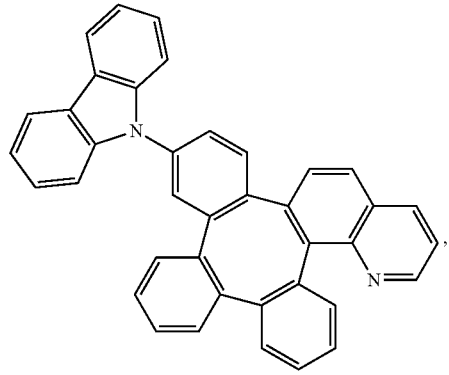
Compound P12
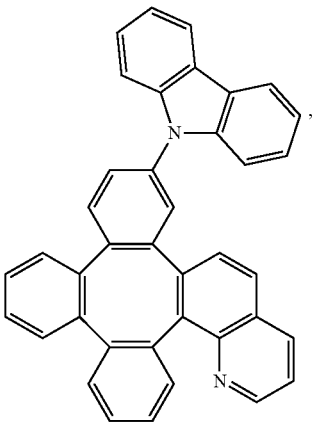
Compound P13
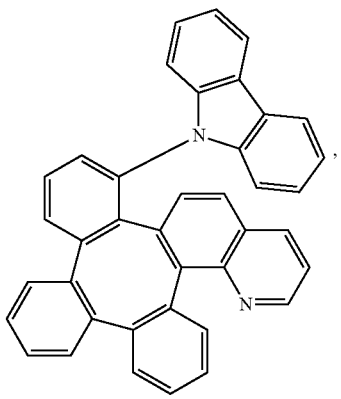
Compound P14

Compound P15
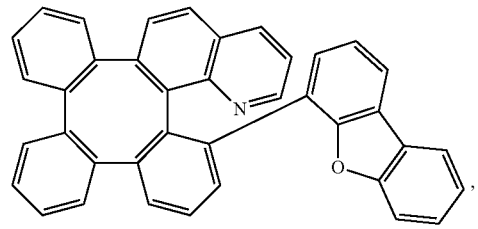
Compound P16
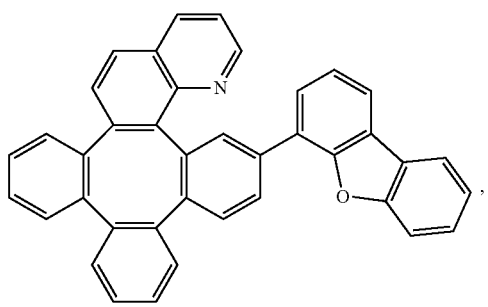
Compound P17
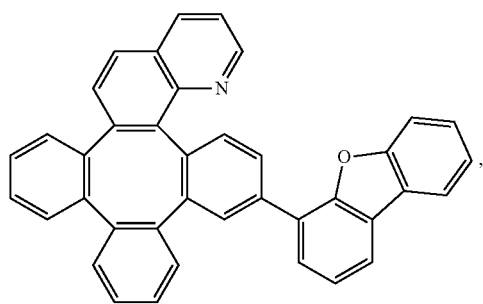
Compound P18
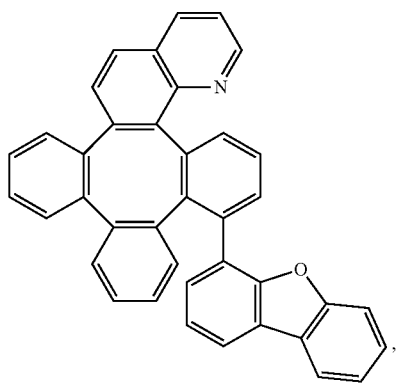
Compound P19
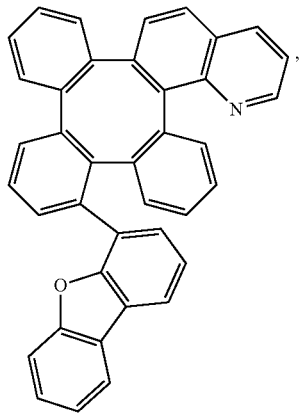
Compound P20
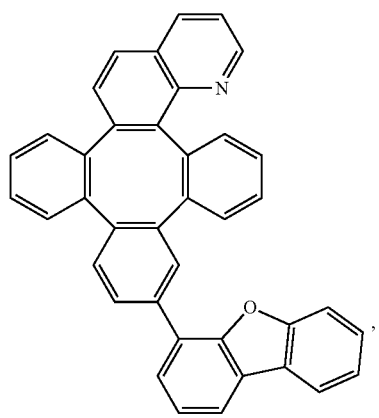
Compound P21
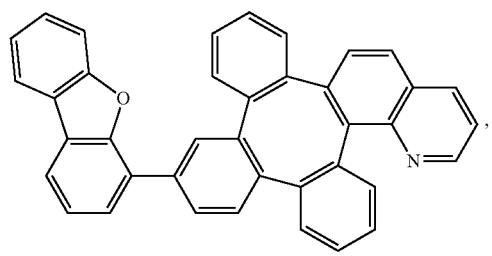
Compound P22
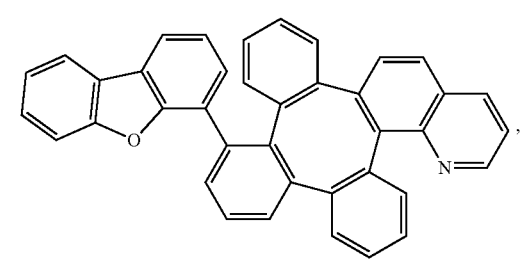

Compound P23
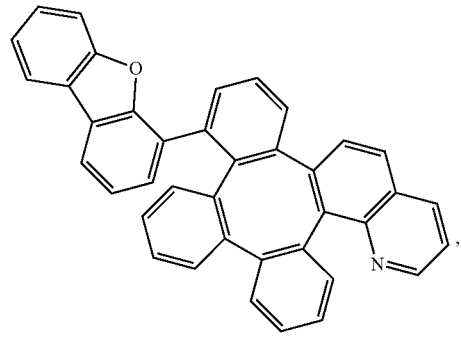
Compound P24
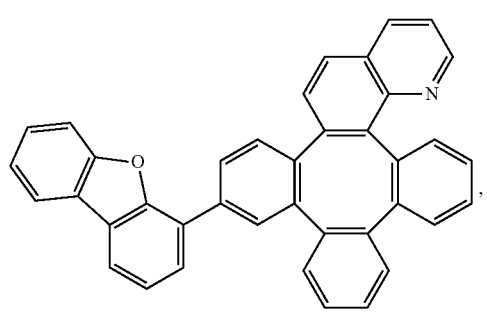
Compound P25
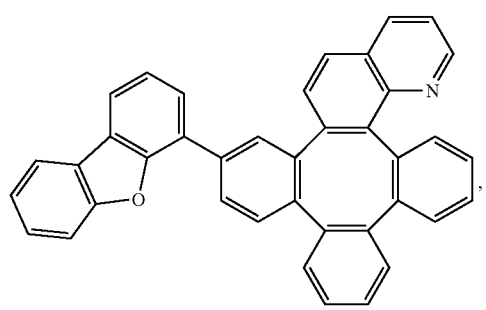
Compound P26
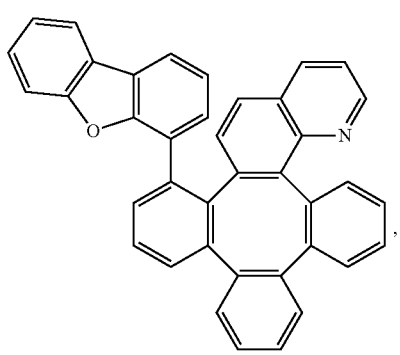
Compound P27
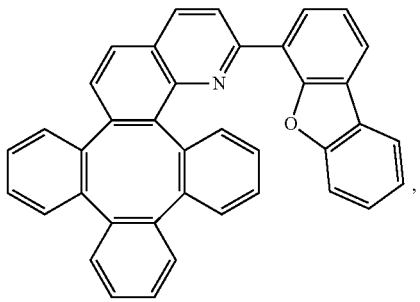
Compound P28
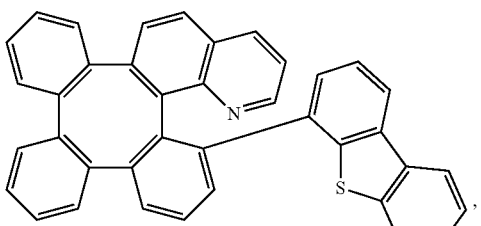
Compound P29
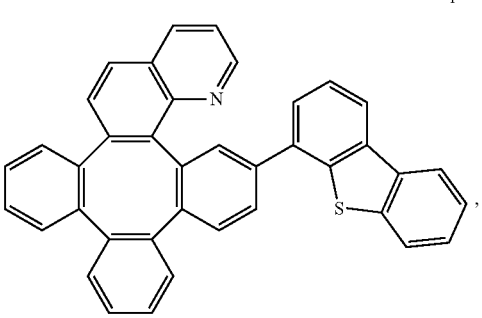
Compound P30
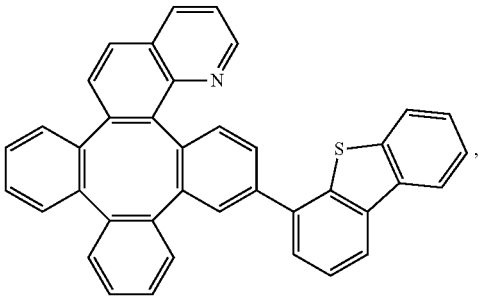
Compound P31

Compound P32
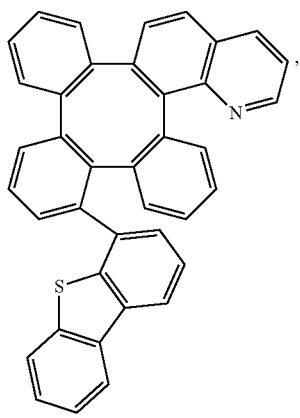
Compound P33
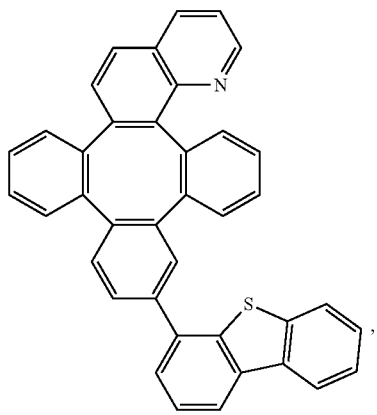
Compound P34
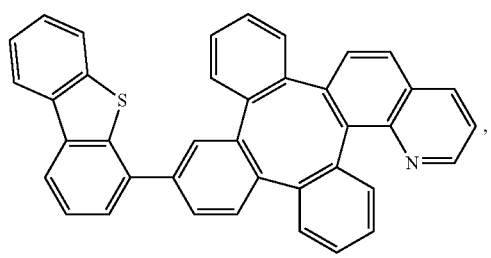
Compound P35
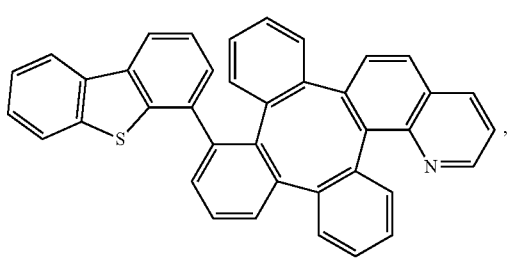
Compound P36
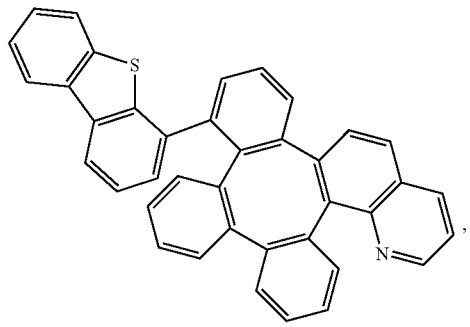
Compound P37
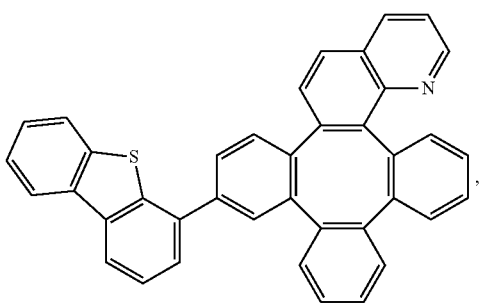
Compound P38
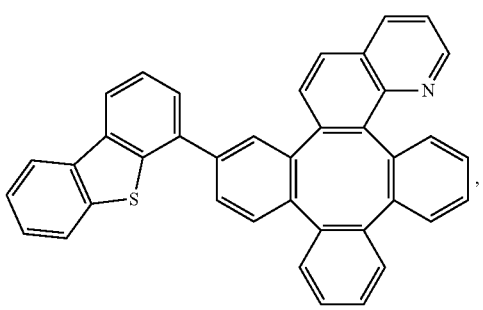
Compound P39
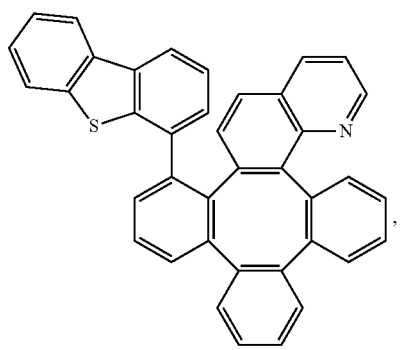

Compound P40
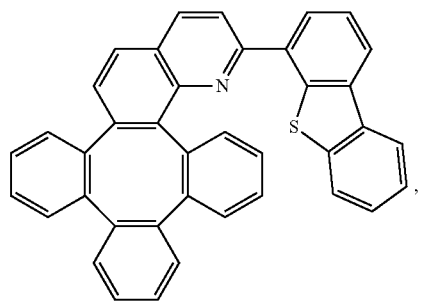
Compound MA1
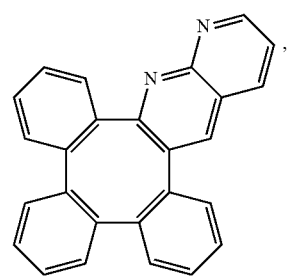
Compound MA2
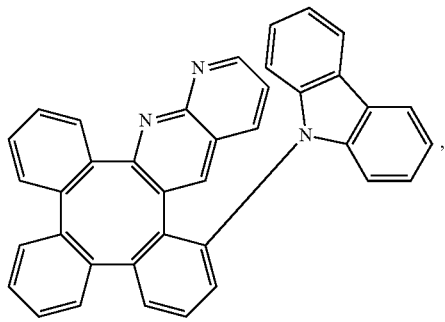
Compound MA3
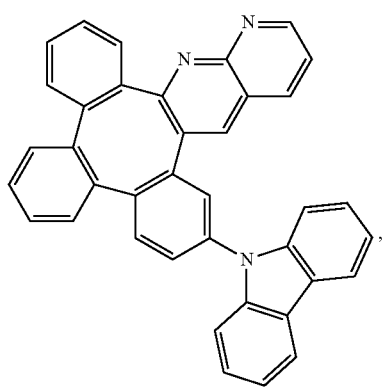
Compound MA4
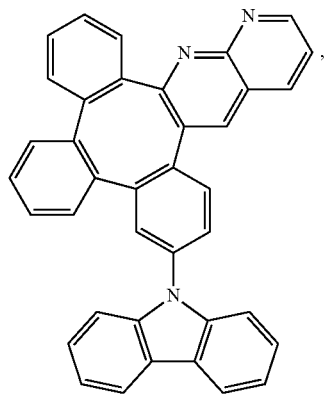
Compound MA5
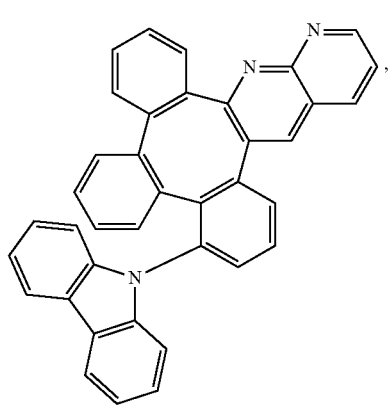
Compound MA6
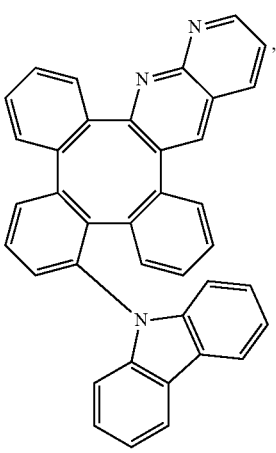
Compound MA7
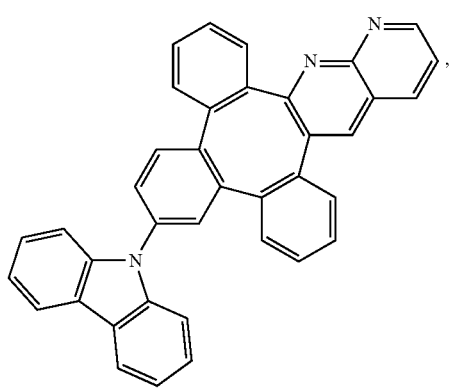

Compound MA8
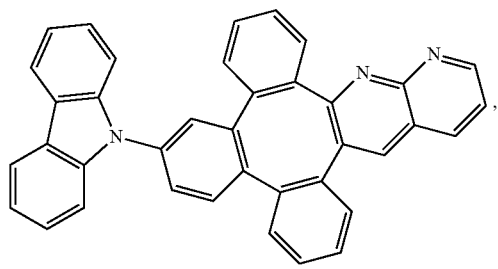
Compound MA9
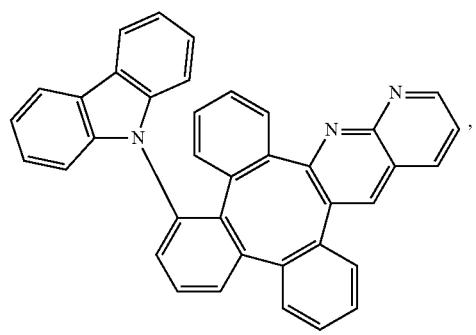
Compound MA10
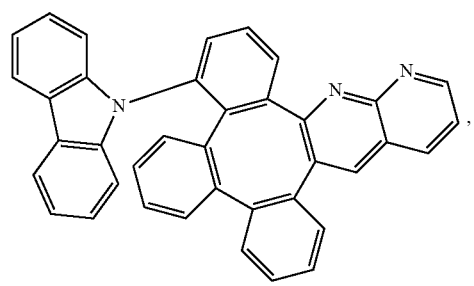
Compound MA11
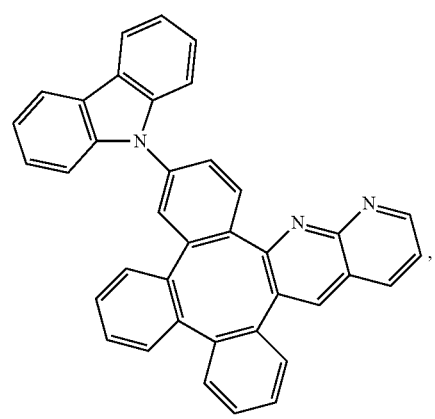
Compound MA12
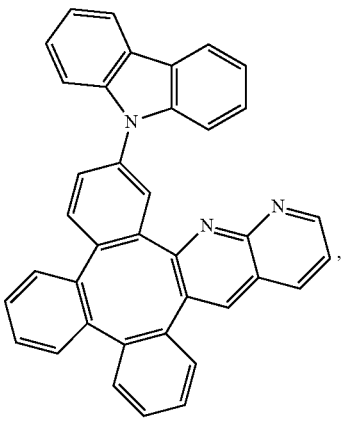
Compound MA13
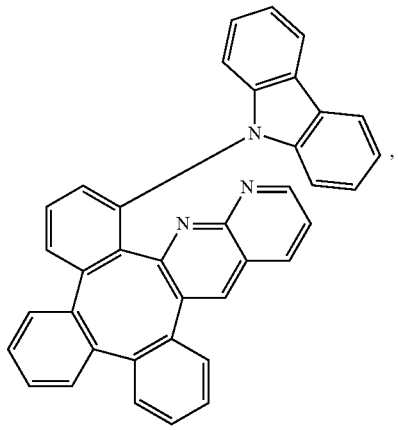
Compound MA14
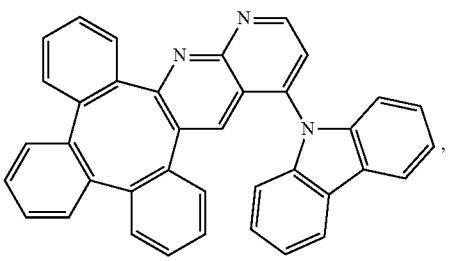
Compound MA15
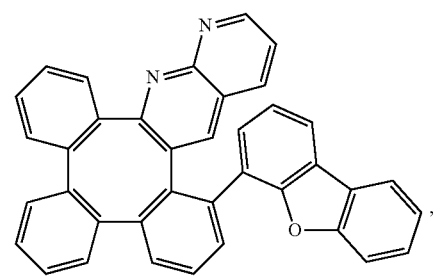

Compound MA16
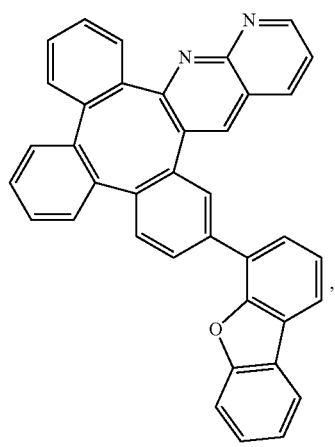
Compound MA17
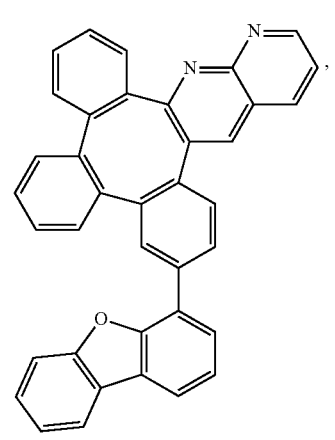
Compound MA18
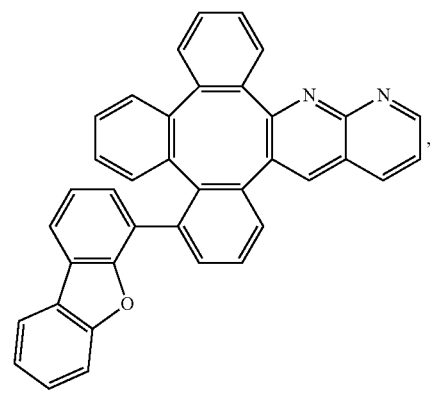
Compound MA19
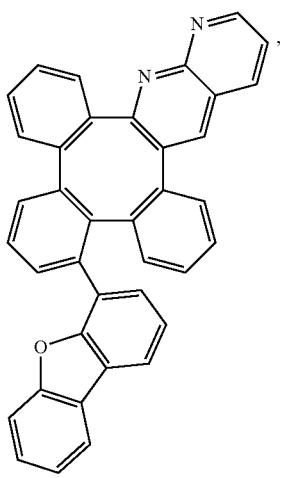
Compound MA20
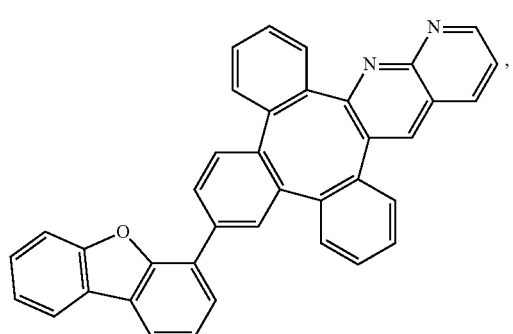
Compound MA21
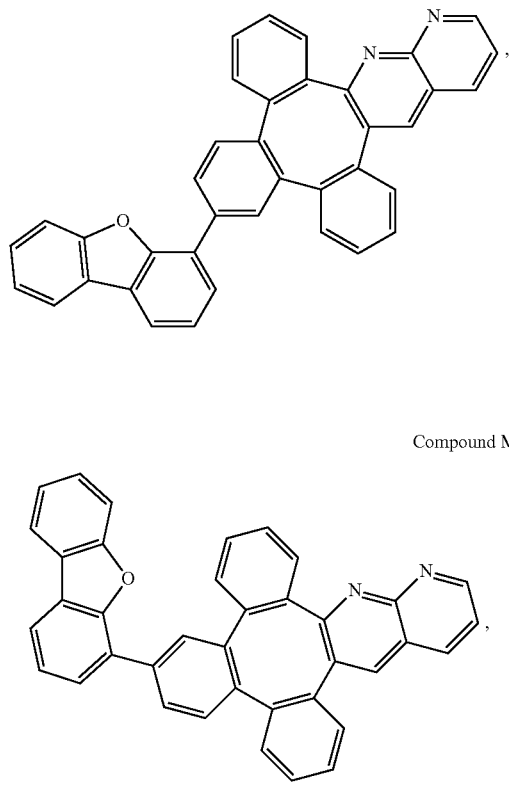
Compound MA22
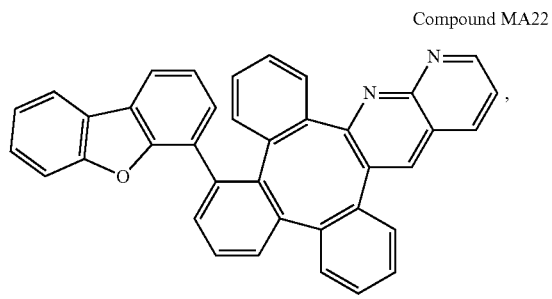

Compound MA23
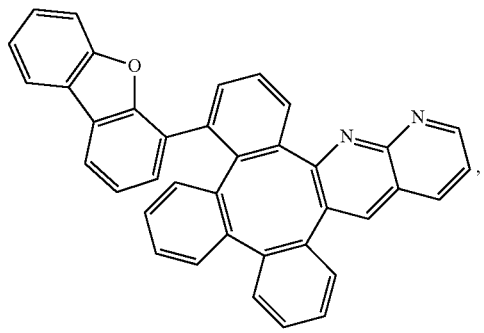
Compound MA24
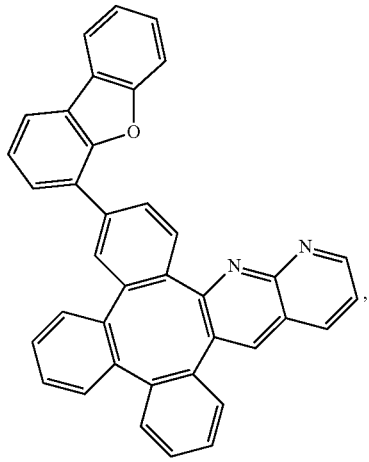
Compound MA25
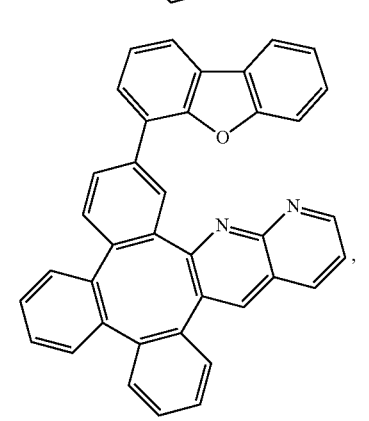
Compound MA26
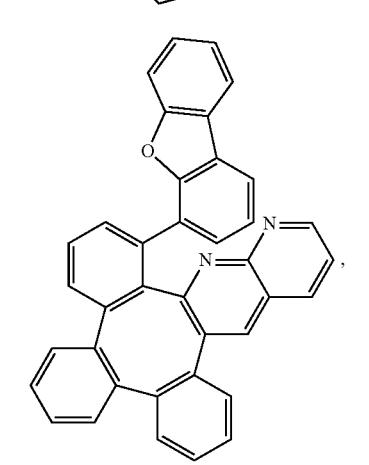
Compound MA27
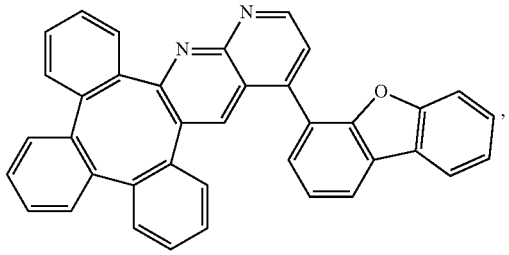
Compound MA28
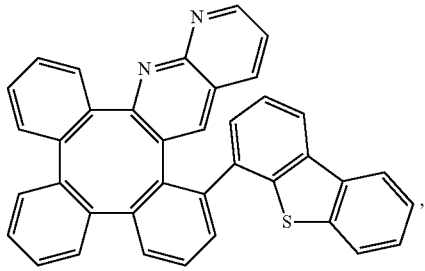
Compound MA29
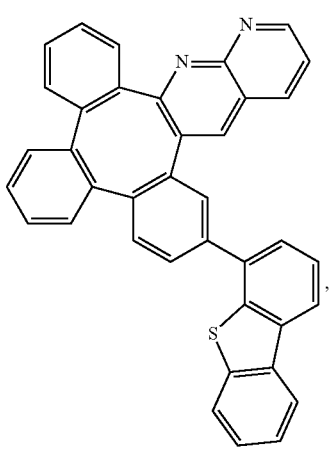
Compound MA30
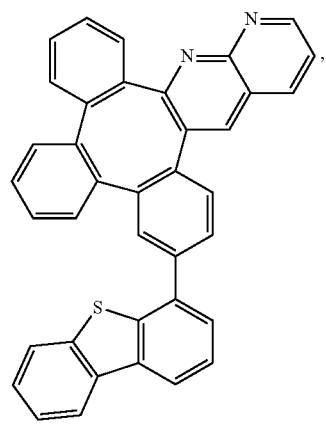

Compound MA31
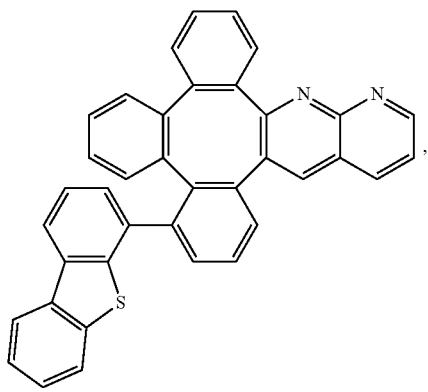
Compound MA32
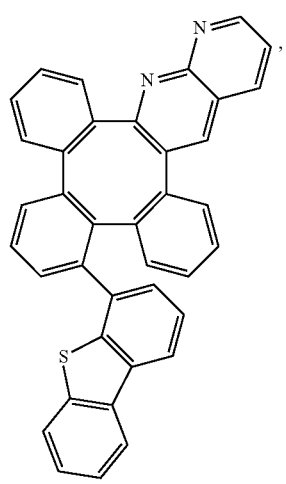
Compound MA33
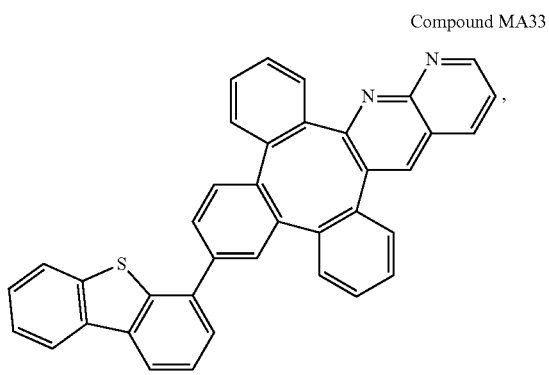
Compound MA34
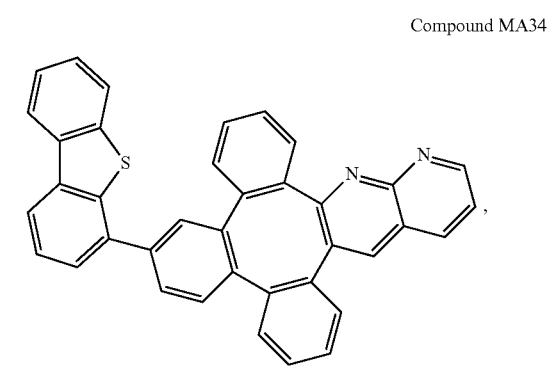
Compound MA35
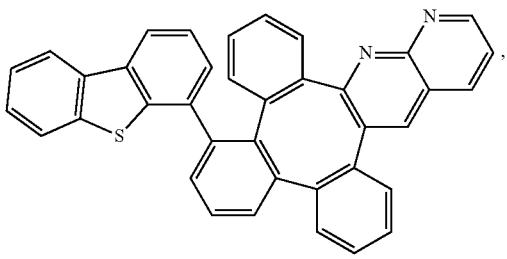
Compound MA36
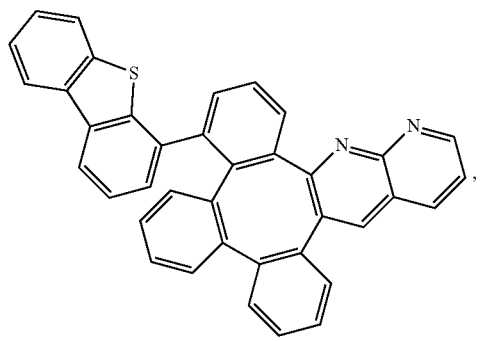
Compound MA37
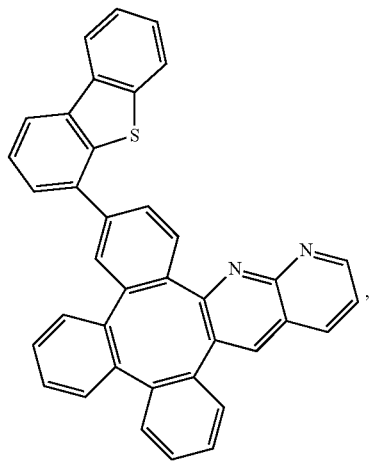
Compound MA38
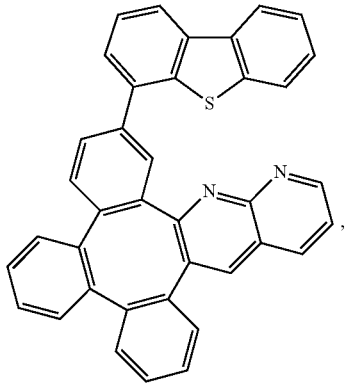

-continued
Compound MA39
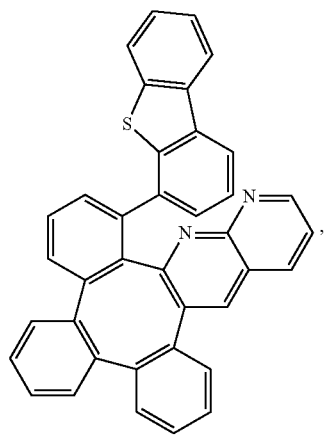
Compound MA40
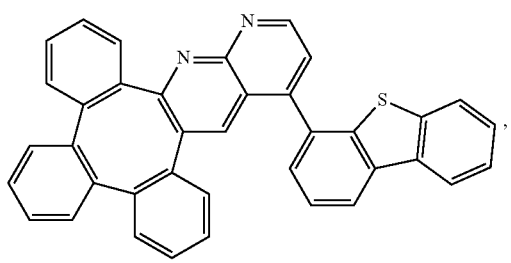
Compound MB1
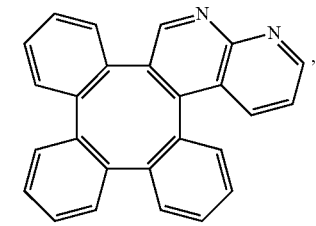
Compound MB2
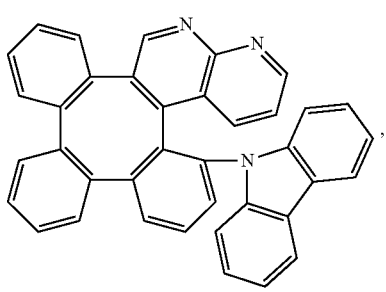
Compound MB3
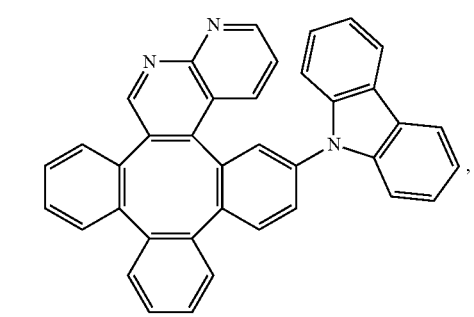
Compound MB4
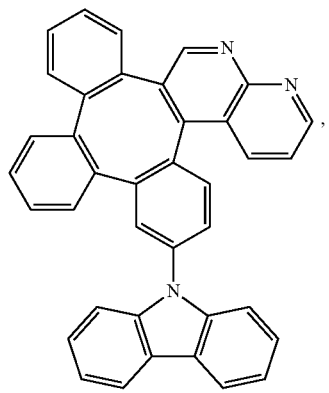
Compound MB5
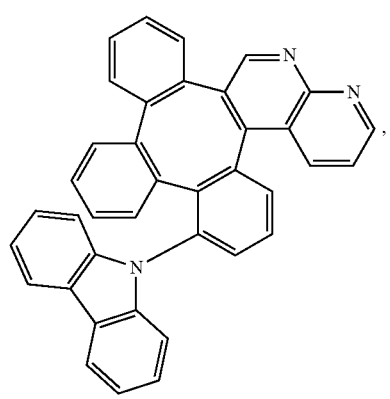
Compound MB6
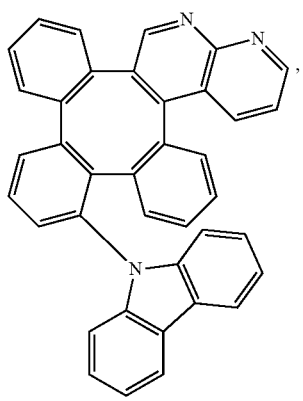
Compound MB7
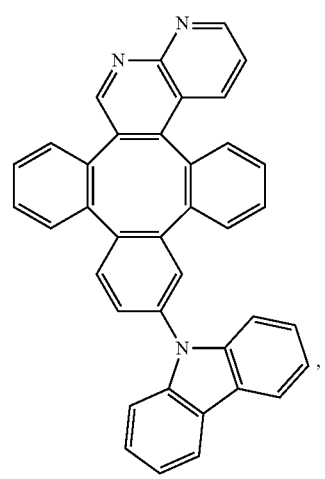

Compound MB8
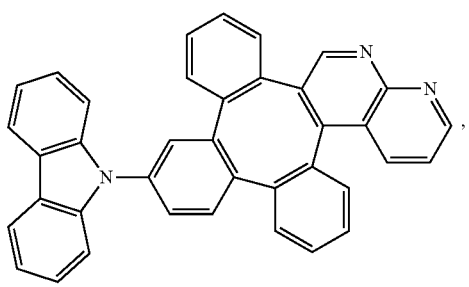
Compound MB9
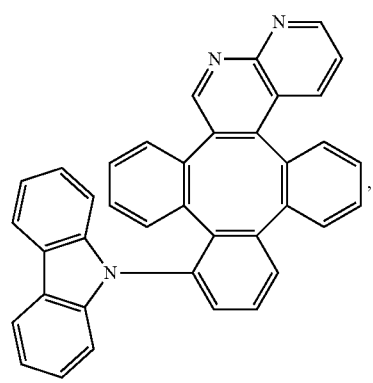
Compound MB10
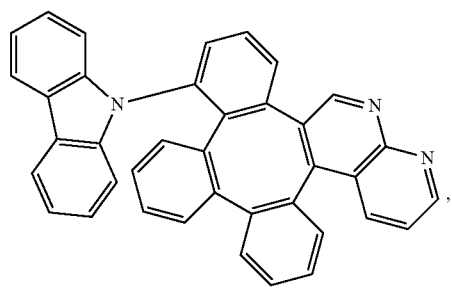
Compound MB11
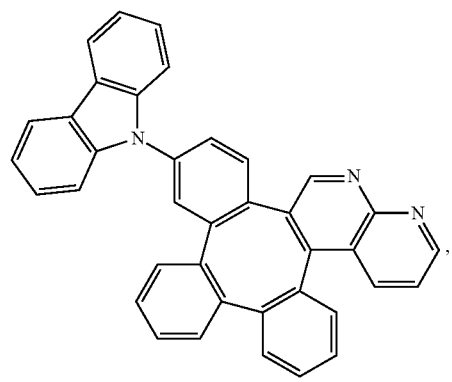
Compound MB12
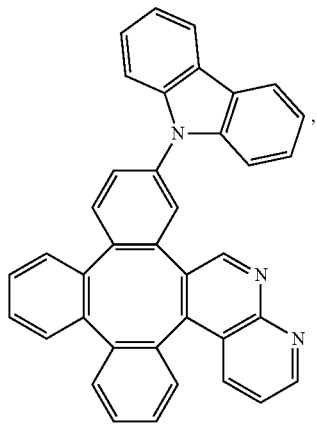
Compound MB13
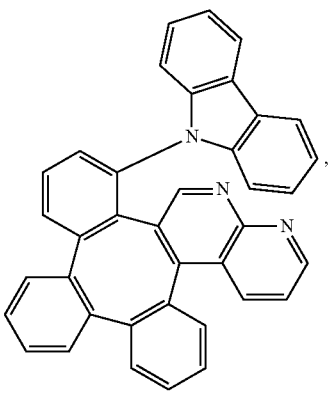
Compound MB14
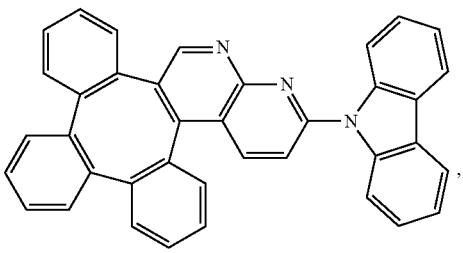
Compound MB15
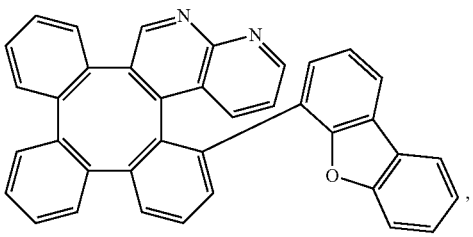

-continued
Compound MB16
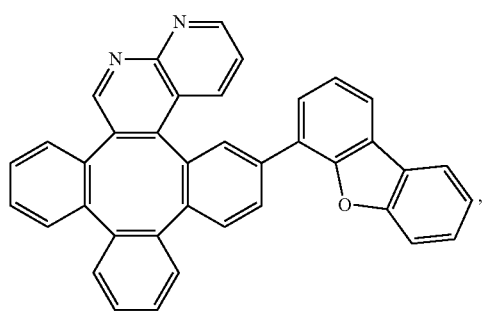
Compound MB17
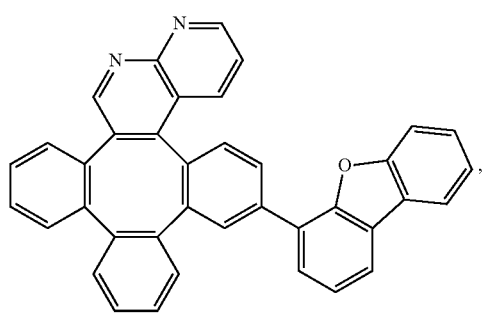
Compound MB18
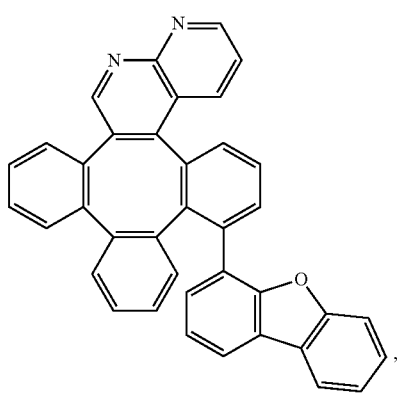
Compound MB19
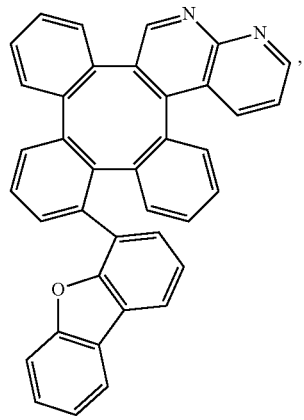
-continued
Compound MB20
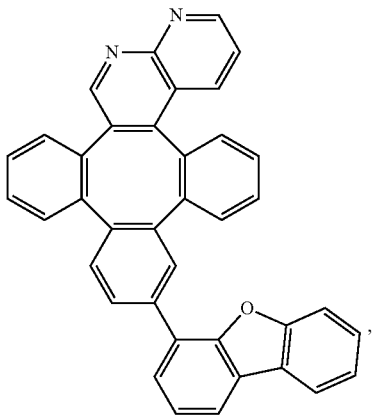
Compound MB21
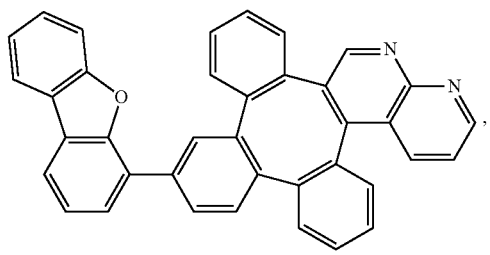
Compound MB22
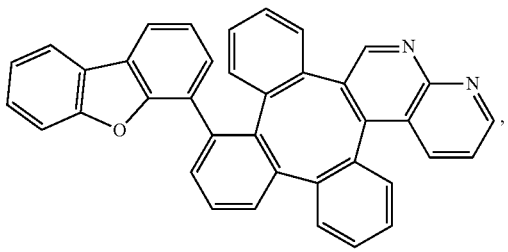
Compound MB23
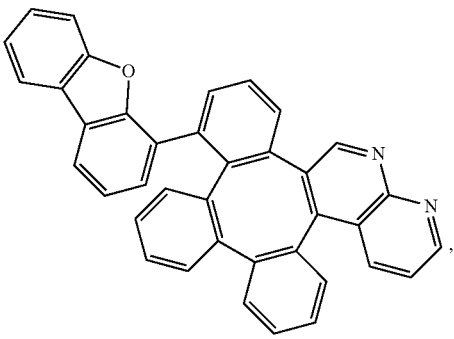

Compound MB24
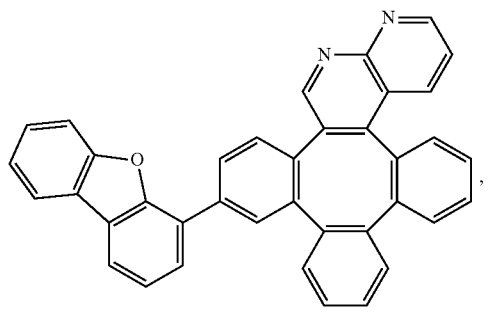
Compound MB25
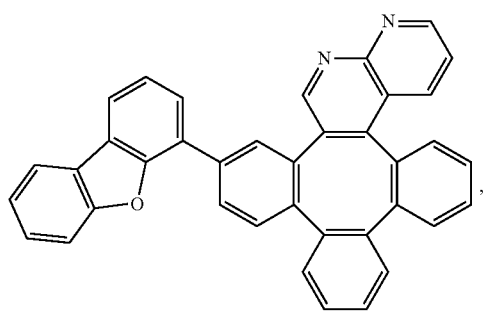
Compound MB26
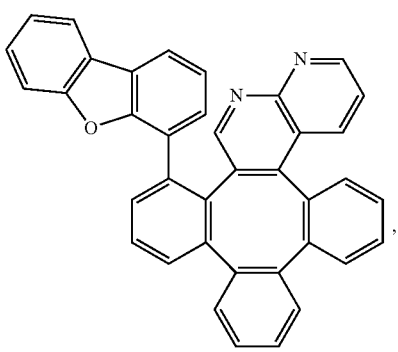
Compound MB27
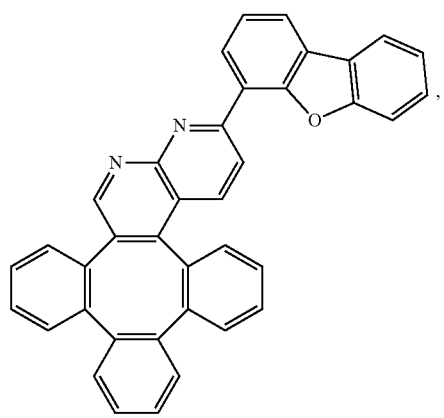
Compound MB28
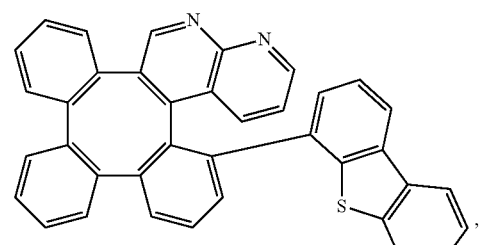
Compound MB29
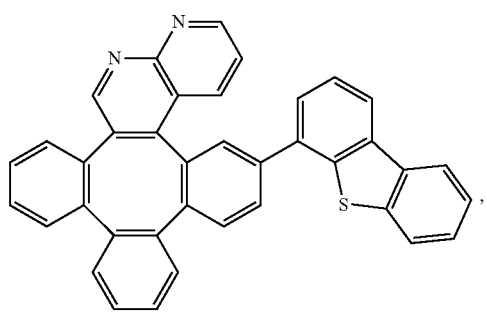
Compound MB30
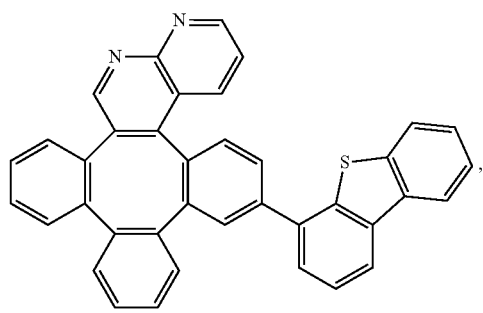
Compound MB31
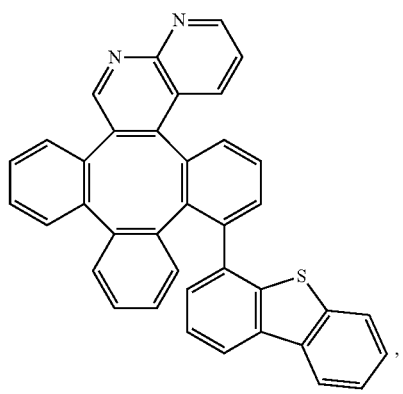

Compound MB32
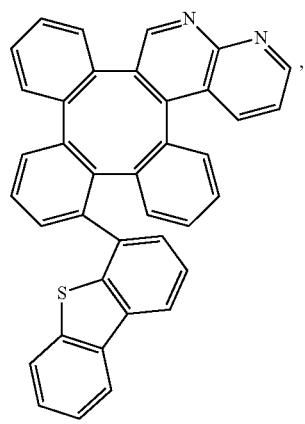
Compound MB33
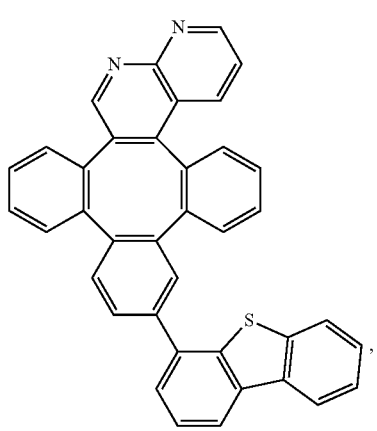
Compound MB34
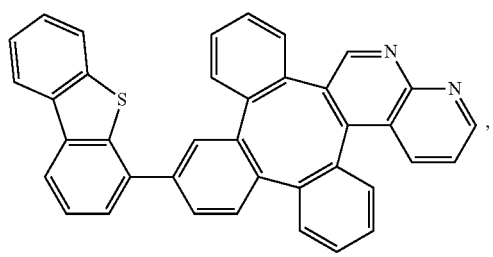
Compound MB35
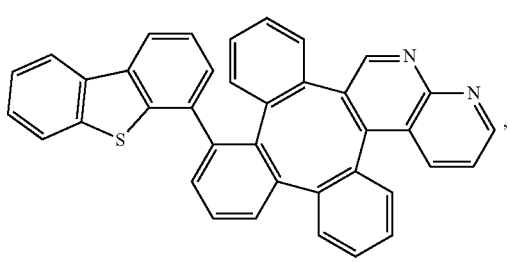
Compound MB36
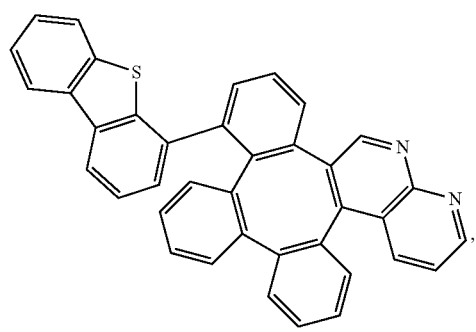
Compound MB37
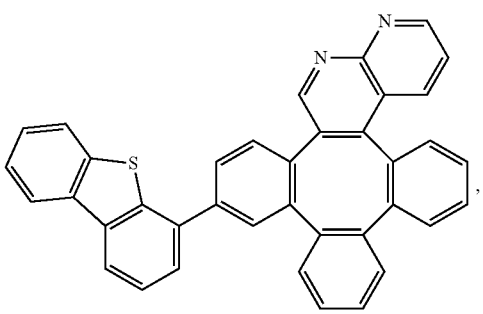
Compound MB38
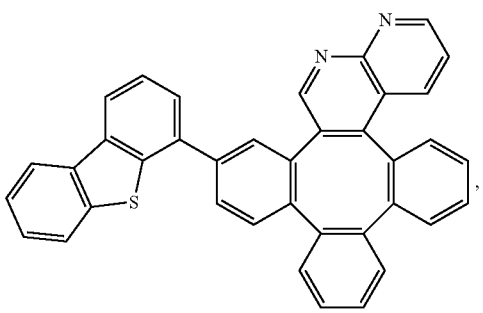
Compound MB39
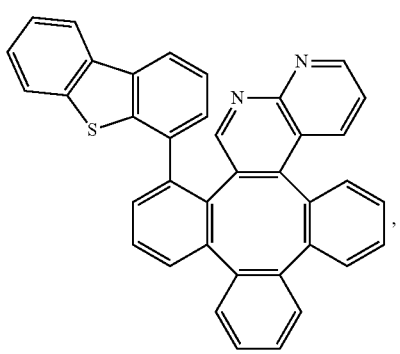

Compound MB40
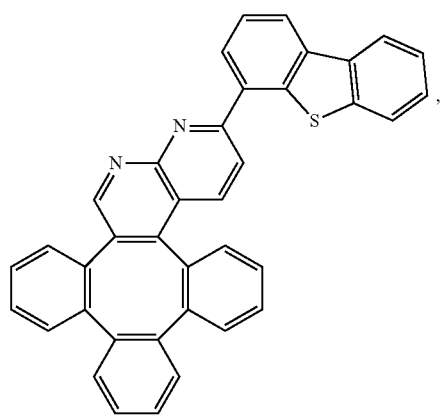
Compound MC1
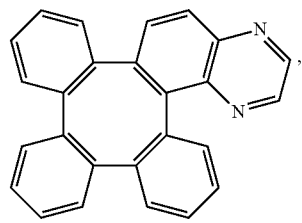
Compound MC2
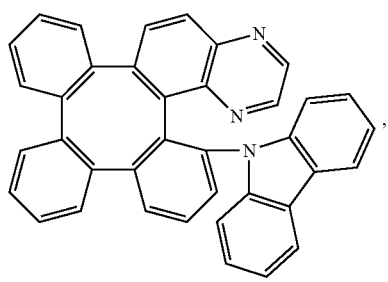
Compound MC3
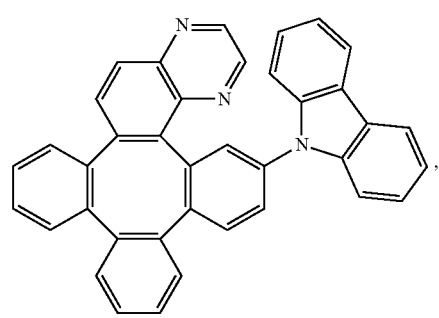
Compound MC4
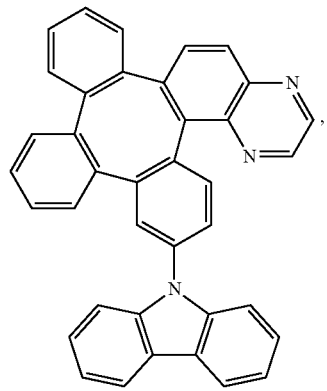
Compound MC5
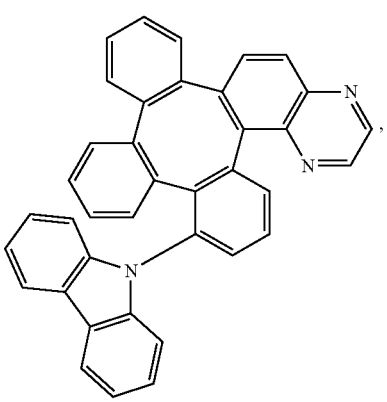
Compound MC6
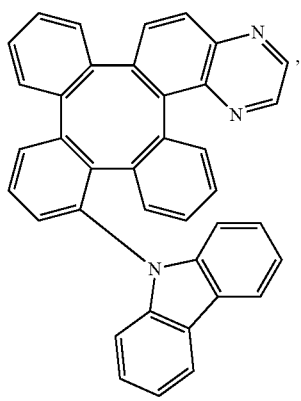

Compound MC7
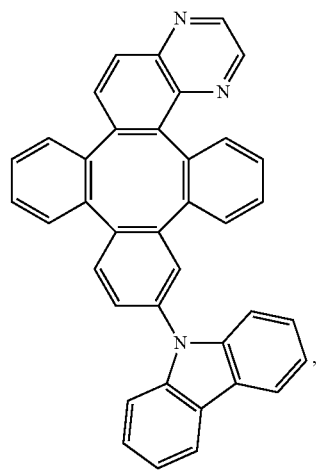
Compound MC8
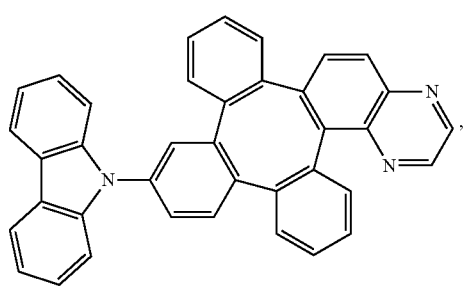
Compound MC9
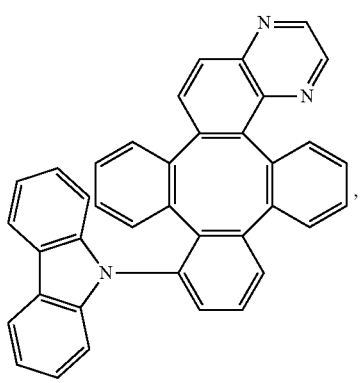
Compound MC10
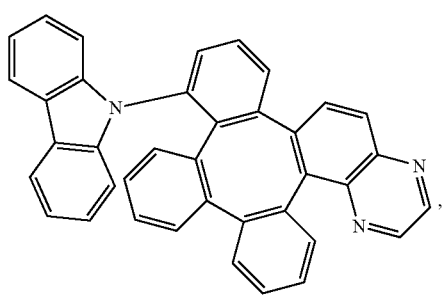
Compound MC11
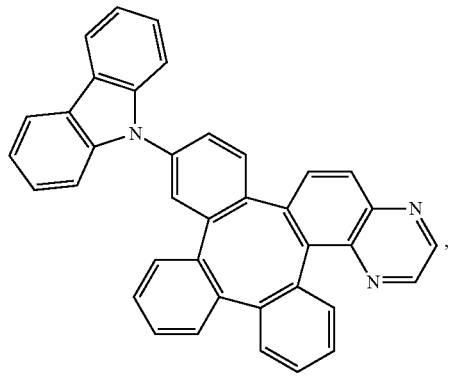
Compound MC12
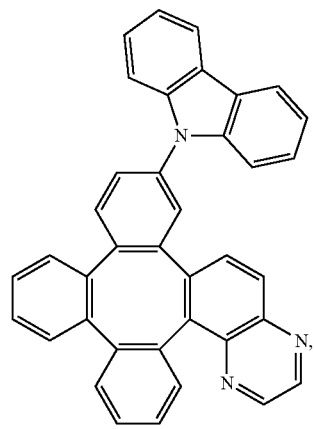
Compound MC13
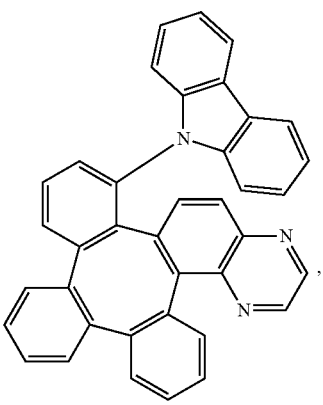
Compound MC14
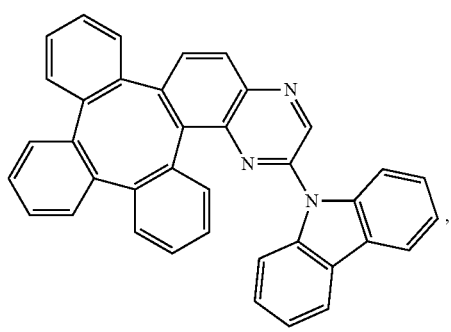

-continued
Compound MC15
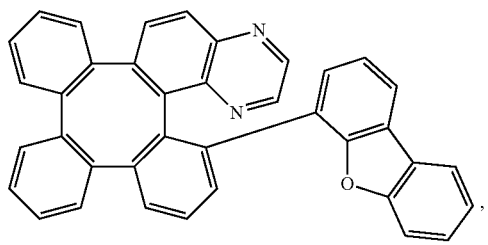
Compound MC16
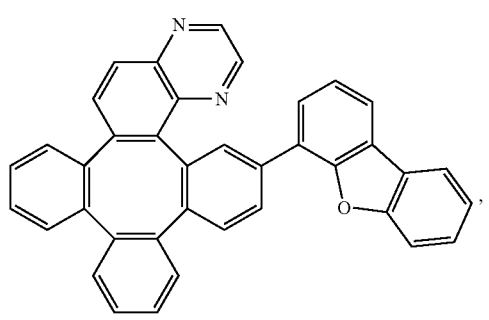
Compound MC17
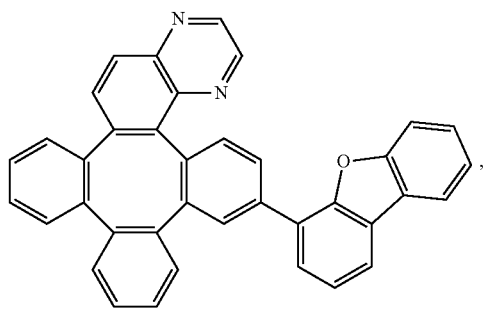
Compound MC18
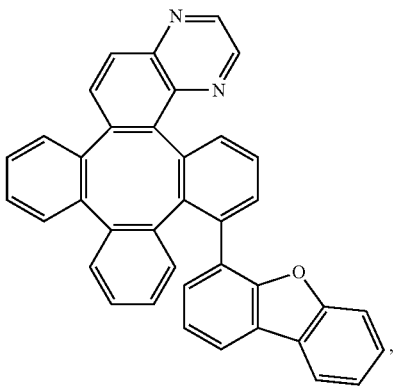
-continued
Compound MC19
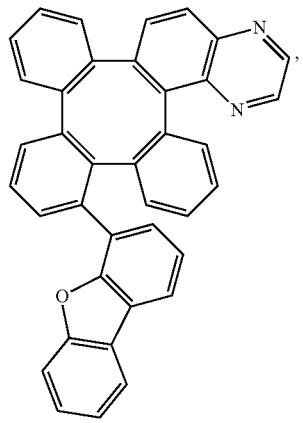
Compound MC20
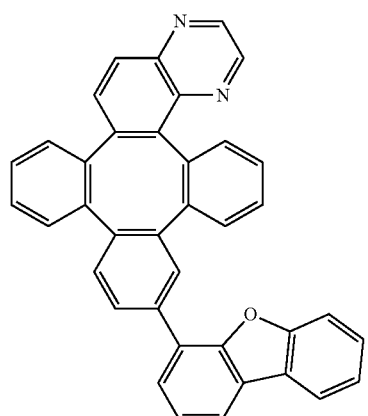
Compound MC21
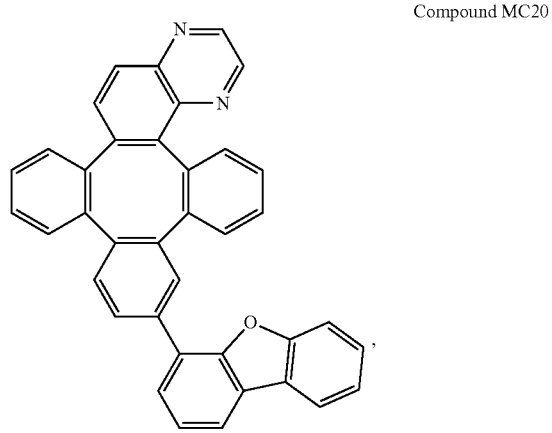
Compound MC22
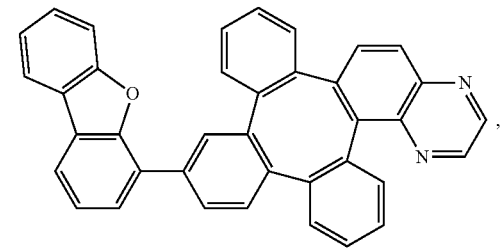

Compound MC23
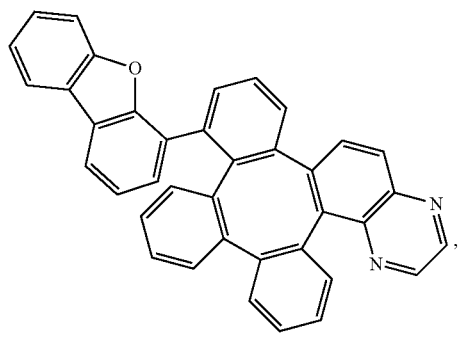
Compound MC24
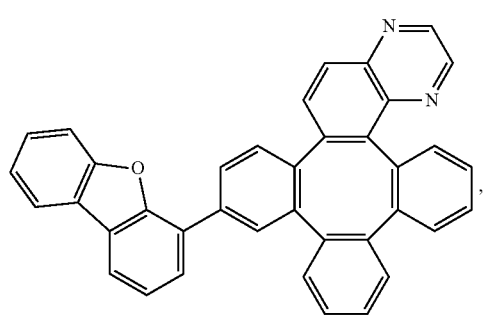
Compound MC25
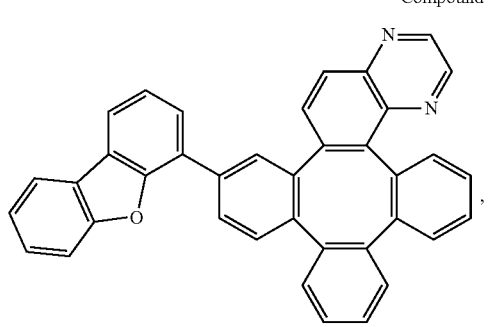
Compound MC26
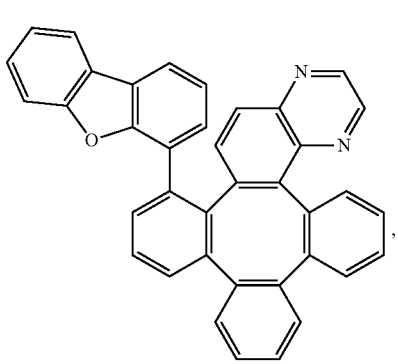
Compound MC27
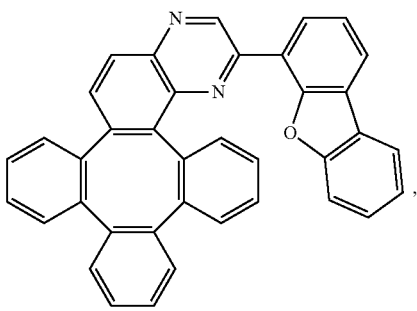
Compound MC28
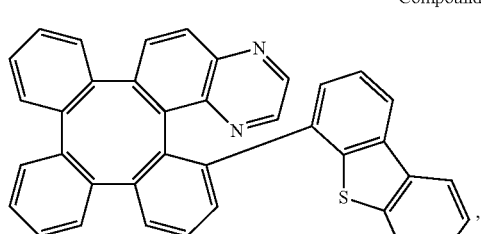
Compound MC29
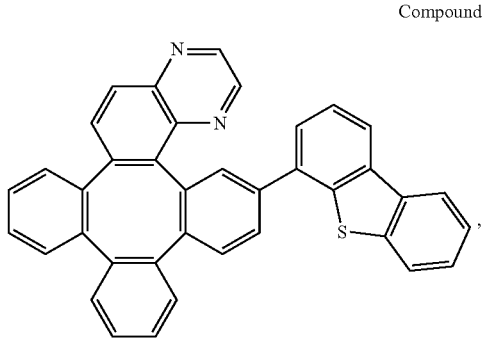
Compound MC30
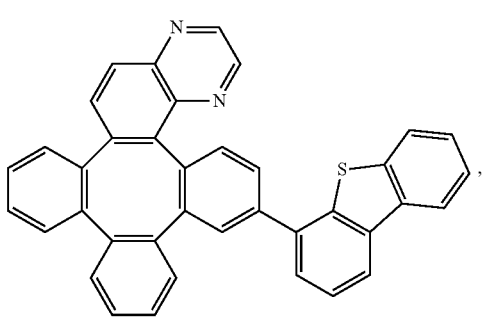

Compound MC31
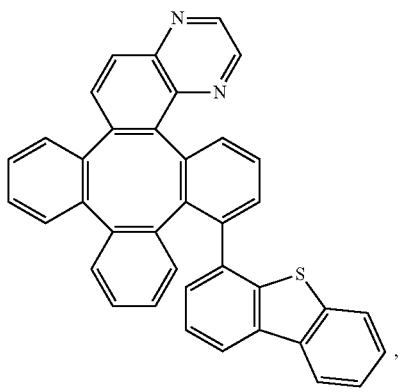
Compound MC32
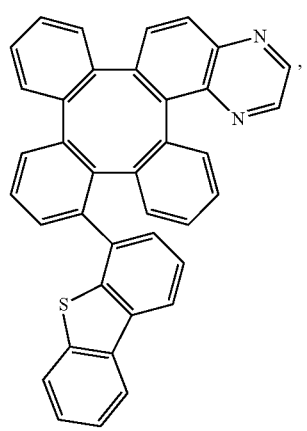
Compound MC33
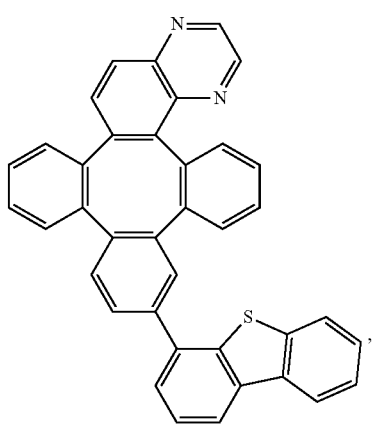
Compound MC34
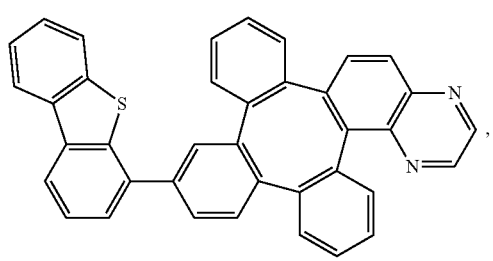
Compound MC35
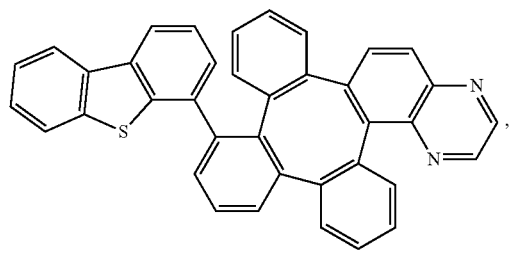
Compound MC36
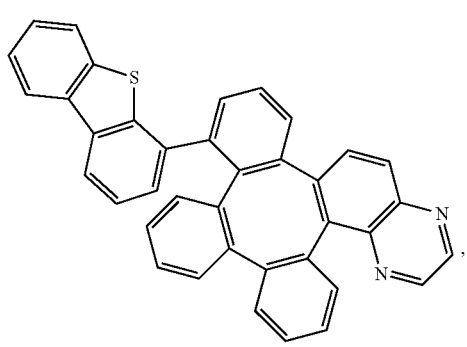
Compound MC37
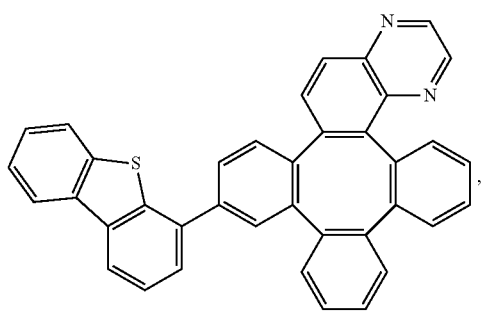
Compound MC38
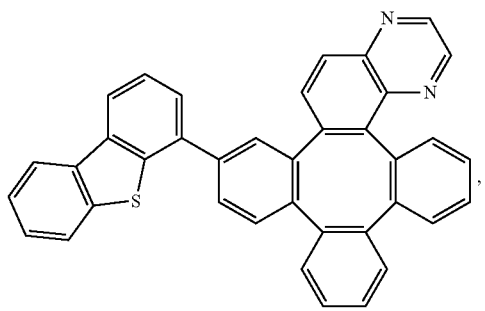

-continued

Compound MC39

Compound MC40

Compound NA1

Compound NA2

Compound NA3

Compound NA4

Compound NA5

Compound NA6

Compound NA7

-continued
Compound NA8
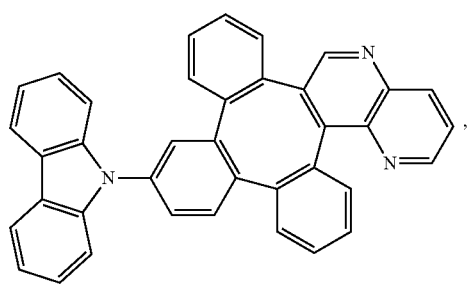
Compound NA9
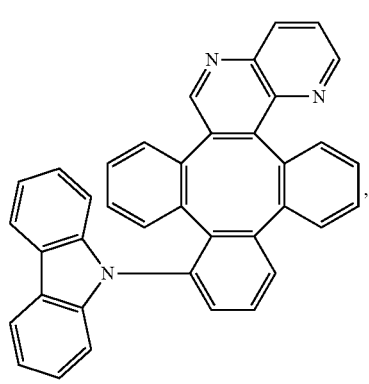
Compound NA10
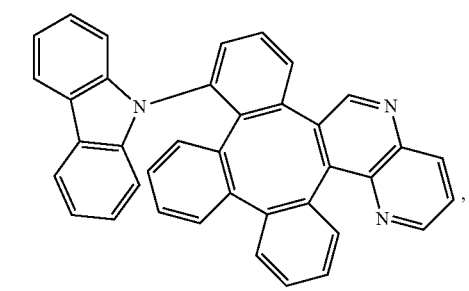
Compound NA11
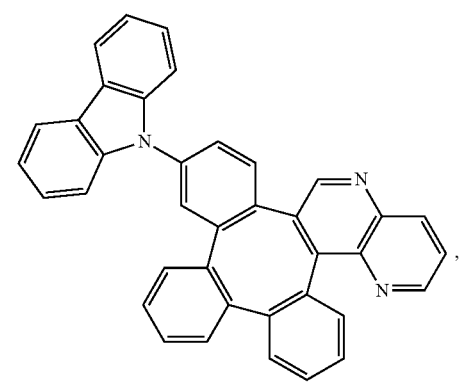
-continued
Compound NA12
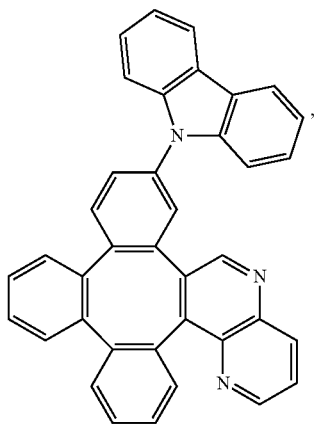
Compound NA13
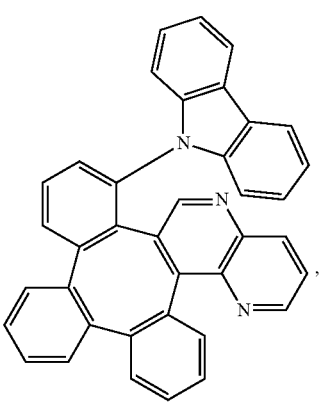
Compound NA14
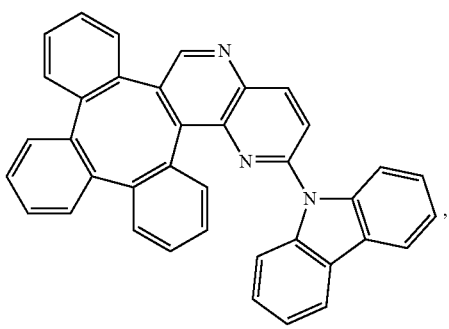
Compound NA15
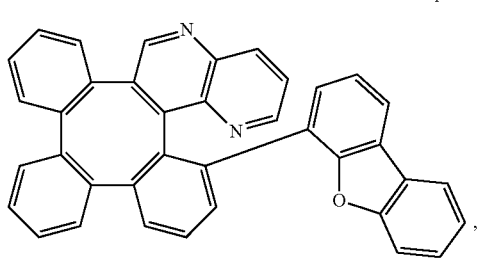

-continued
Compound NA16
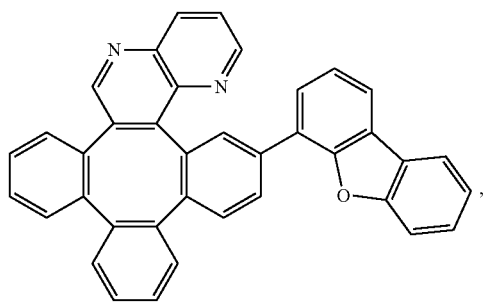
Compound NA17
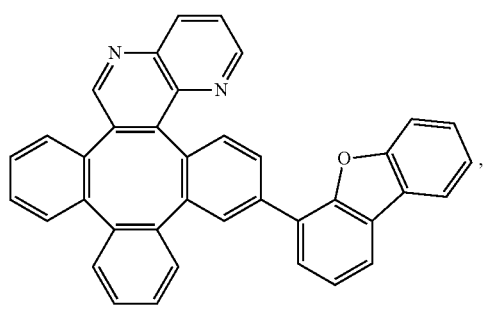
Compound NA18
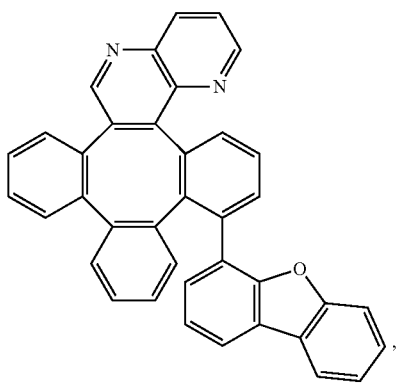
Compound NA19
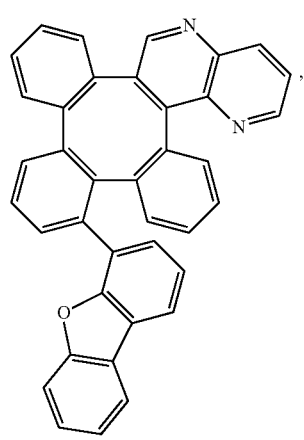
Compound NA20
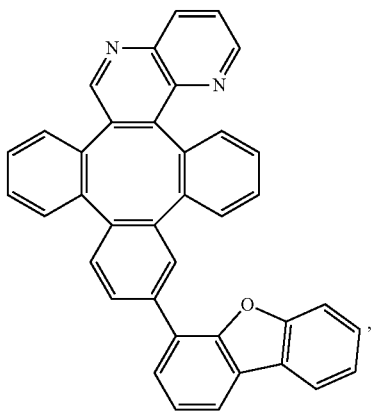
Compound NA21
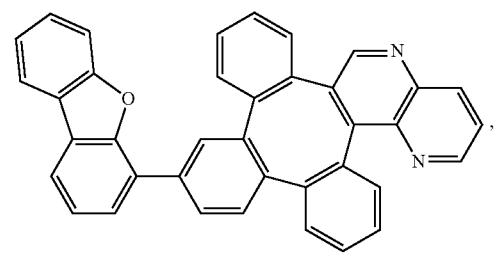
Compound NA22
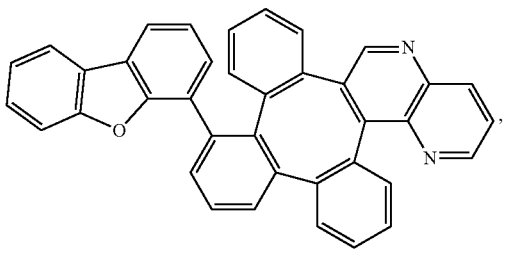
Compound NA23
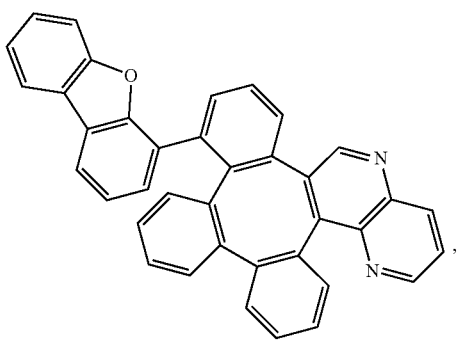

Compound NA24
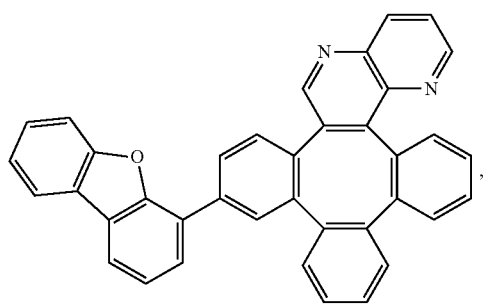
Compound NA25
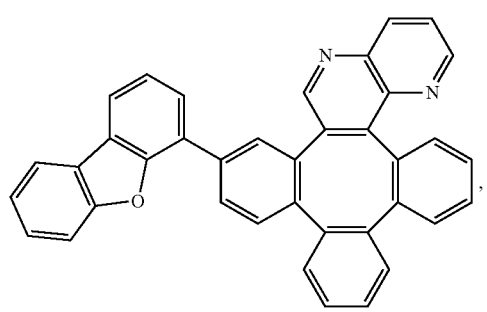
Compound NA26
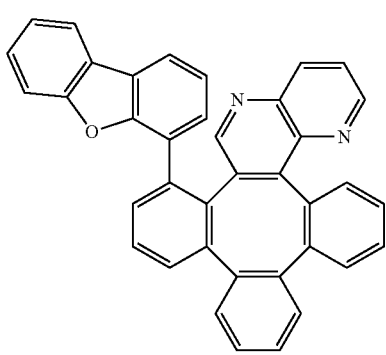
Compound NA27
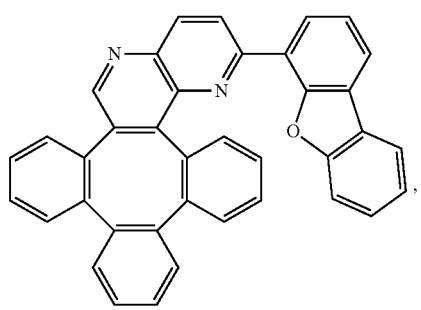
Compound NA28
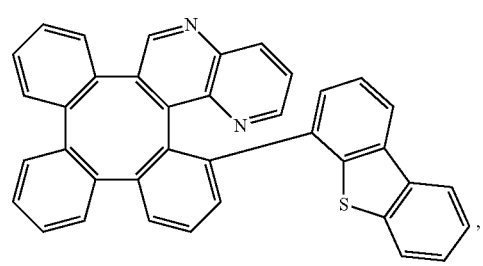
Compound NA29
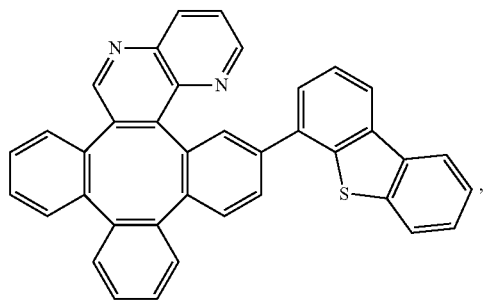
Compound NA30
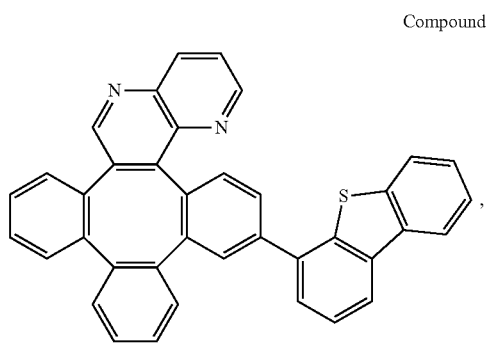
Compound NA31
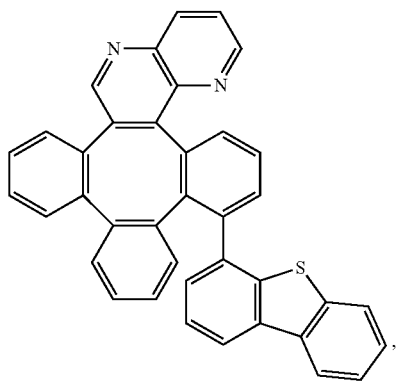
Compound NA32
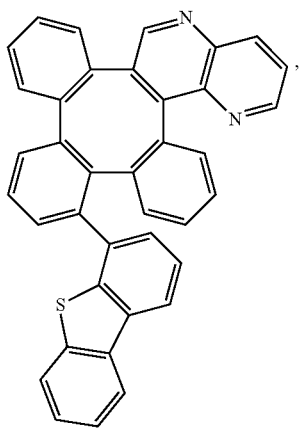

Compound NA33
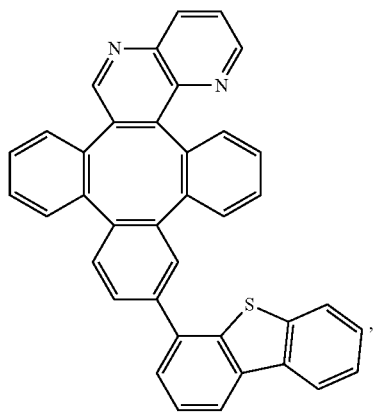
Compound NA34
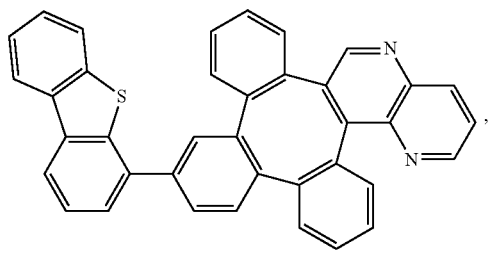
Compound NA35
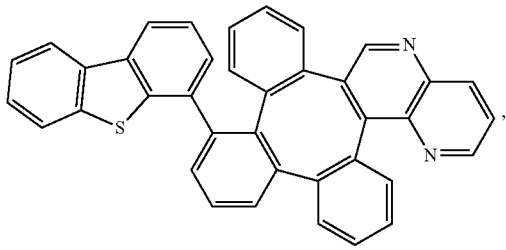
Compound NA36
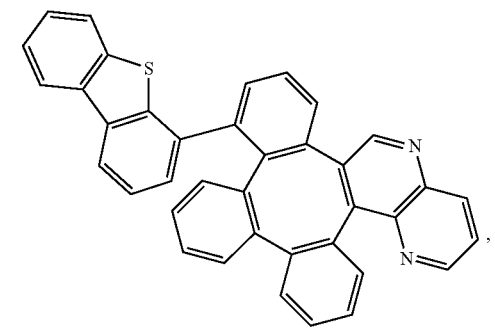
Compound NA37
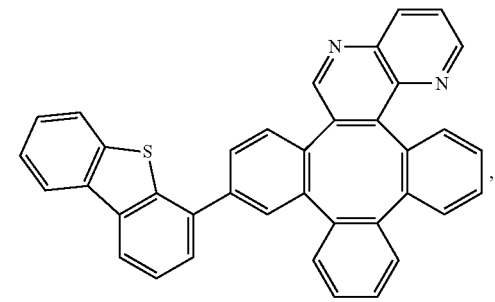
Compound NA38
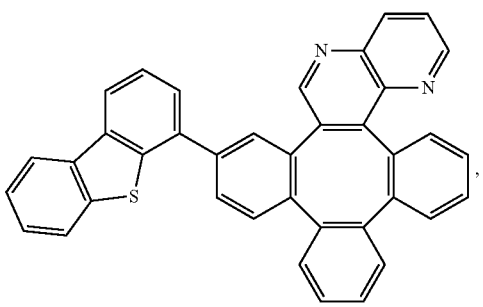
Compound NA39
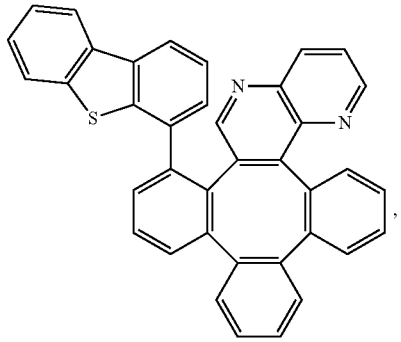
Compound NA40
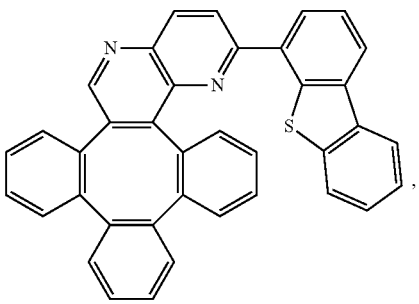
Compound R1
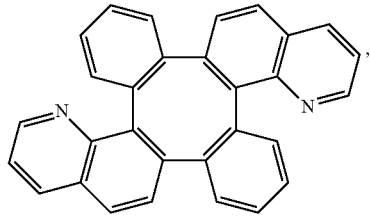
Compound R2
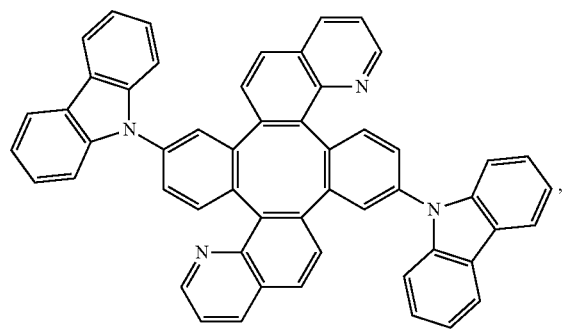

Compound R3
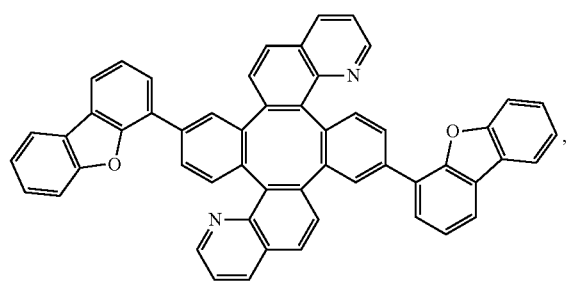
Compound R4
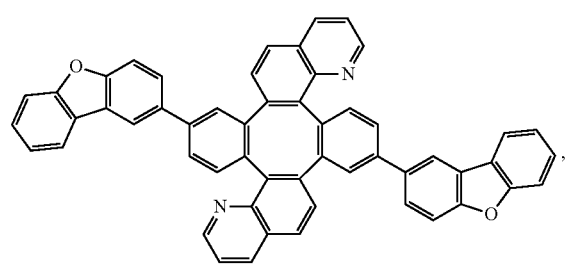
Compound R5
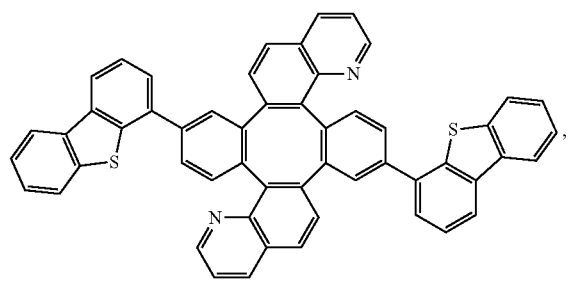
Compound R6
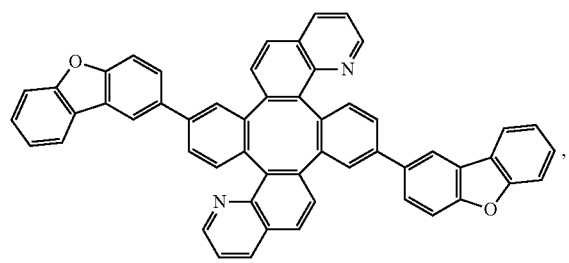
Compound R7
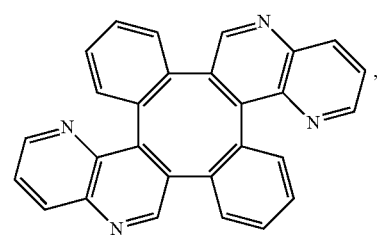
Compound R8
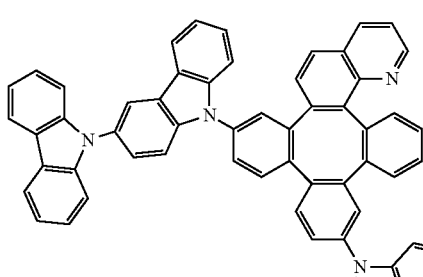
Compound R9
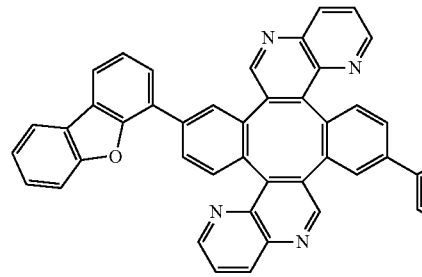
Compound R10
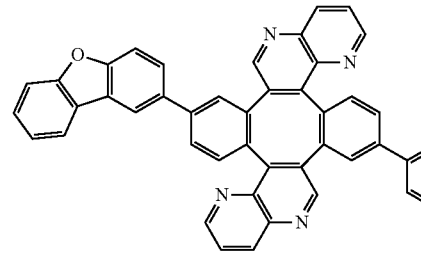
Compound R11
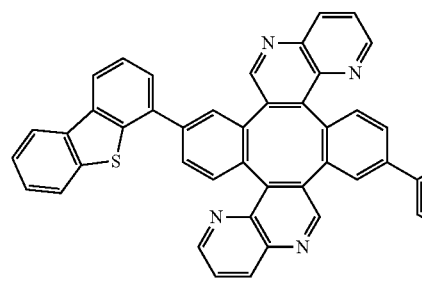
Compound R12
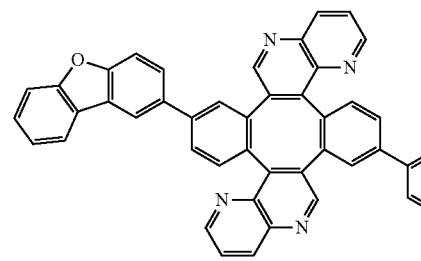

Compound R13
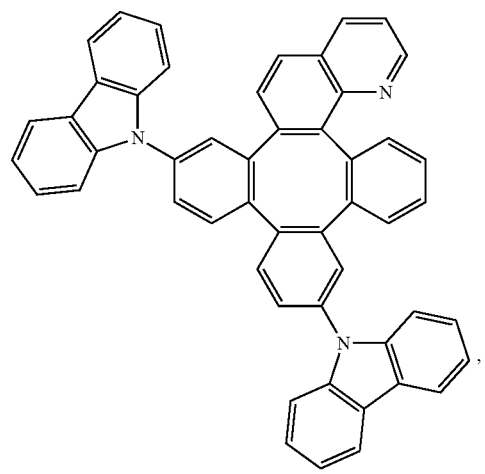
Compound R14
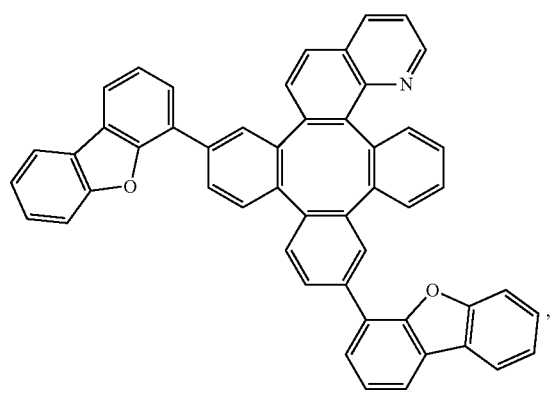
Compound R15
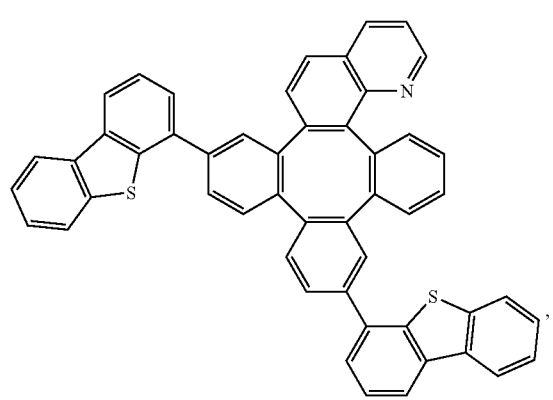
Compound R16
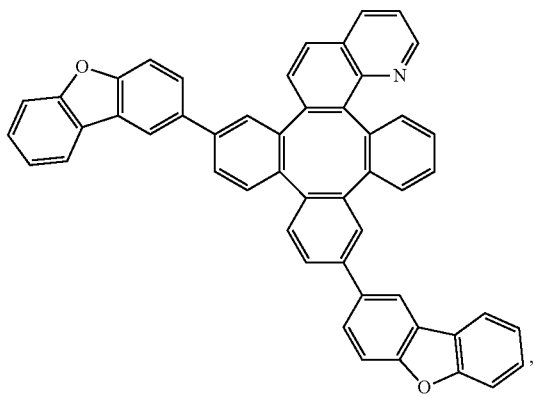
Compound R17
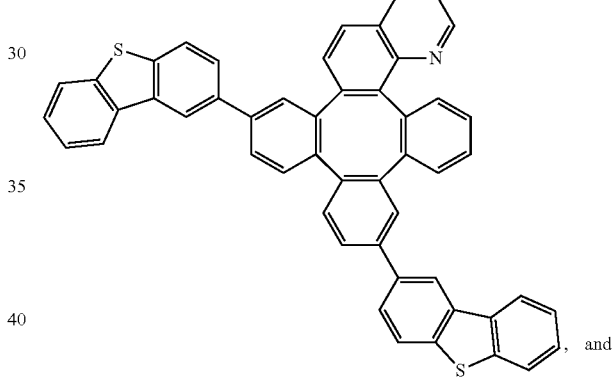
, and
Compound R18
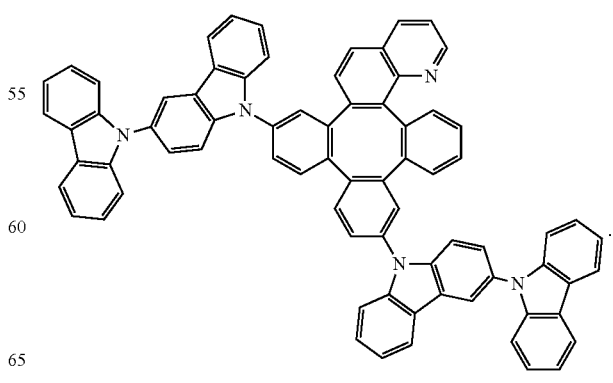
.

In one embodiment, the compound is selected from the group consisting of:
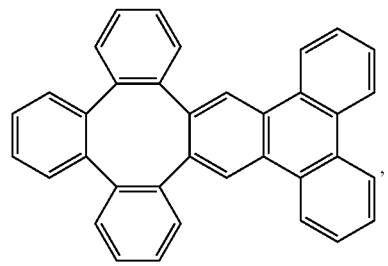
Compound 1t
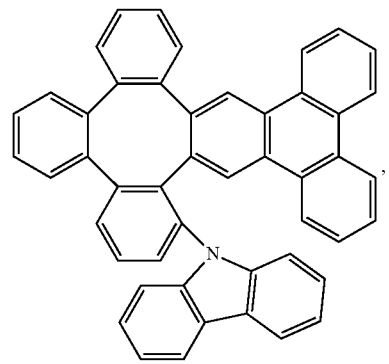
Compound 1
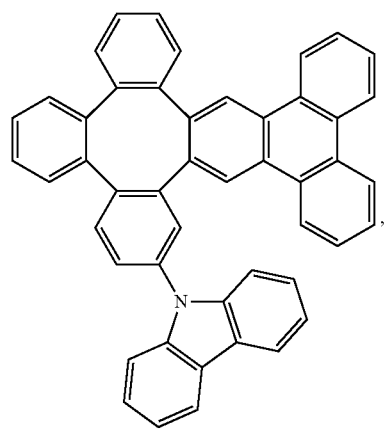
Compound 2
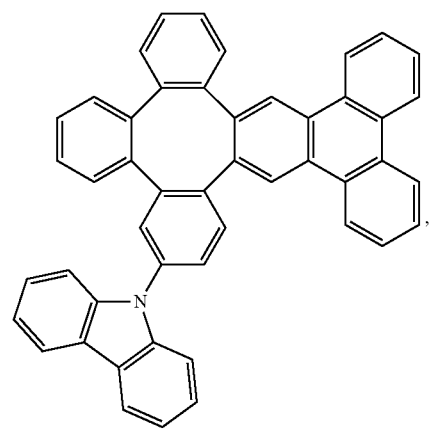
Compound 3
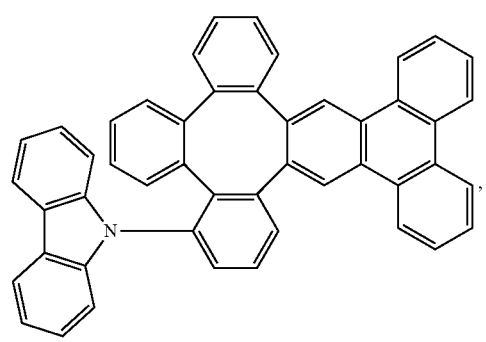
Compound 4
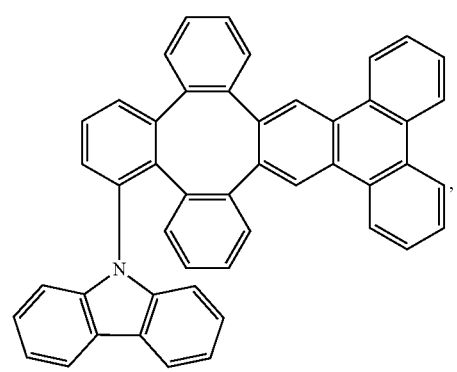
Compound 5

-continued
Compound 6
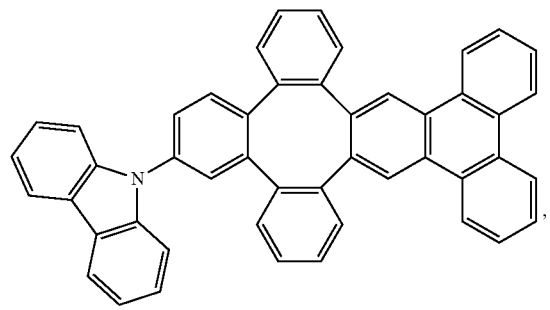
Compound 7
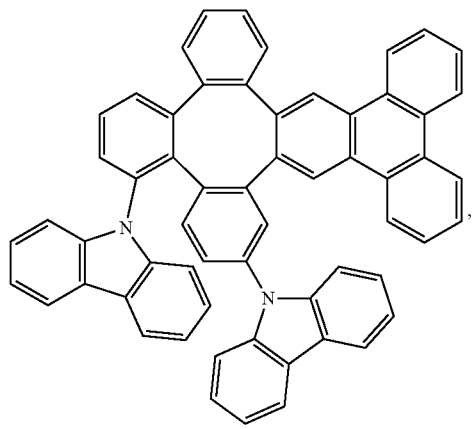
Compound 8
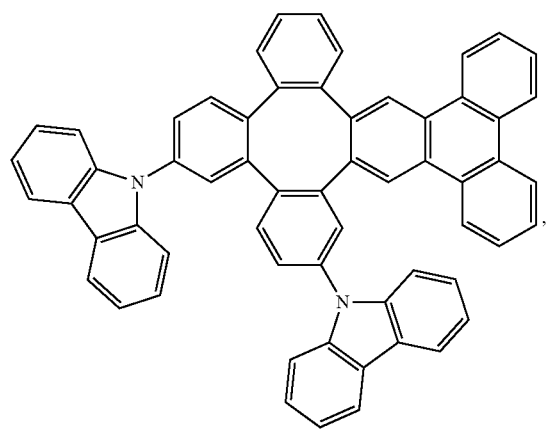
Compound 9
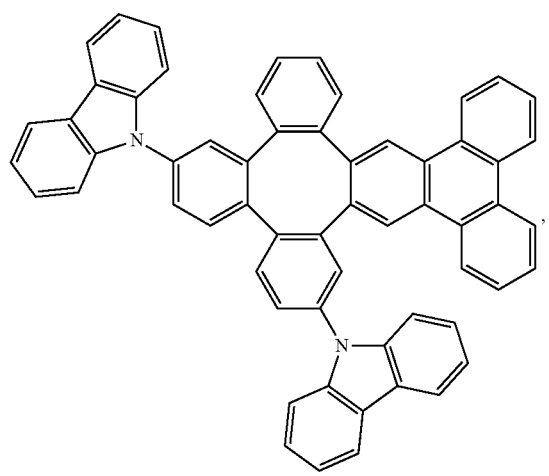
Compound 10
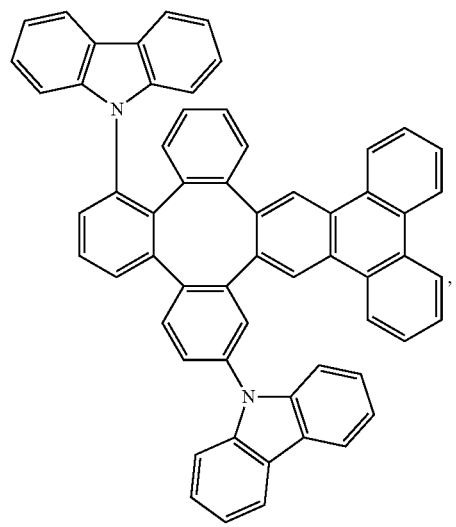
Compound 11
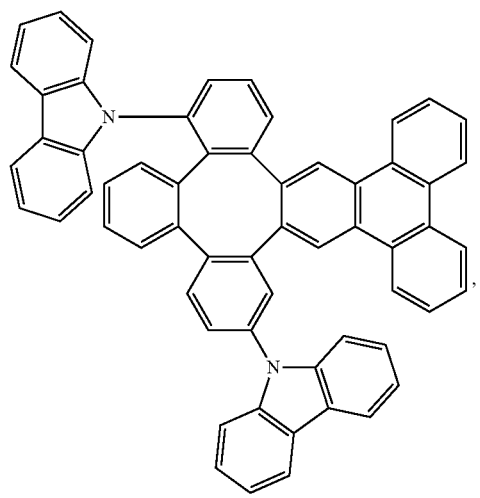

-continued
Compound 12
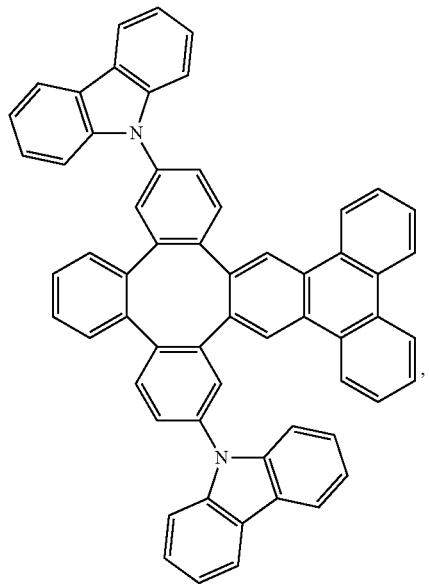
Compound 13
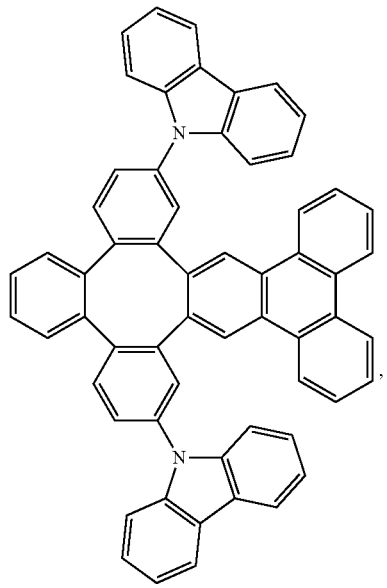
Compound 14
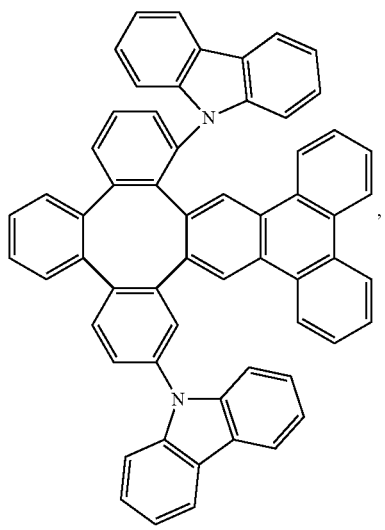
Compound 15
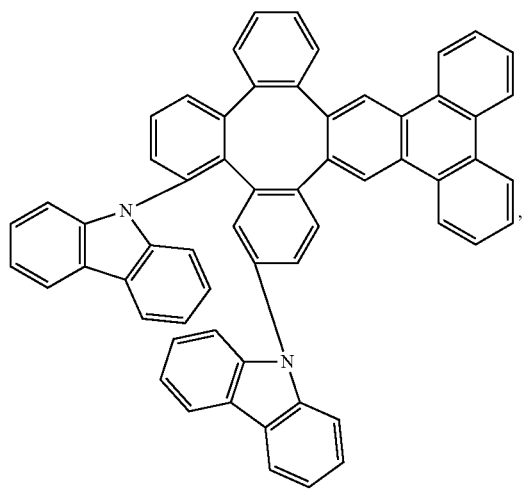
Compound 16
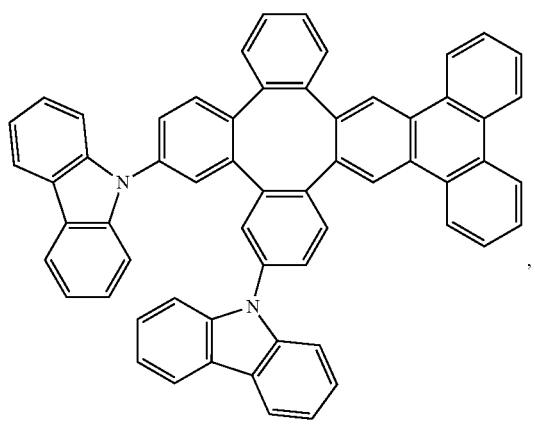
Compound 17
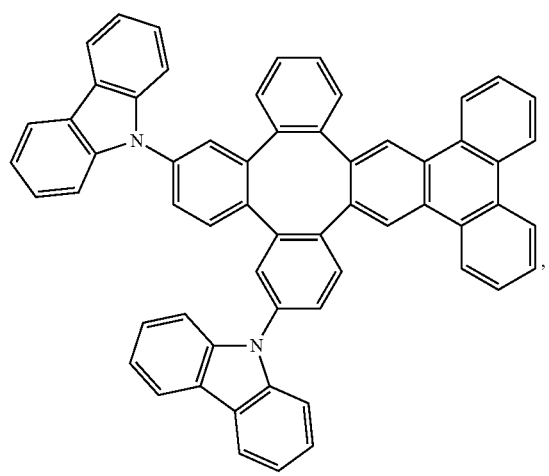

-continued
Compound 18
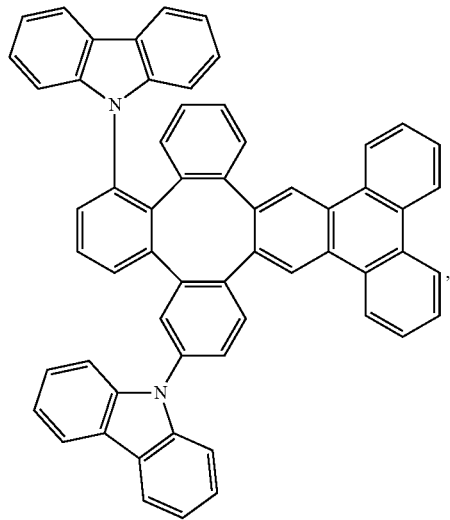
Compound 19
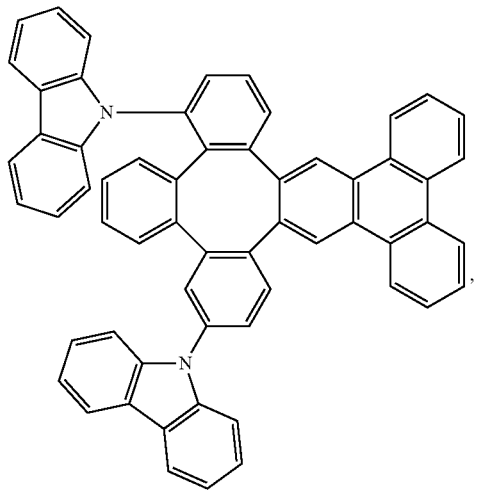
Compound 20
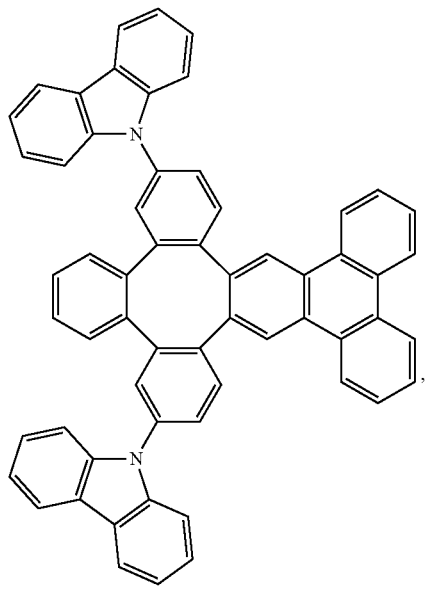
Compound 21
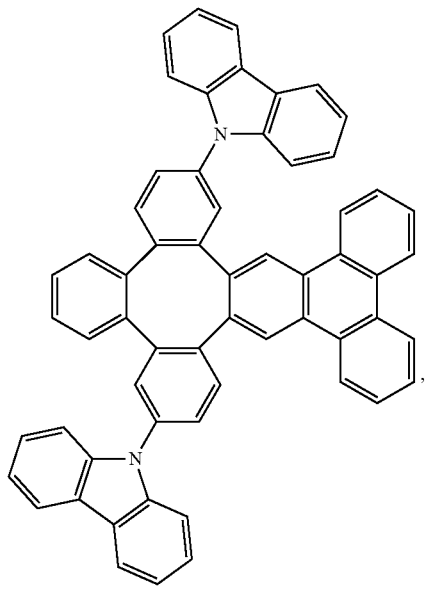
Compound 22
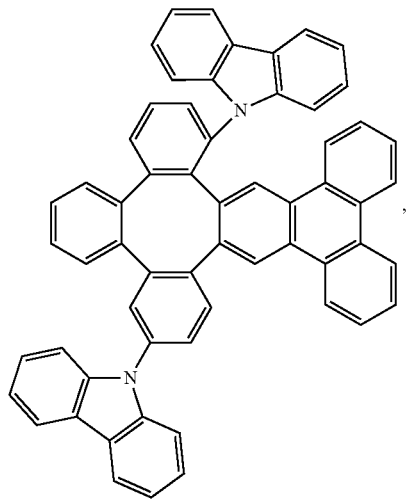
Compound 23
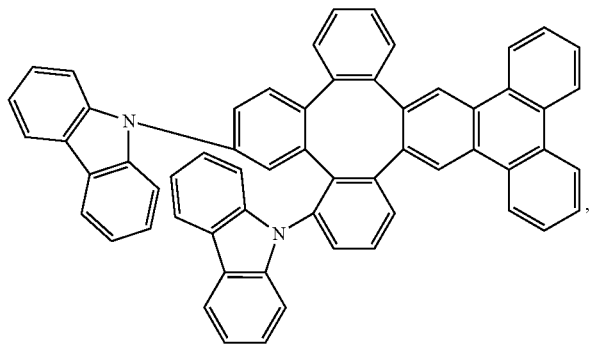

Compound 24
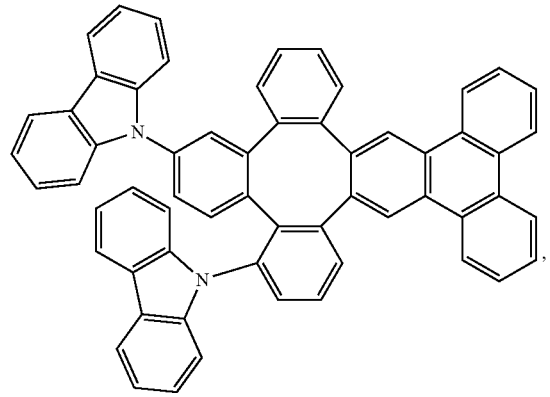
Compound 25
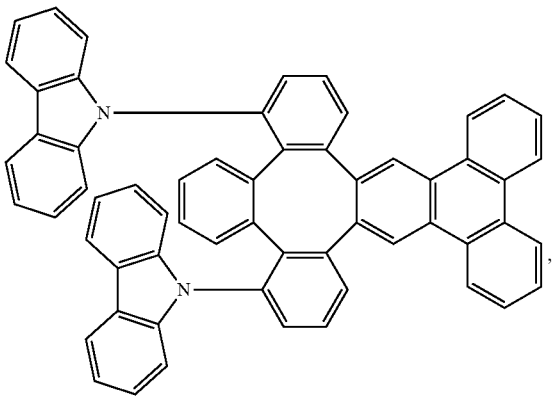
Compound 26
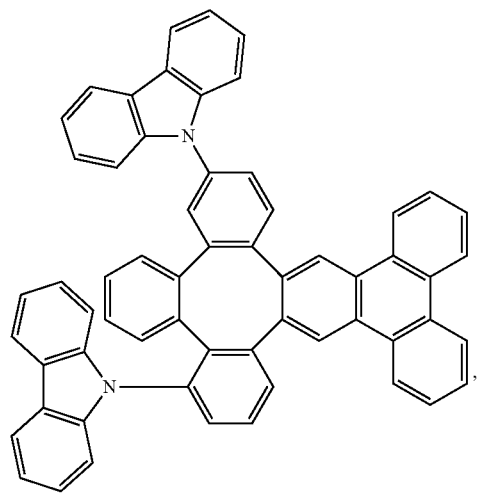
Compound 27
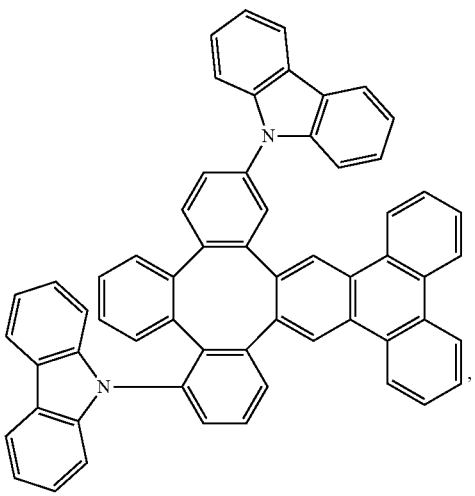
Compound 28
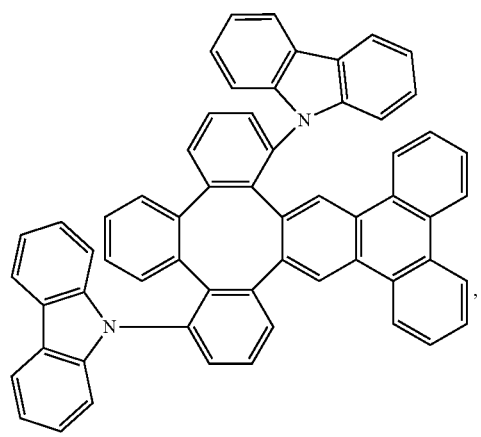
Compound 29
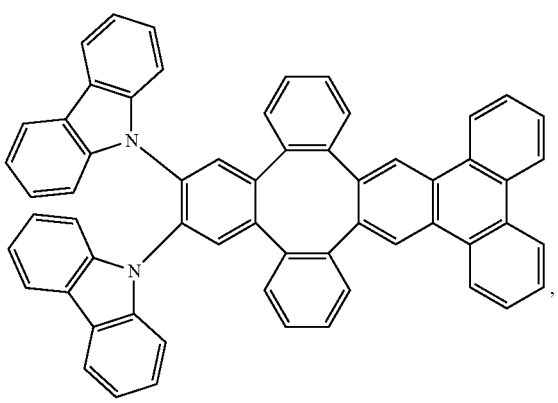

-continued
Compound 30
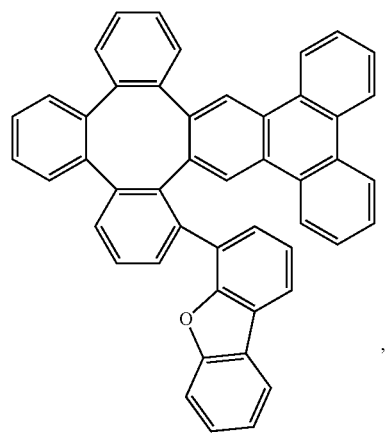
Compound 31
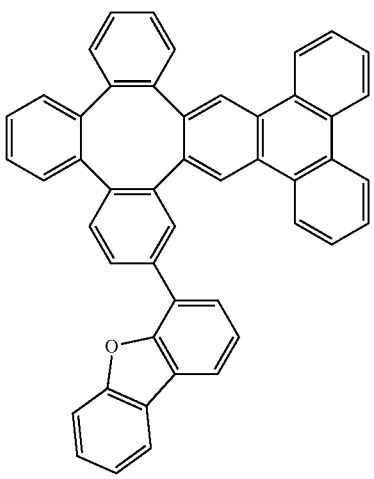
Compound 32
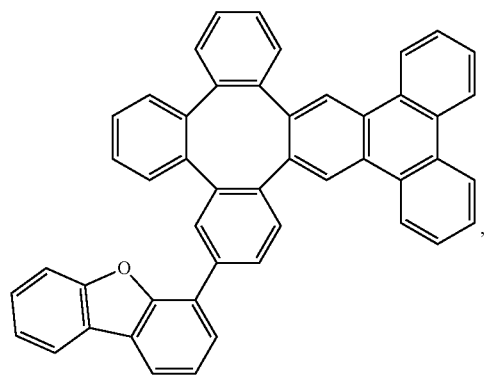
Compound 33
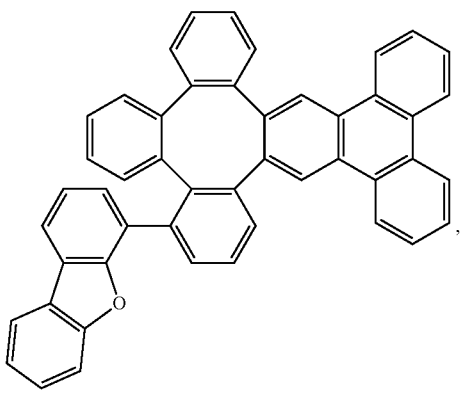
Compound 34
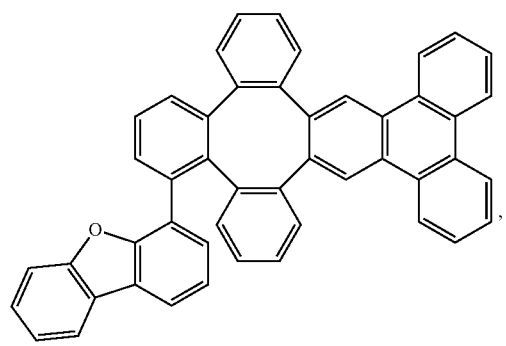
Compound 35
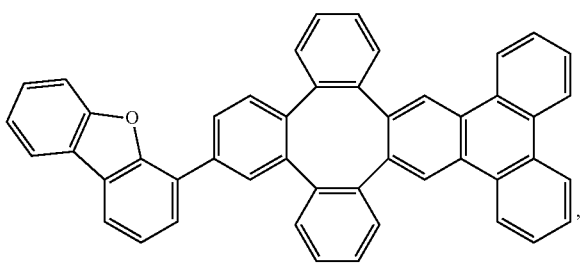

-continued
Compound 36
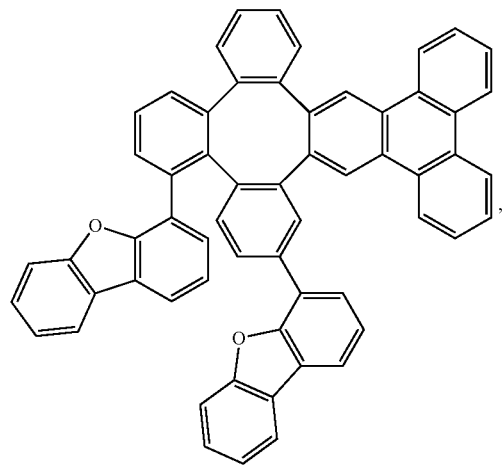
Compound 37
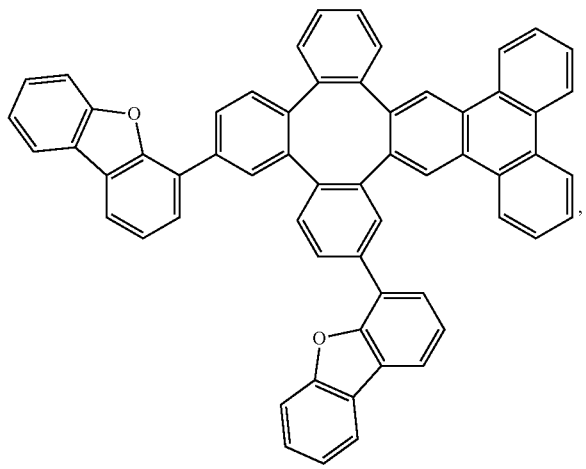
Compound 38
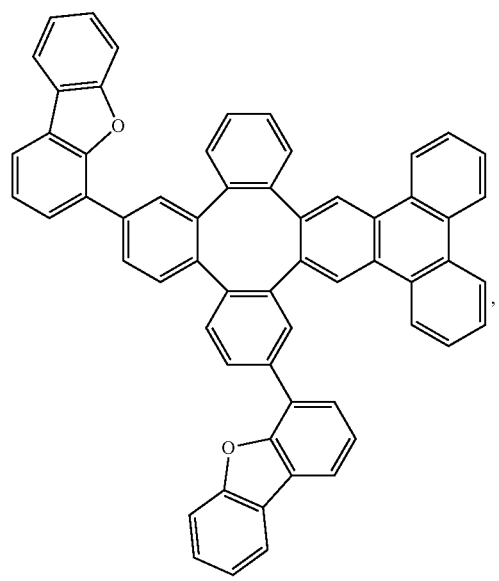
Compound 39
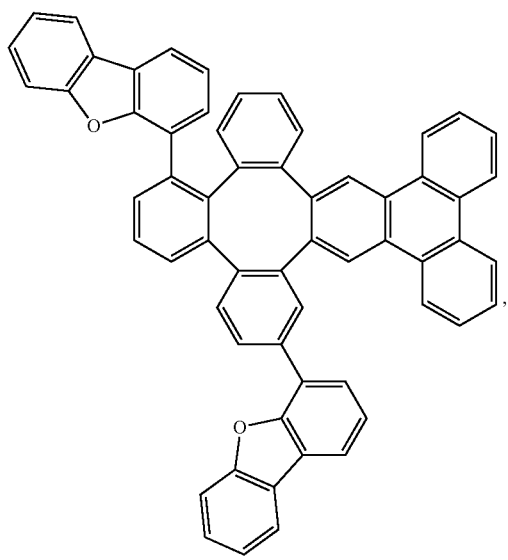

-continued
Compound 40
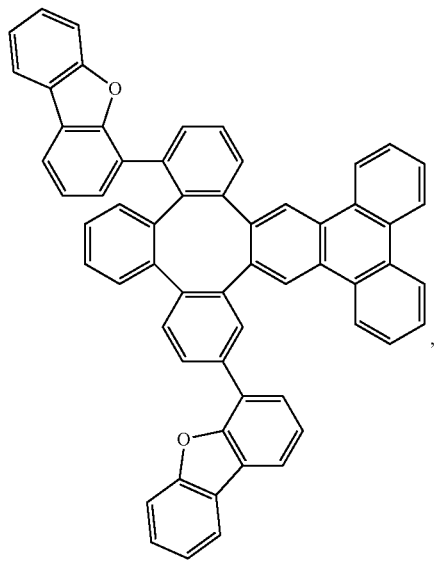
Compound 41
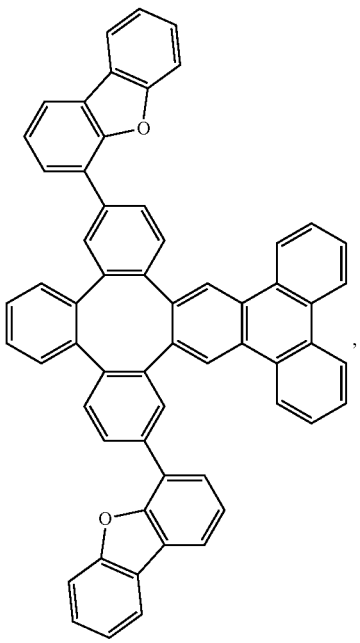
Compound 42
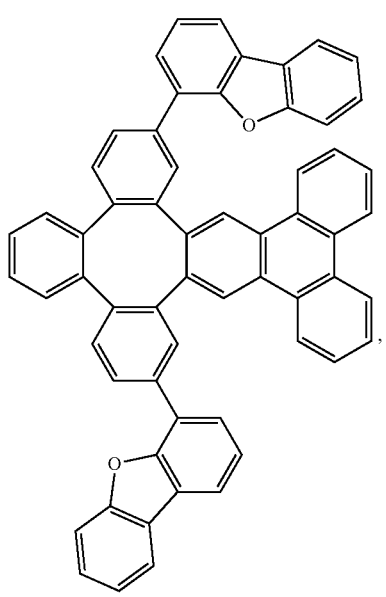
Compound 43
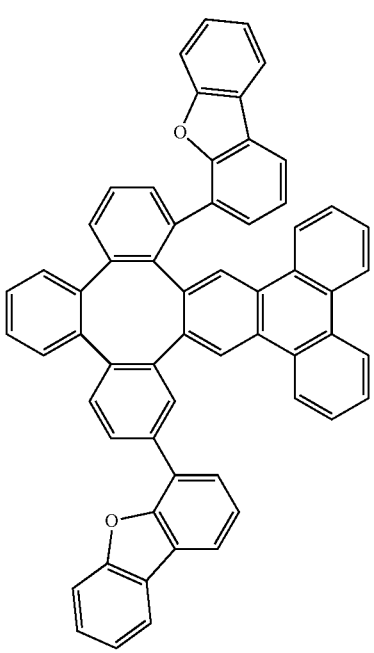

-continued
Compound 44
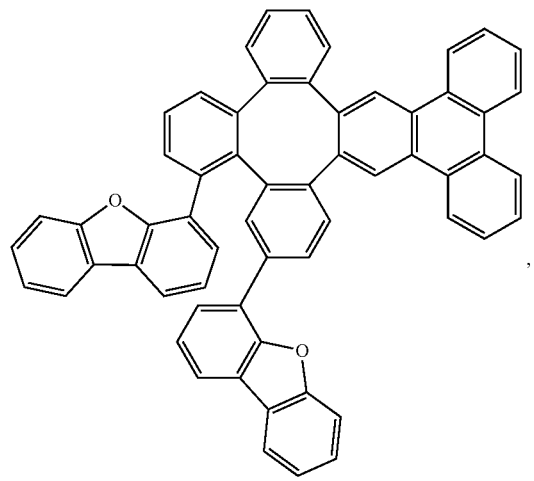
Compound 45
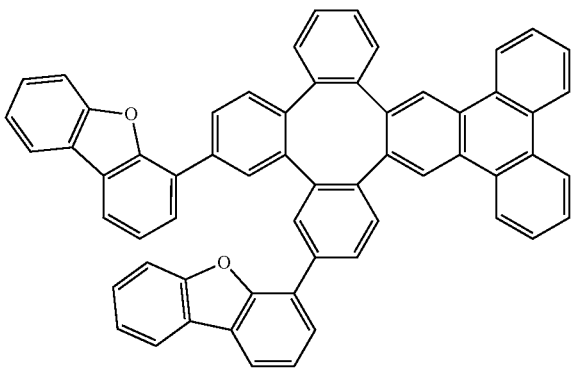
Compound 46
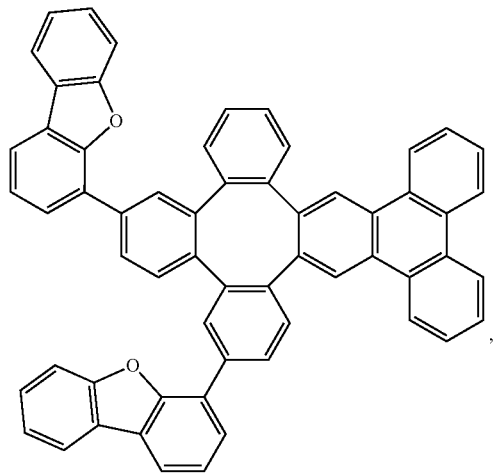
Compound 47
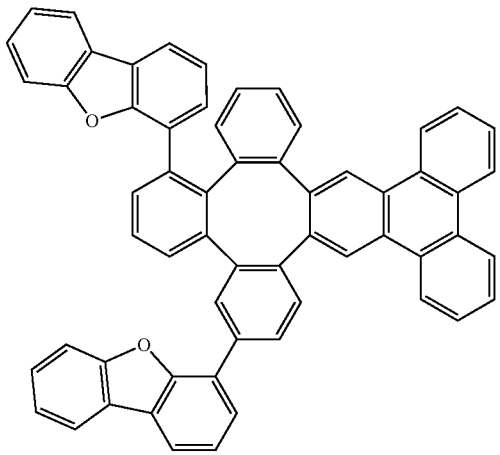
Compound 48
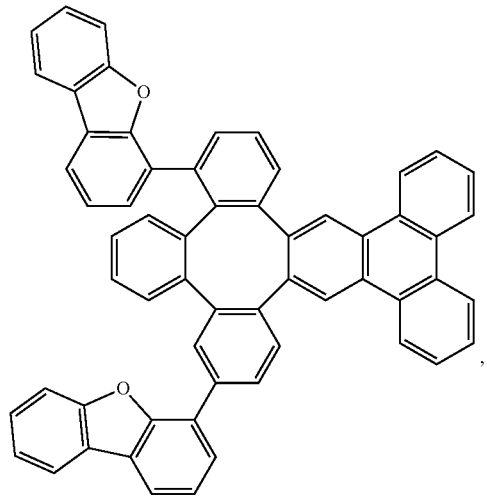
Compound 49
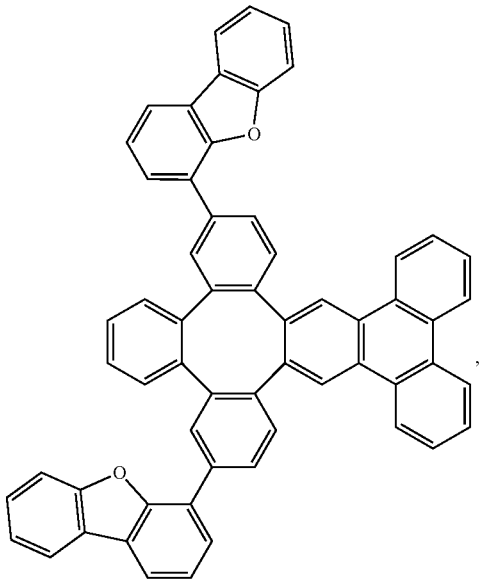

-continued
Compound 50
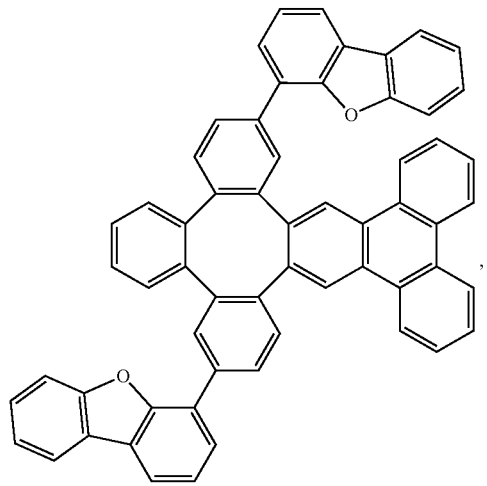
Compound 51
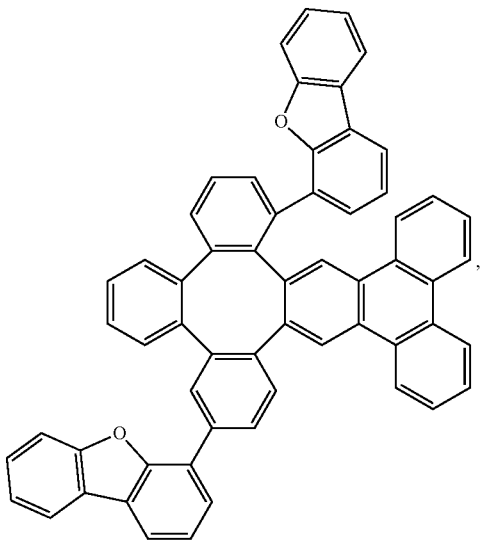
Compound 52
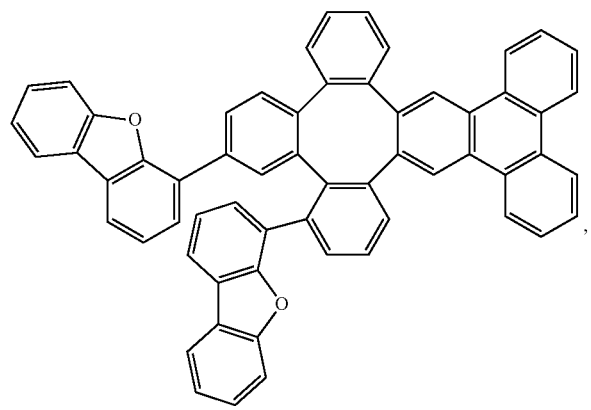
Compound 53
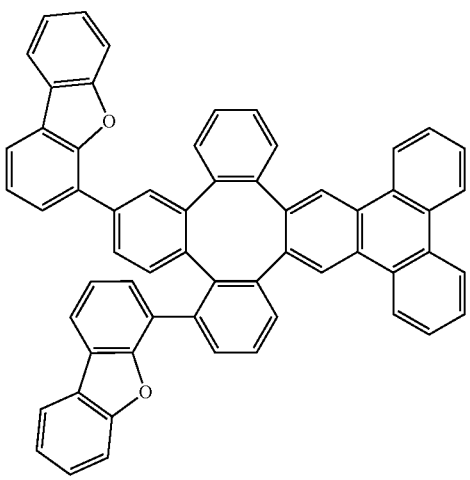
Compound 54
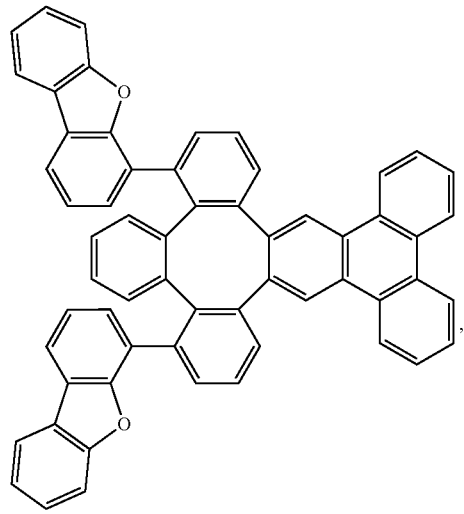
Compound 55
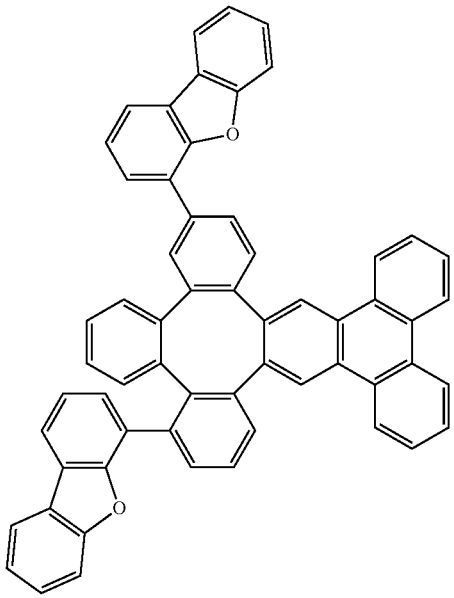

-continued
Compound 56
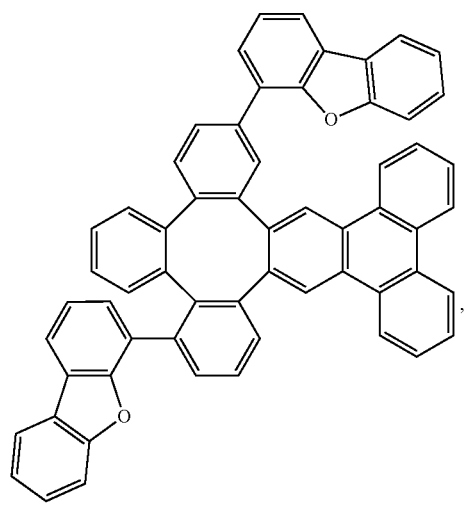
Compound 57
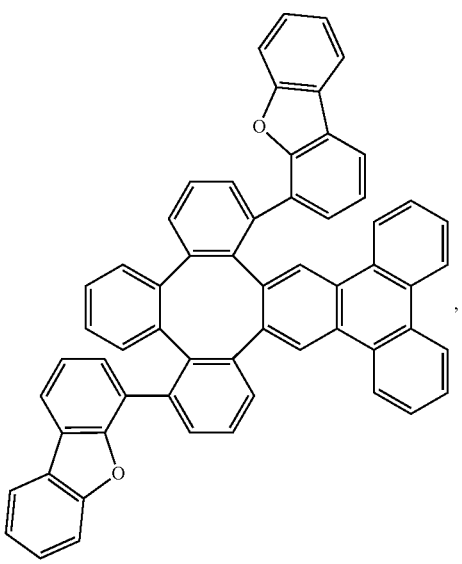
Compound 58
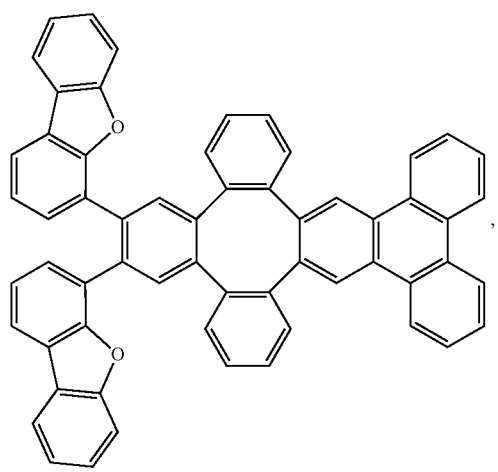
Compound 59
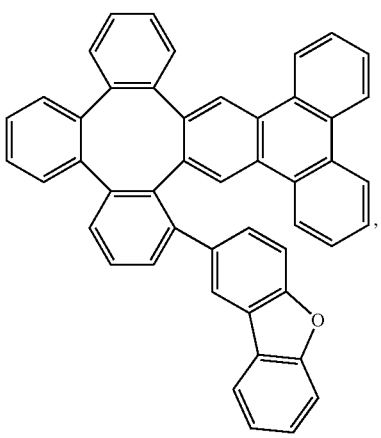
Compound 60
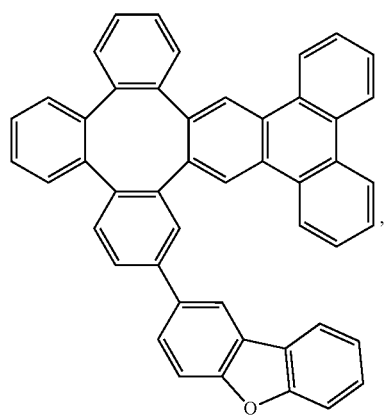
Compound 61
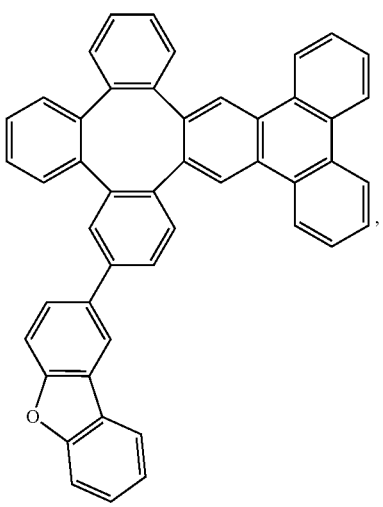

-continued
Compound 62
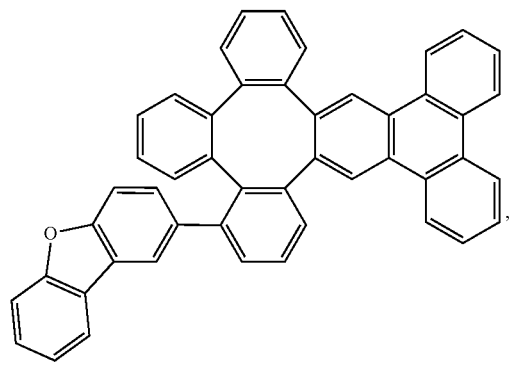
Compound 63
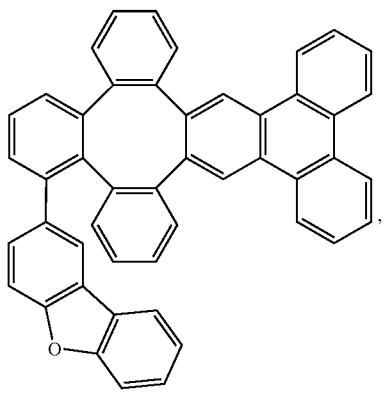
Compound 64
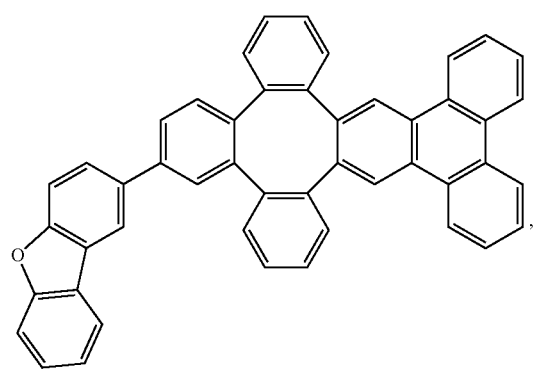
Compound 65
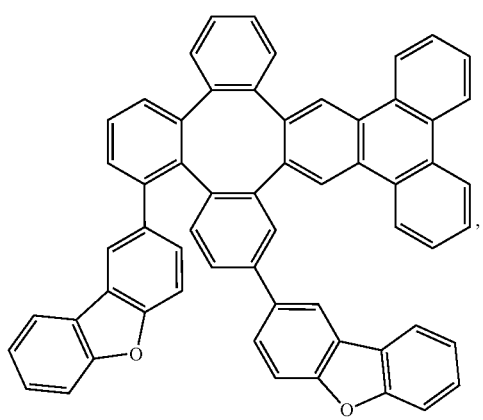
Compound 66
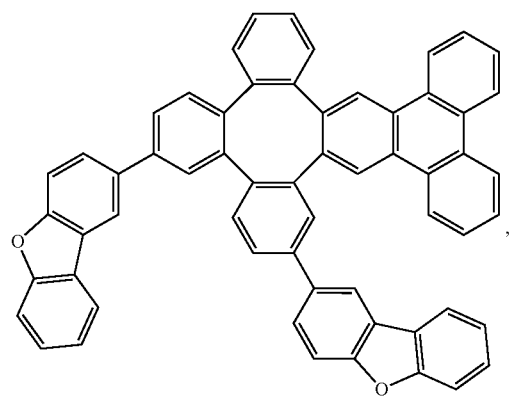
Compound 67
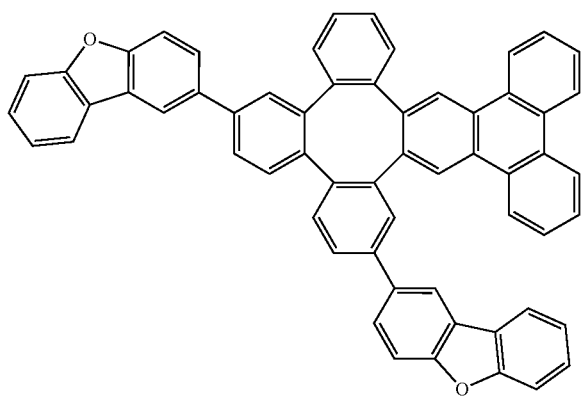

-continued
Compound 68
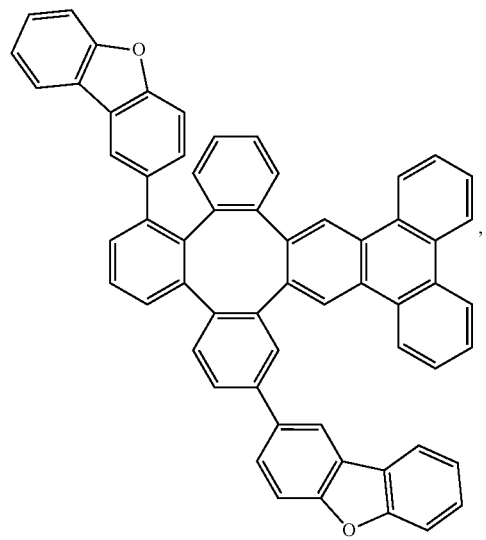
Compound 69
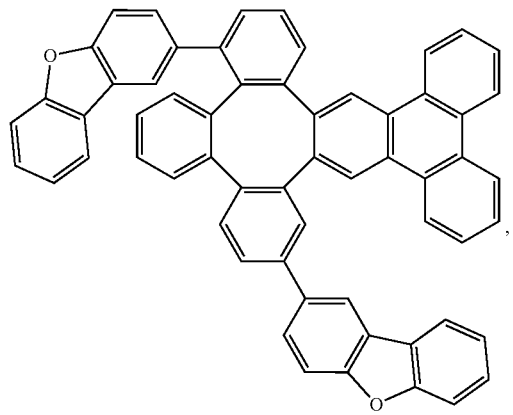
Compound 70
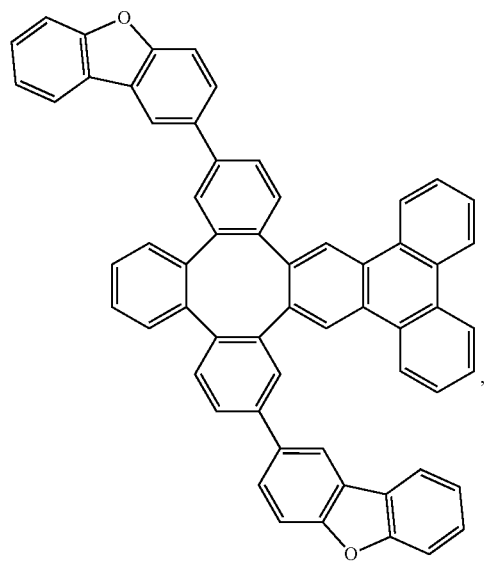
Compound 71
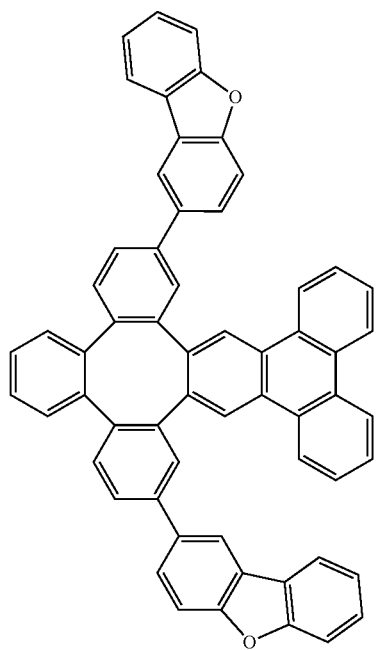

-continued
Compound 72
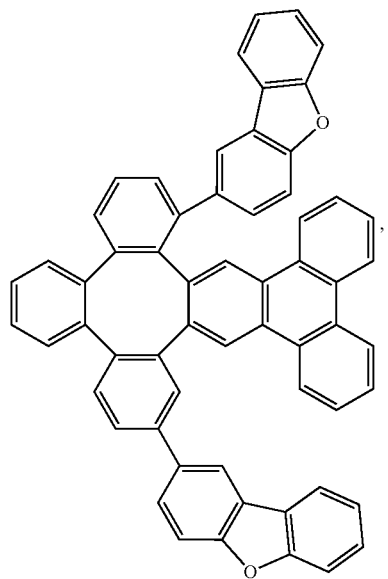
Compound 73
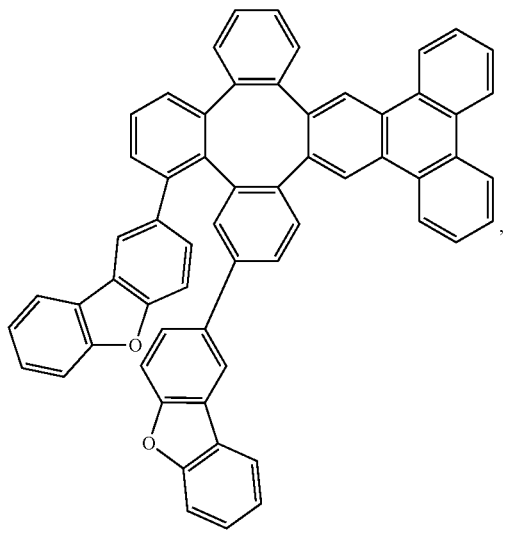
Compound 74
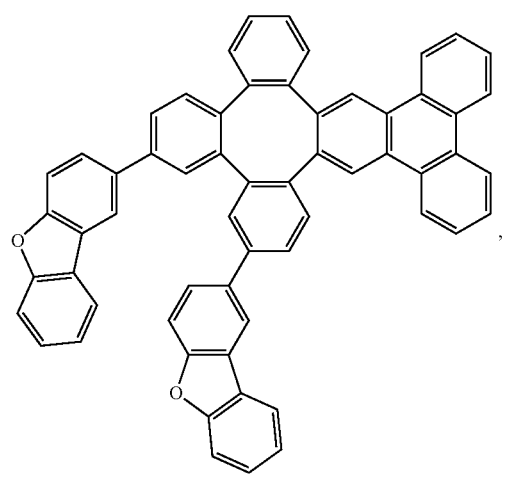
Compound 75
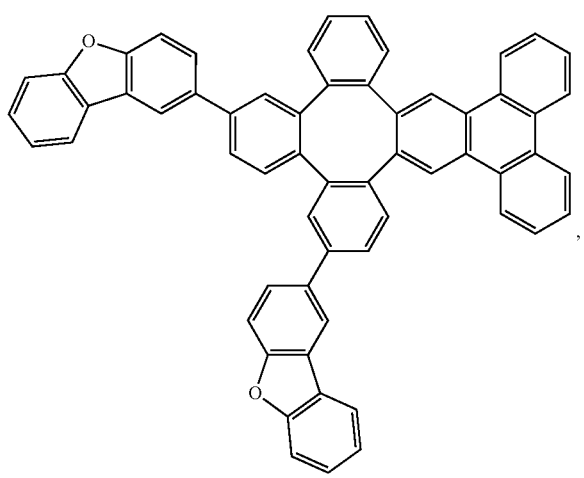

-continued
Compound 76
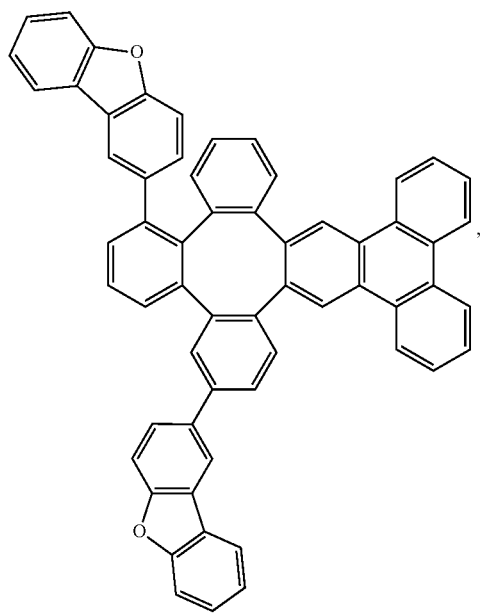
Compound 77
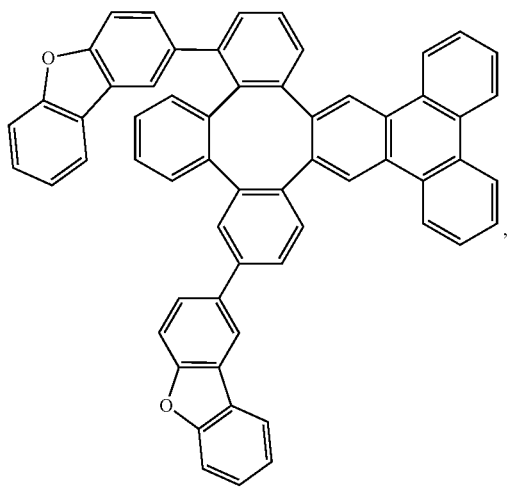
Compound 78
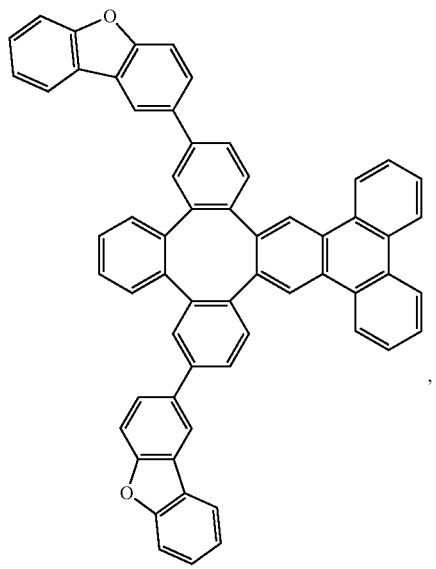
Compound 79
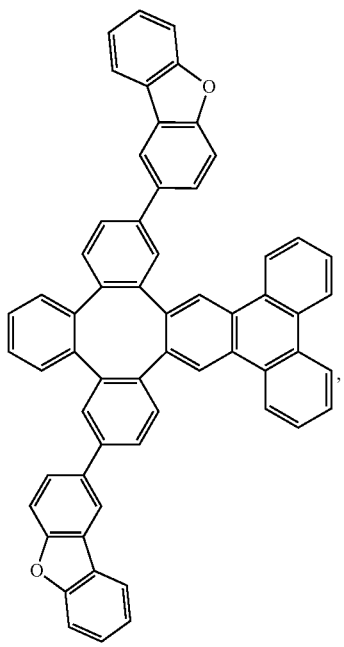

-continued
Compound 80
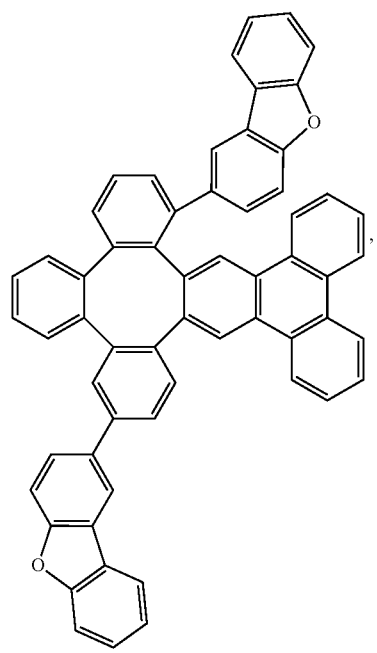
Compound 81
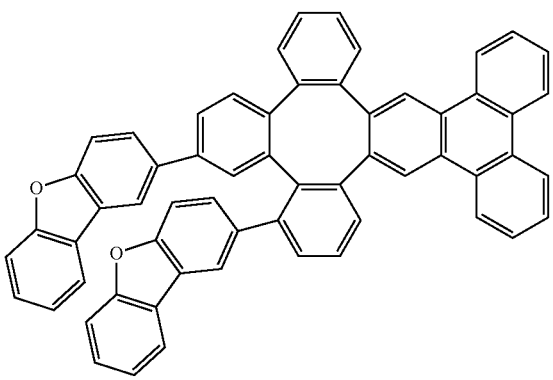
Compound 82
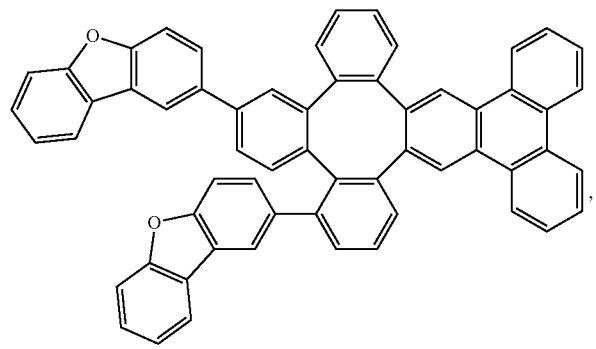
Compound 83
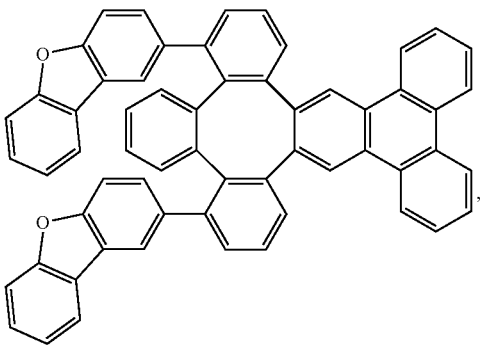
Compound 84
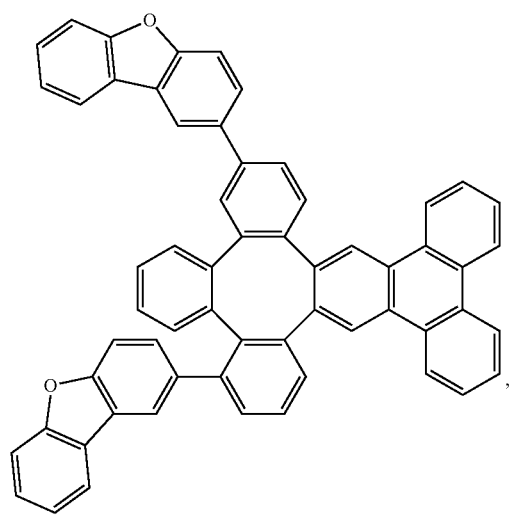
Compound 85
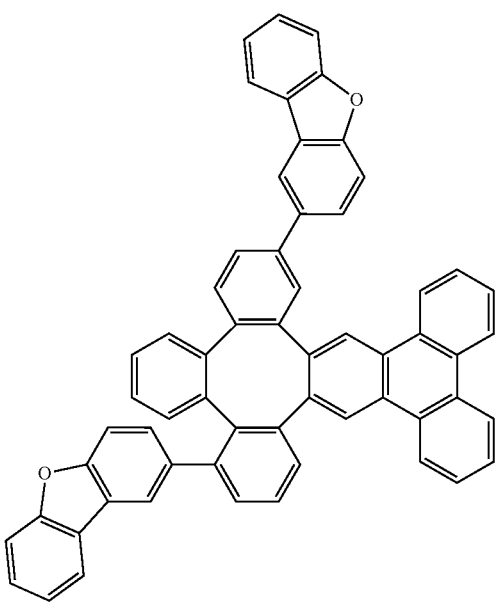

Compound 86
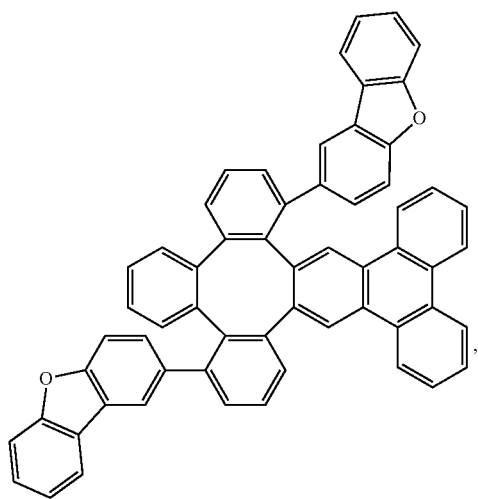
Compound 87
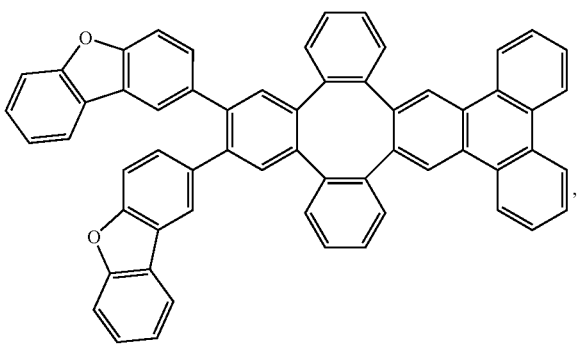
Compound 88
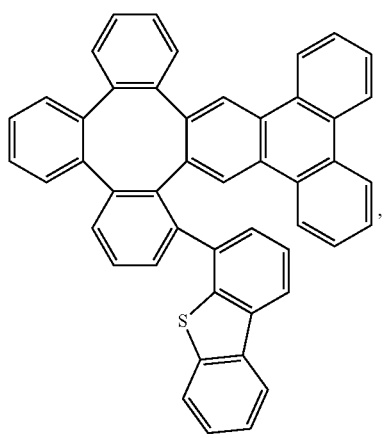
Compound 89
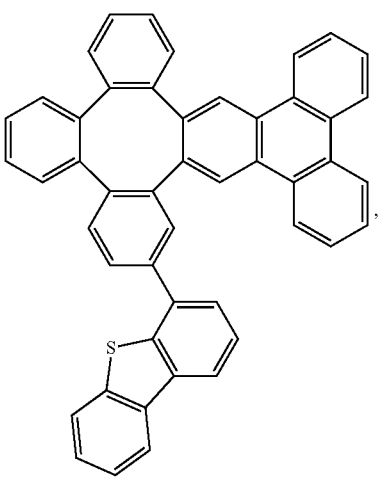
Compound 90
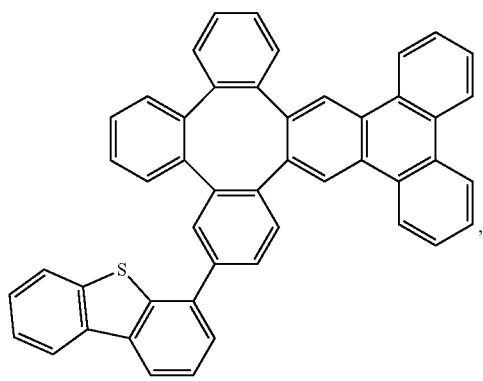
Compound 91
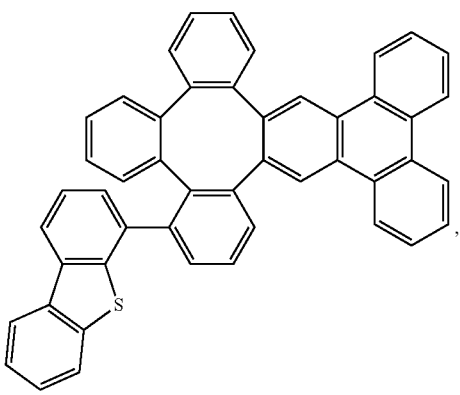

-continued
Compound 92
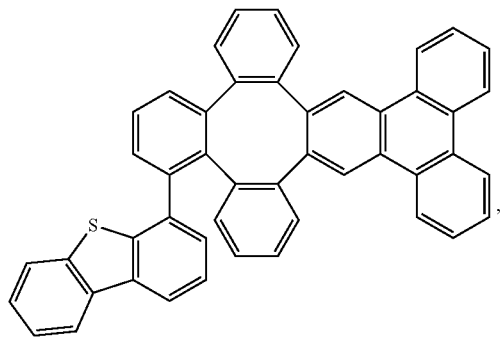
Compound 93
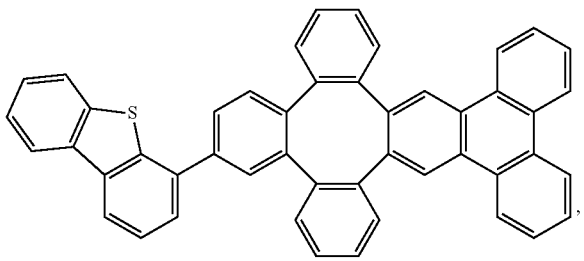
Compound 94
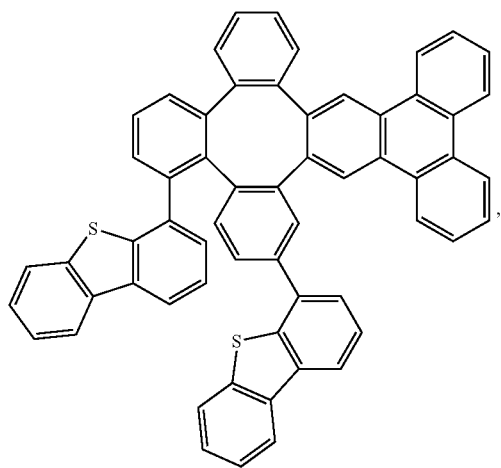
Compound 95
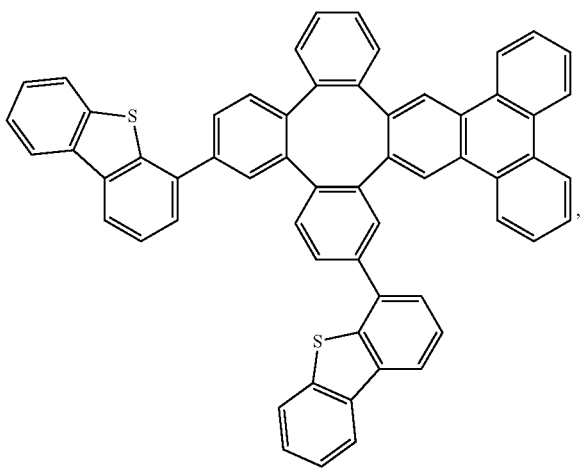
Compound 96
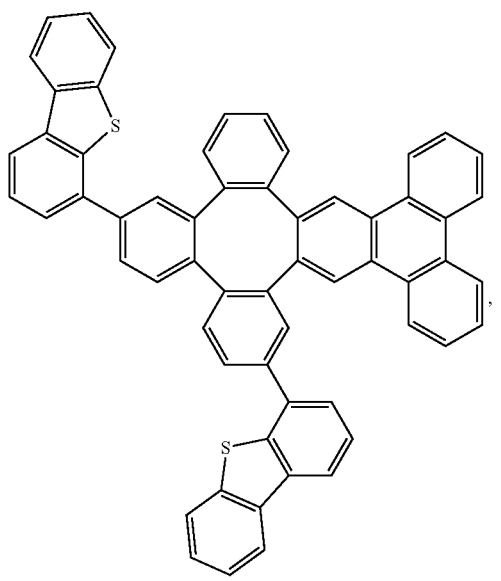
Compound 97
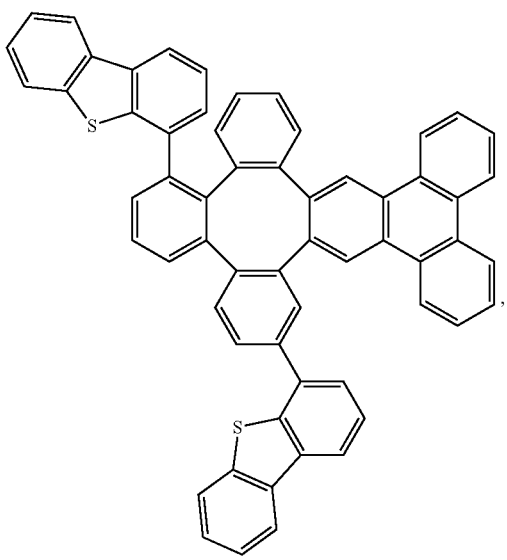

Compound 98
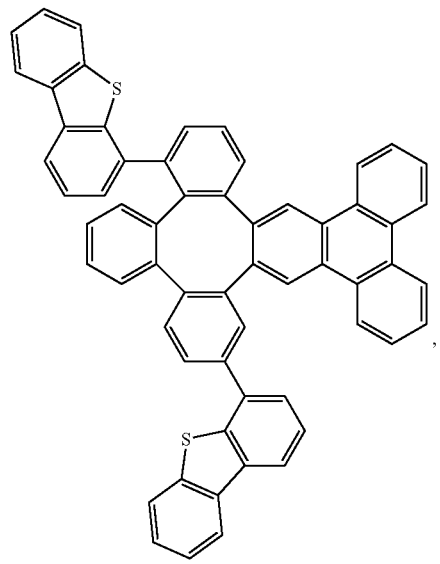
Compound 99
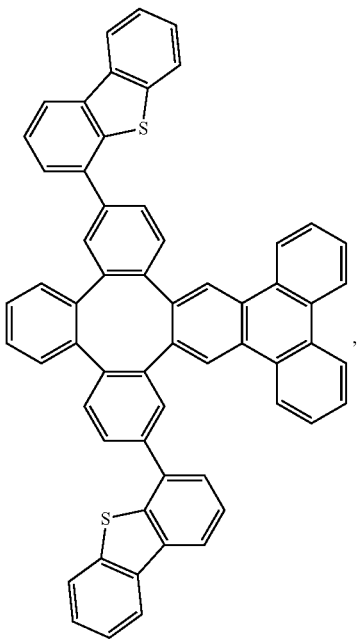
Compound 100
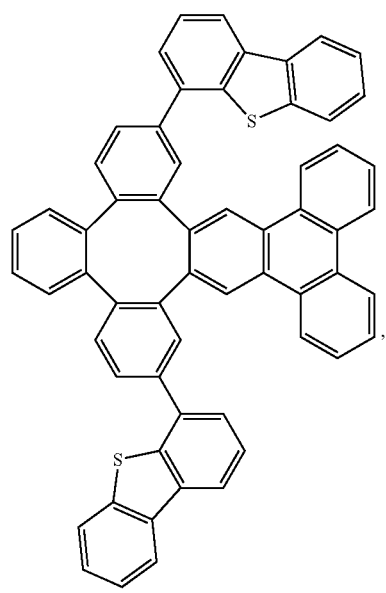
Compound 101
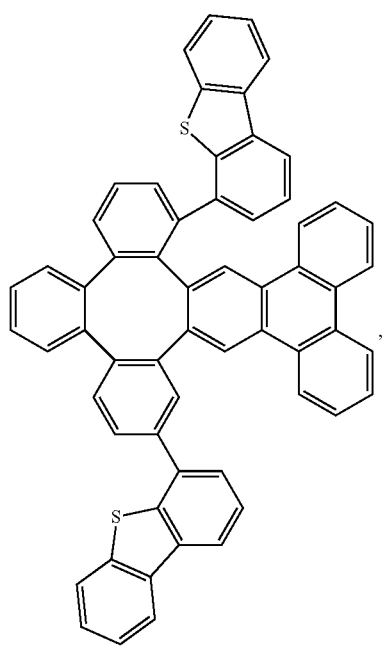

-continued
Compound 102
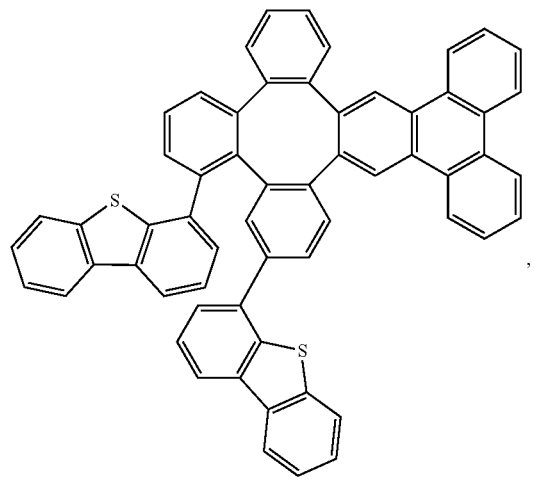
Compound 103
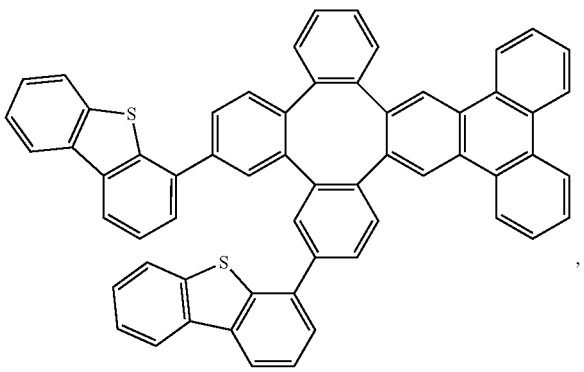
Compound 104
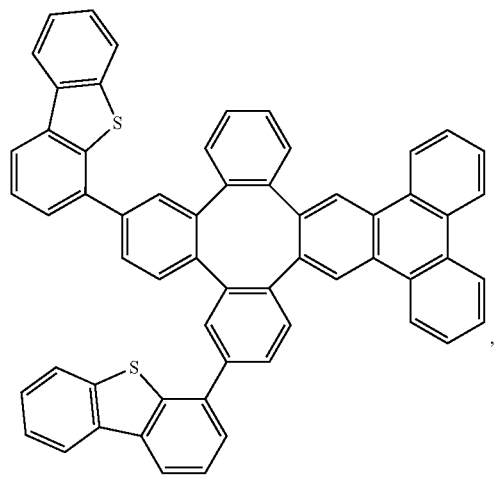
Compound 105
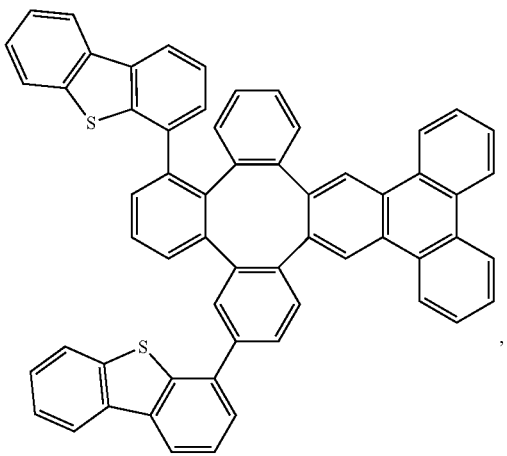
Compound 106
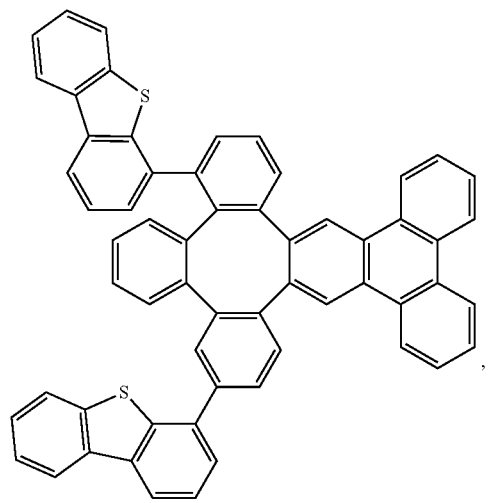
Compound 107
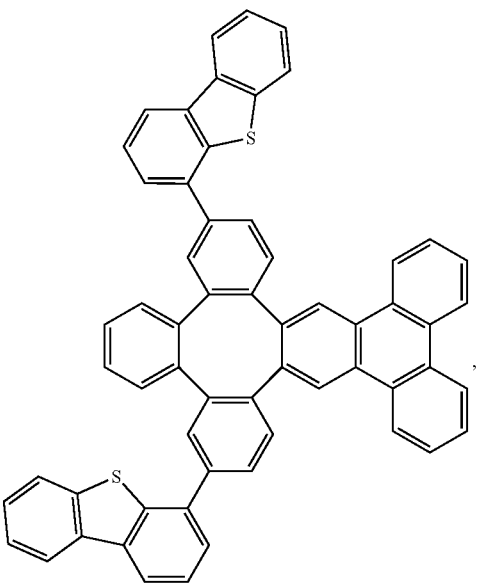

-continued
Compound 108
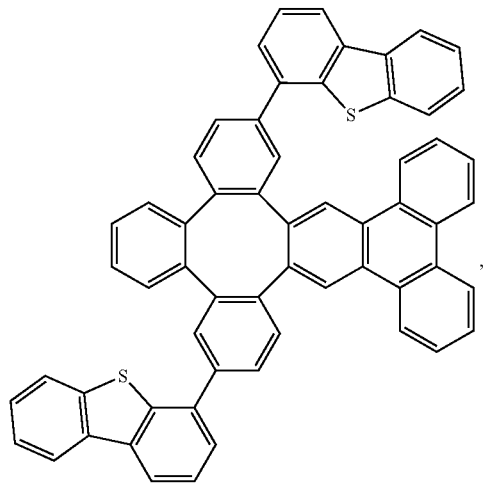
Compound 109
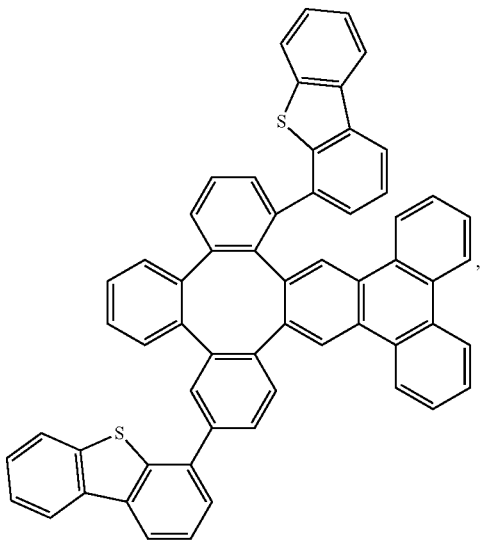
Compound 110
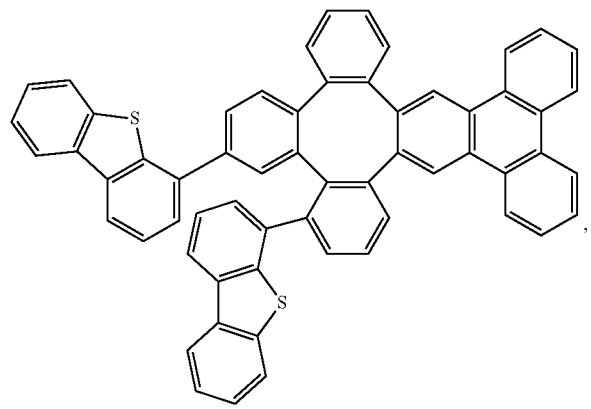
Compound 111
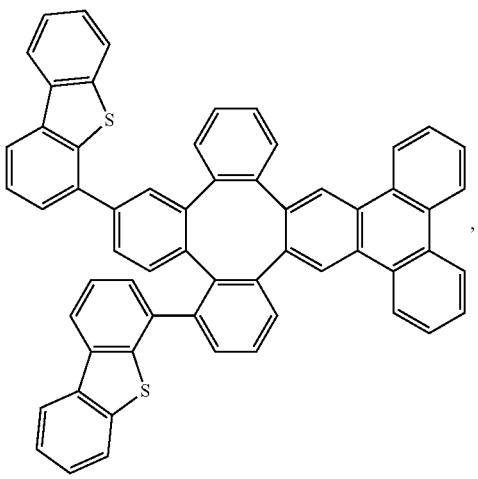
Compound 112
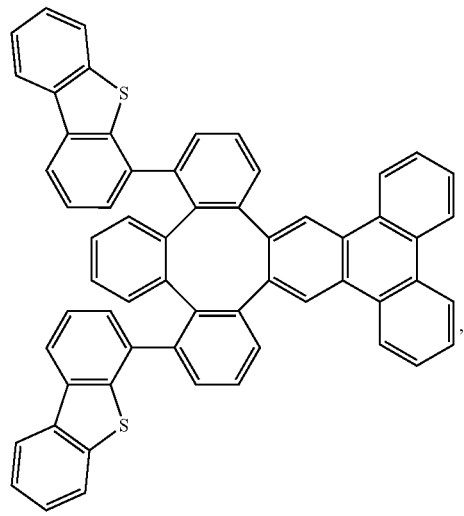
Compound 113
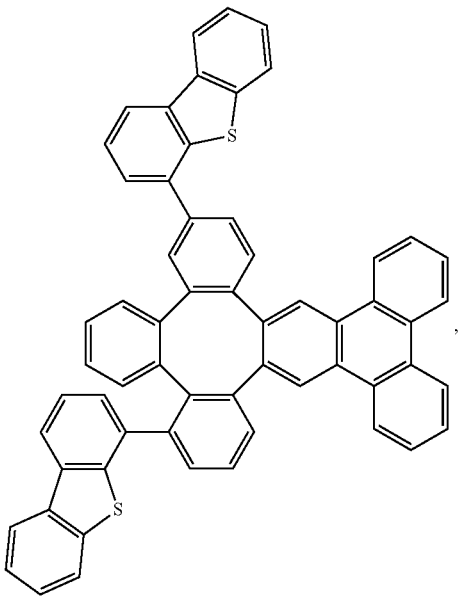

-continued
Compound 114
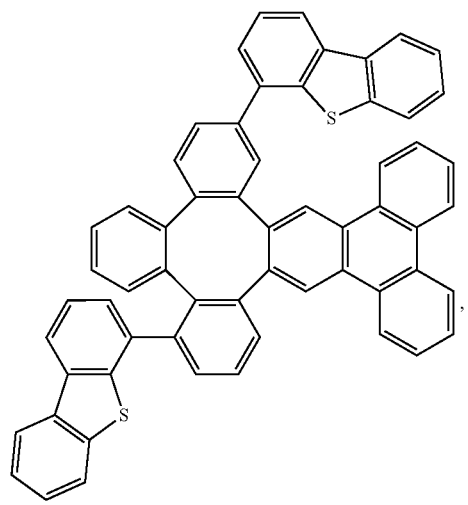
Compound 115
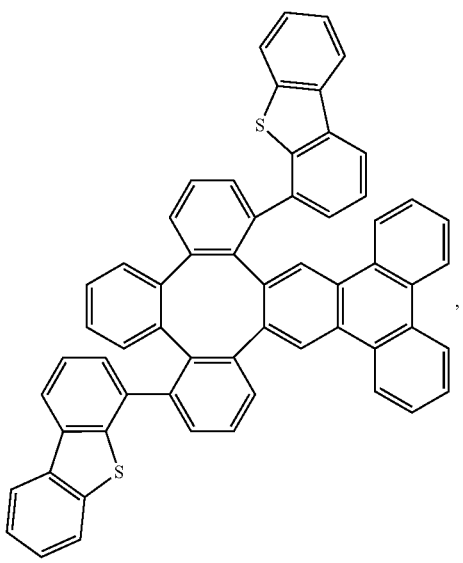
Compound 116
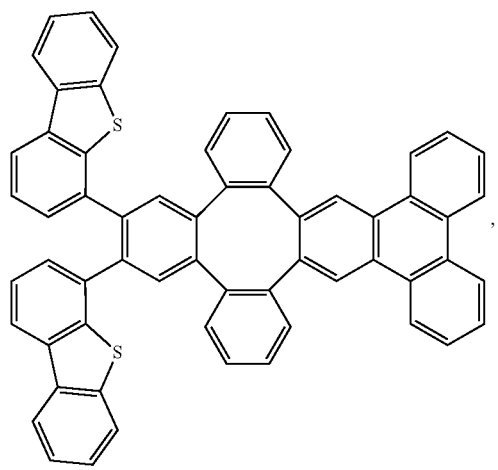
Compound 117
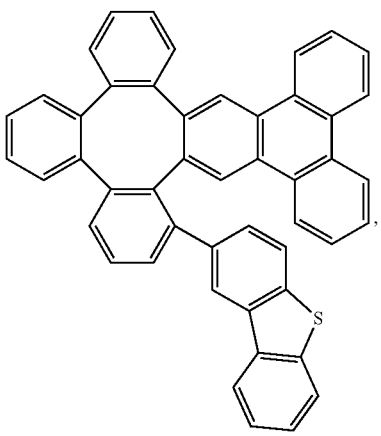
Compound 118
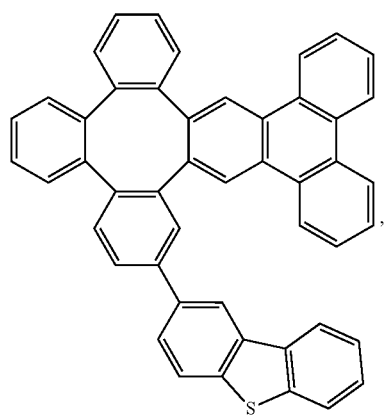
Compound 119
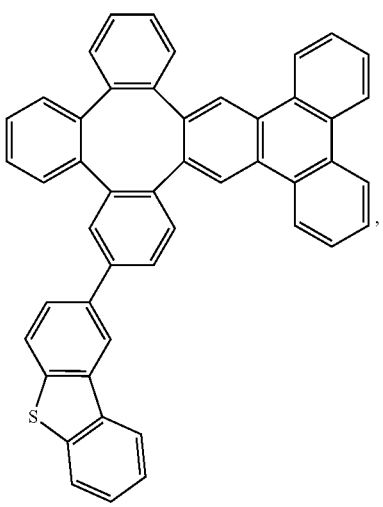

-continued
Compound 120
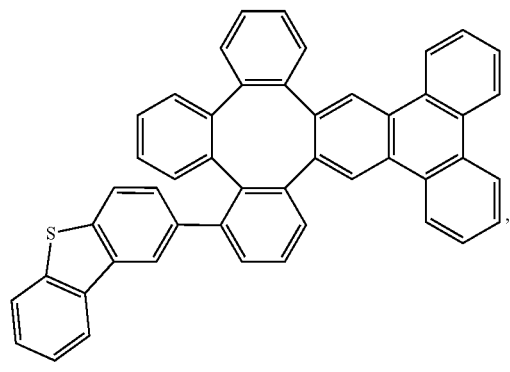
Compound 121
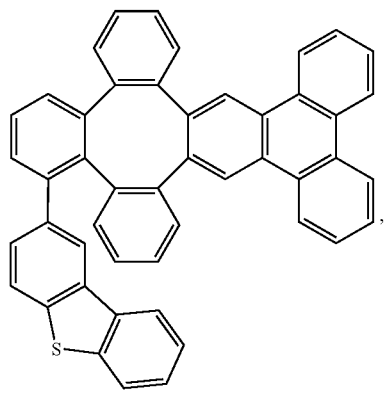
Compound 122
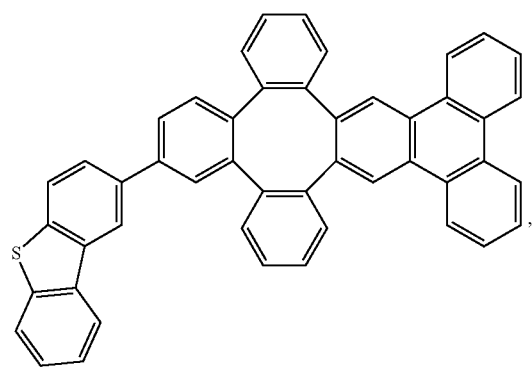
Compound 123
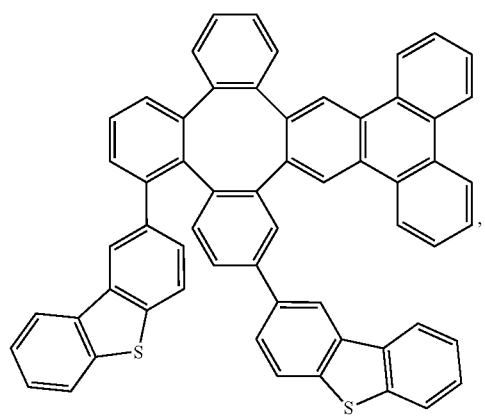
Compound 124
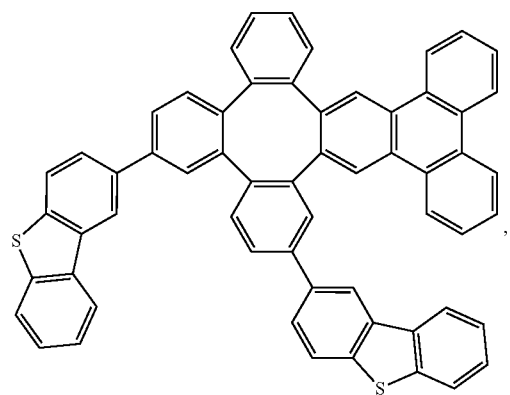
Compound 125
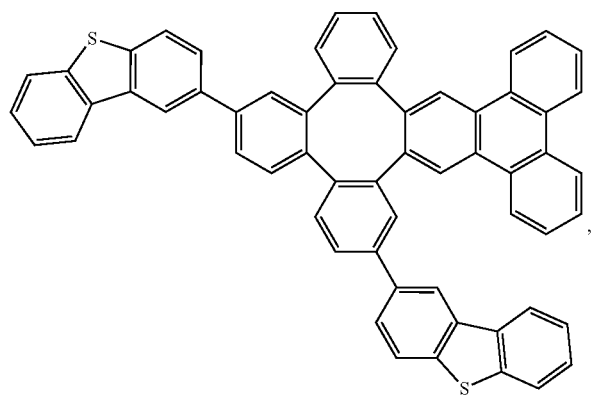

-continued
Compound 126
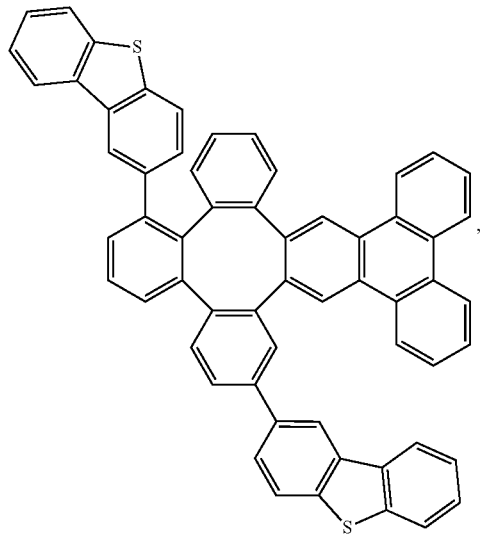
Compound 127
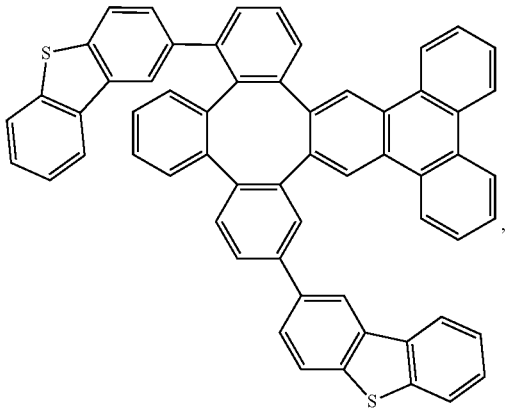
Compound 128
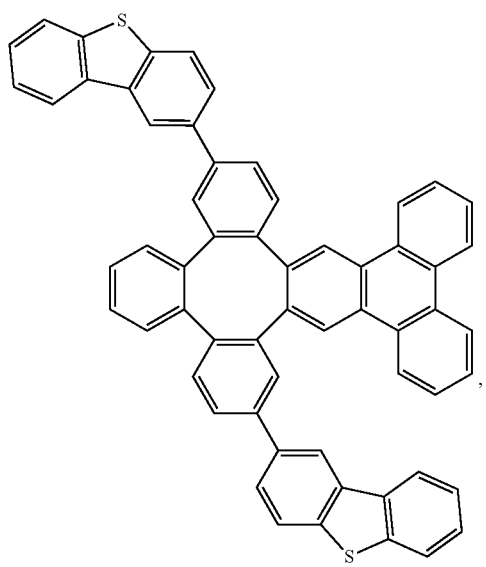
Compound 129
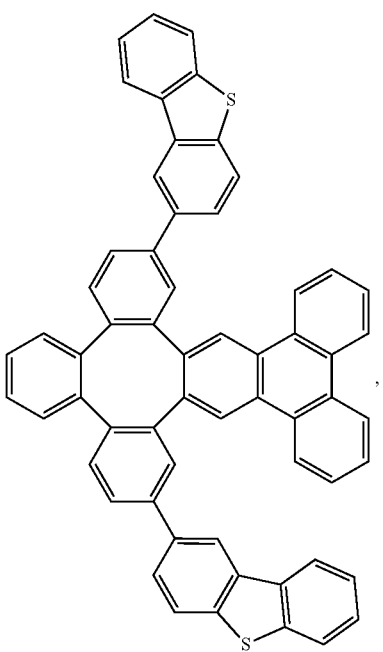

-continued
Compound 130
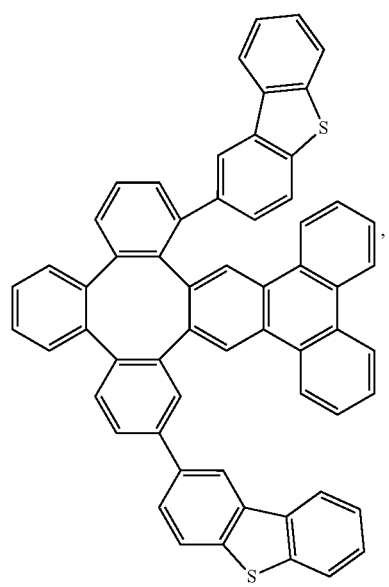
Compound 131
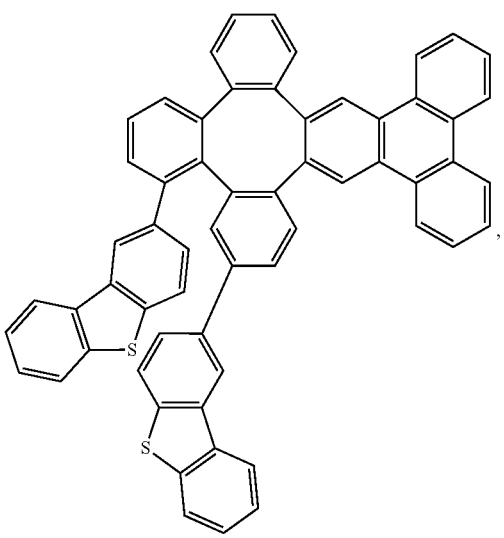
Compound 132
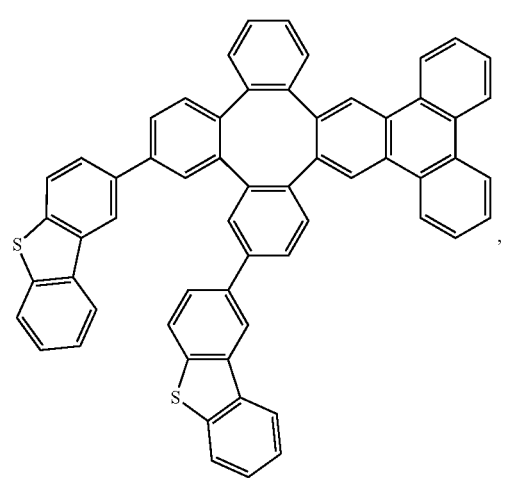
Compound 133
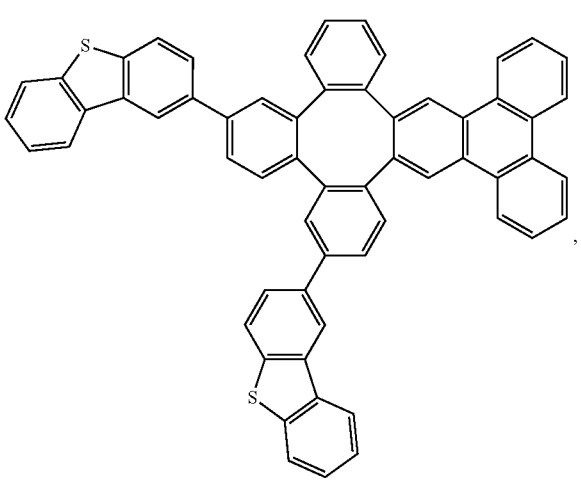

-continued
Compound 134
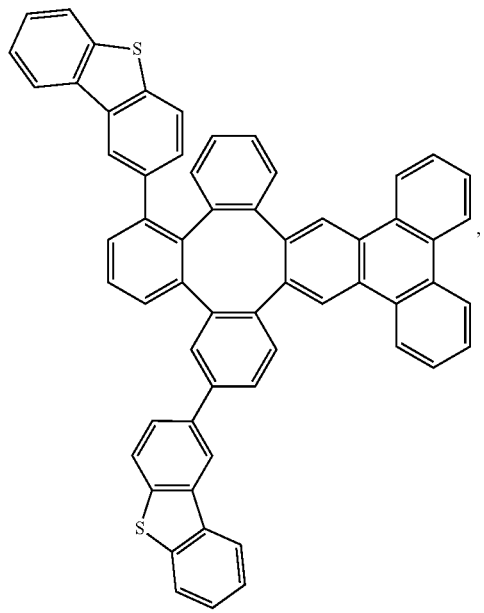
Compound 135
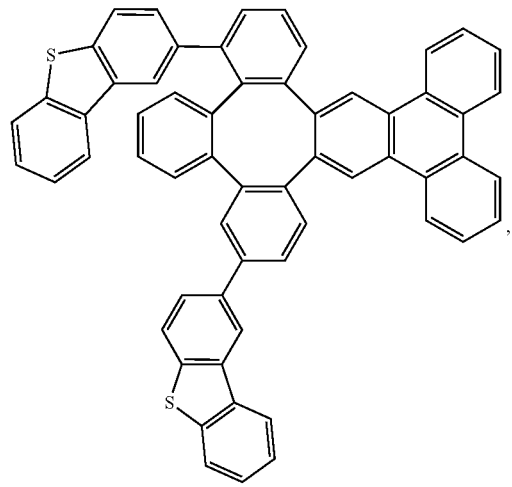
Compound 136
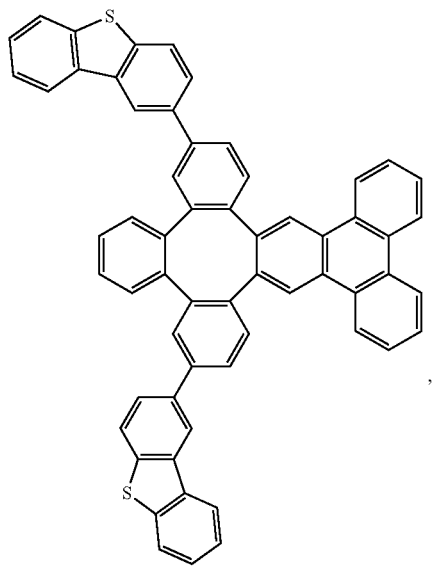
Compound 137
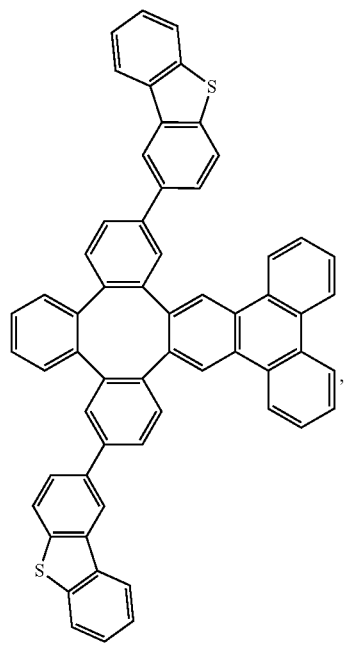

-continued
Compound 138
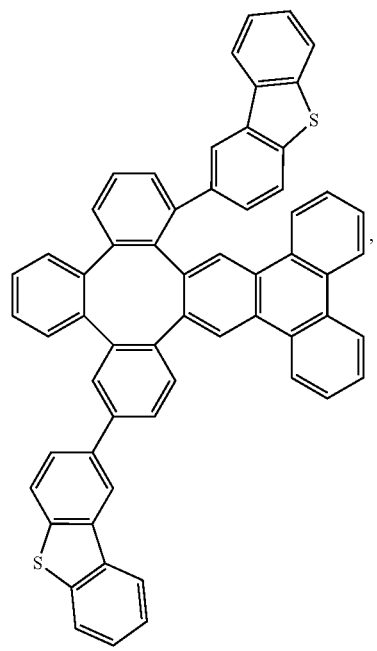
Compound 139
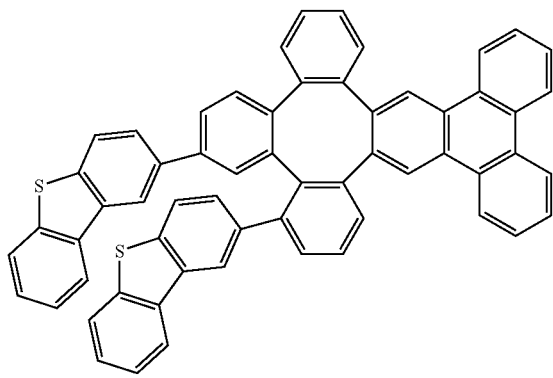
Compound 140
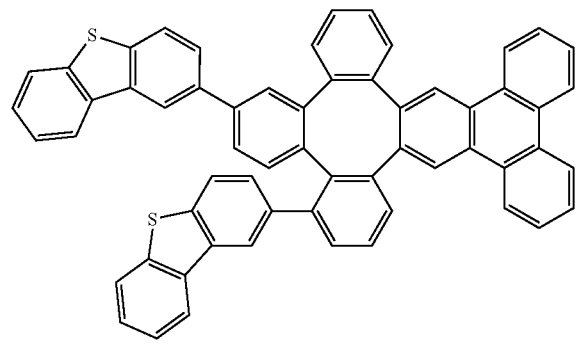
Compound 141
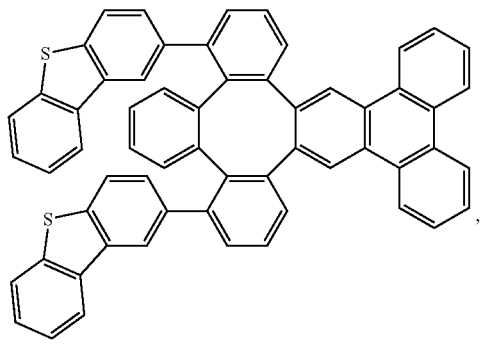
Compound 142
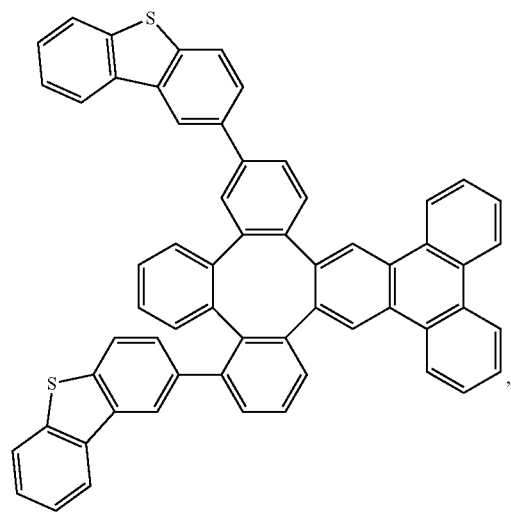
Compound 143
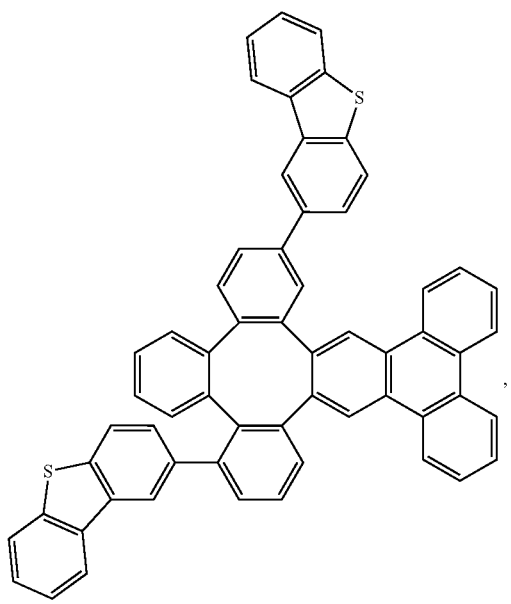

-continued
Compound 144
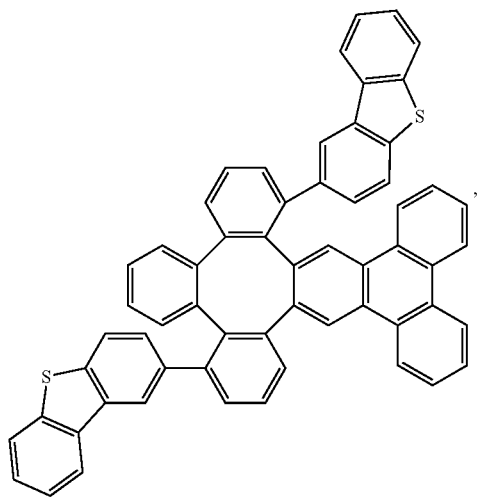
Compound 145
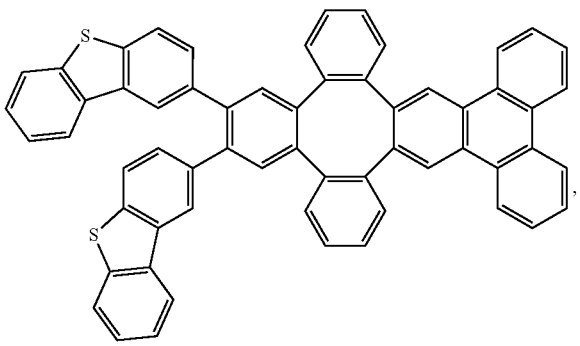
Compound 146
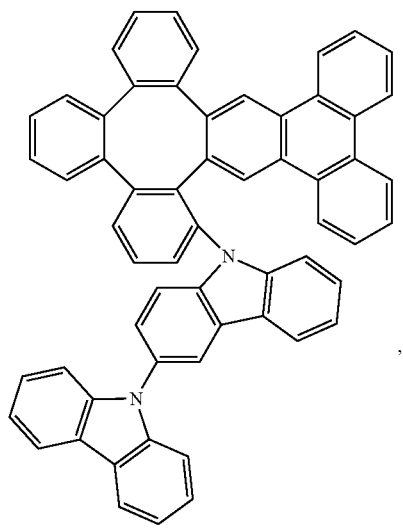
Compound 147
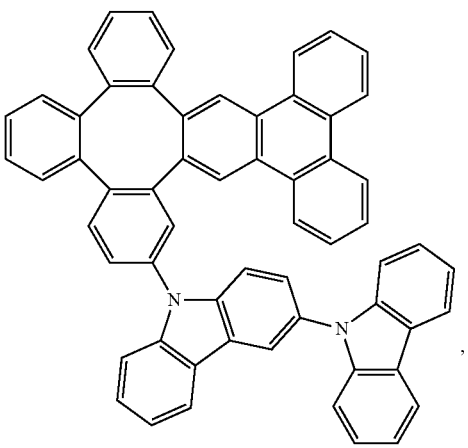
Compound 148
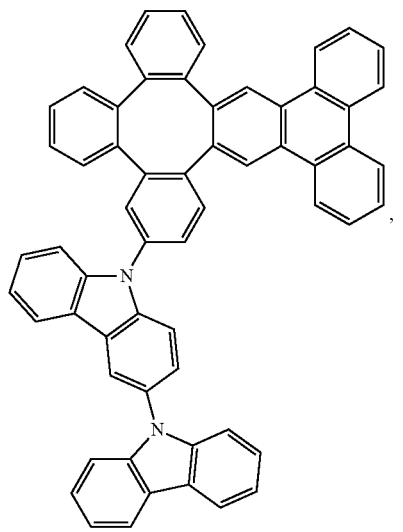
Compound 149
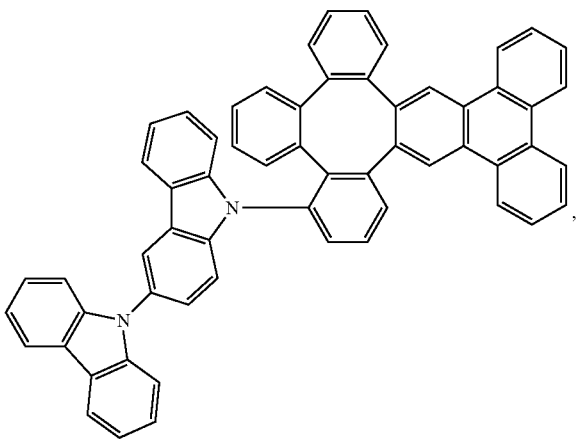

-continued
Compound 150
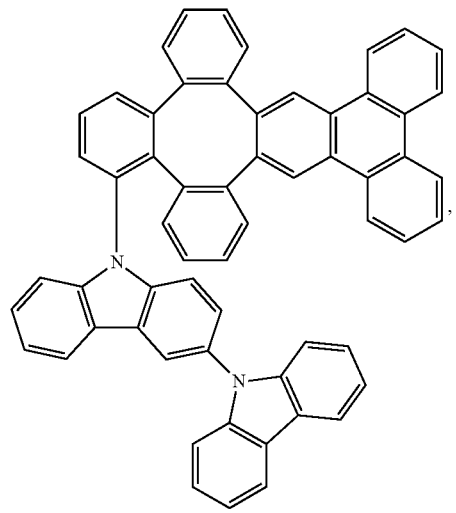
Compound 151
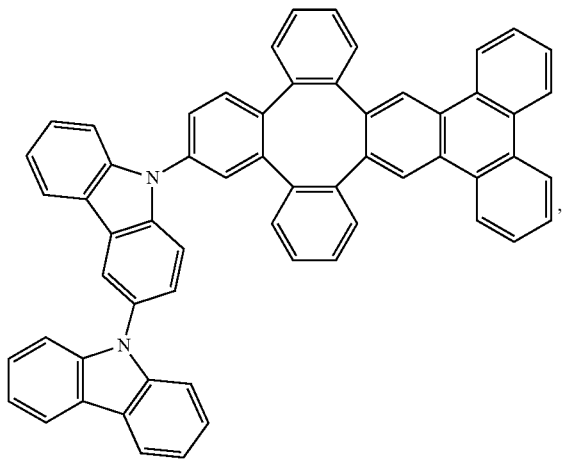
Compound 152 Compound 153
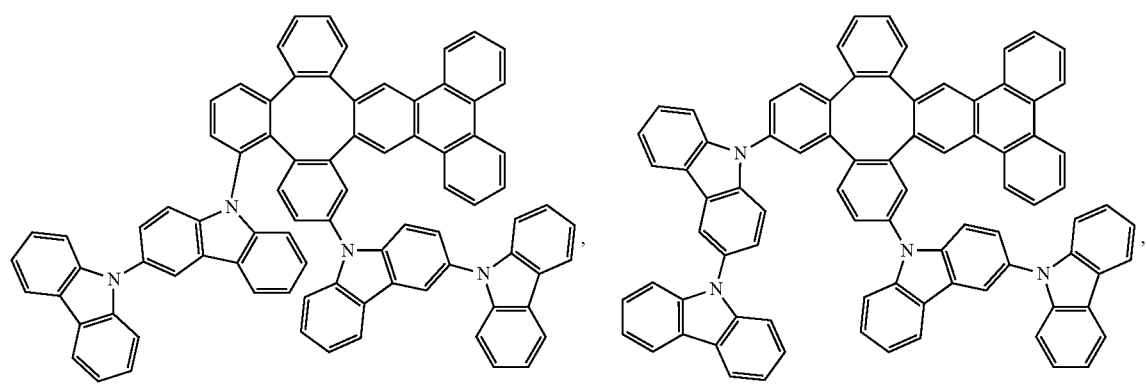
Compound 154
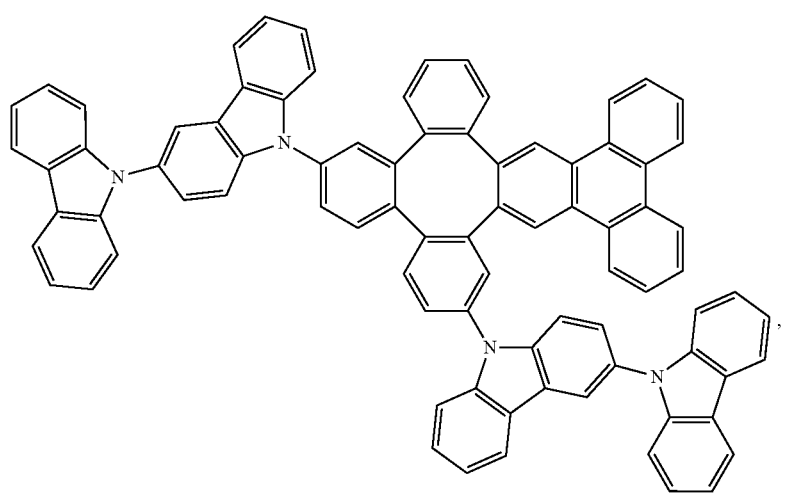

Compound 155
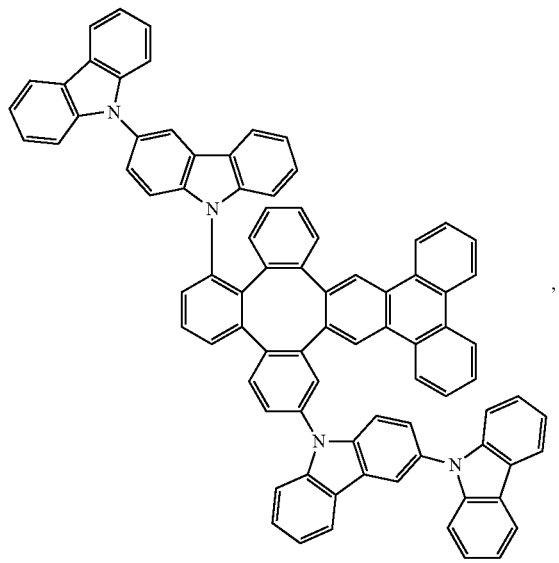
Compound 156
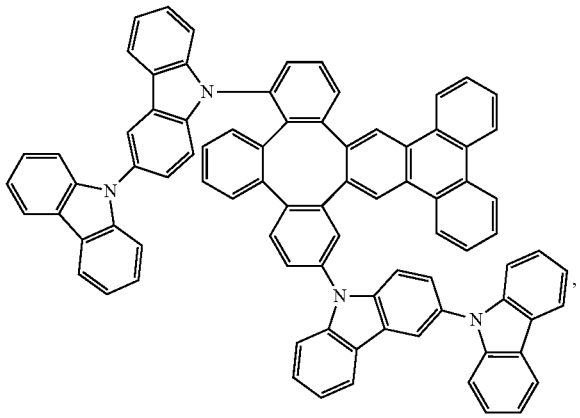
Compound 157
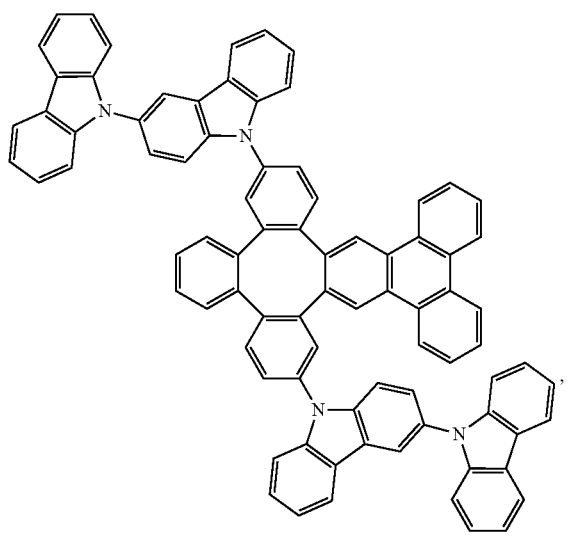
Compound 158
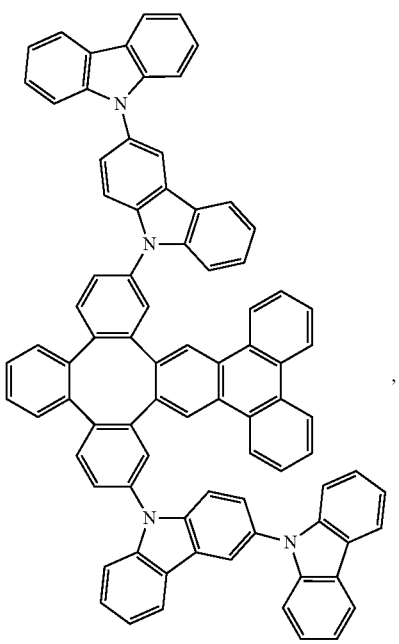

Compound 159
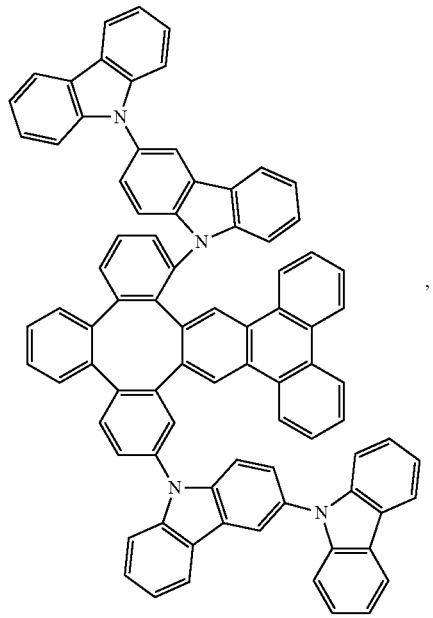
Compound 160
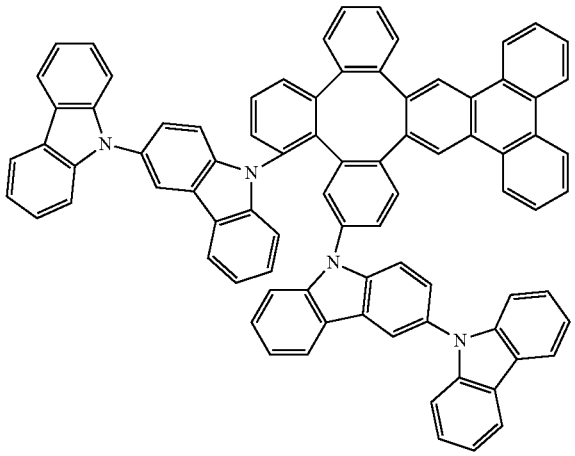
Compound 161
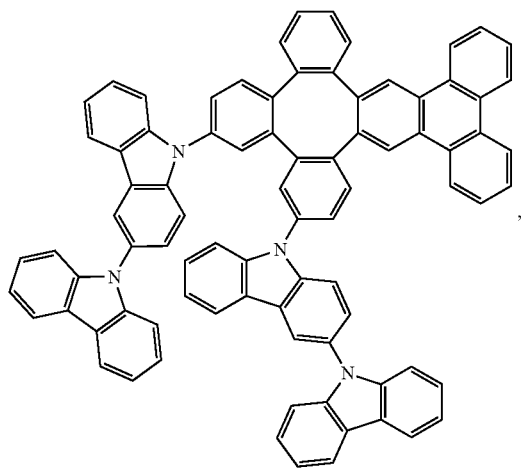
Compound 162
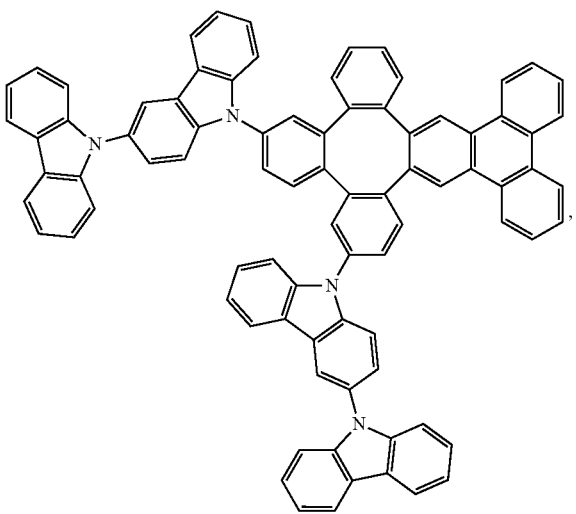

-continued
Compound 163
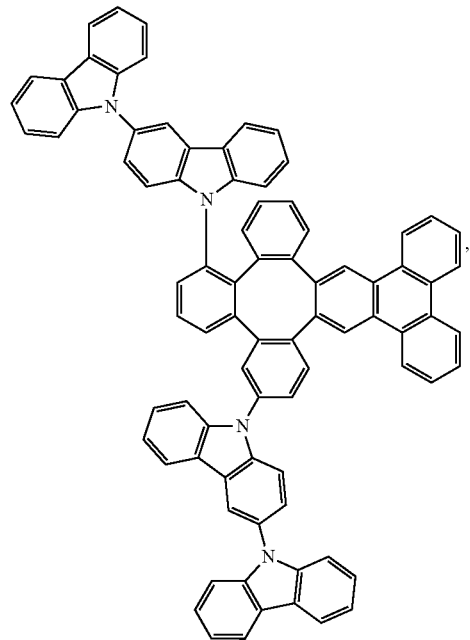
Compound 164
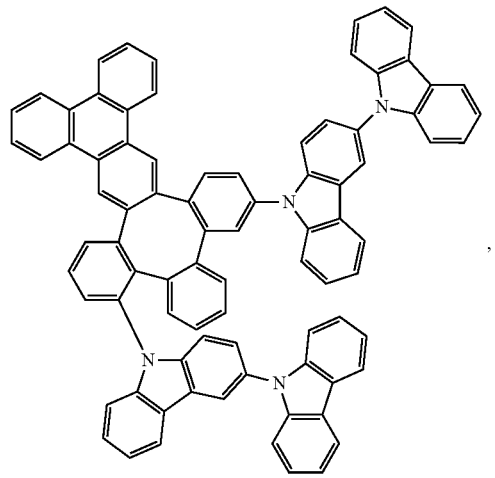
Compound 165
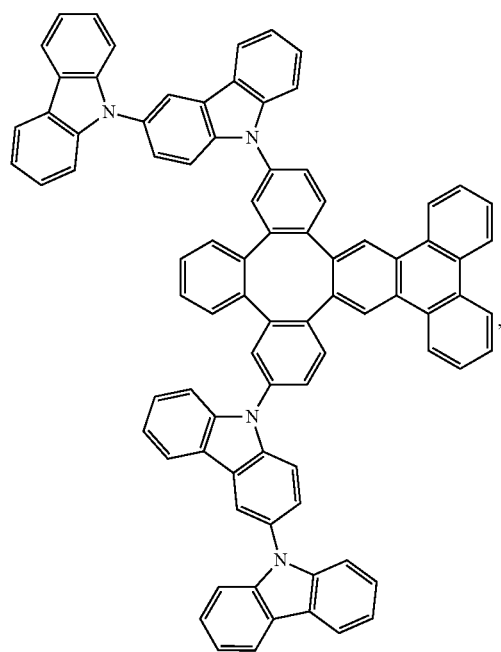
Compound 166
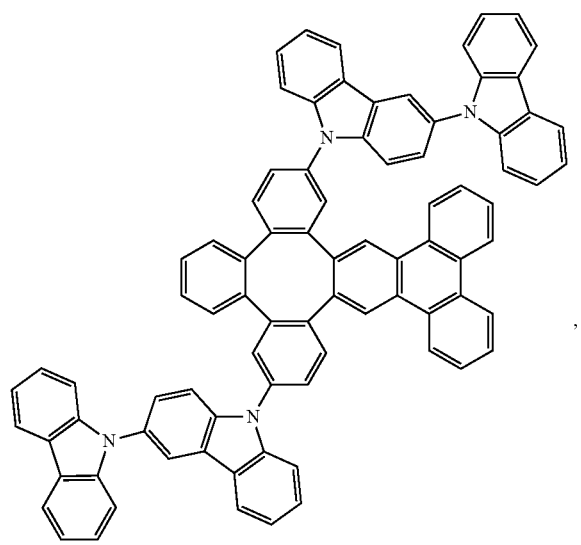

-continued
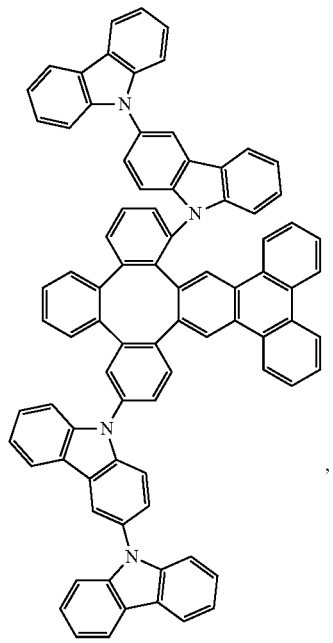
Compound 167
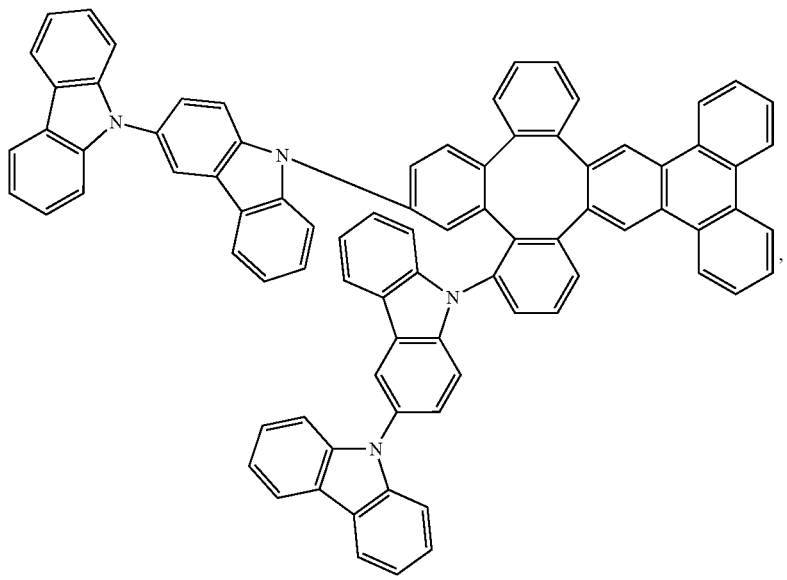
Compound 168

Compound 169
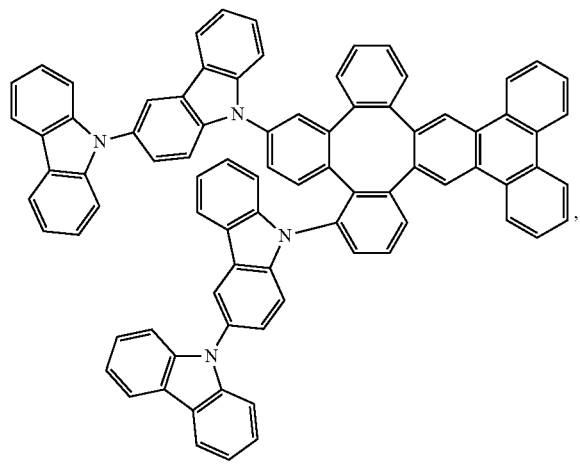
Compound 170
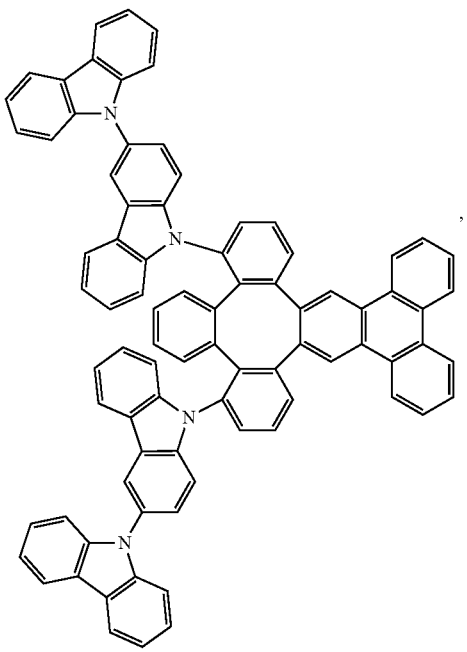
Compound 171
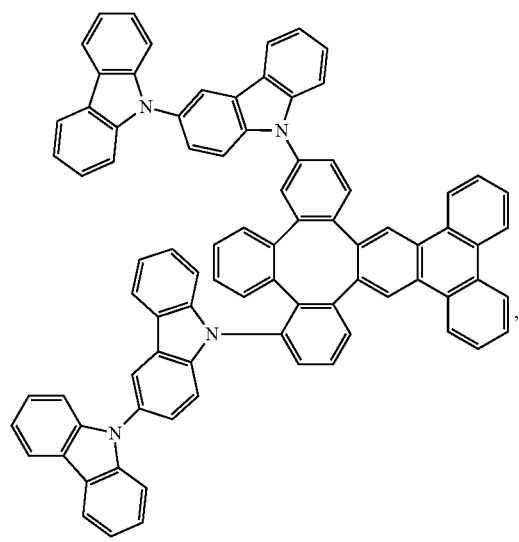
Compound 172
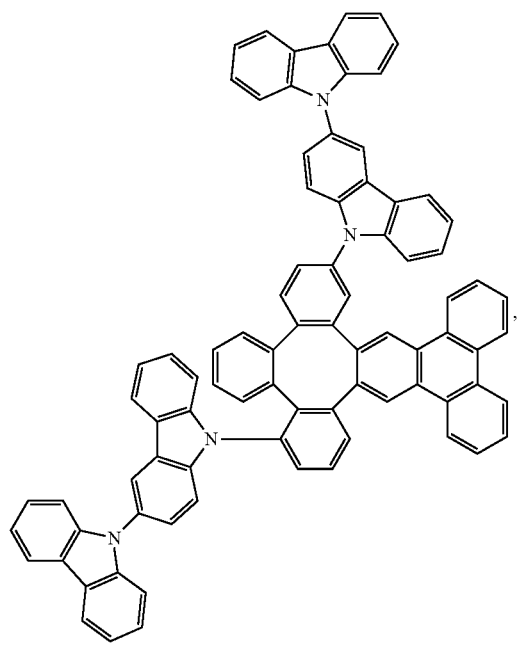

-continued
Compound 173
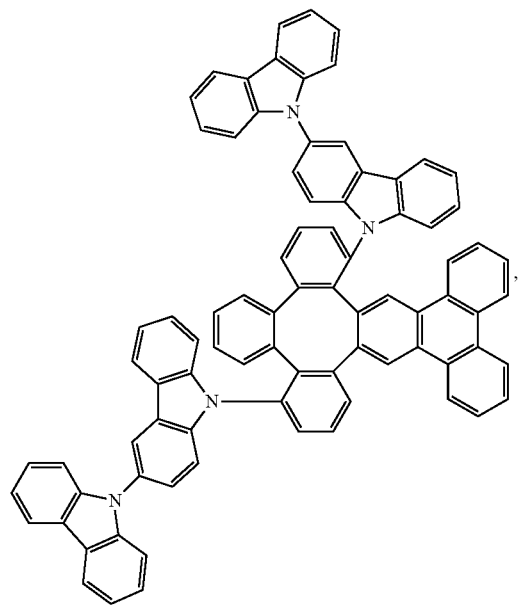
Compound 174
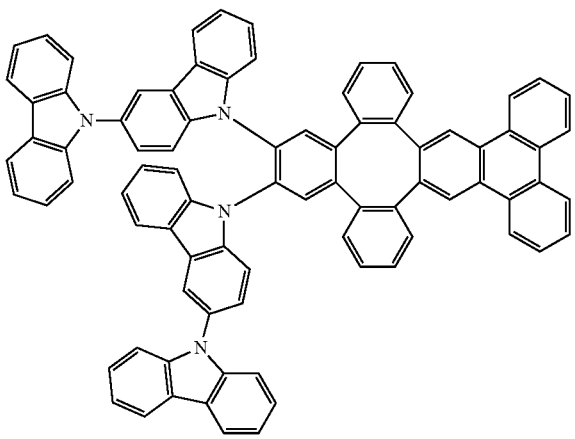
Compound 175
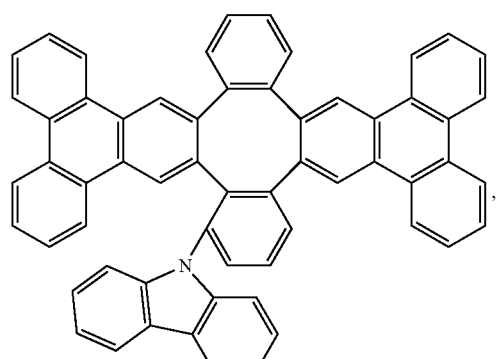
Compound 176
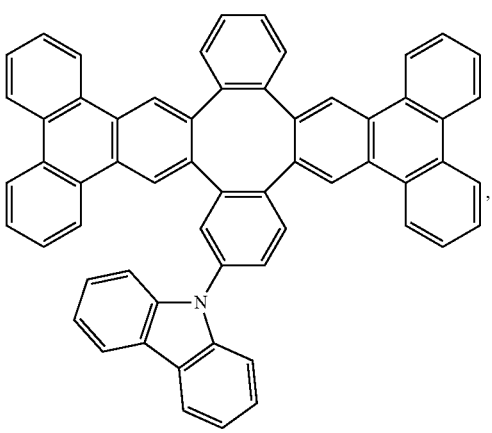

-continued
Compound 177
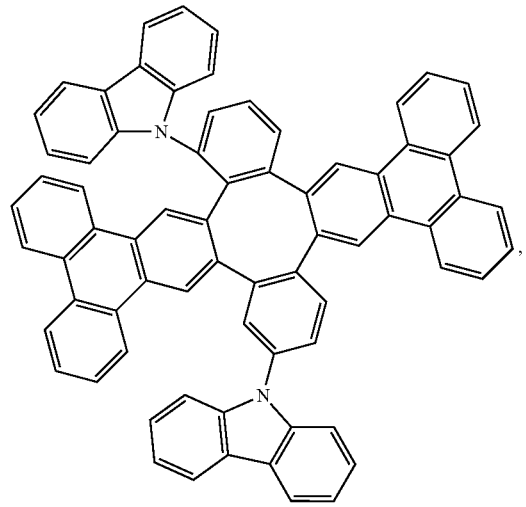
Compound 178
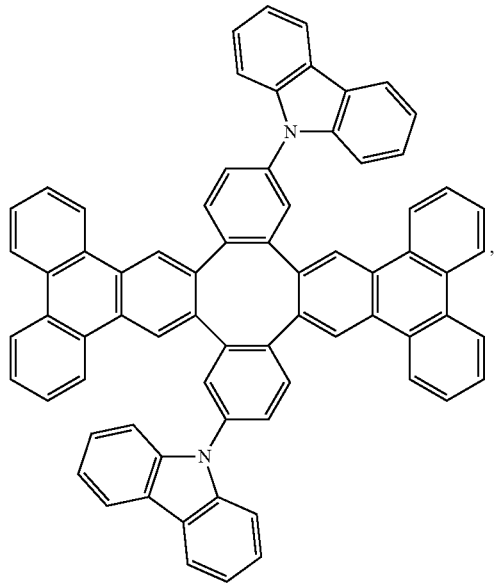
Compound 179
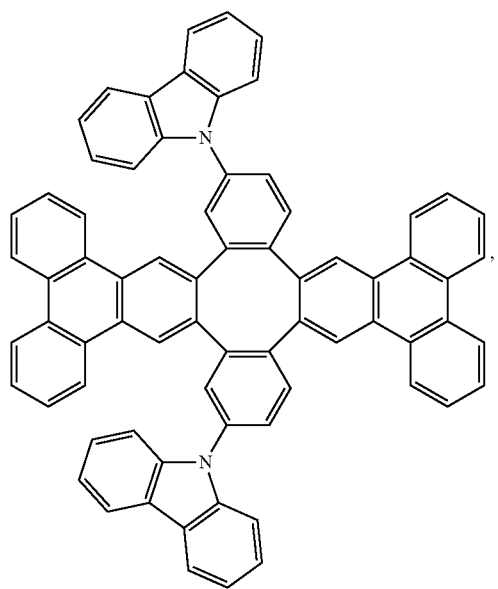
Compound 180
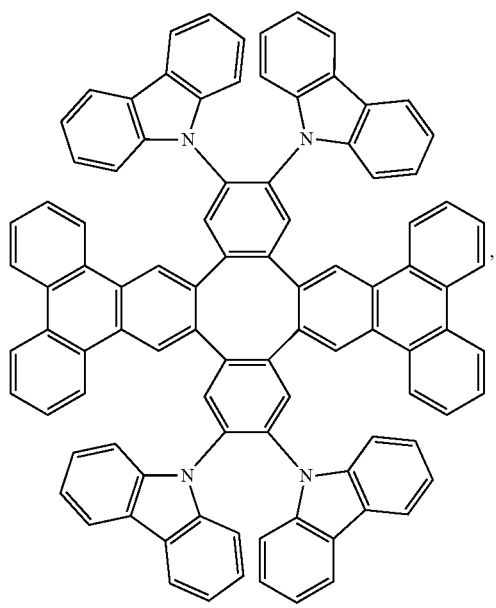

-continued
Compound 181
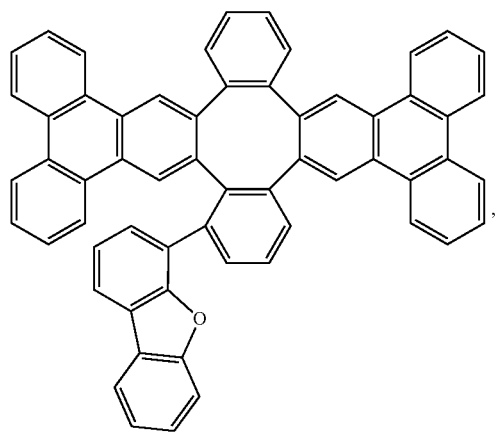
Compound 182
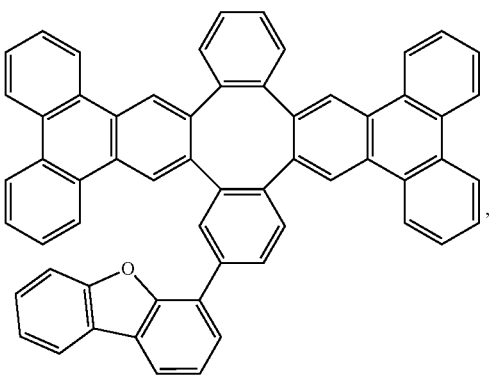
Compound 183
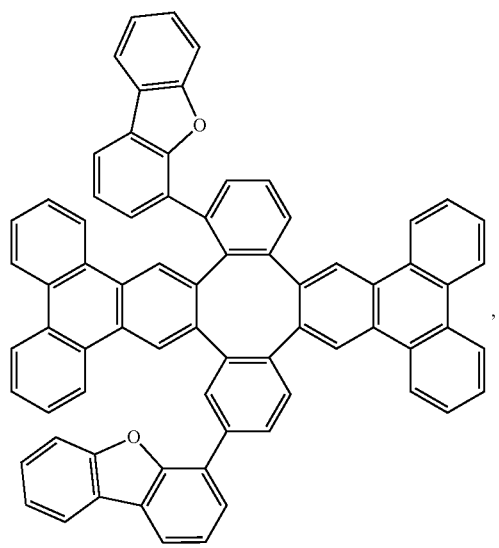
Compound 184
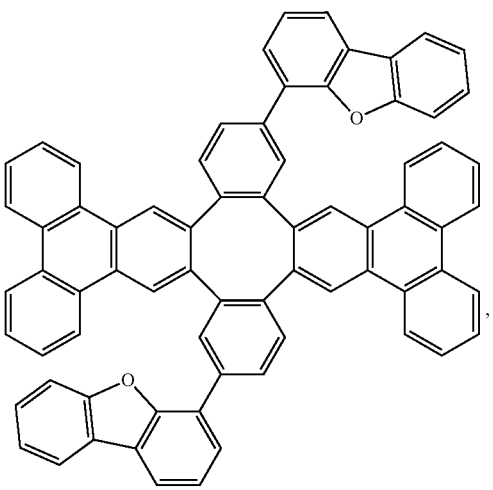
Compound 185
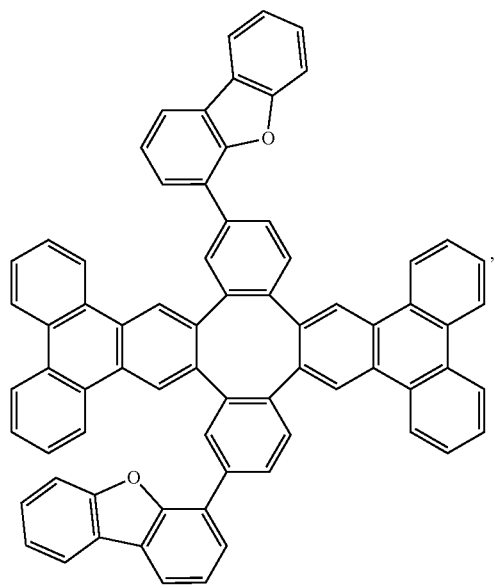
Compound 186
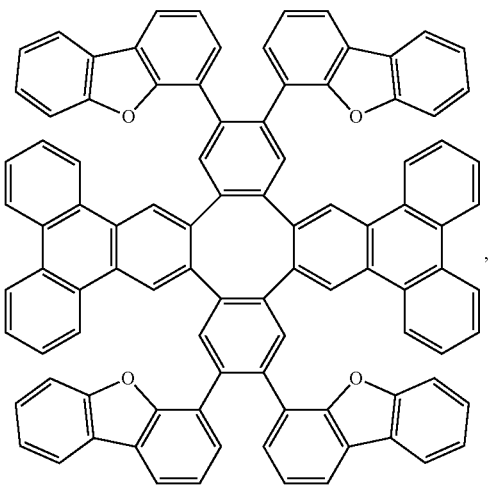

Compound 187
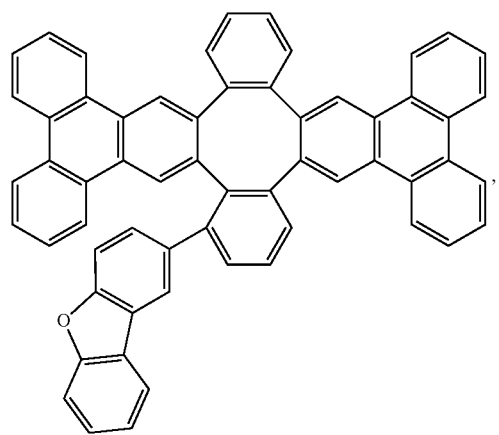
Compound 188
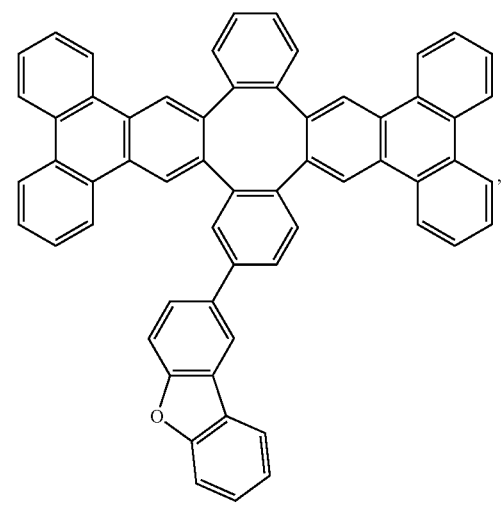
Compound 189
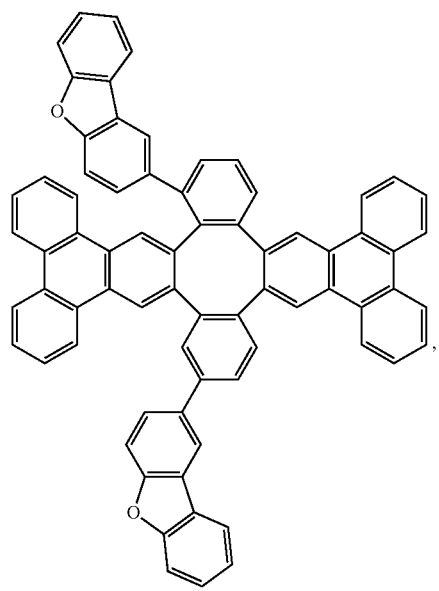
Compound 190
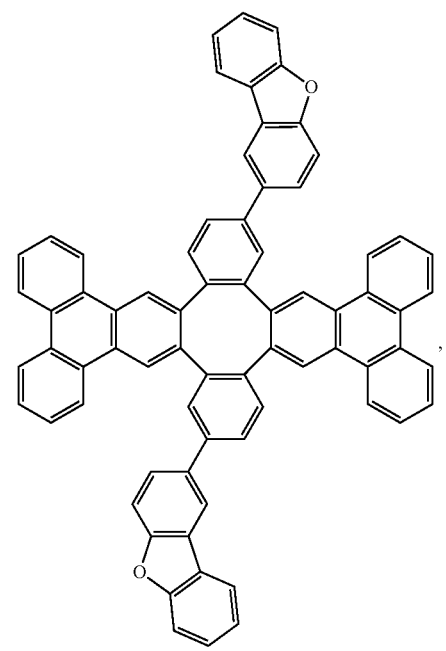

-continued
Compound 191
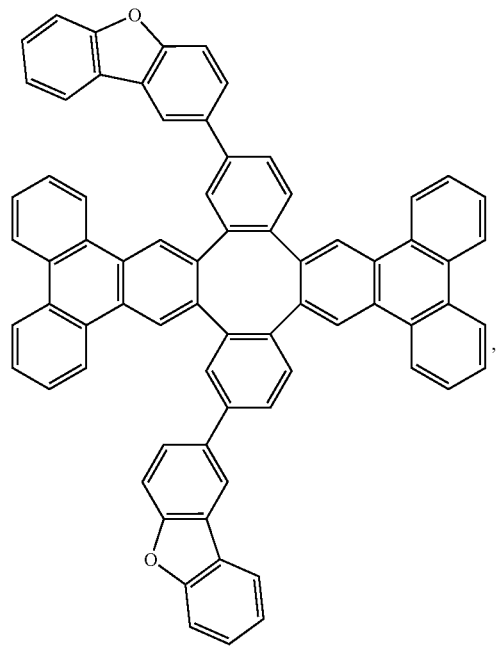
Compound 192
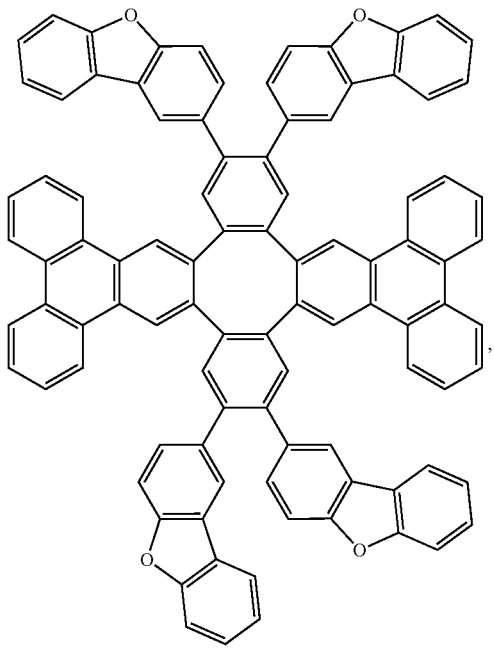
Compound 193
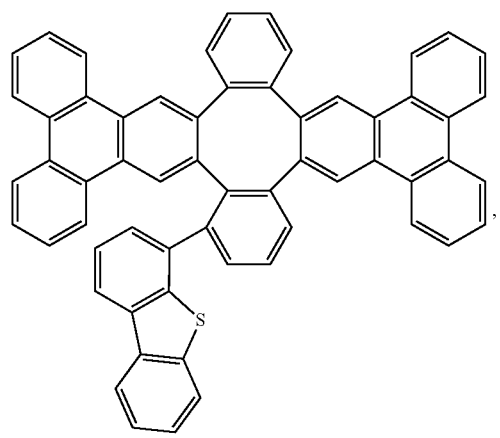
Compound 194
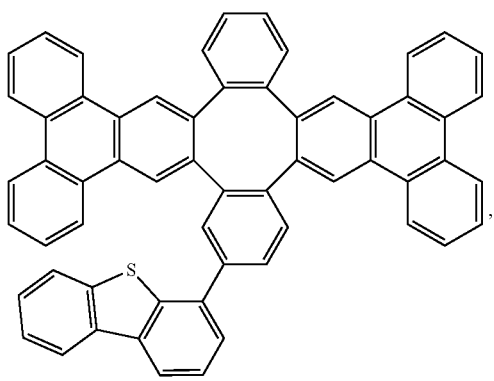

-continued
Compound 195
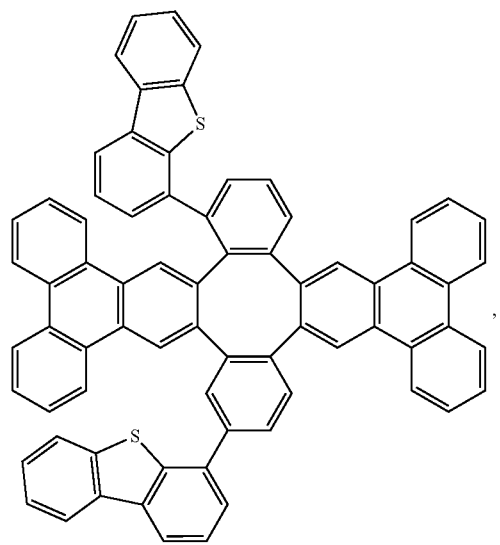
Compound 196
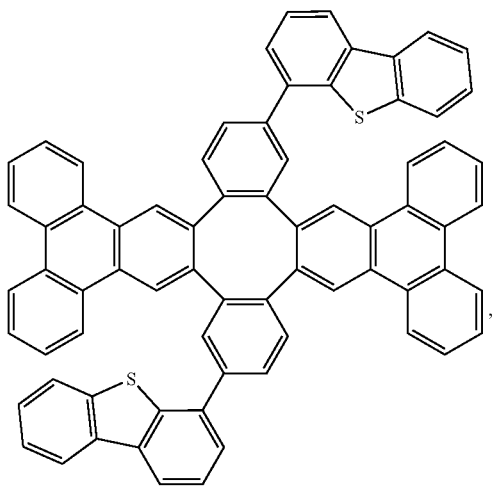
Compound 197
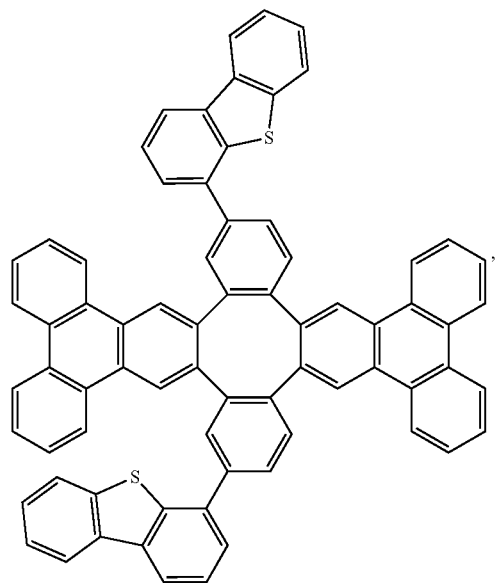
Compound 198
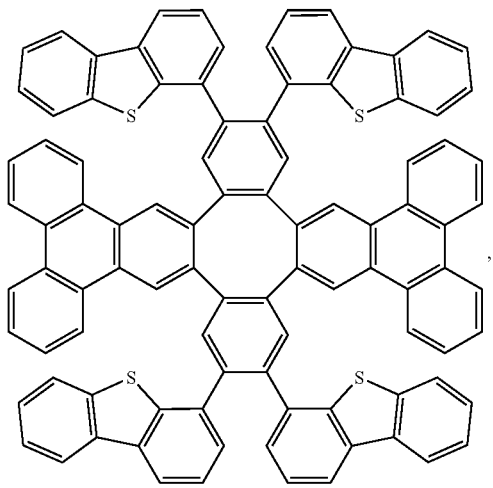

-continued
Compound 199
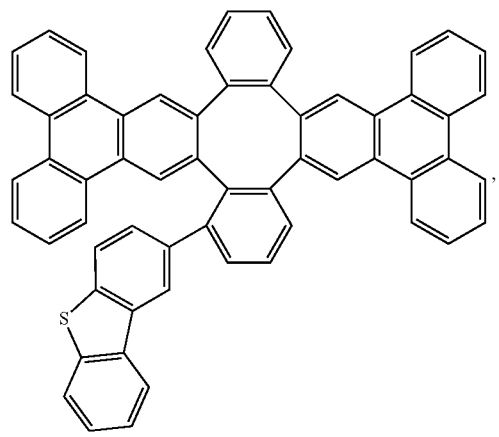
Compound 200
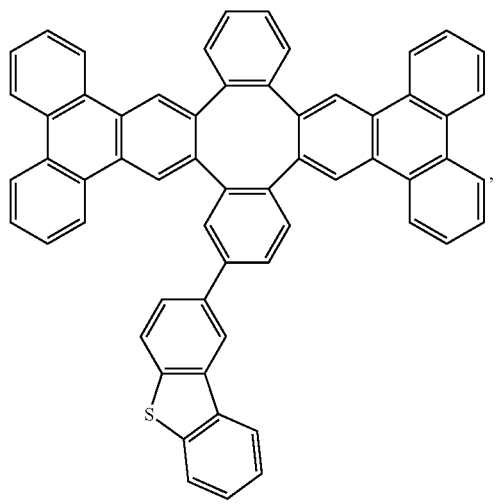
Compound 201
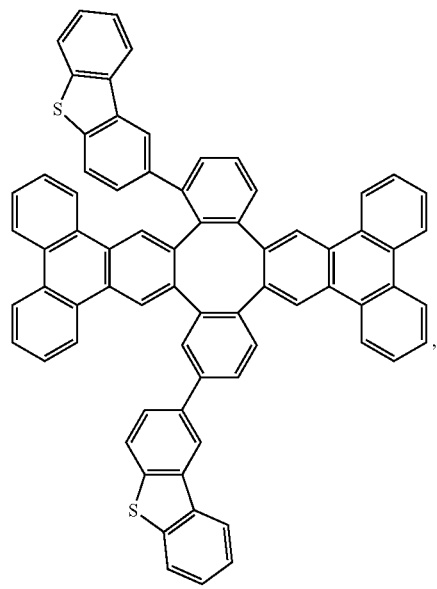
Compound 202
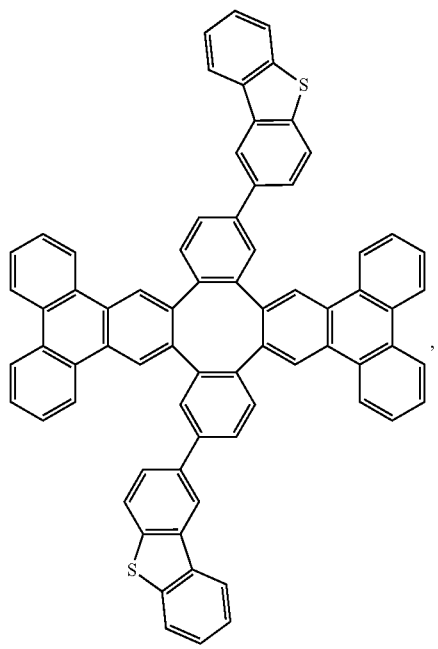

Compound 203
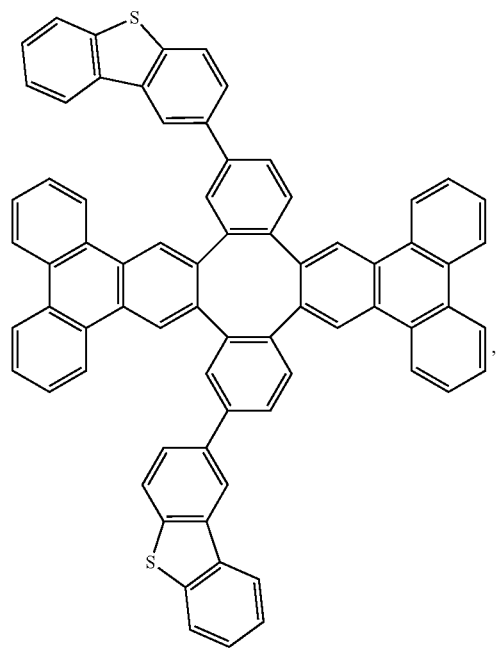
Compound 204
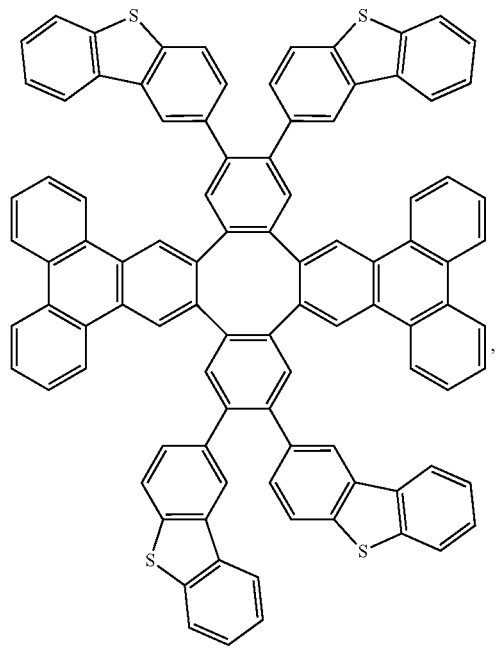
Compound 205
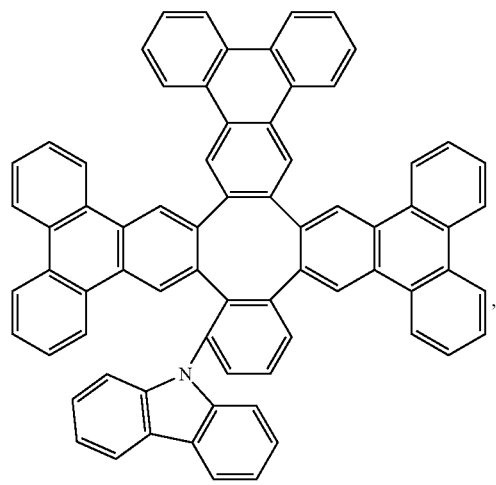
Compound 206
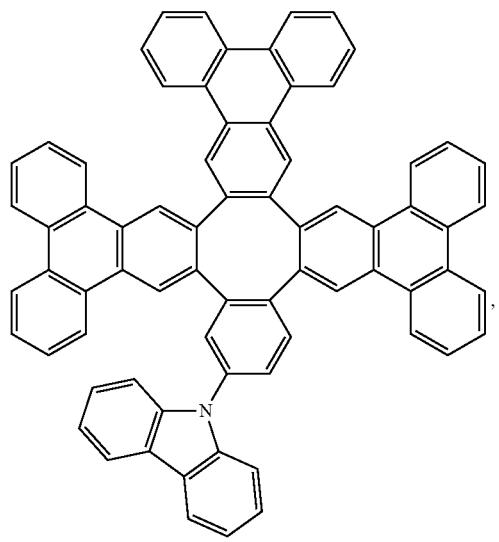

-continued
Compound 207
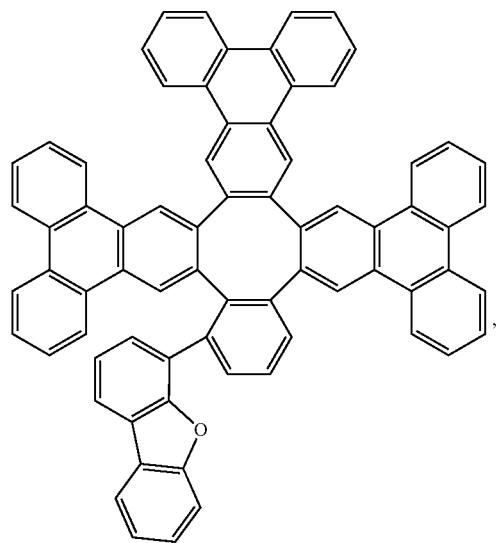
Compound 208
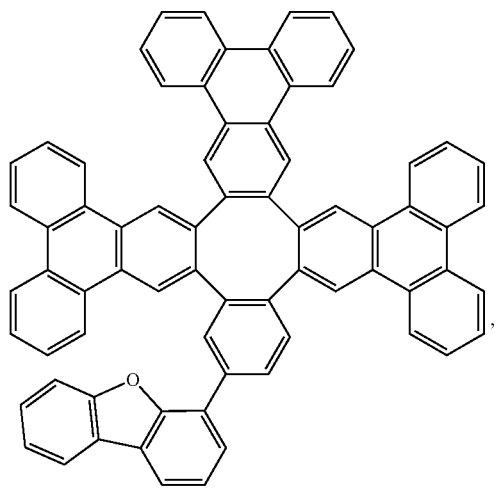
Compound 209
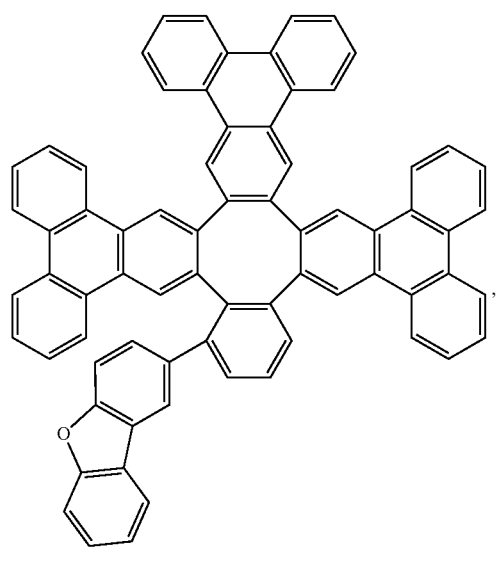
Compound 210
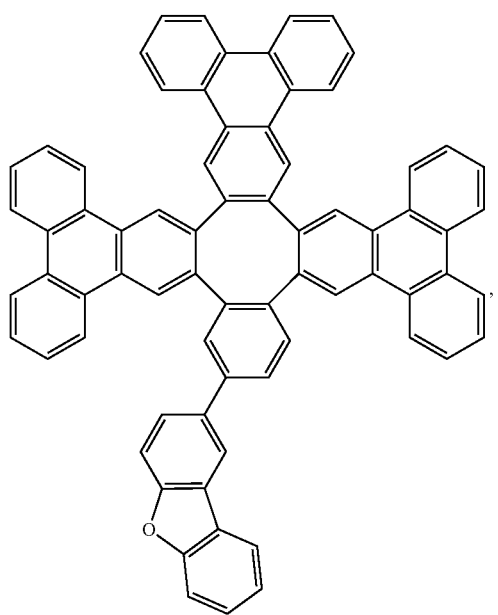

-continued
Compound 211
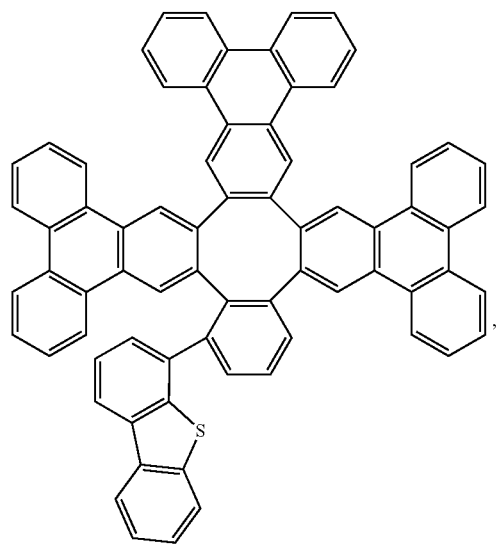
Compound 212
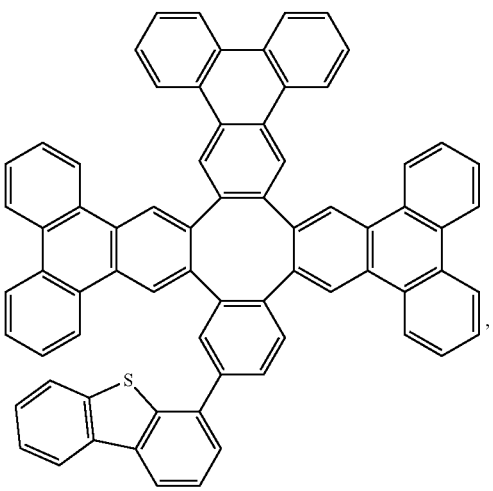
Compound 213
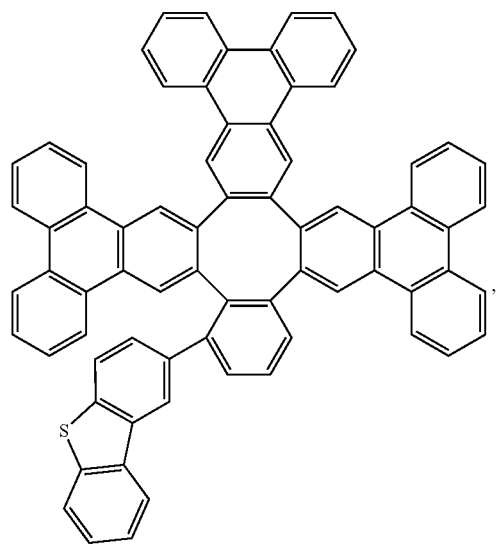
Compound 214
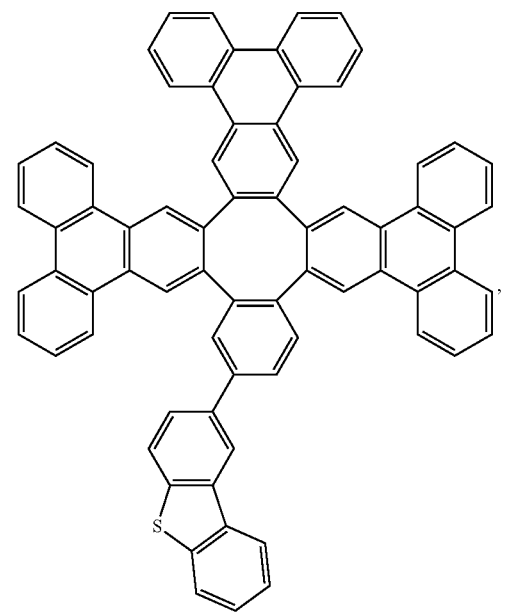
Compound 215
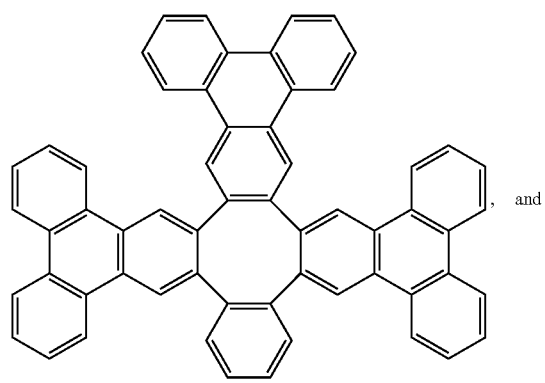, and
Compound 216
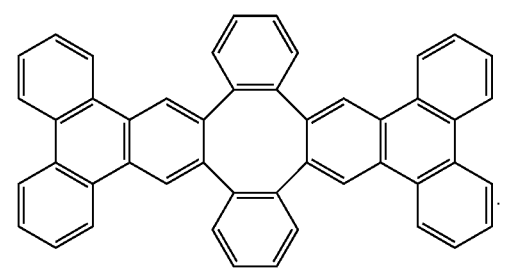, In one embodiment, the compound is selected from the group consisting of:
Compound T1
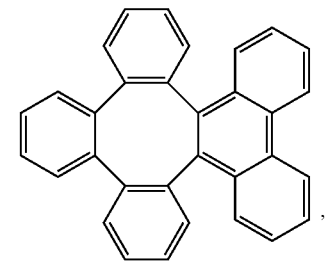
Compound T2
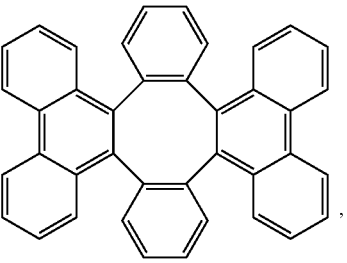
Compound T3
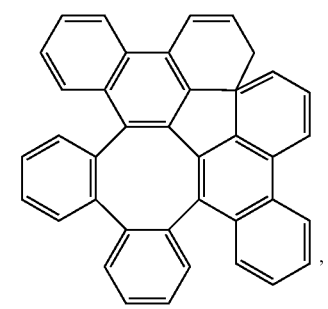
Compound T4
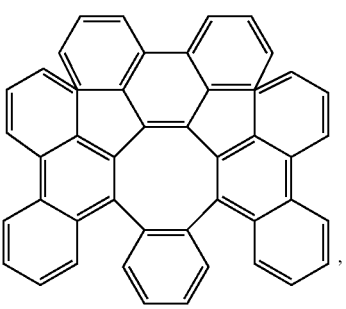
Compound T5
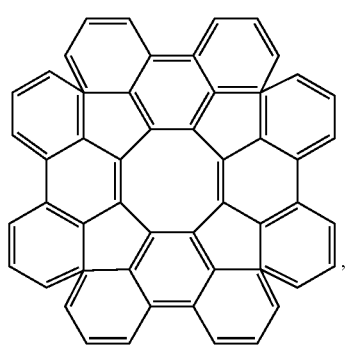
Compound T6
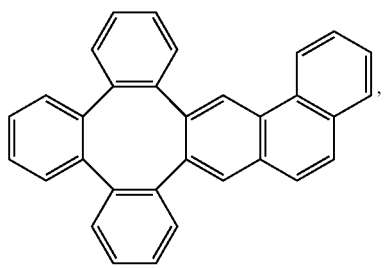
Compound T7
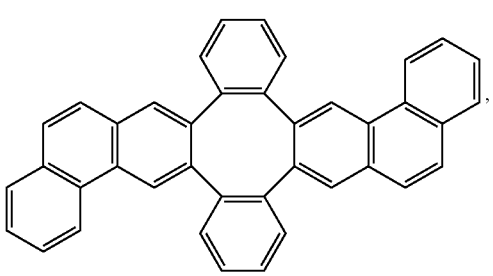
Compound T8
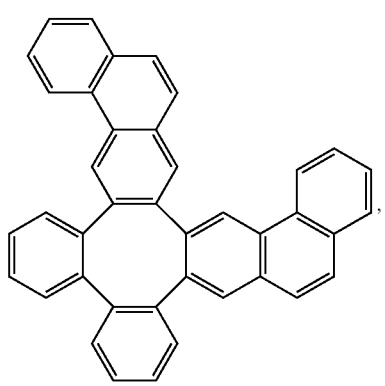
Compound T9
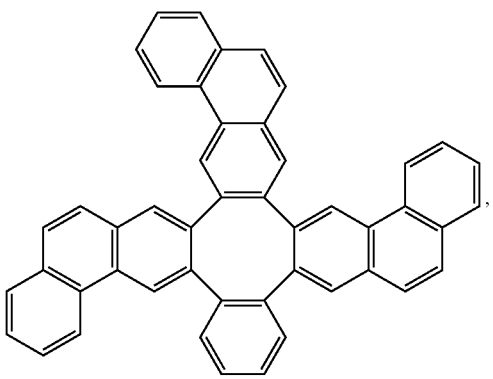

Compound T10
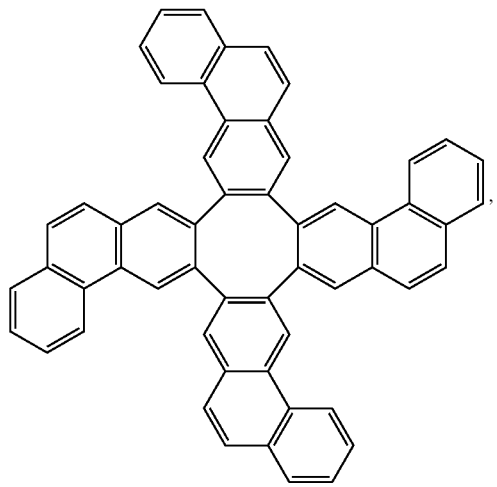
Compound T11
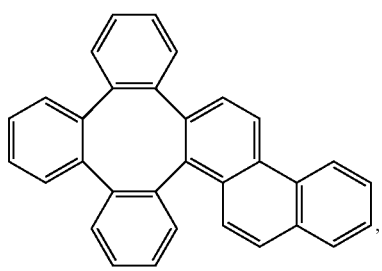
Compound T12
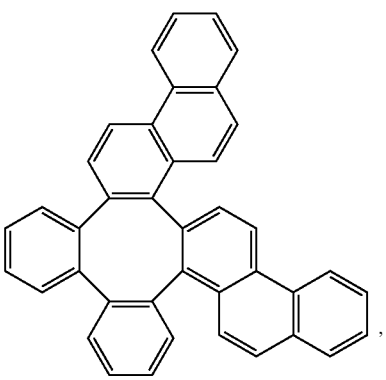
Compound T13
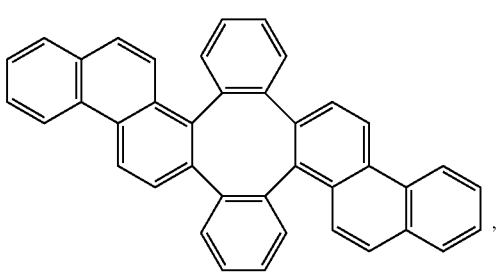
Compound T14
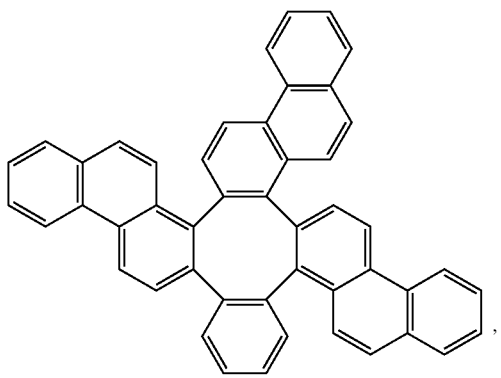
Compound T15
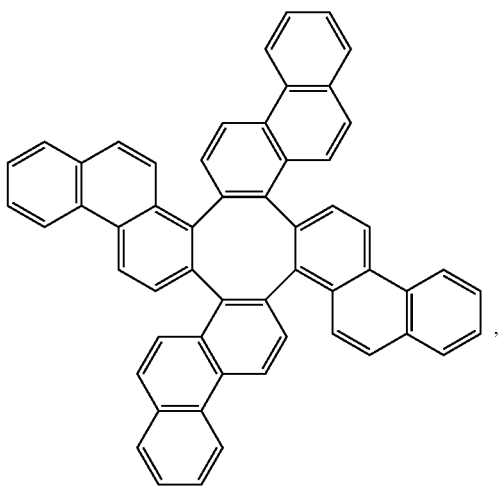
Compound T16
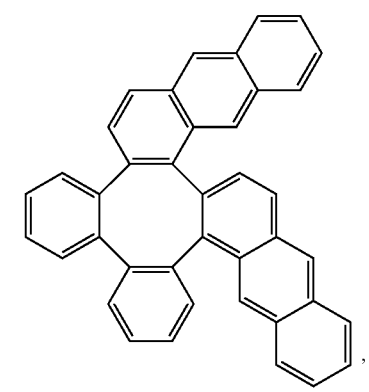
Compound T17
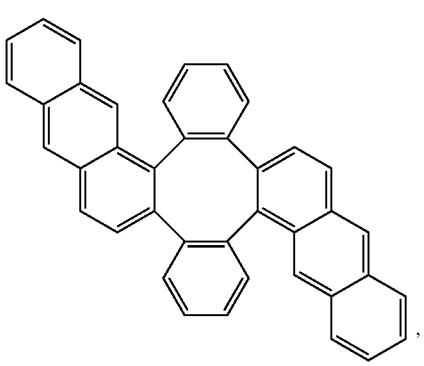

Compound T18
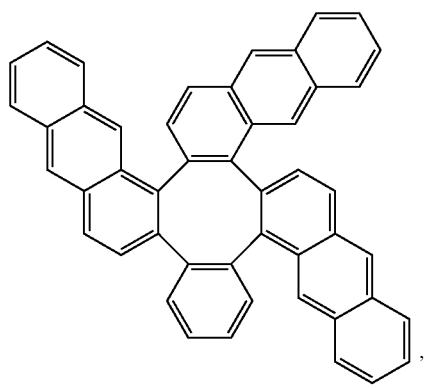
Compound T22
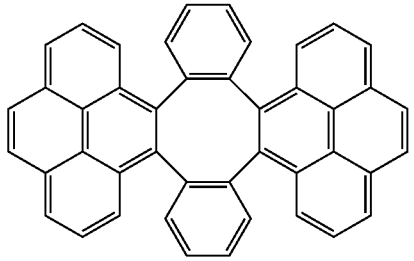
Compound T19
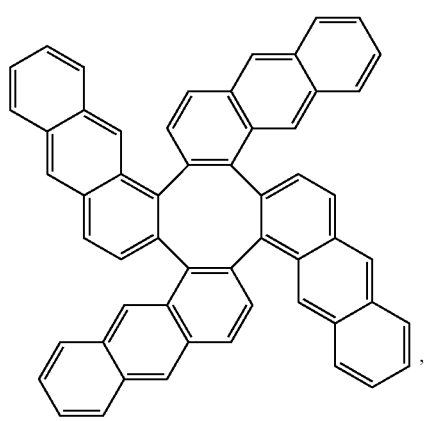
Compound T23
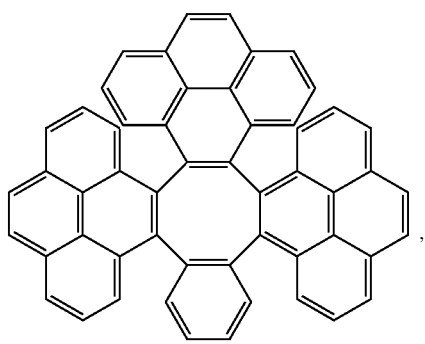
Compound T20
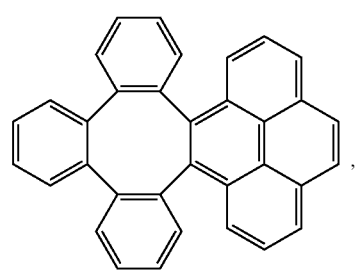
Compound T24
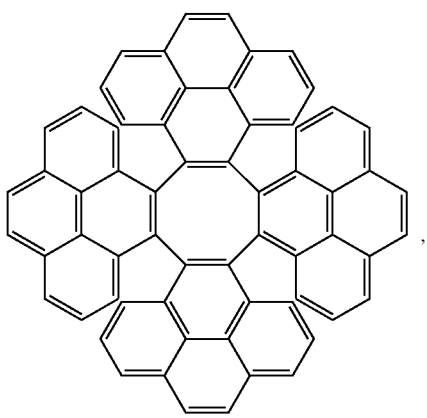
Compound T21
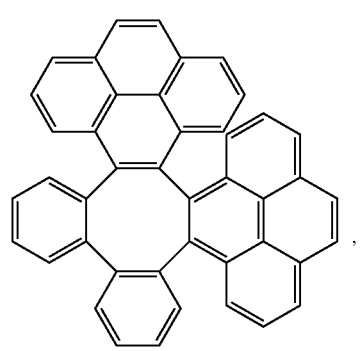
Compound T25
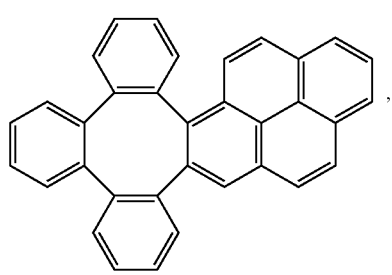

Compound T26
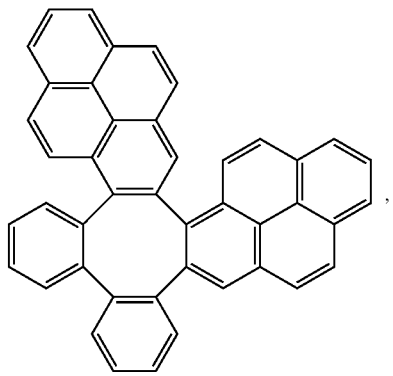
Compound T27
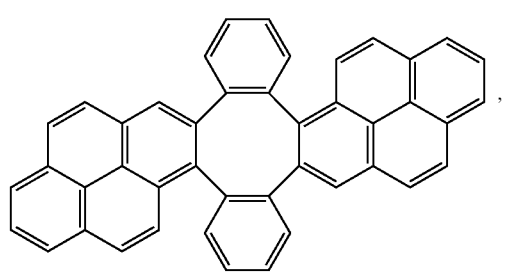
Compound T28
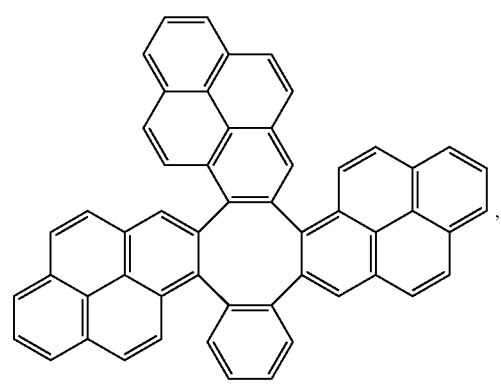
Compound T29
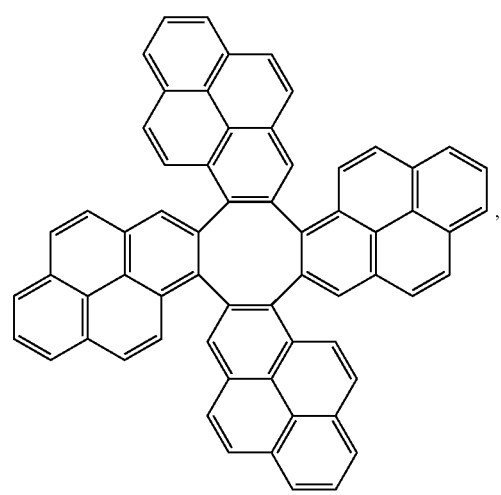
Compound T30
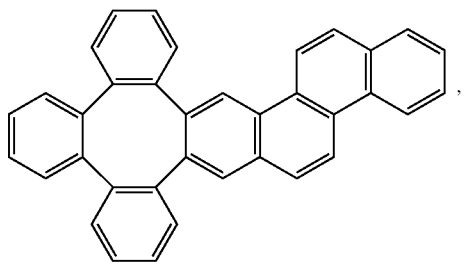
Compound T31
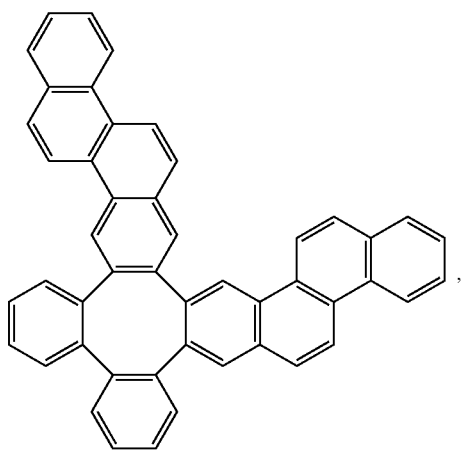
Compound T32
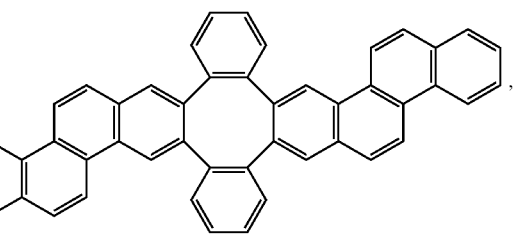
Compound T33
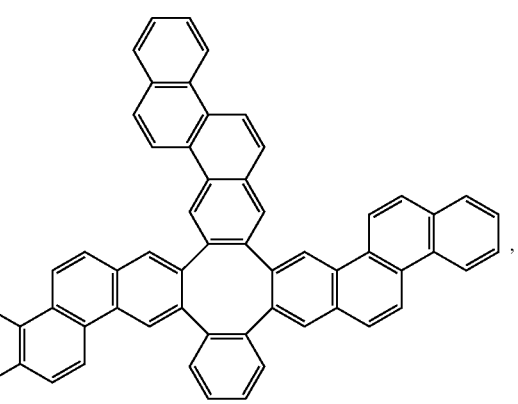

-continued
Compound T34
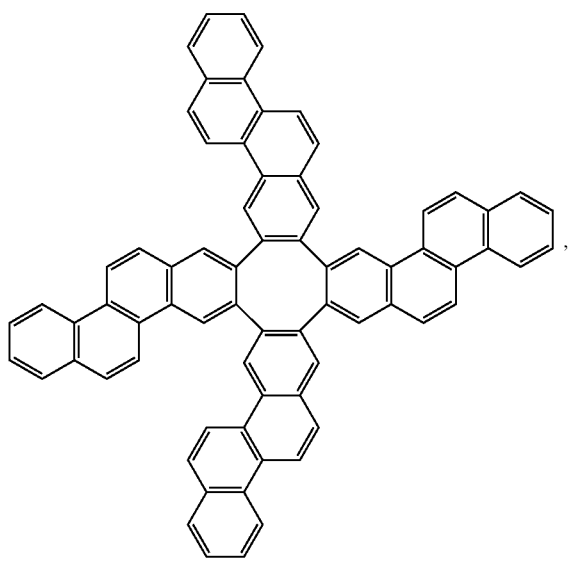
Compound T35
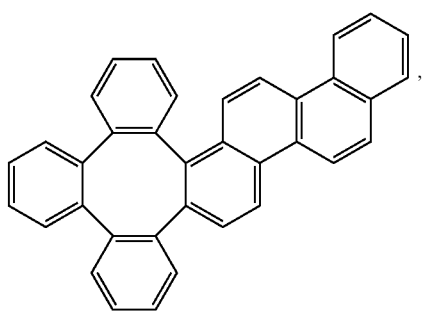
Compound T36
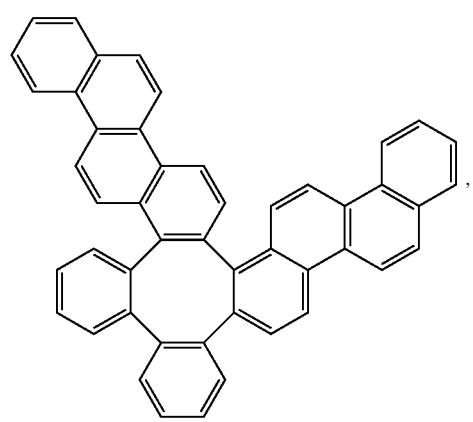
-continued
Compound T37
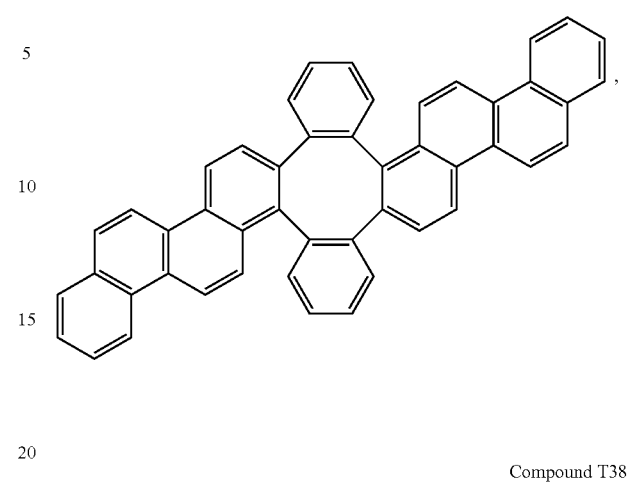
Compound T38
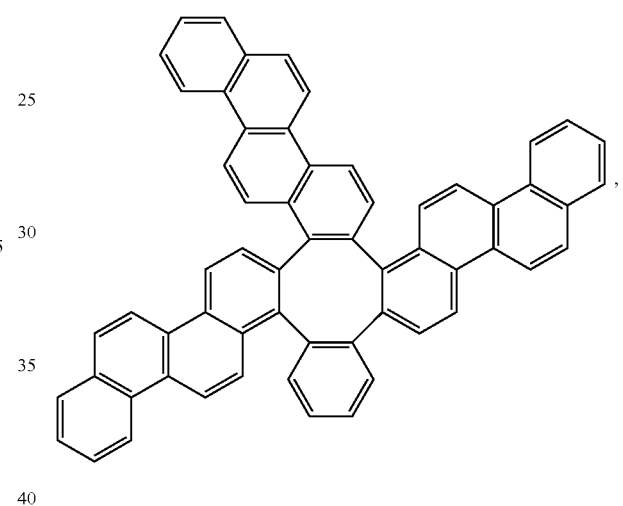
Compound T39
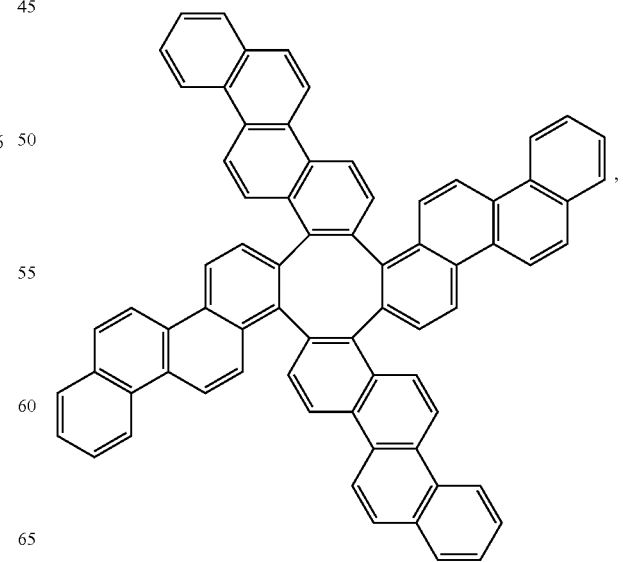

-continued
Compound T40
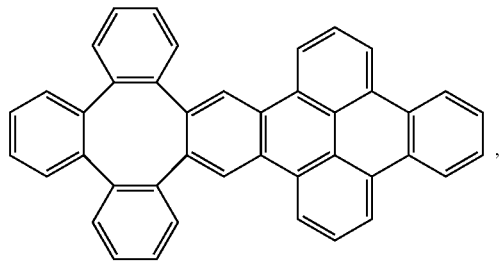
Compound T41
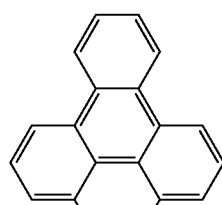
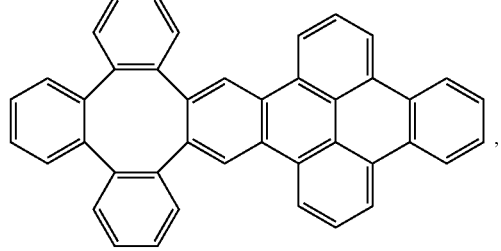
Compound T42
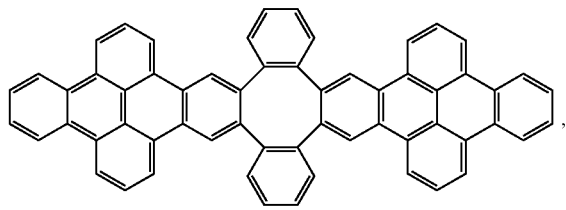
Compound T43
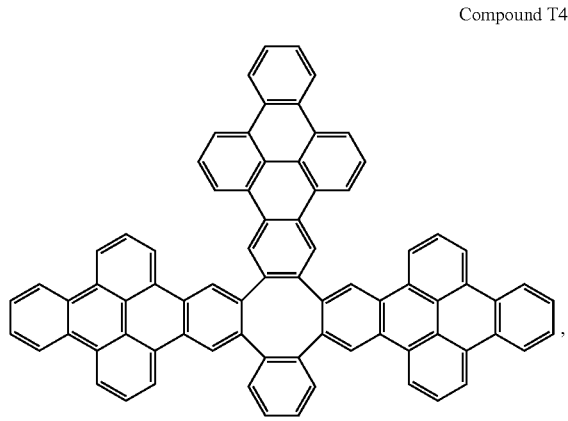
-continued
Compound T44
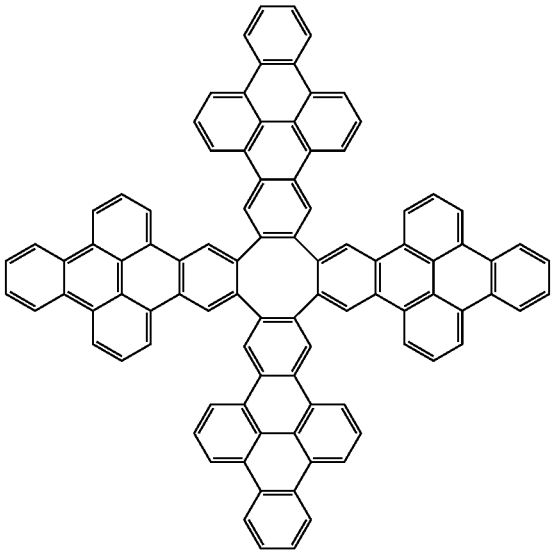
Compound U1
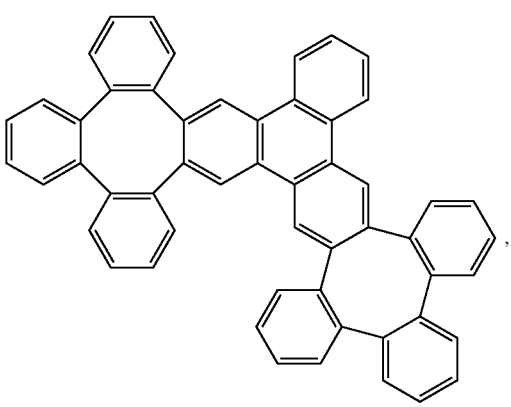
Compound U2
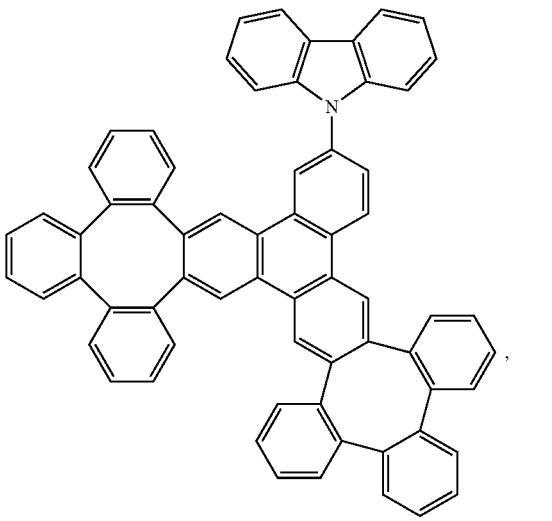

Compound U3

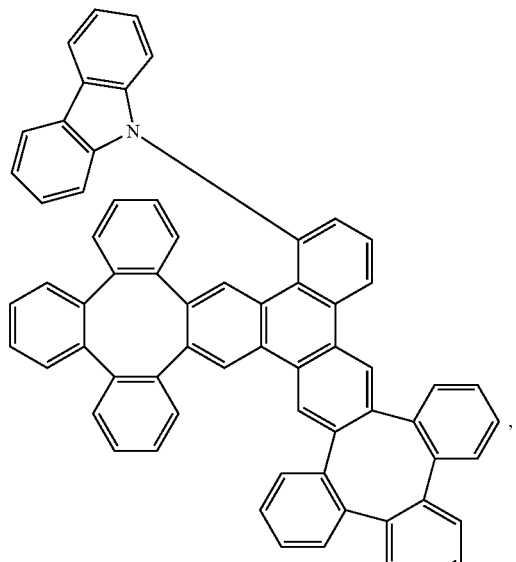

Compound U4

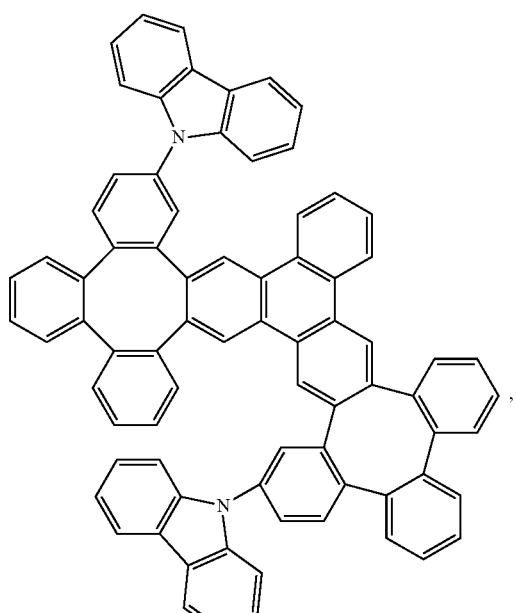

Compound U5

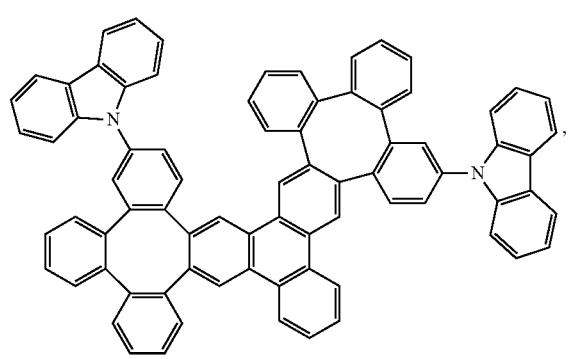

Compound U6

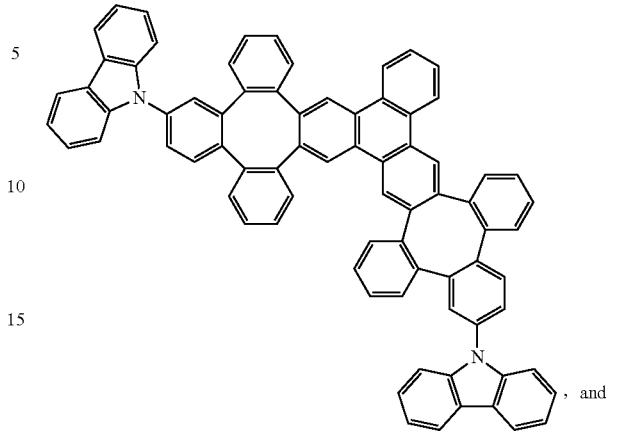

, and

Compound U7

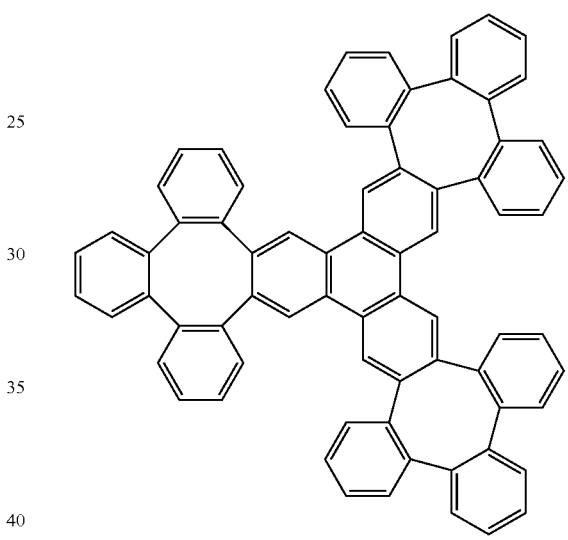

According to another aspect of the present disclosure, an OLED is also provided. The OLED includes an anode, a cathode, and an organic layer disposed between the anode and the cathode. The organic layer may include a host and one or more emitter dopants. In one embodiment, the organic layer is a blocking layer and the compound of Formula I is a blocking material in the organic layer. In one embodiment, the organic layer is a transporting layer and the compound of Formula I is a transporting material in the organic layer. In one embodiment, the organic layer is an emissive layer and the compound of Formula I is an emitter.

In one embodiment, the compound comprising a structure according to Formula I emits a blue light with a peak wavelength of about 400 nm to about 500 nm. In one embodiment, the compound comprising a structure according to Formula I emits a yellow light with a peak wavelength of about 530 nm to about 580 nm.

In one embodiment, the OLED emits a luminescent radiation at room temperature when a voltage is applied across the organic light emitting device, and wherein the luminescent radiation comprises a delayed fluorescence process.

In one embodiment, the emissive layer further comprises a host material. In one embodiment, the emissive layer further comprises a first phosphorescent emitting material.

In one embodiment, the emissive layer further comprises a second phosphorescent emitting material. In one embodiment, the OLED emits a white light at room temperature when a voltage is applied across the organic light emitting device.

In one embodiment, the organic layer further comprises a phosphorescent emissive dopant; wherein the emissive dopant is a transition metal complex having at least one ligand or part of the ligand if the ligand is more than bidentate selected from the group consisting of:

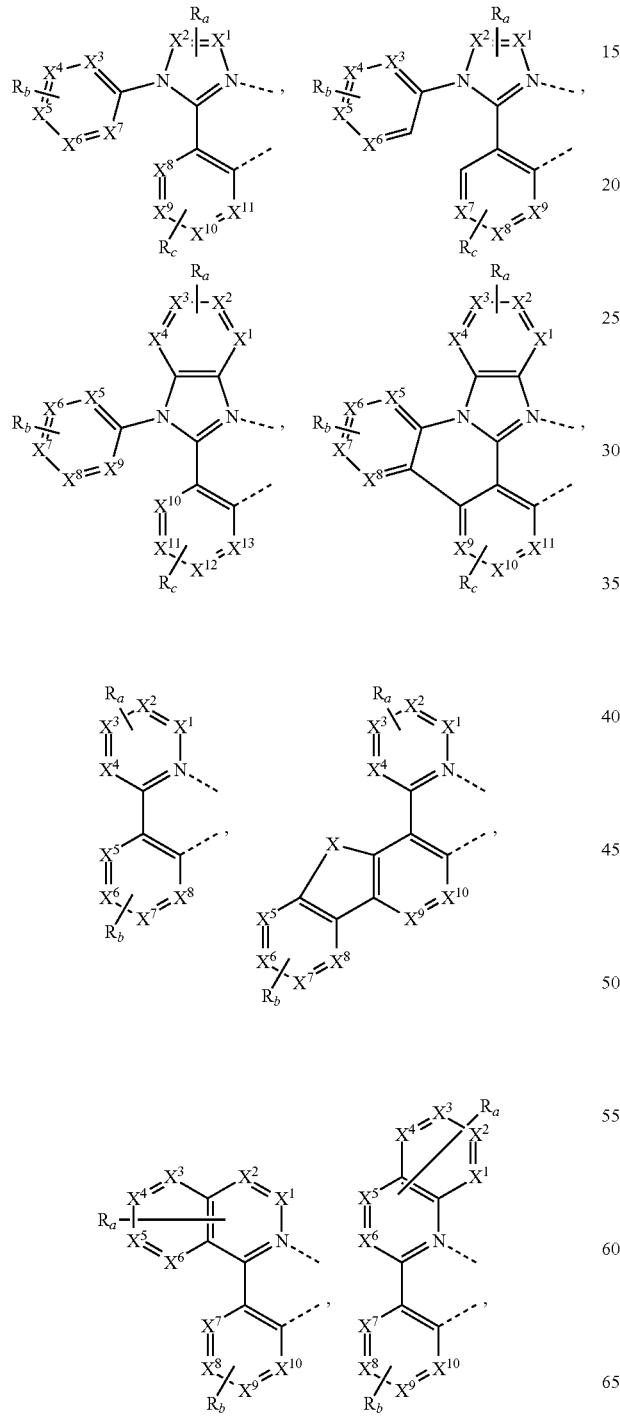

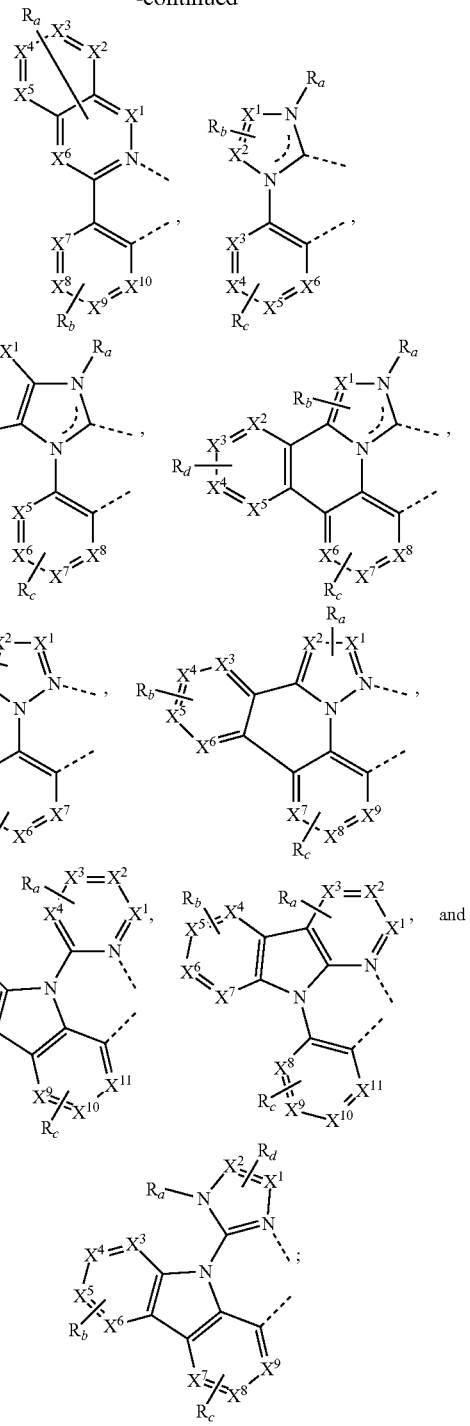

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

The emitter dopants can be delayed fluorescent dopants and/or fluorescent dopants. The organic layer can include a compound according to Formula I and its variations as described herein as a host.

The OLED can be incorporated into one or more of a consumer product, an electronic component module, and a lighting panel.

According to another aspect of the present disclosure, a consumer product comprising an OLED is provided. The OLED may include an anode, a cathode, and an organic layer disposed between the anode and the cathode. The organic layer may include a host and one or more emitter dopants. In one embodiment, the organic layer includes a compound of Formula I.

Non-limiting examples of consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays that are less than 2 inches diagonal, 3-D displays, virtual reality or augmented reality displays, vehicles, video walls comprising multiple displays tiled together, theater or stadium screens, and/or signs.

In yet another aspect of the present disclosure, a formulation that comprises a compound of Formula I is described. The formulation can include one or more components selected from the group consisting of a solvent, a host, a hole injection material, hole transport material, and an electron transport layer material, disclosed herein.

Combination with other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

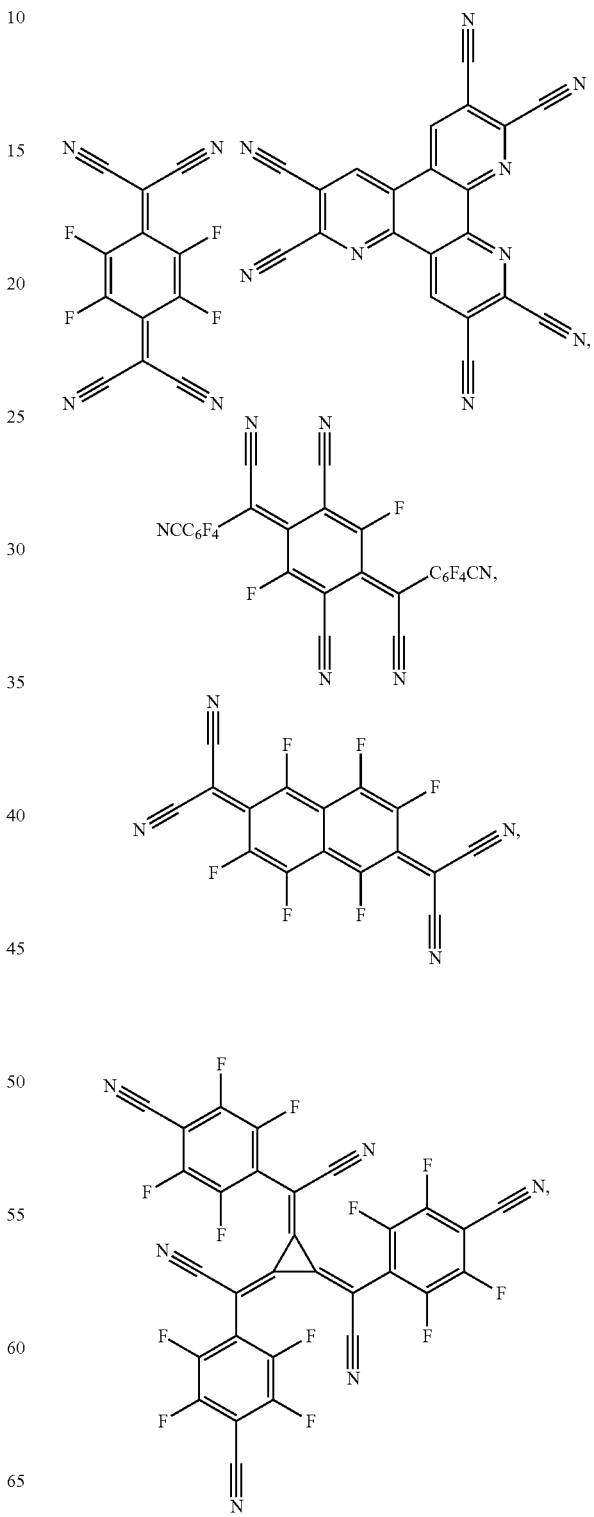

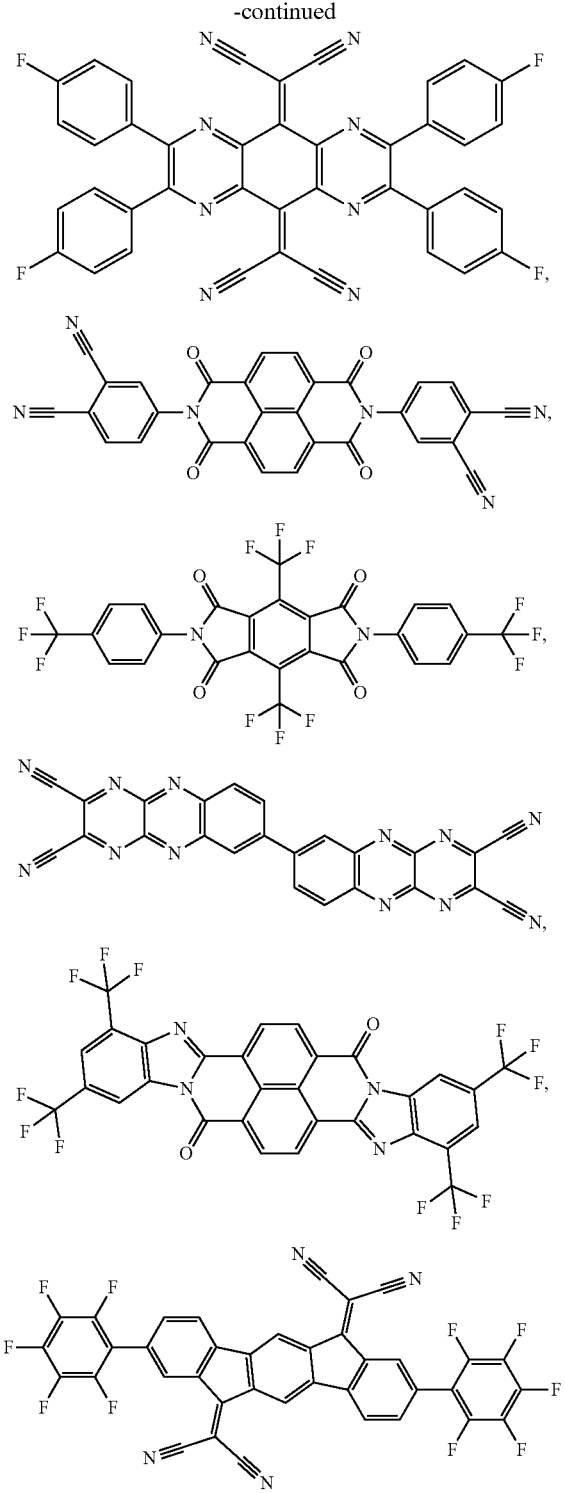

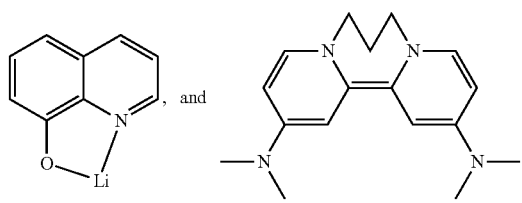

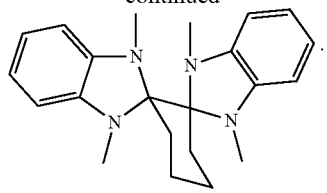

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

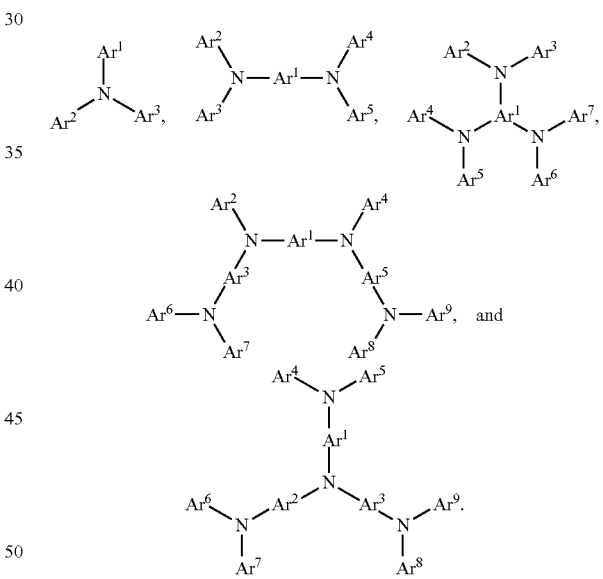

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

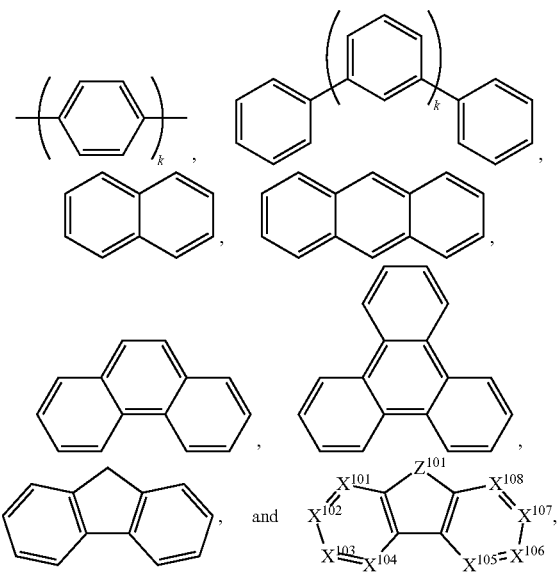

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

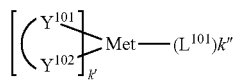

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, US06517957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

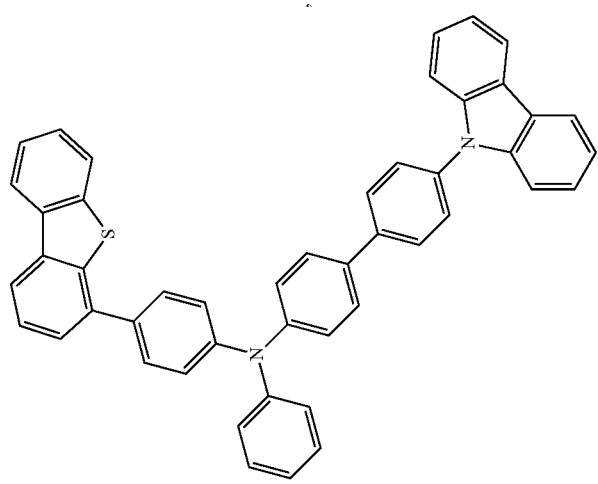
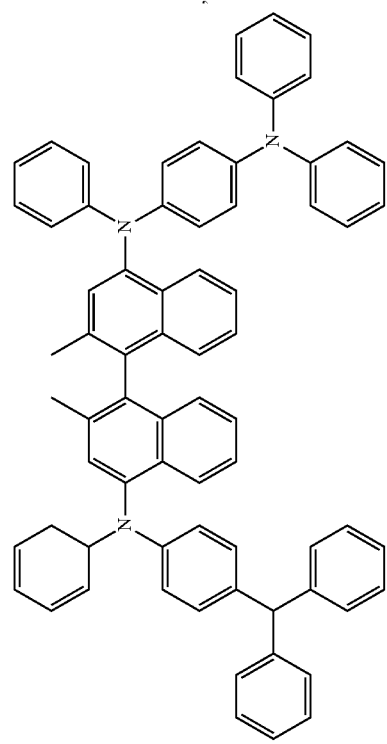

-continued
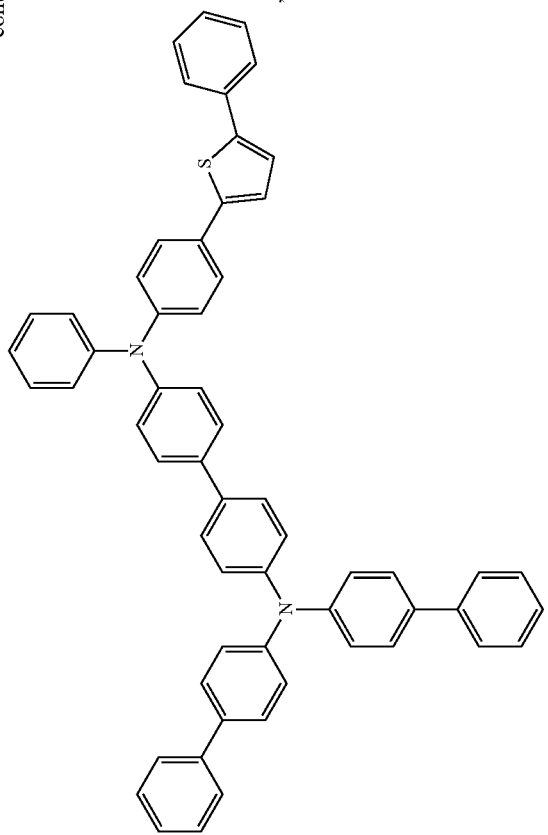
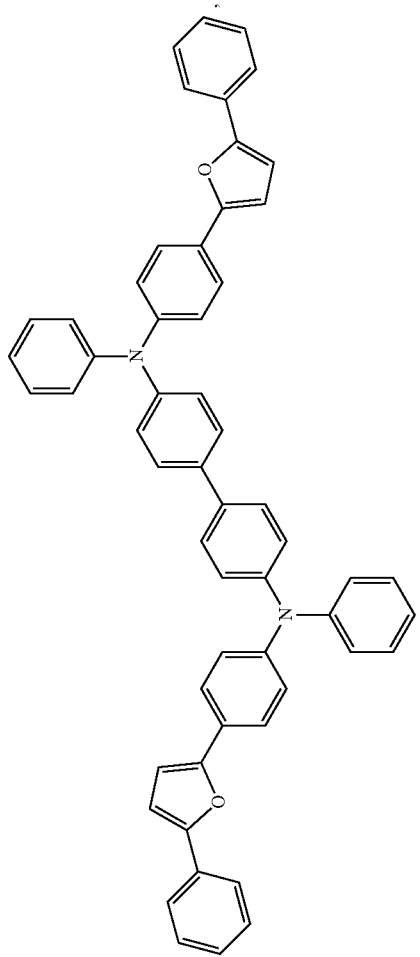

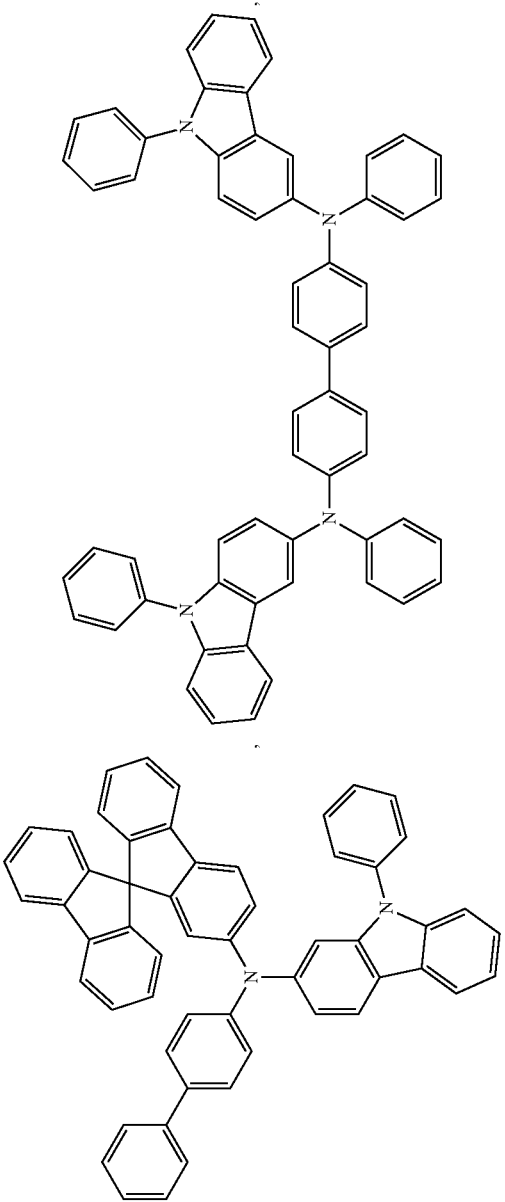
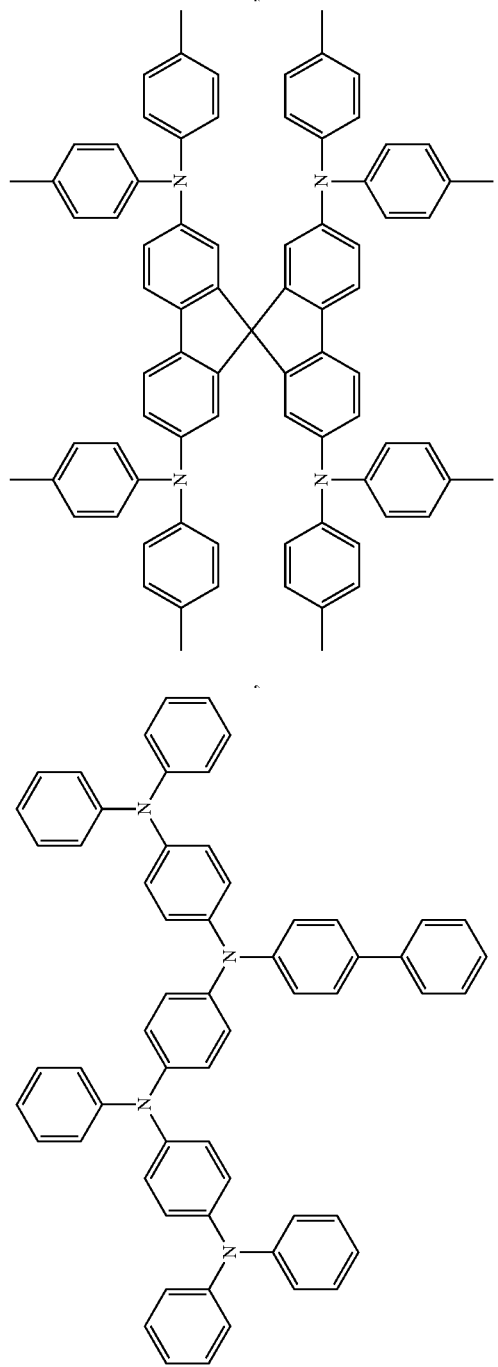

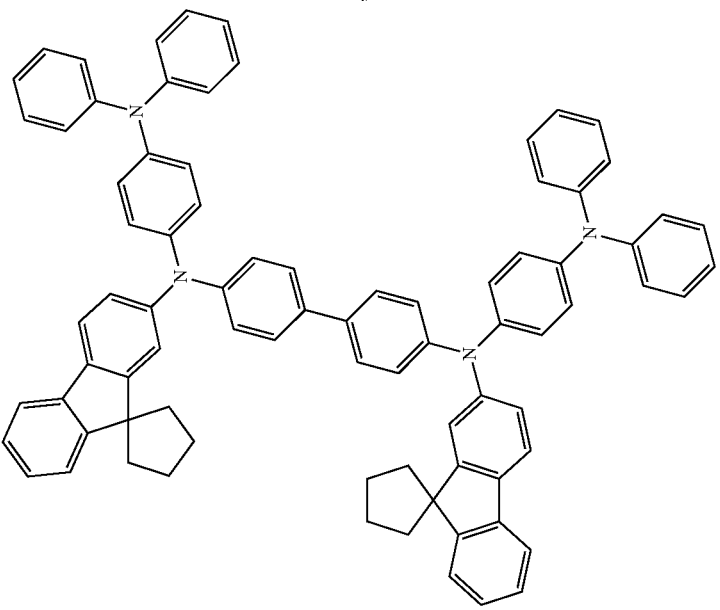
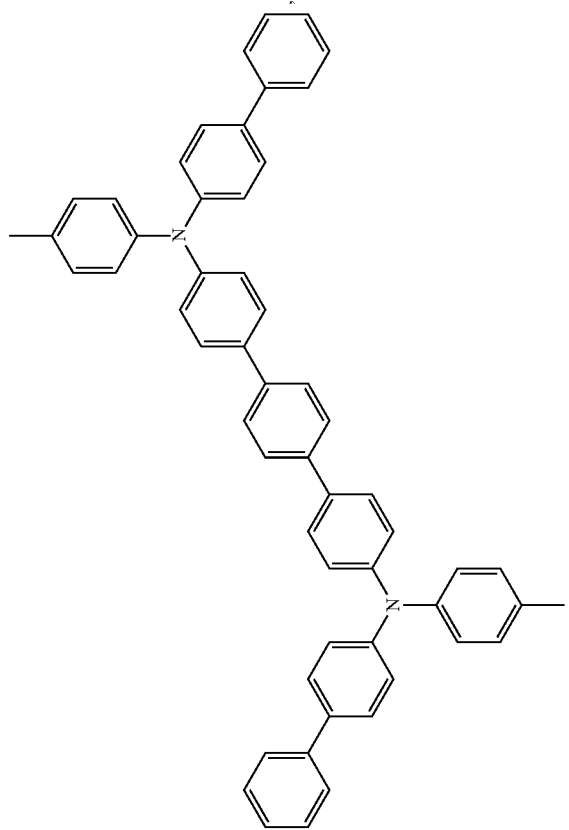

-continued
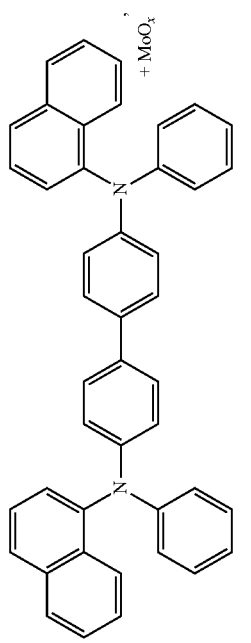
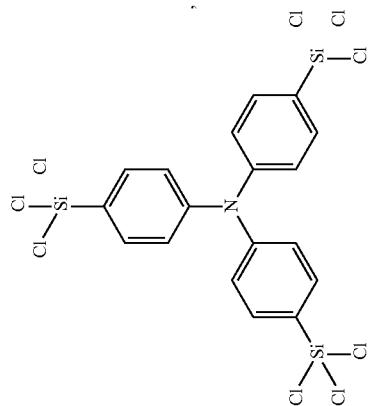
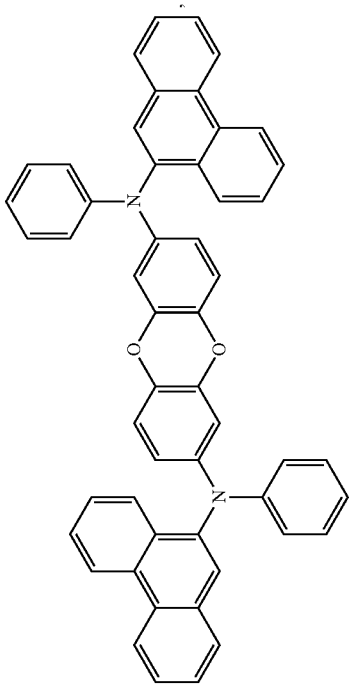
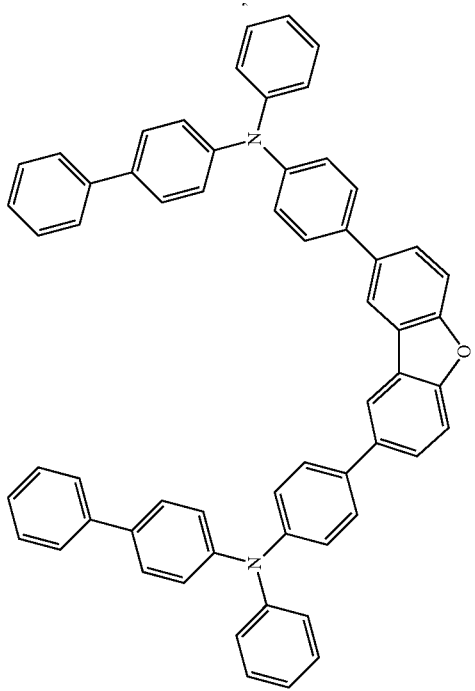

-continued
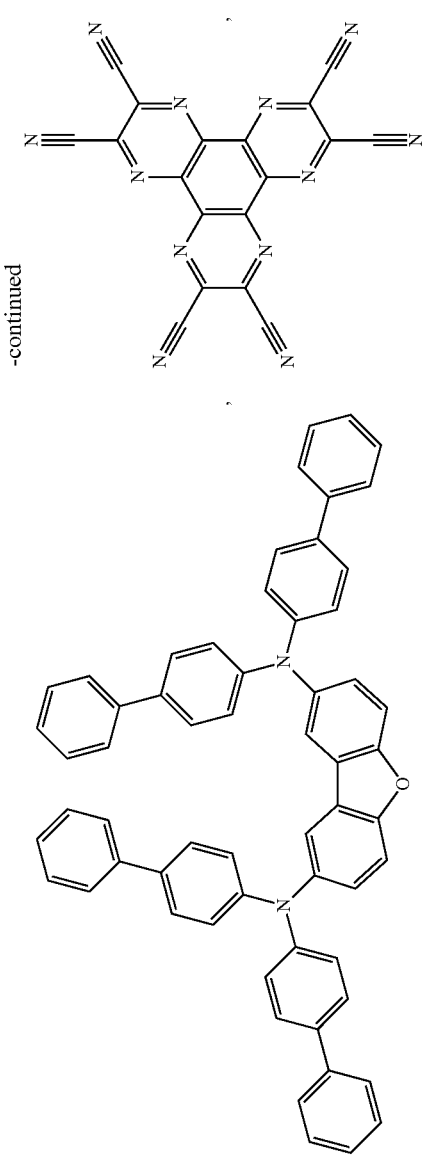
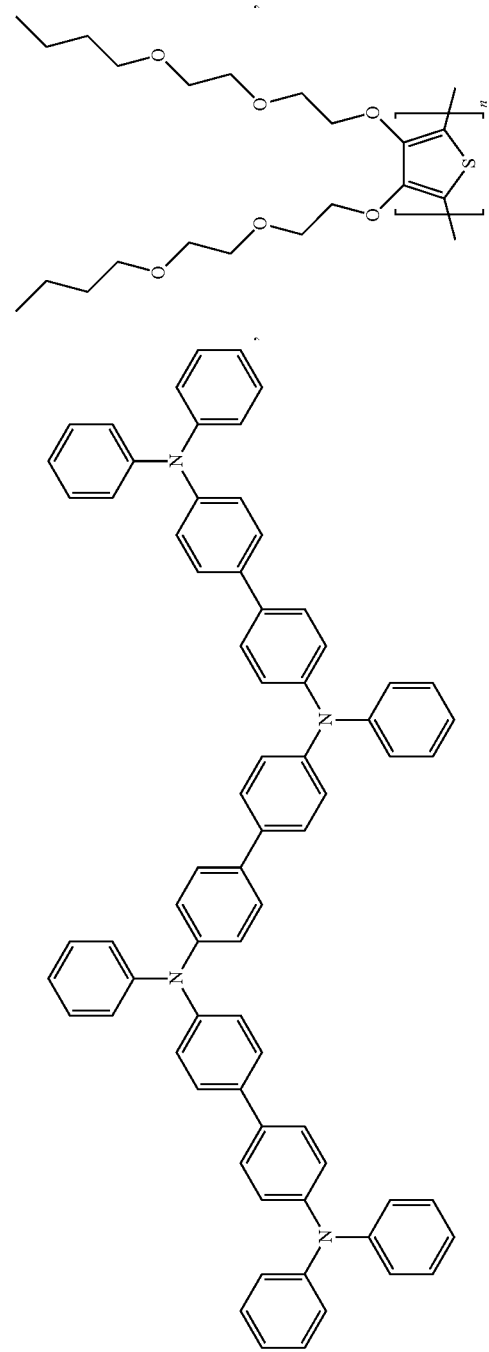

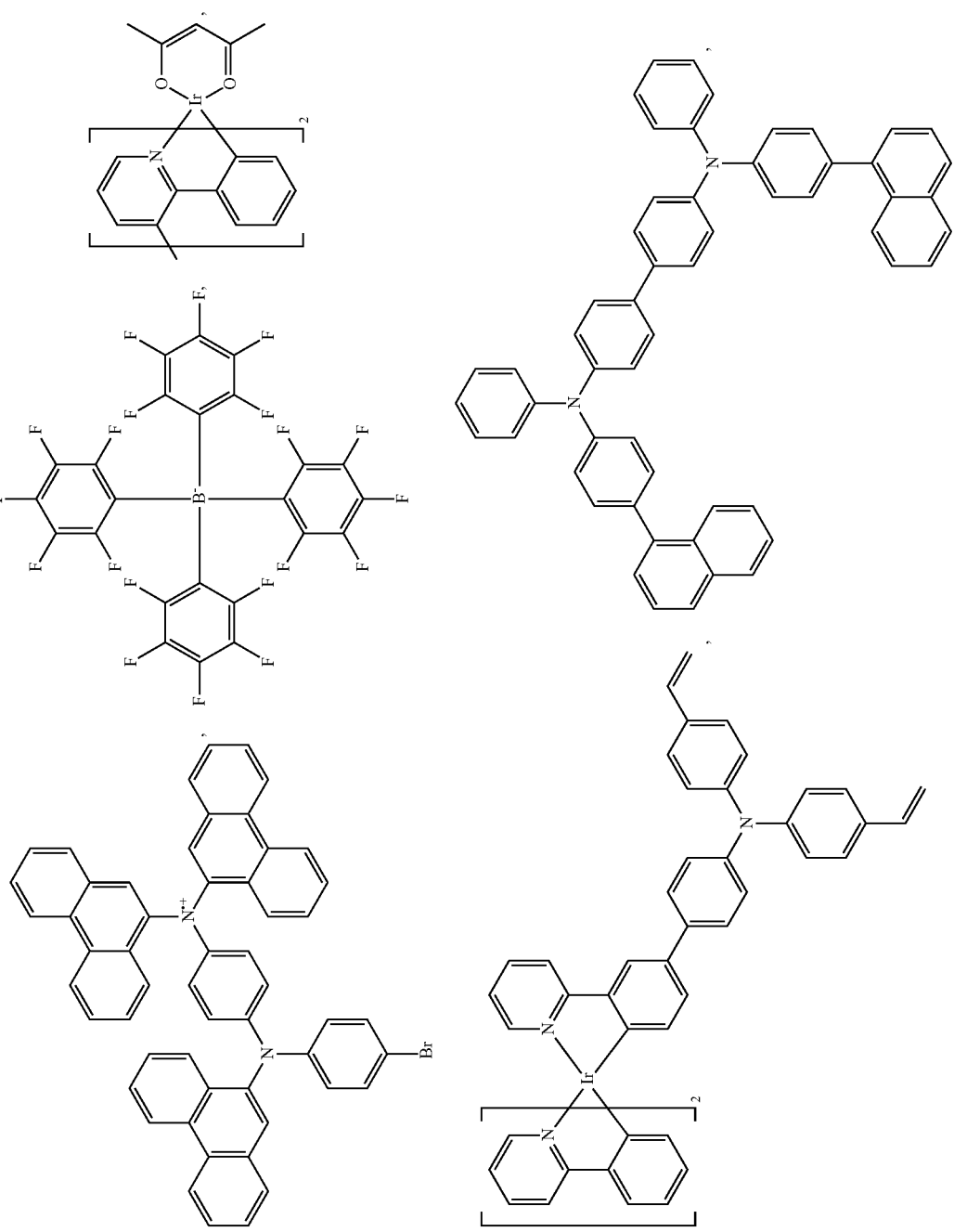

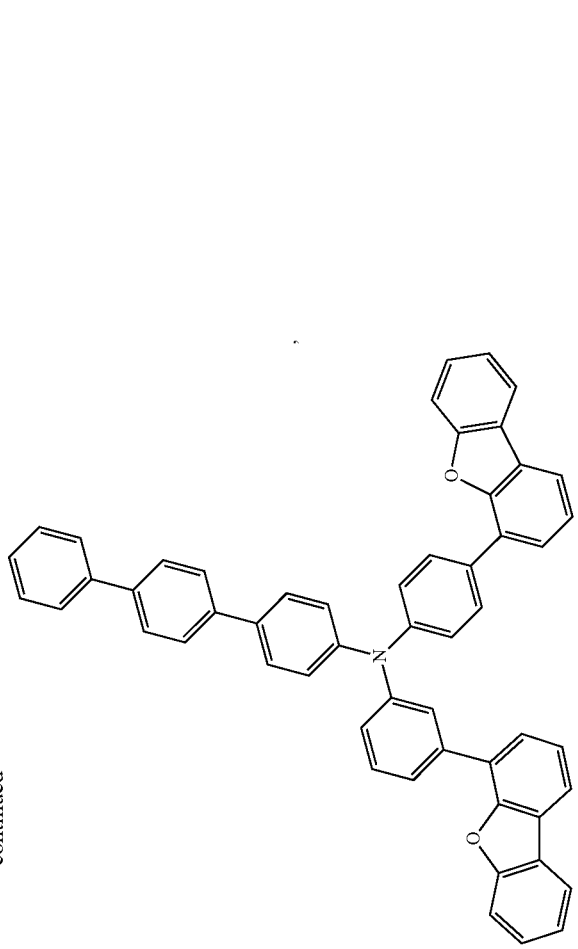
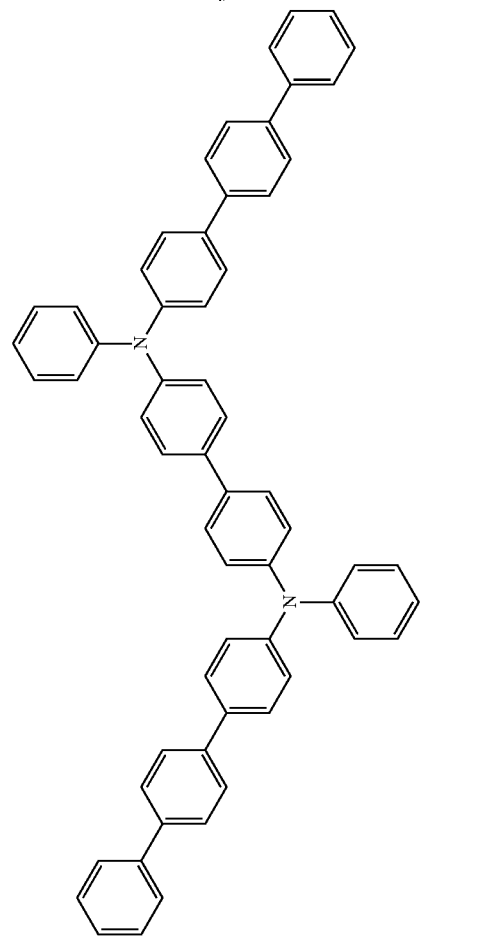
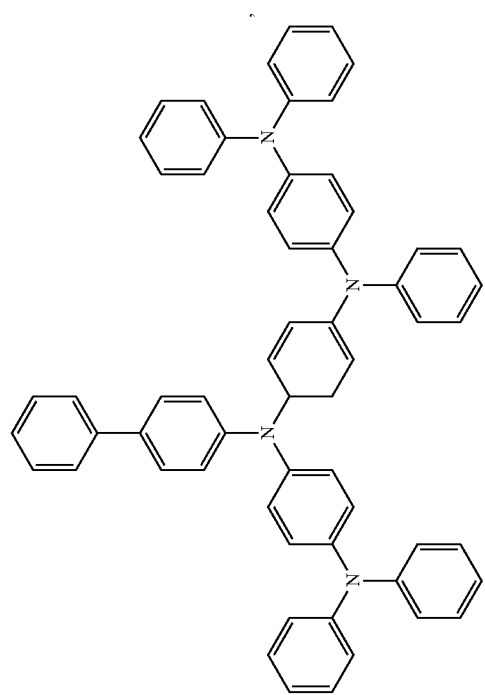
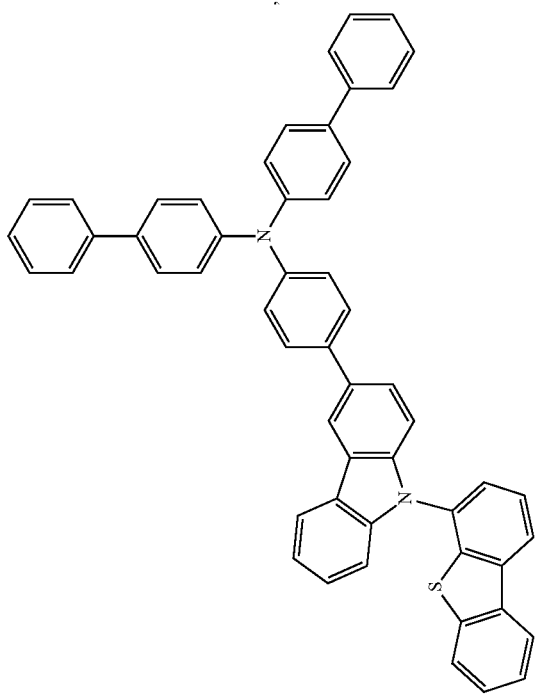

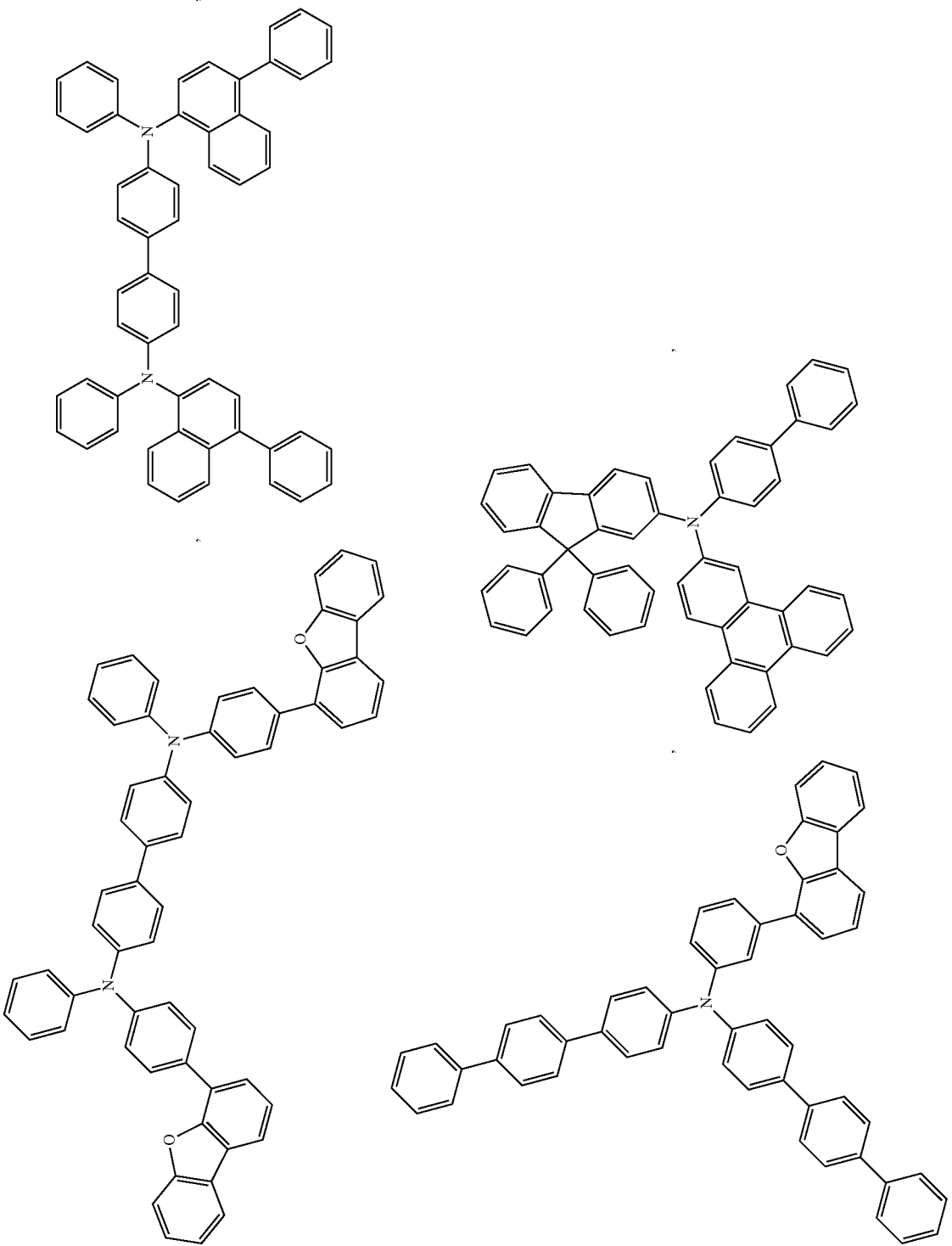

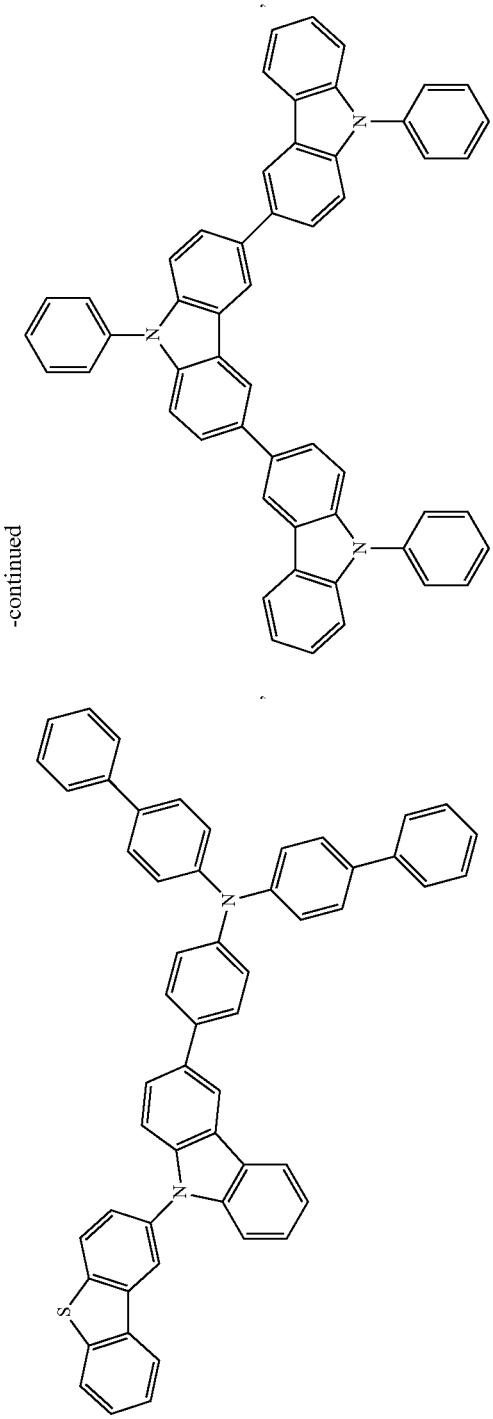
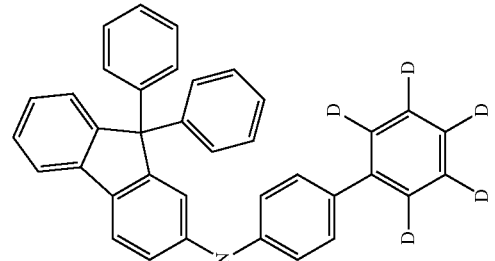
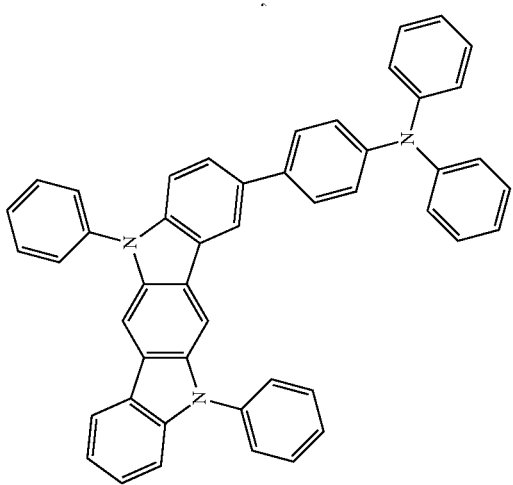

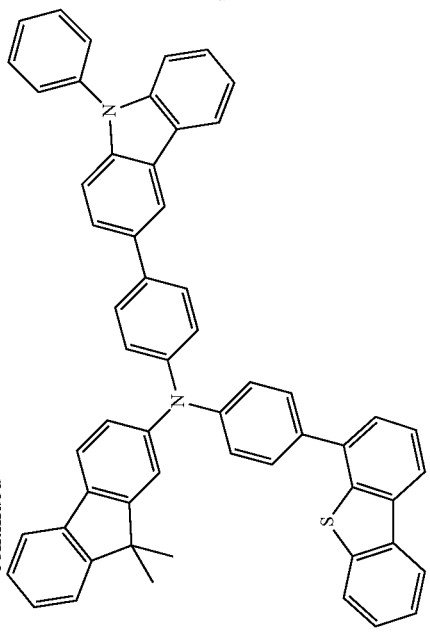
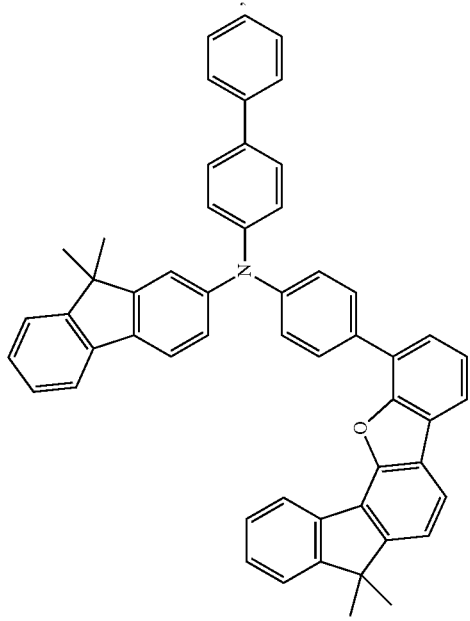
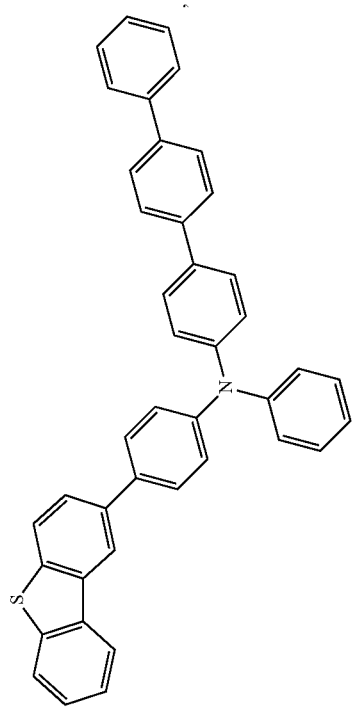
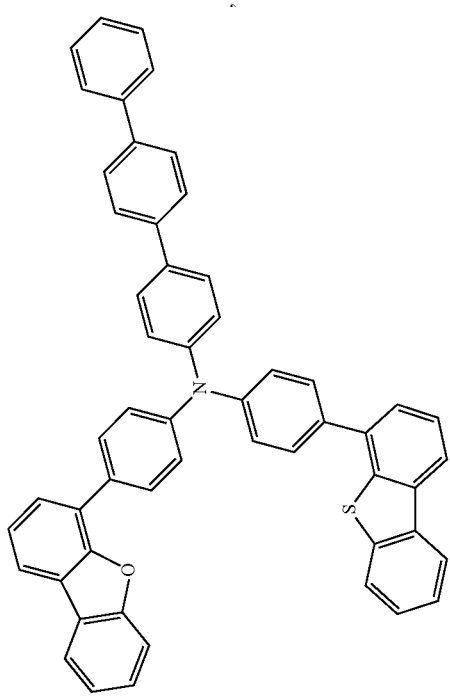

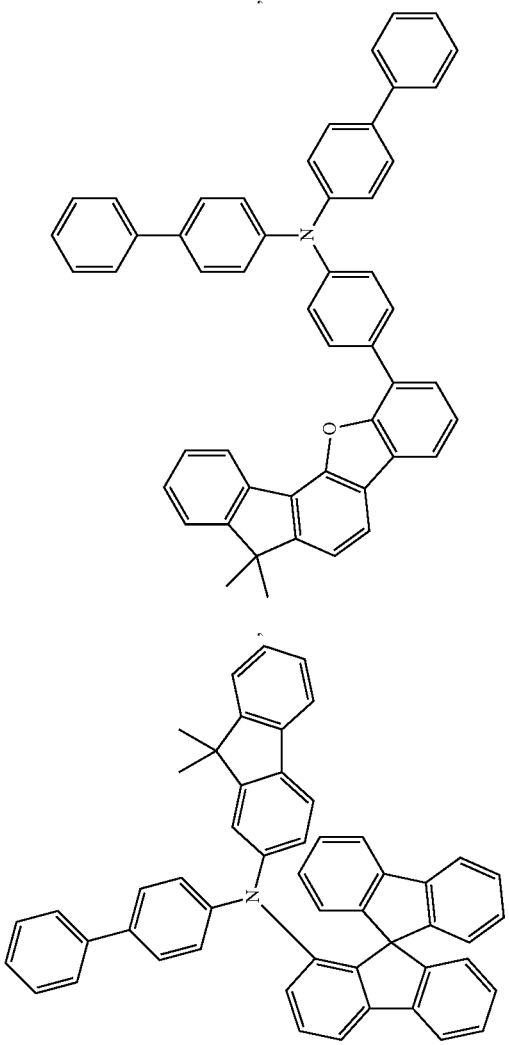
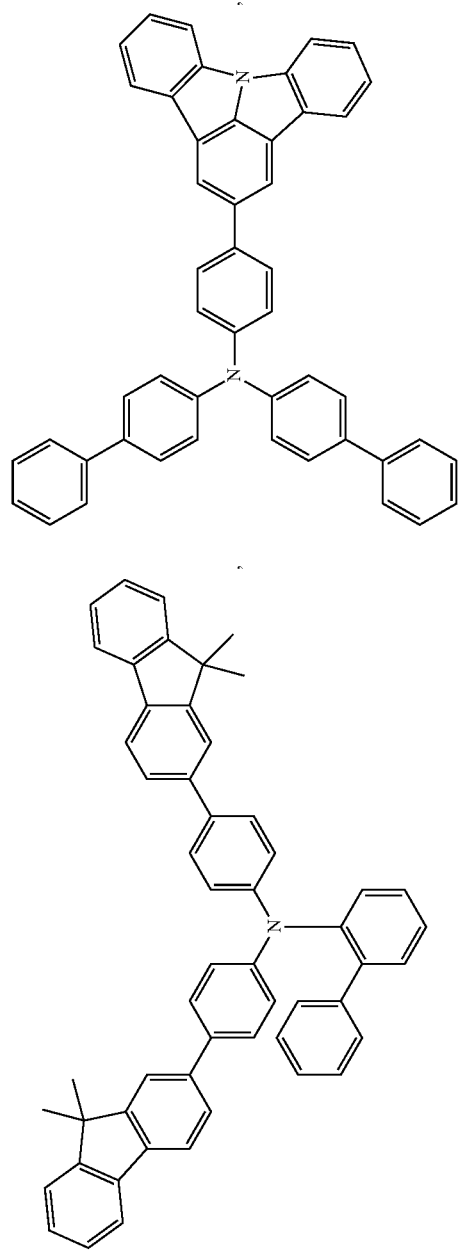

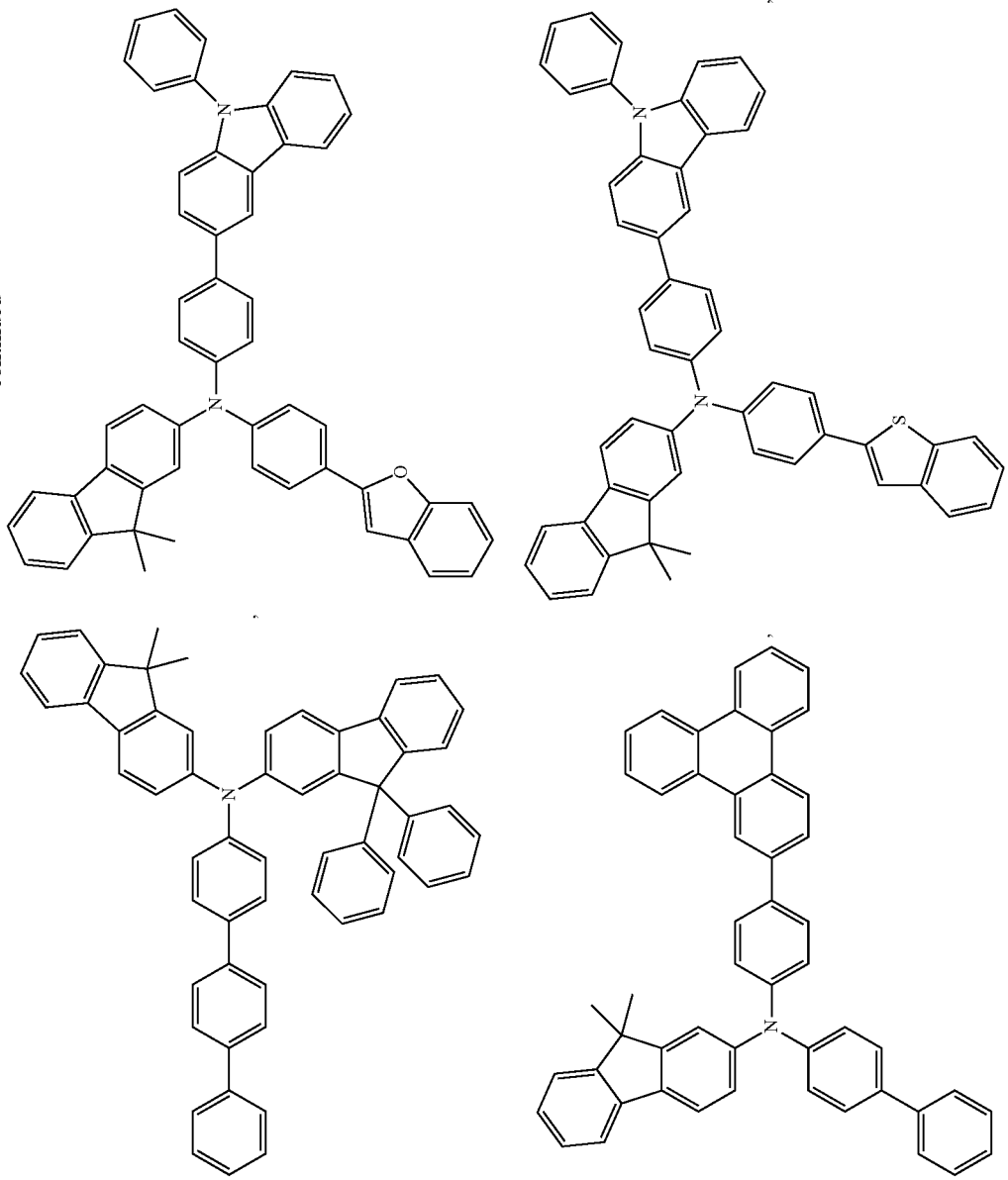

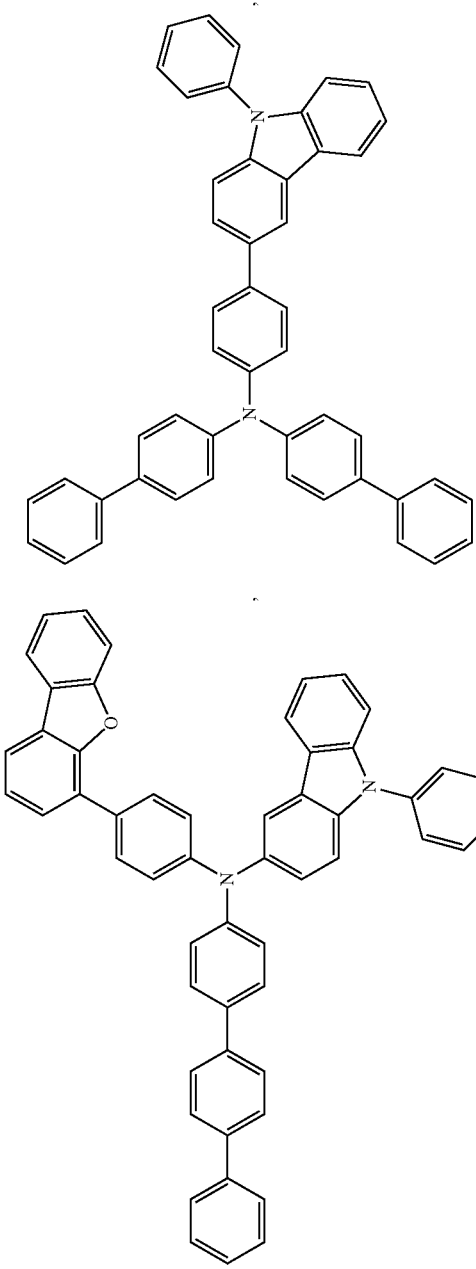
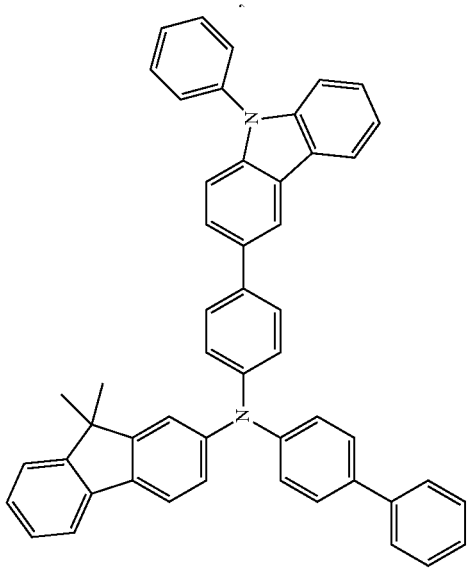
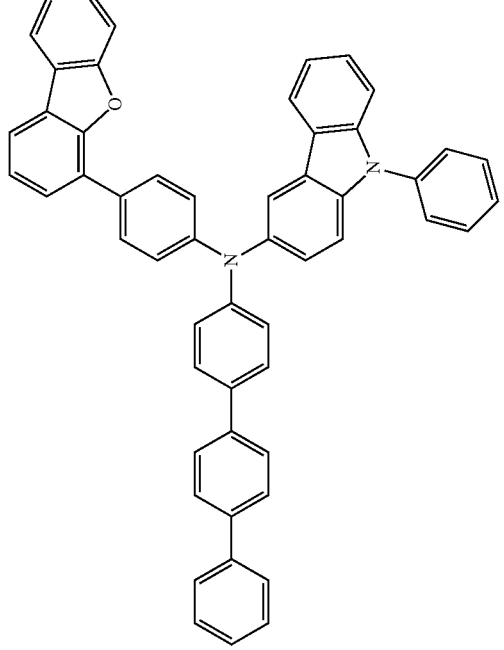
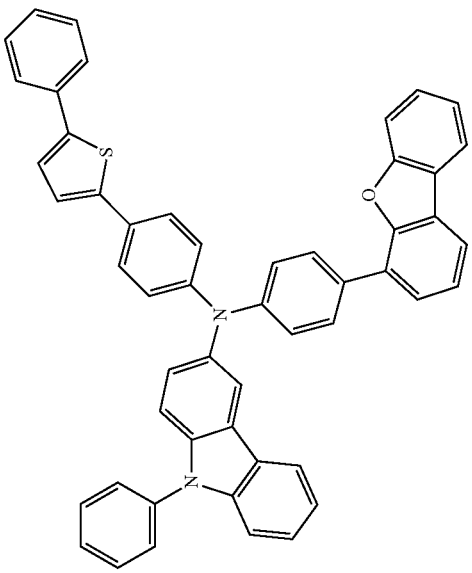

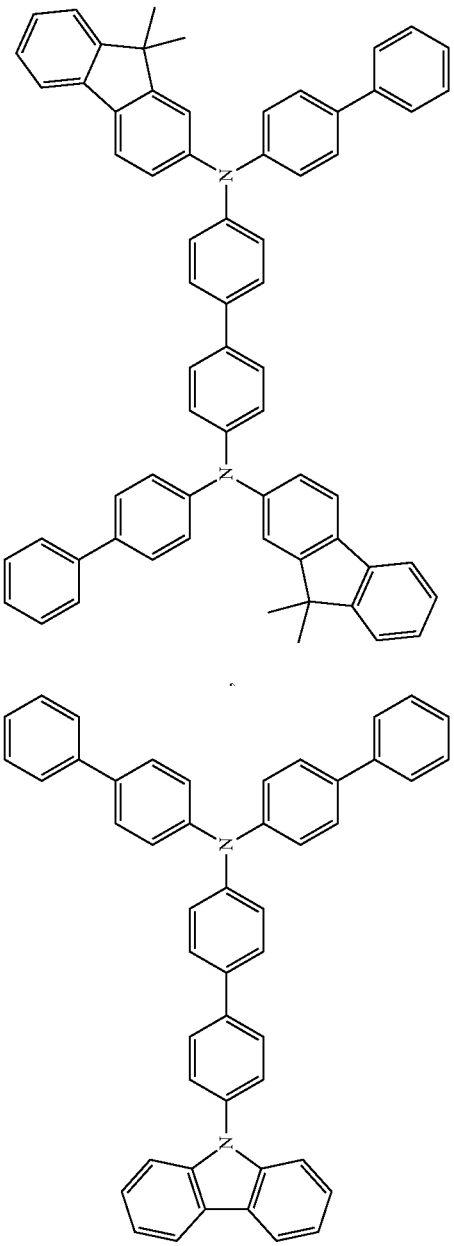
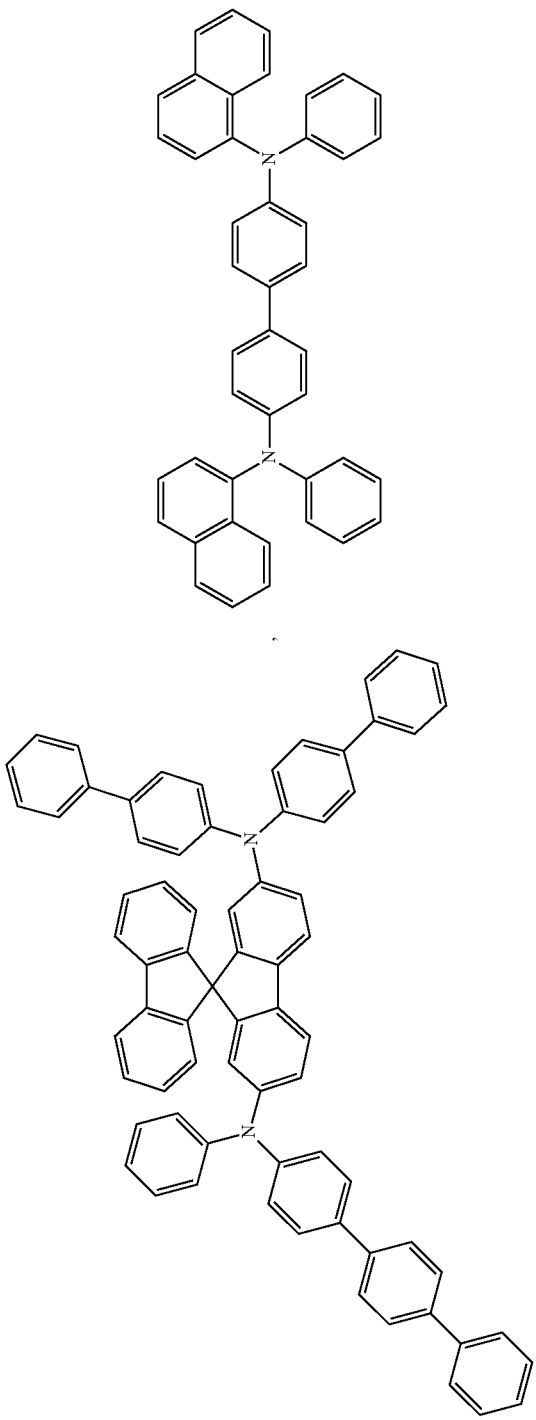

401
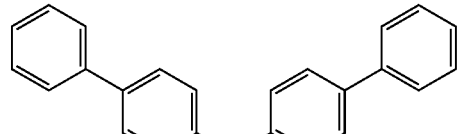
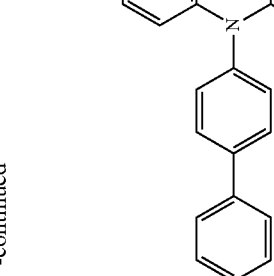
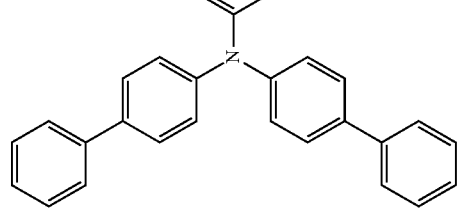
402
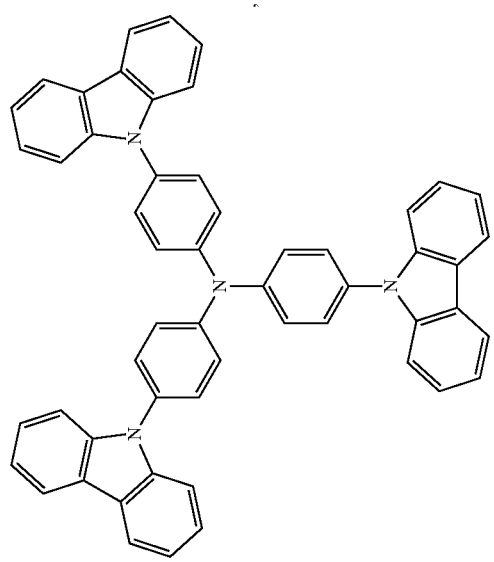
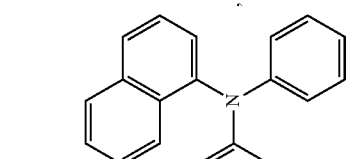
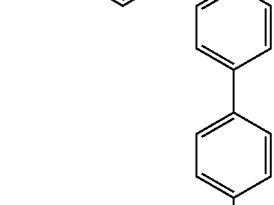
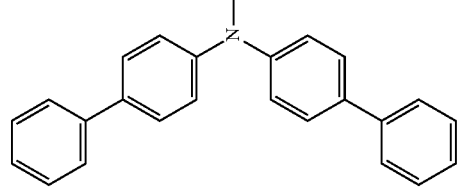
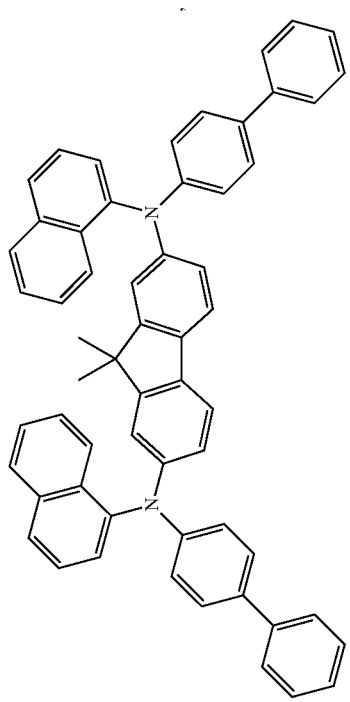

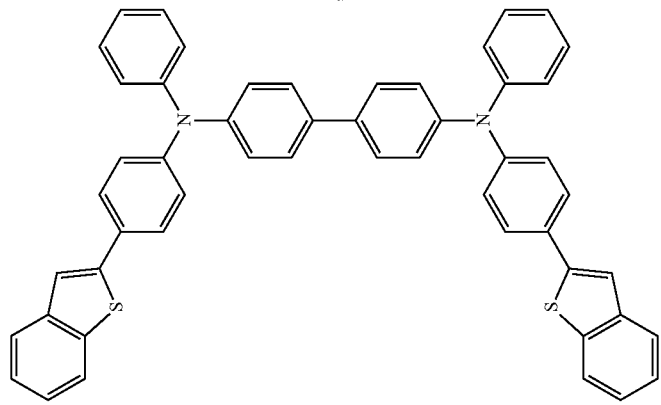
and
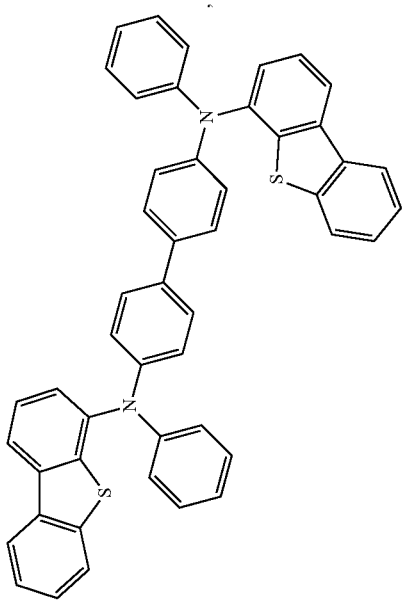
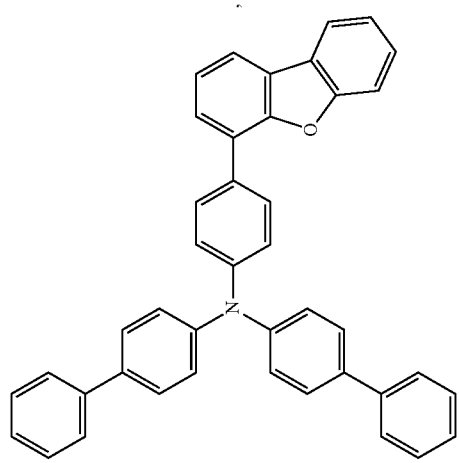

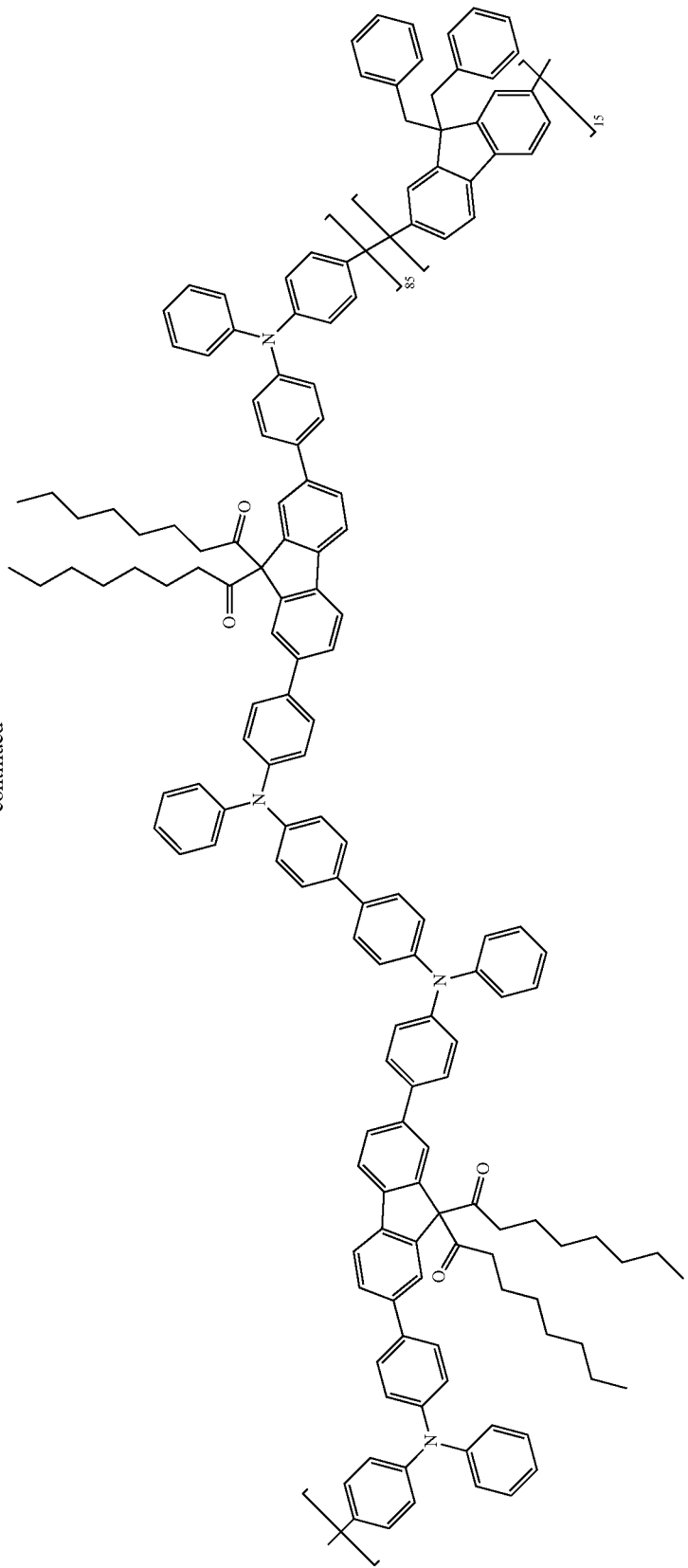

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting dopant material, and may contain one or more additional host materials using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

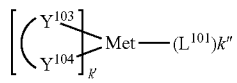

wherein Met is a metal; ($Y^{102}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

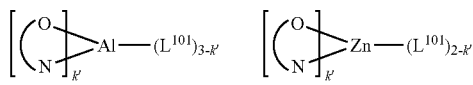

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of other organic compounds used as additional host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

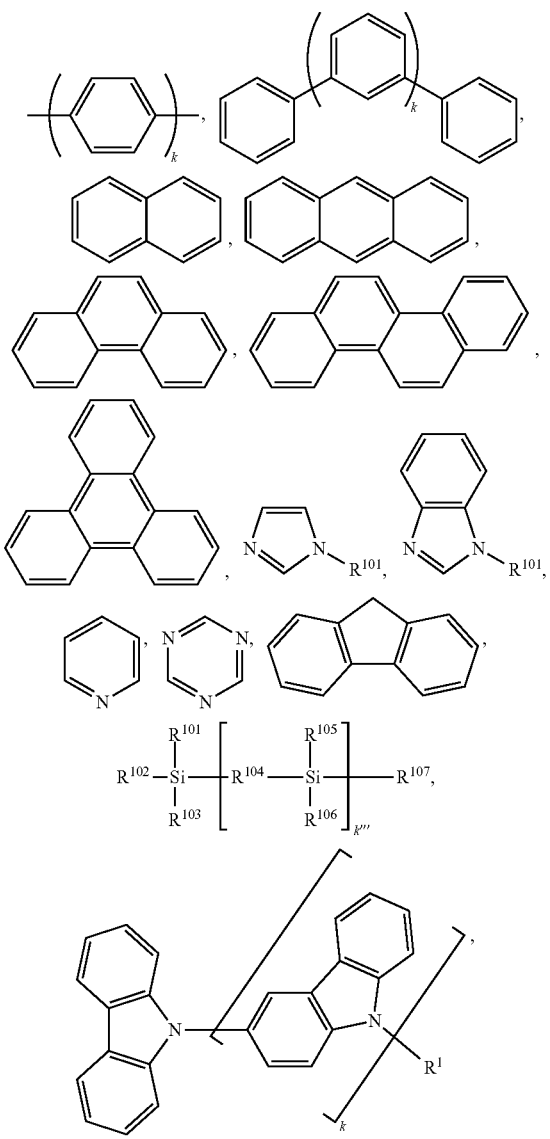

-continued

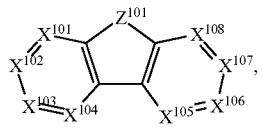

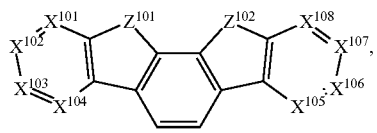

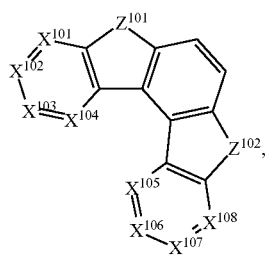

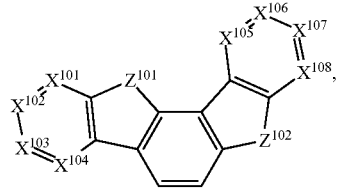

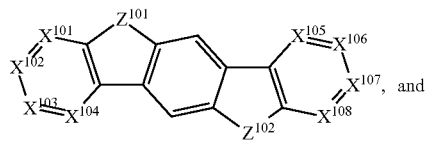

-continued

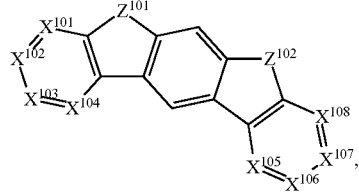

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

Non-limiting examples of the additional host materials that may be used in an OLED in combination with the host compound disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472,

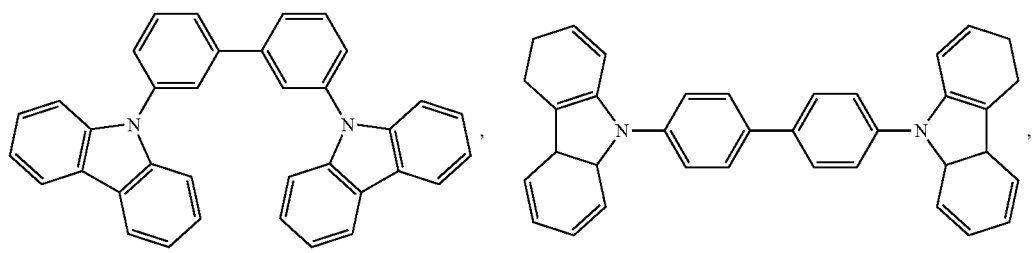

-continued
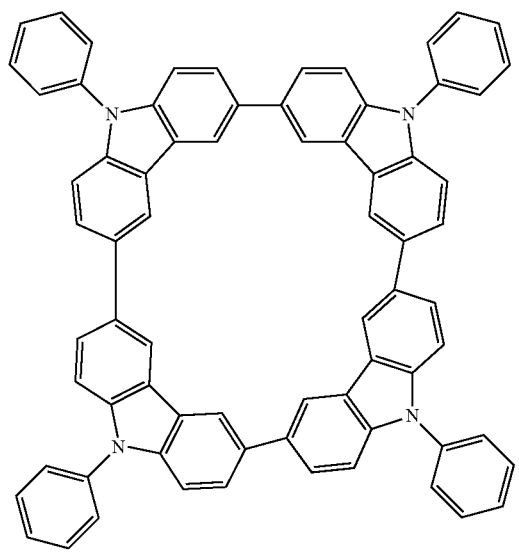
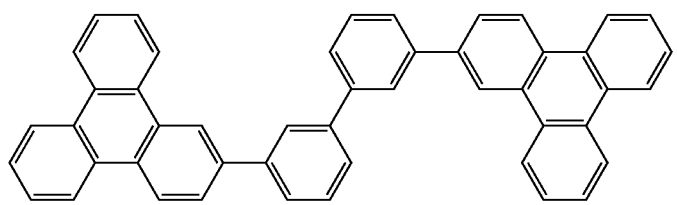
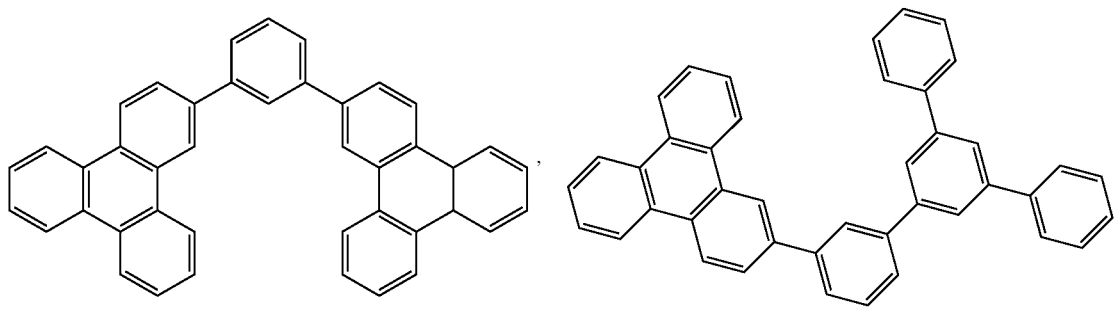
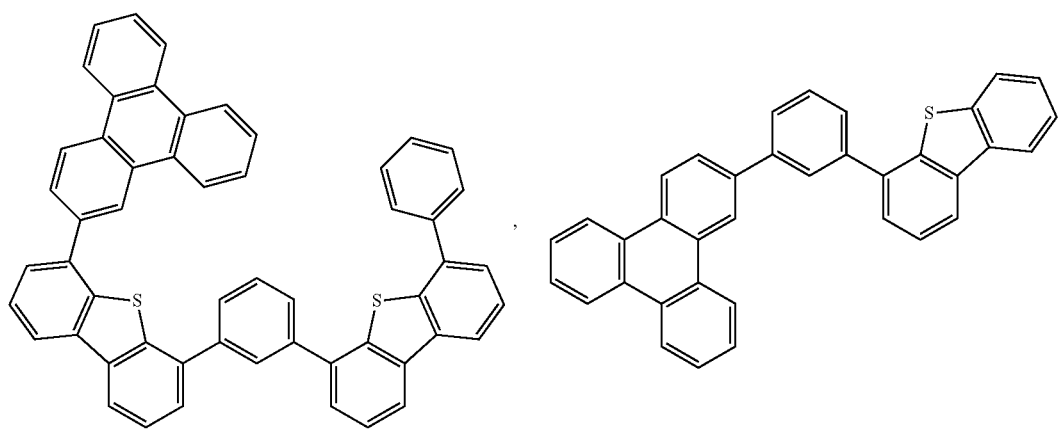

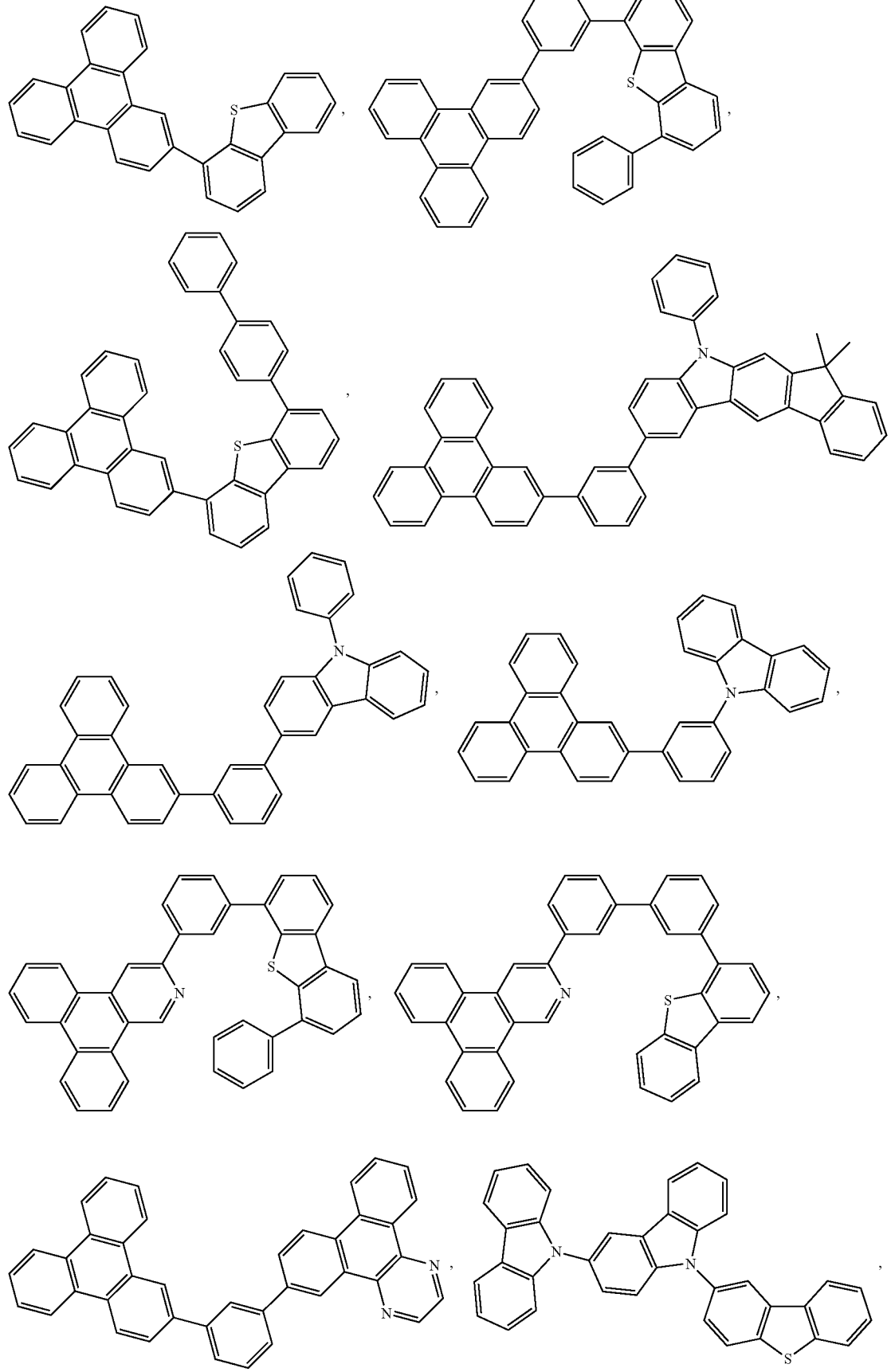

415 416
-continued
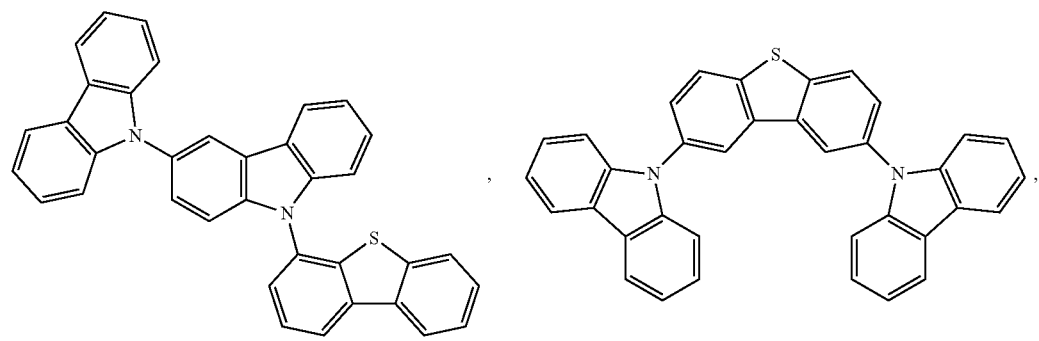
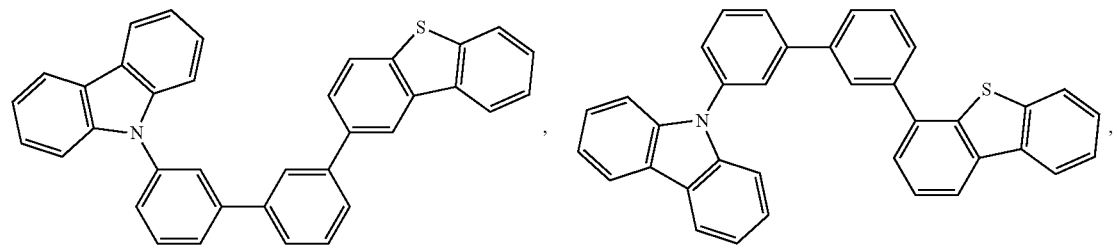
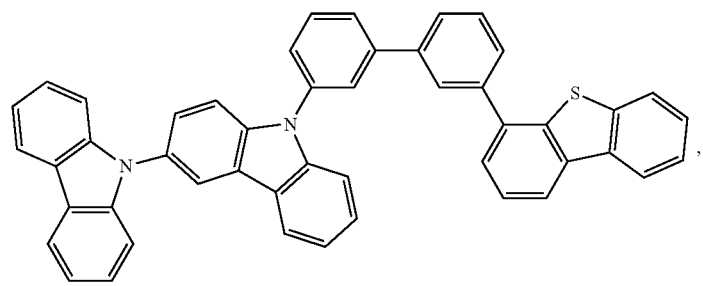
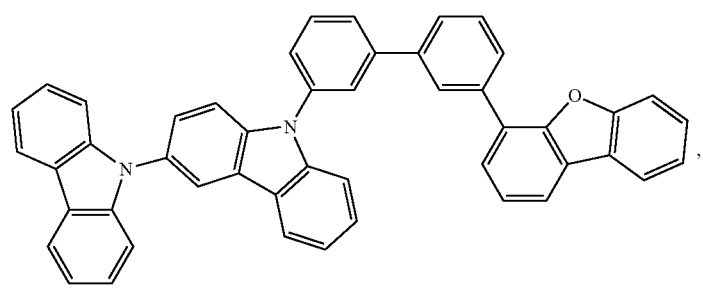
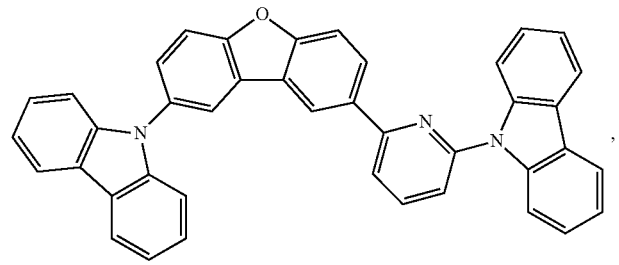
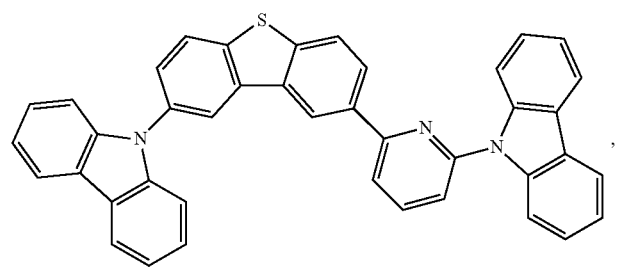

417                                           418
-continued
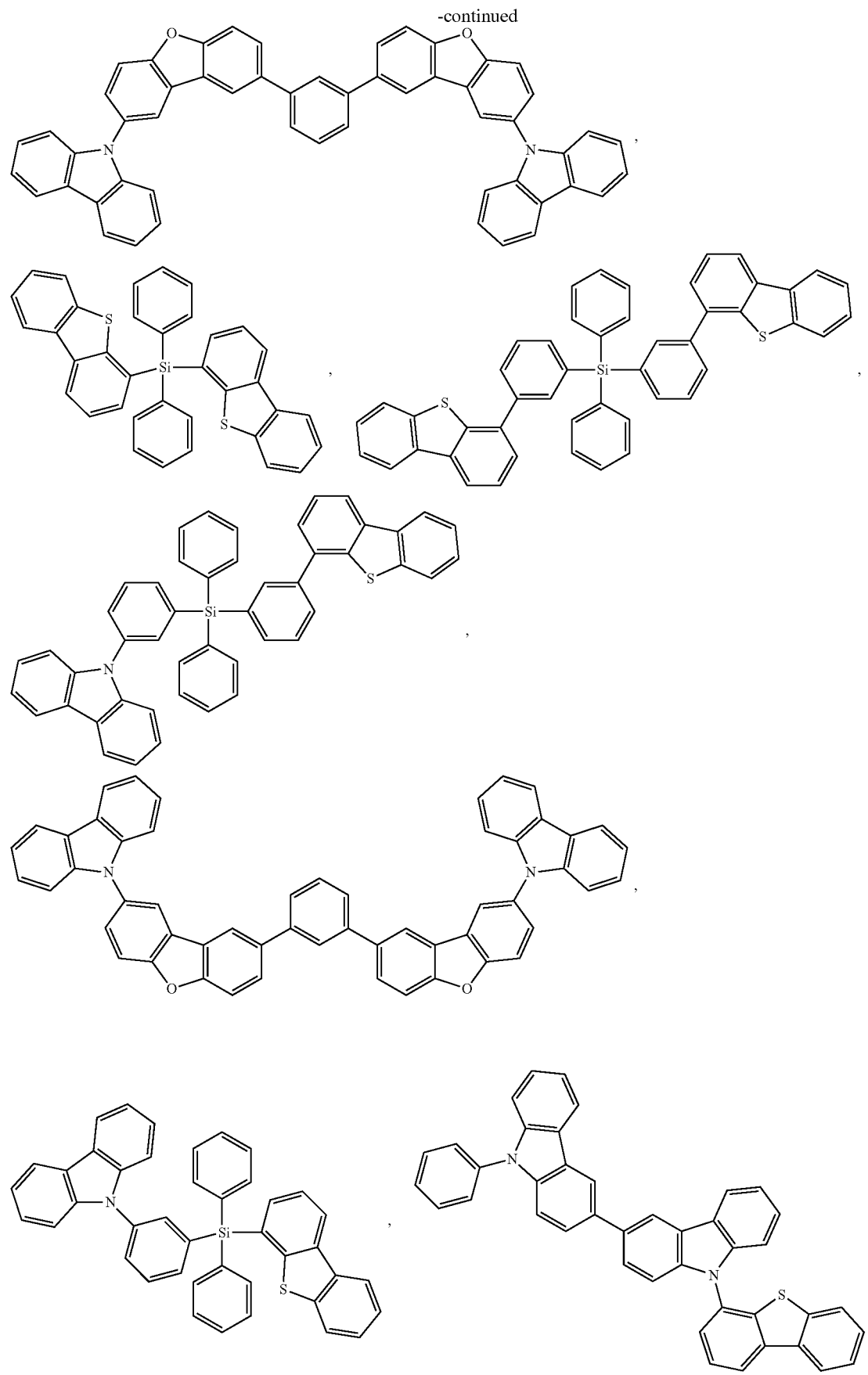

419
420
-continued
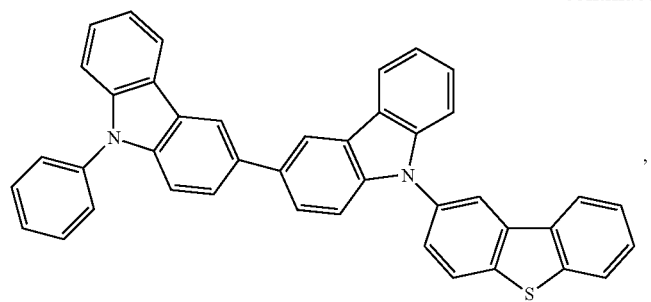
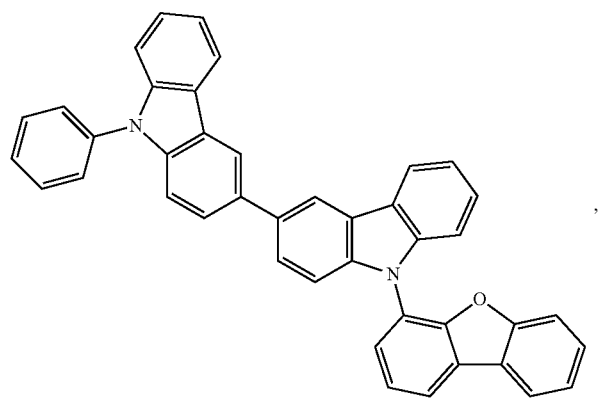
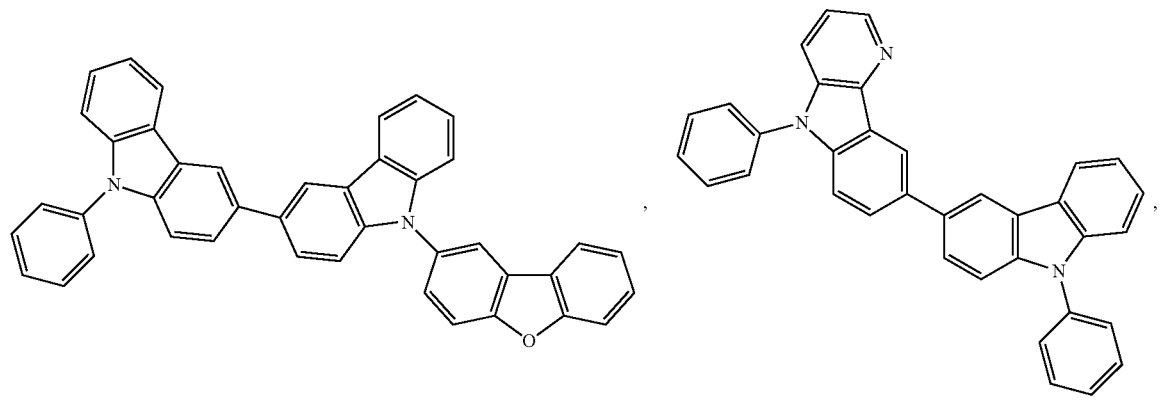
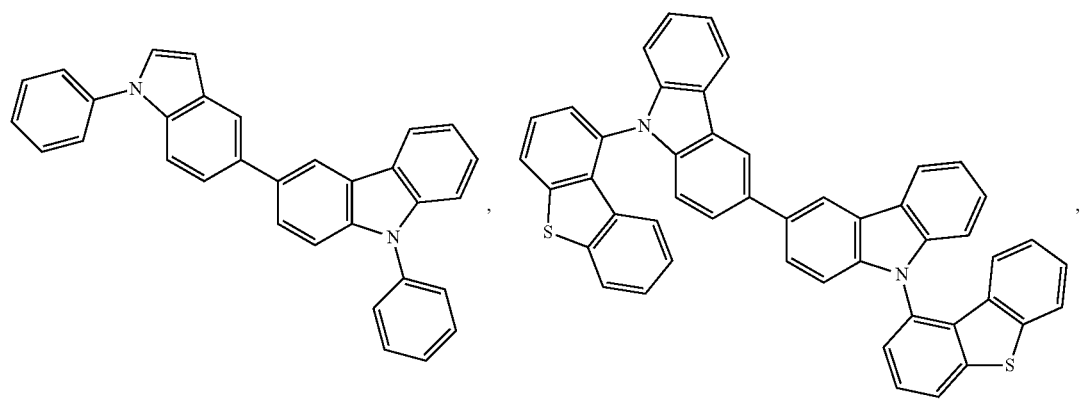

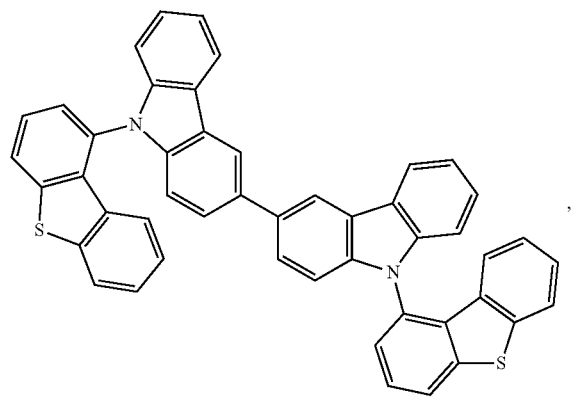
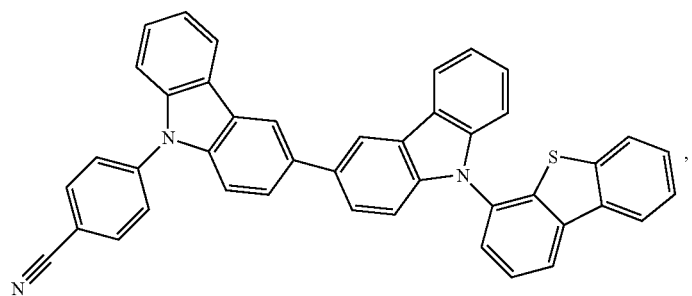
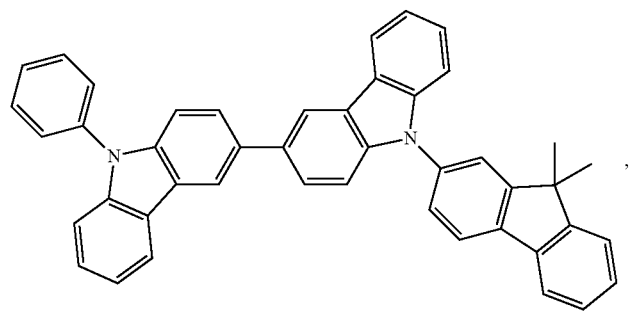
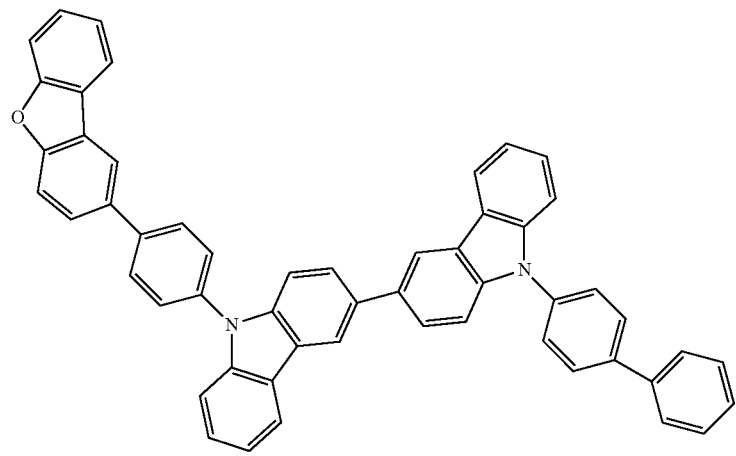

423
-continued
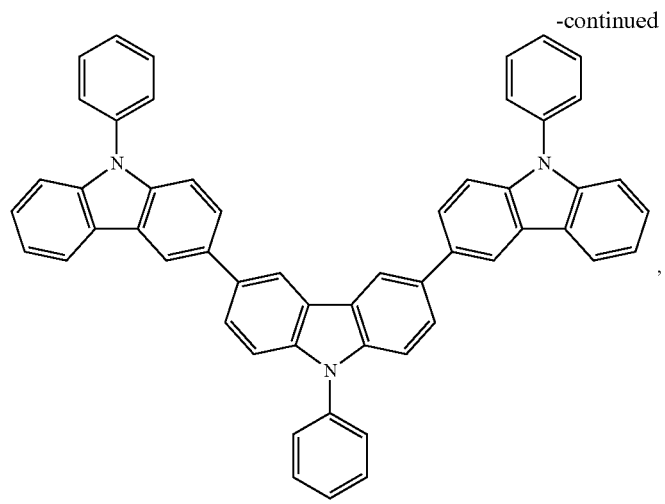
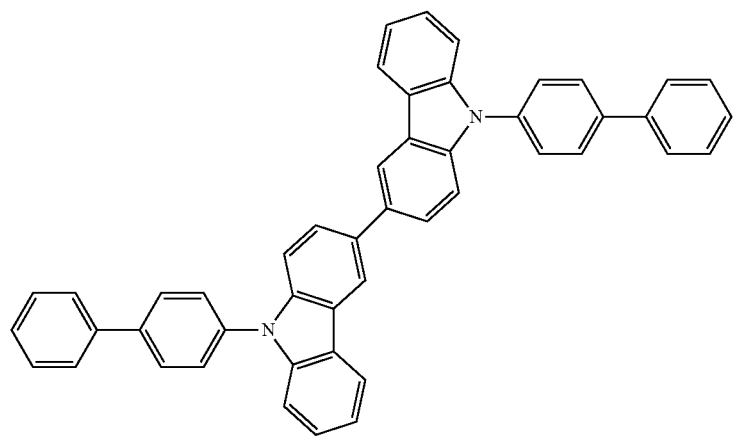
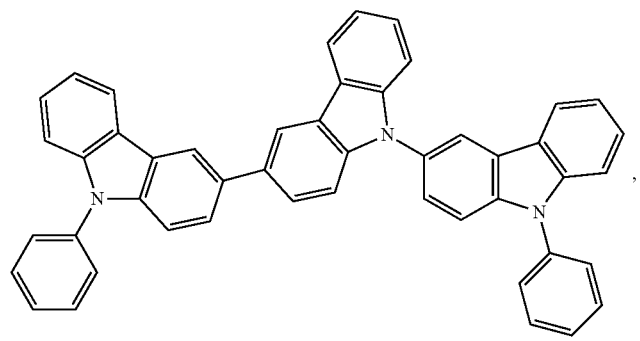
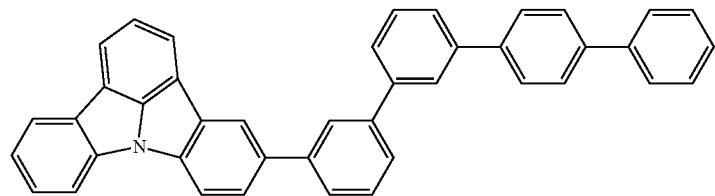

-continued
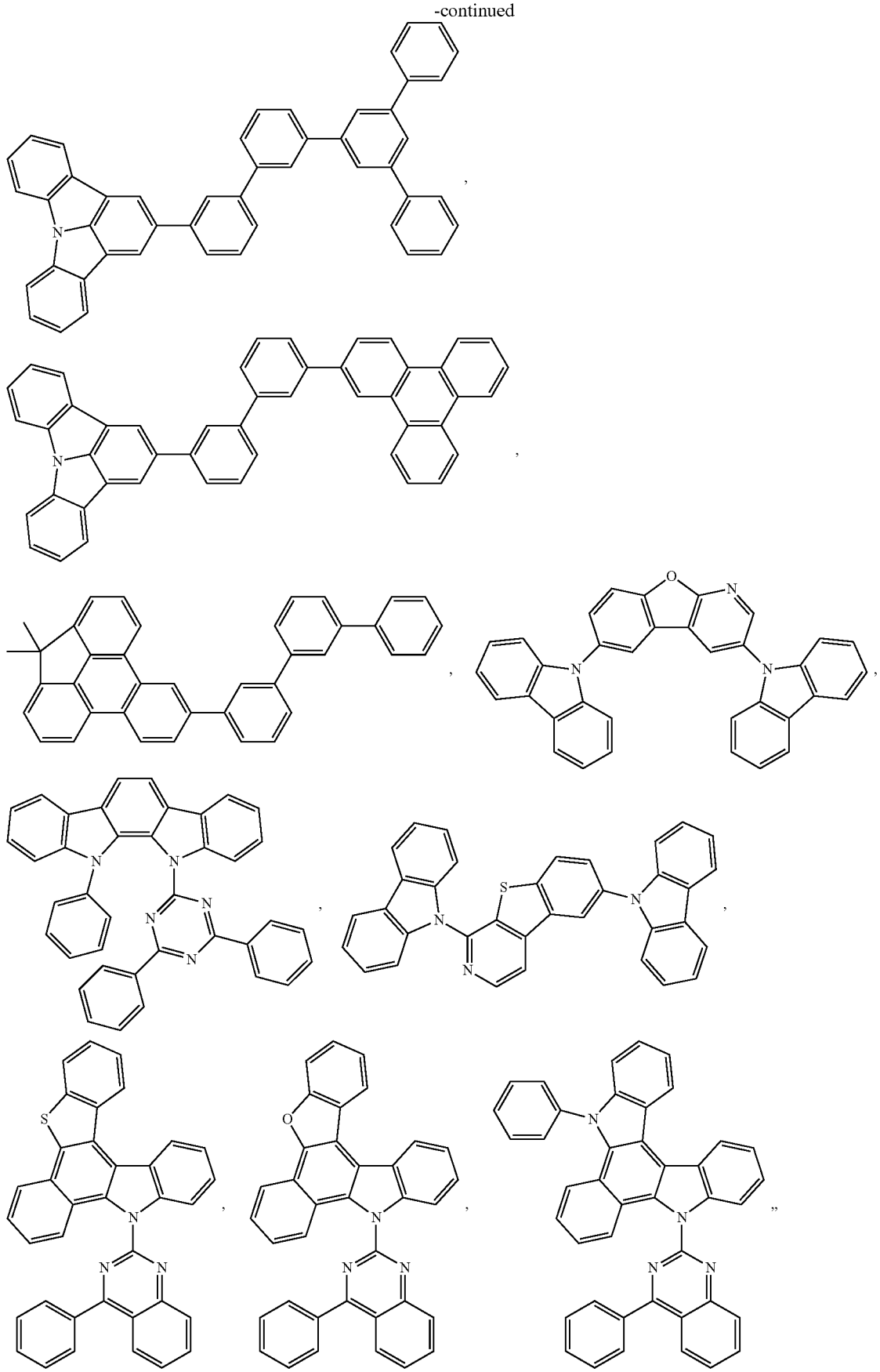

-continued
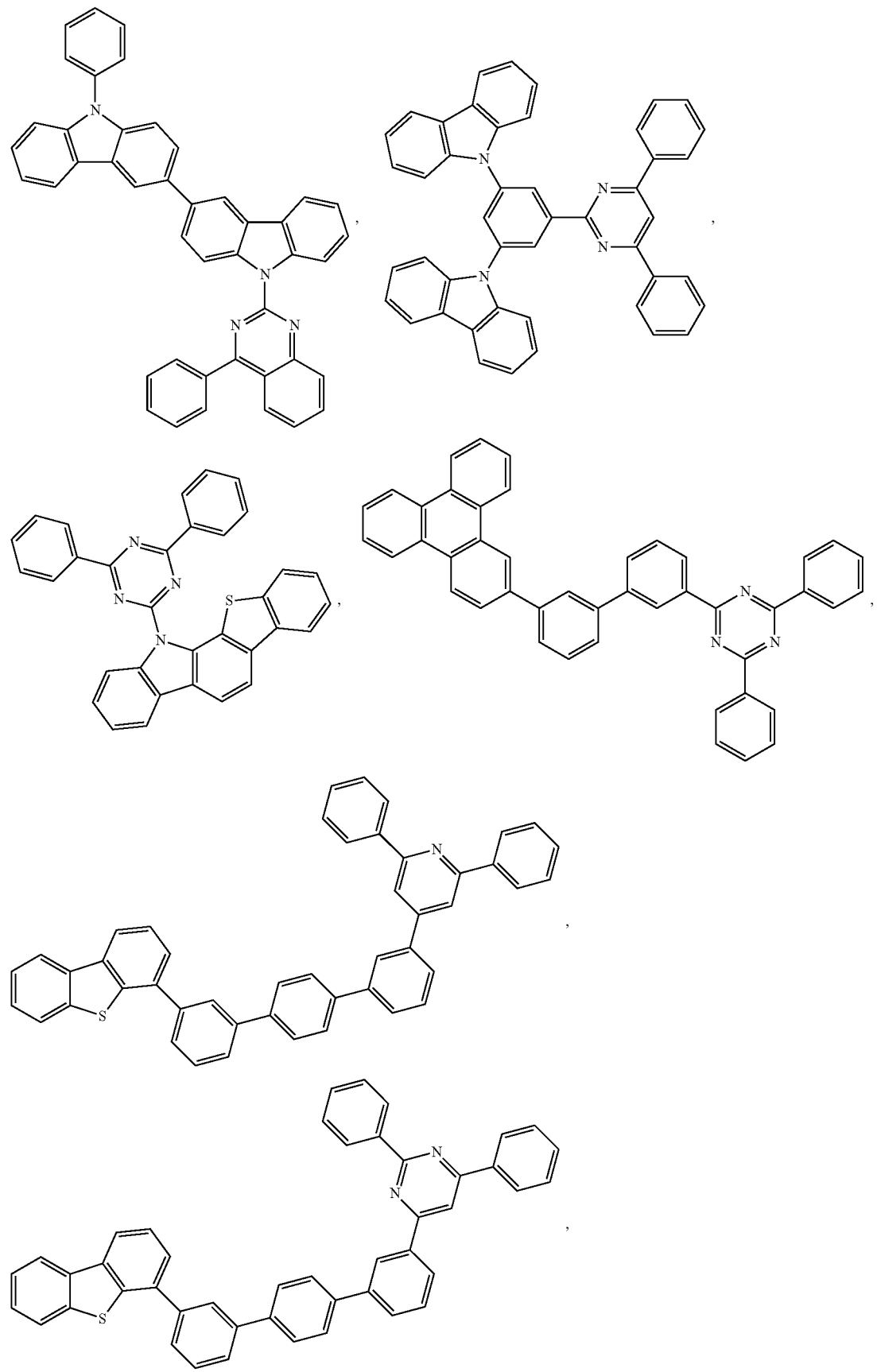

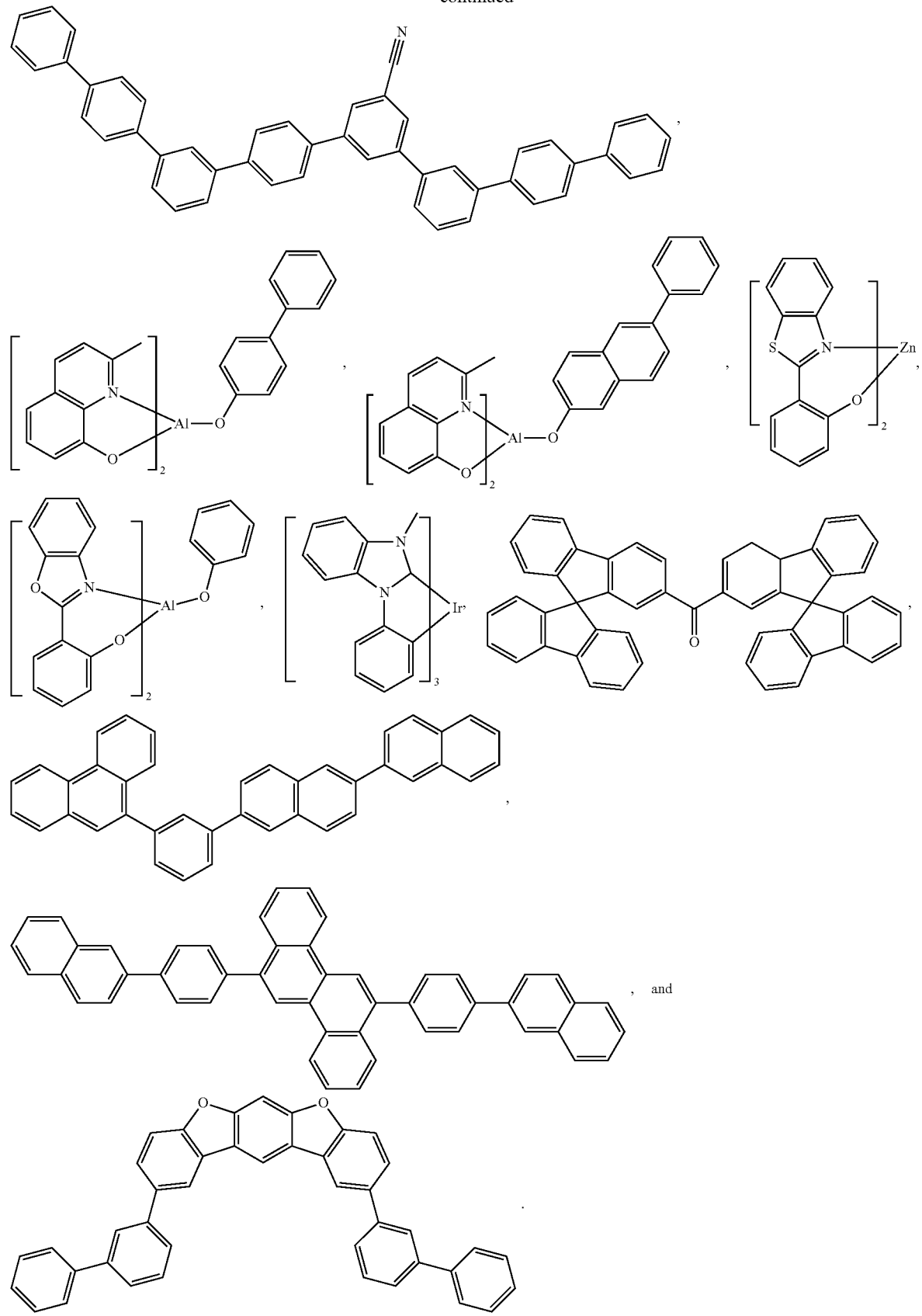

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, US06699599, US06916554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,8713,61, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450,

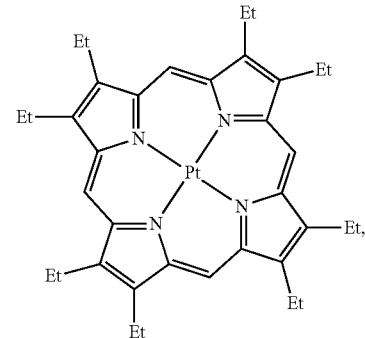

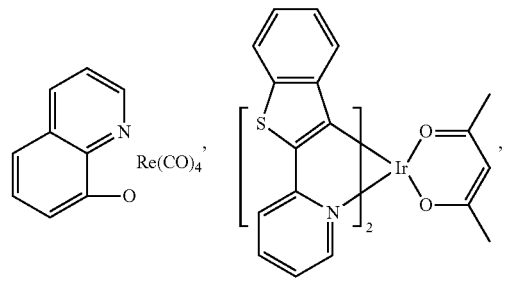

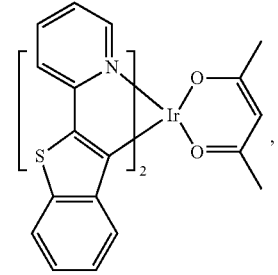

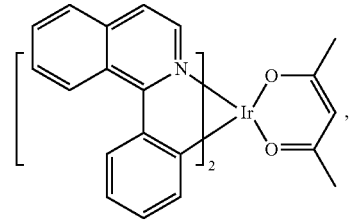

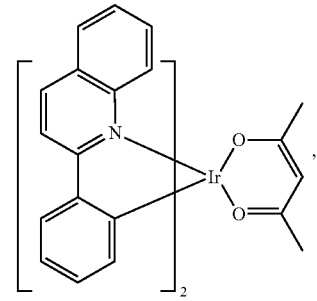

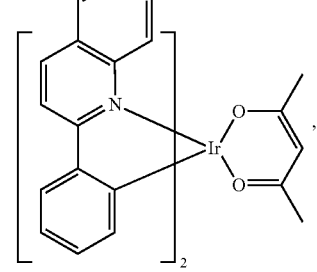

433
-continued
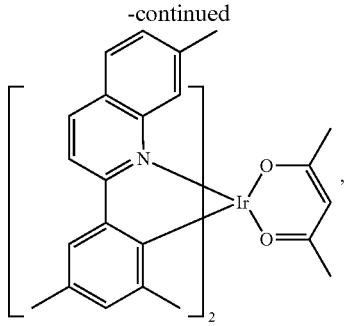
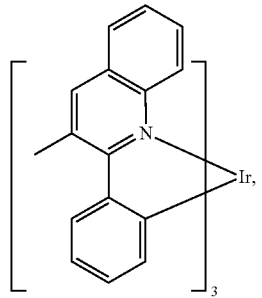
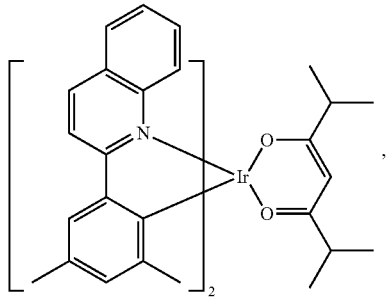
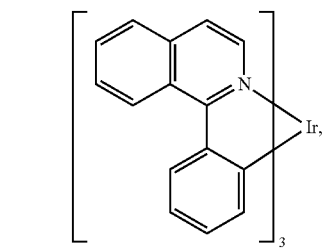
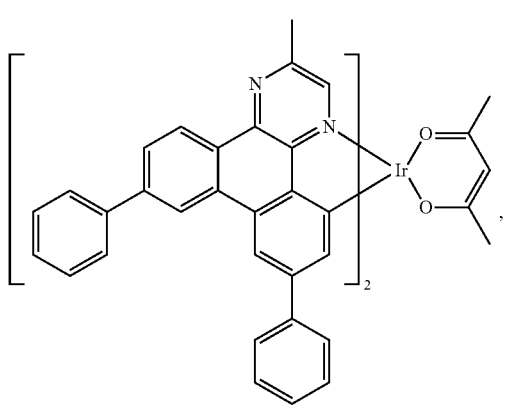
434
-continued
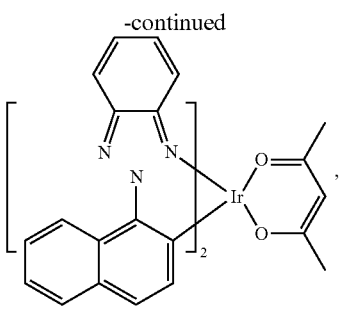
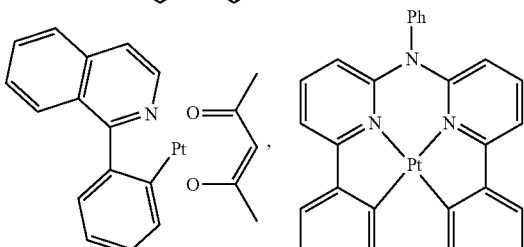
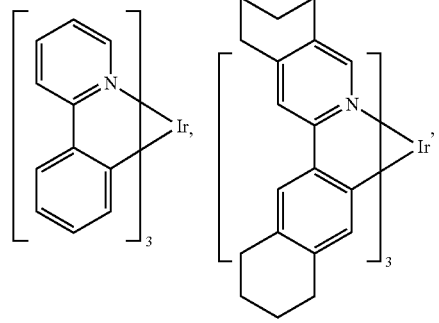
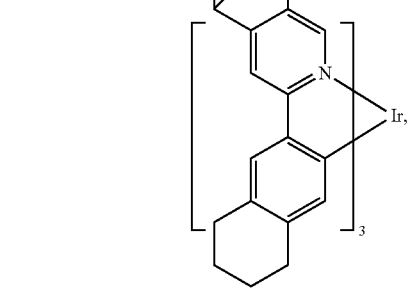
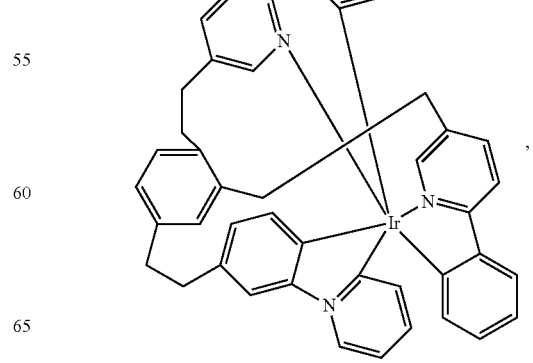

-continued
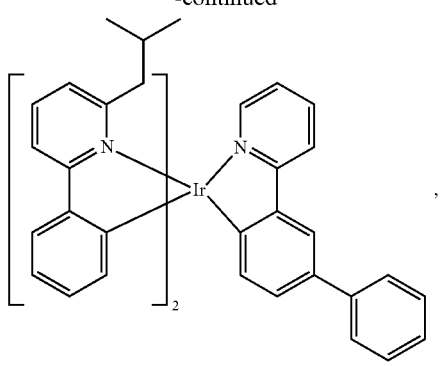
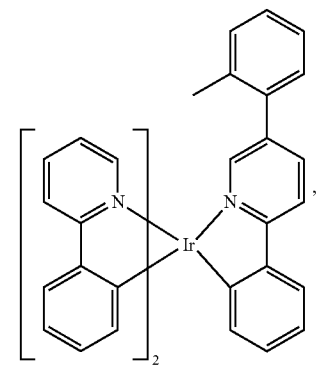
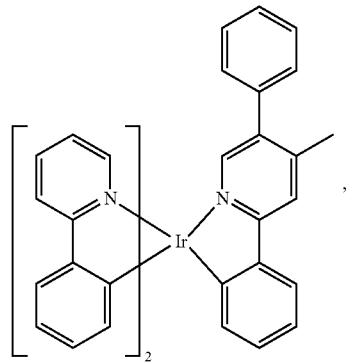
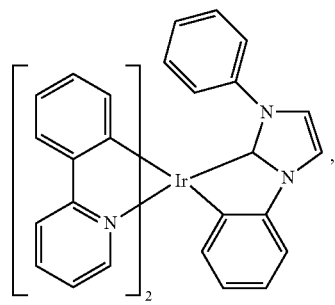
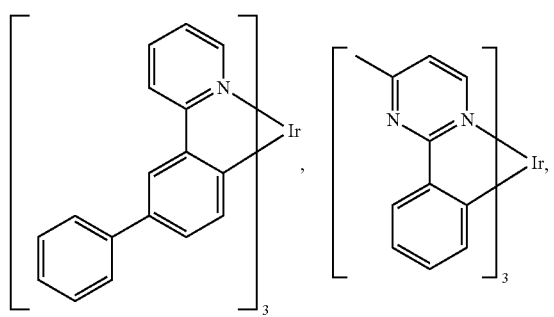
-continued
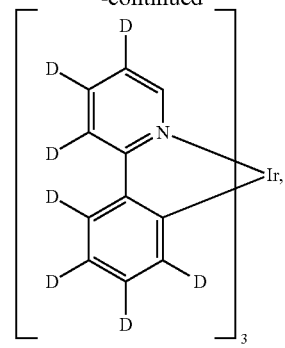
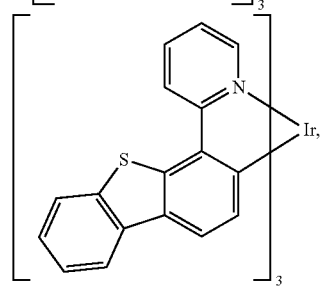
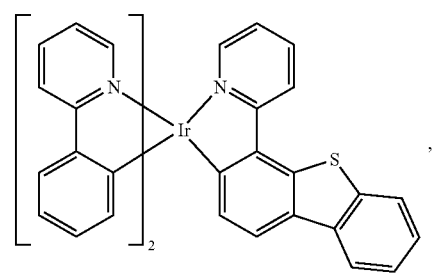
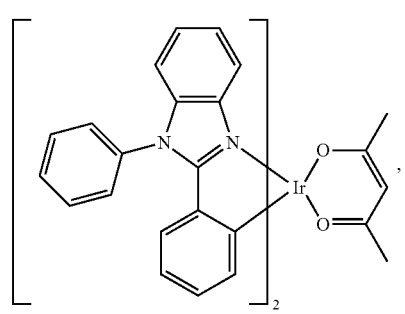
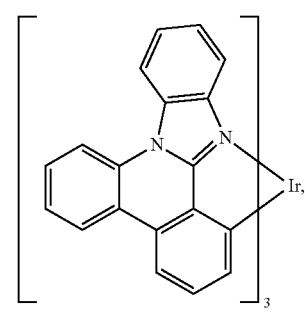

-continued
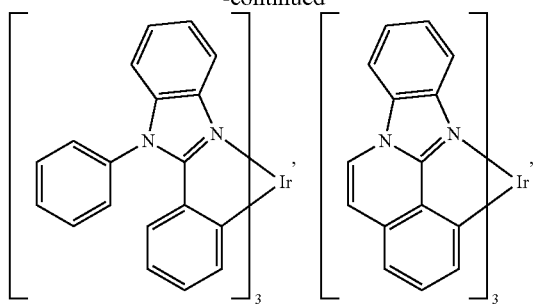
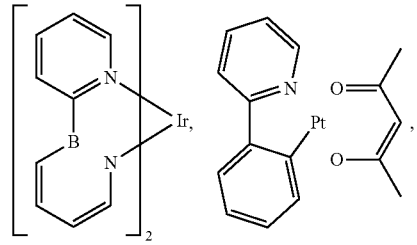
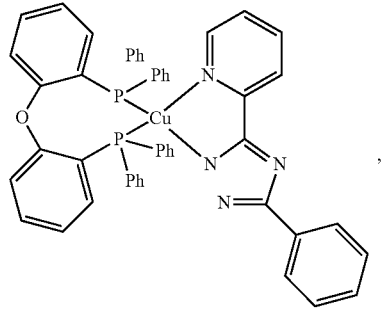
-continued
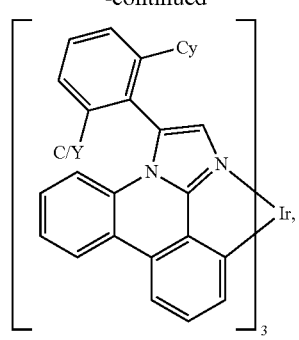
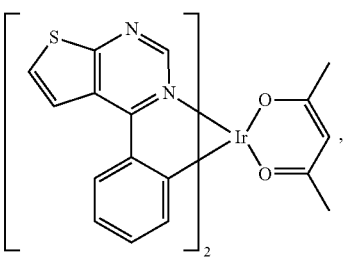
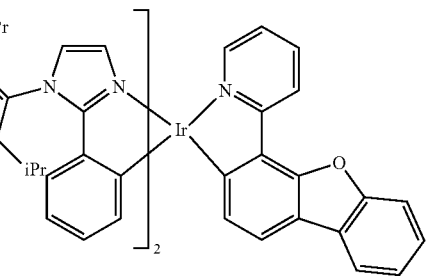
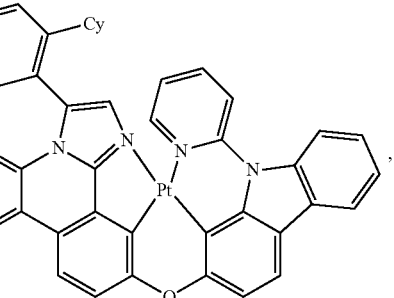
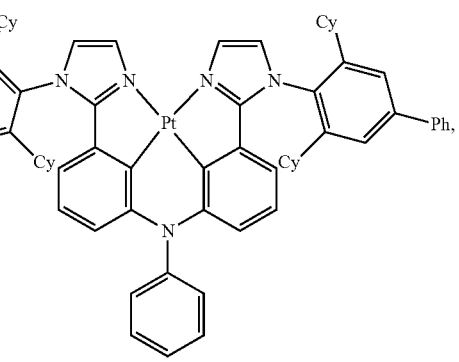
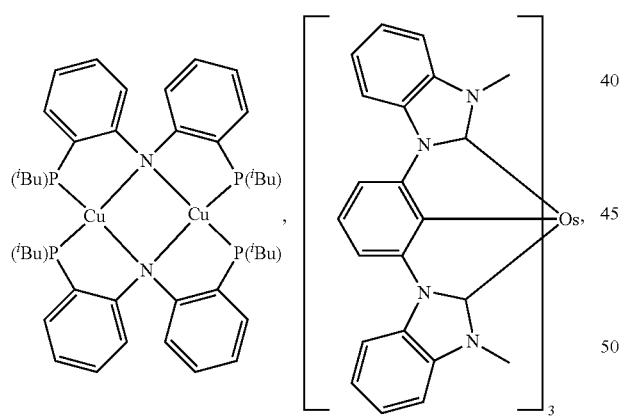
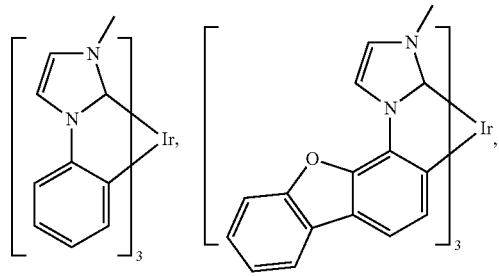

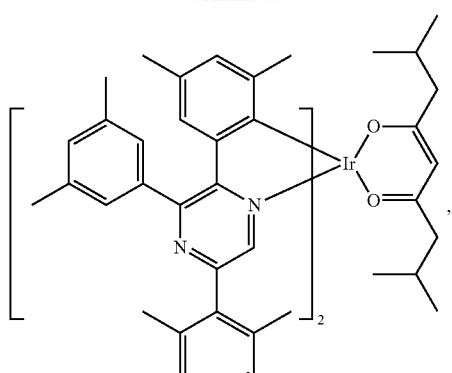
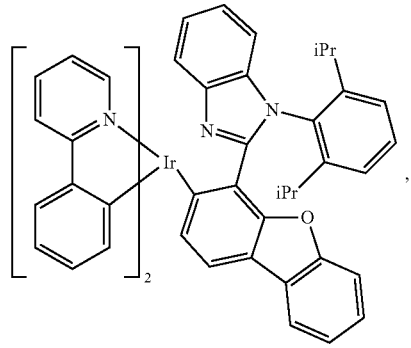
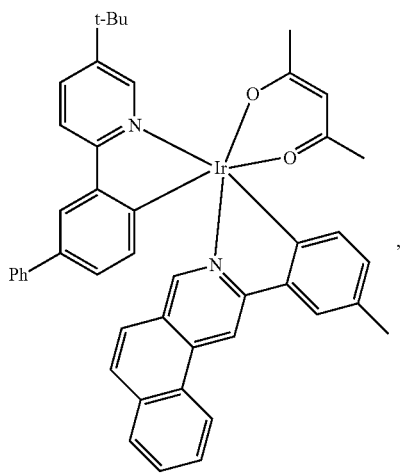
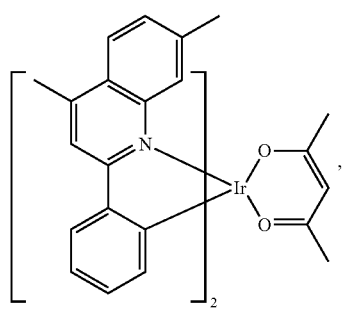
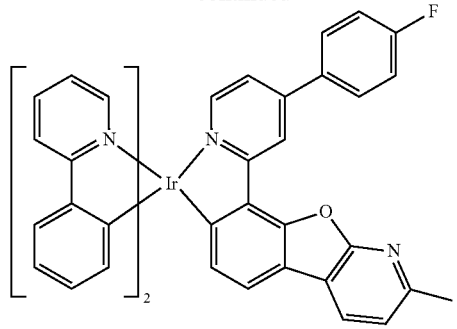
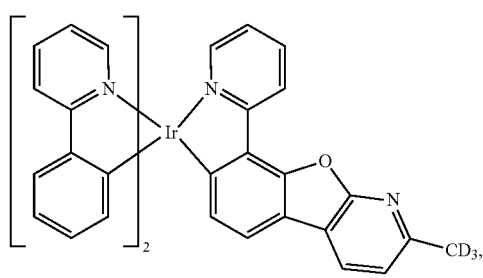
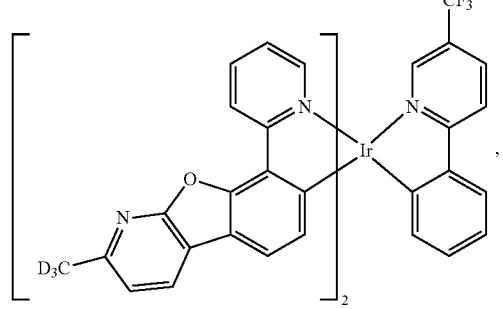
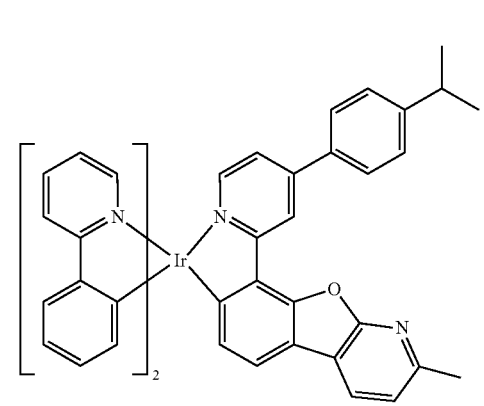
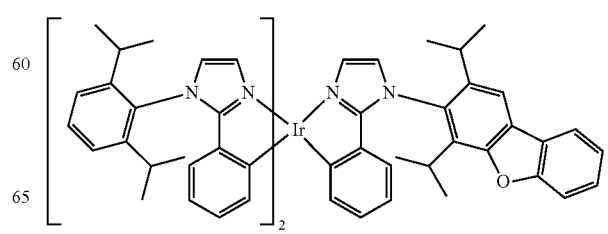

441
-continued
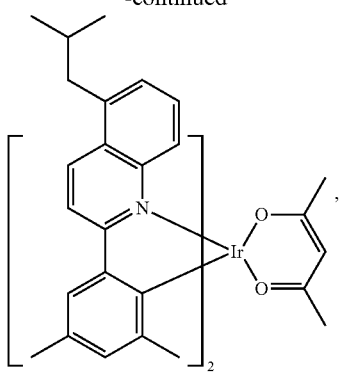
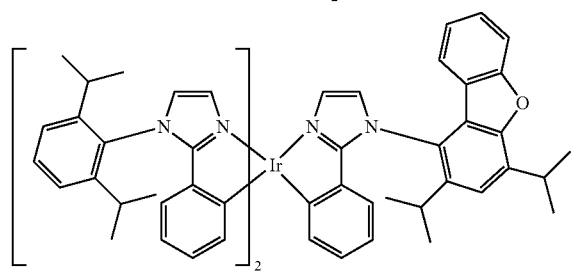
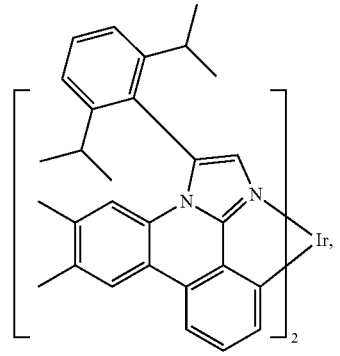
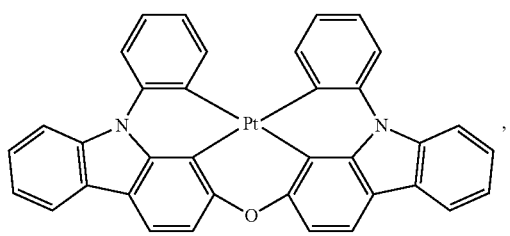
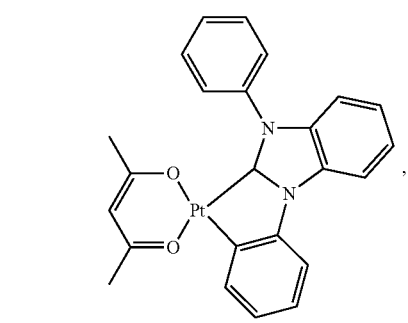
442
-continued
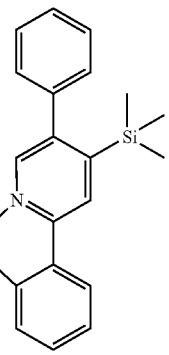
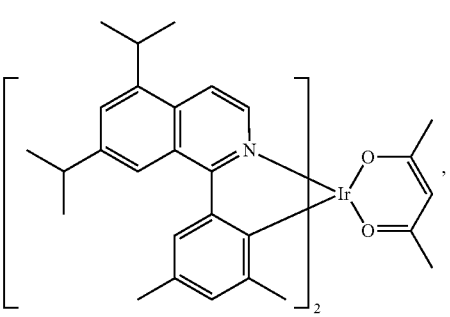
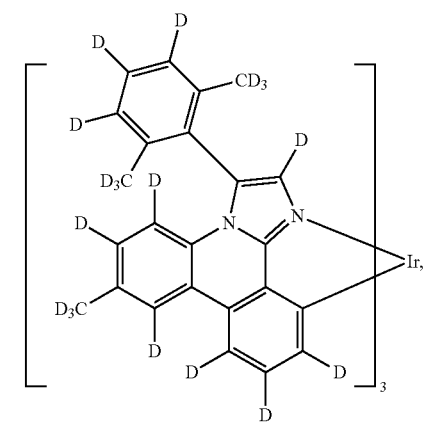

443
-continued
444
-continued
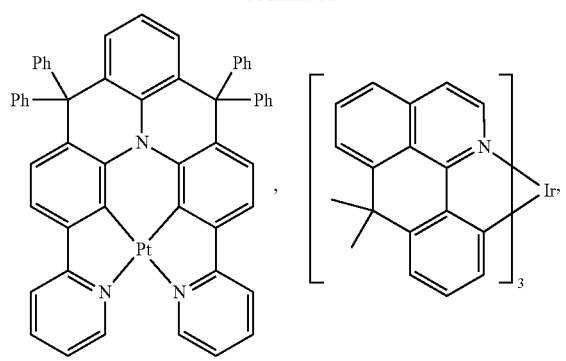
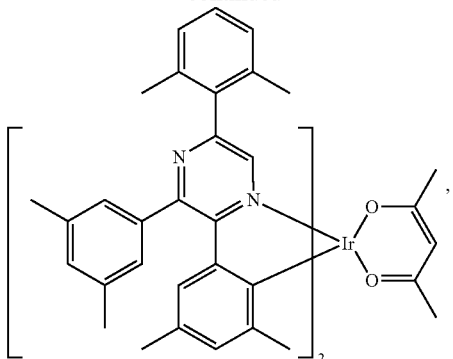
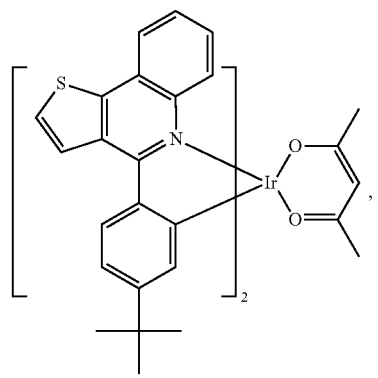
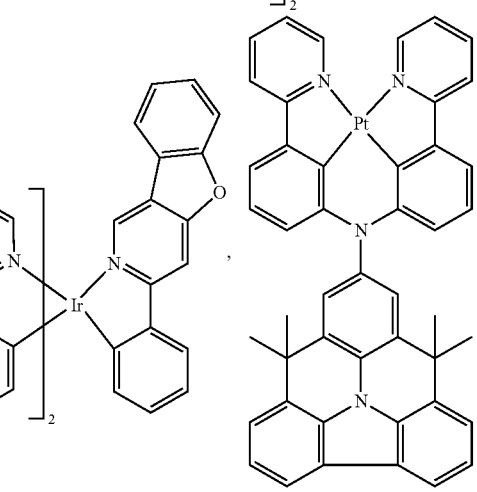
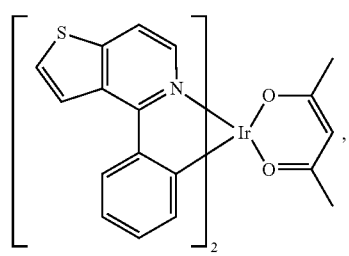
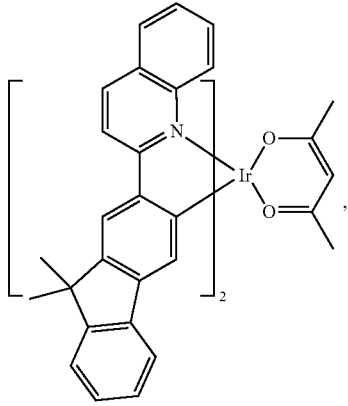
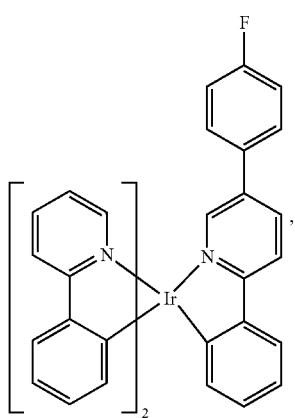
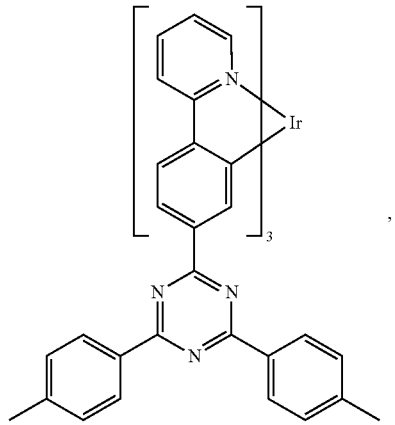

445
-continued
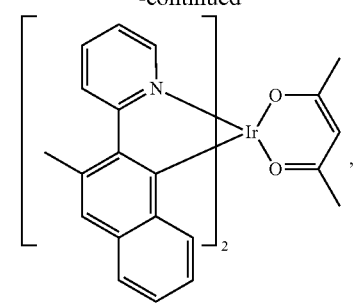
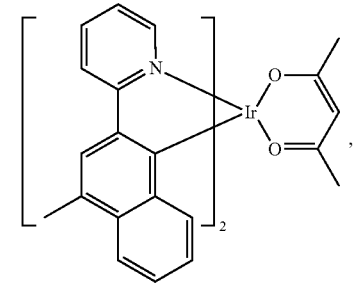
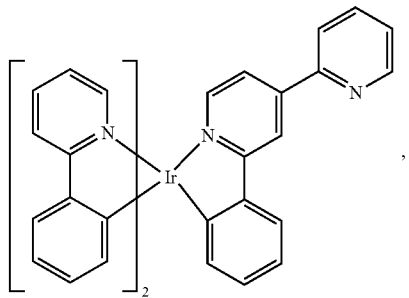
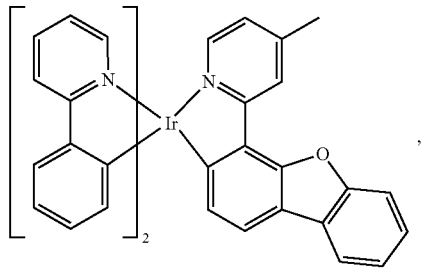
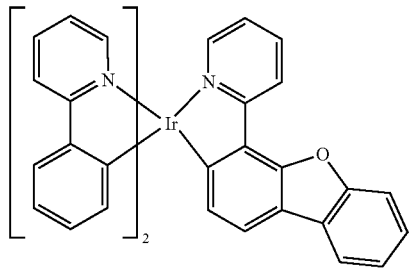
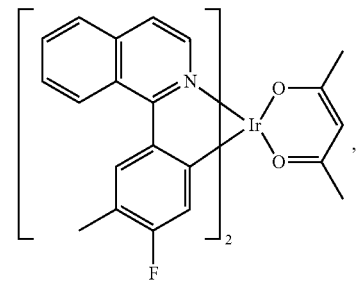
446
-continued
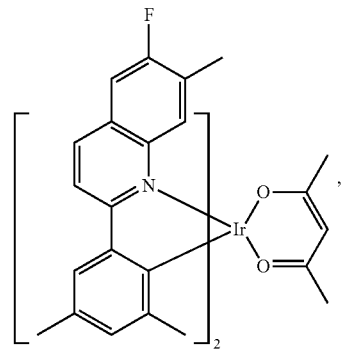
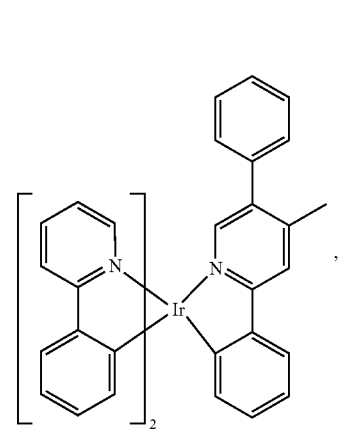
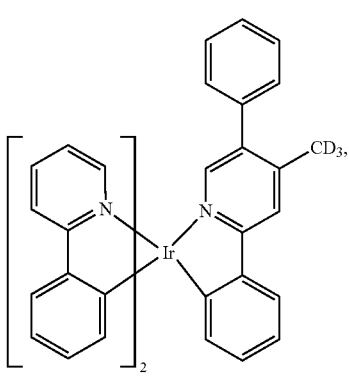
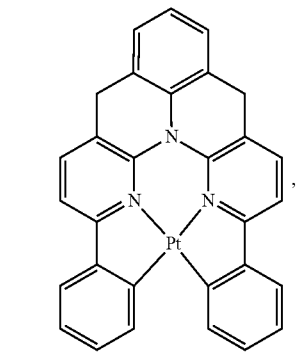

-continued
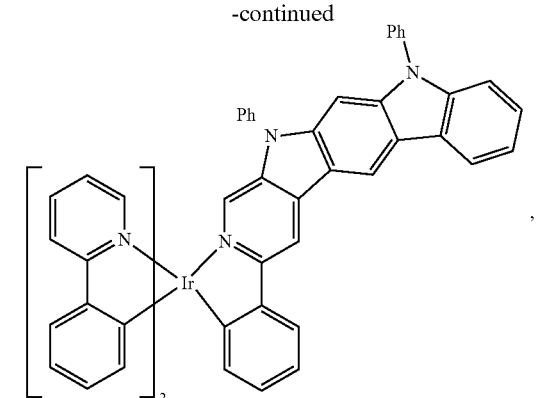
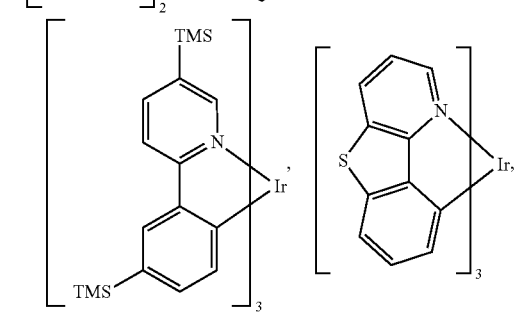
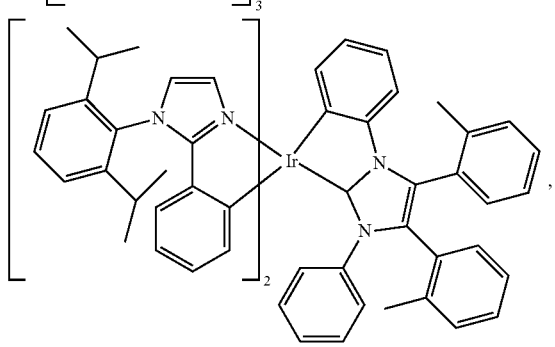
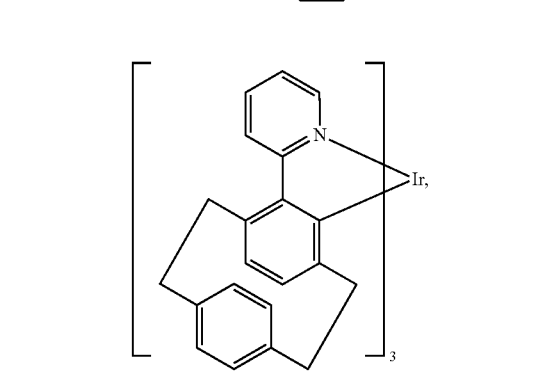
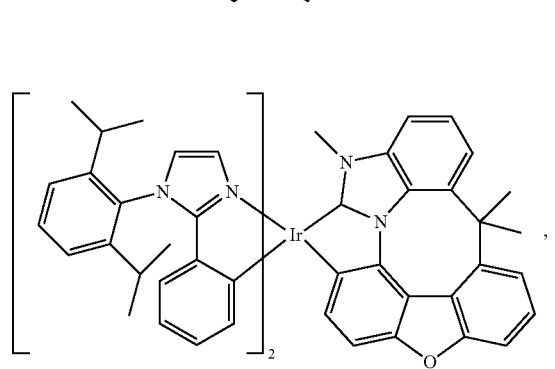
-continued
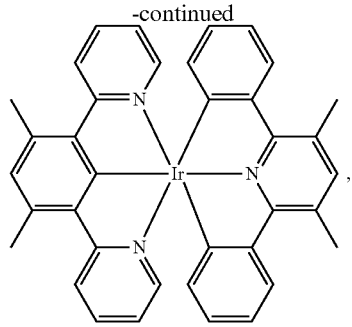
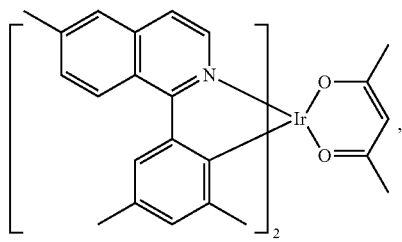
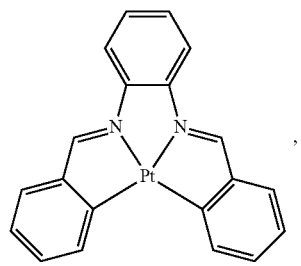
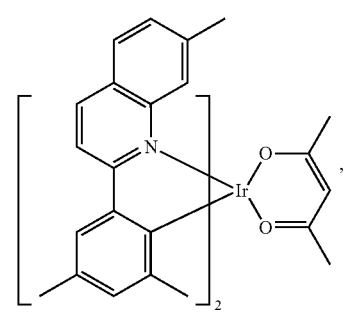
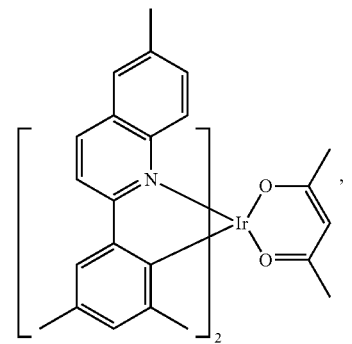

449
-continued
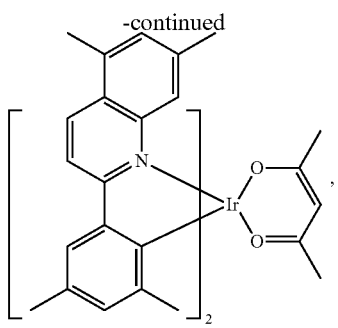,
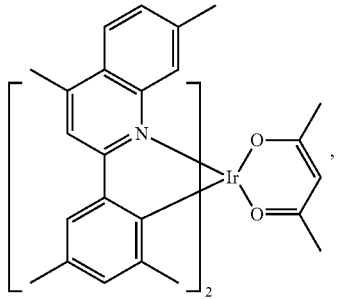,
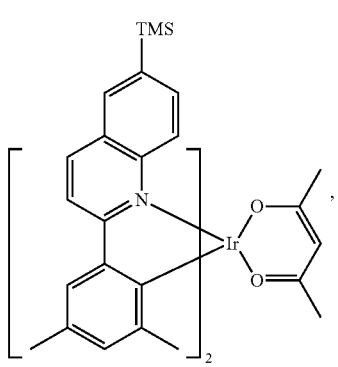,
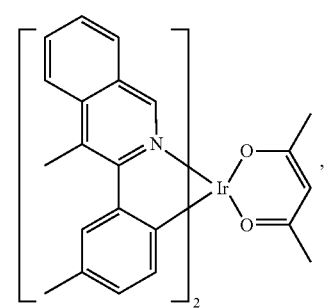,
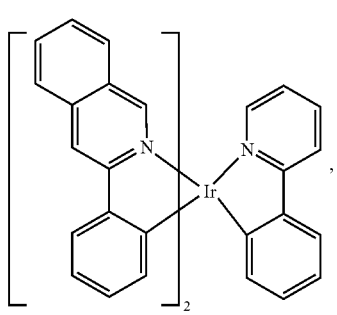,
450
-continued
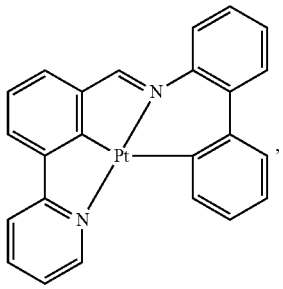,
,
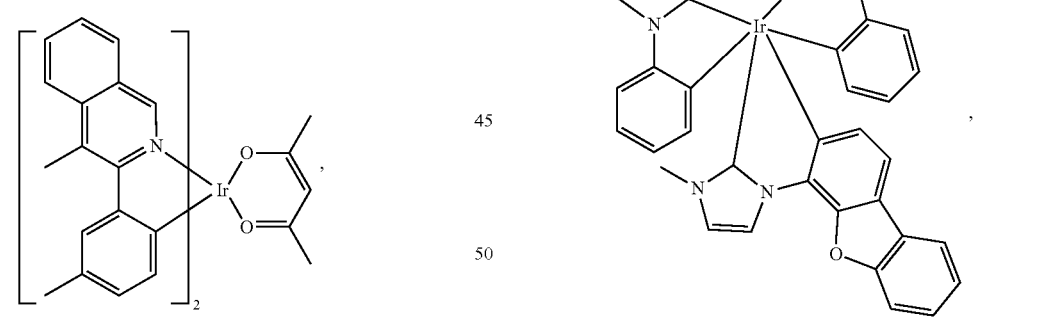,
, -continued
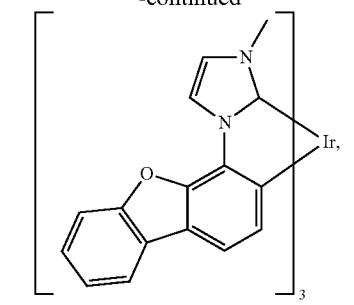
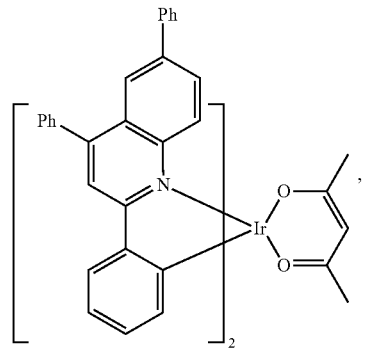
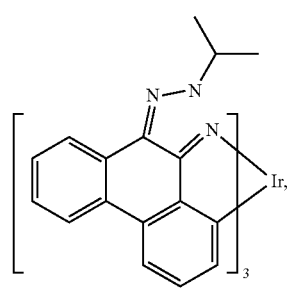
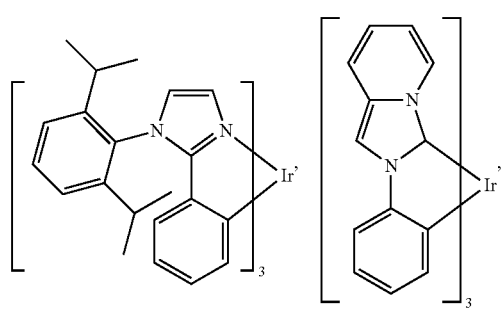
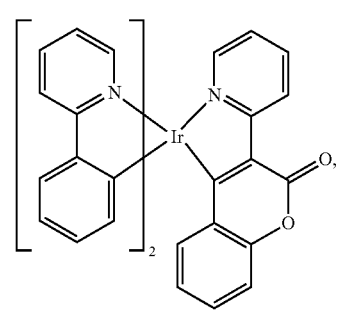
-continued
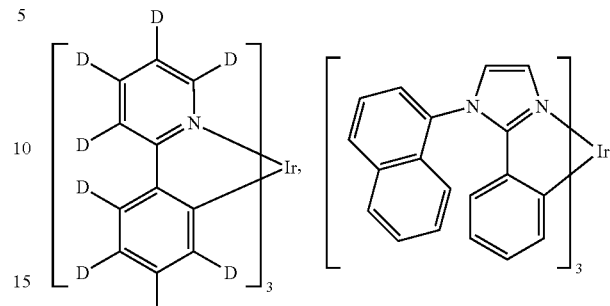
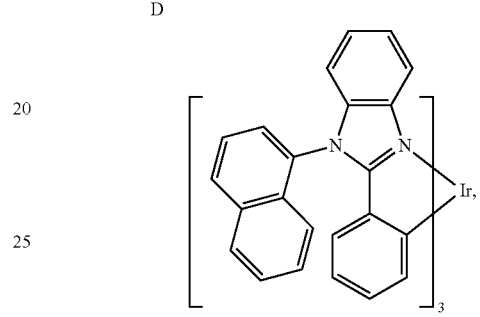
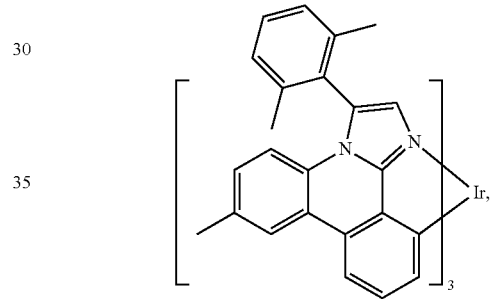
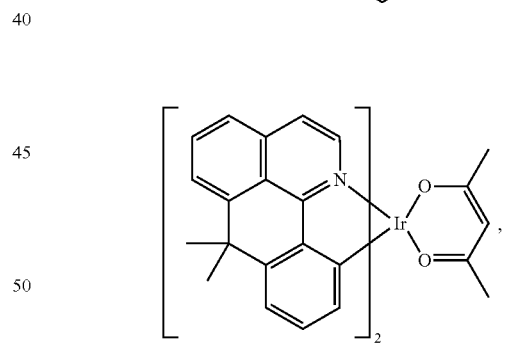
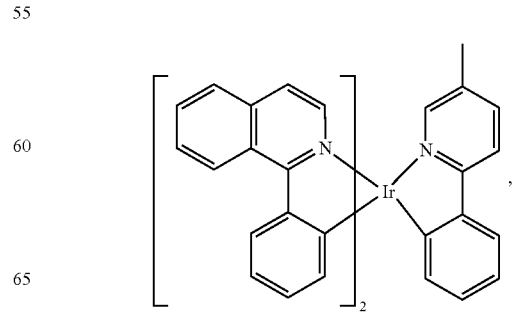

453

-continued

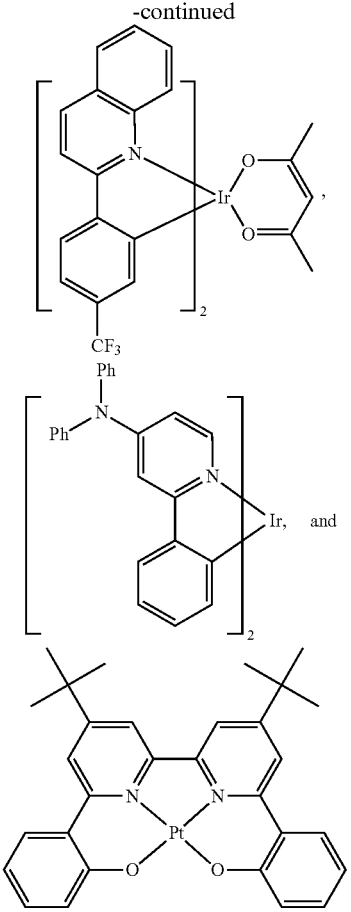

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

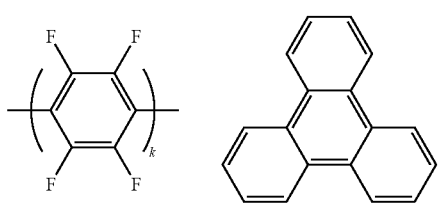

454

-continued

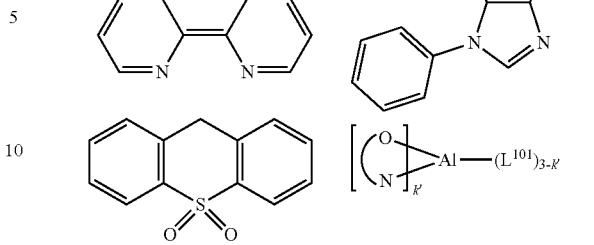

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

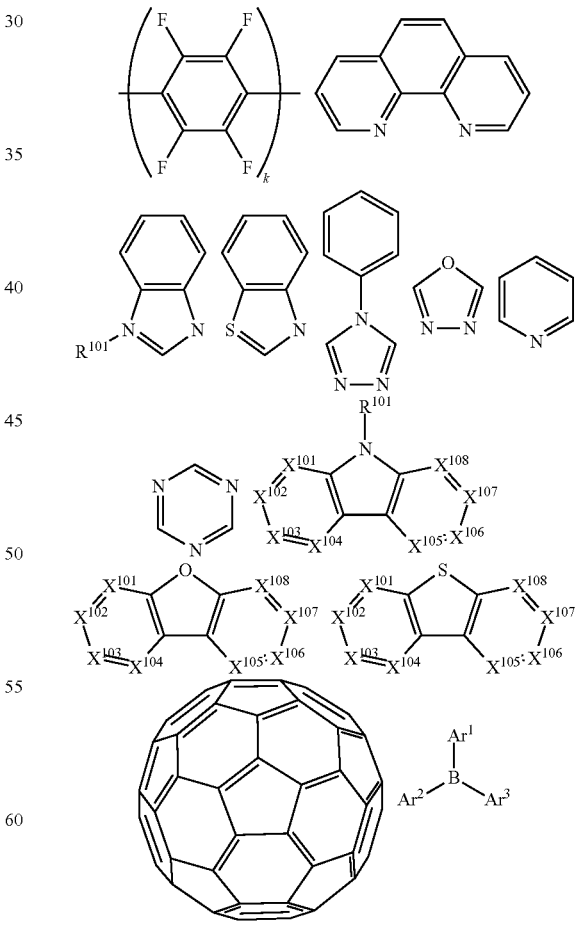

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

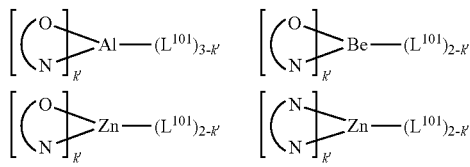

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

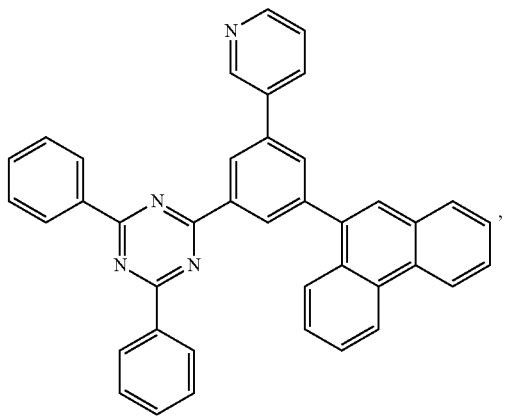

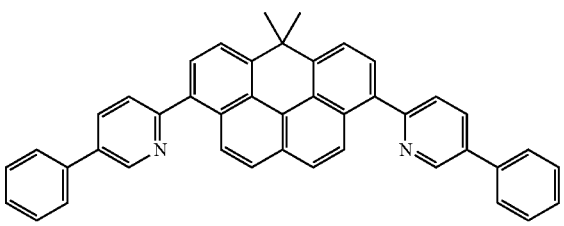

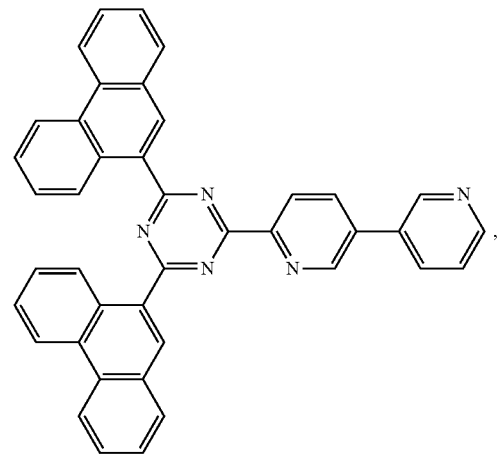

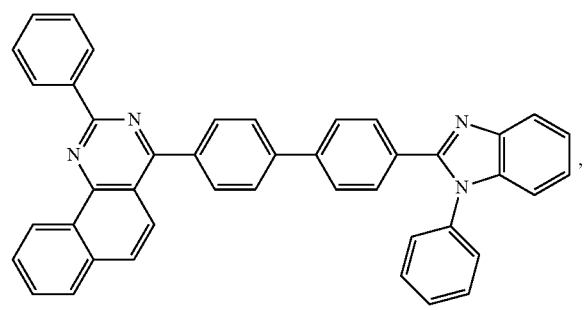

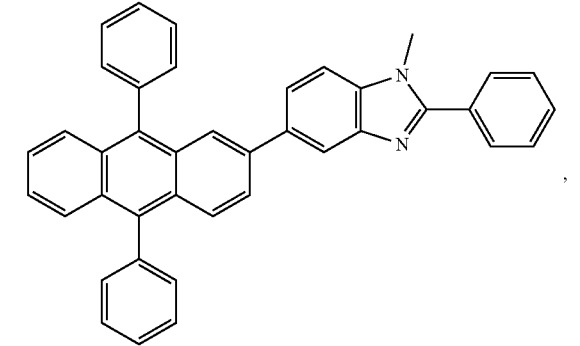

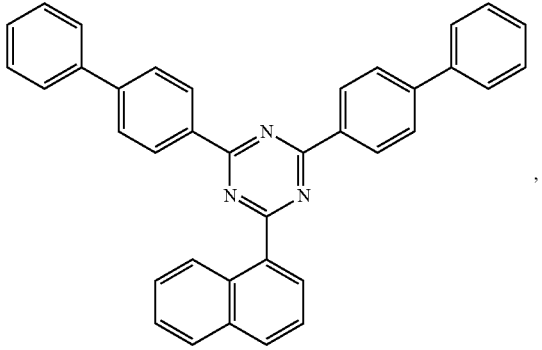

457
-continued
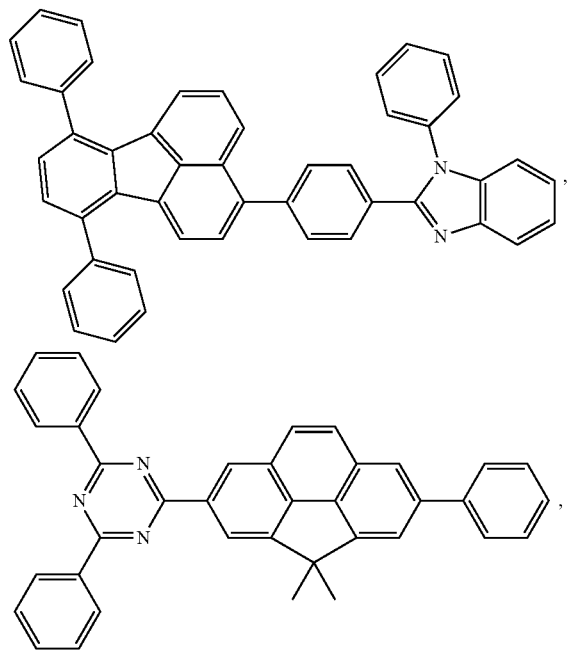
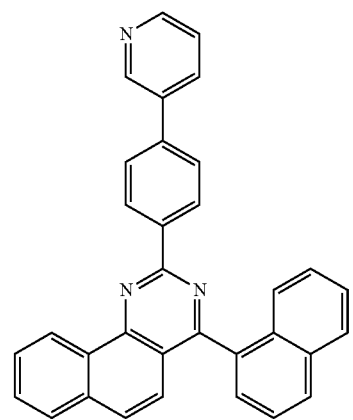
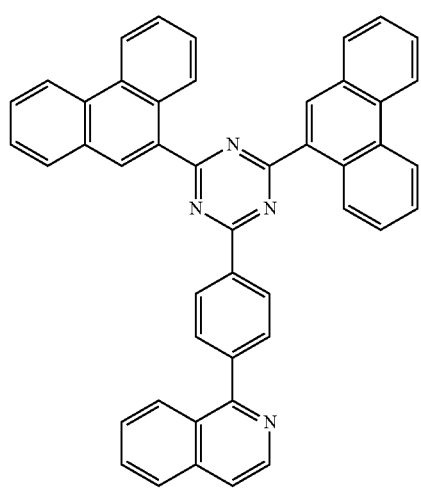
458
-continued
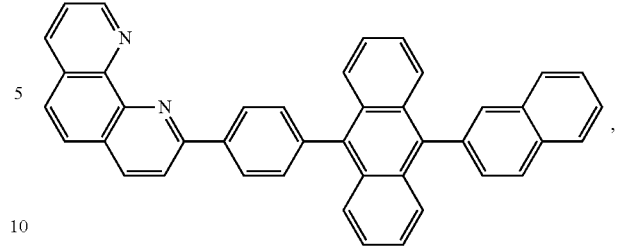
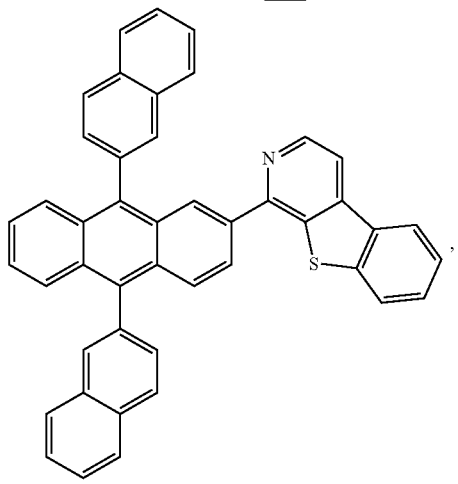
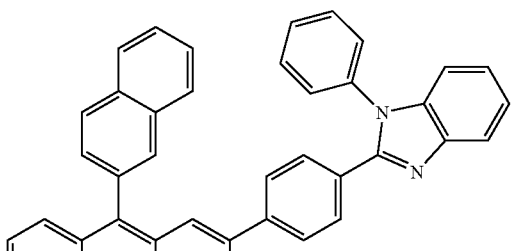
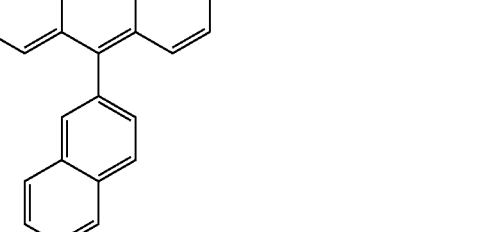
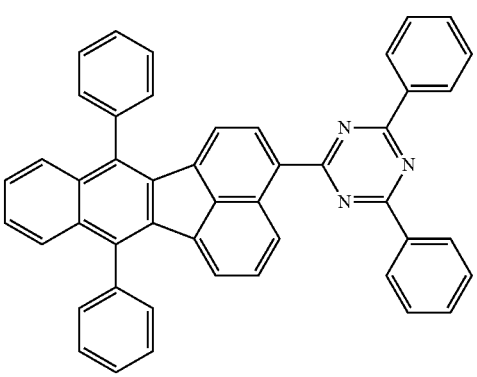

459
-continued
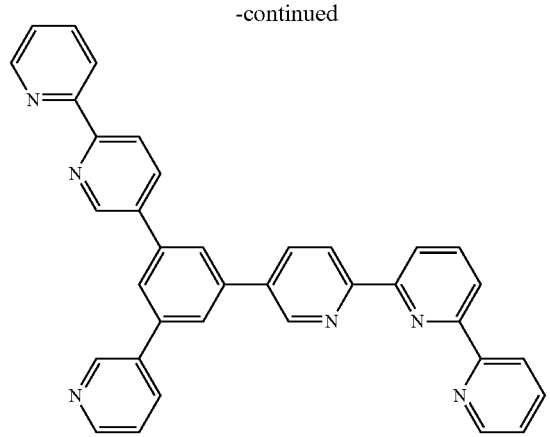
,
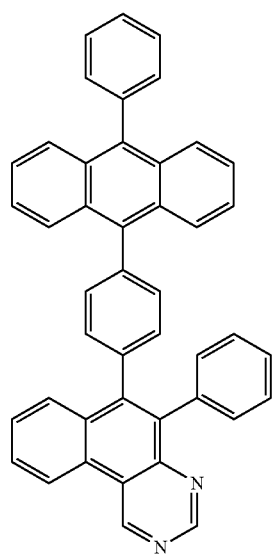
,
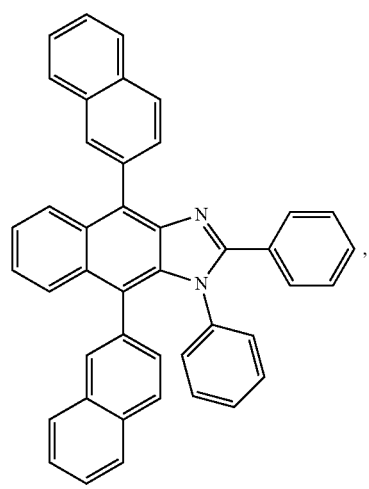
,
460
-continued
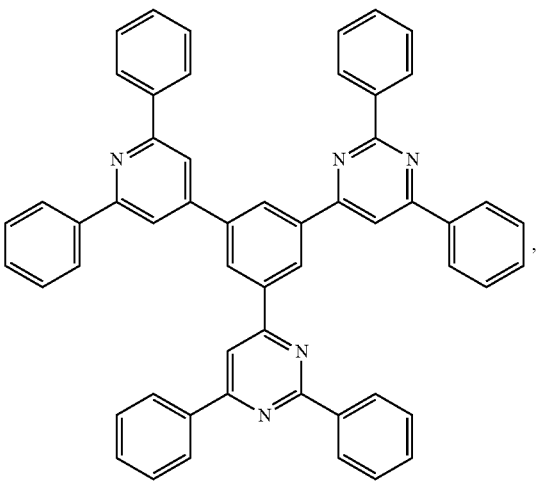
,
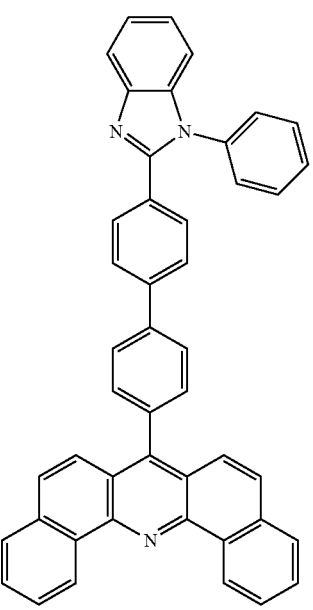
,
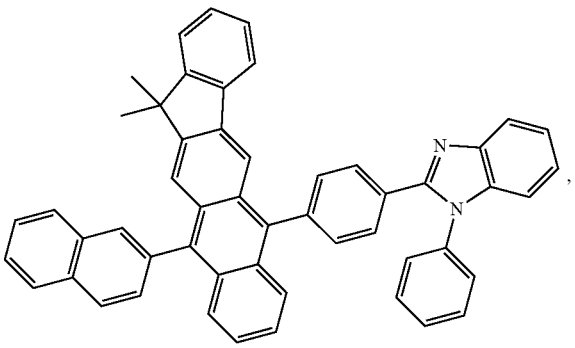
, 461
-continued
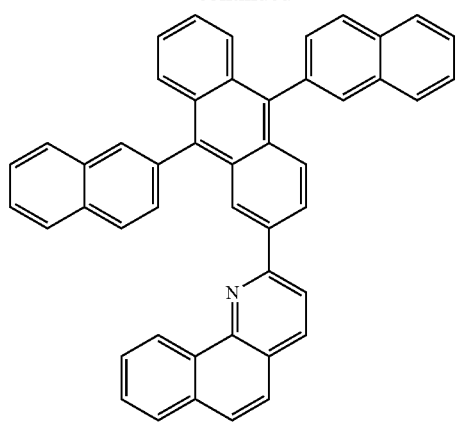
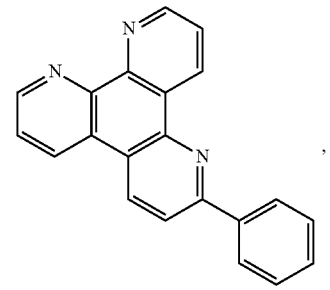
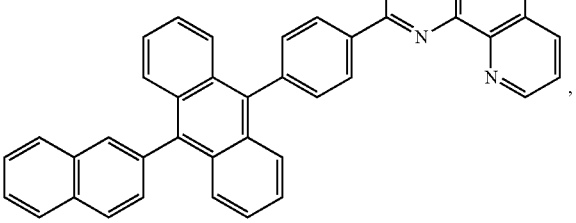
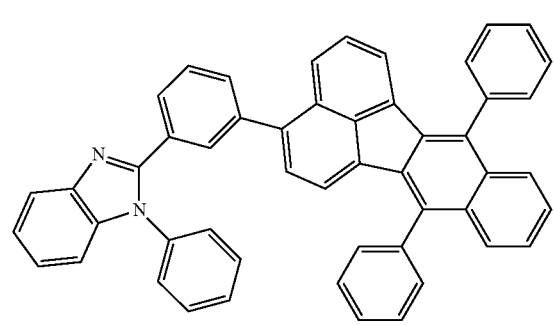
462
-continued
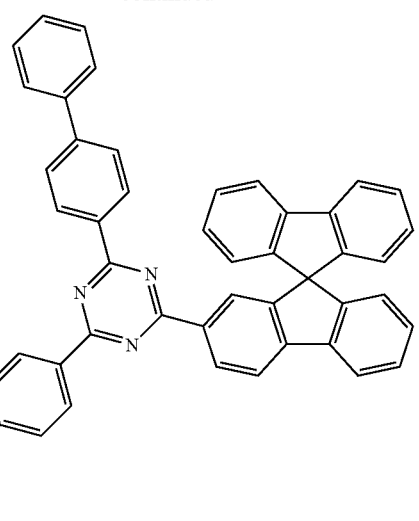
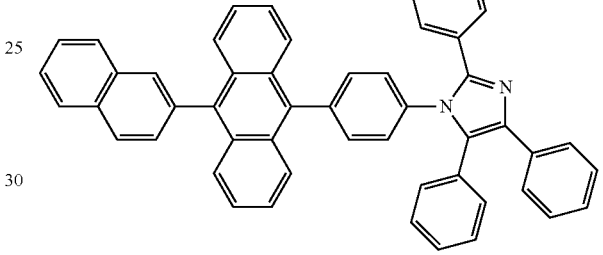
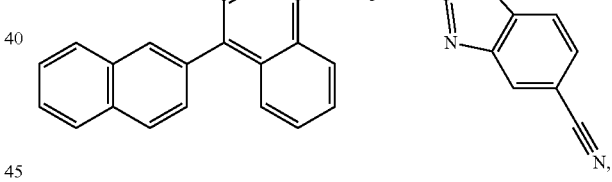
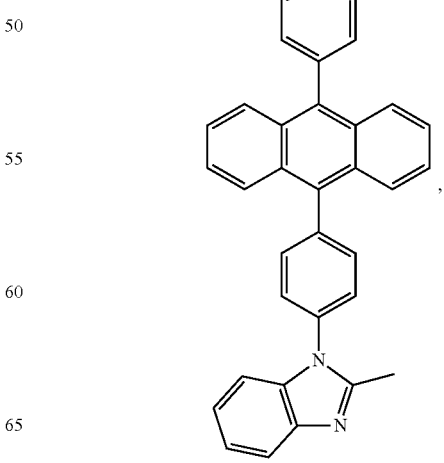

463
-continued

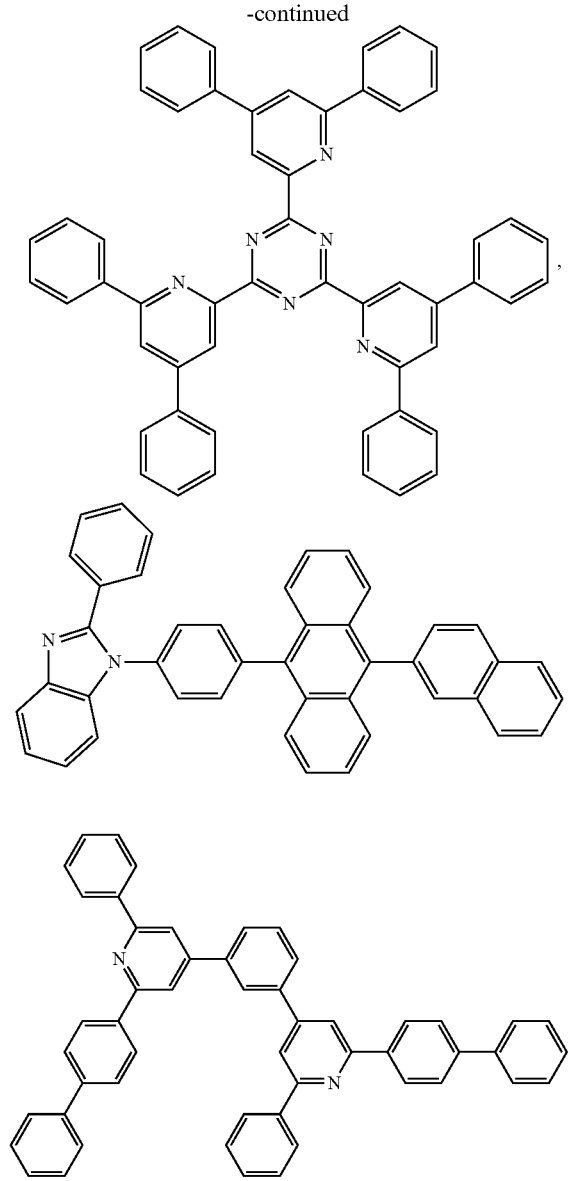

464
-continued

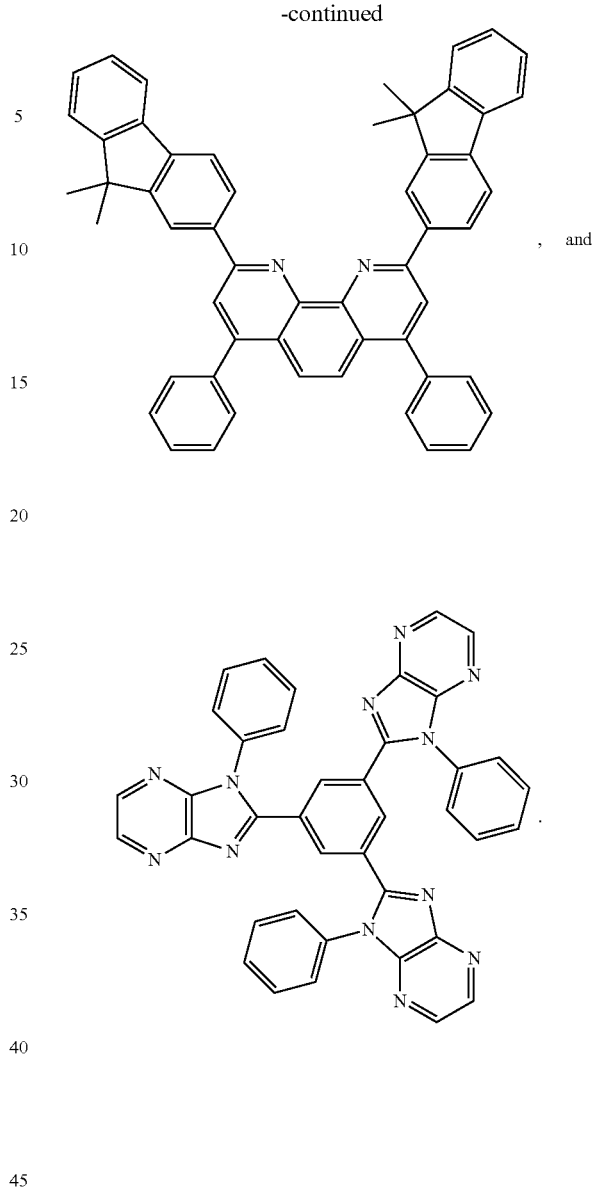
, and

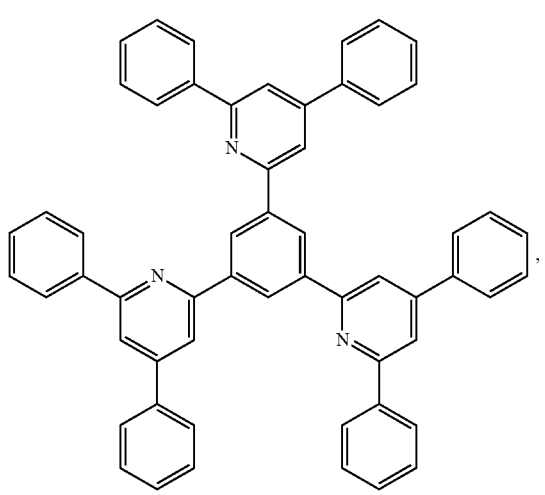

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

EXPERIMENTAL

Synthesis of 2-(2-iodophenyl)triphenylene

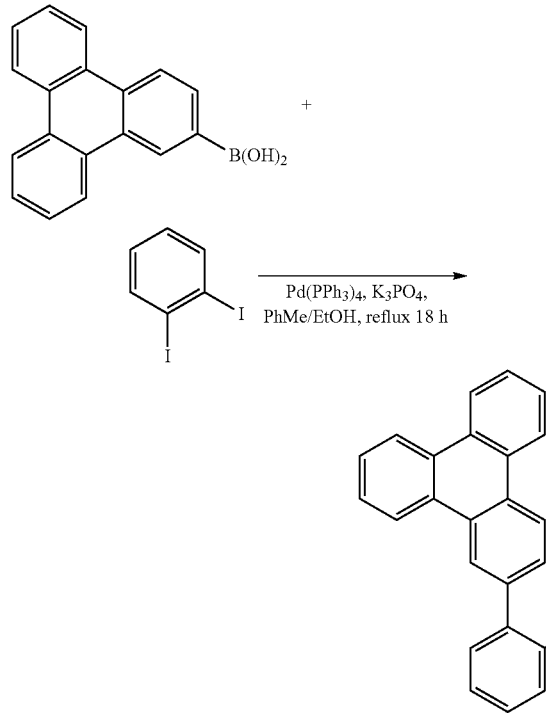

A solution of toluene (450 mL) and ethanol (150 mL) was bubbled with nitrogen gas for 10 min. Triphenylen-2-ylboronic acid (10.0 g g, 36.7 mmol), 1,2-diiodobenzene (36.4 g, 110 mmol), tetrakis(triphenylphosphine)palladium(0) (2.1 g, 1.8 mmol), and tripotassium phosphate (39.0 g, 184 mmol) were added. The mixture was bubbled with nitrogen gas for 15 minutes and refluxed for 18 hours. After cooling (~22° C.), the reaction mixture was filtered through a silica pad and washed with toluene. The solvent was removed in vacuo and the residue was purified by flash column chromatography using hexane to 30% DCM in hexane to yield the desired product 2-(2-iodophenyl)triphenylene (9.2 g, 21.4 mmol, 58.2% yield) as a pale yellow solid.

Synthesis of phenanthro[9,10-b]tetraphenylene [Compound 1t]

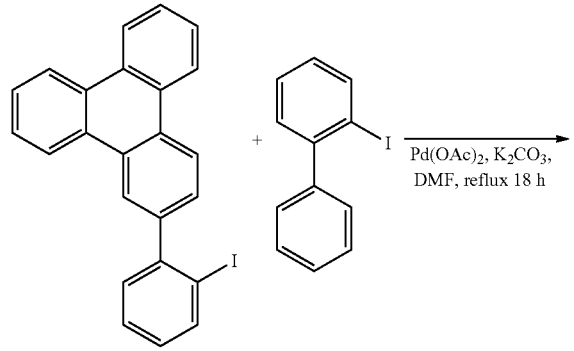

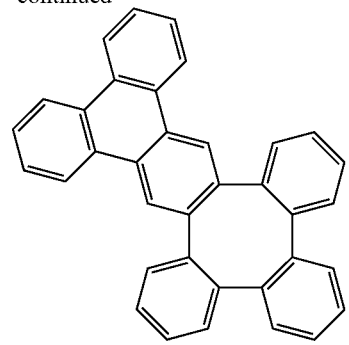

A solution of DMF (100 mL) was bubbled with nitrogen gas for 10 min. 2-(2-iodophenyl)triphenylene (9.2 g, 21.4 mmol), 2-iodo-1,1'-biphenyl (18.0 g, 64.1 mmol), palladium (II) acetate (192 mg, 0.9 mmol), and potassium carbonate (17.7 g, 128 mmol) were added. The mixture was bubbled with nitrogen gas for 15 minutes and refluxed for 18 hours. After cooling (~22° C.), the reaction mixture was filtered through a silica pad and washed with toluene. The solvent was removed in vacuo and the residue was purified by flash column chromatography using hexane to 30% DCM in hexane to yield the desired product phenanthro[9,10-b] tetraphenylene (3.0 g, 6.6 mmol, 30.9% yield) as a pale yellow solid. Compound 1t has a triplet energy of 436 nm measured at 77K in a dilute 2-MeTHF solution. The reduction potential is −2.78 V (reversible) vs Fc/Fc⁻ measured by cyclic voltammetry.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having Formula I:

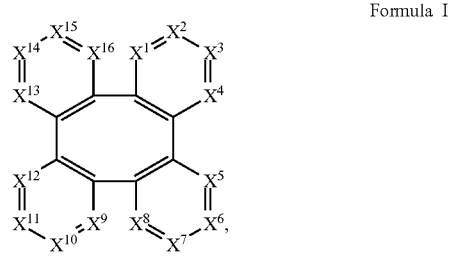

Formula I wherein $X^1$-$X^{16}$ are each independently selected from the group consisting of CR and N;
wherein at least two adjacent $X^1$-$X^{16}$ are CR;
wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, phosphino, and combinations thereof;

wherein at least one pair of adjacent Rs is

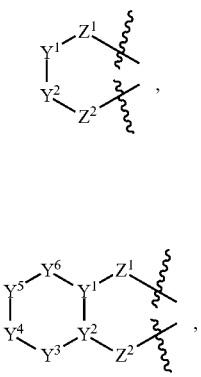

Attachment A

Attachment B

Attachment C or is fused with two or more aromatic rings such that no acene unit of more than 3 fused rings is formed;

wherein in Attachments A and B, $Y^1$-$Y^2$, $Y^2$-$Y^3$, $Y^3$-$Y^4$, $Y^4$-$Y^5$ and $Y^5$-$Y^6$ are connected by single or double bonds;

wherein $Y^1$-$Y^6$ are each independently selected from the group consisting of C and N;

wherein any unsaturated C in $Y^1$-$Y^6$ is substituted by one or two $R^1$;

wherein in Attachment A, $Z^1$ and $Z^2$ are each independently selected from the group consisting of C=$CR^2R^3$, C=$NR^2$, O, SO, $SO_2$, $BR^2$, $PR^2$, $SiR^2R^3$, and Se;

wherein in Attachment B, $Z^1$ and $Z^2$ are each independently selected from the group consisting of $CR^2R^3$, C=$CR^2R^3$, C=O, C=$NR^2$, $NR^2$, O, S, SO, $SO_2$, $BR^2$, P, $SiR^2R^3$, and Se;

wherein in Attachment C, at least one of $Y^1$-$Y^4$ is N;

wherein $R^1$-$R^3$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrite, isonitrile, suifanyl, sulfinyl, sulfonyl, phosphino, and combinations thereof; and wherein

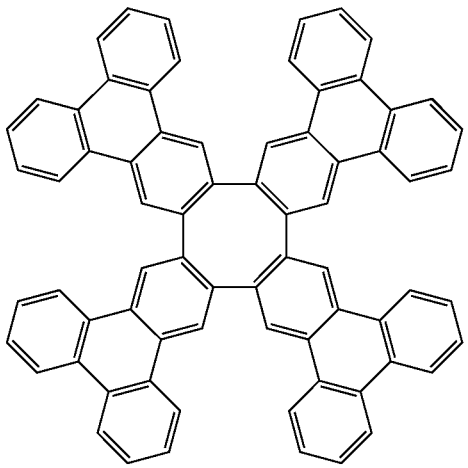 [SMILES: c1ccc2c(c1)c1ccccc1c1cc3c(cc21)-c1cc2c4ccccc4c4ccccc4c2cc1-c1cc2c4ccccc4c4ccccc4c2cc1-c1cc2c4ccccc4c4ccccc4c2cc1-3]

is excluded.

2. The compound of claim 1, wherein $X^1$-$X^{16}$ are CR.

3. The compound of claim 1, wherein $X^1$-$X^{16}$ are CR and in Attachments A and B, $Y^1$-$Y^6$ are C.

4. The compound of claim 1, wherein at least two pairs of adjacent Rs are attachment A, B, C, or are fused with two or more aromatic rings such that no acene unit of more than 3 fused rings is formed.

5. The compound of claim 1, wherein at least three pairs of adjacent Rs are attachment A, B, C, or are fused with two or more aromatic rings such that no acene unit of more than 3 fused rings is formed.

6. The compound of claim 1, wherein at least four pairs of adjacent Rs are attachment A, B, C, or are fused with two or more aromatic rings such that no acene unit of more than 3 fused rings is formed.

7. The compound of claim 1, wherein the compound is selected from the group consisting of:

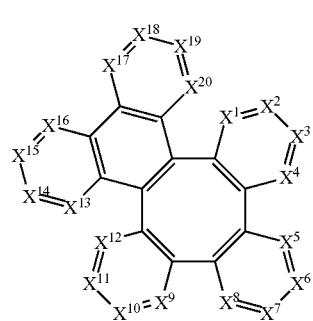

Formula 2

-continued
Formula 3
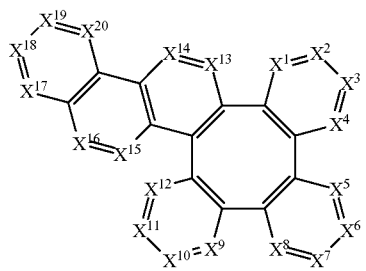
Formula 4
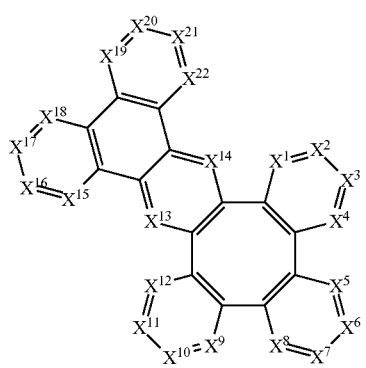
Formula 5
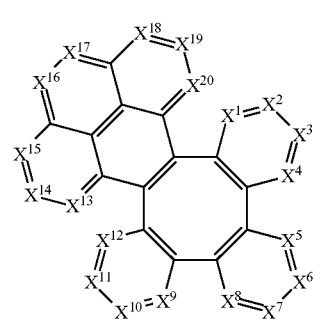
Formula 6
-continued
Formula 7
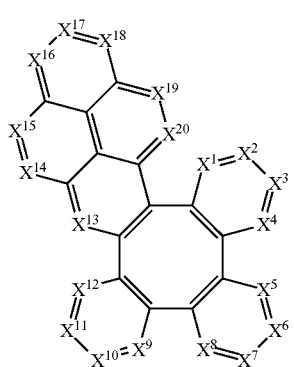
Formula 8
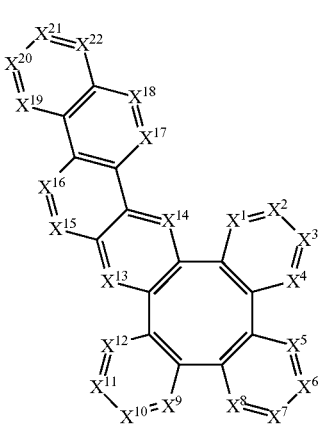
Formula 9
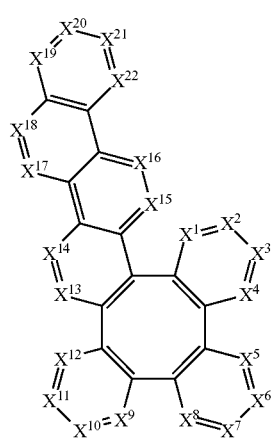
wherein $X^1$-$X^{22}$ are each independently selected from the group consisting of CR and N.

8. The compound of claim 1, wherein the compound is selected from the group consisting of:
Compound A1
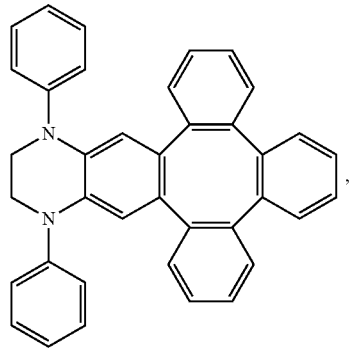
Compound A2
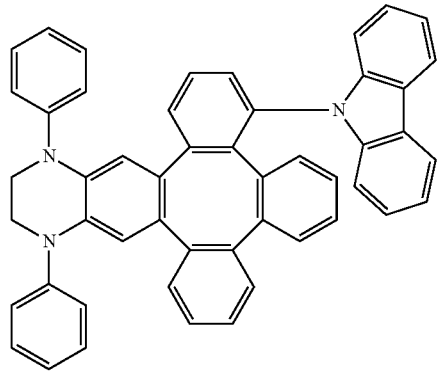
Compound A3
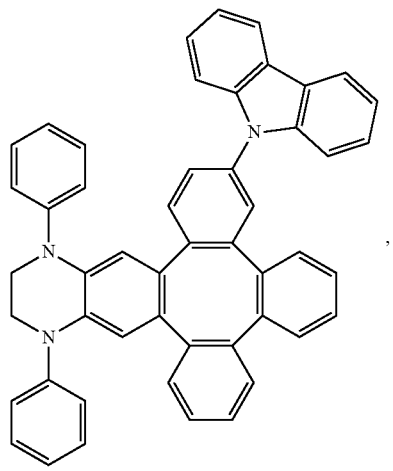
Compound A4
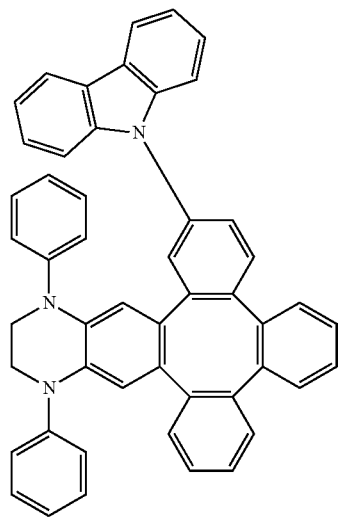
Compound A5
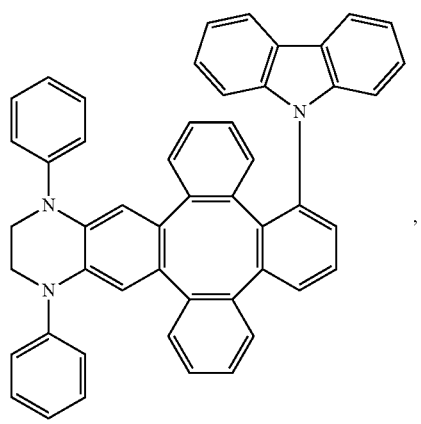
Compound A6
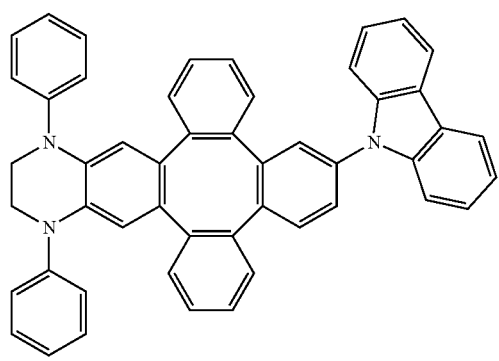

-continued
Compound A7
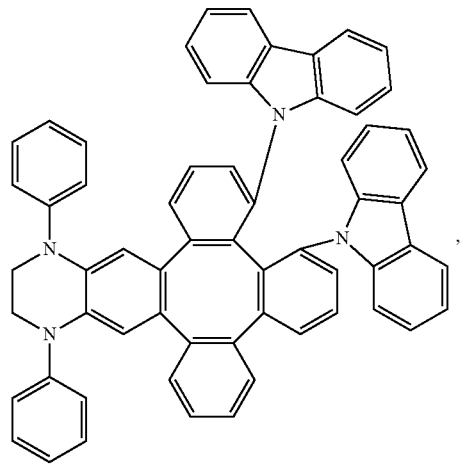
Compound A8
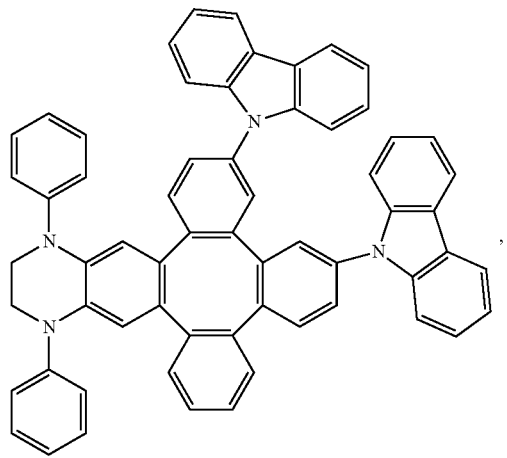
Compound A9
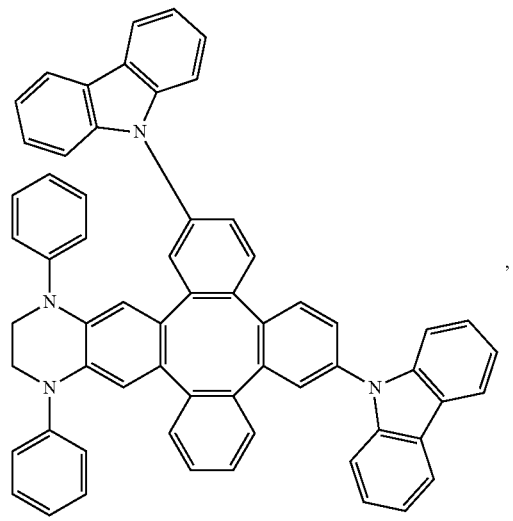
Compound A10
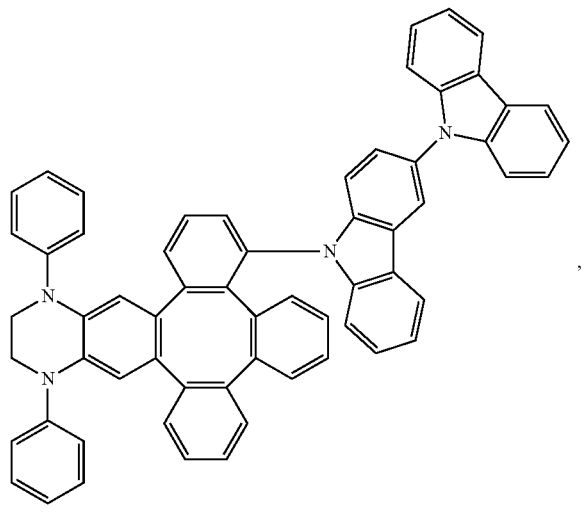
Compound A11
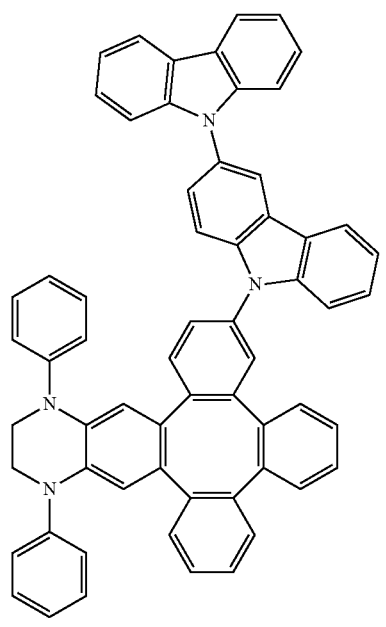
Compound A12
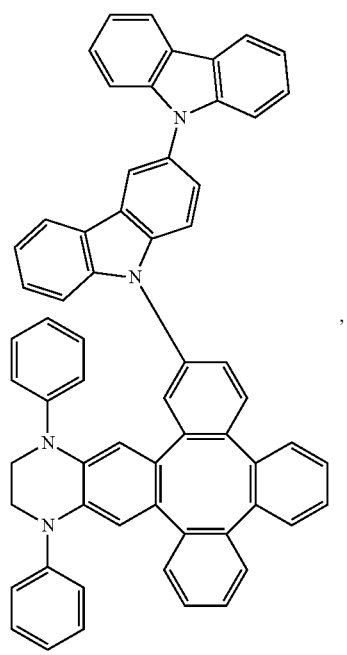

-continued
Compound A13
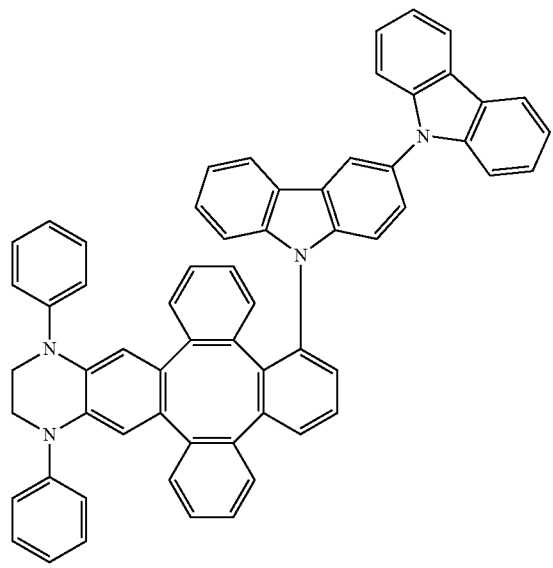
Compound A14
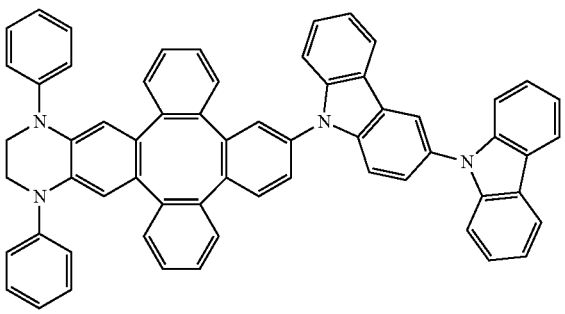
Compound A15
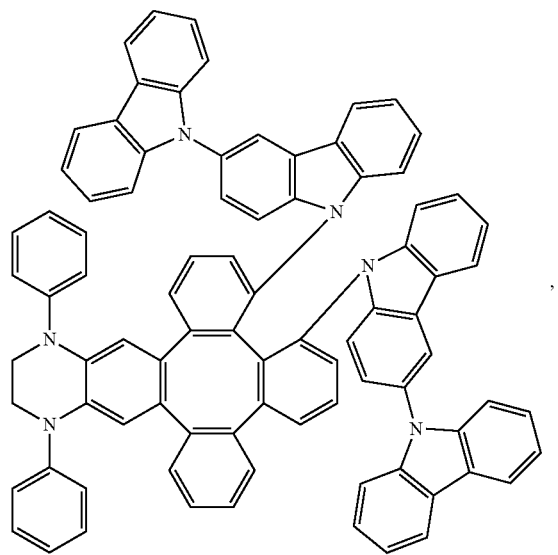
Compound A16
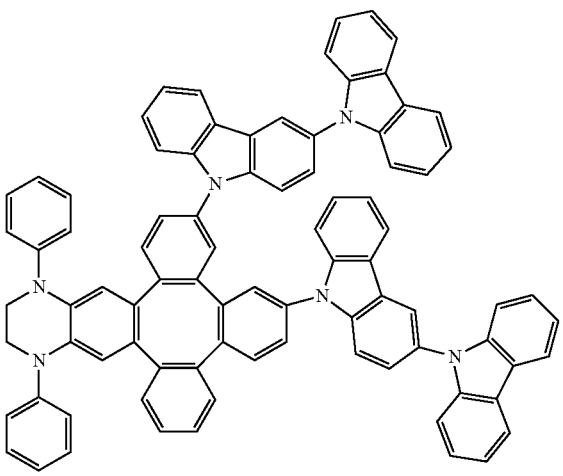

-continued
Compound A17
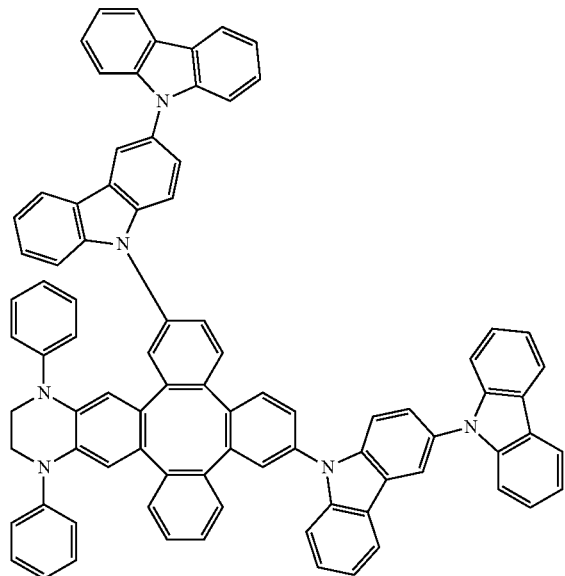
Compound A18
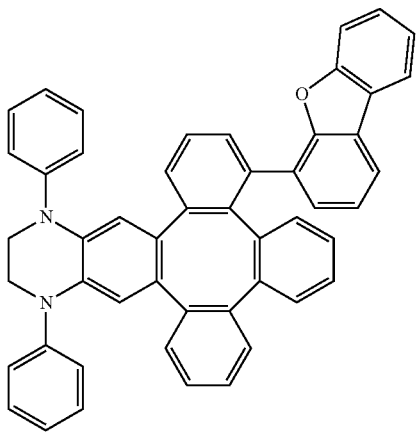
Compound A19
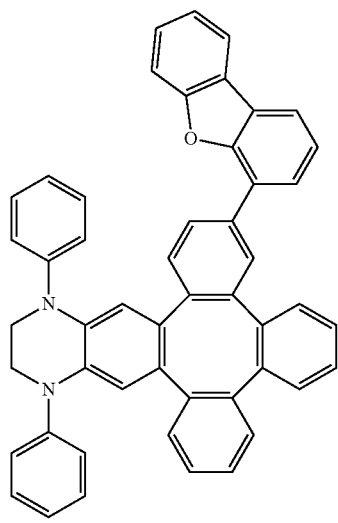
Compound A20
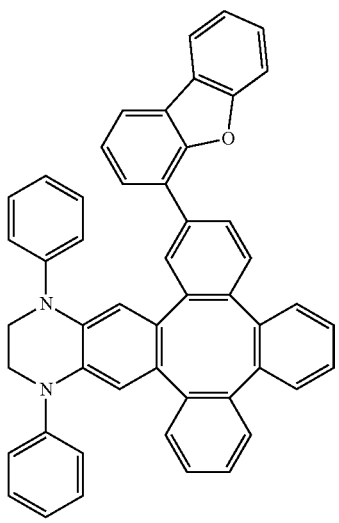
Compound A21
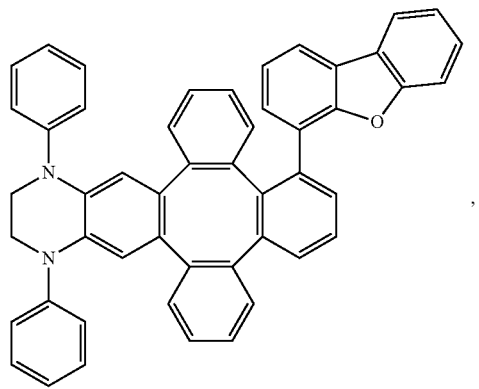
Compound A22
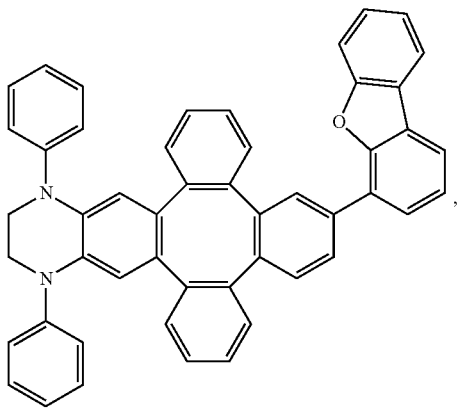

-continued
Compound A23
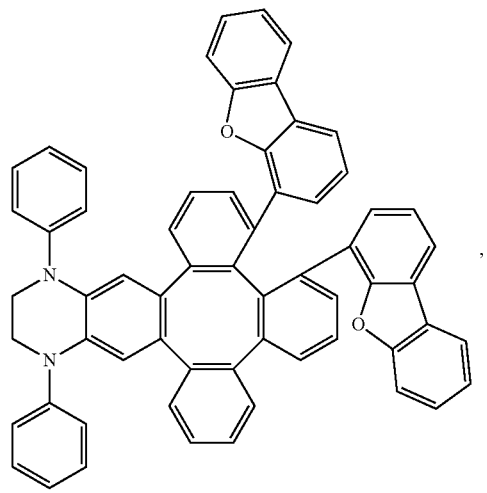
Compound A24
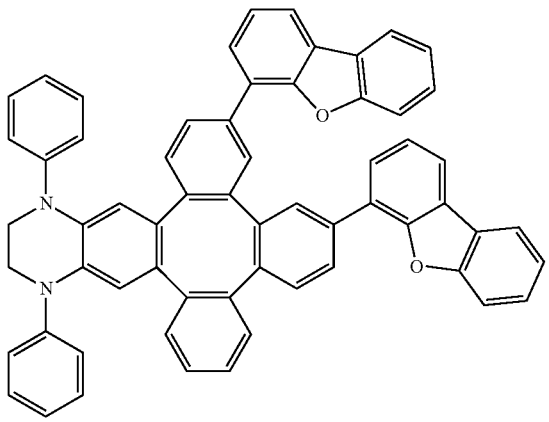
Compound A25
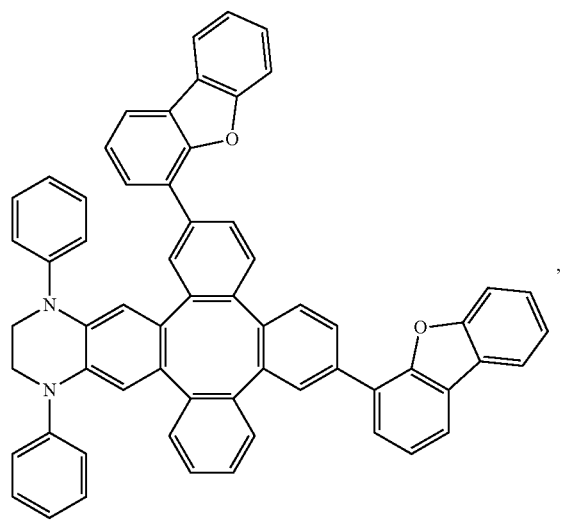
Compound A26
Compound A27
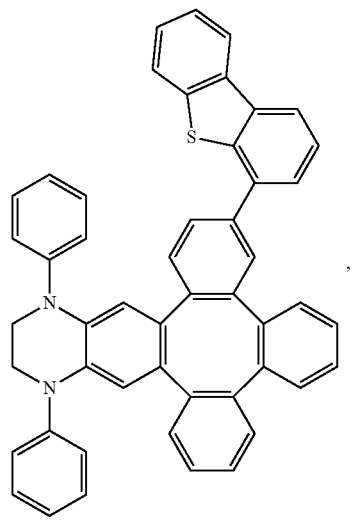
Compound A28
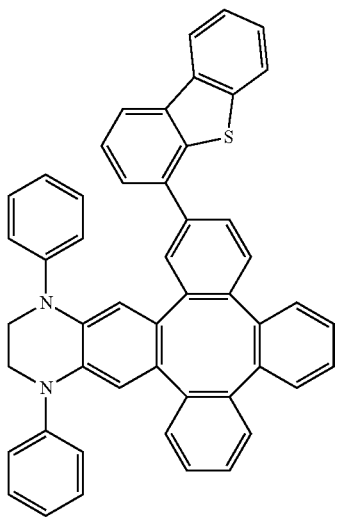

-continued
Compound A29
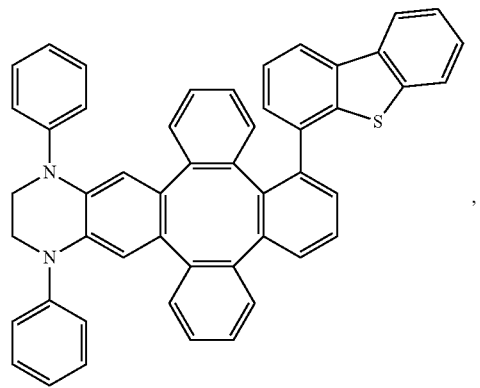
Compound A30
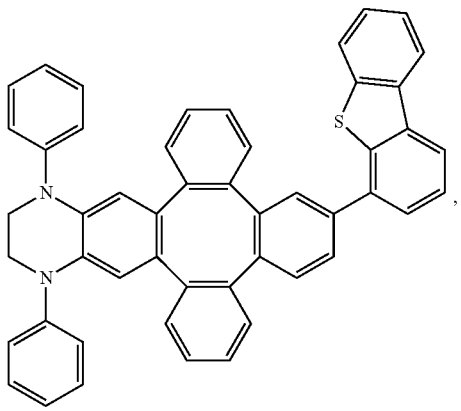
Compound A31
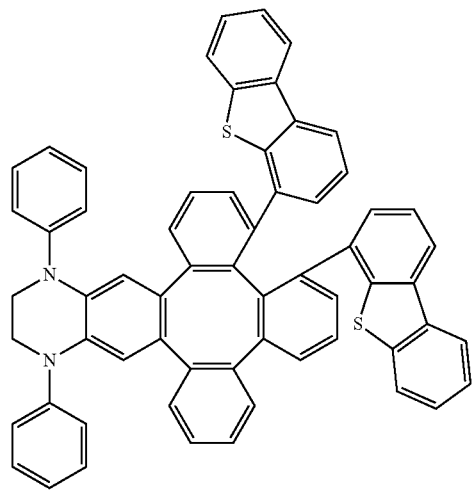
Compound A32
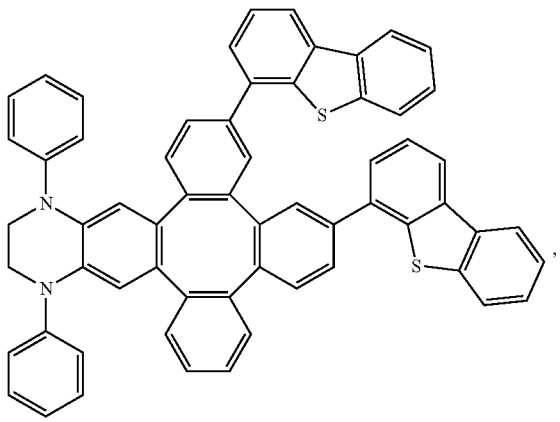
Compound A33
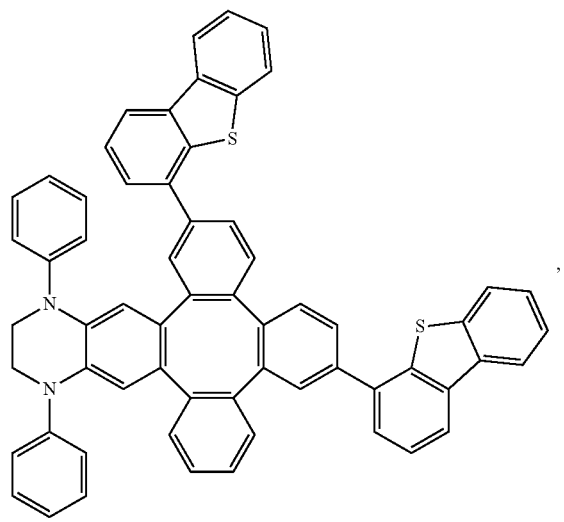
Compound C1
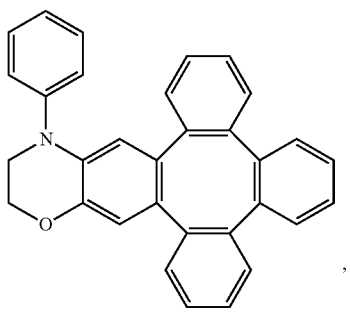

-continued
Compound C2
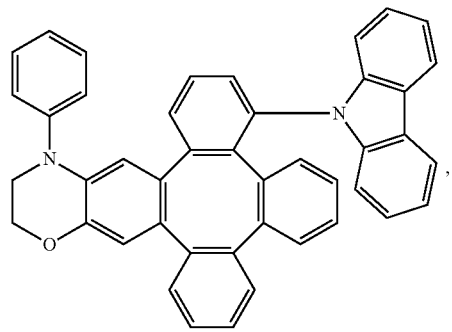
Compound C3
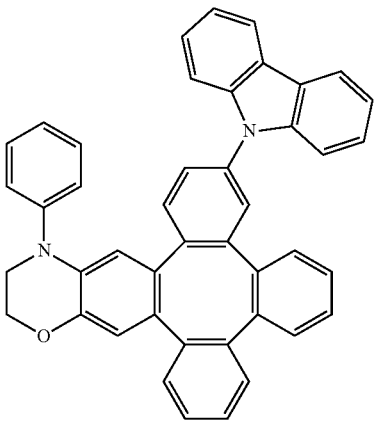
Compound C4
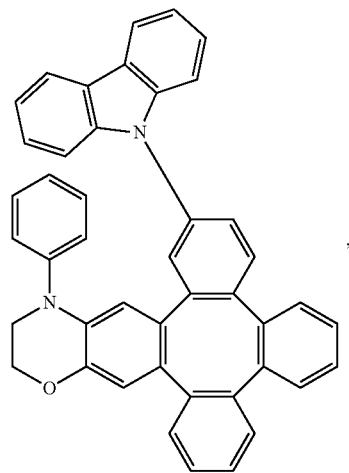
Compound C5
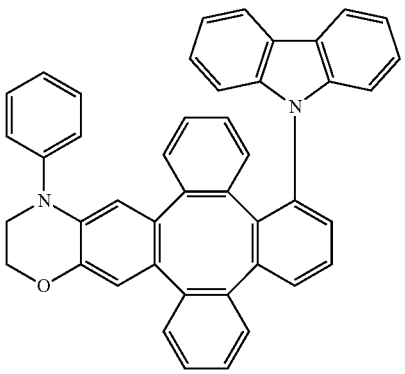
Compound C6
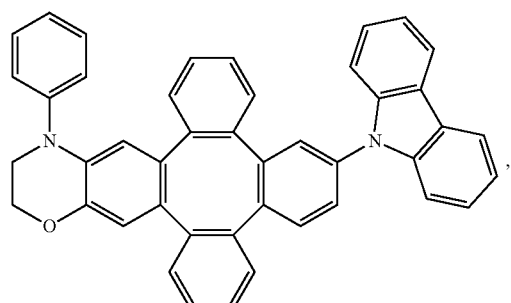
Compound C7
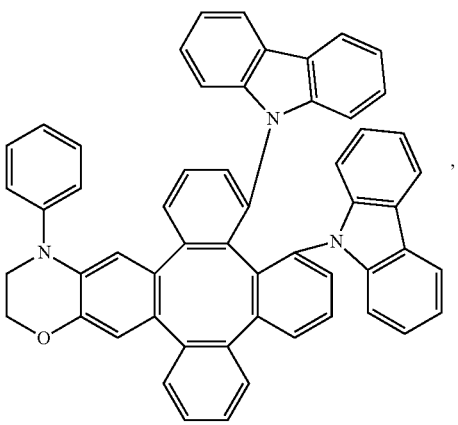

-continued
Compound C8
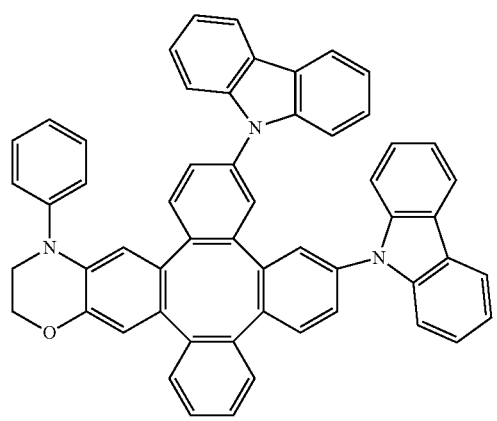
Compound C9
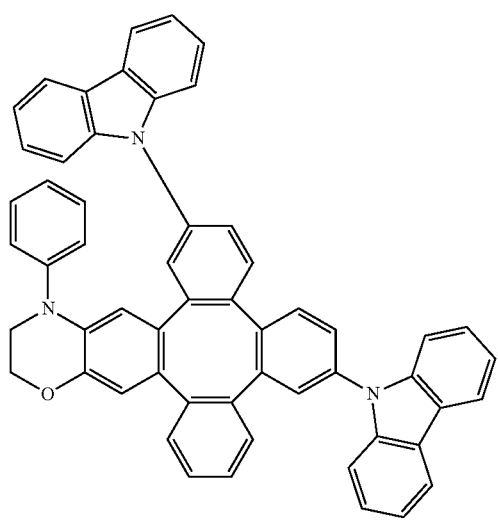
Compound C10
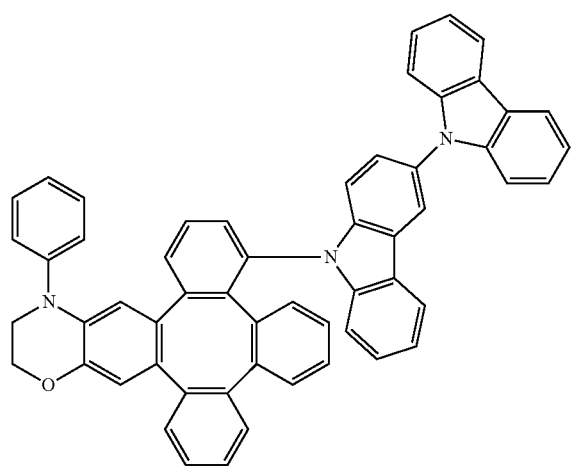
Compound D1
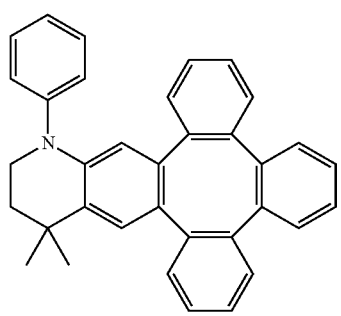
Compound D2
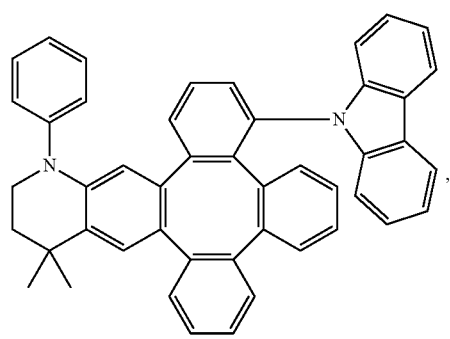
Compound D3
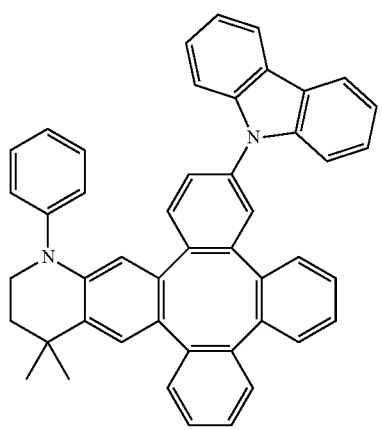

-continued
Compound D4
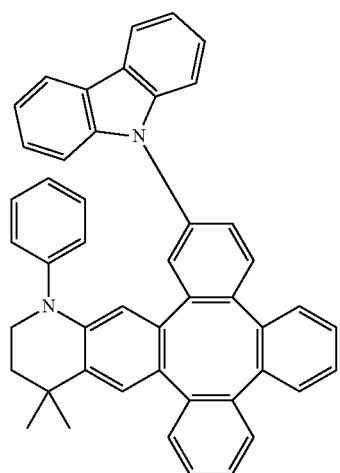
Compound D5
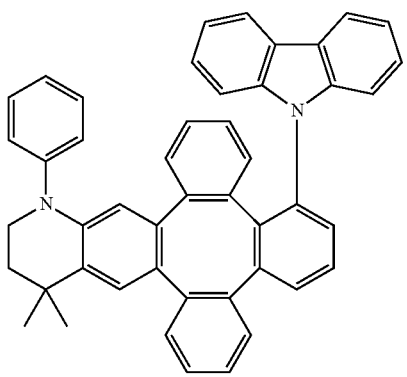
Compound D6
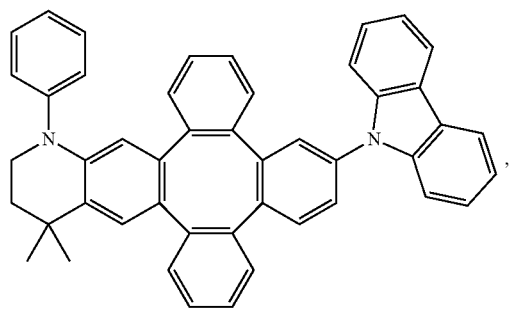
Compound D7
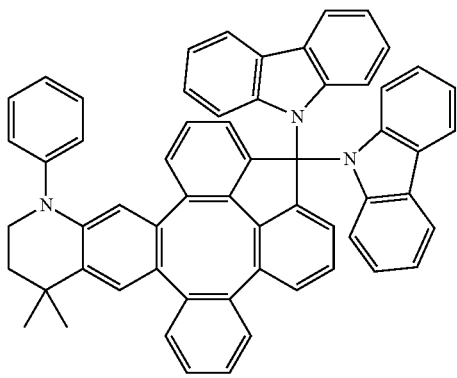
Compound D8
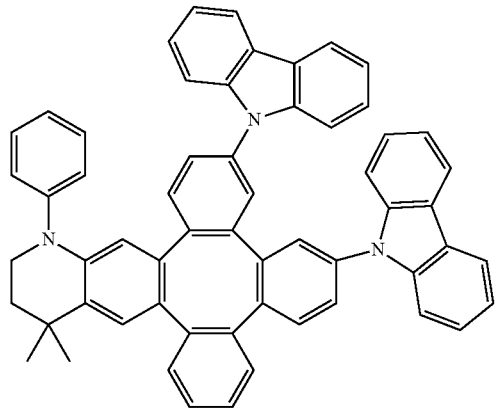
Compound D9
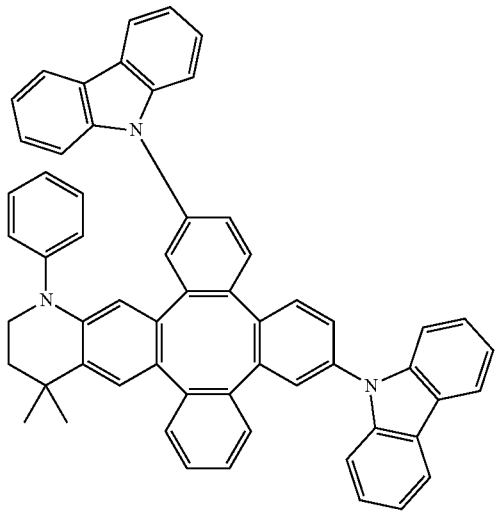

Compound D10
Compound B1
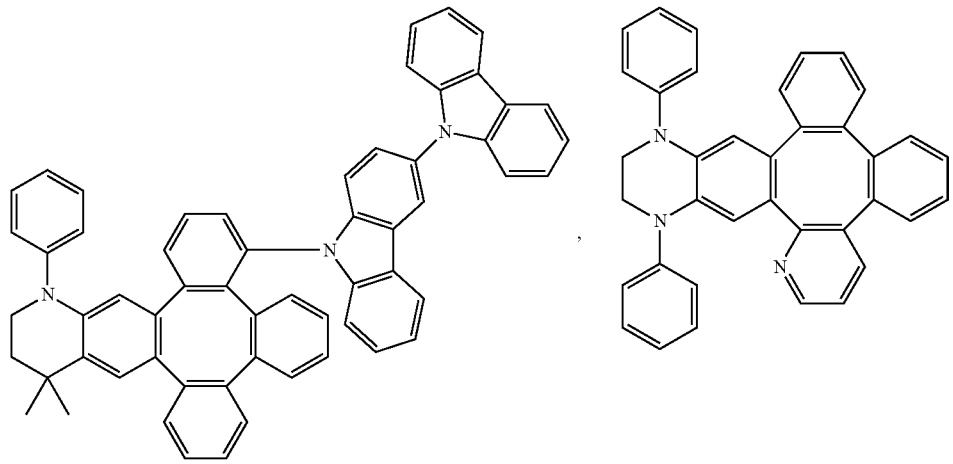
Compound B2
Compound B3
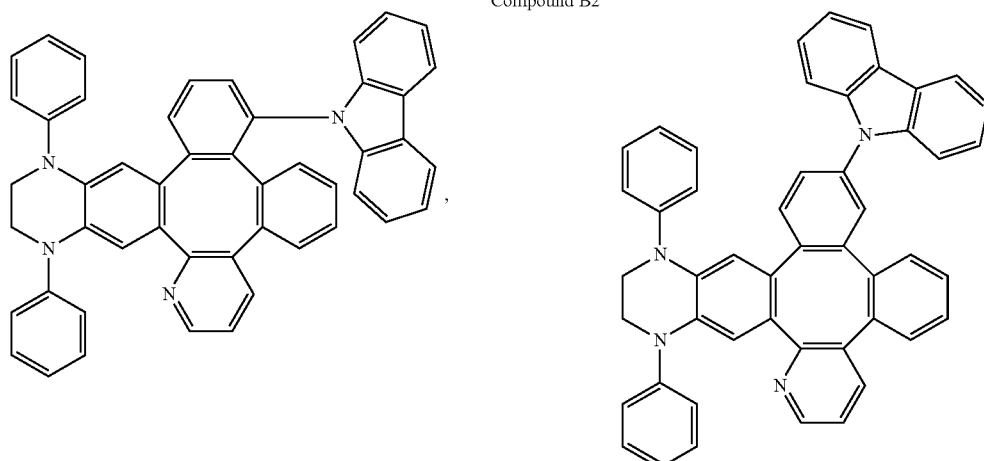
Compound B4
Compound B5
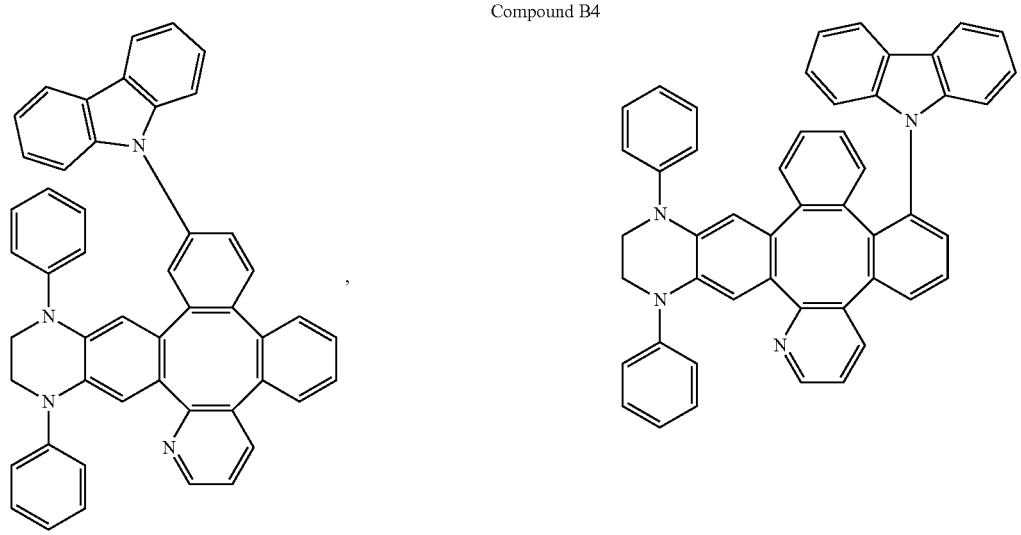

-continued
Compound B6
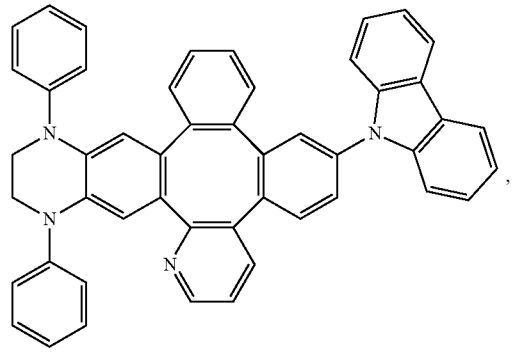
Compound B7
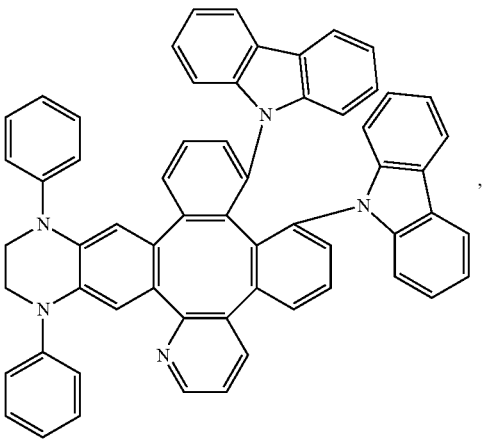
Compound B8
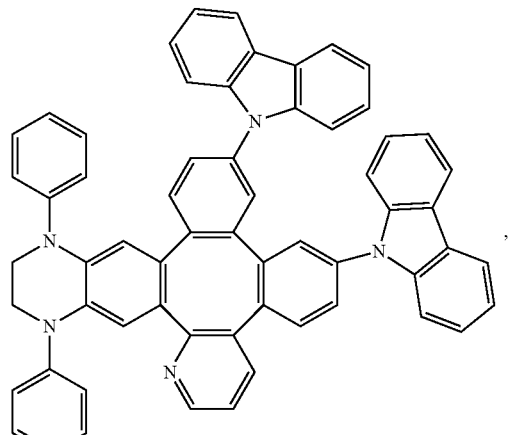
Compound B9
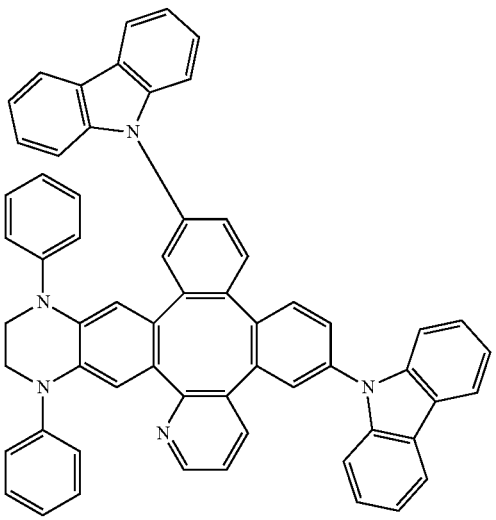
Compound B10
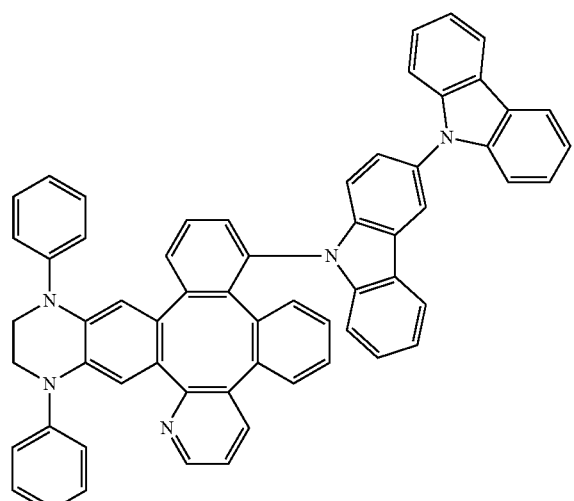
Compound B11
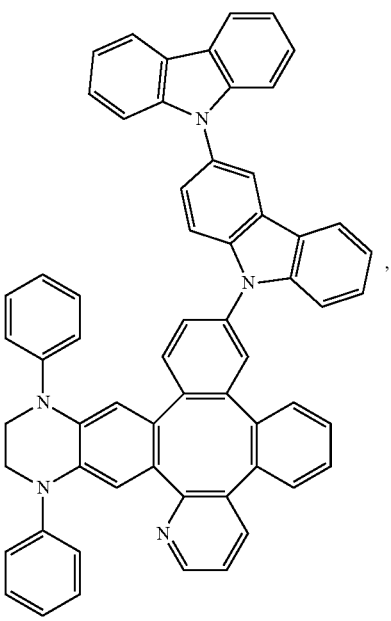

Compound B12
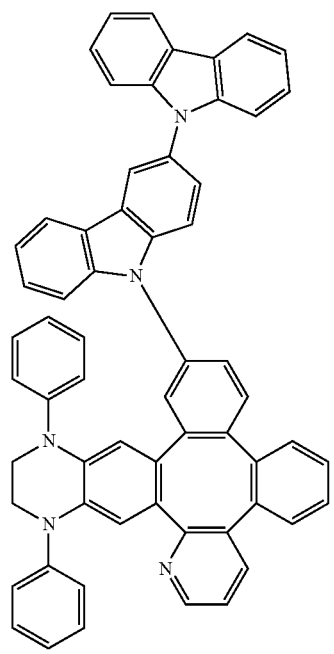
Compound B13
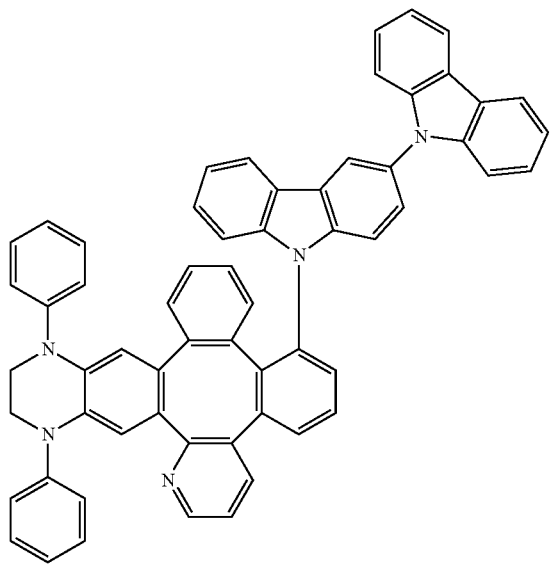
Compound B14
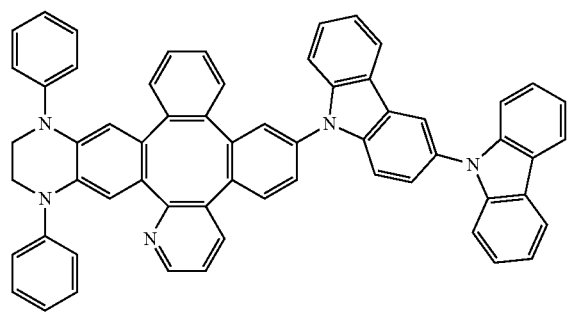
Compound B15
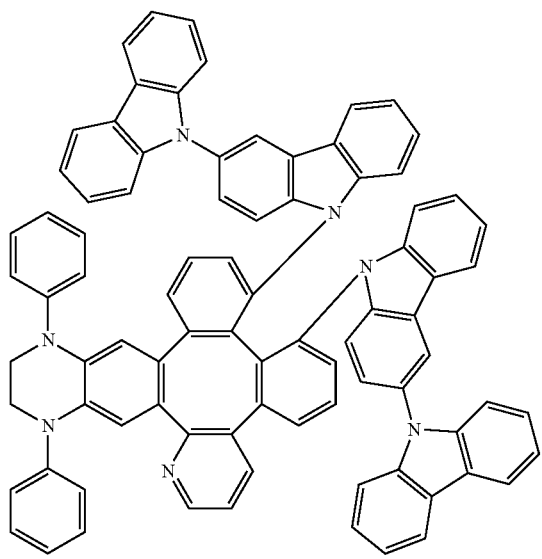

-continued
Compound B16
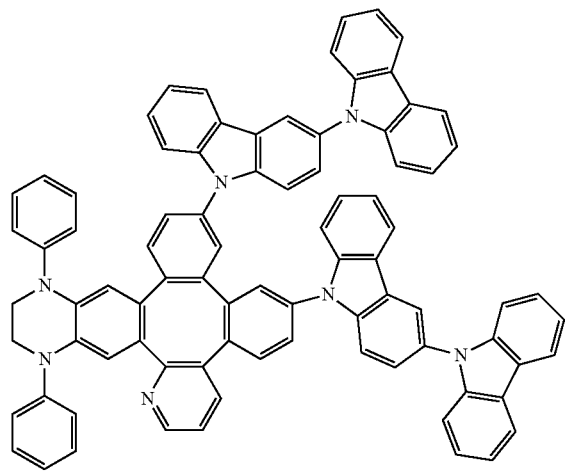
Compound B17
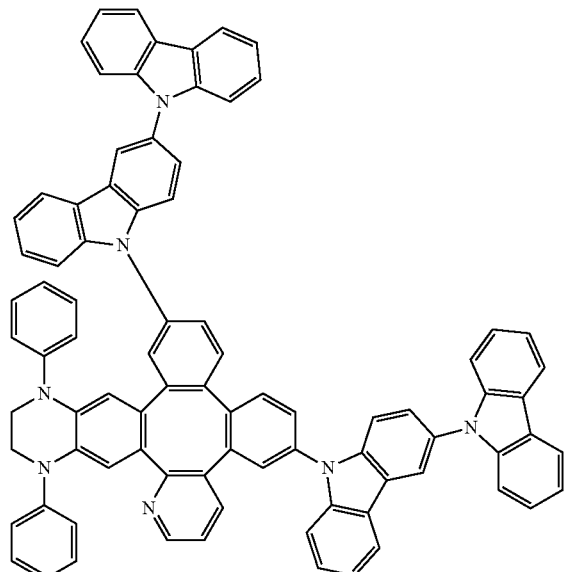
Compound B18
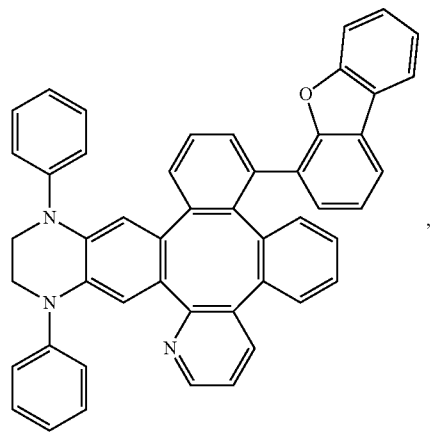
Compound B19
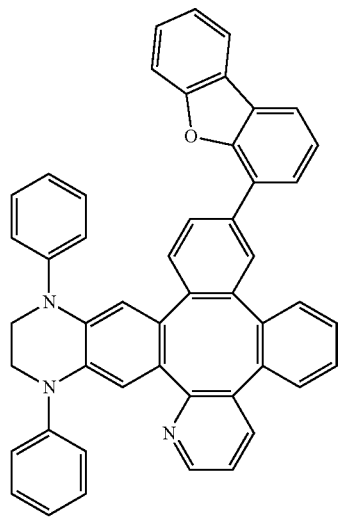
Compound B20
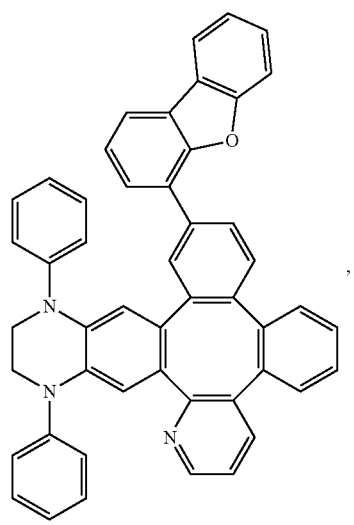
Compound B21
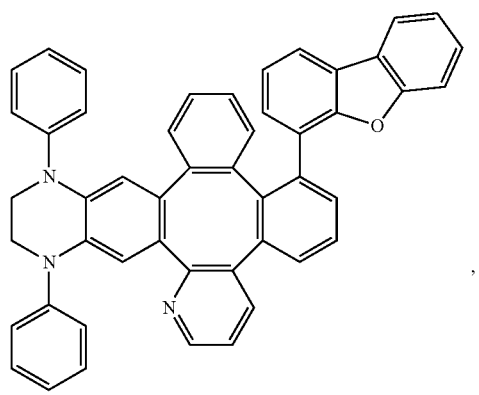

-continued
Compound B22
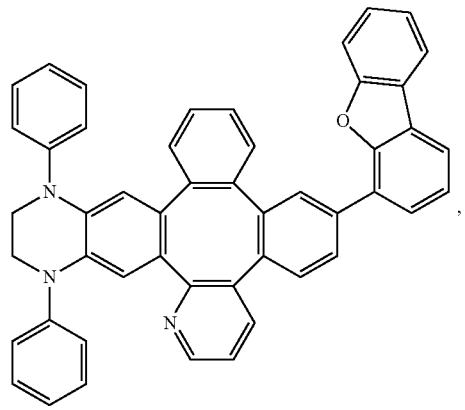
Compound B23
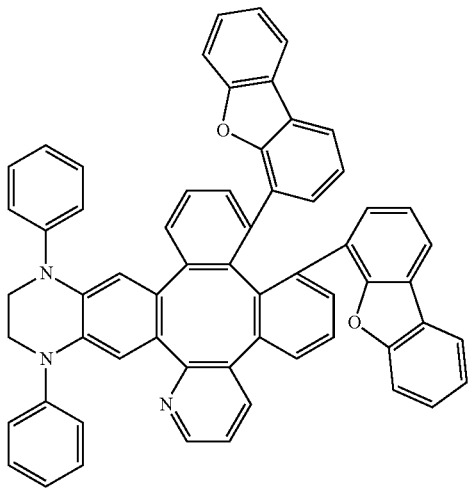
Compound B24
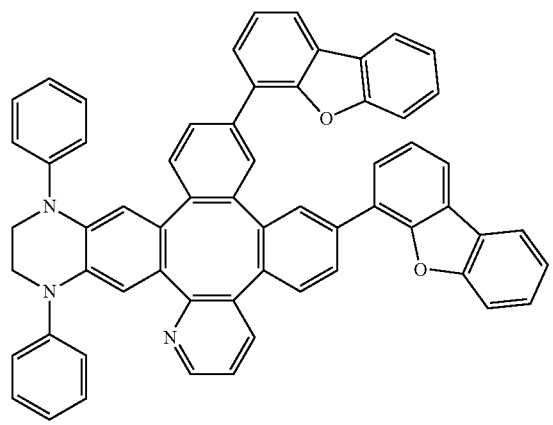
Compound B25
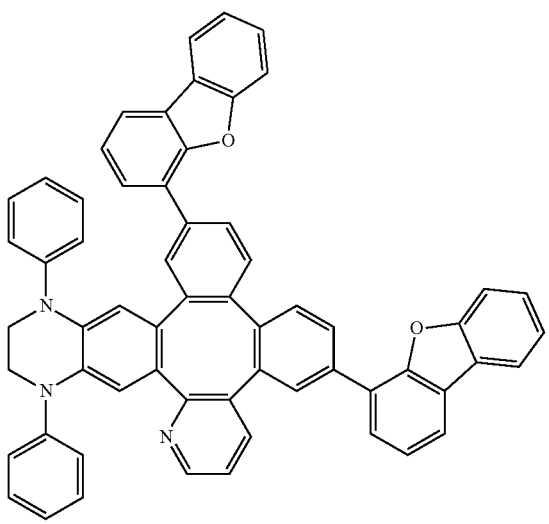
Compound B26
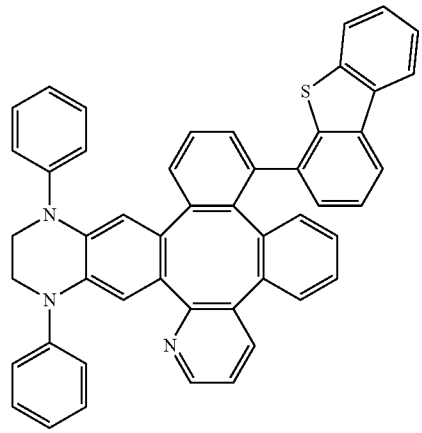
Compound B27
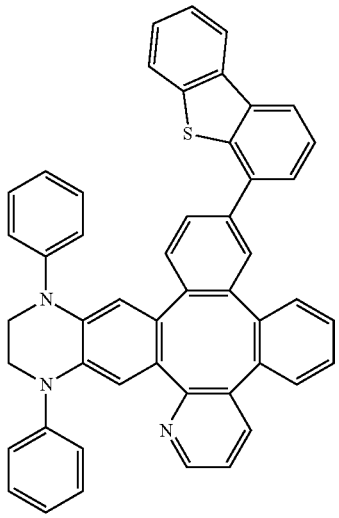

-continued
Compound B28
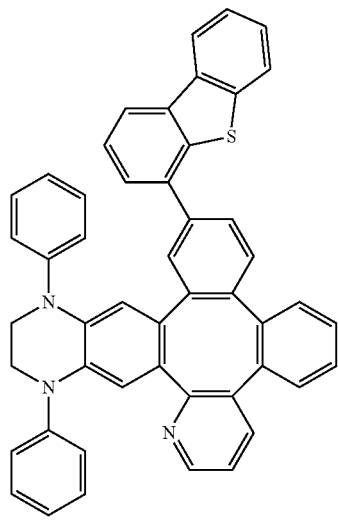
Compound B29
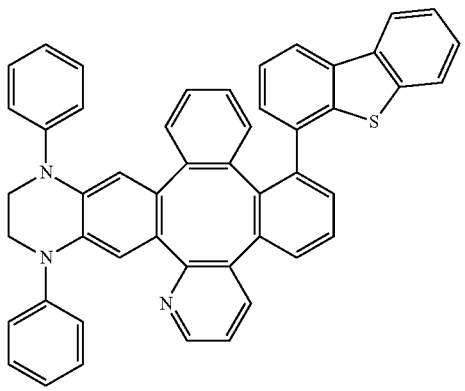
Compound B30
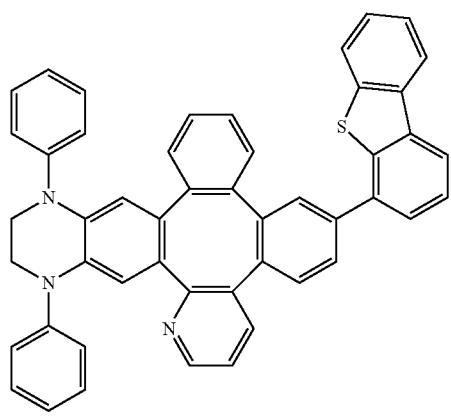
Compound B31
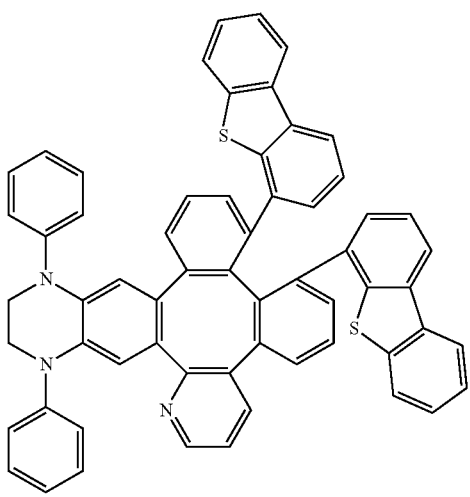
Compound B32
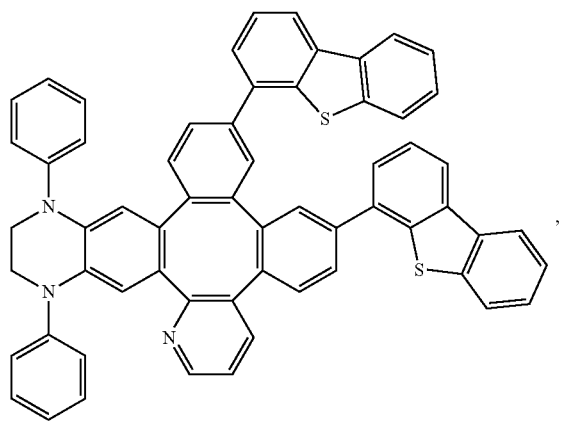
Compound B33
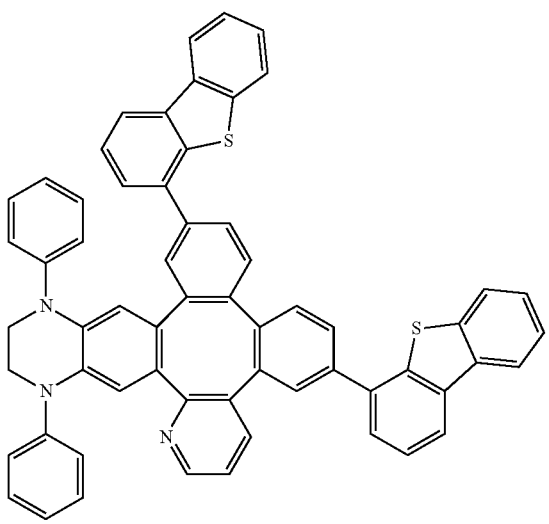

-continued
Compound CC1
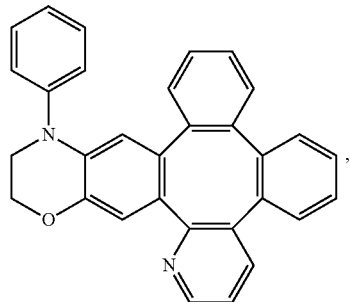
Compound CC2
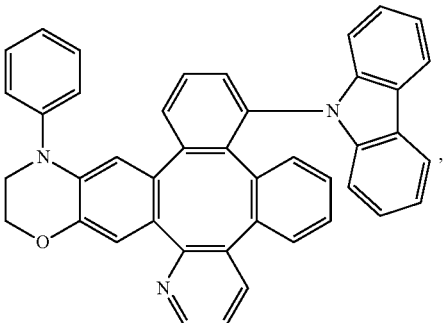
Compound CC3
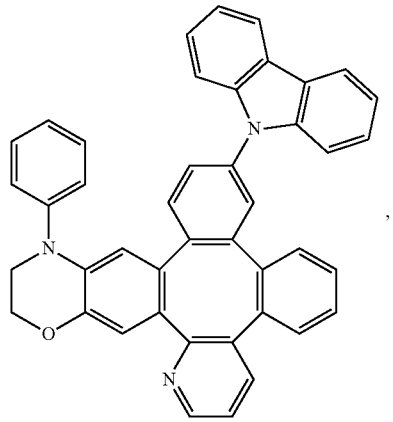
Compound CC4
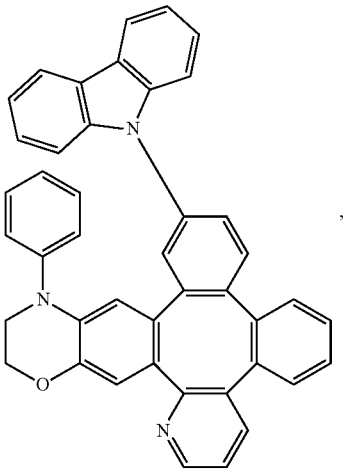
Compound CC5
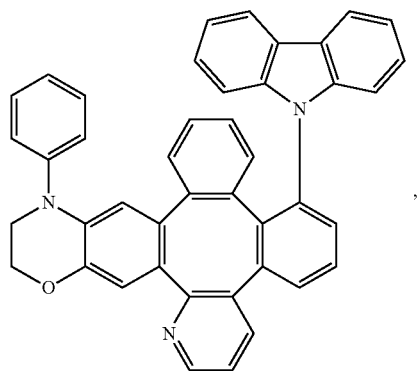
Compound CC6
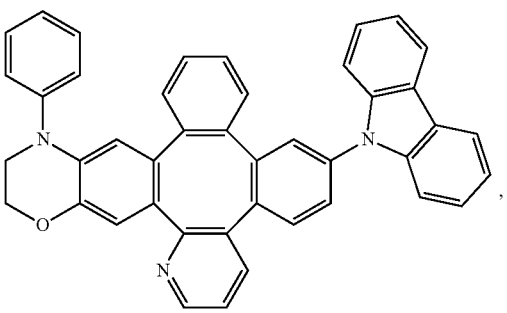
Compound CC7
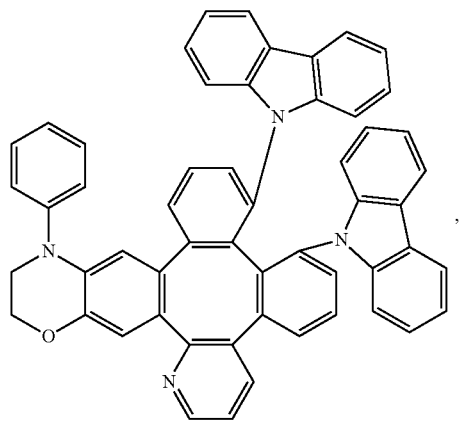
Compound CC8
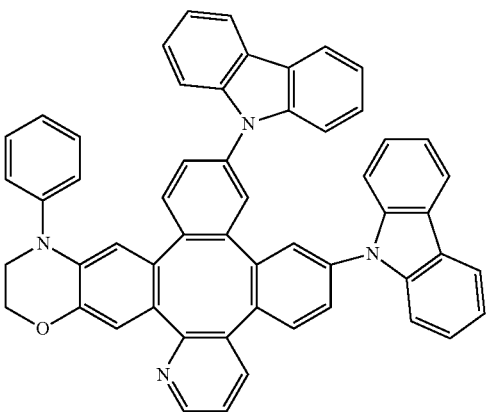

-continued
Compound CC9
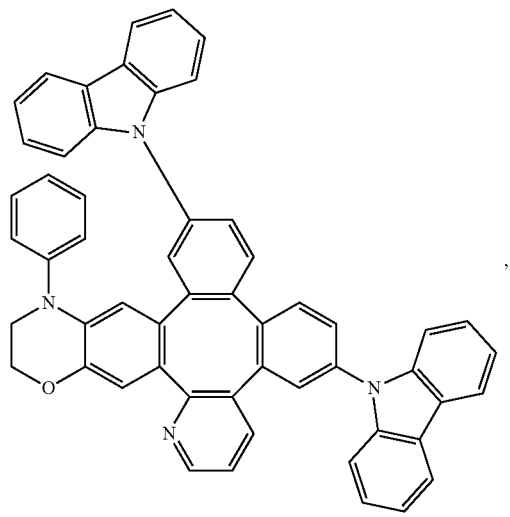
Compound CC10
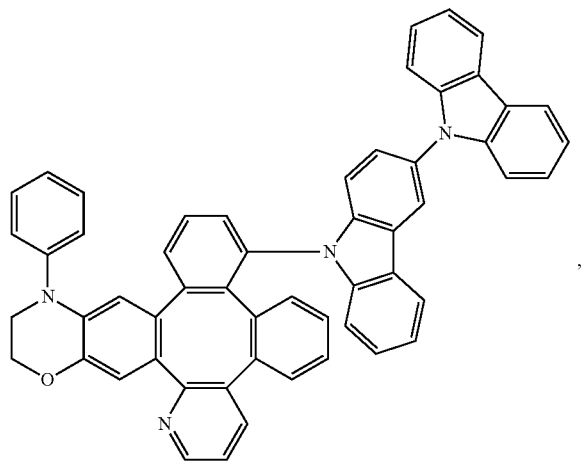
Compound DD1
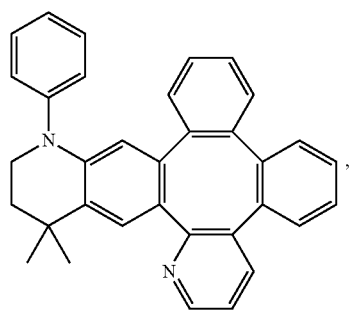
Compound DD2
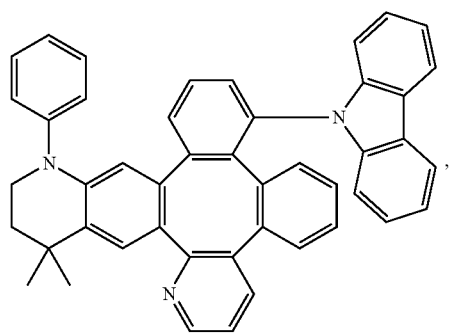
Compound DD3
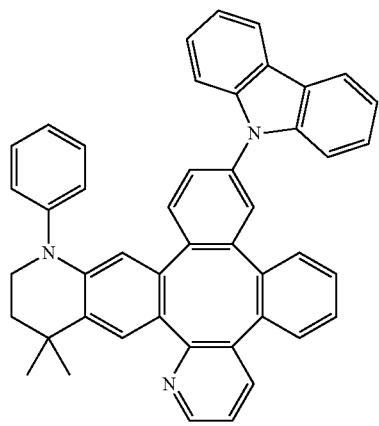
Compound DD4
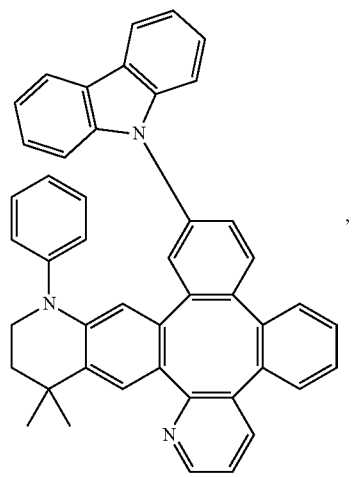

-continued
Compound DD5
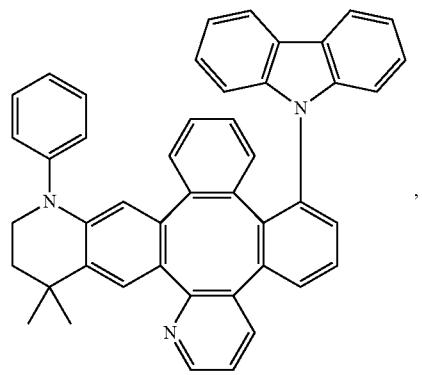
Compound DD6
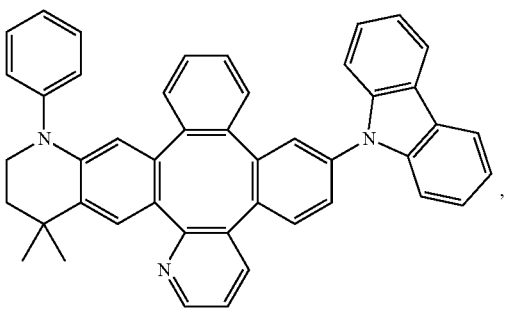
Compound DD7
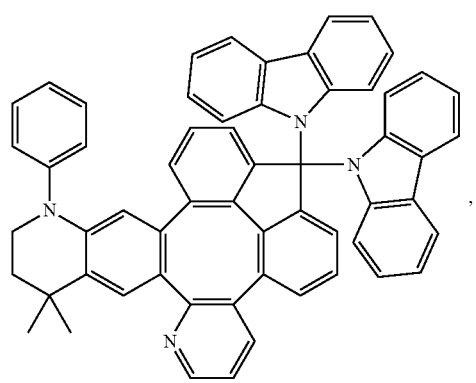
Compound DD8
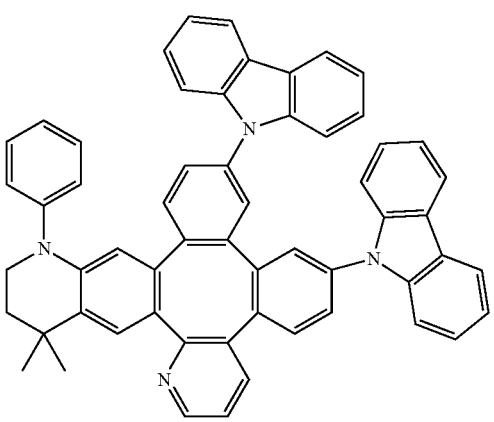
Compound DD9
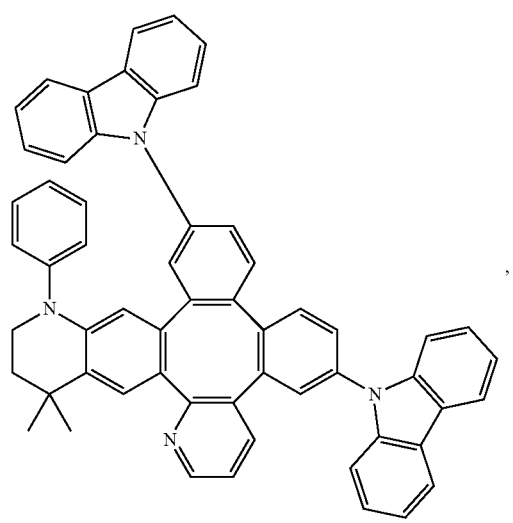
Compound DD10
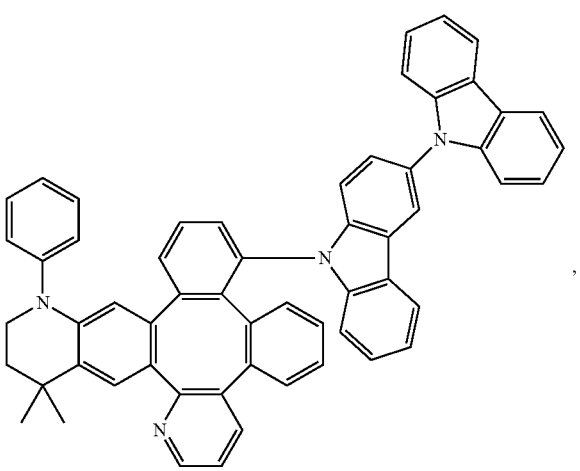

-continued
Compound A34
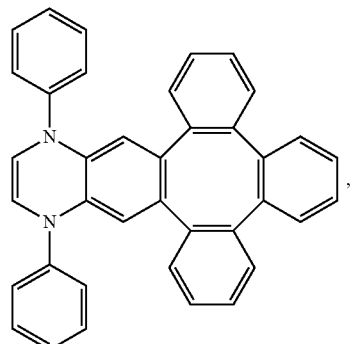
Compound A35
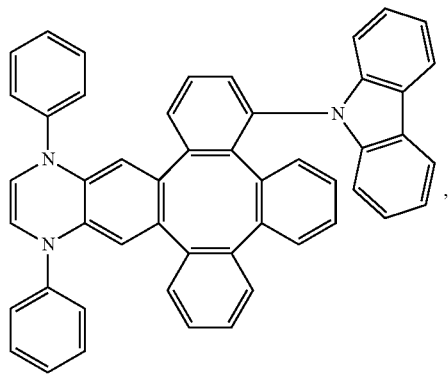
Compound A36
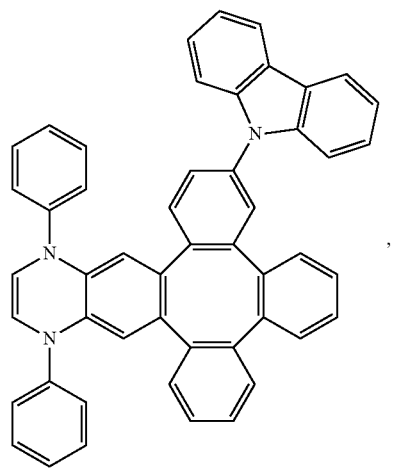
Compound A37
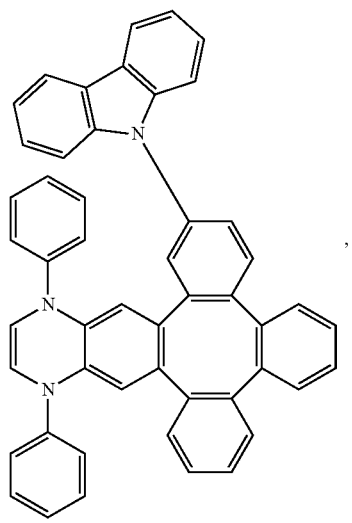
Compound A38
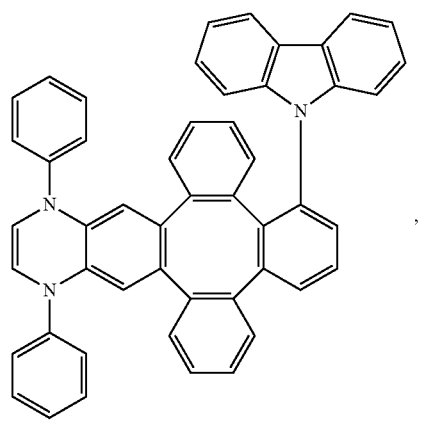
Compound A39
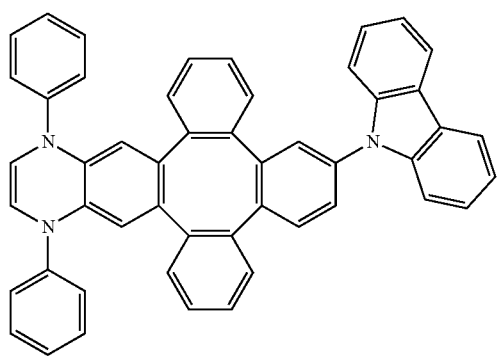

-continued
Compound A40
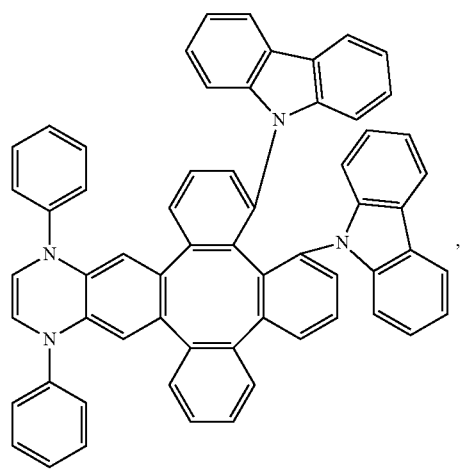
Compound A41
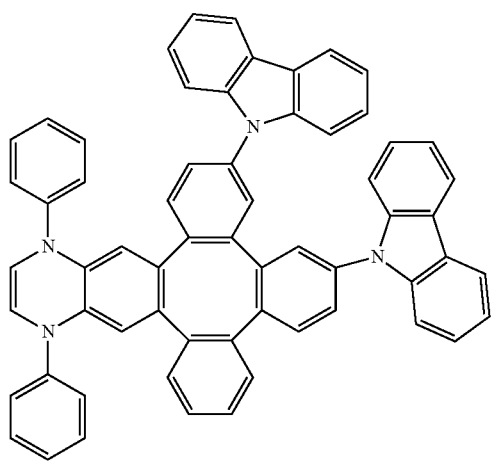
Compound A42
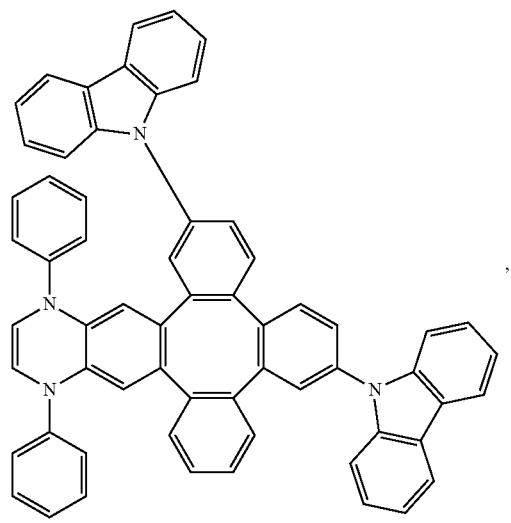
Compound A43
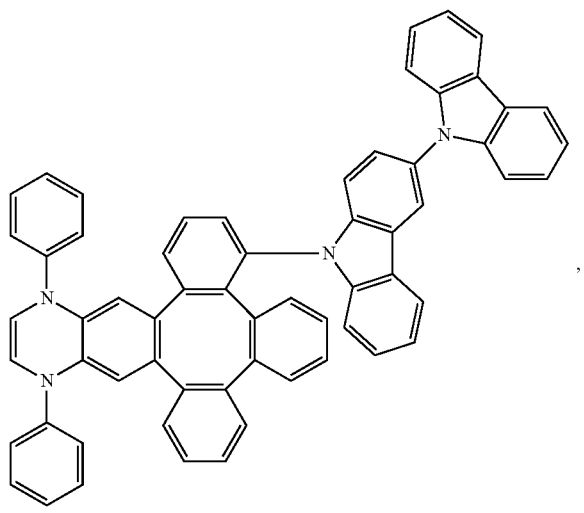
Compound A44
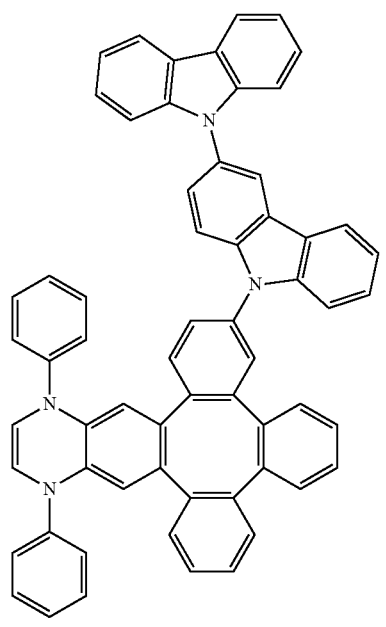
Compound A45
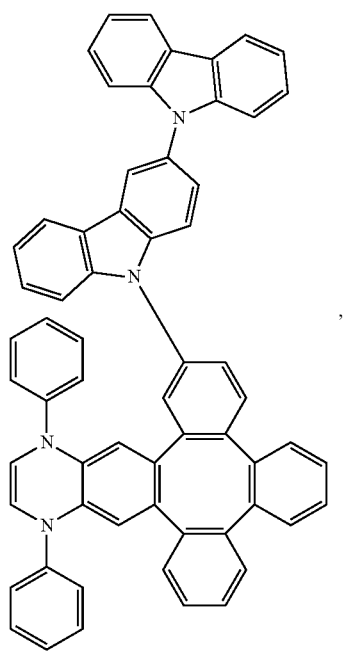

-continued
Compound A46
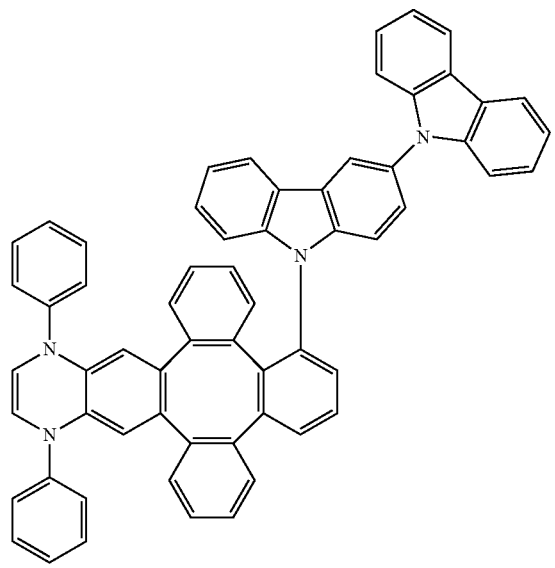
Compound A47
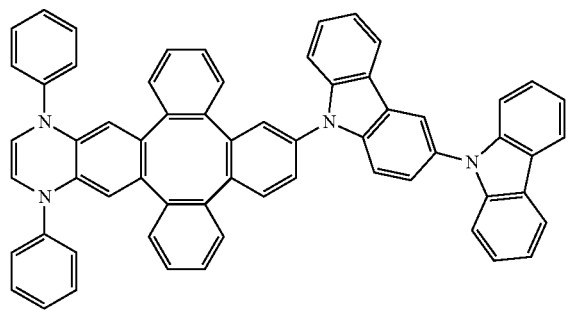
Compound A48
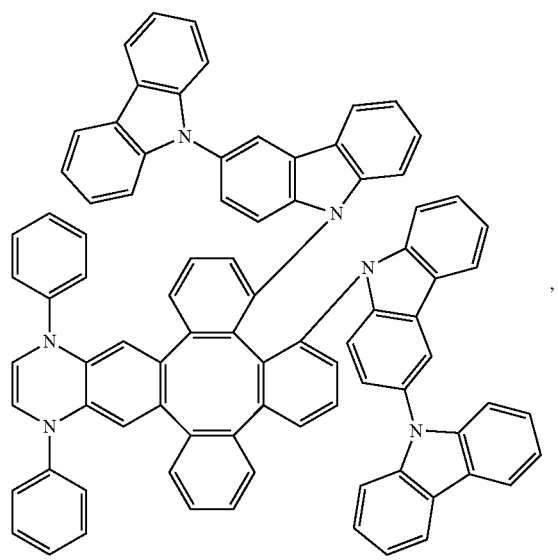
Compound A49
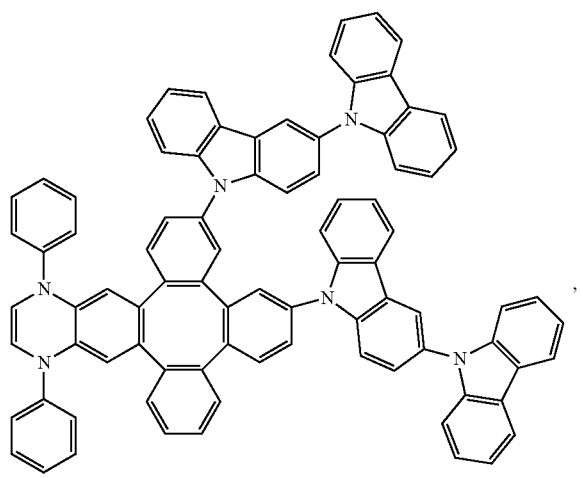

-continued
Compound A50
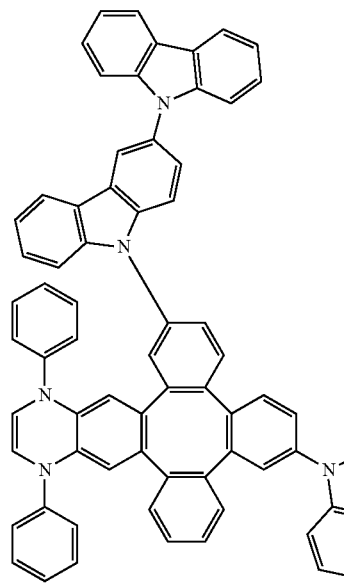
Compound A51
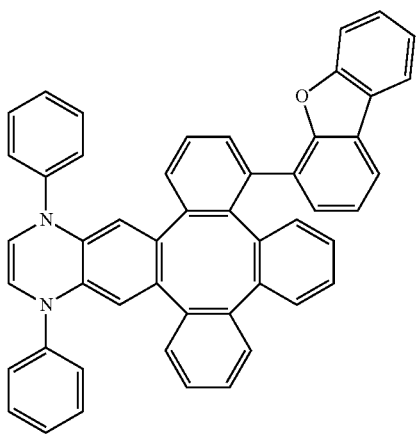
Compound A52
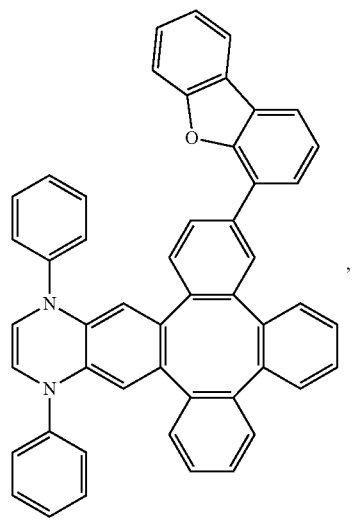
Compound A53
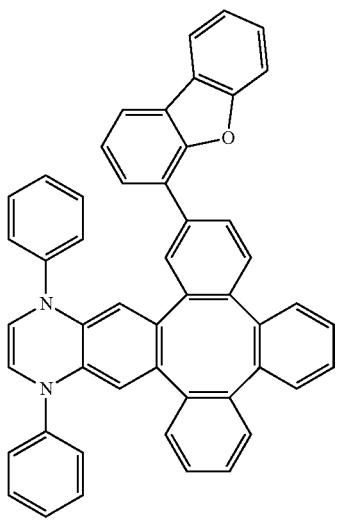
Compound A54
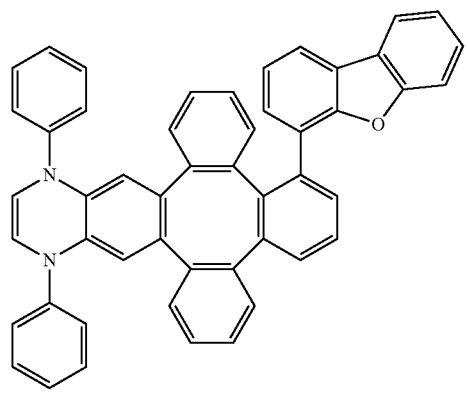
Compound A55
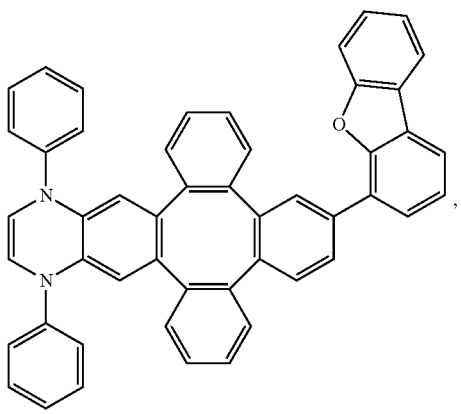

-continued
Compound A56
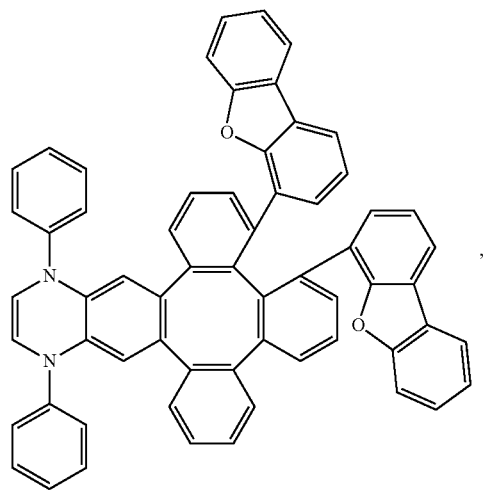
Compound A57
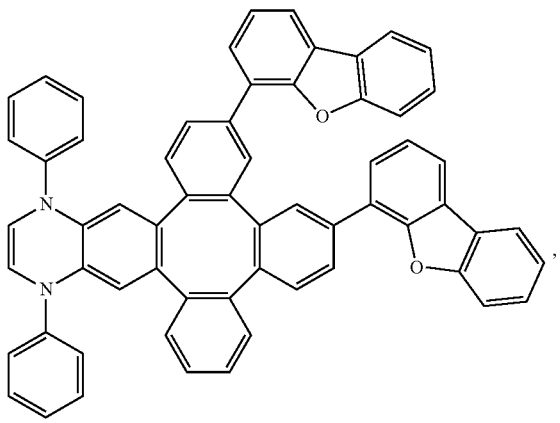
Compound A58
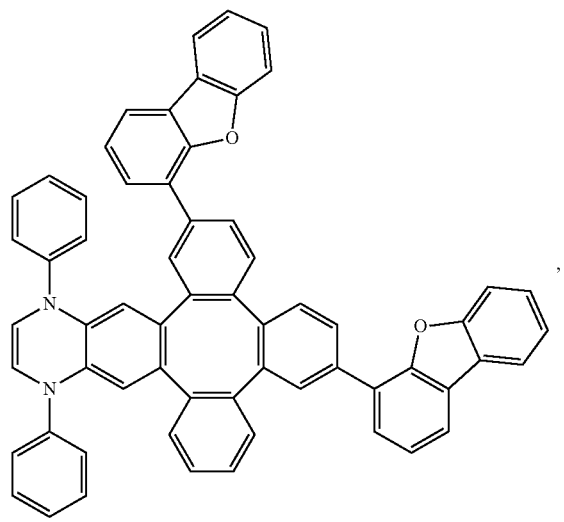
Compound A59
Compound A60
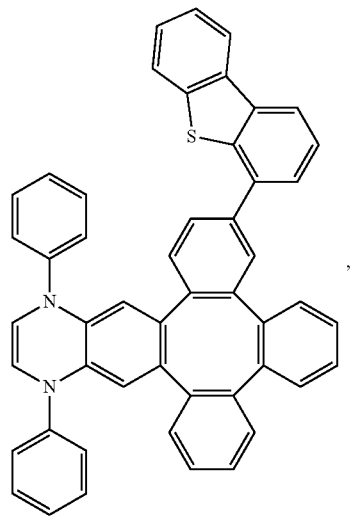
Compound A61
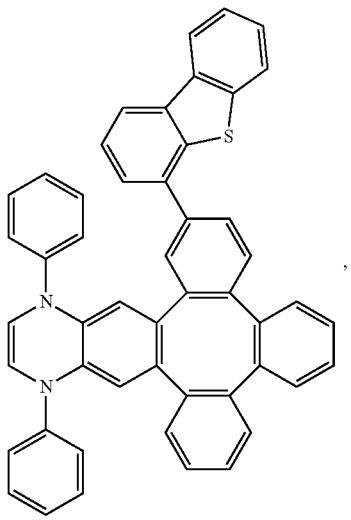

-continued
Compound A62
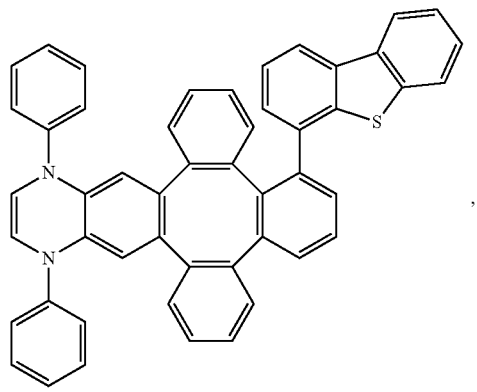
Compound A63
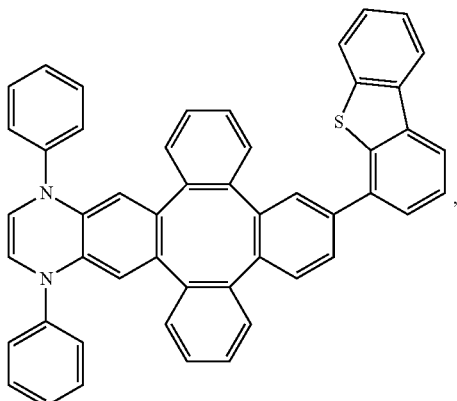
Compound A64
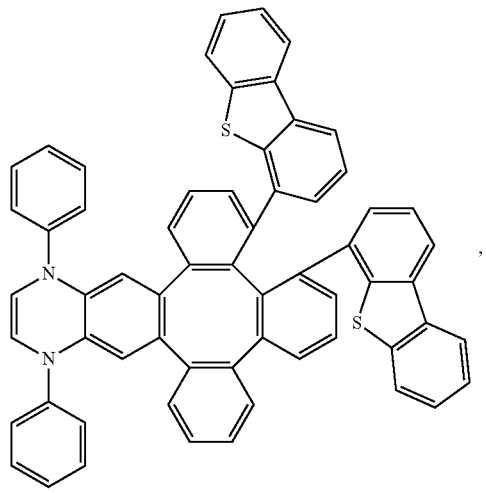
Compound A65
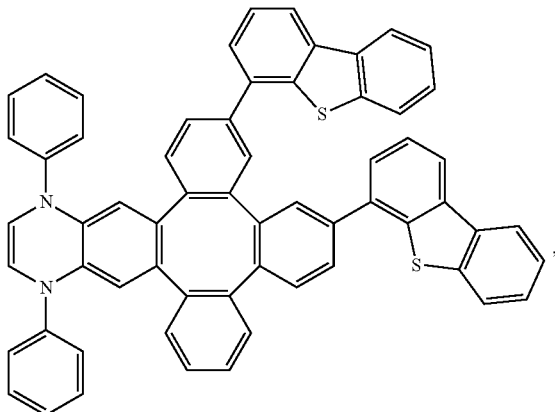
Compound A66
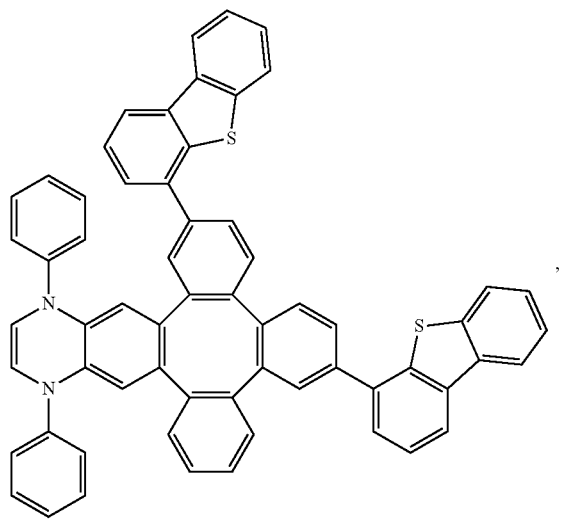
Compound C34
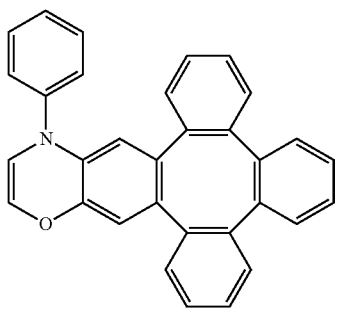

-continued
Compound C35
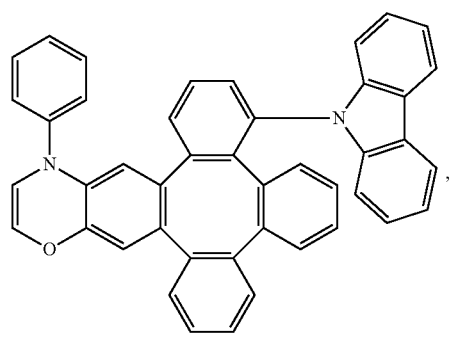
Compound C36
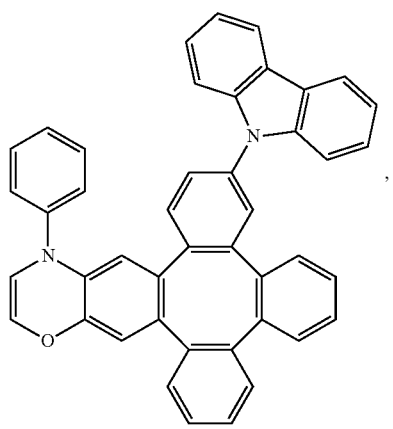
Compound C37
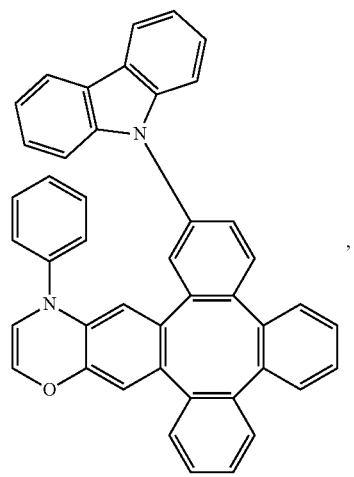
Compound C38
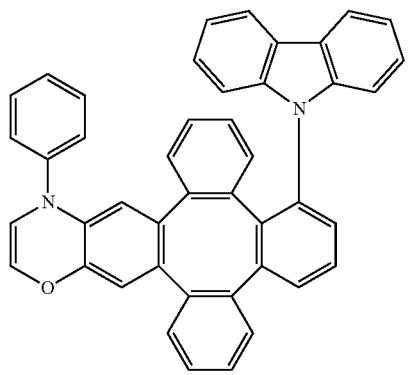
Compound C39
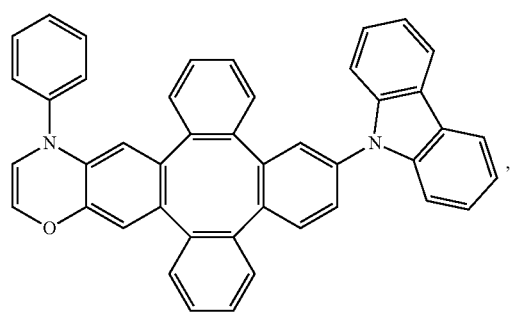
Compound C40
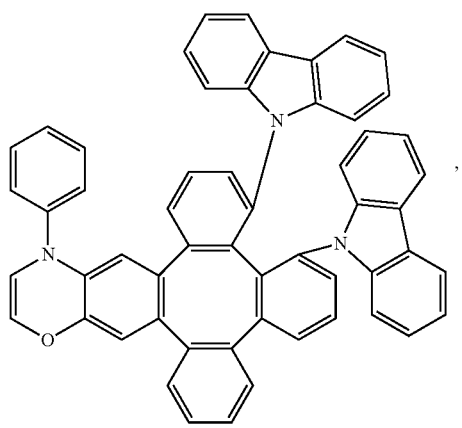

-continued
Compound C41
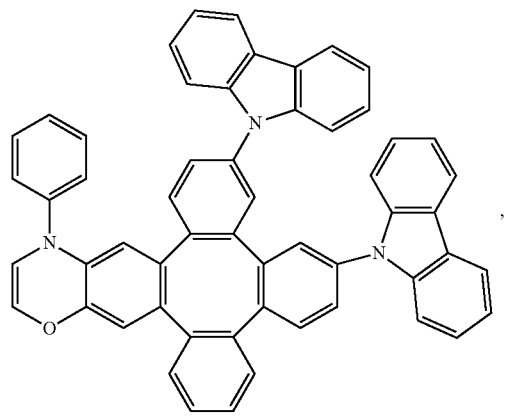
Compound C42
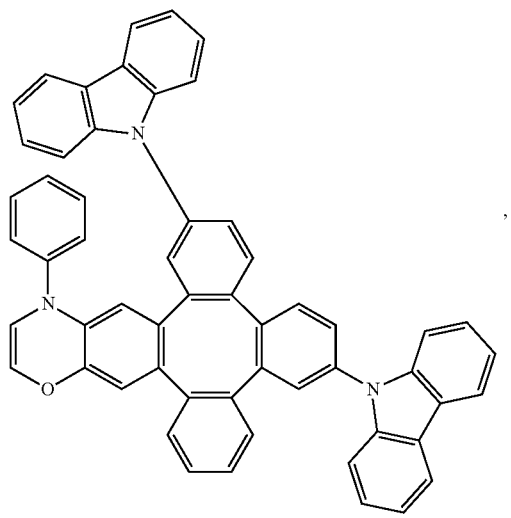
Compound C43
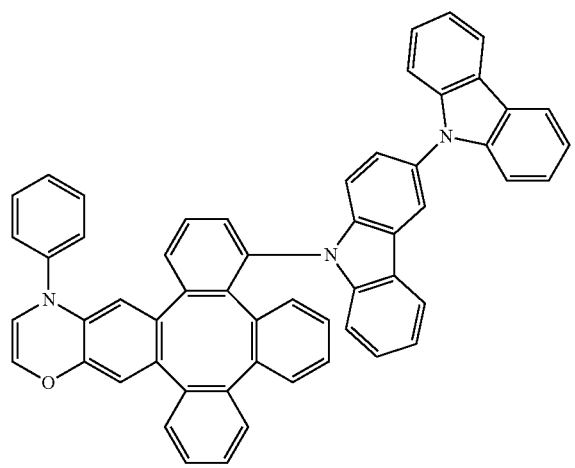
Compound D34
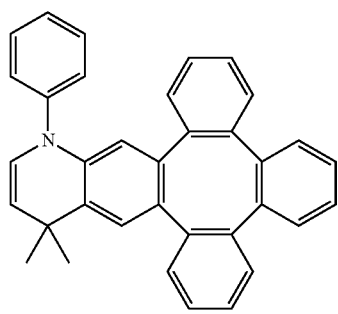
Compound D35
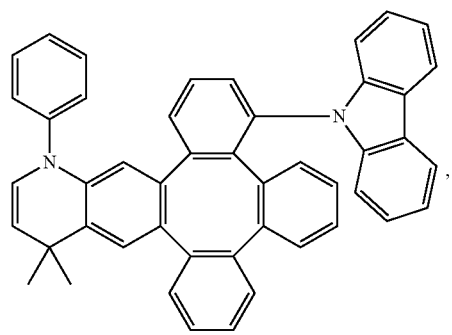
Compound D36
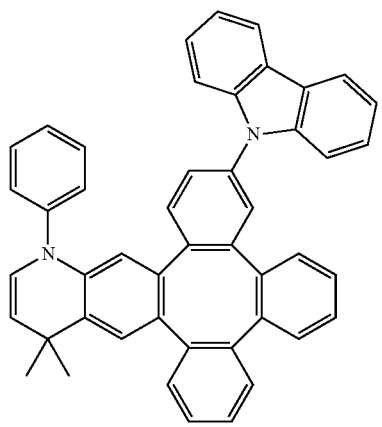

Compound D37
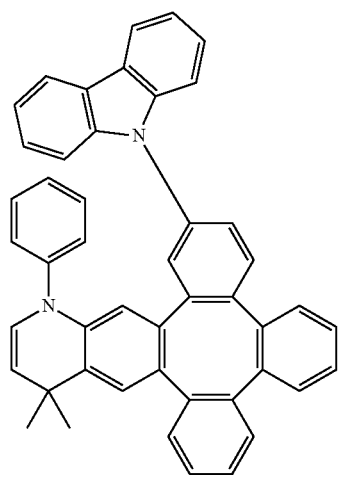
Compound D38
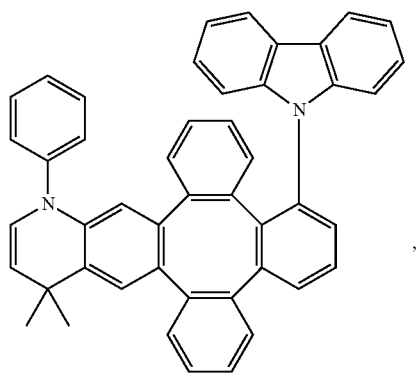
Compound D39
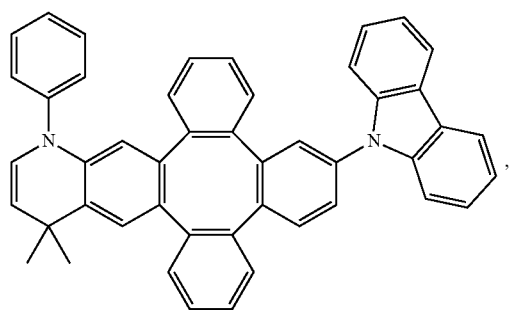
Compound D40
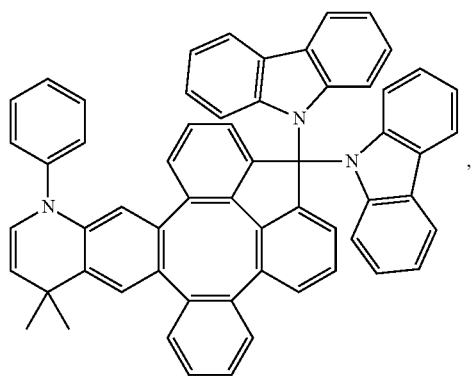
Compound D41
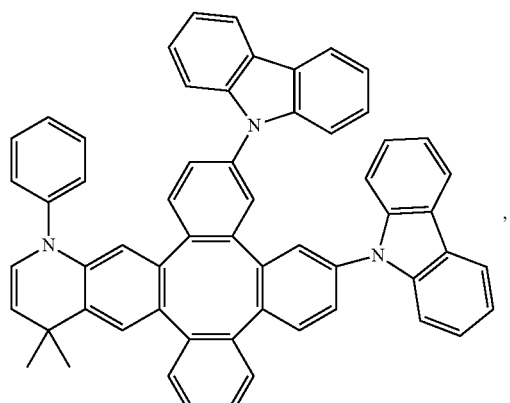
Compound D42
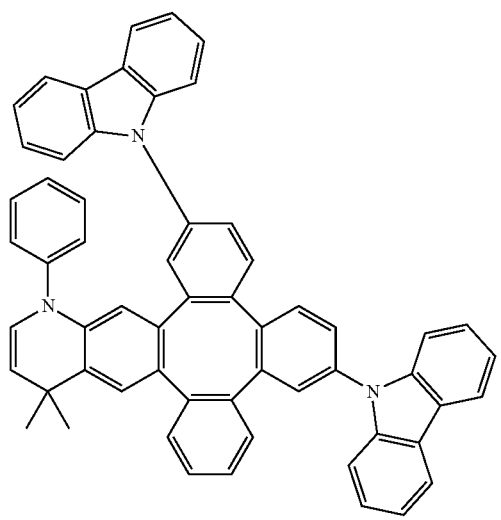

-continued
Compound D43
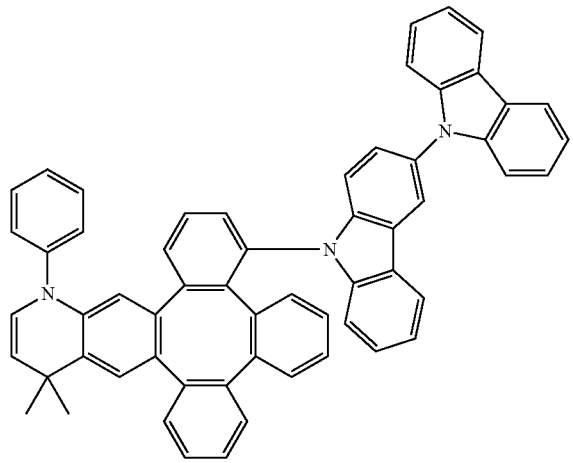
Compound B34
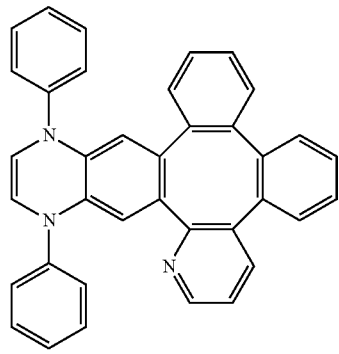
Compound B35
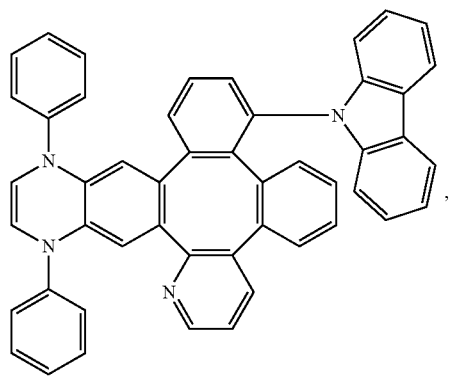
Compound B36
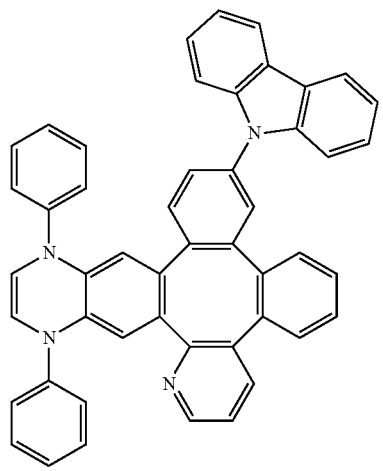
Compound B37
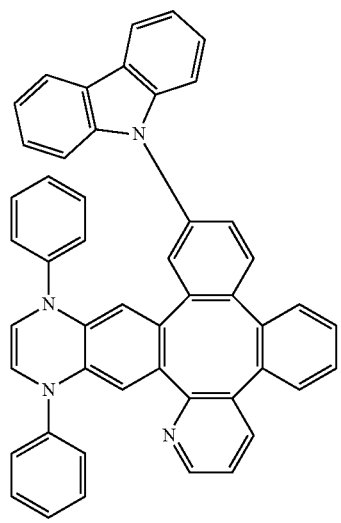
Compound B38
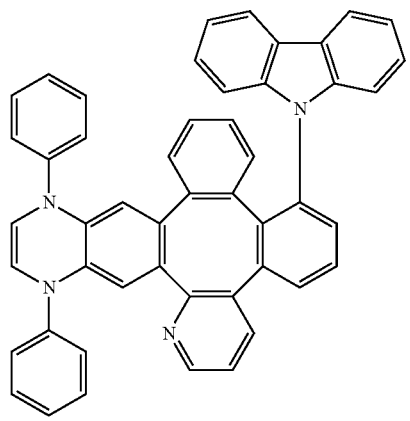

-continued
Compound B39
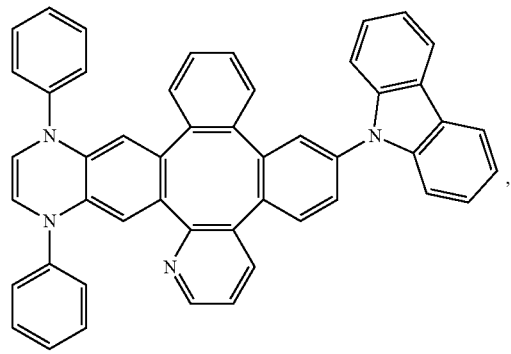
Compound B40
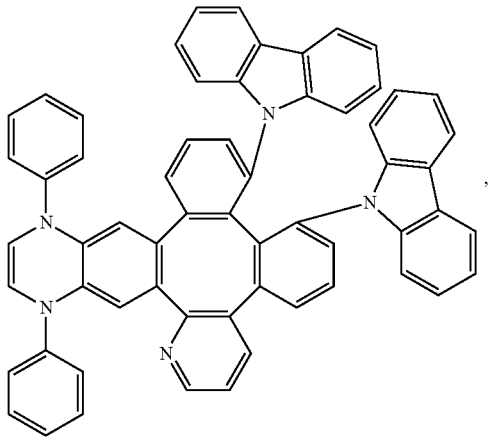
Compound B41
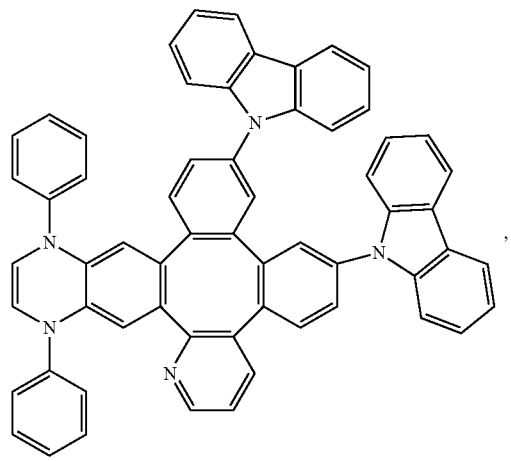
Compound B42
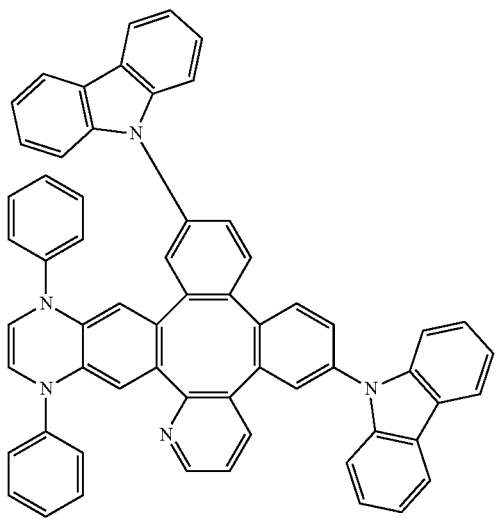
Compound B43
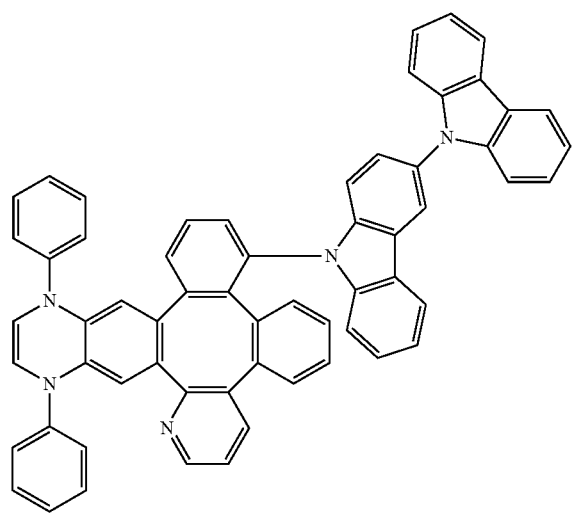
Compound B44
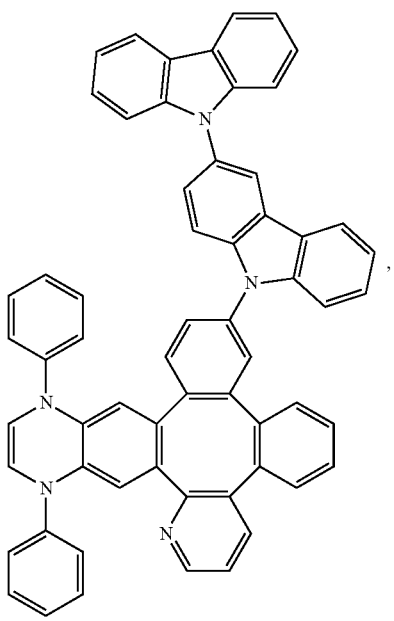

Compound B45
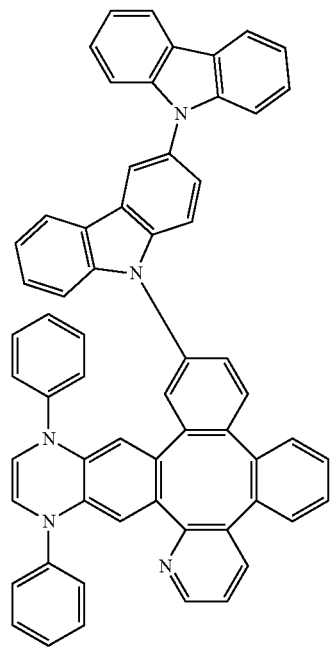
Compound B46
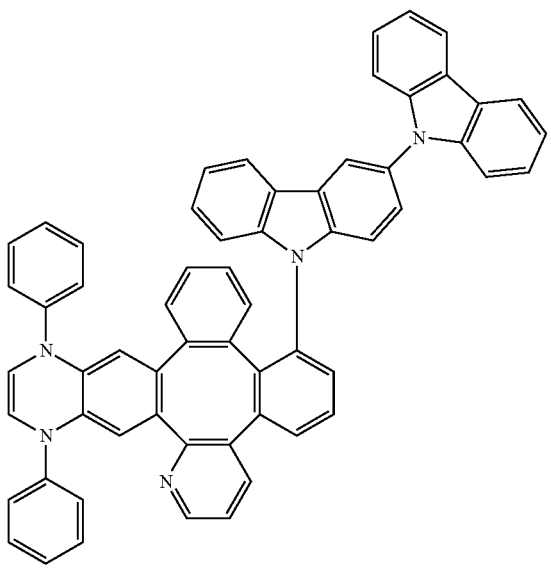
Compound B47
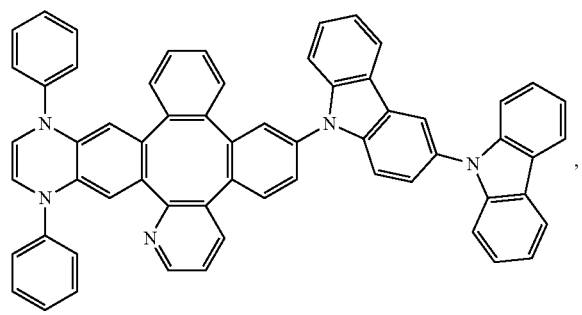
Compound B48
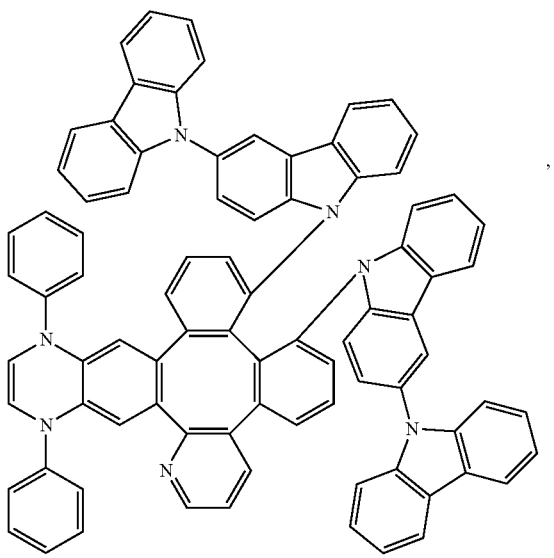

-continued
Compound B49
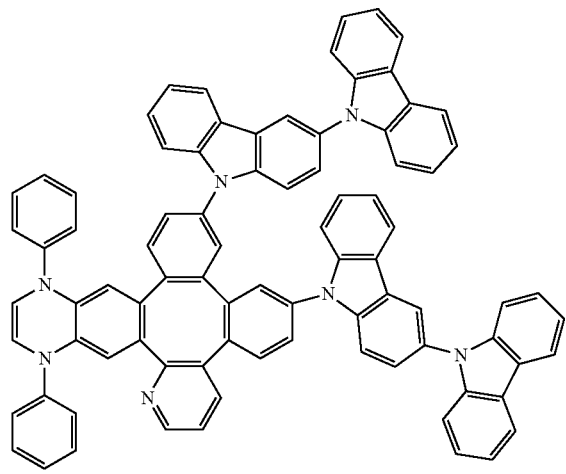
Compound B50
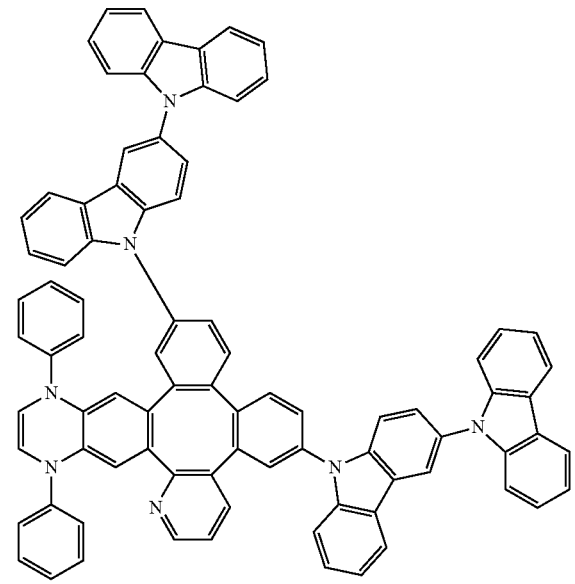
Compound B51
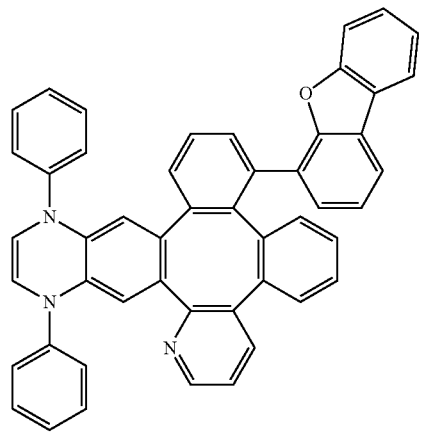
Compound B52
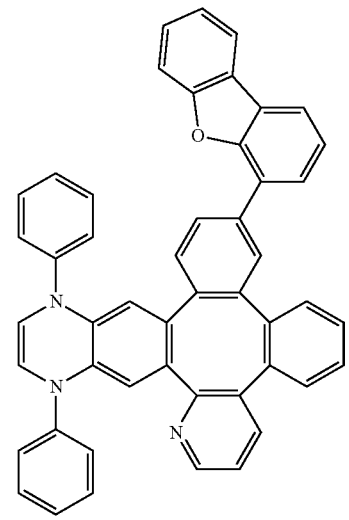
Compound B53
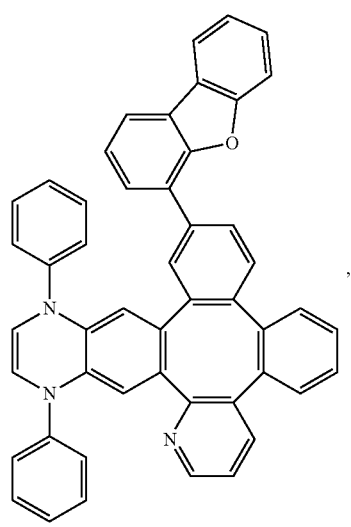
Compound B54
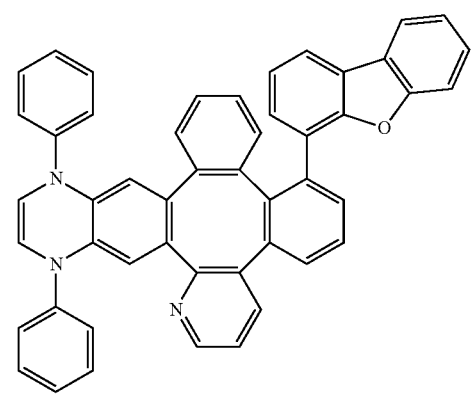

-continued
Compound B55
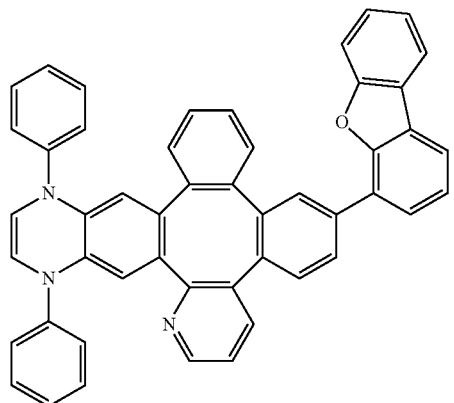
Compound B56
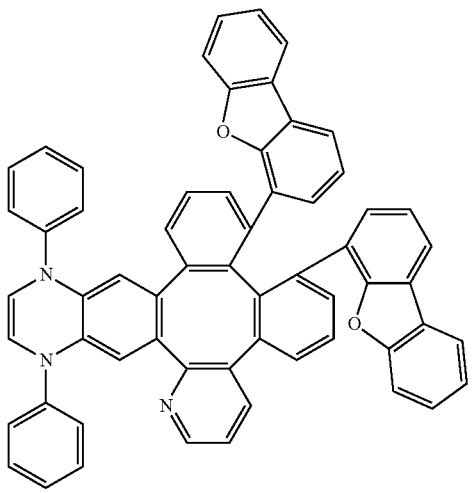
Compound B57
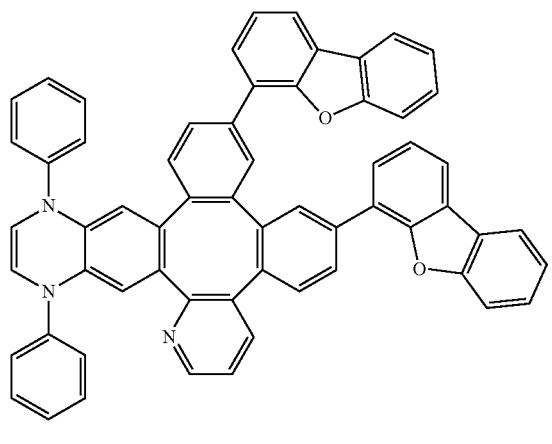
Compound B58
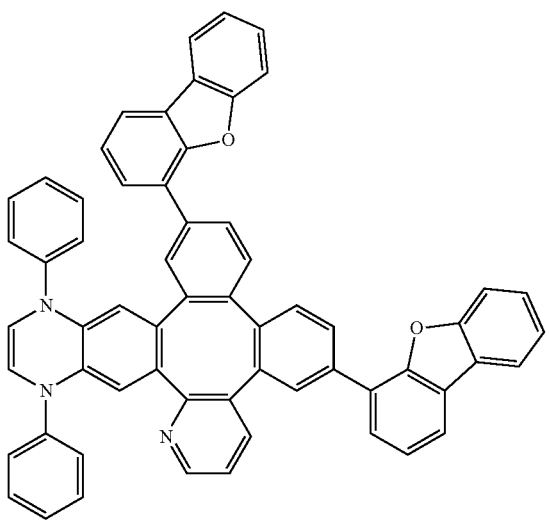
Compound B59
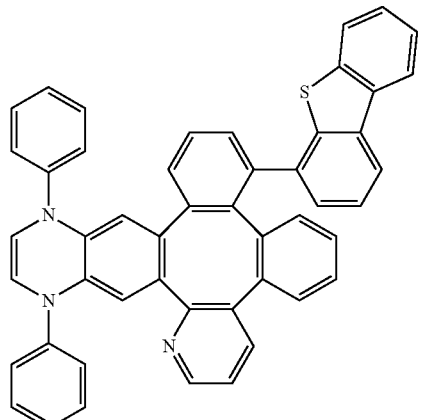
Compound B60
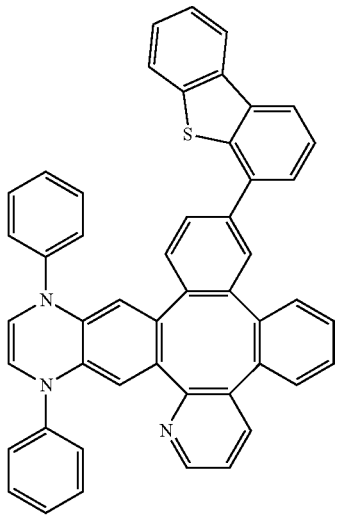

-continued
Compound B61
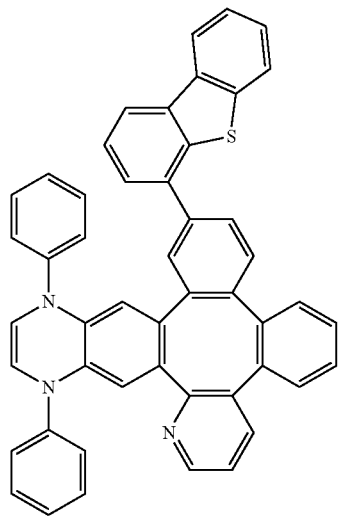
Compound B62
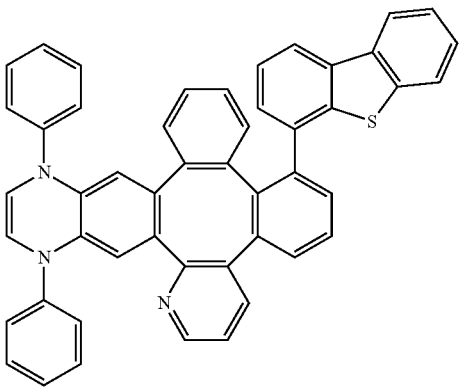
Compound B63
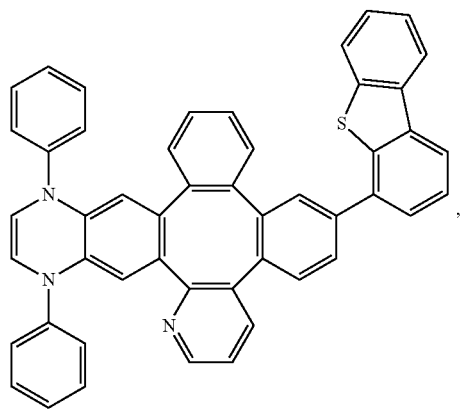
Compound B64
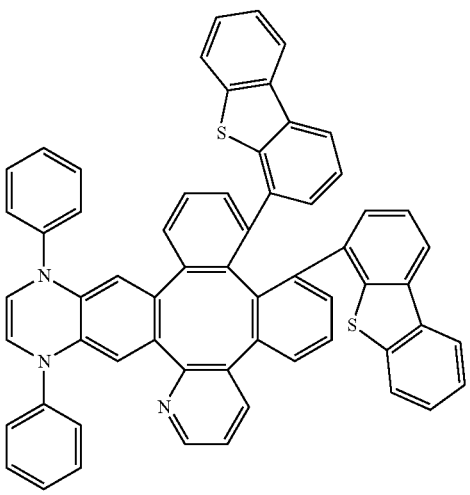
Compound B65
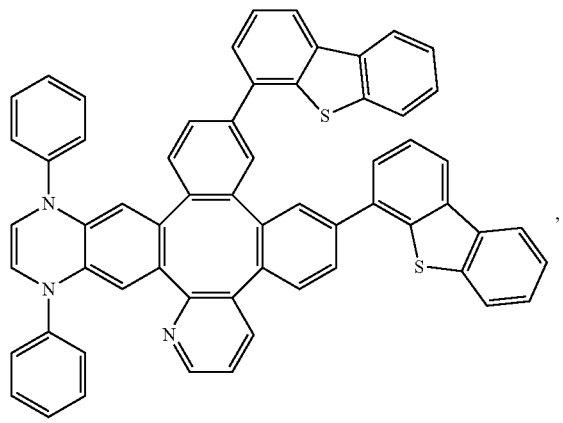
Compound B66
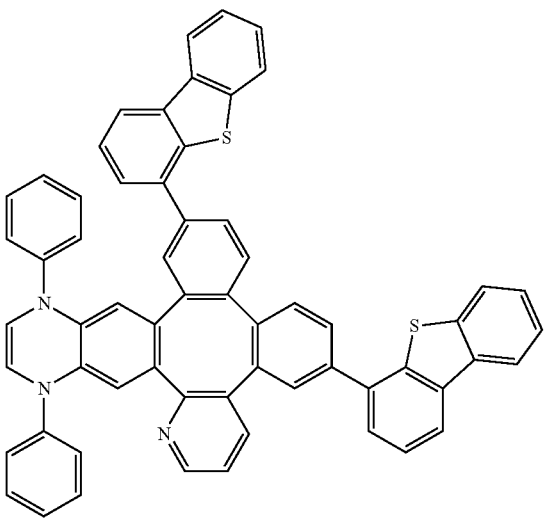

-continued
Compound CC34
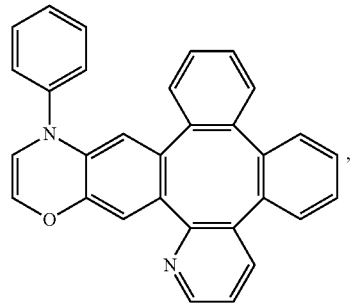
Compound CC35
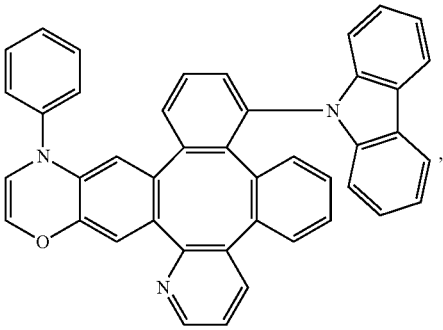
Compound CC36
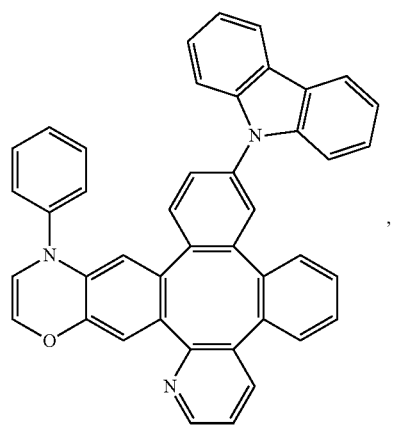
Compound CC37
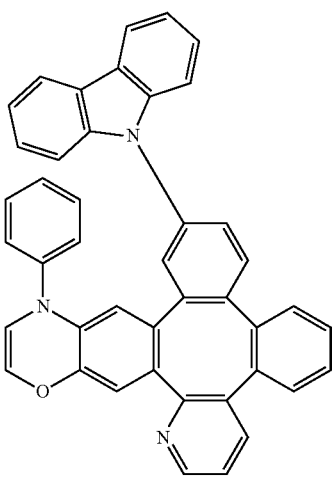
Compound CC38
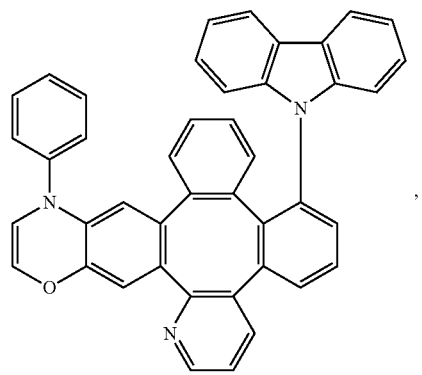
Compound CC39
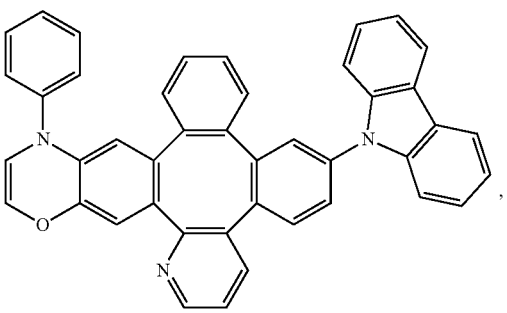
Compound CC40
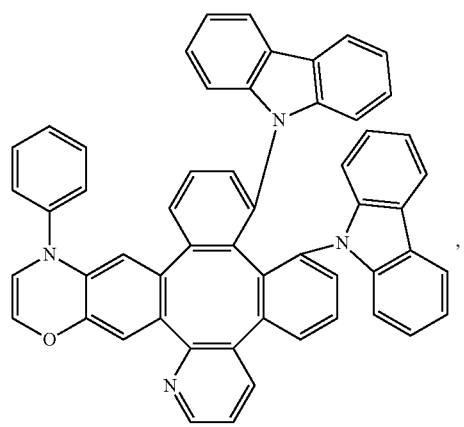
Compound CC41
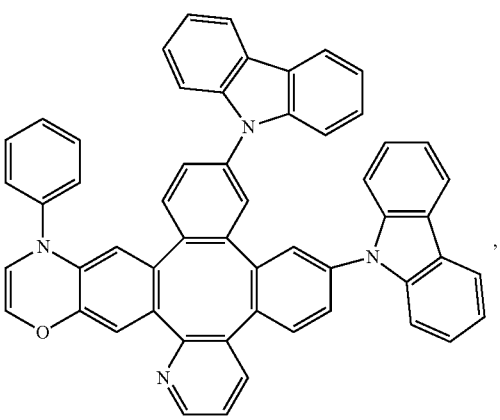

-continued
Compound CC42
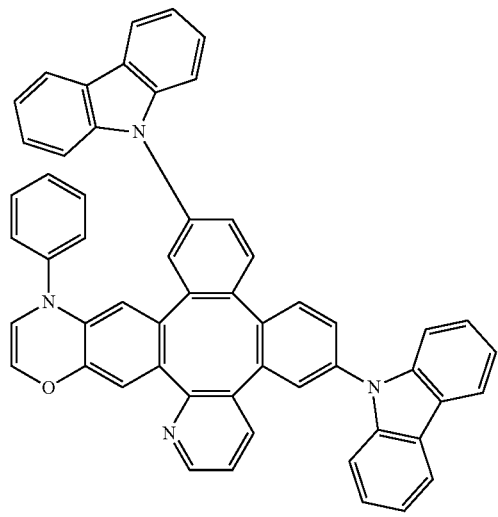
Compound CC43
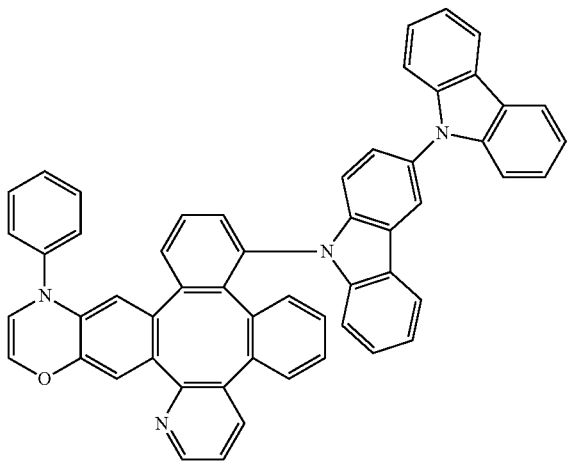
Compound DD34
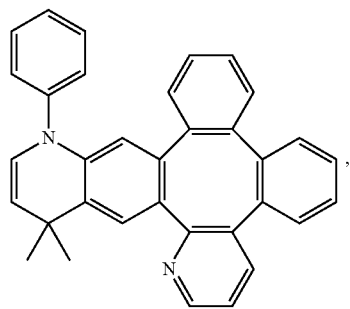
Compound DD35
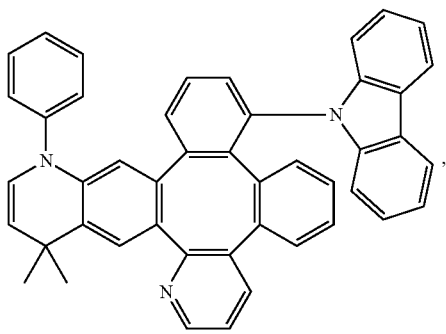
Compound DD36
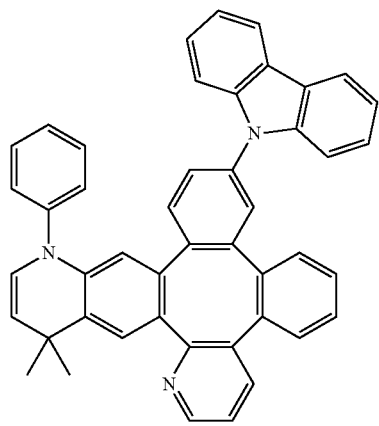
Compound DD37
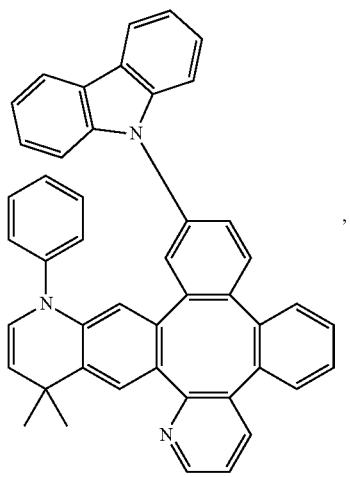

-continued
Compound DD38
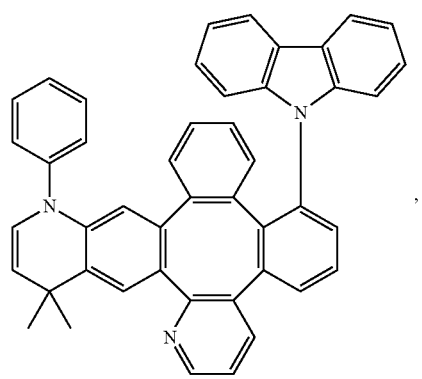
Compound DD39
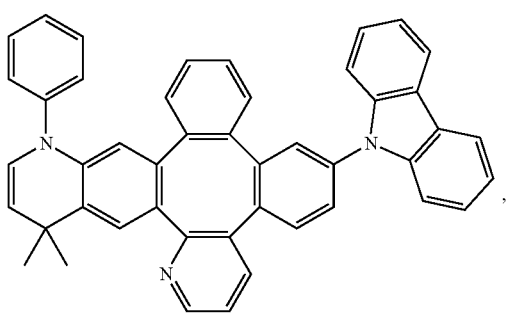
Compound DD40
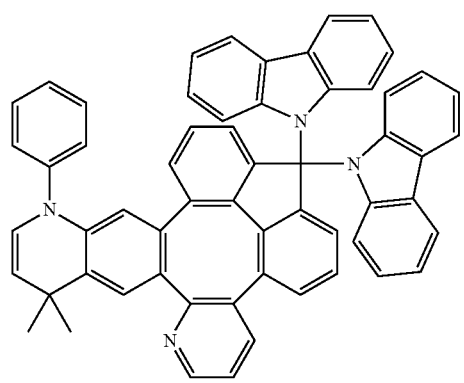
Compound DD41
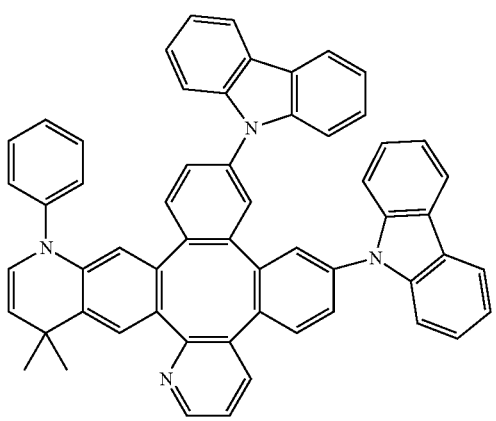
Compound DD42
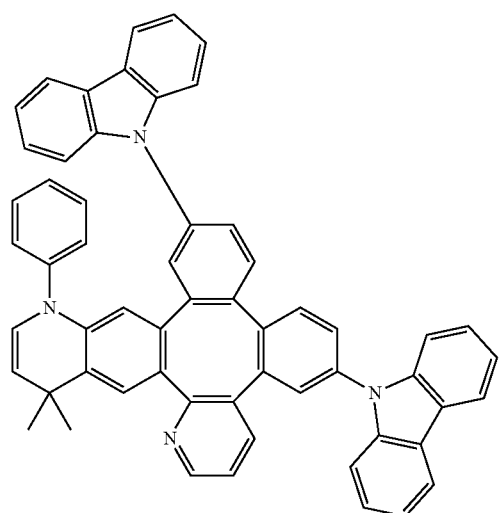
Compound DD43
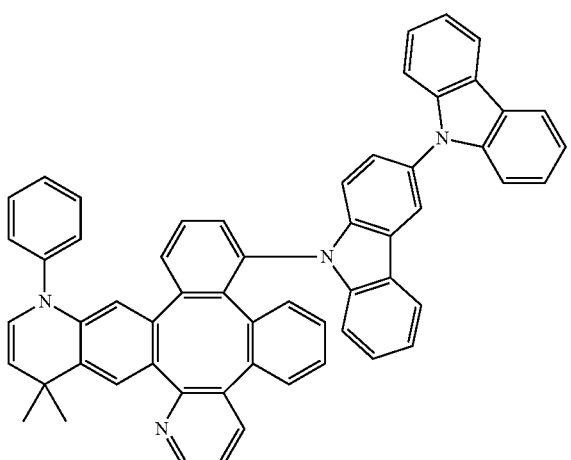

-continued
Compound A67
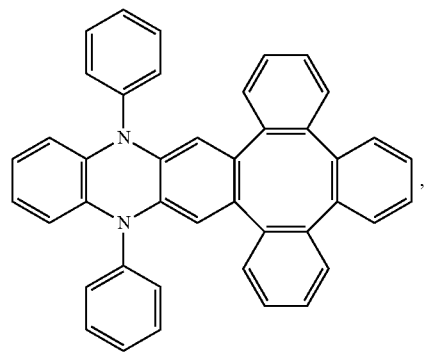
Compound A68
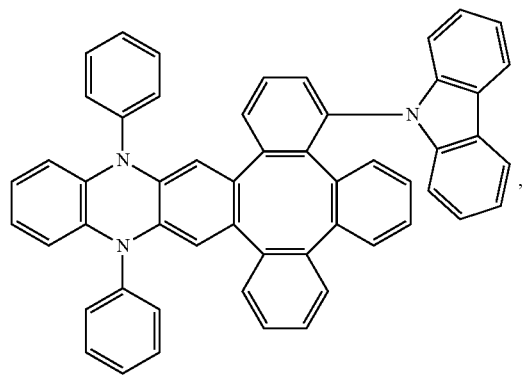
Compound A69
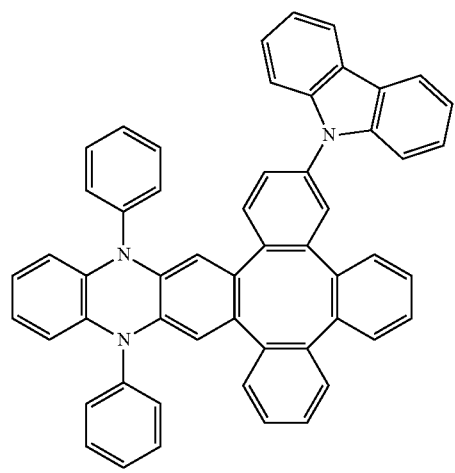
Compound A70
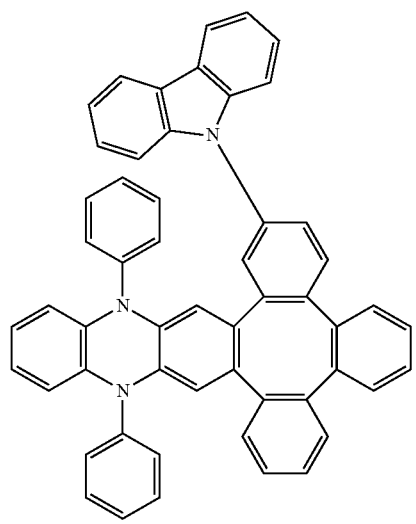
Compound A71
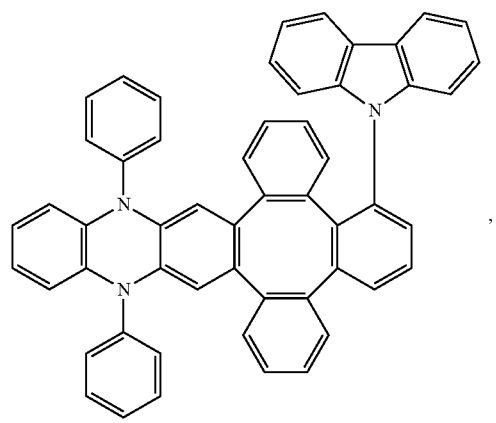
Compound A72
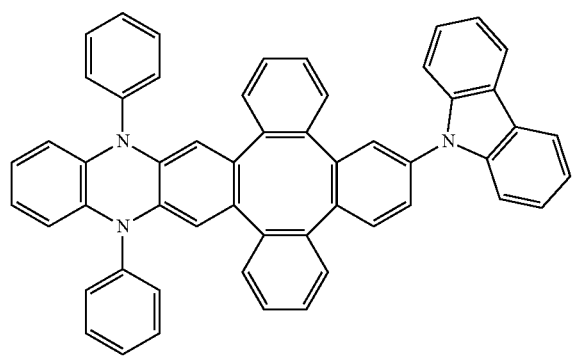

-continued
Compound A73
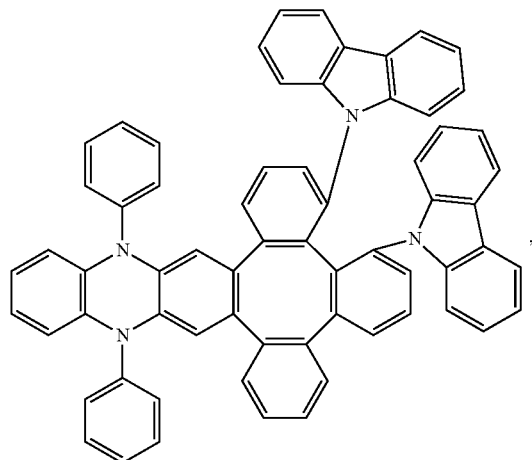
Compound A74
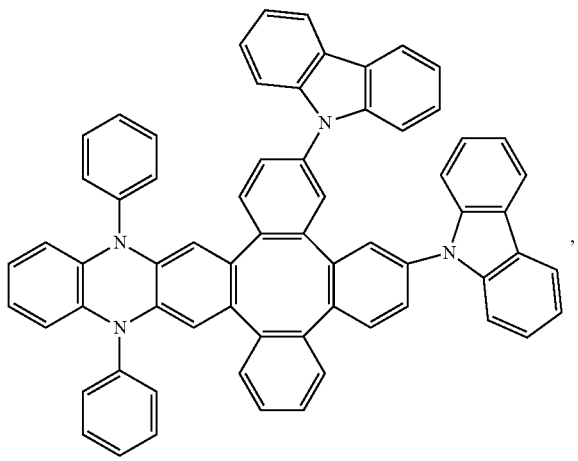
Compound A75
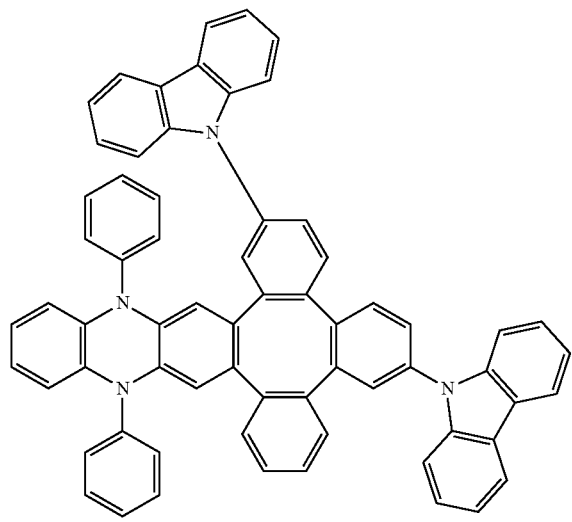
Compound A76
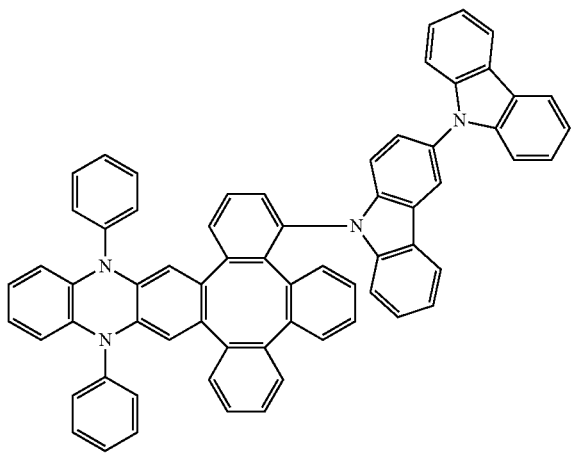

Compound A77
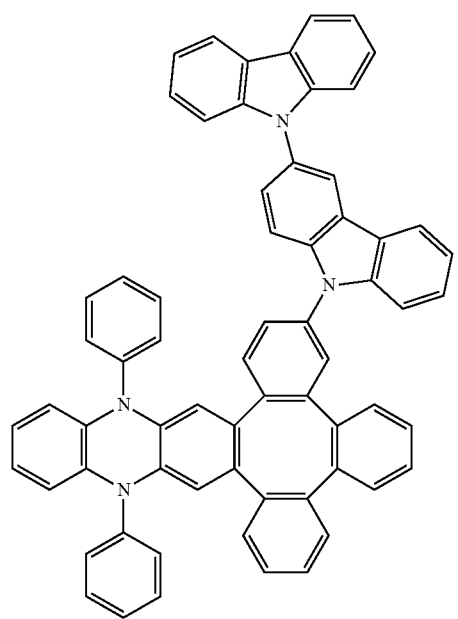
Compound A78
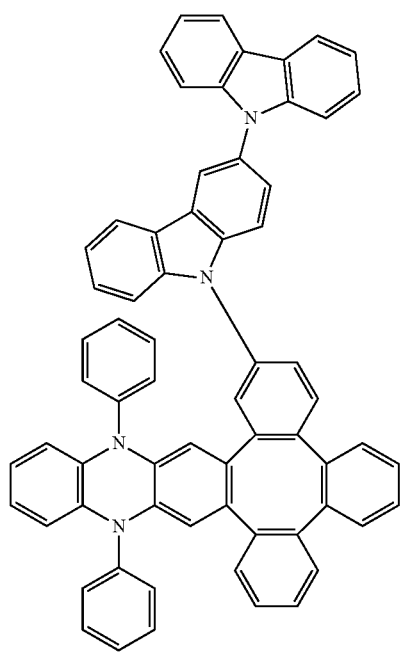
Compound A79
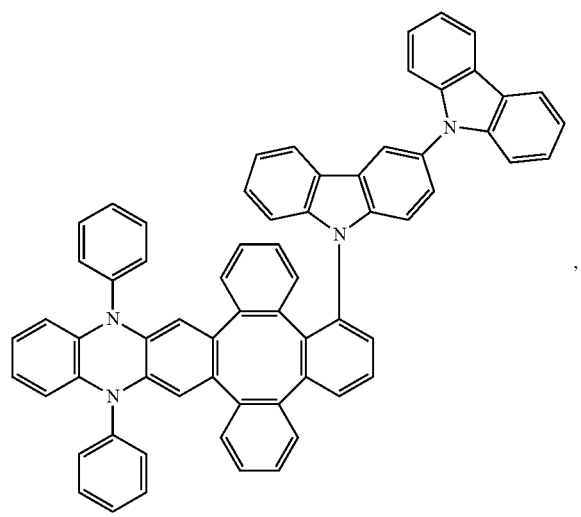
Compound A80
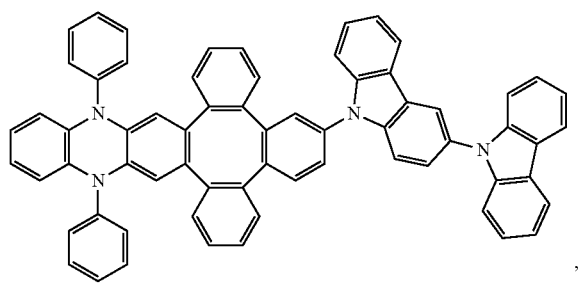

-continued
Compound A81
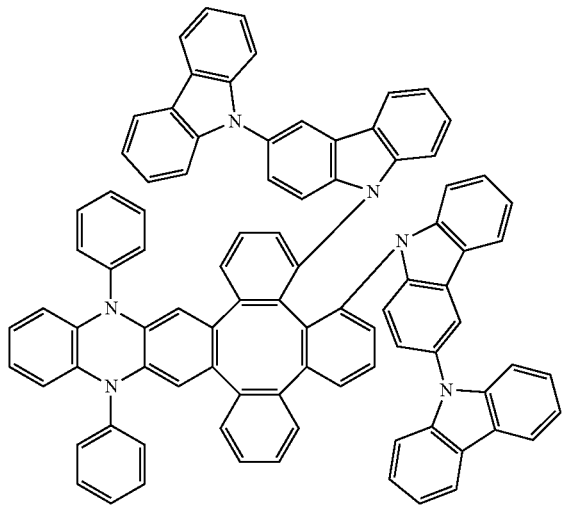
Compound A82
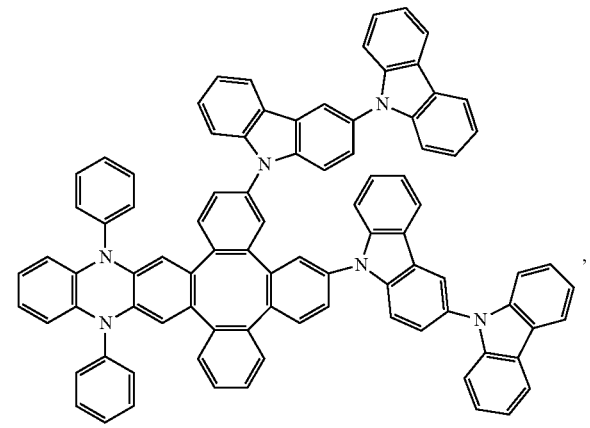
Compound A83
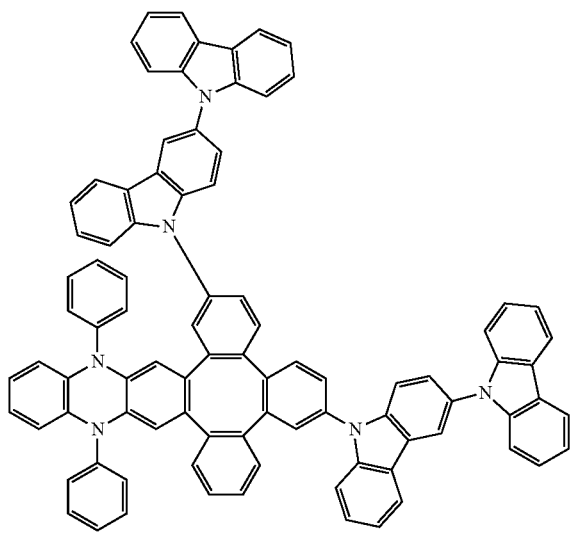
,
Compound A84
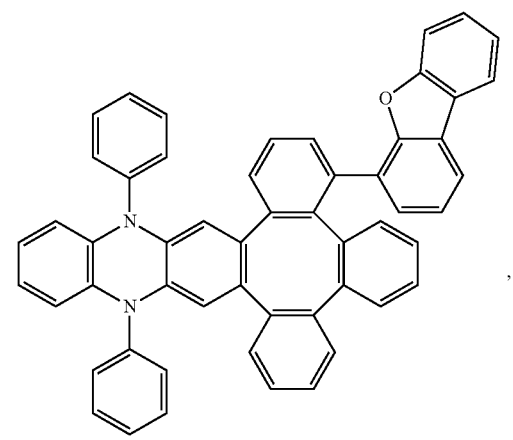
,
Compound A85
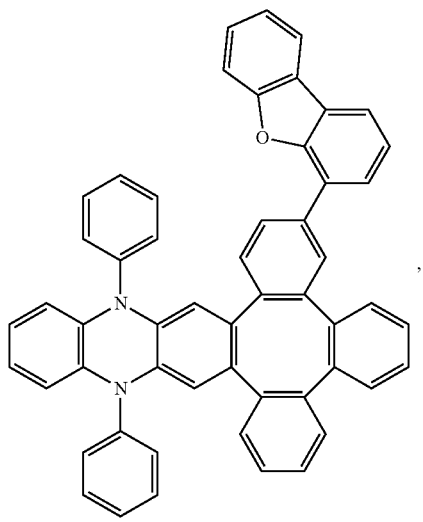
,
Compound A86
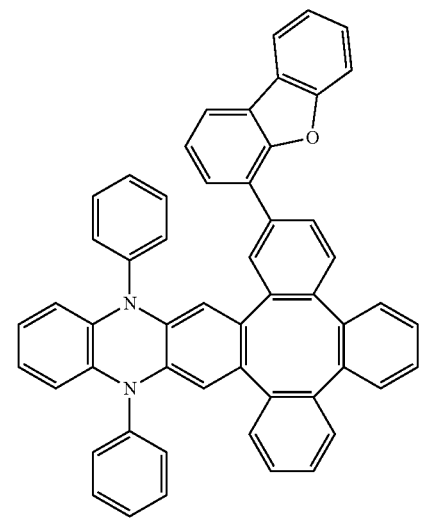
, -continued
Compound A87
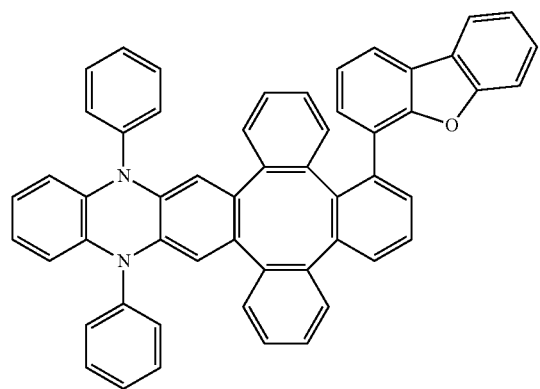
Compound A88
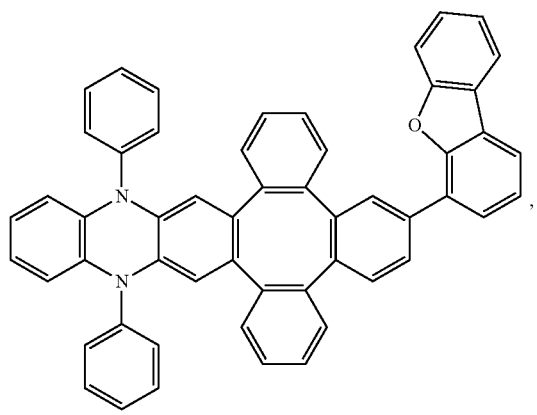
Compound A89
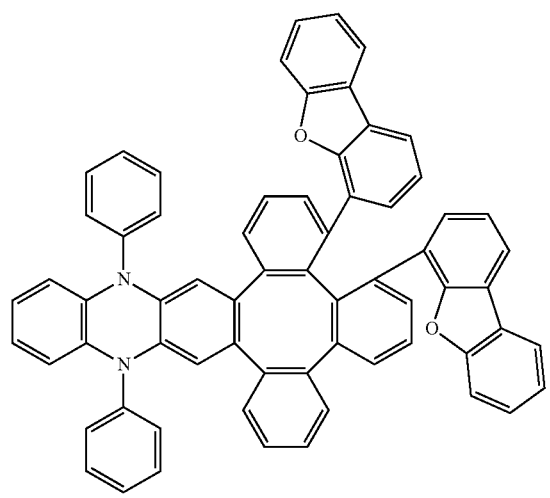
Compound A90
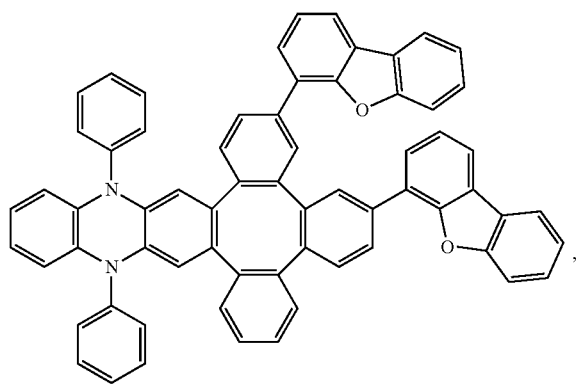
Compound A91
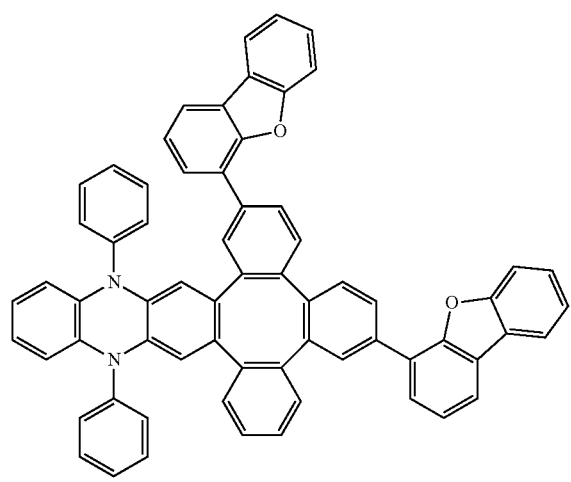
Compound A92
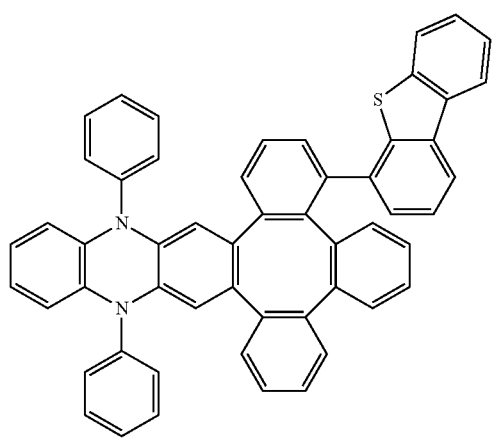

-continued
Compound A93
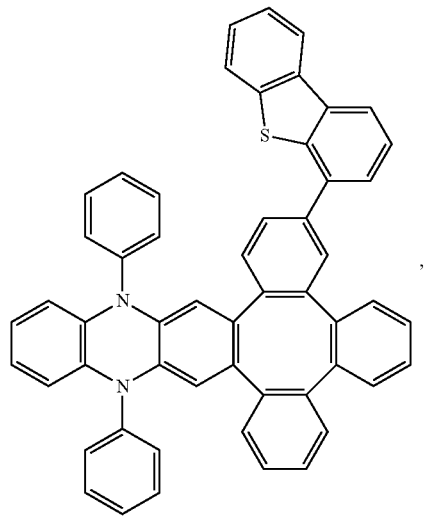
Compound A94
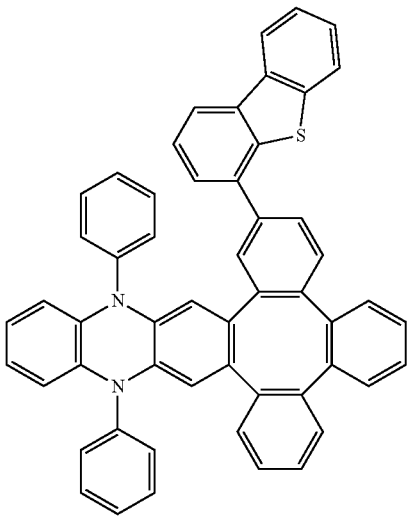
Compound A95
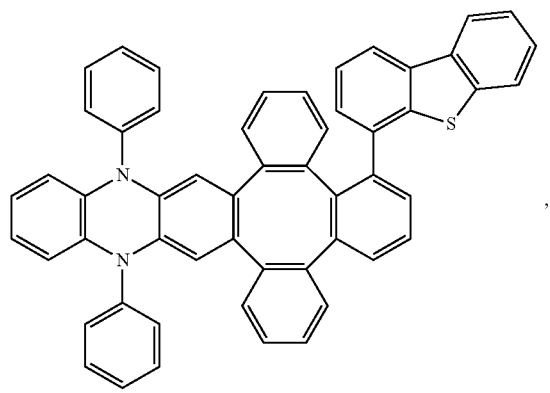
Compound A96
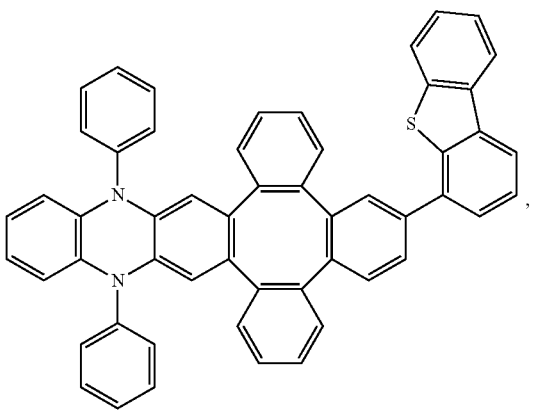
Compound A97
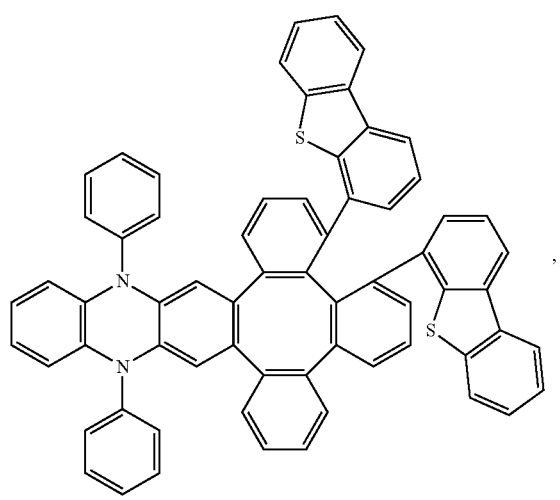
Compound A98
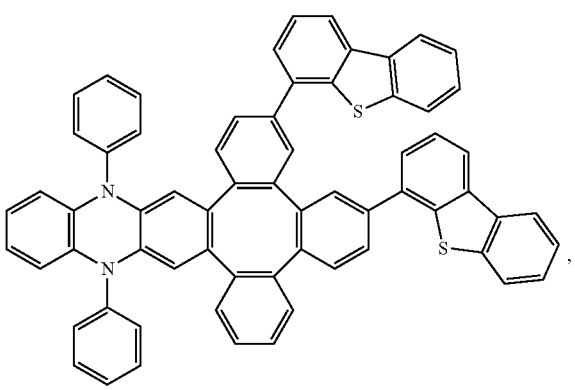

-continued
Compound A99
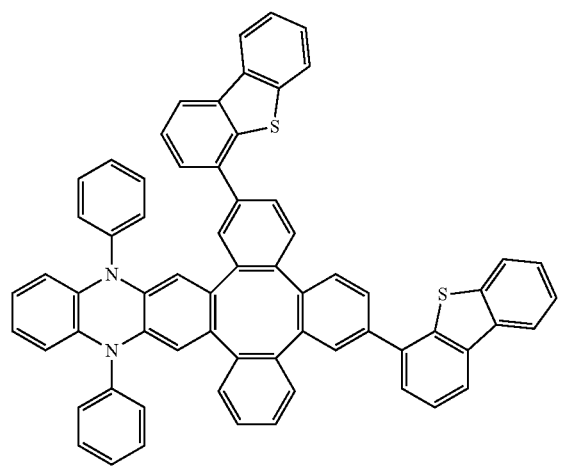
Compound C67
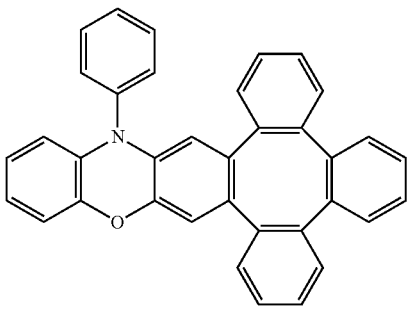
Compound C68
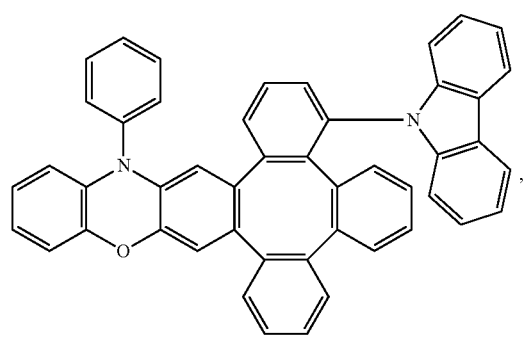
Compound C69
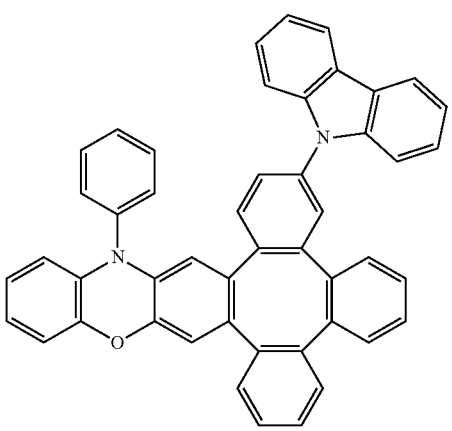
Compound C70
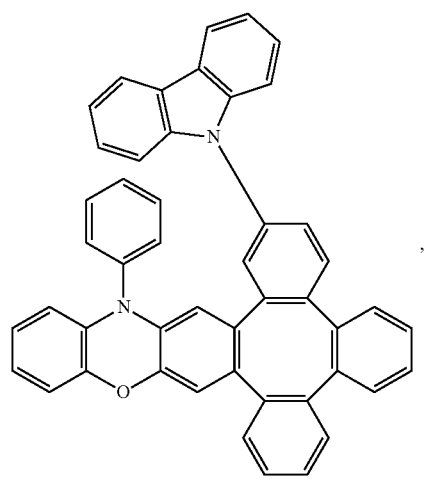
Compound C71
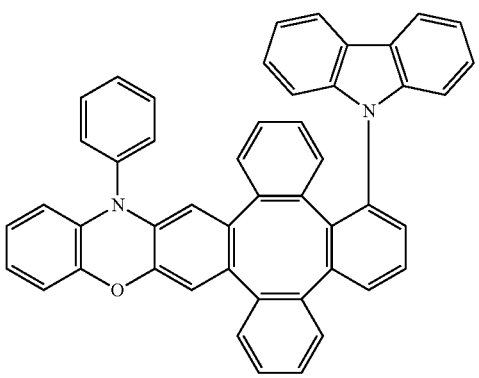

-continued
Compound C72
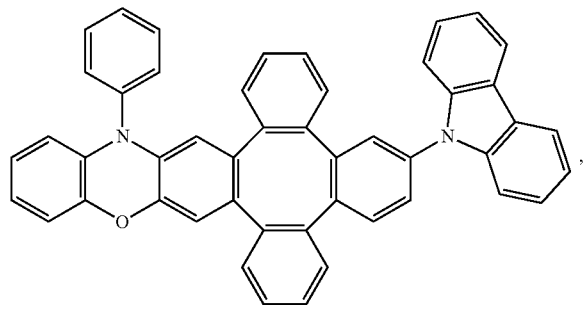
Compound C73
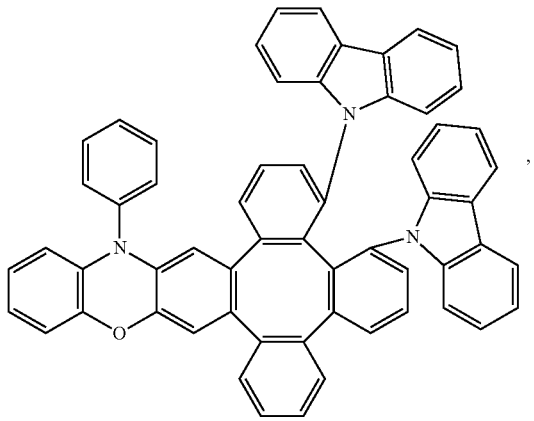
Compound C74
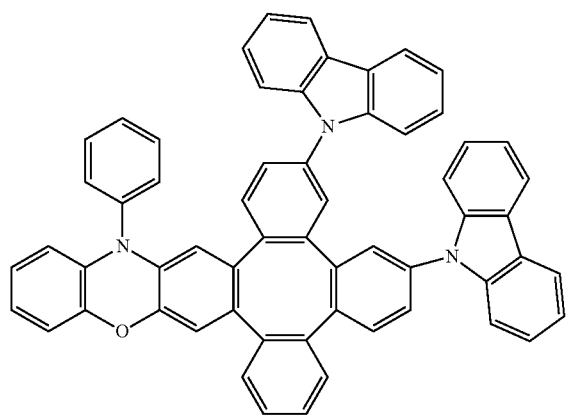
Compound C75
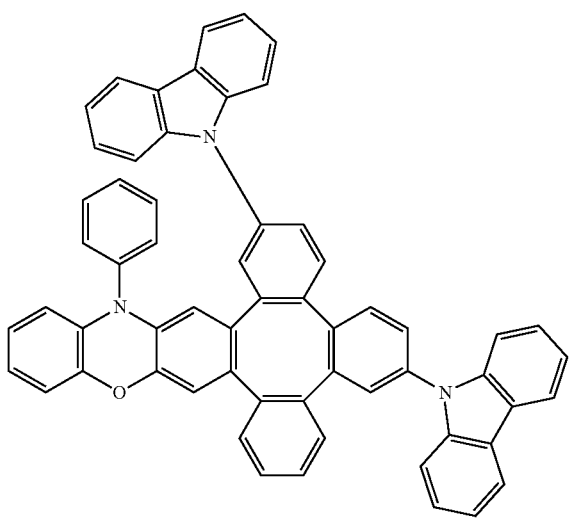
Compound C76
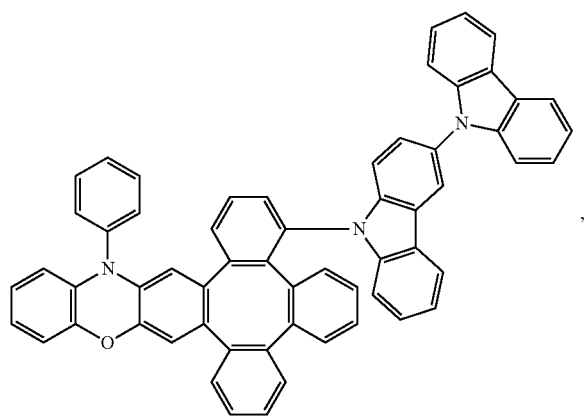
Compound D67
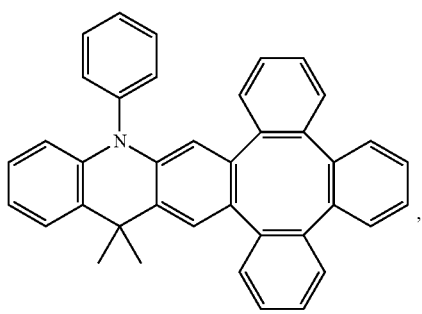

-continued
Compound D68
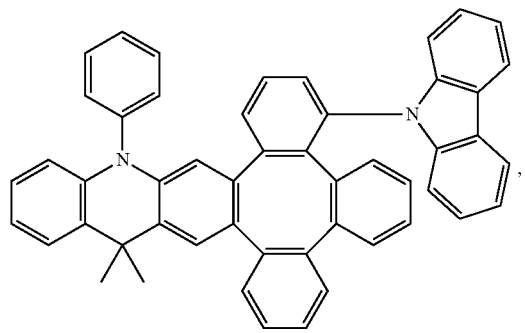
Compound D69
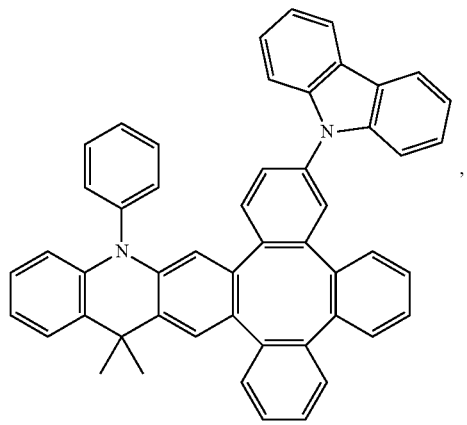
Compound D70
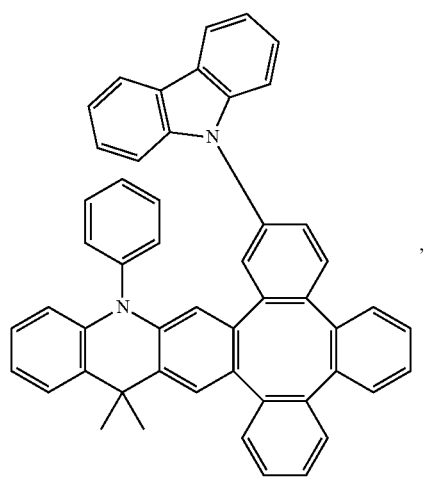
Compound D71
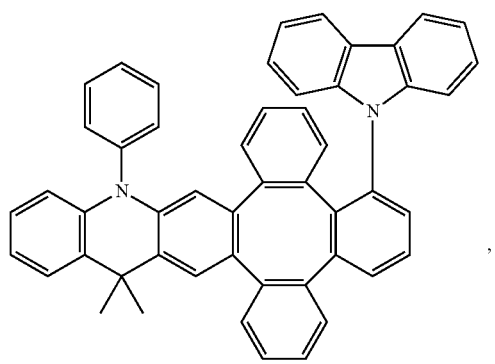
Compound D72
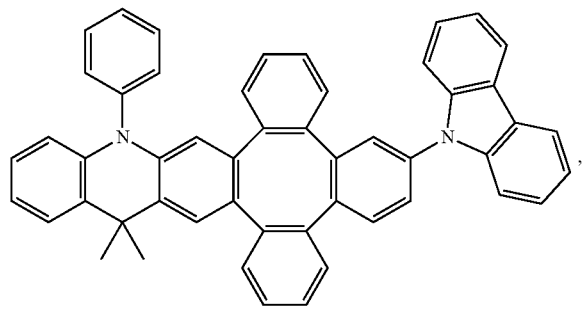
Compound D73
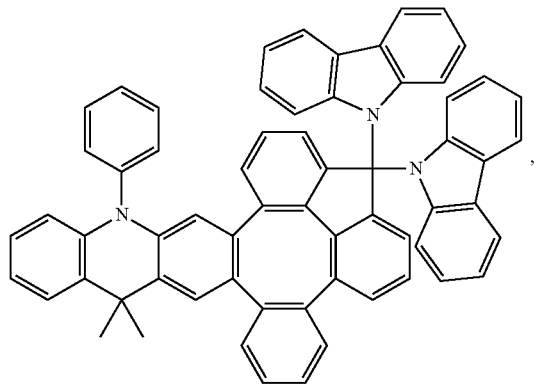

-continued
Compound D74
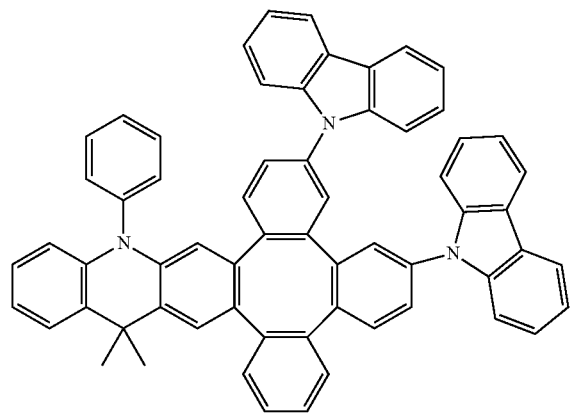
Compound D75
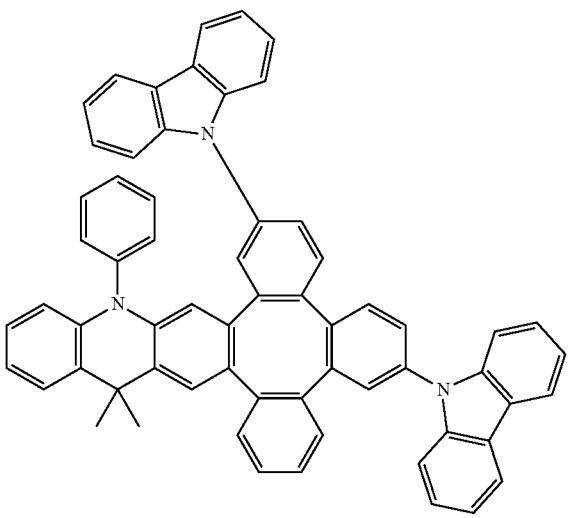
Compound D76
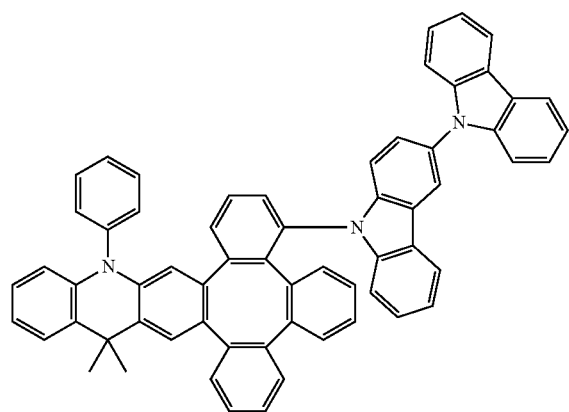
Compound E67
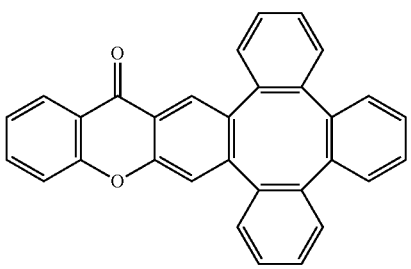
Compound E68
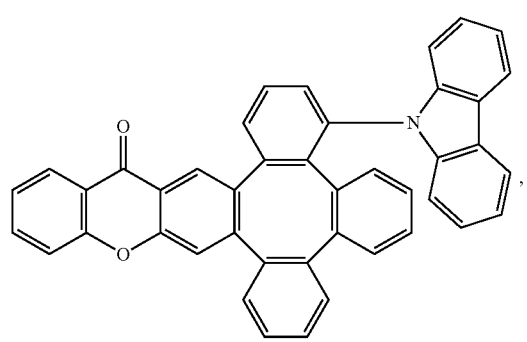
Compound E69
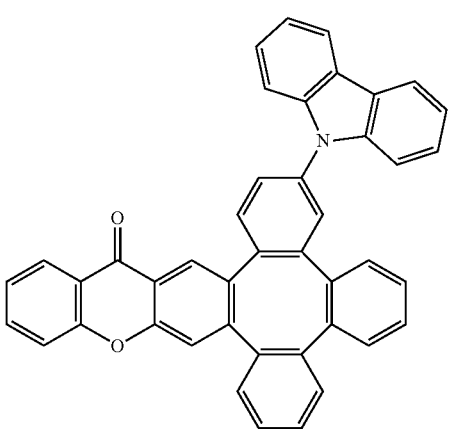

-continued
Compound E70
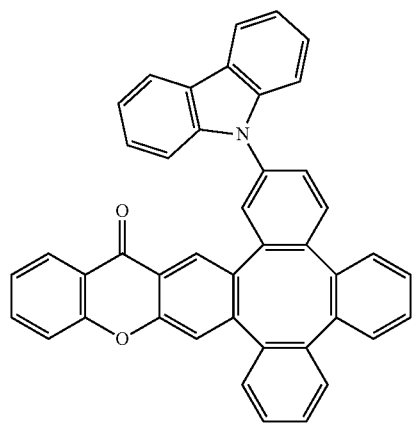
Compound E71
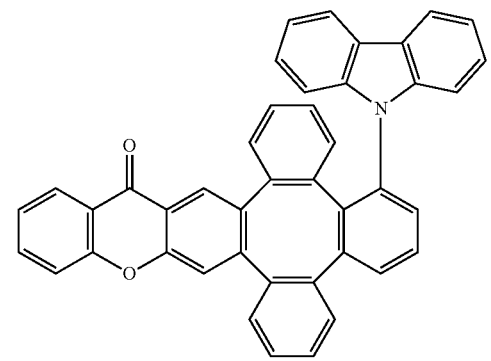
Compound E72
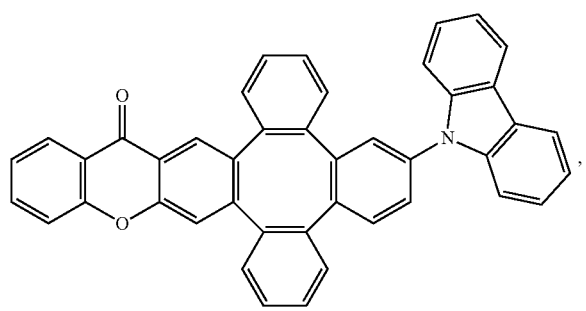
Compound E73
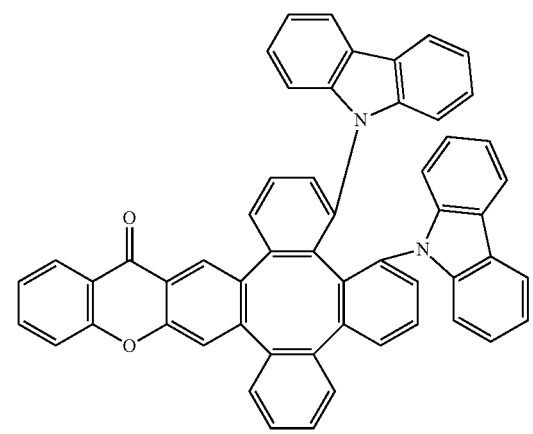
Compound E74
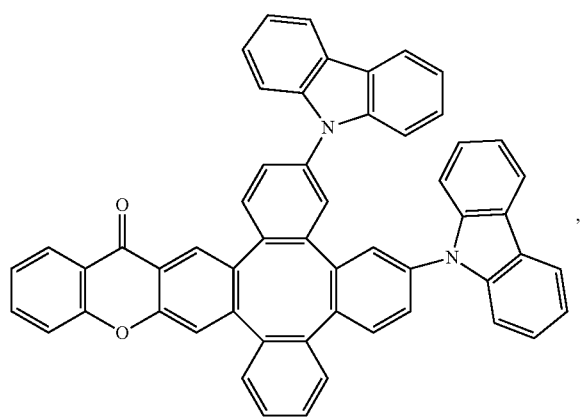
Compound E75
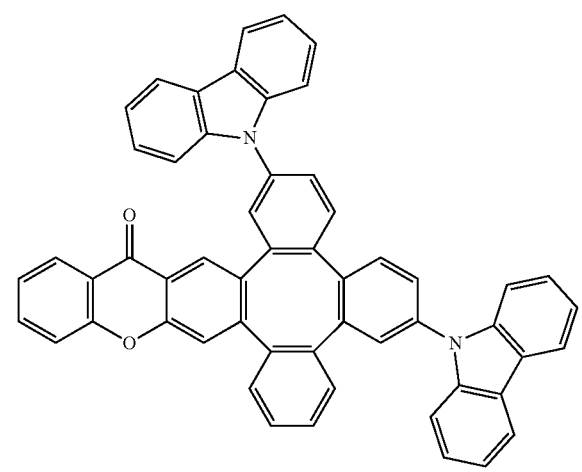

-continued
Compound E76
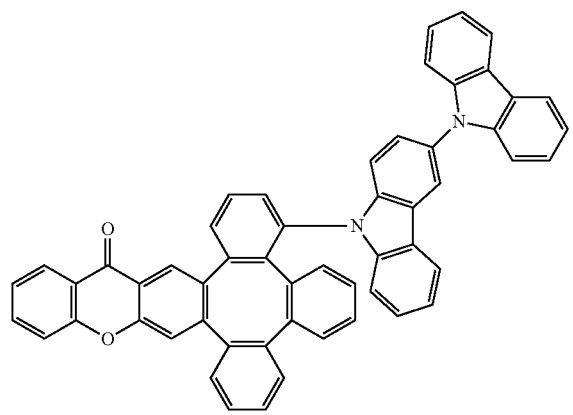
Compound F67
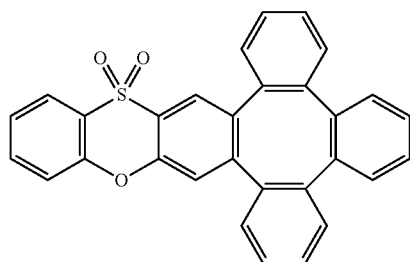
Compound F68
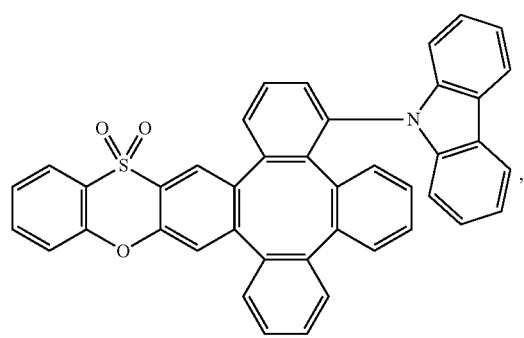
Compound F69
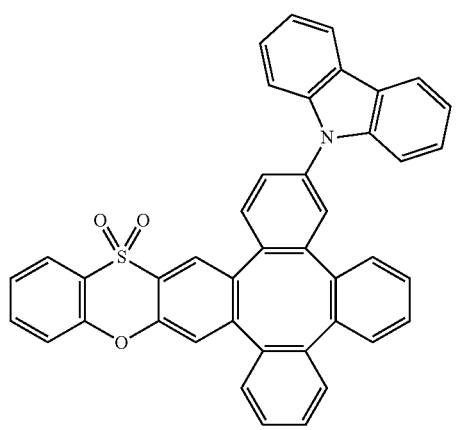
Compound F70
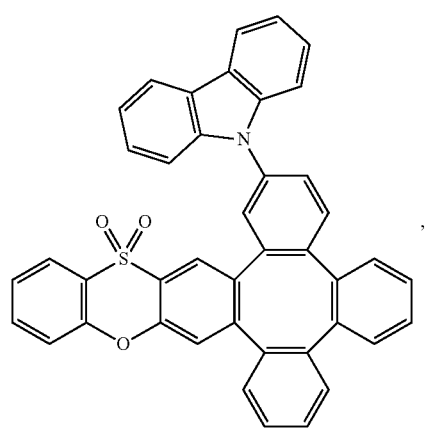
Compound F71
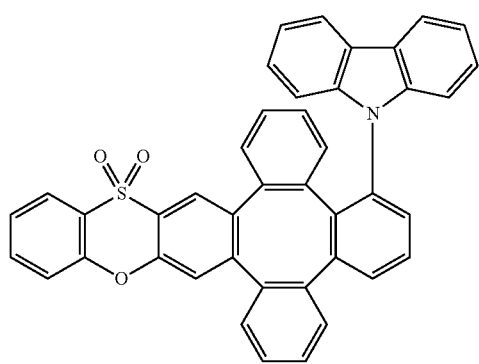

-continued
Compound F72
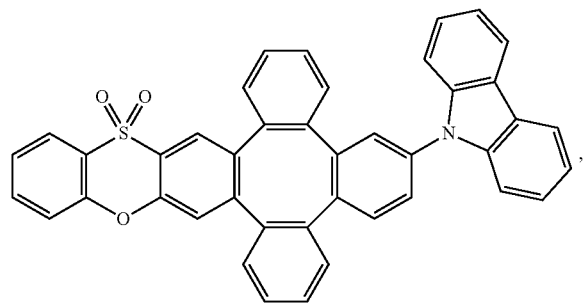
Compound F73
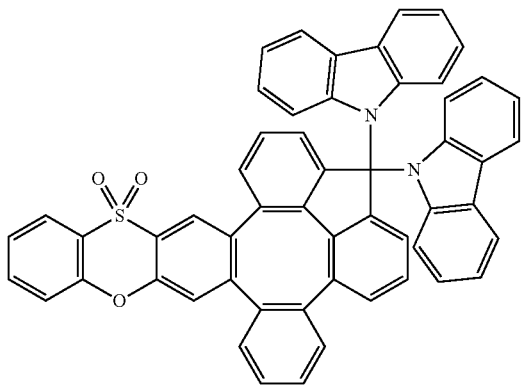
Compound F74
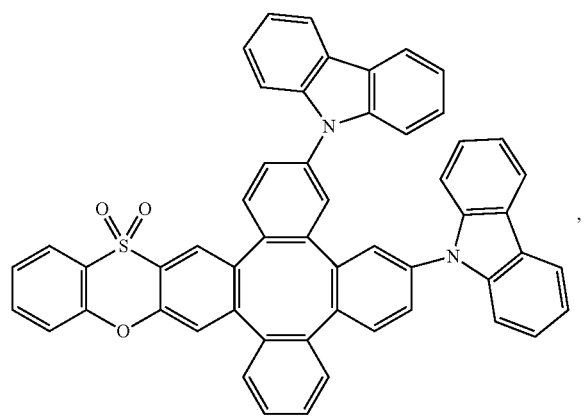
Compound F75
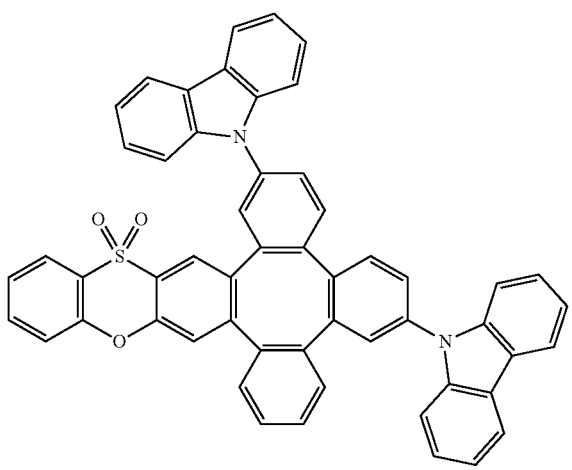
Compound F76
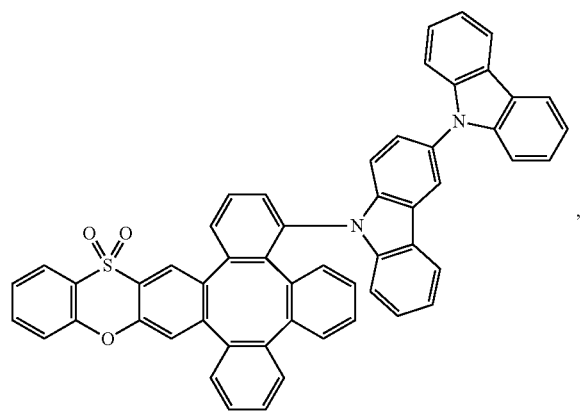
Compound B67
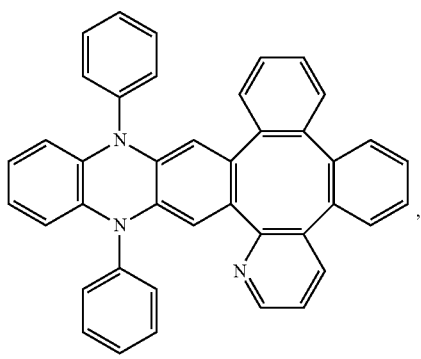

-continued
Compound B68
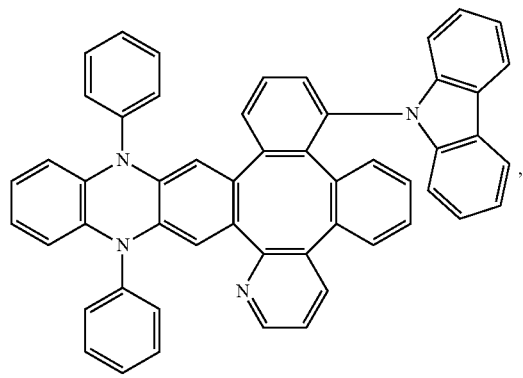
Compound B69
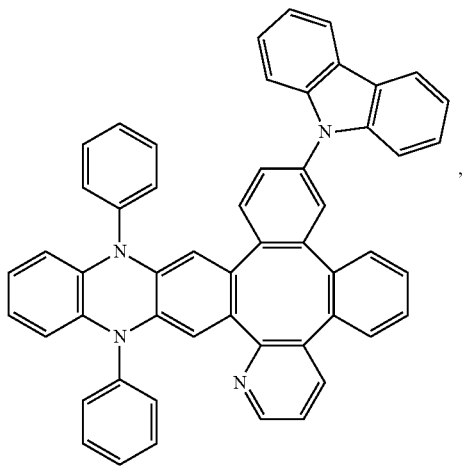
Compound B70
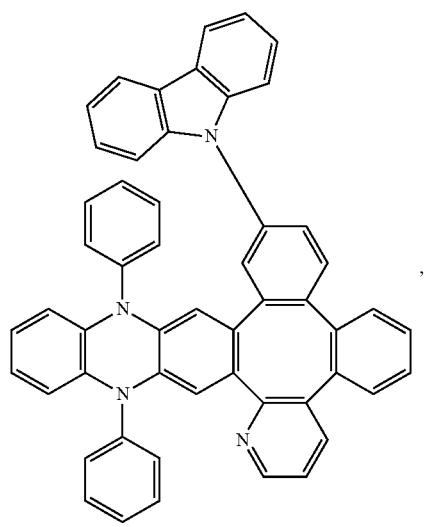
Compound B71
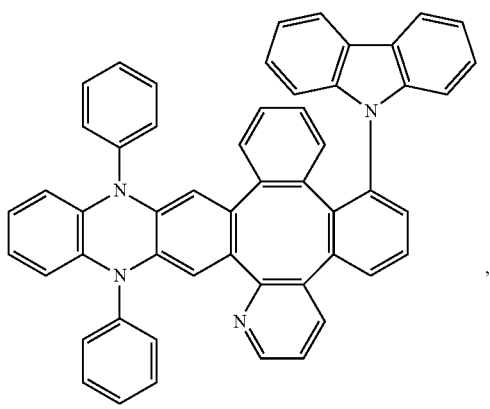
Compound B72
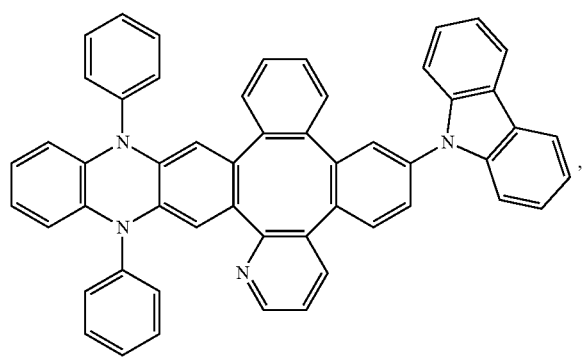
Compound B73
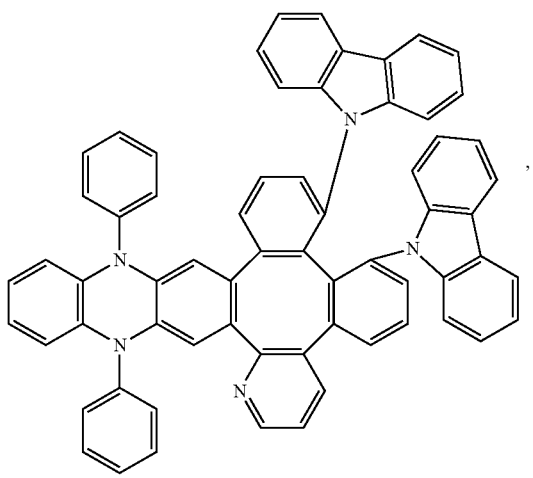

Compound B74
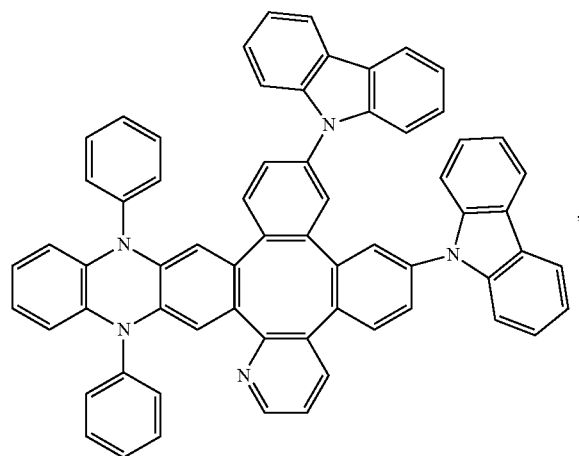
Compound B75
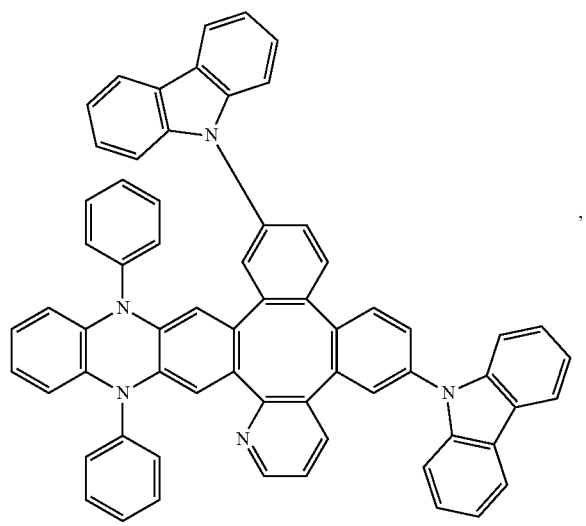
Compound B76
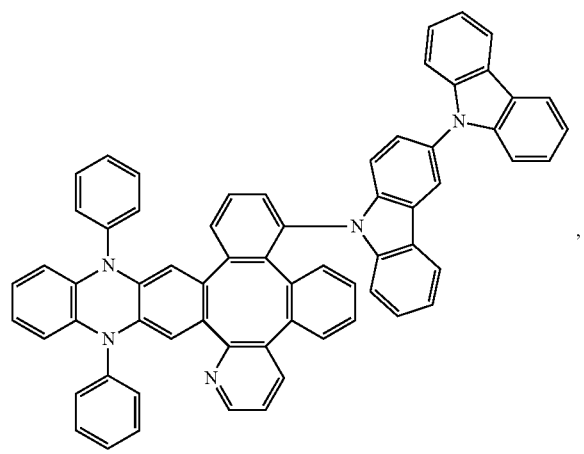
Compound B77
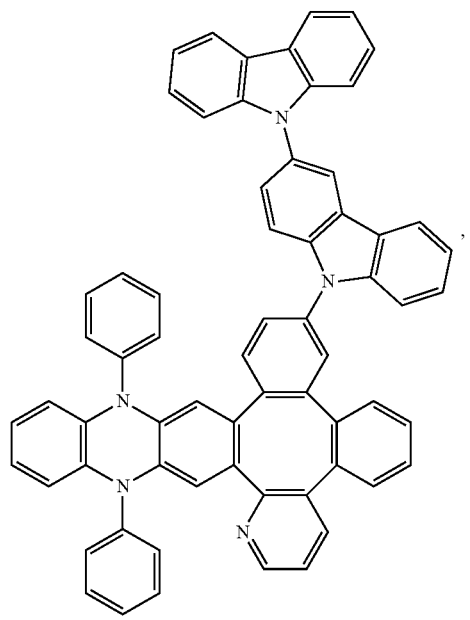

-continued
Compound B78
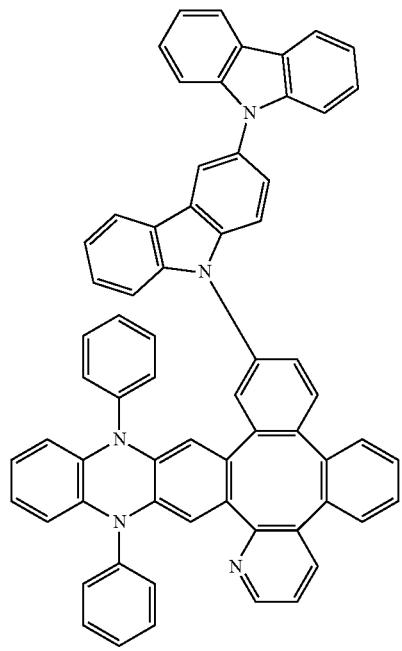
Compound B79
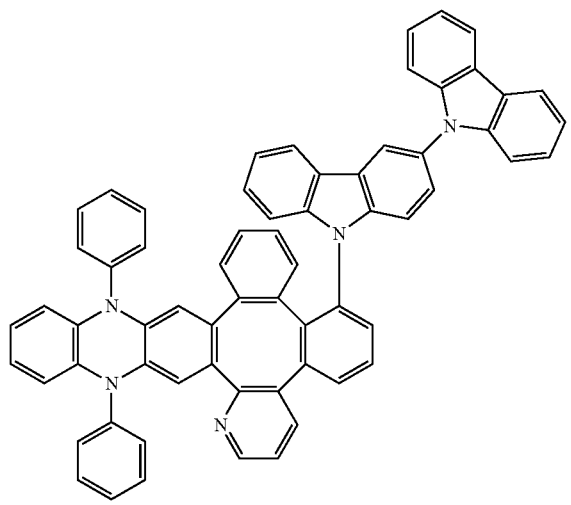
Compound B80
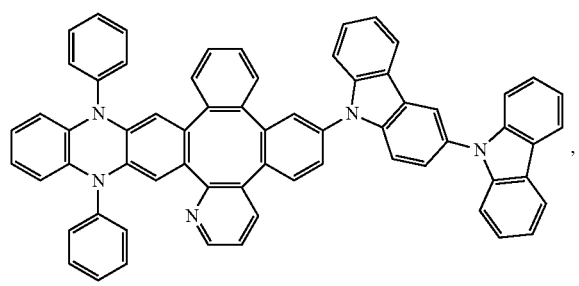
Compound B81
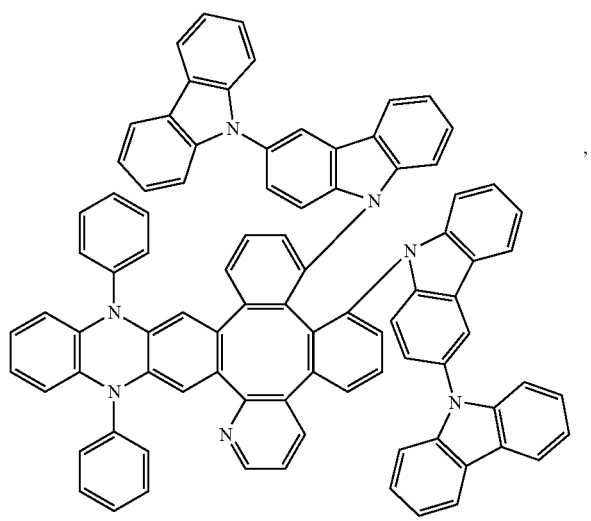

-continued
Compound B82
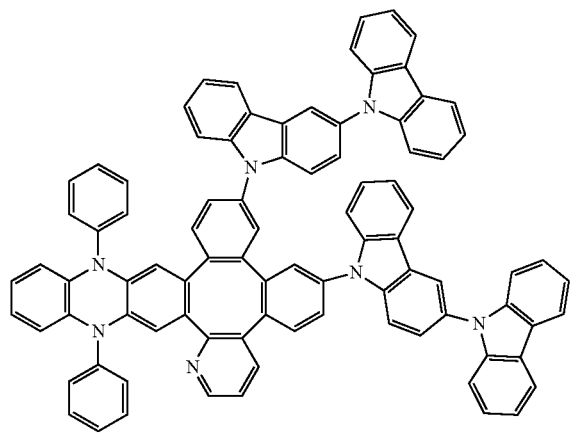
Compound B83
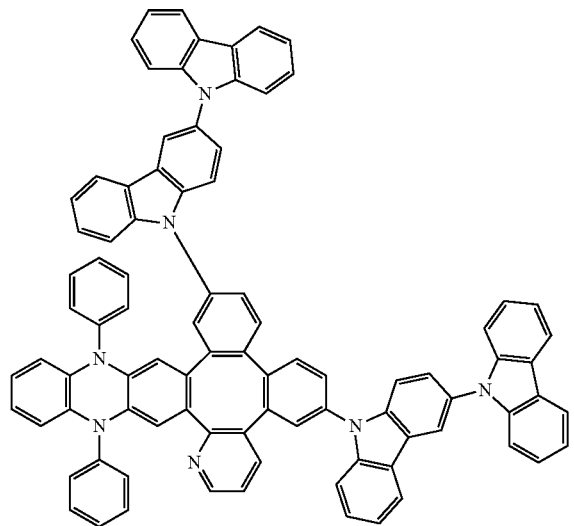
Compound B84
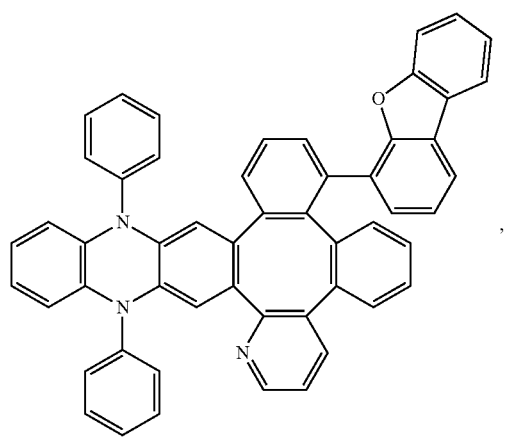
Compound B85
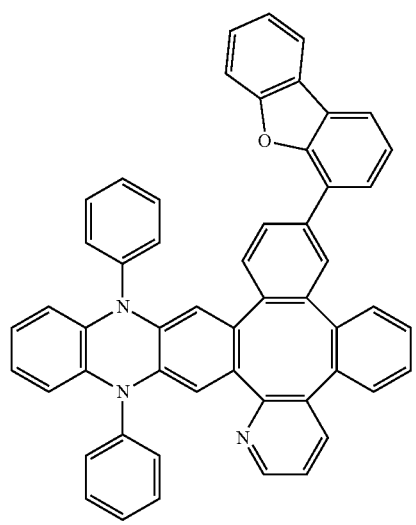
Compound B86
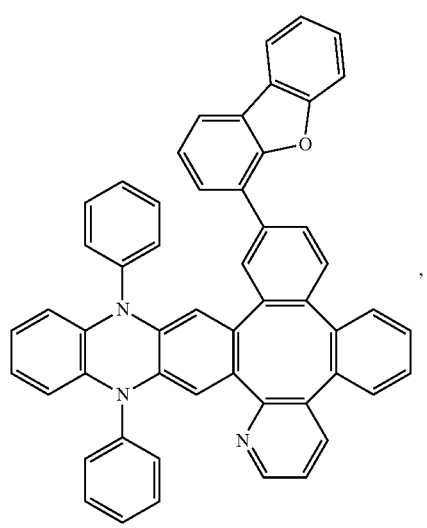
Compound B87
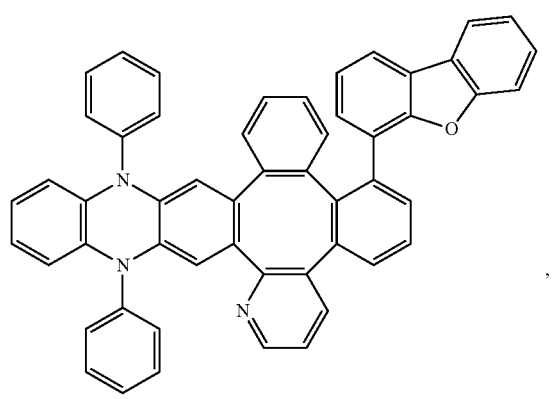

-continued
Compound B88
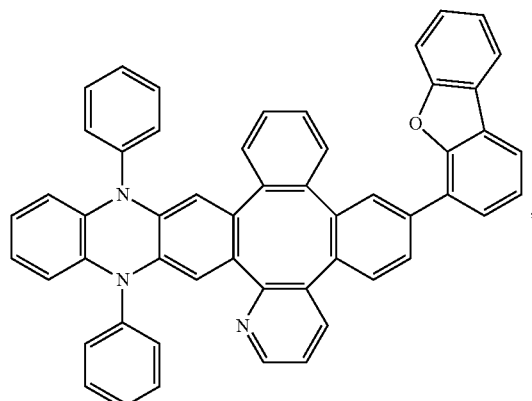
Compound B89
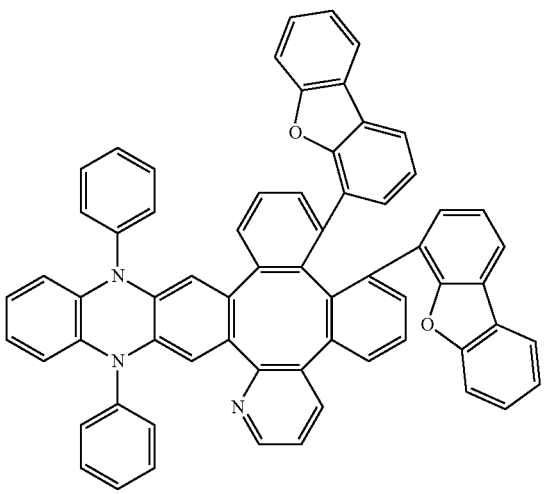
Compound B90
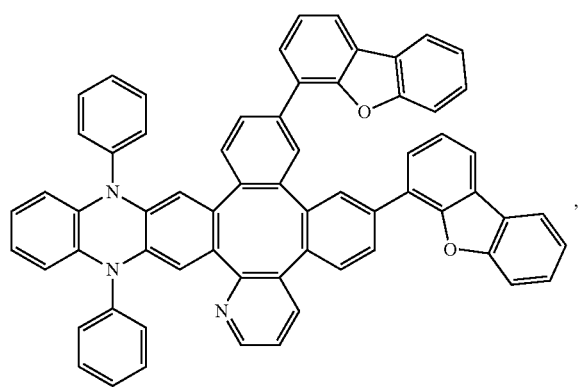
Compound B91
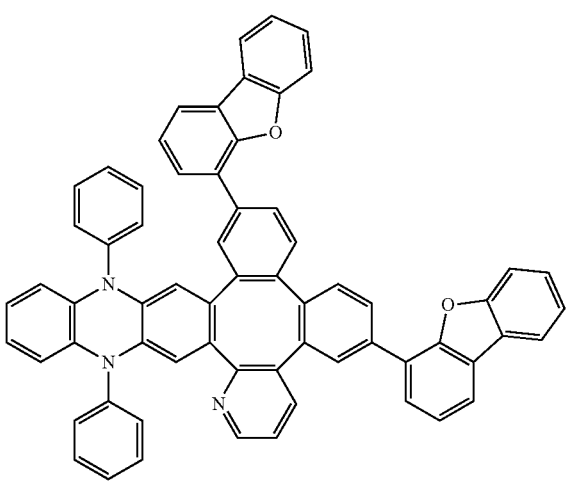
Compound B92
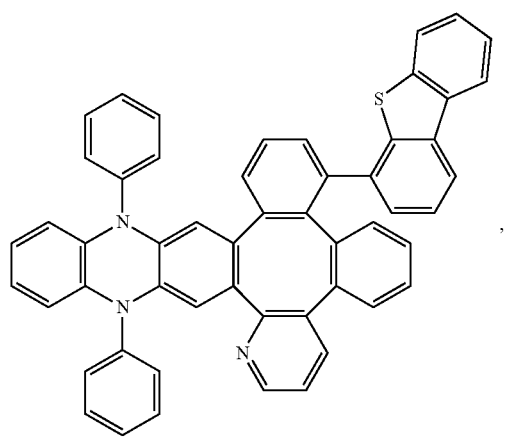
Compound B93
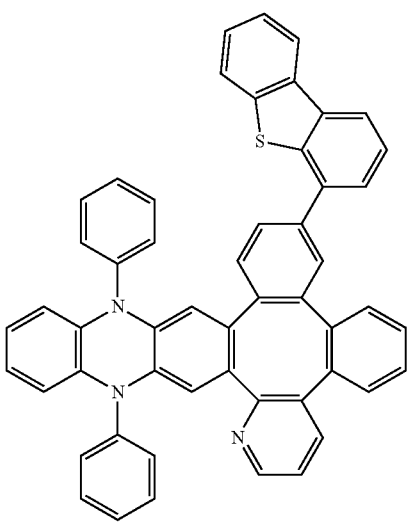

-continued
Compound B94
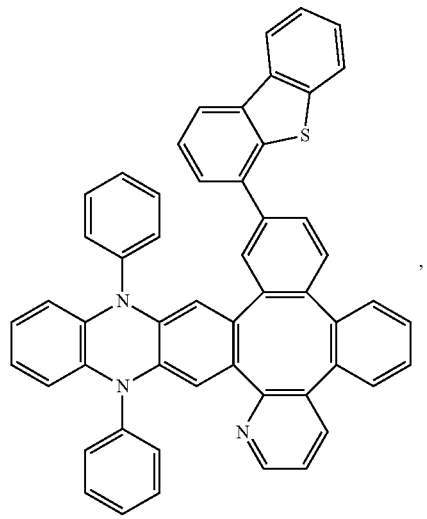
Compound B95
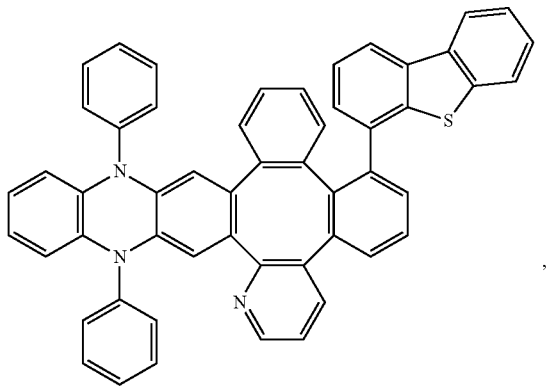
Compound B96
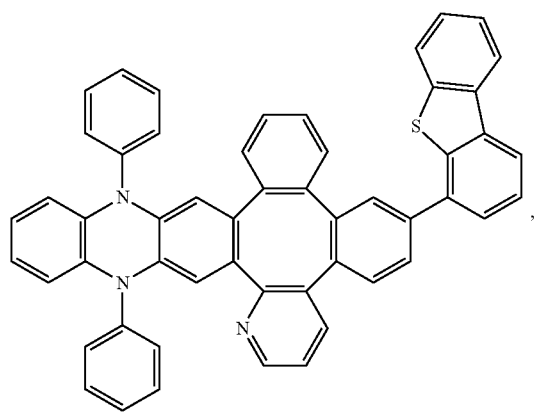
Compound CC67
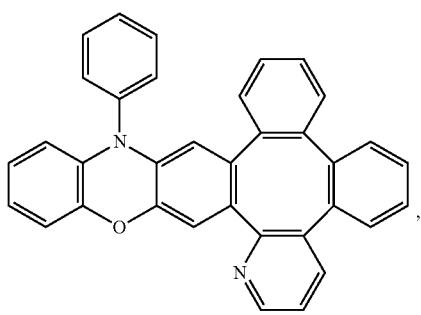
Compound CC68
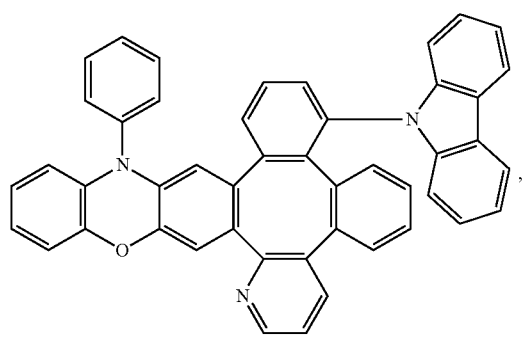
Compound CC69
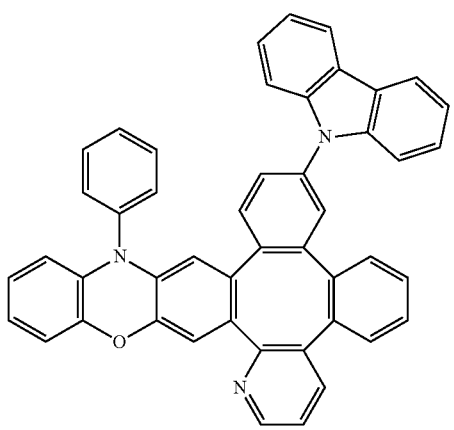

Compound CC70
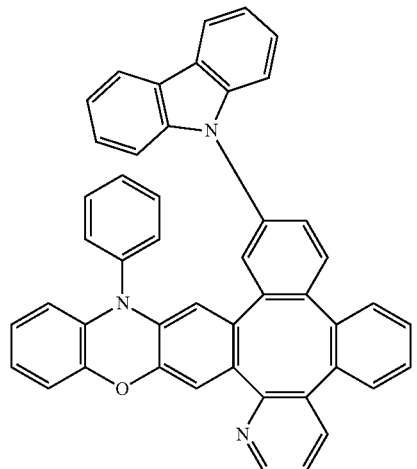
Compound CC71
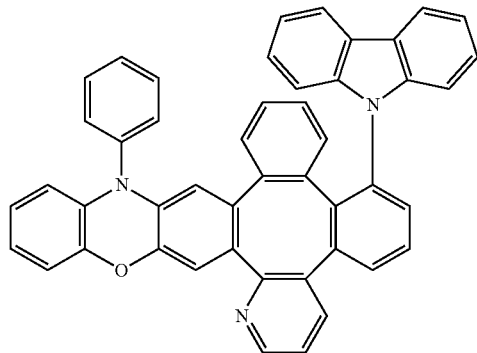
Compound CC72
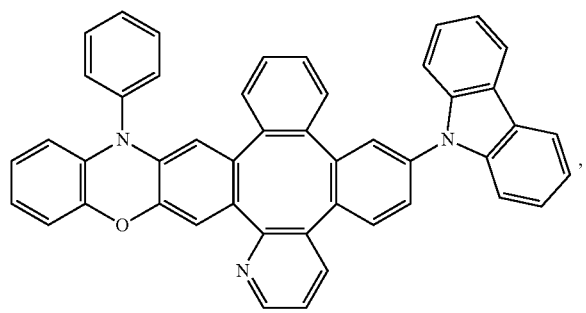
Compound CC73
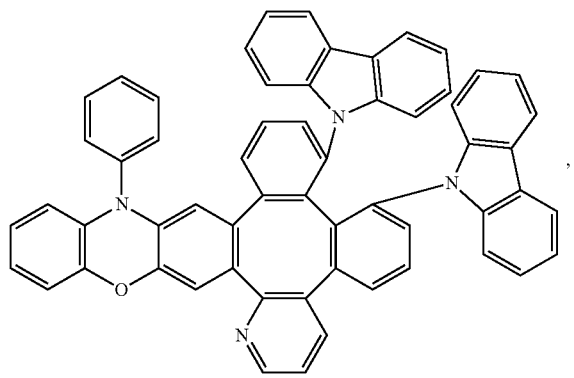
Compound CC74
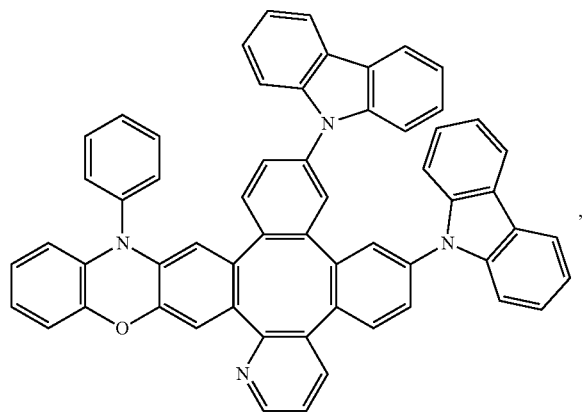
Compound CC75
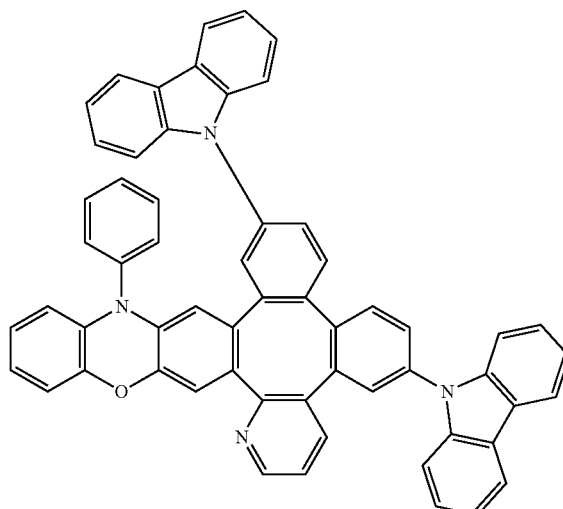

Compound CC76
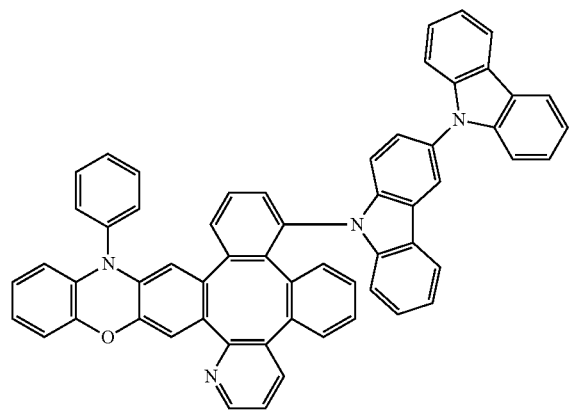
Compound DD67
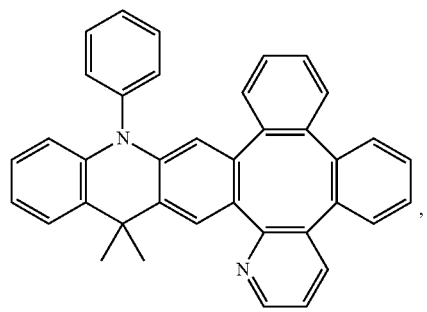
Compound DD68
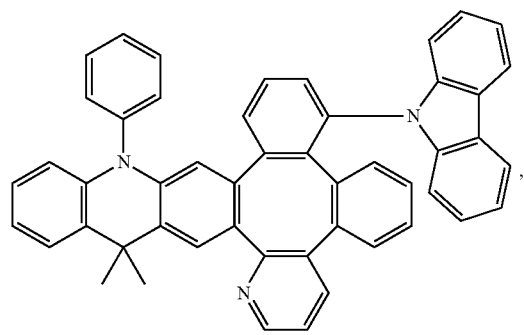
Compound DD69
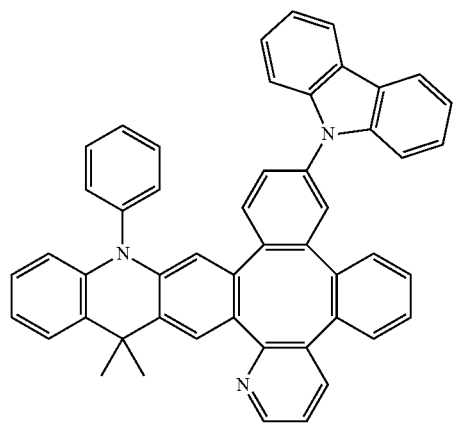
Compound DD70
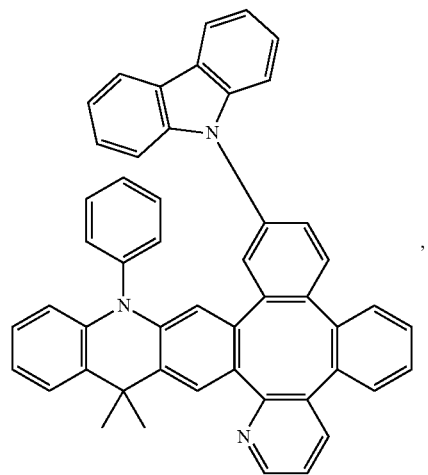
Compound DD71
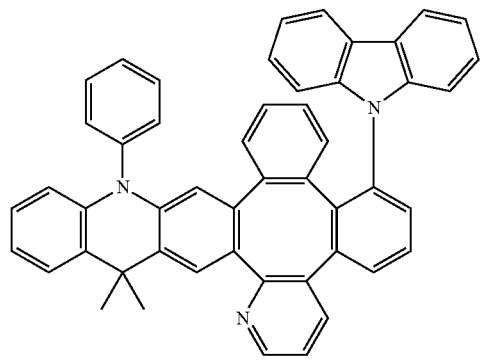

-continued
Compound DD72
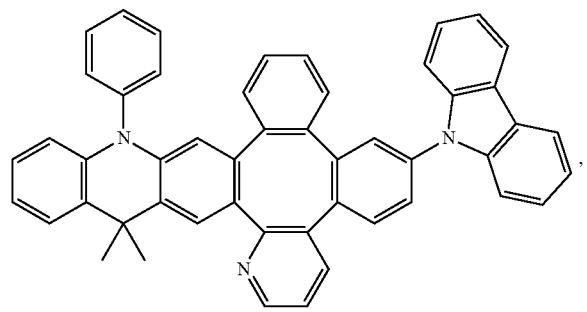
Compound DD73
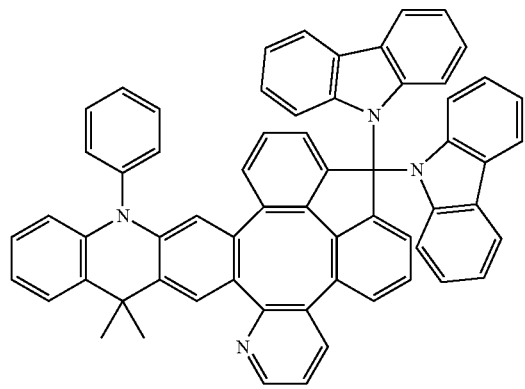
Compound DD74
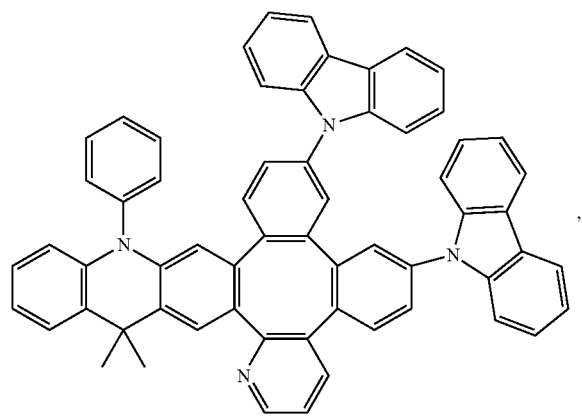
Compound DD75
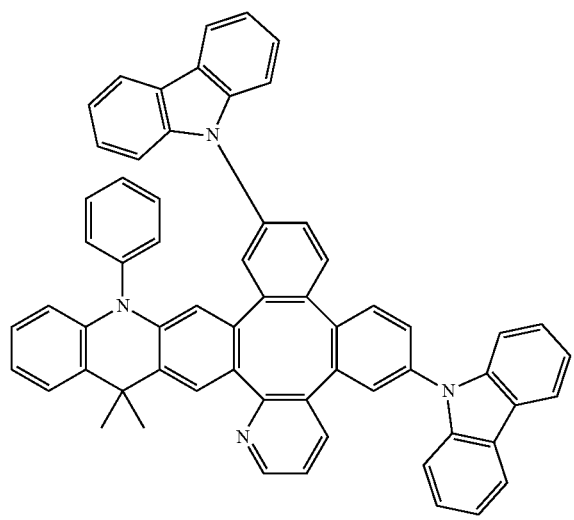
Compound DD76
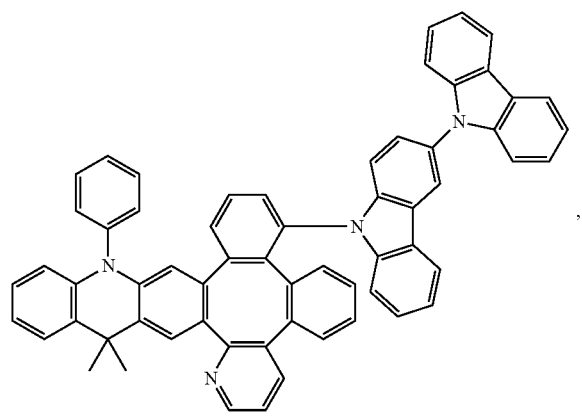
Compound EE67
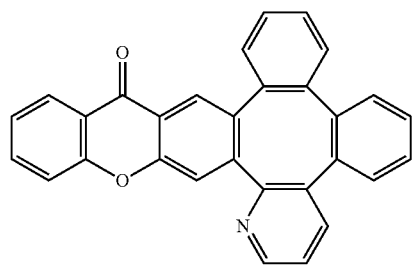

-continued
Compound EE68
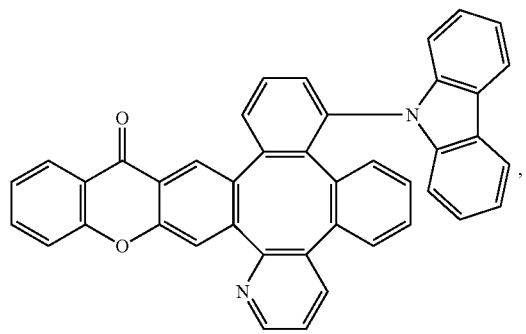
Compound EE69
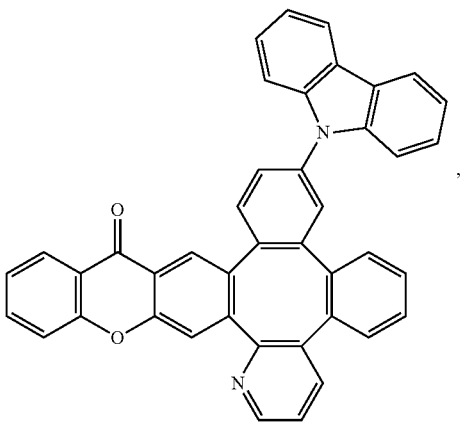
Compound EE70
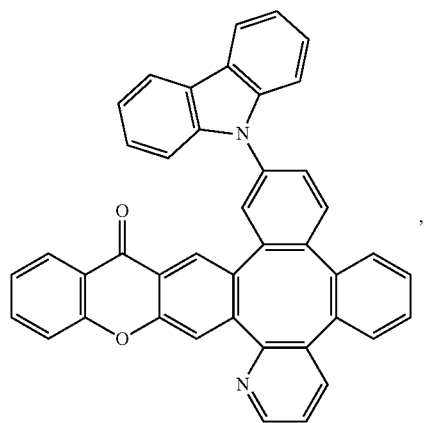
Compound EE71
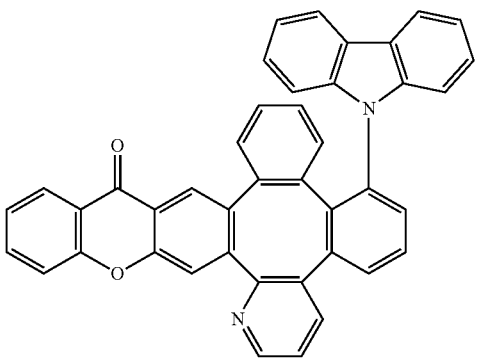
Compound EE72
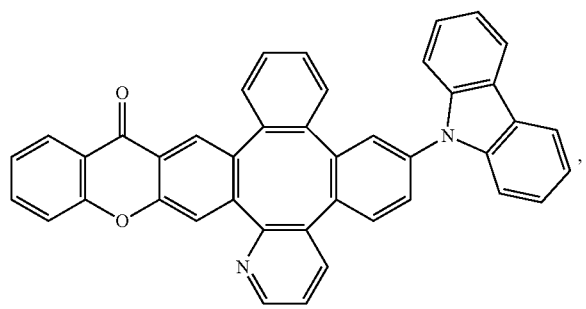
Compound EE73
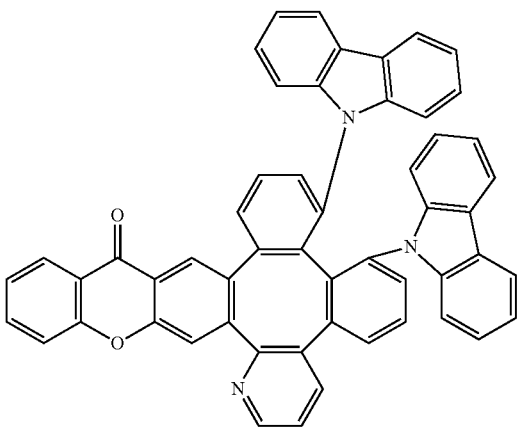

-continued
Compound EE74
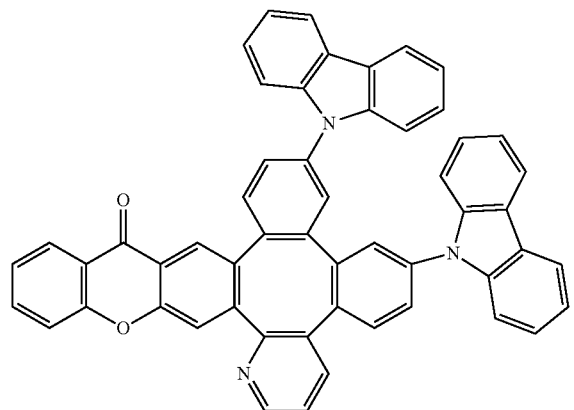
Compound EE75
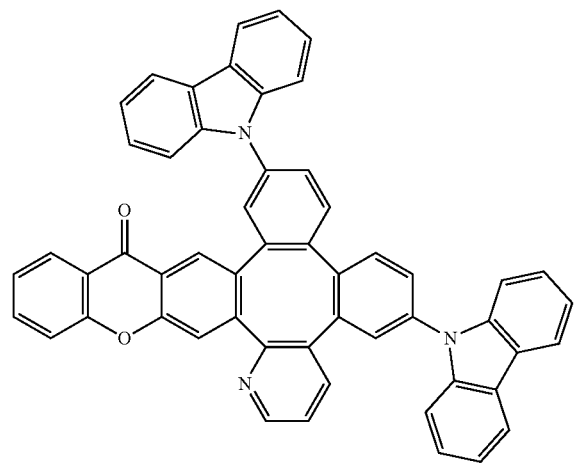
Compound EE76
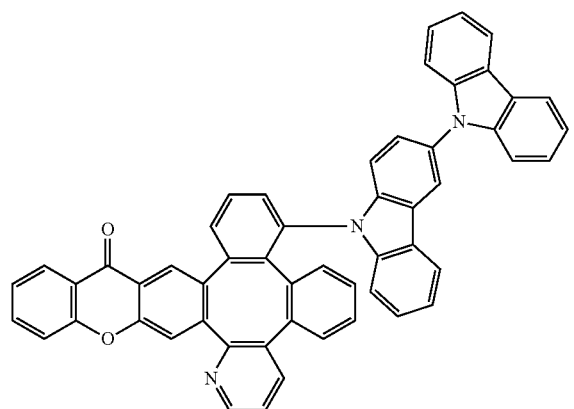
Compound FF67
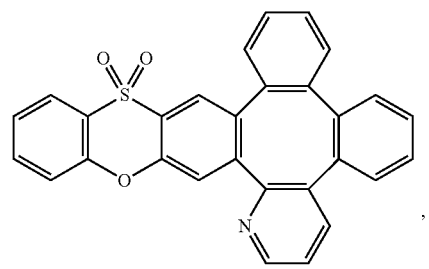
Compound FF68
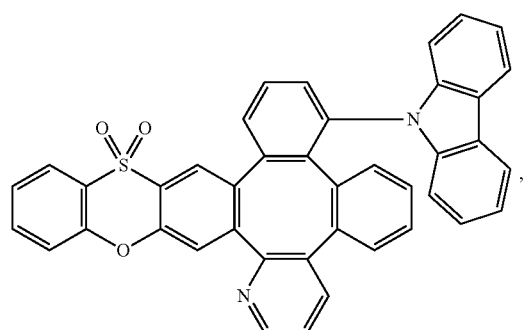
Compound FF69
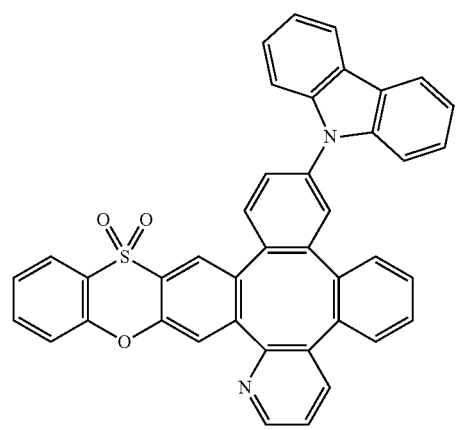

Compound FF70
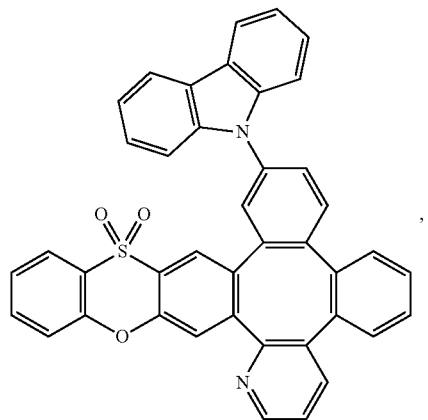
Compound FF71
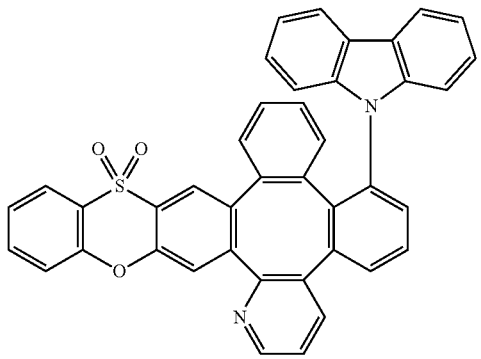
,
Compound FF72
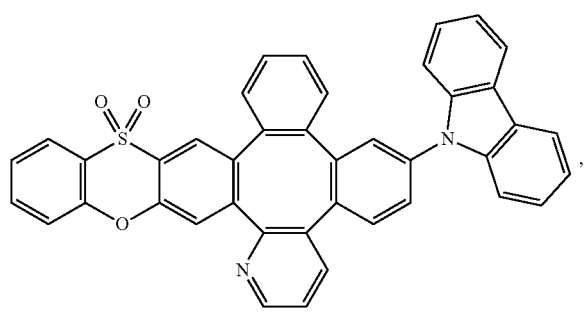
Compound FF73
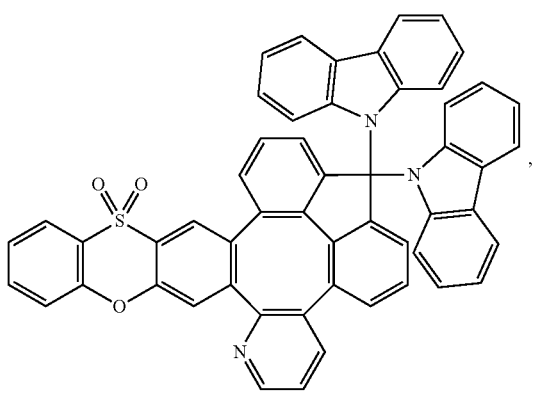
,
Compound FF74
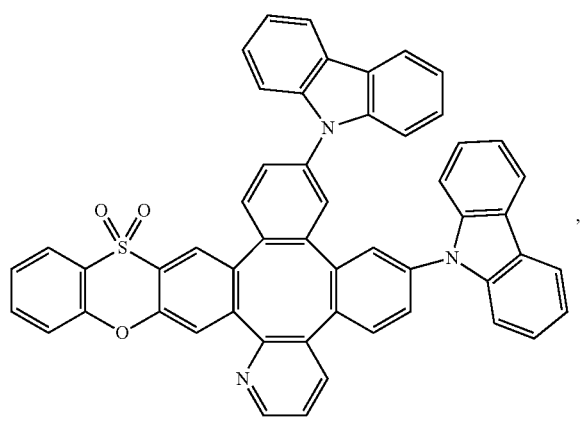
Compound FF75
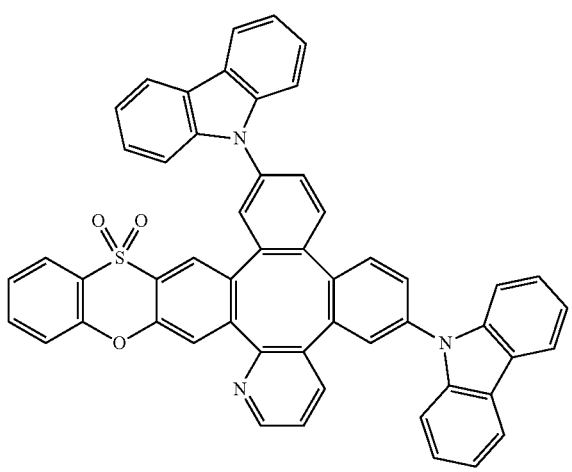
, -continued
Compound FF76
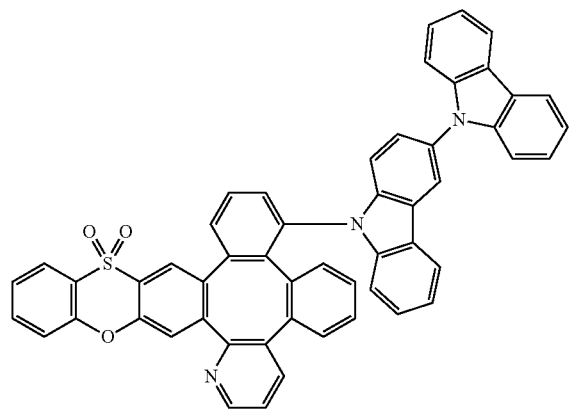
Compound A97
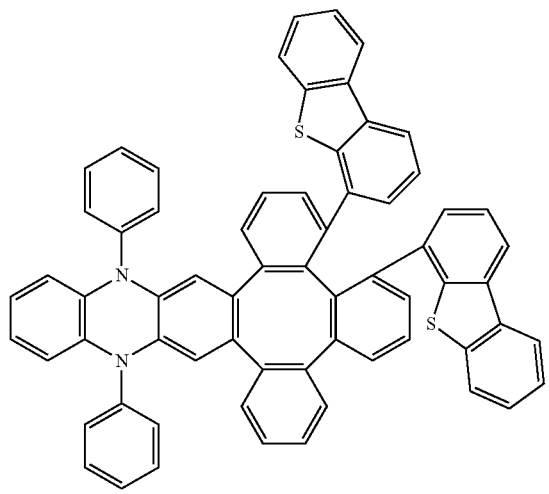
Compound A98
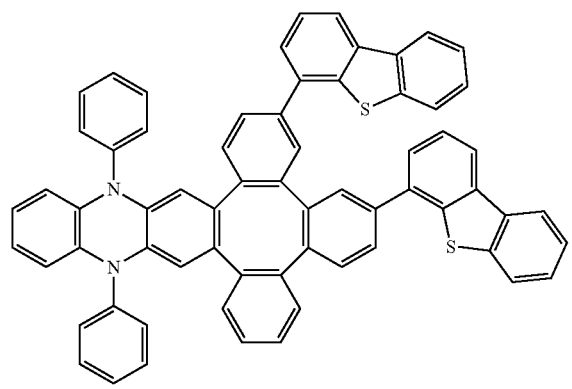
Compound A99
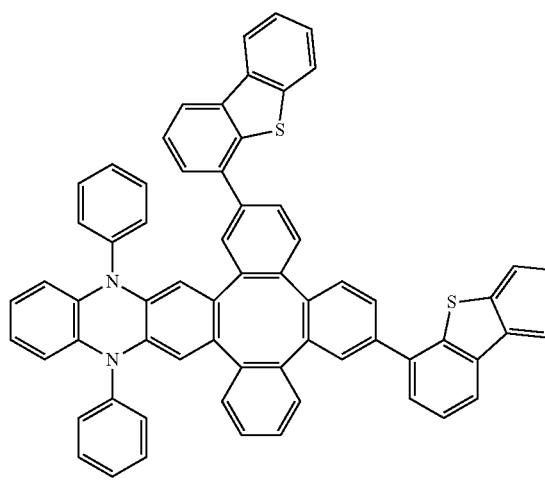
Compound A100
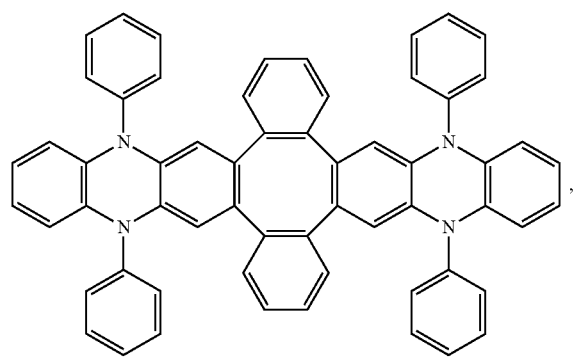
Compound A101
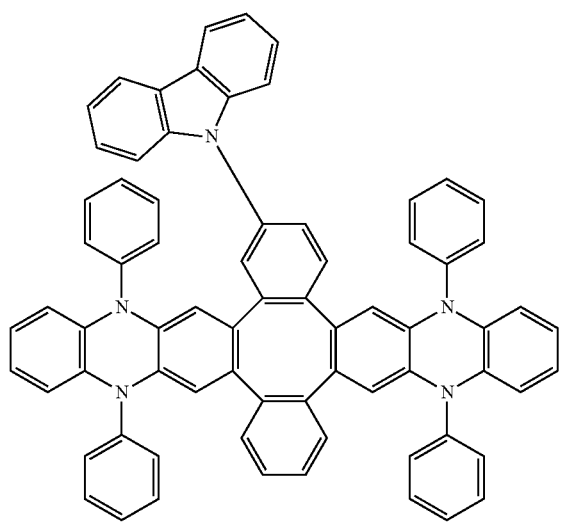

-continued
Compound A102
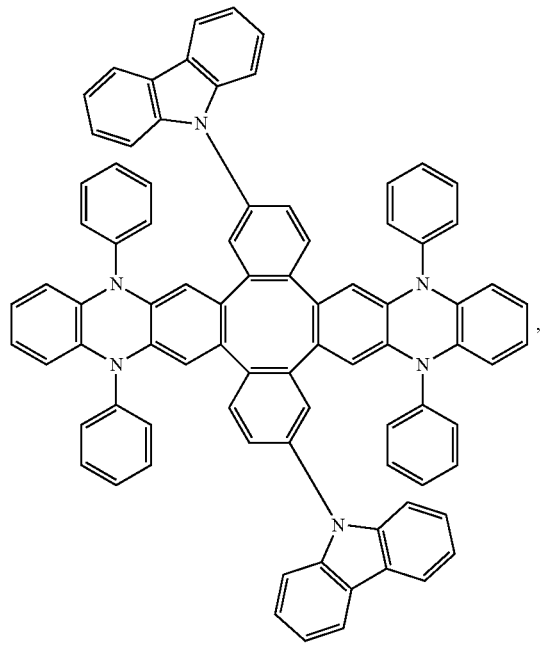
Compound A103
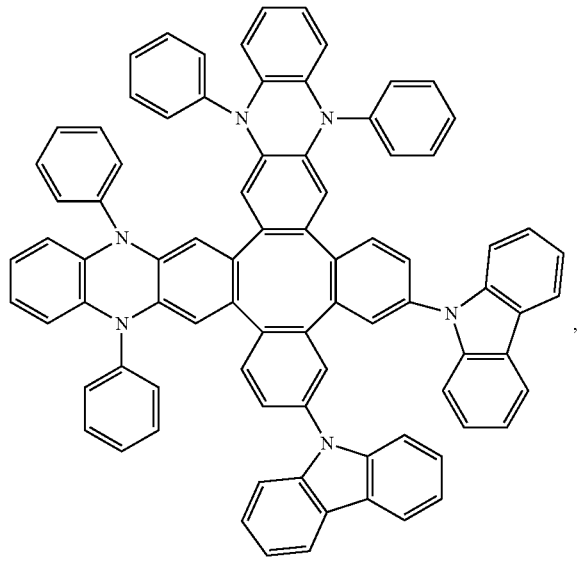
Compound A104
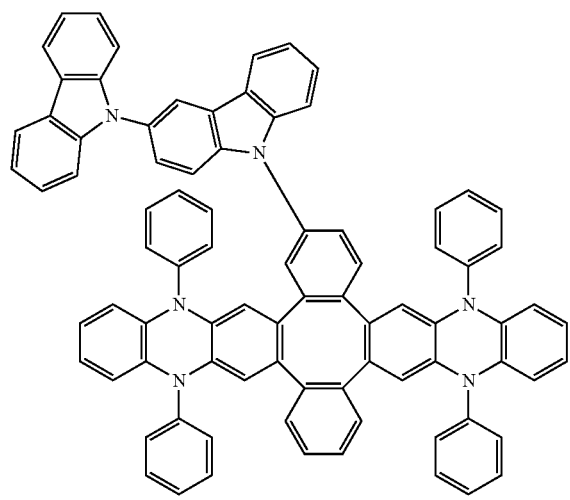
Compound A105
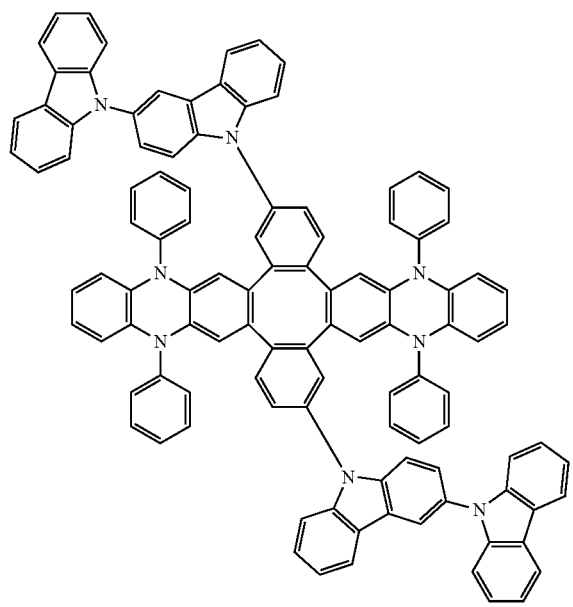

-continued
Compound A106
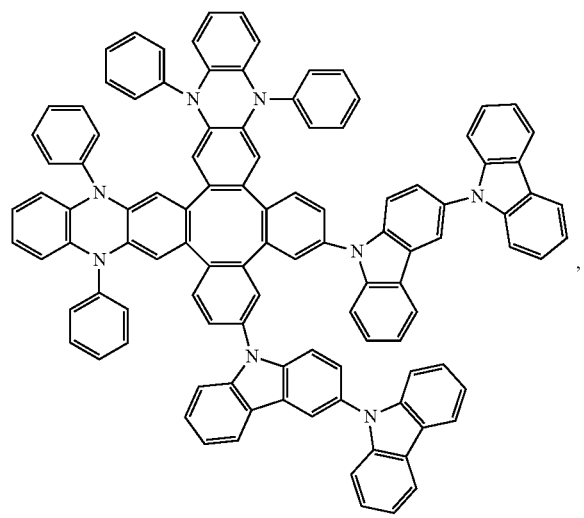
Compound A107
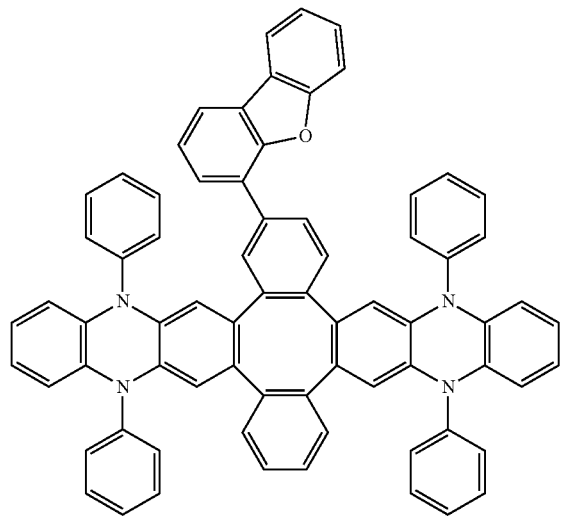
Compound A108
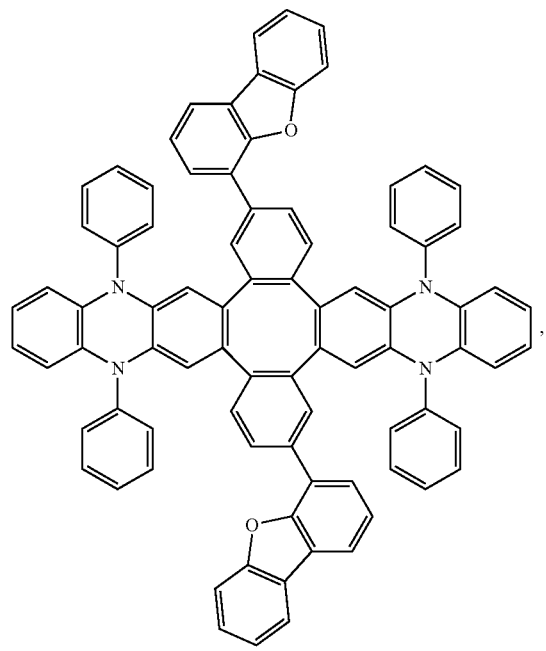
Compound A109
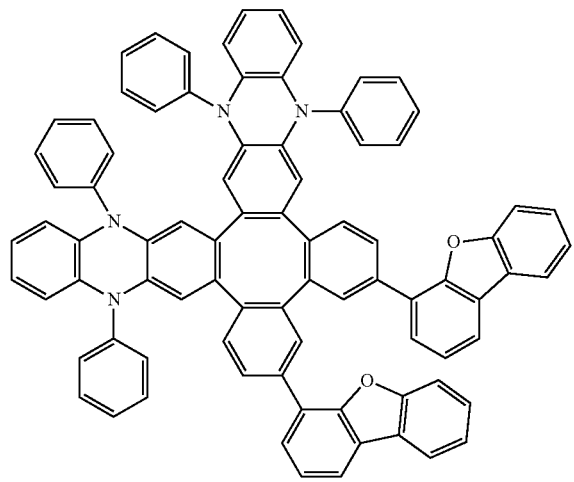

Compound A110
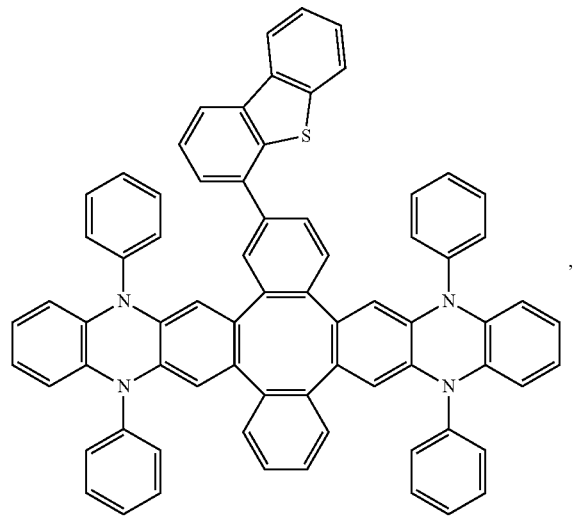
Compound A111
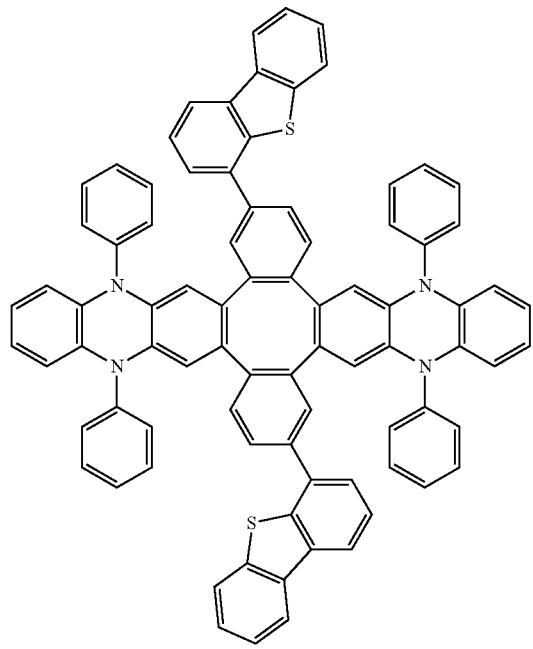
Compound A112
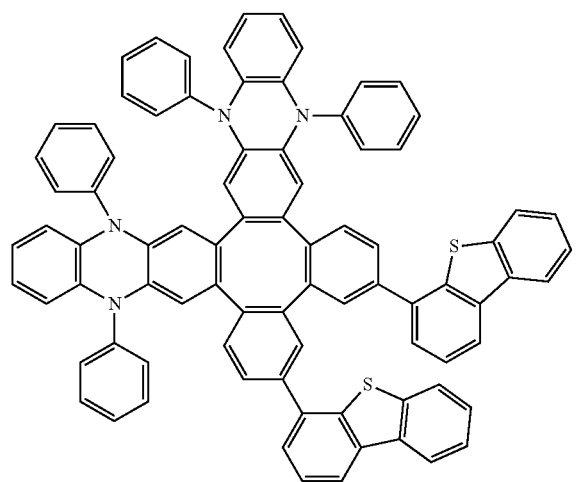
Compound C100
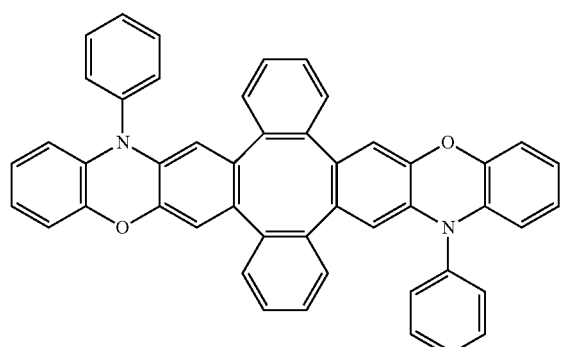

Compound C101
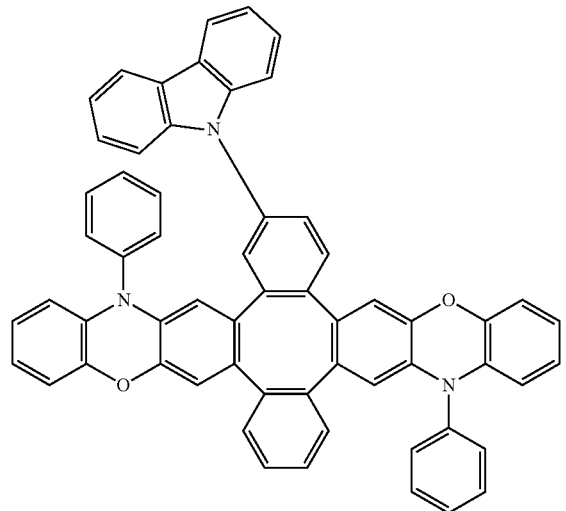
Compound C102
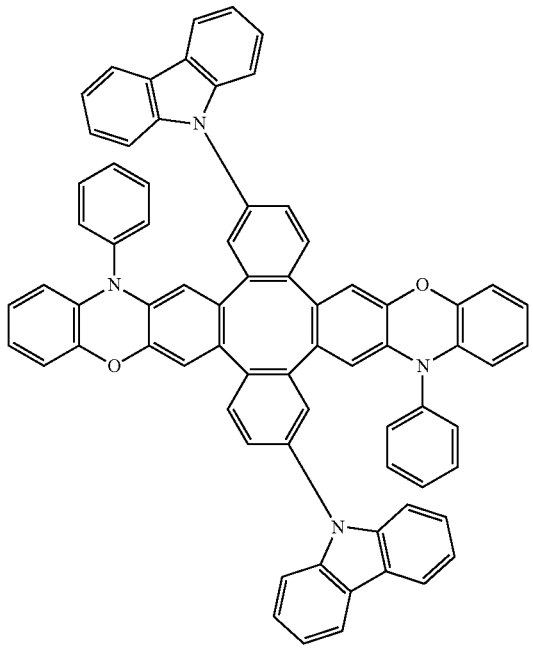
Compound C103
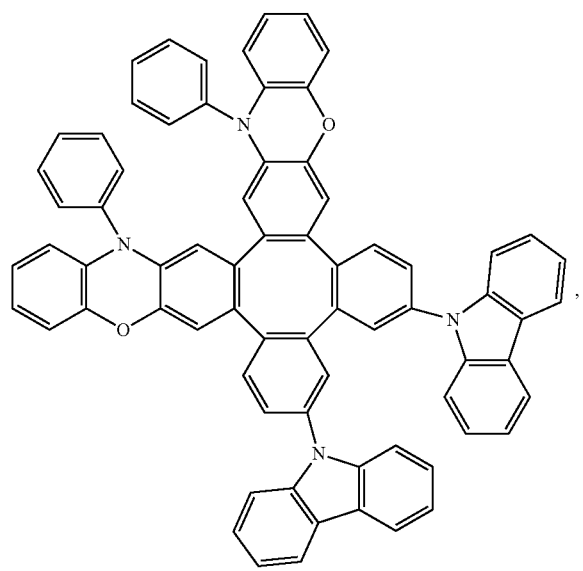
Compound C104
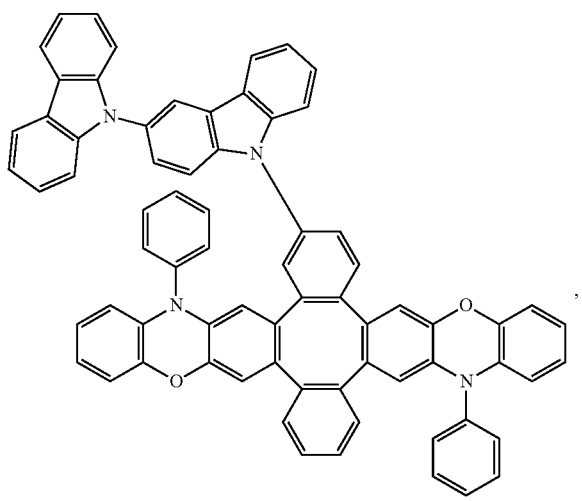

-continued
Compound C105
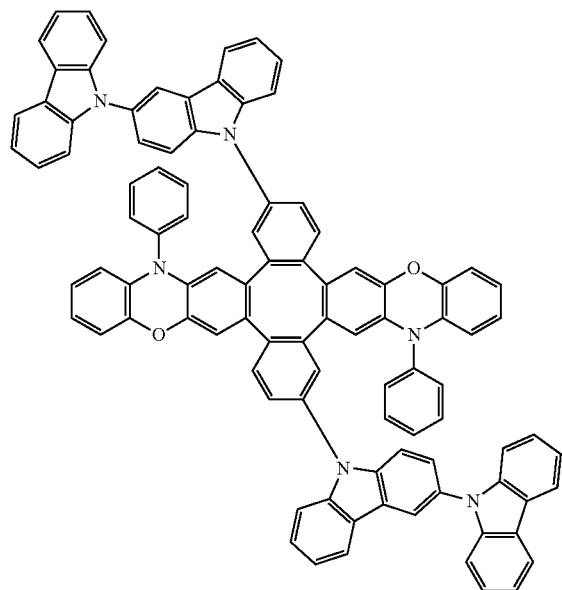
Compound C106
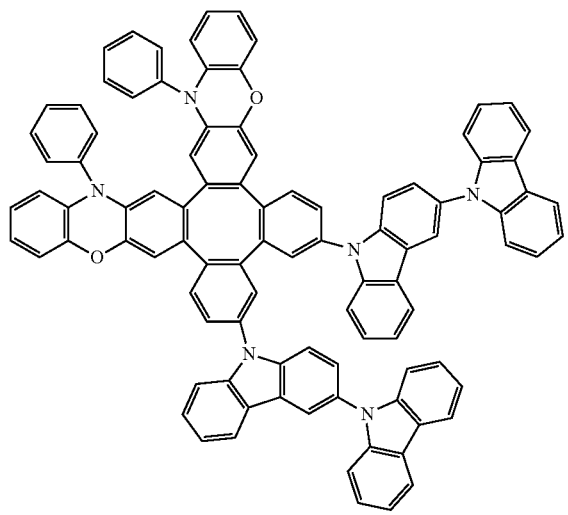
Compound C107
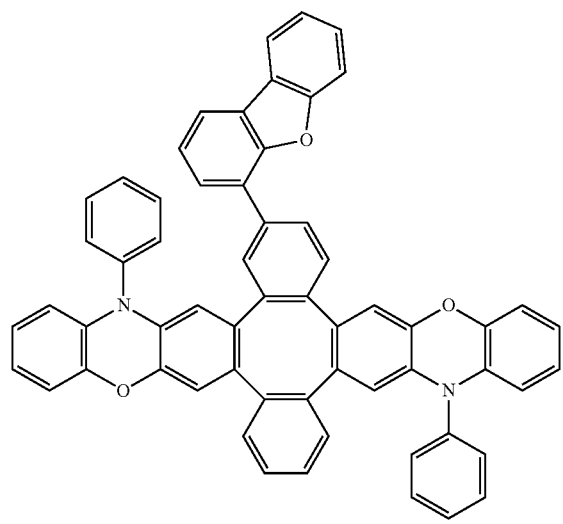
Compound C108
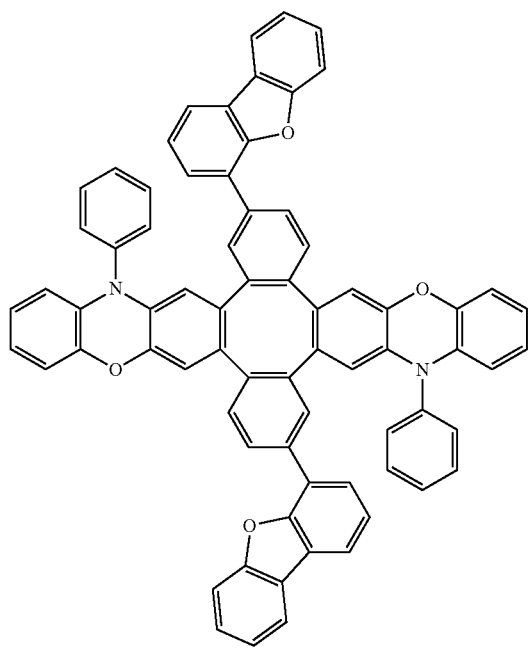

-continued
Compound D100
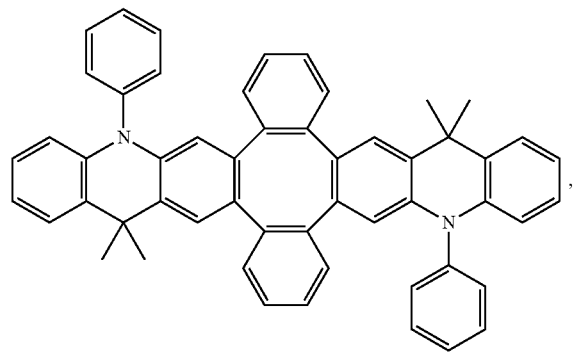
Compound D101
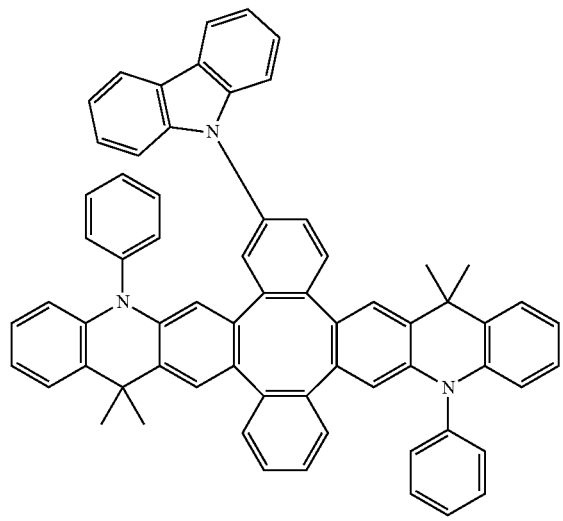
Compound D102
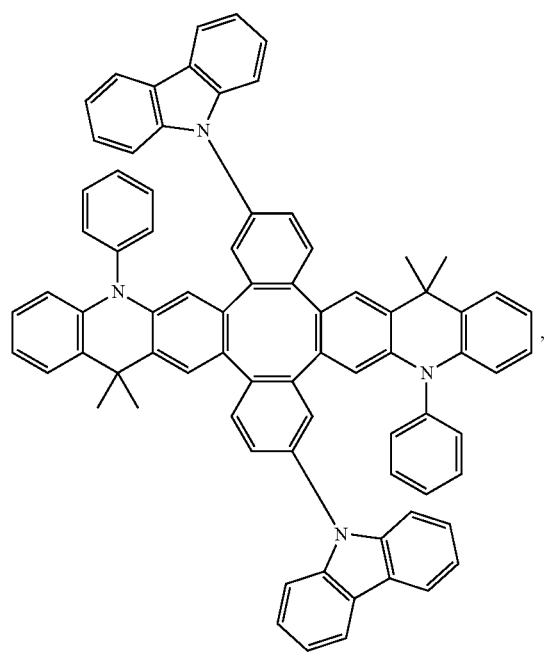
Compound D103
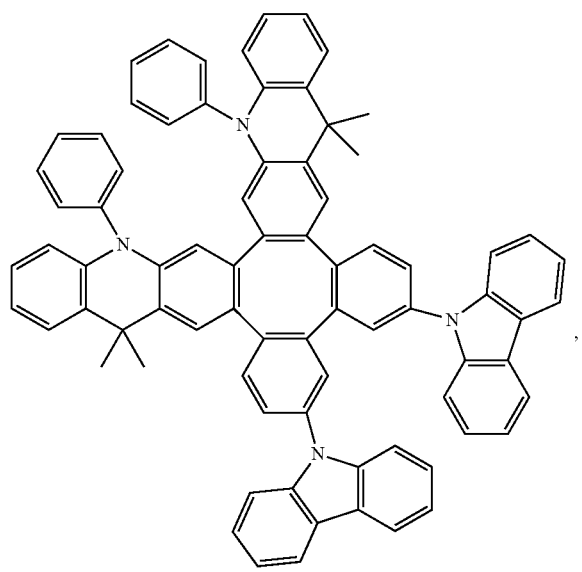

Compound D104
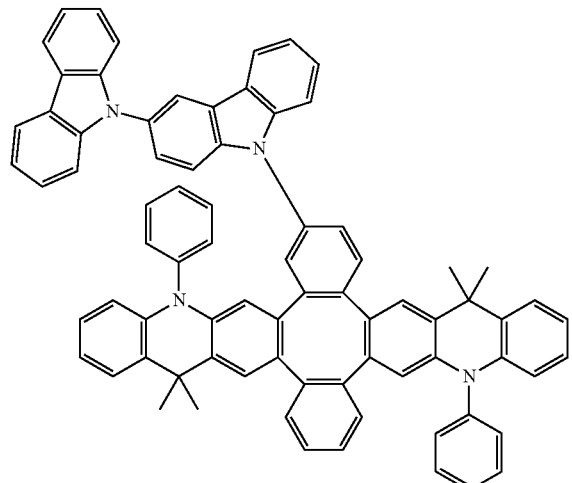
Compound D105
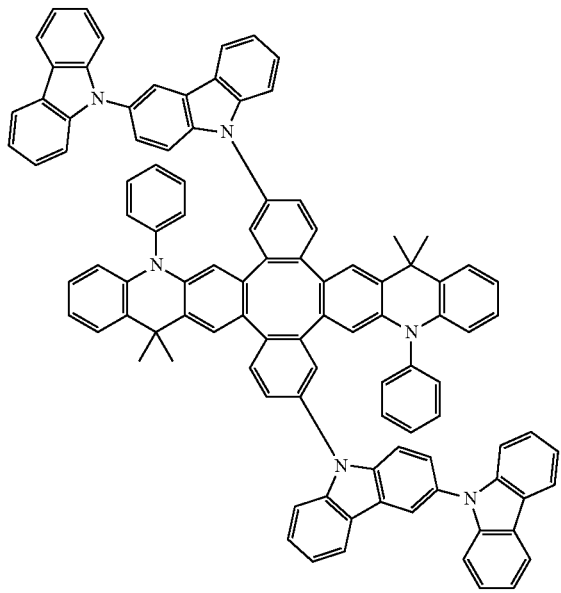
Compound D106
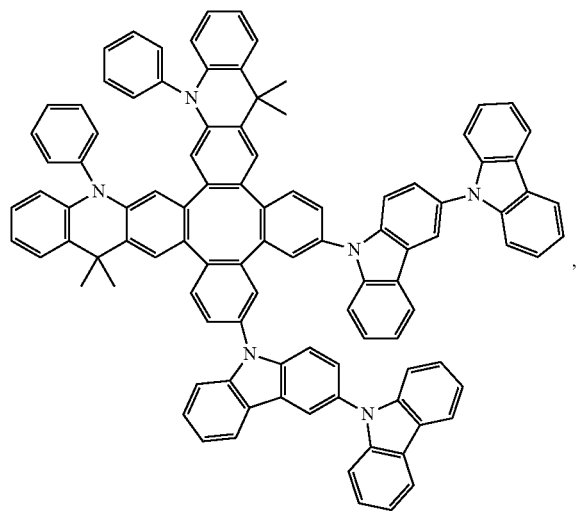
Compound D107
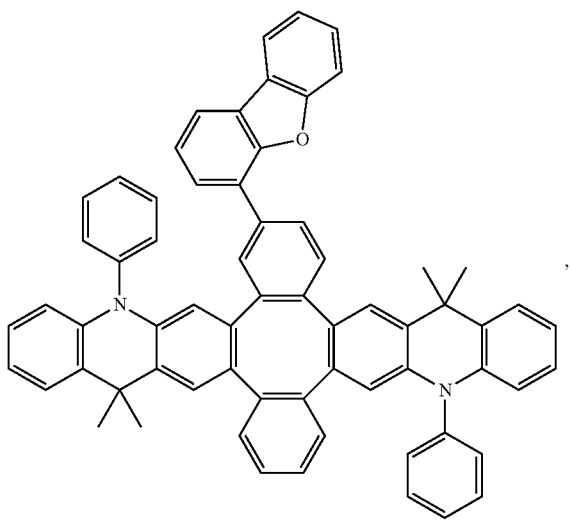

Compound D108
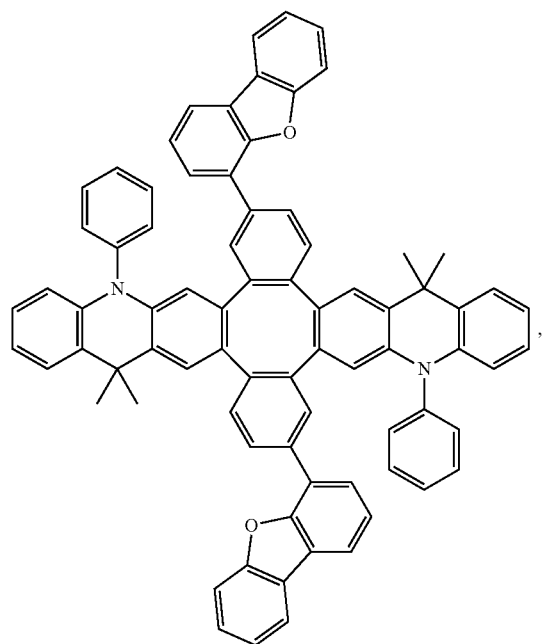
Compound E100
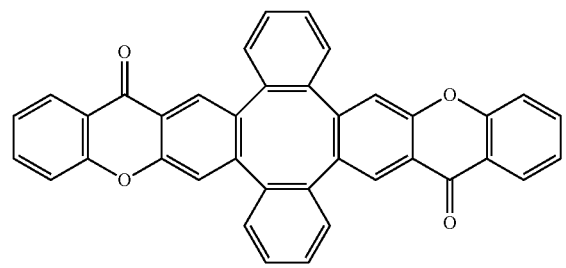
Compound E101
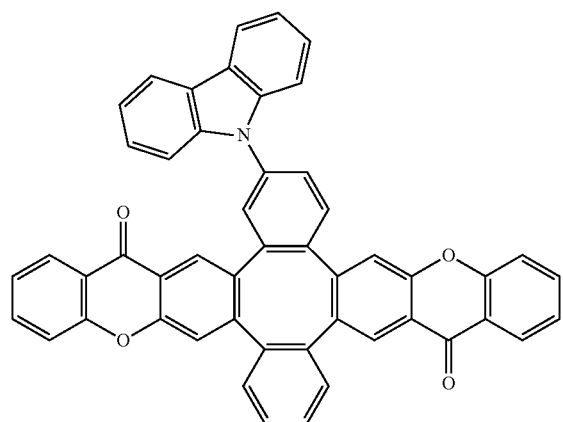
Compound E102
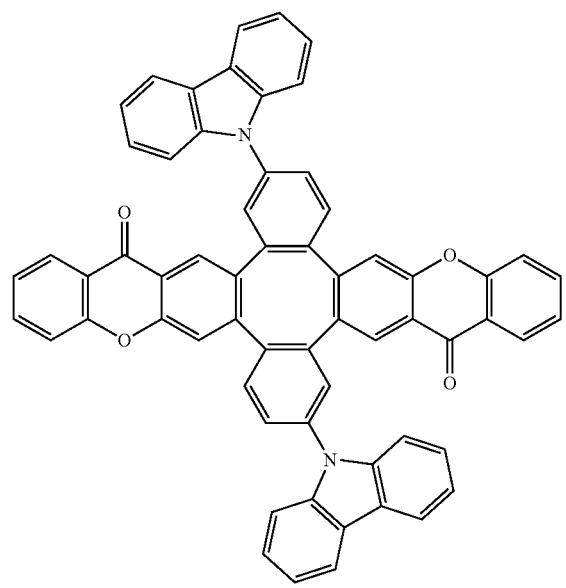

-continued
Compound E103
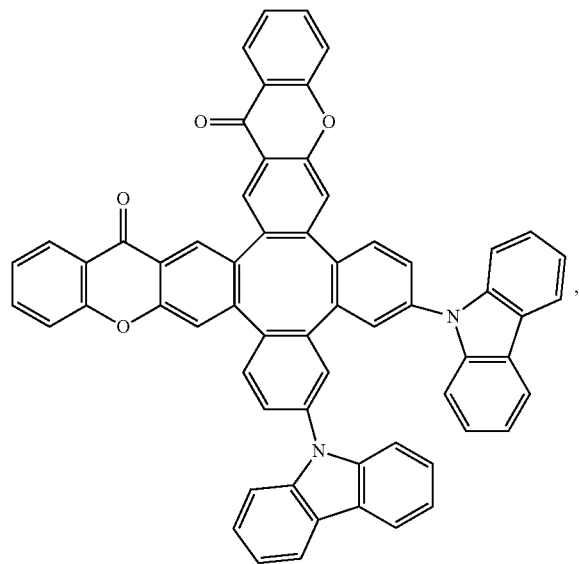
Compound E104
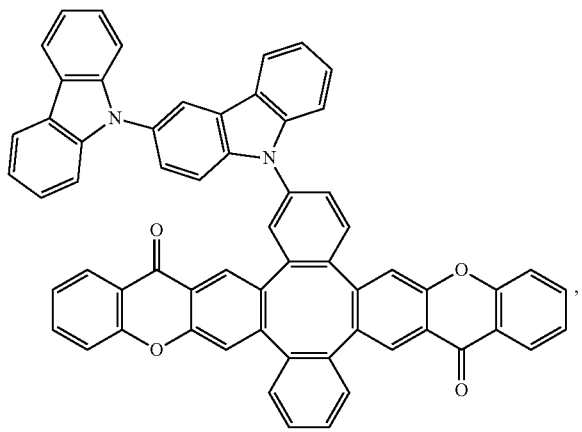
Compound E105
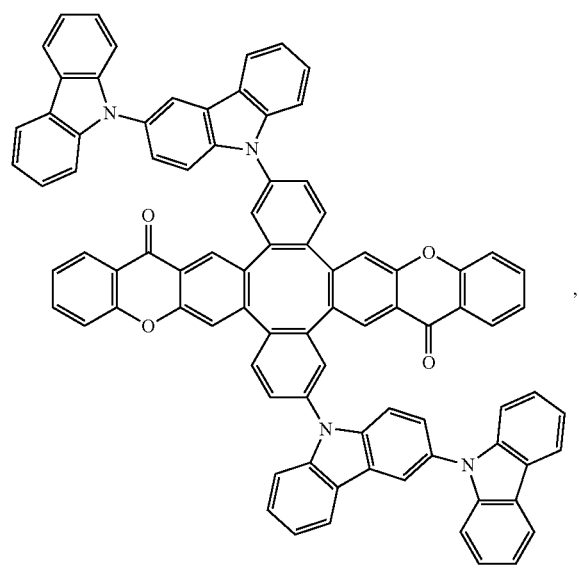
Compound E106
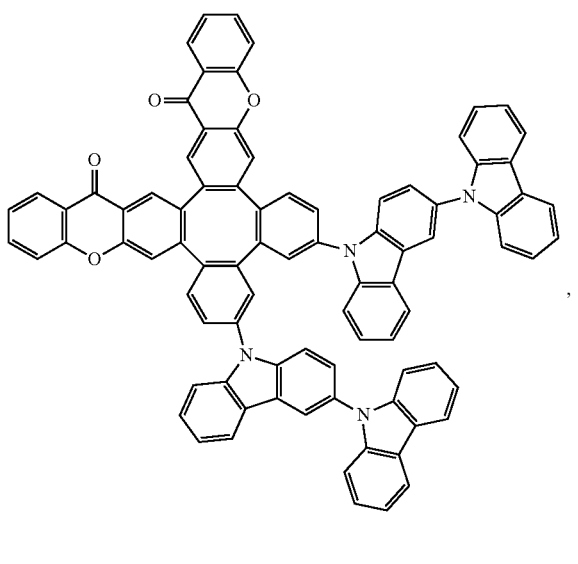

Compound E107
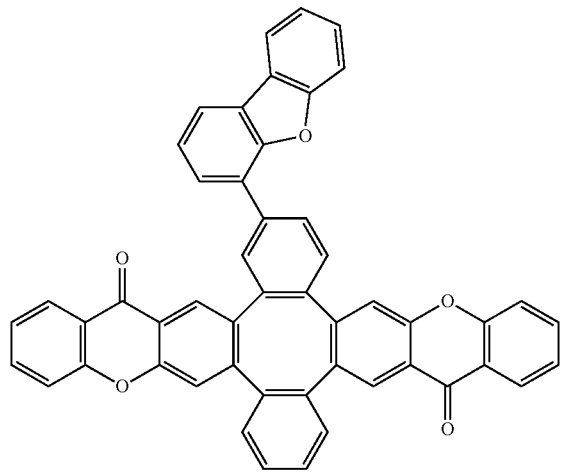
Compound E108
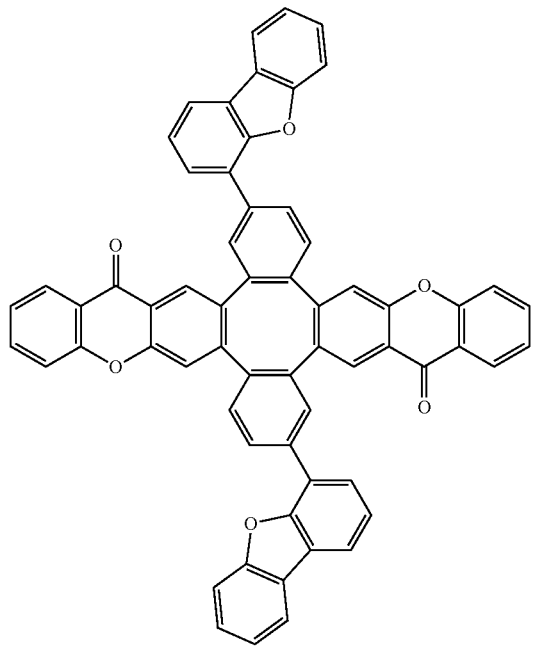
Compound F100
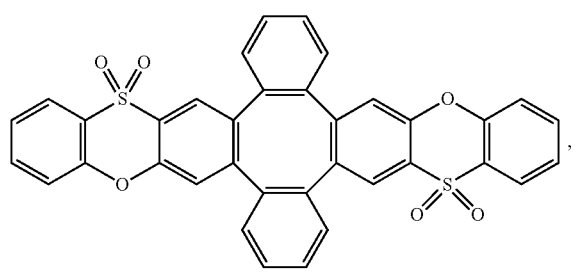
Compound F101
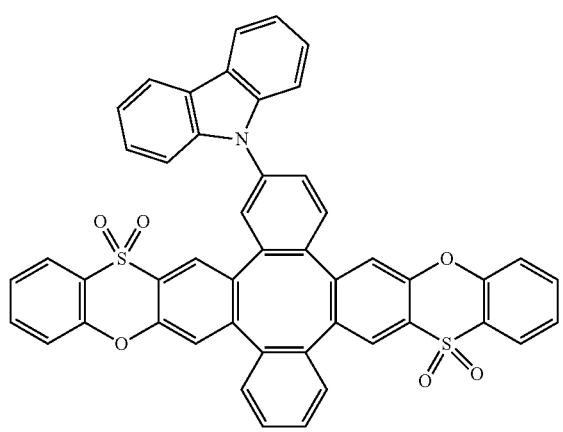

-continued
Compound F102
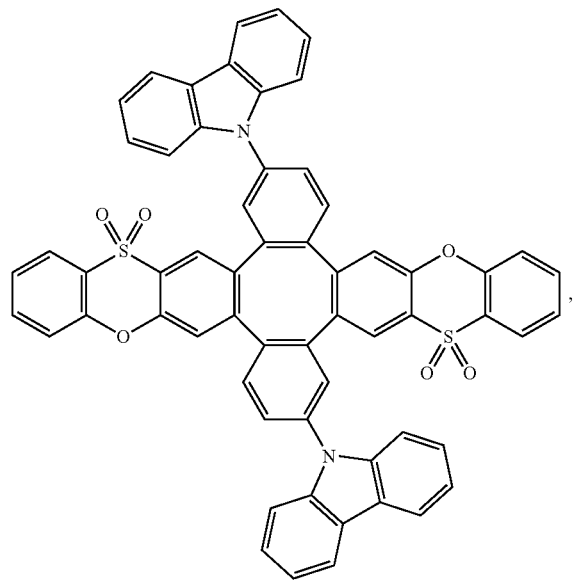
Compound F103
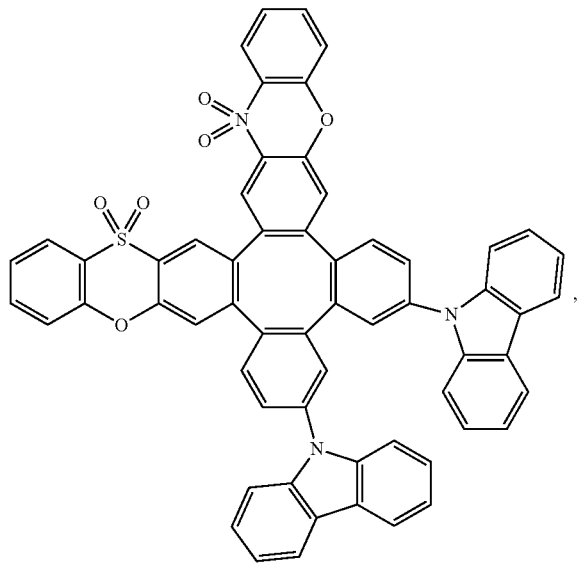
Compound F104
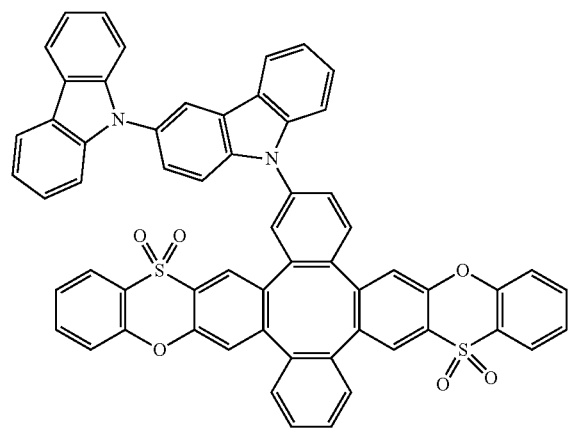
Compound F105
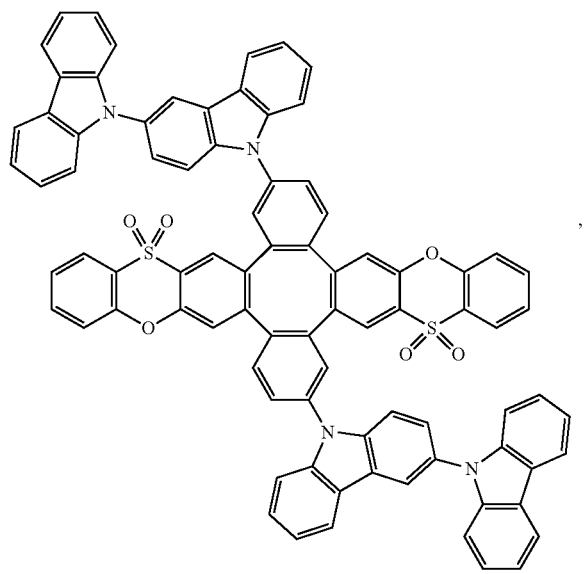

-continued
Compound F106
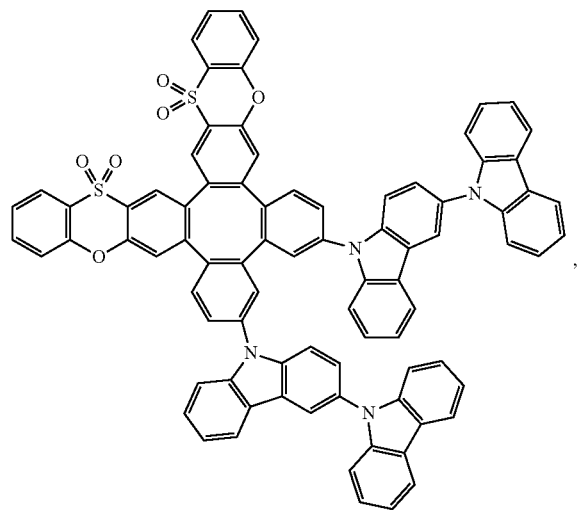
Compound F107
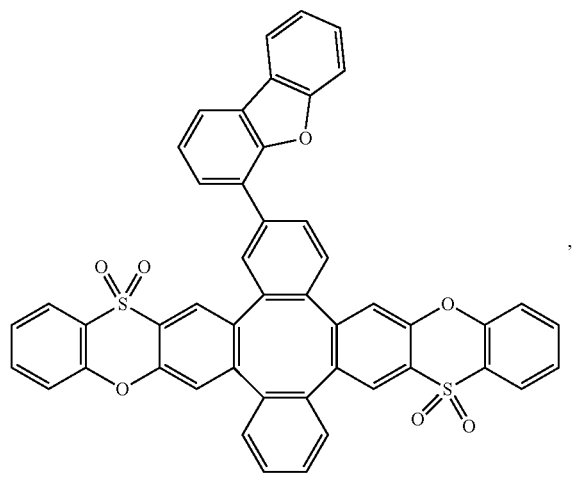
Compound F108
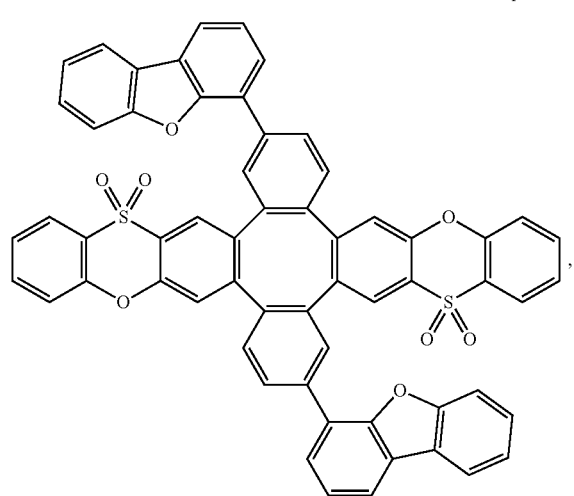
Compound B100
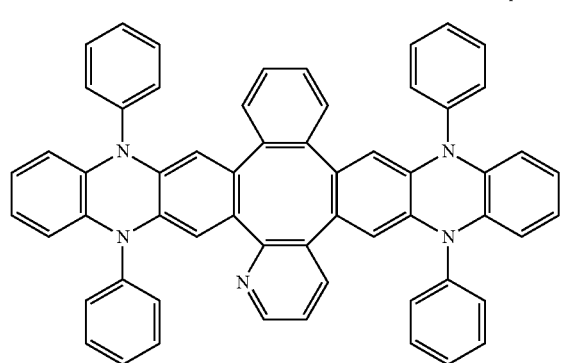

-continued
Compound B101
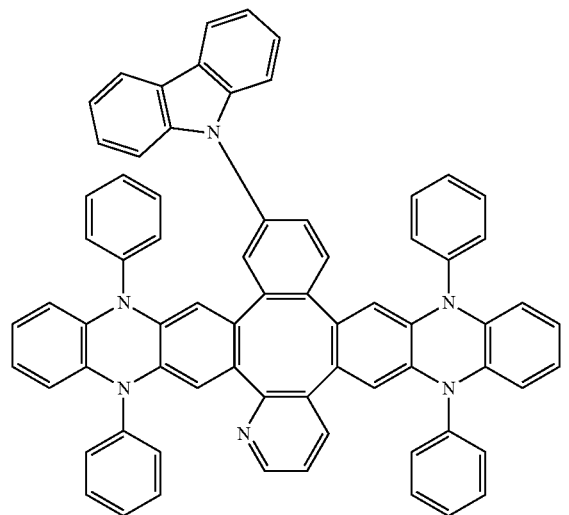
Compound B102
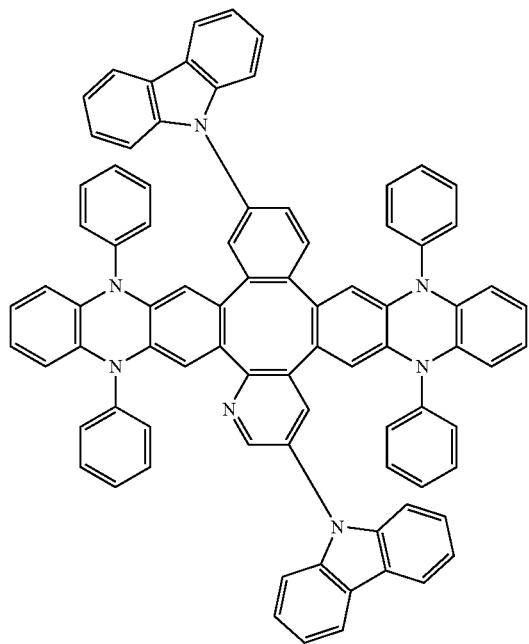
Compound B103
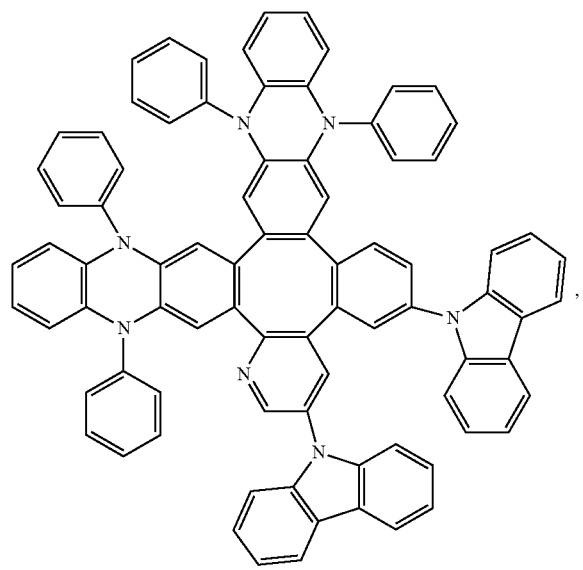
Compound B104
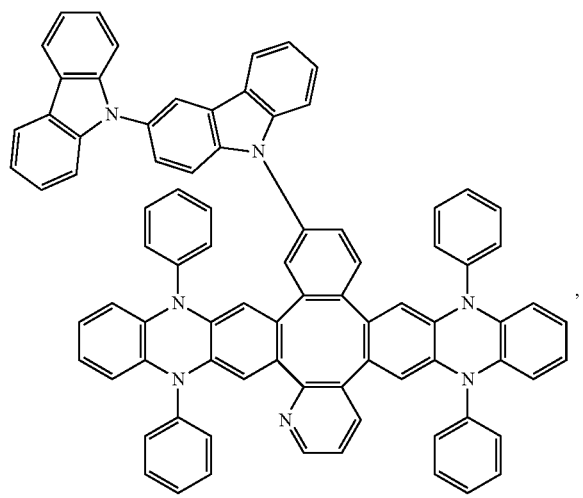

-continued
Compound B105
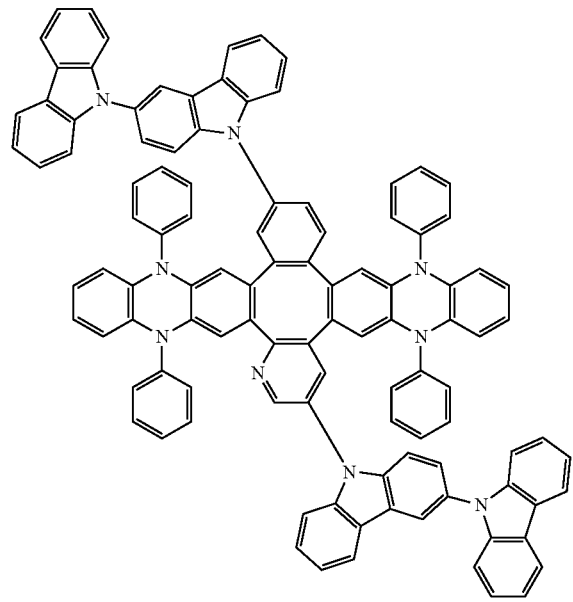
Compound B106
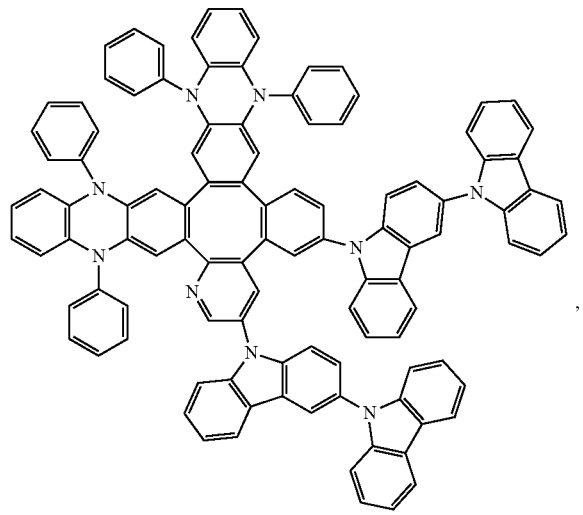
Compound B107
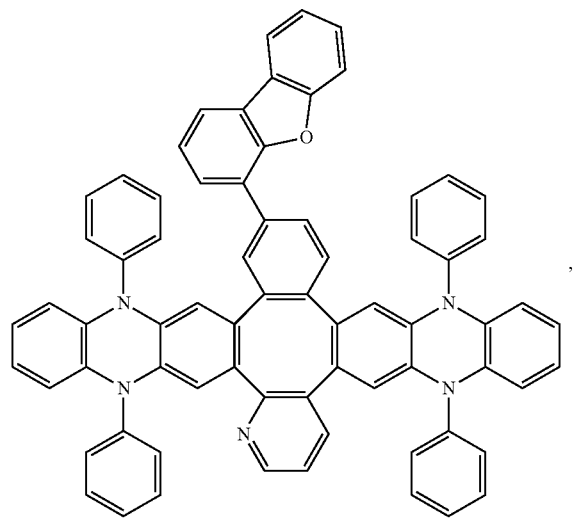
Compound B108
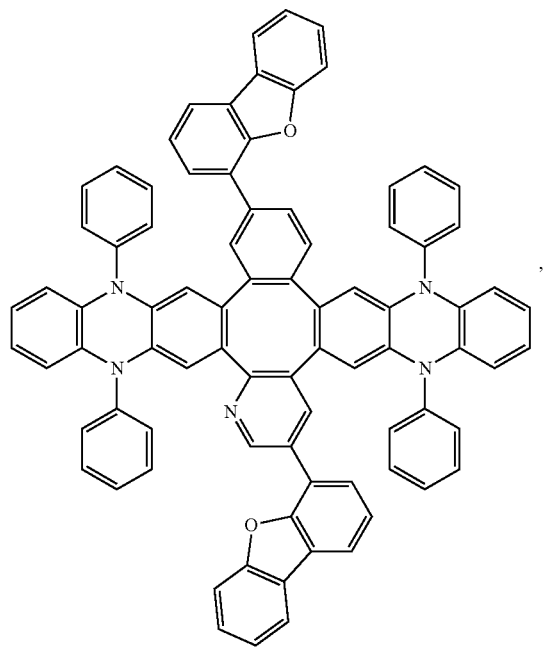

-continued
Compound B109
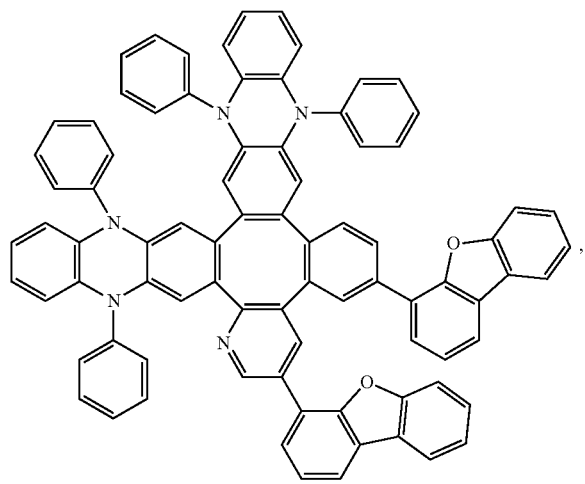
Compound B110
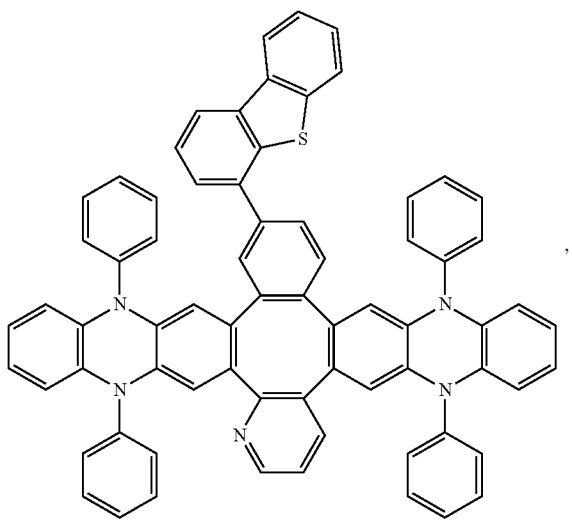
Compound B111
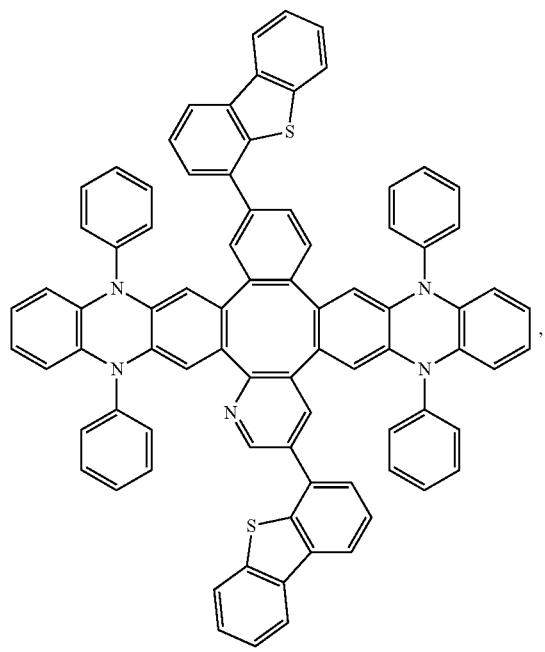
Compound B112
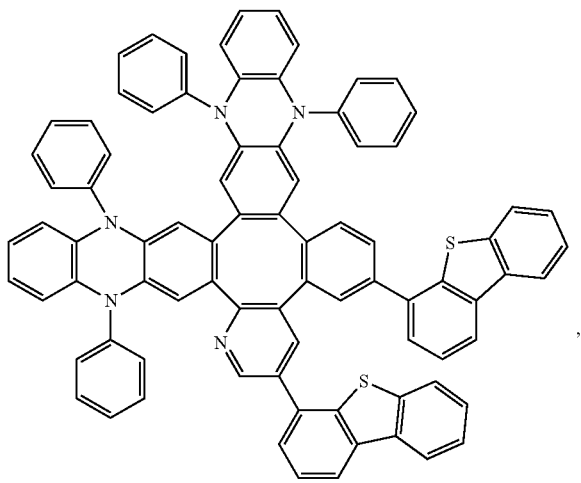
Compound B113
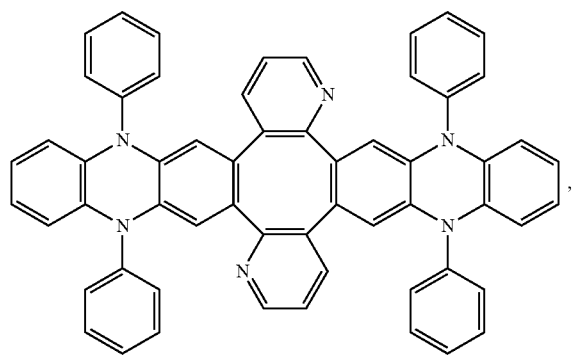
Compound CC100
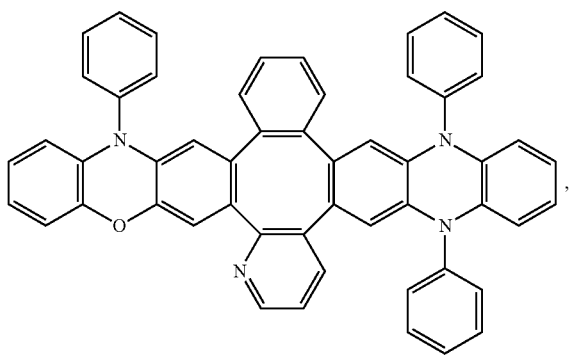

Compound CC101
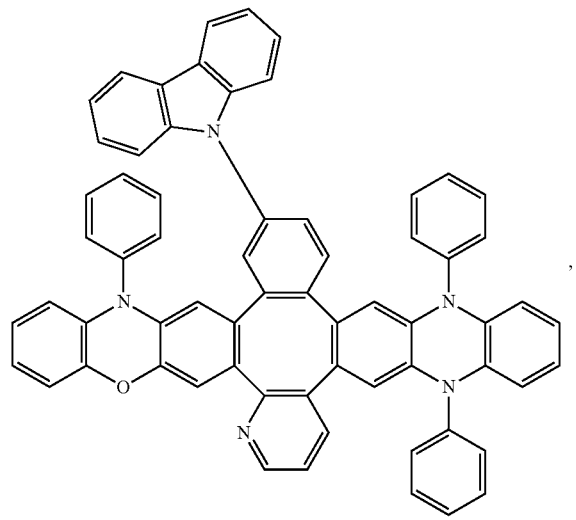
Compound CC102
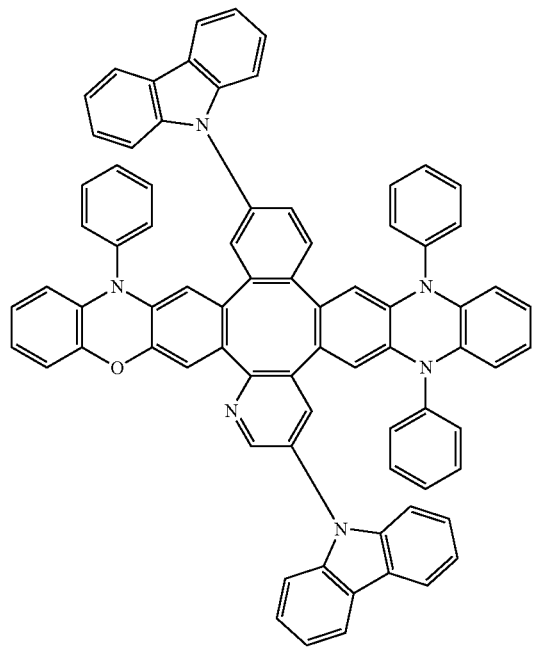
,
Compound CC103
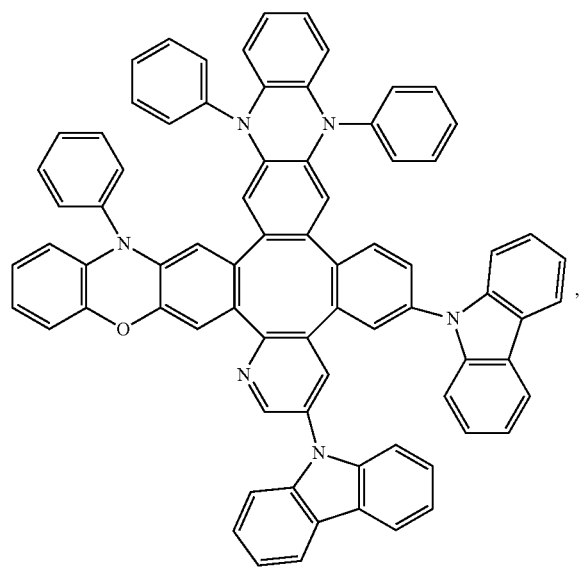
,
Compound CC104
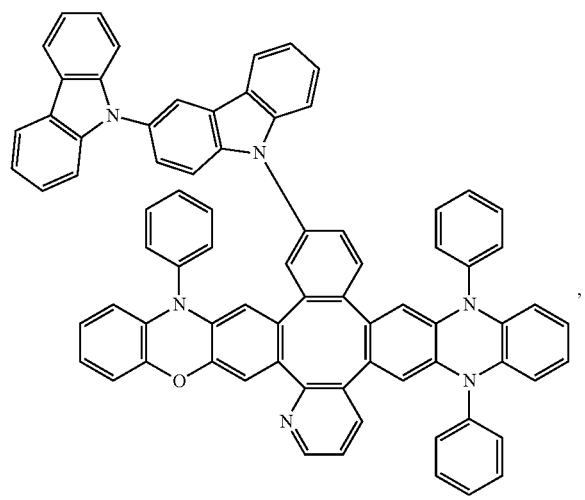
, -continued
Compound CC105
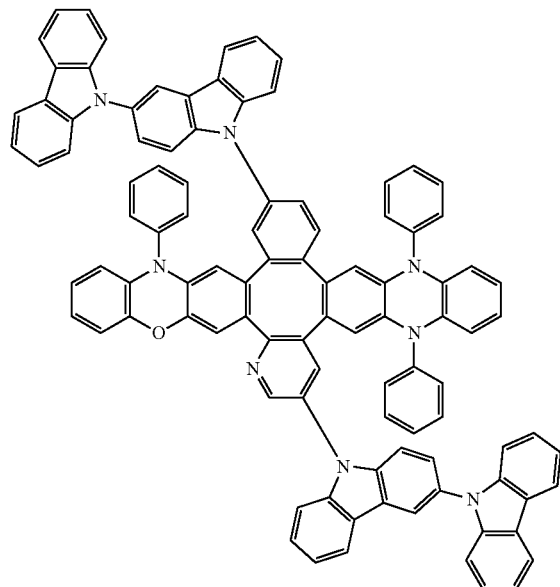
Compound CC106
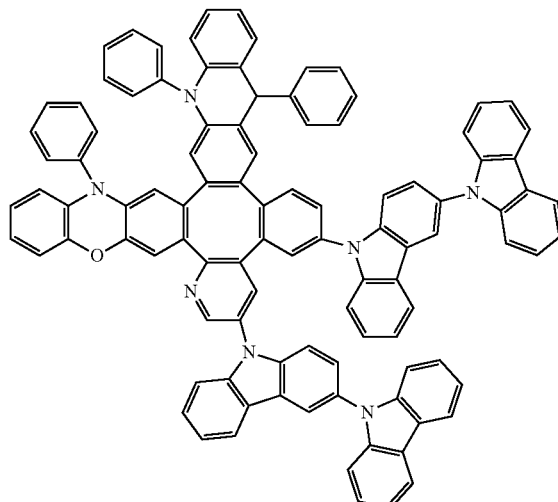
Compound CC107
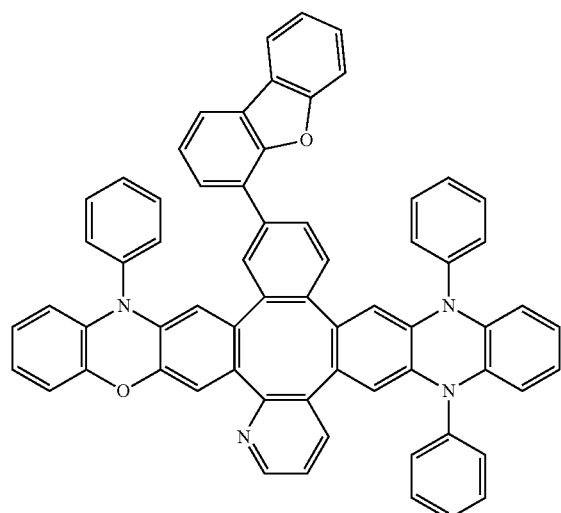
Compound CC108
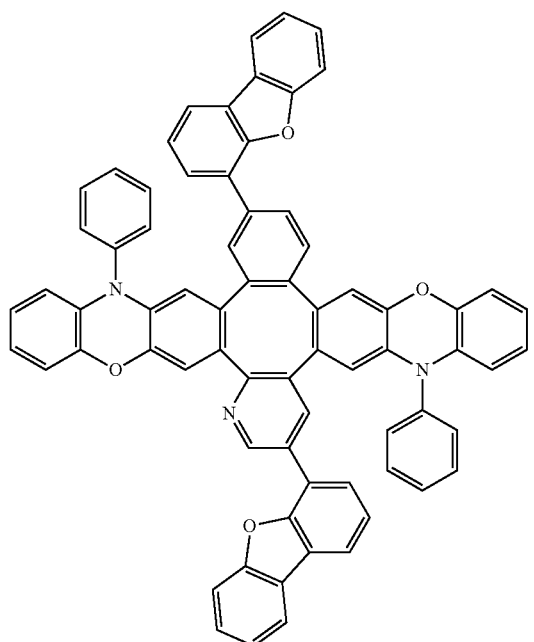

-continued
Compound DD100
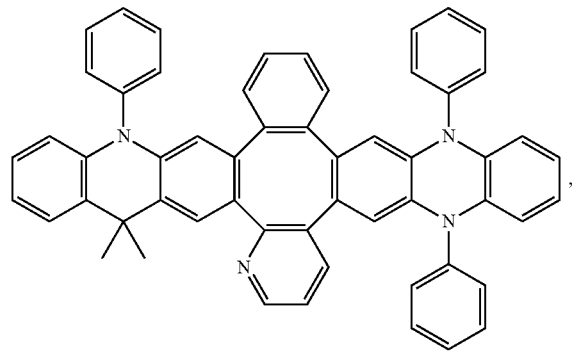
Compound DD101
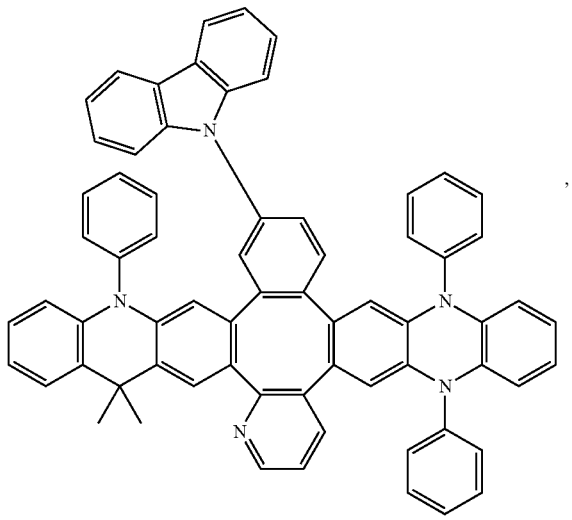
Compound DD102
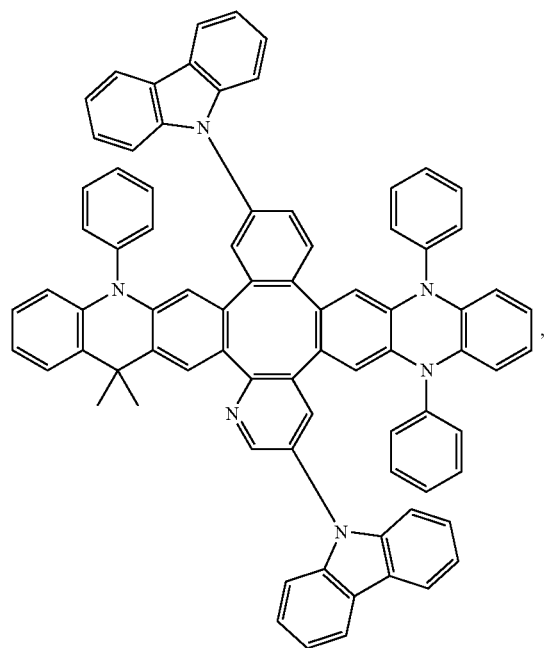
Compound DD103
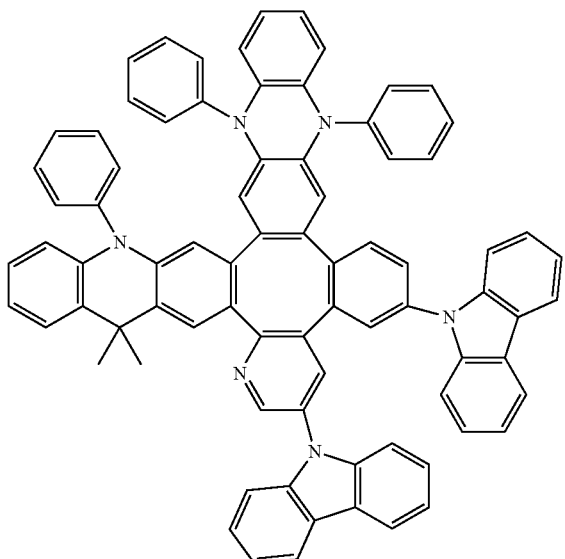

-continued
Compound DD104
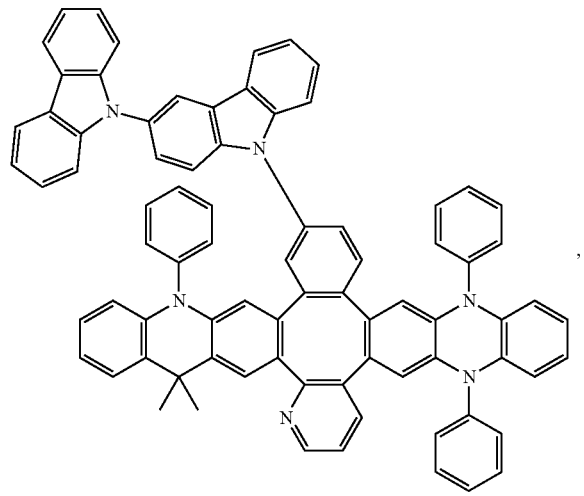
Compound DD105
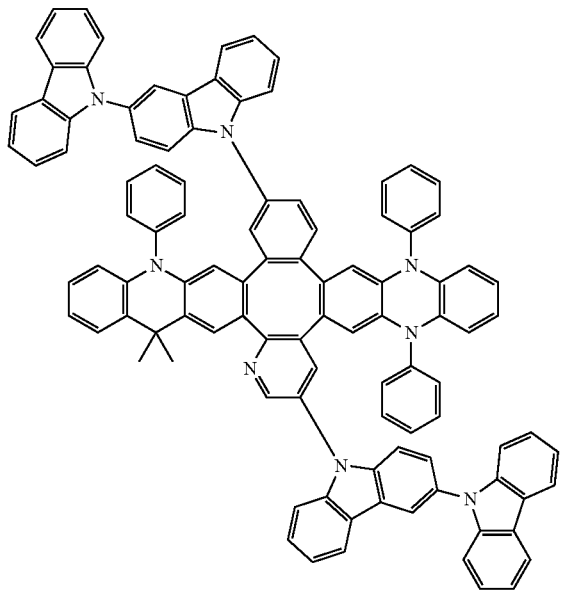
Compound DD106
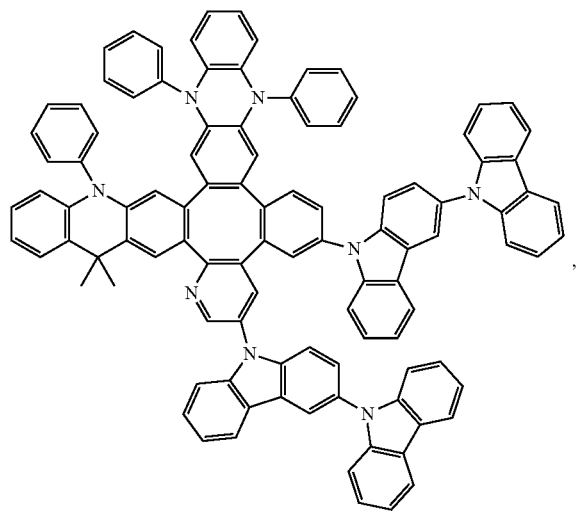
Compound DD107
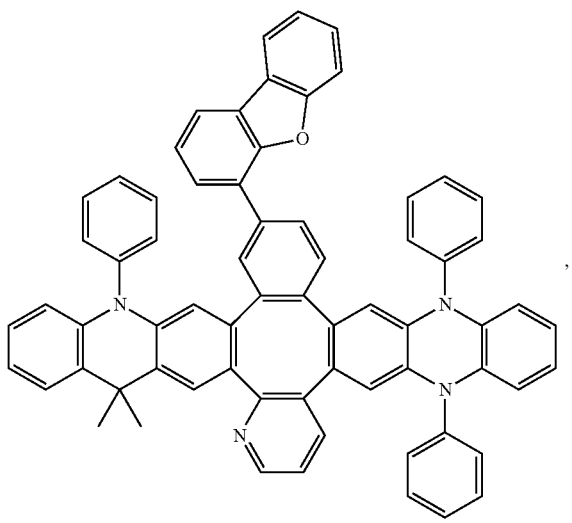

-continued
Compound DD108
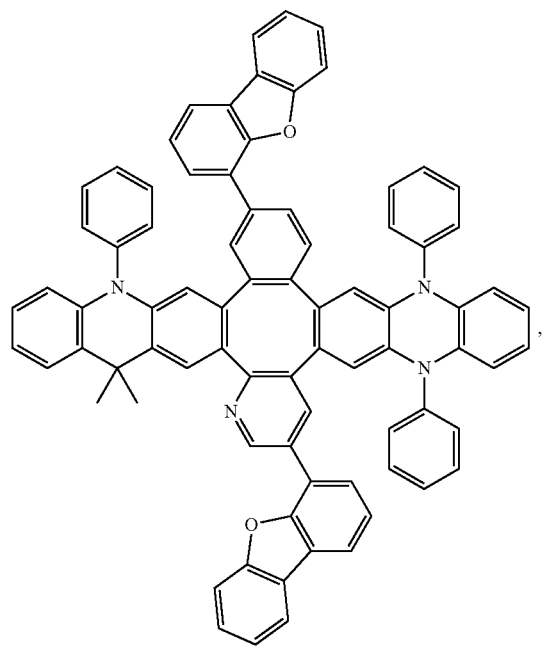
Compound EE100
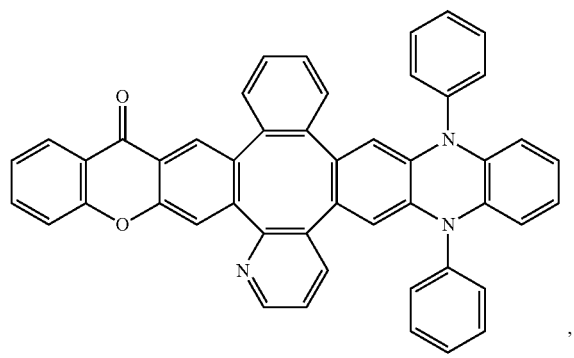
Compound EE101
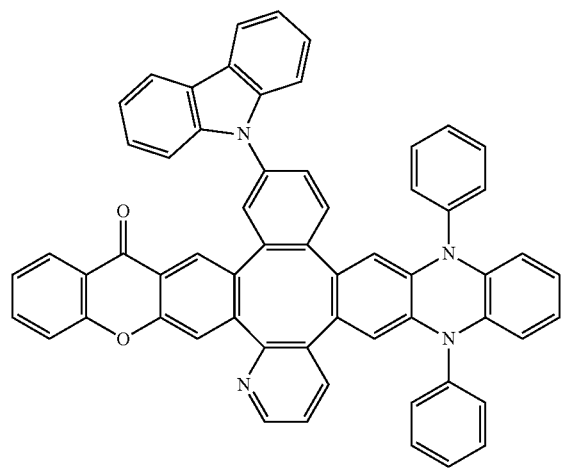
Compound EE102
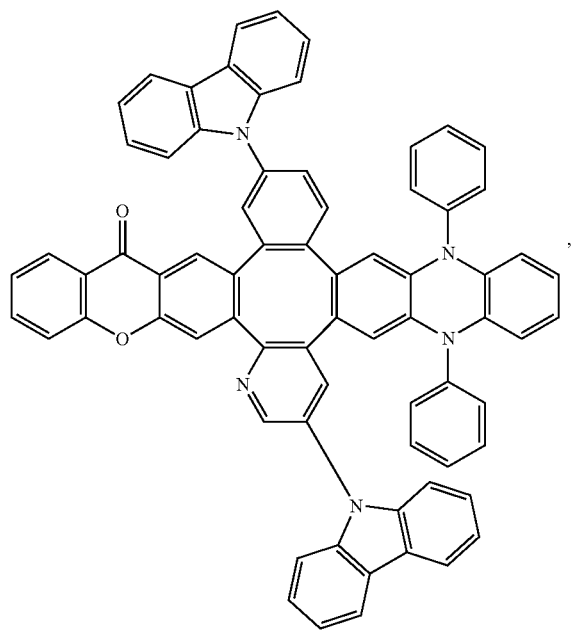

-continued
Compound EE103
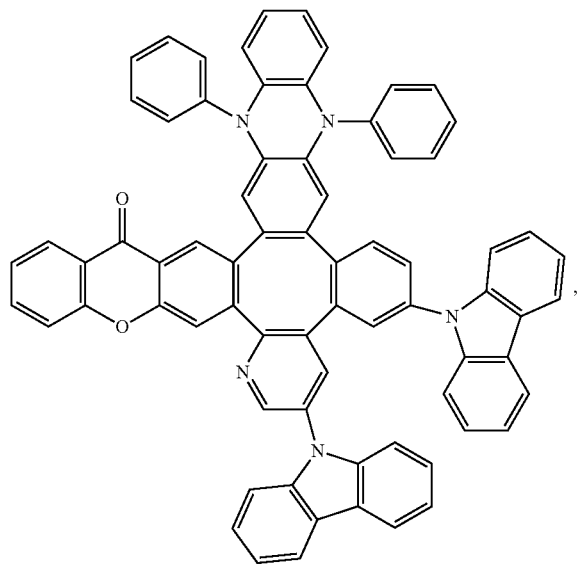
Compound EE104
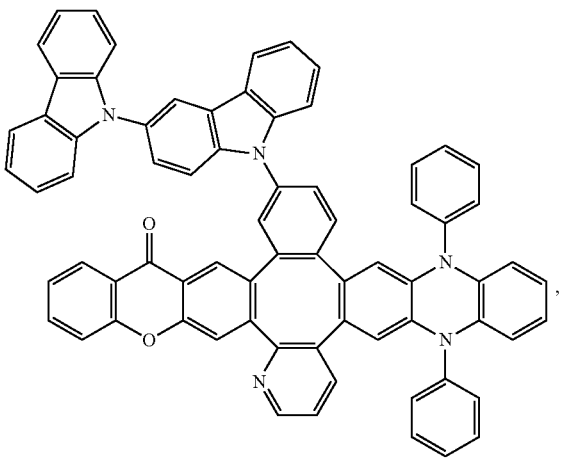
Compound EE105
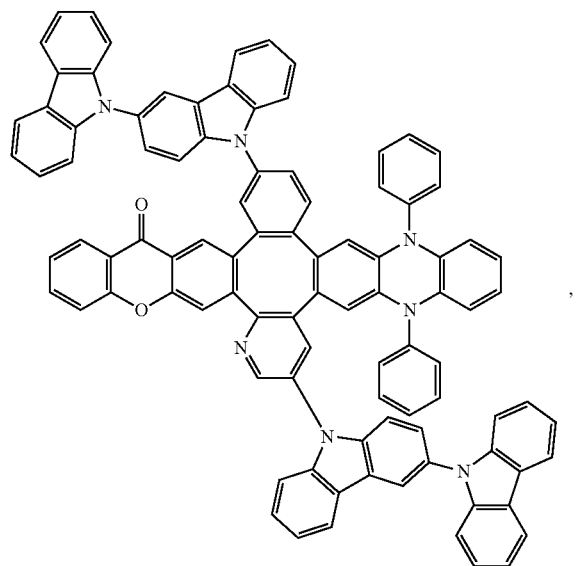
Compound EE106
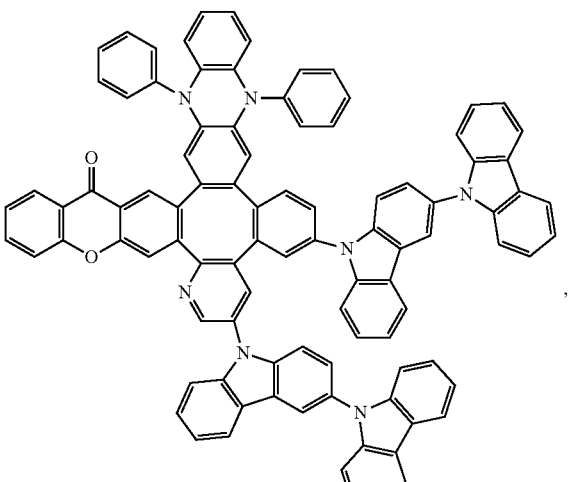

-continued
Compound EE107
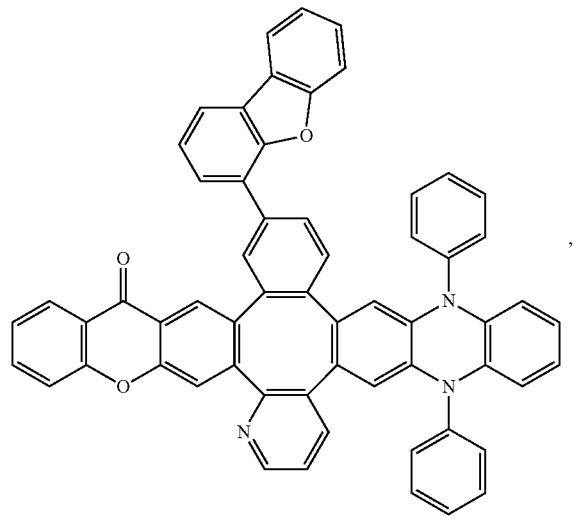
Compound EE108
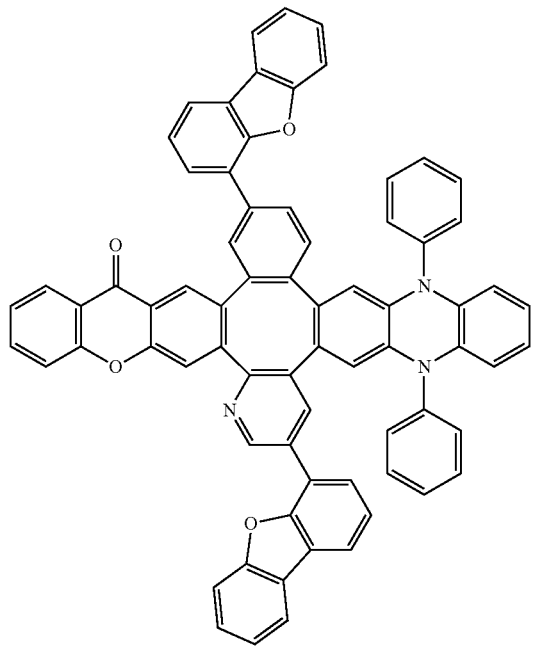
Compound FF100
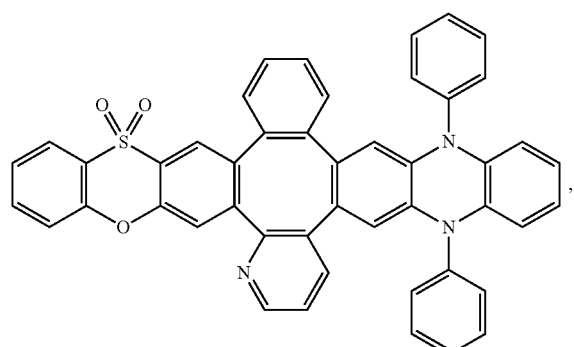
Compound FF101
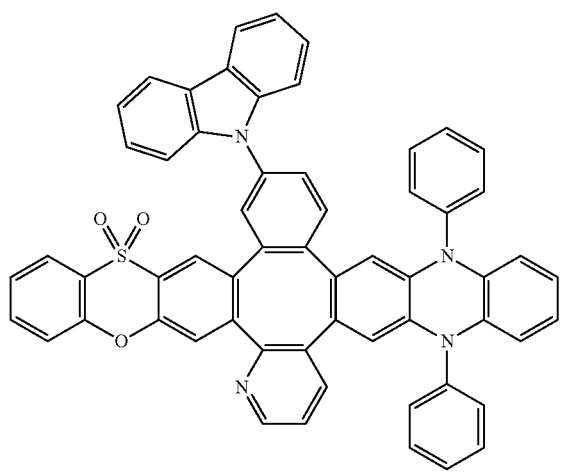

-continued
Compound FF102
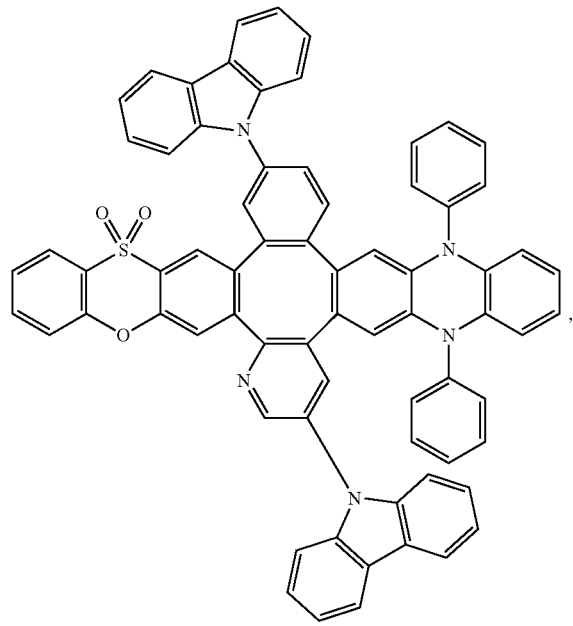
Compound FF103
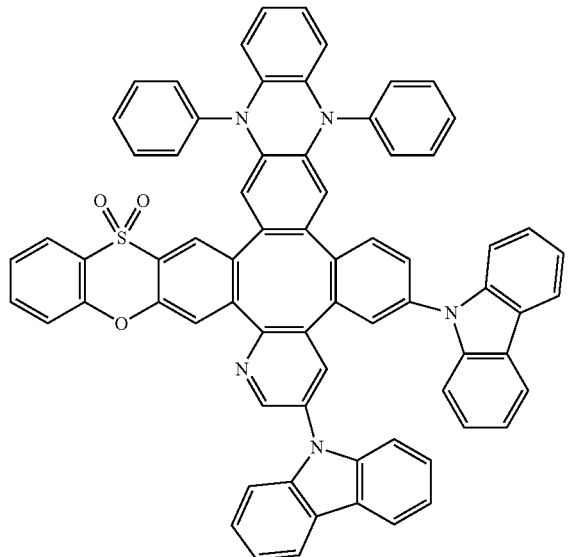
Compound FF104
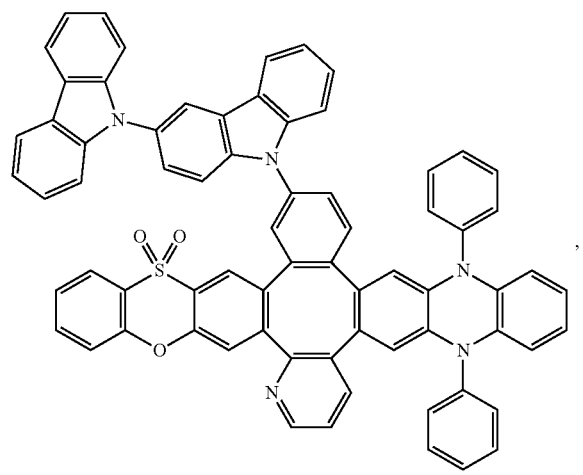
Compound FF105
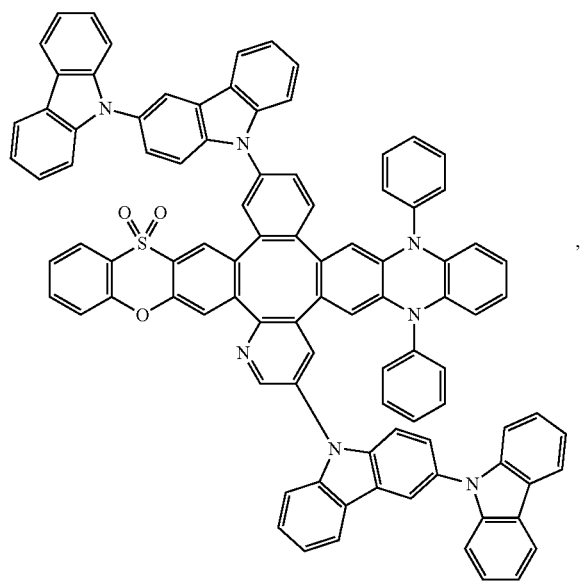

-continued
Compound FF106
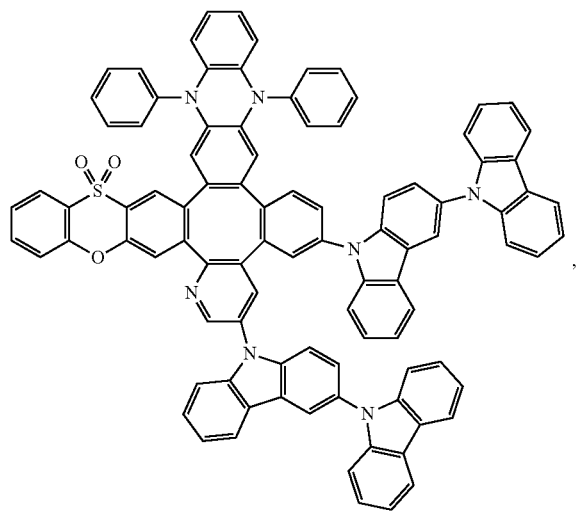
Compound FF107
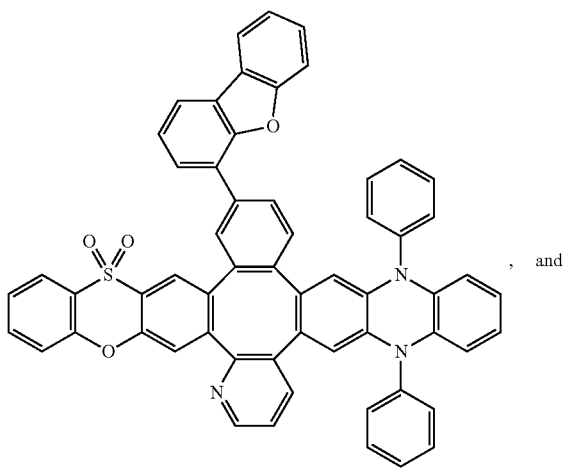
, and
Compound FF108
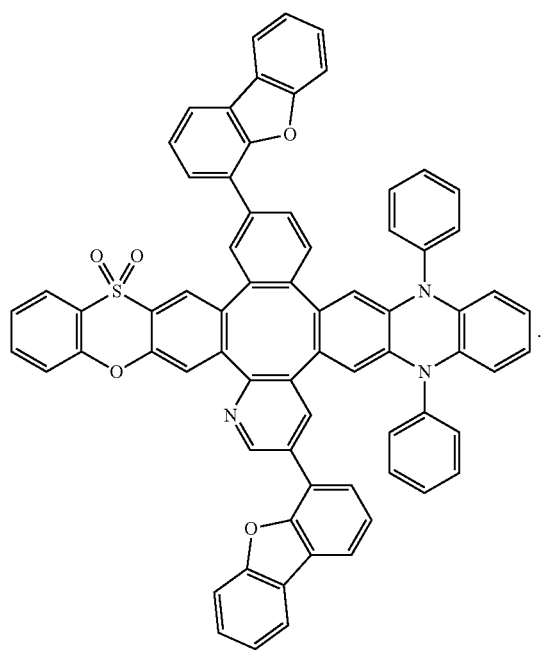
9. The compound of claim 1, wherein the compound is selected from the group consisting of:
Compound M1
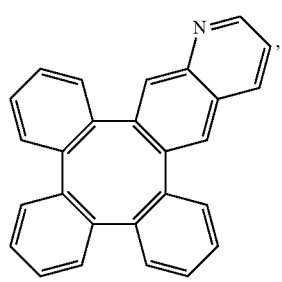
Compound M2
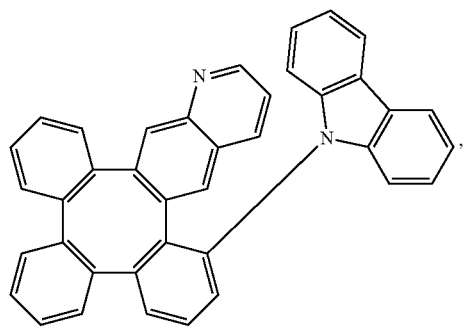

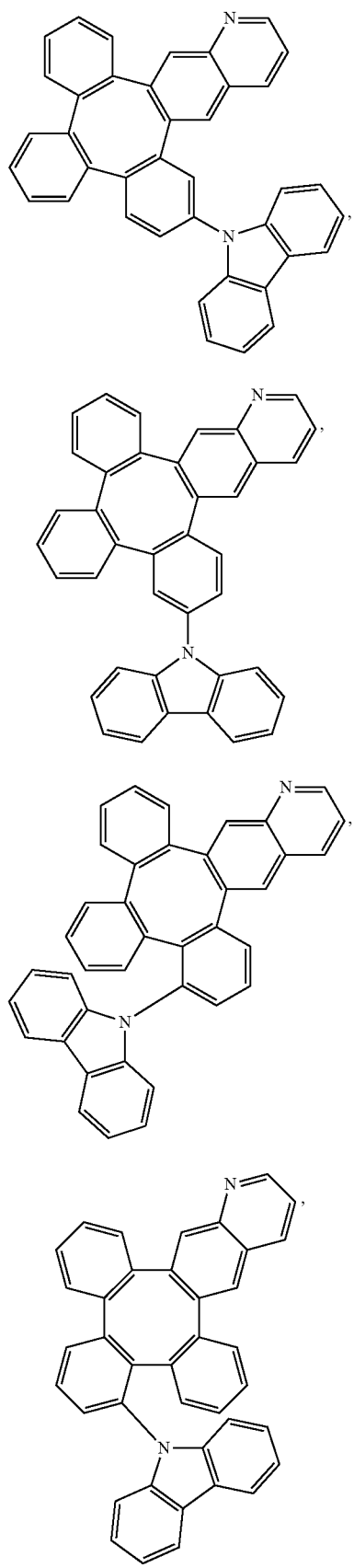
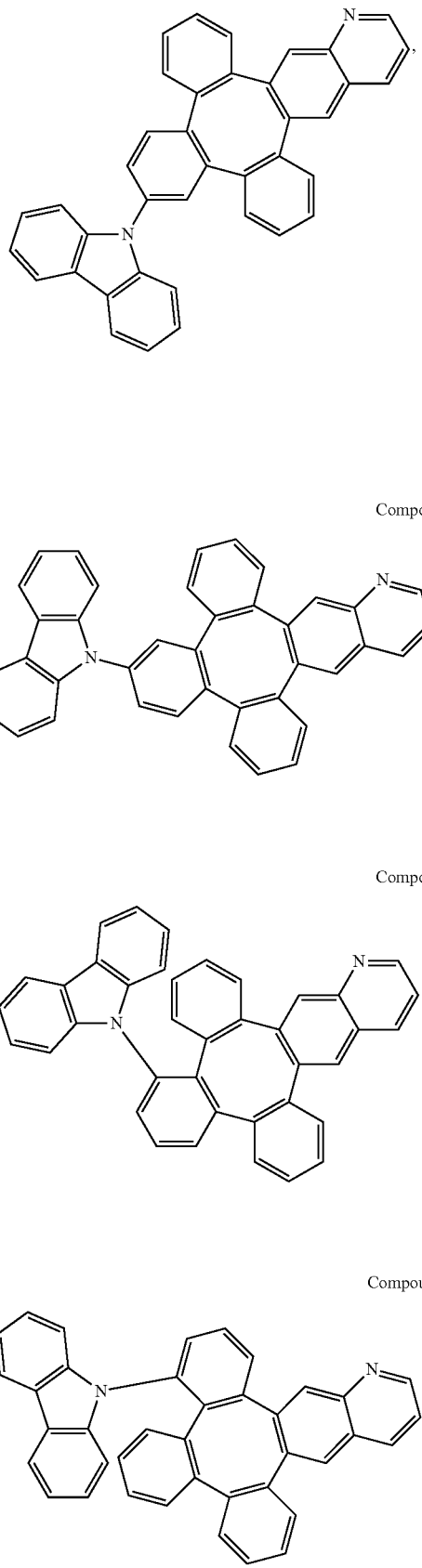

Compound M11
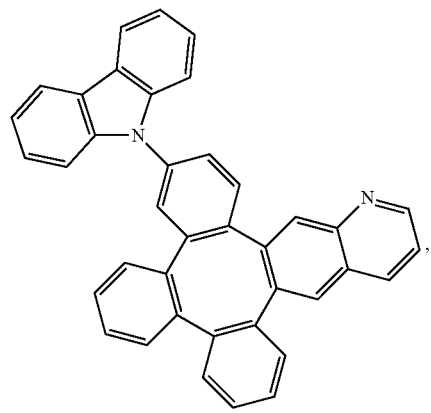
Compound M12
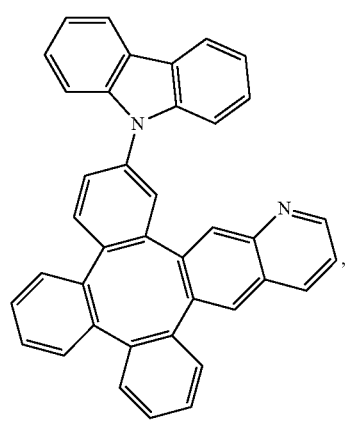
Compound M13
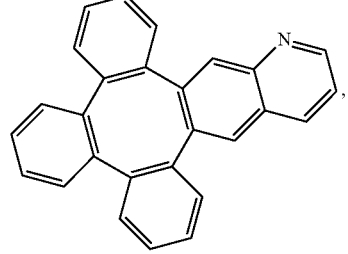
Compound M14
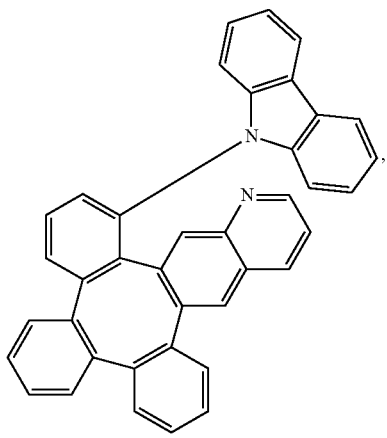
Compound M15
Compound M16
Compound M17
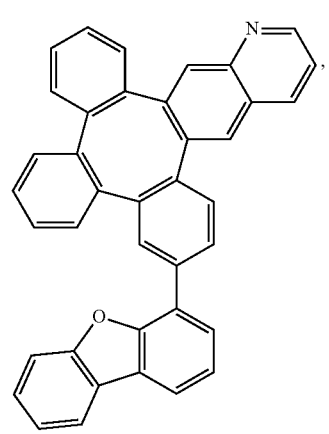
Compound M18
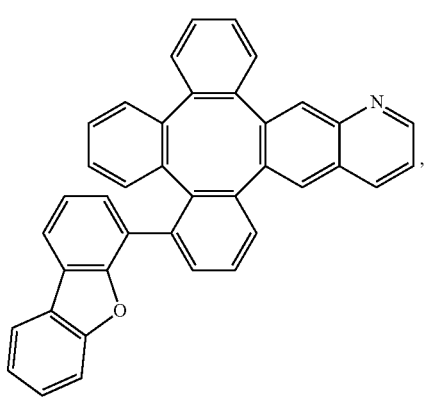

Compound M19
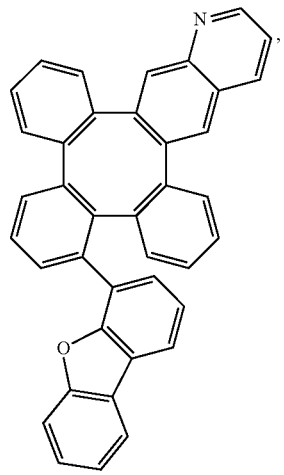
Compound M20
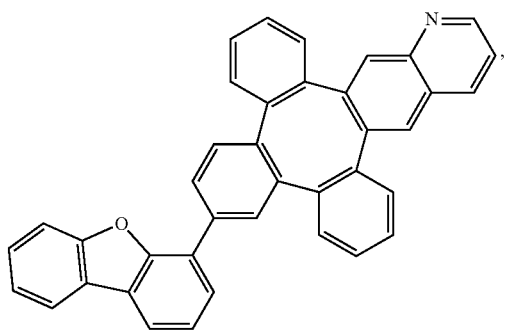
Compound M21
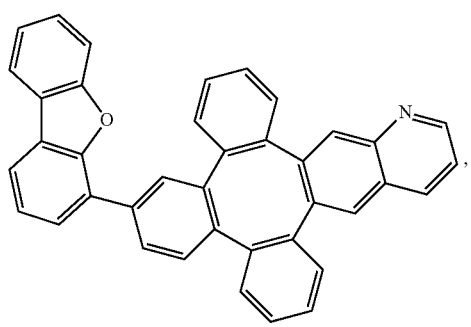
Compound M22
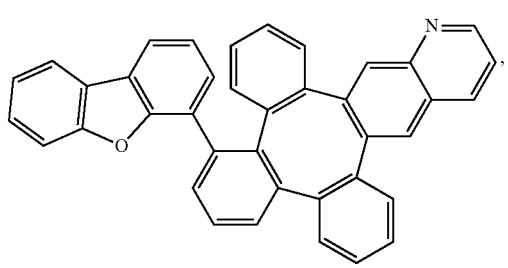
Compound M23
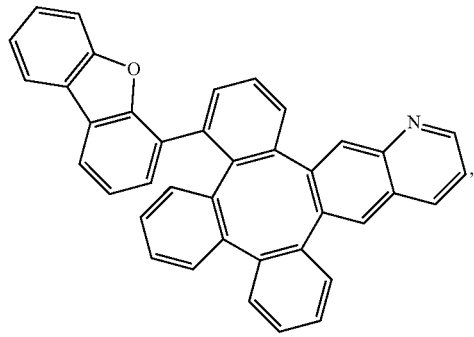
Compound M24
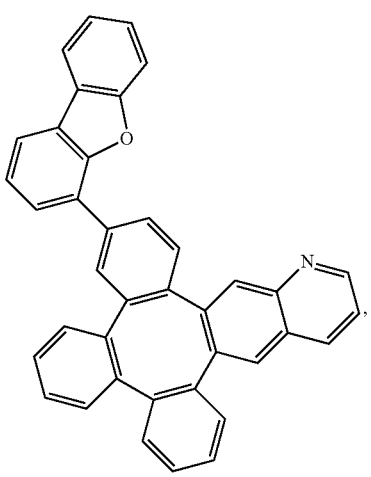
Compound M25
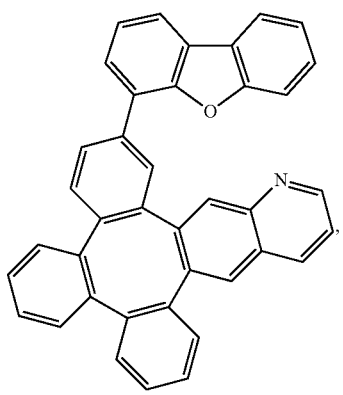

Compound M26
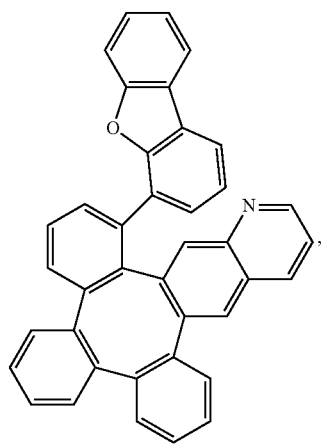
Compound M27
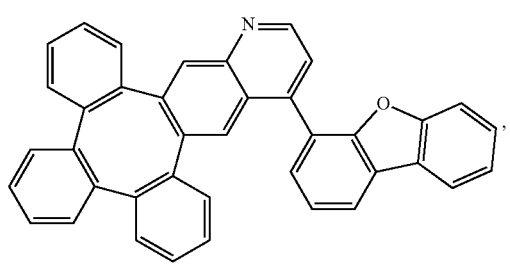
Compound M28
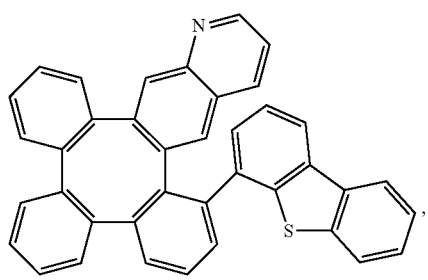
Compound M29
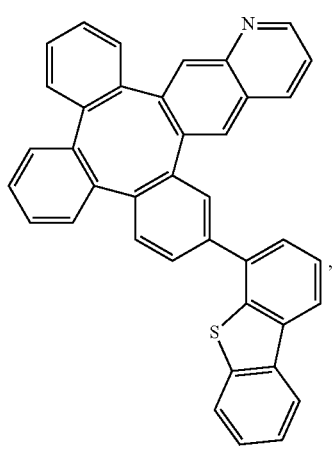
Compound M30
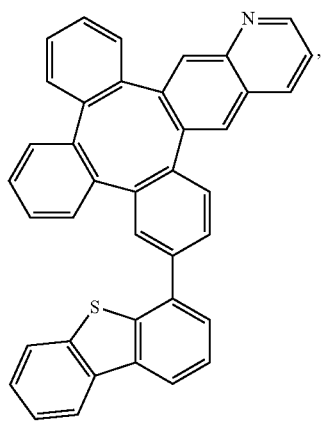
Compound M31
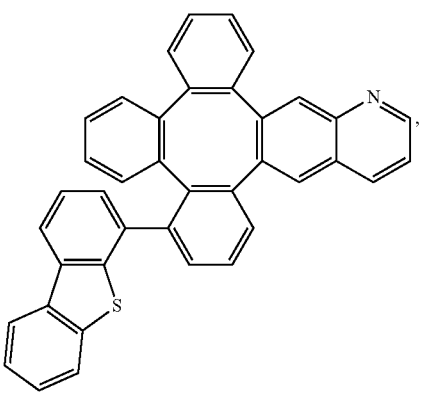
Compound M32
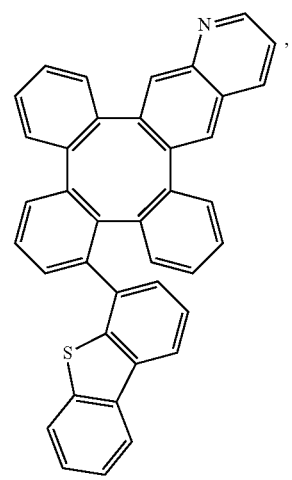
Compound M33
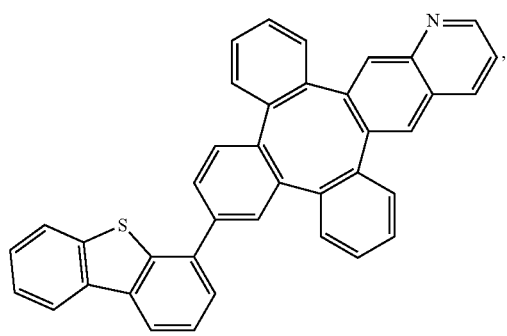

-continued
Compound M34
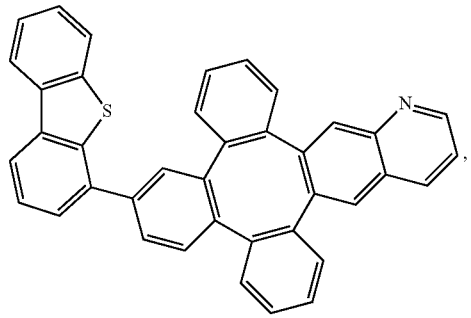
Compound M35
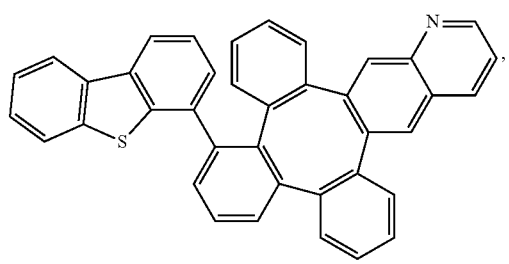
Compound M36
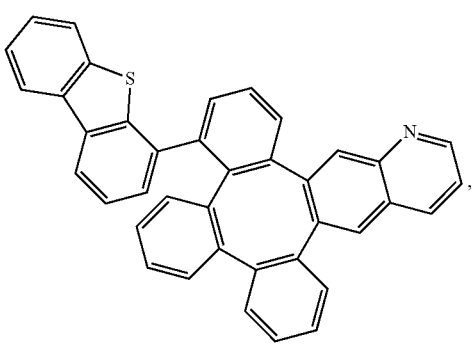
Compound M37
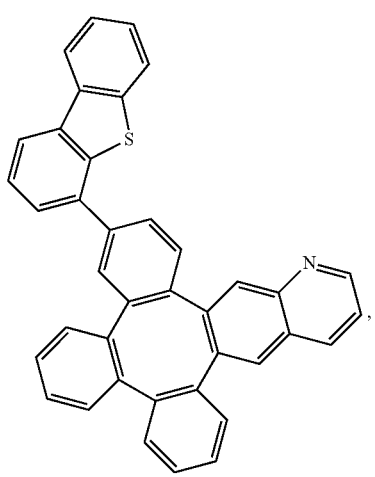
-continued
Compound M38
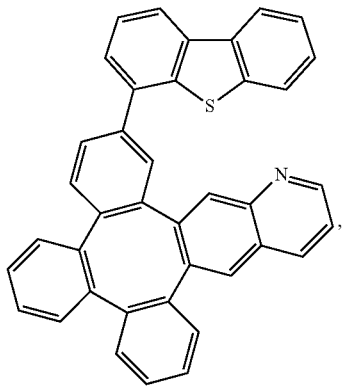
Compound M39
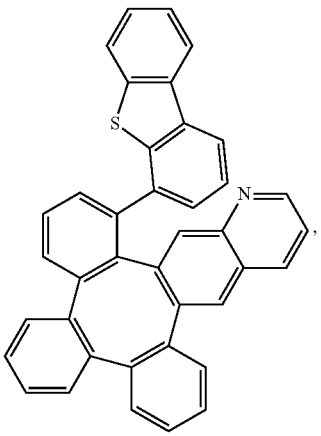
Compound M40
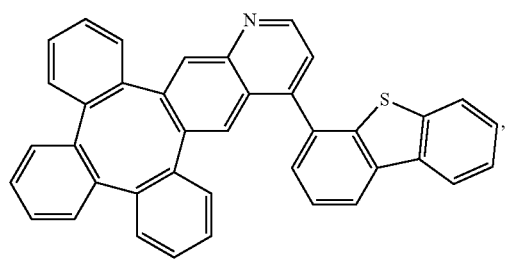
Compound N1
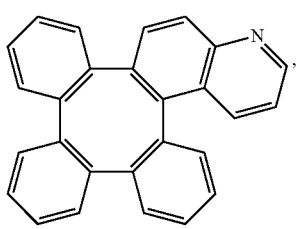

Compound N2
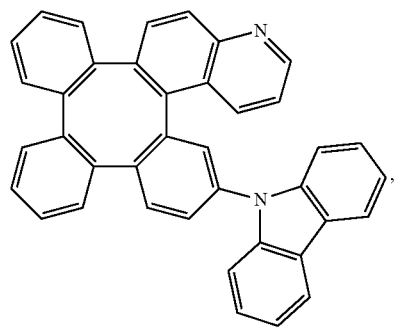
Compound N3
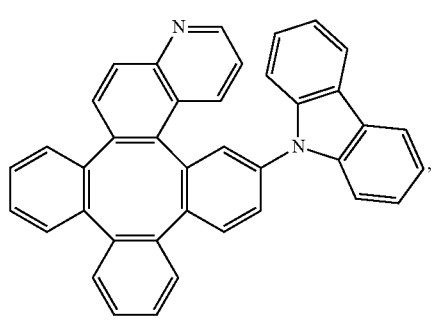
Compound N4
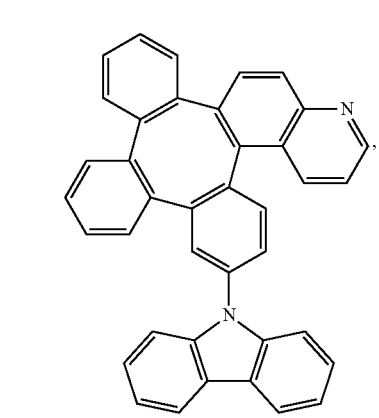
Compound N5
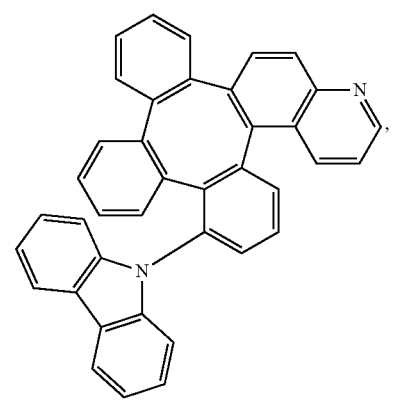
Compound N6
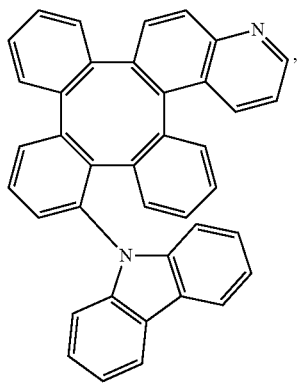
Compound N7
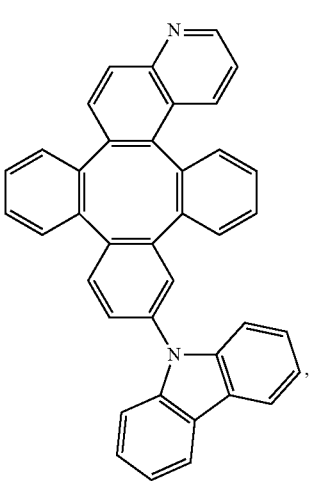
Compound N8
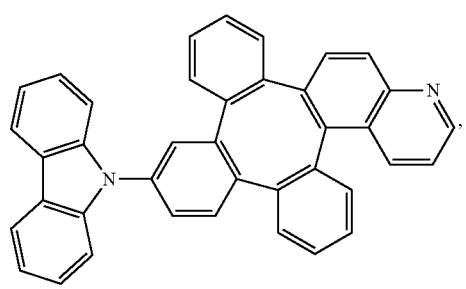
Compound N9
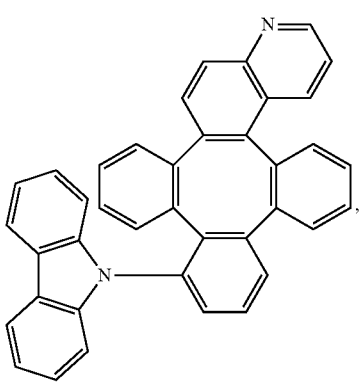

Compound N10
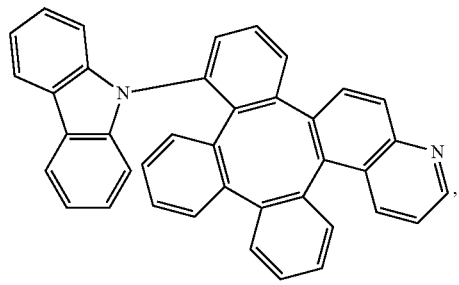
Compound N11
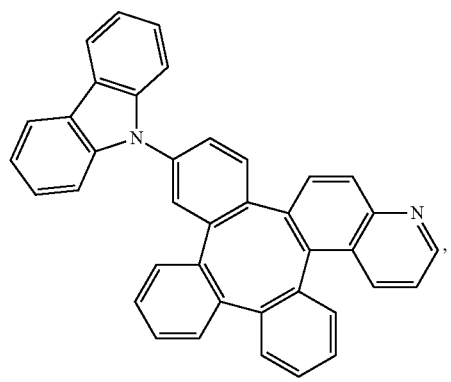
Compound N12
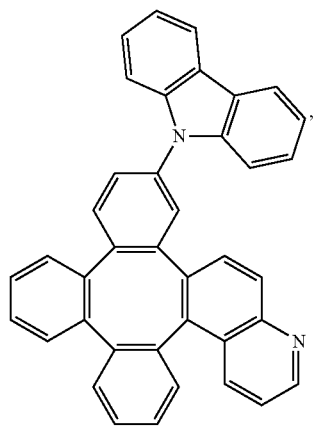
Compound N13
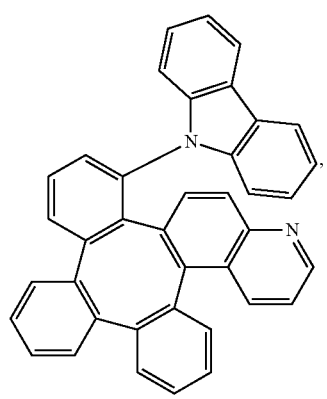
Compound N14
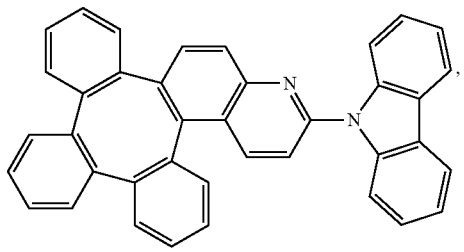
Compound N15
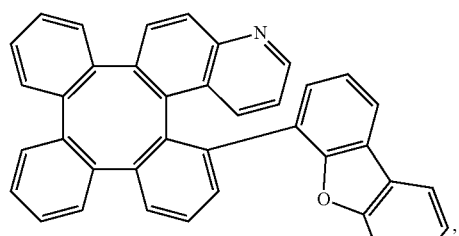
Compound N16
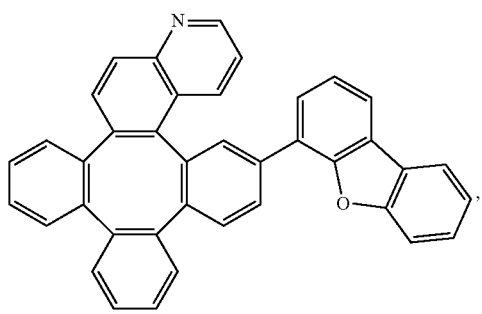
Compound N17
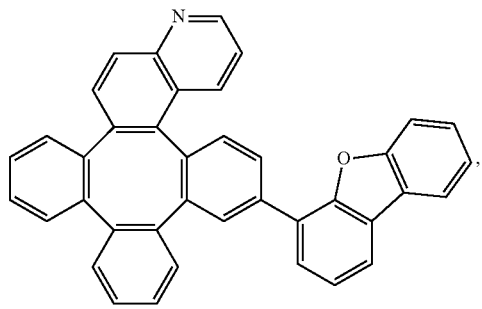
Compound N18
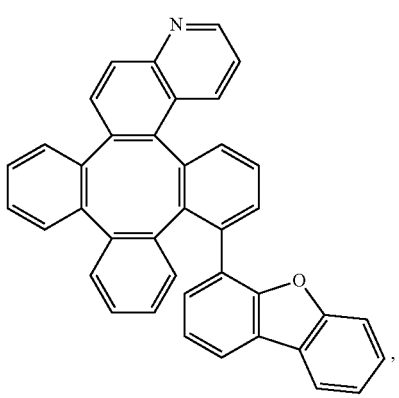

Compound N19
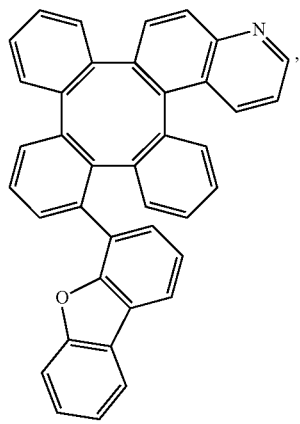
Compound N20
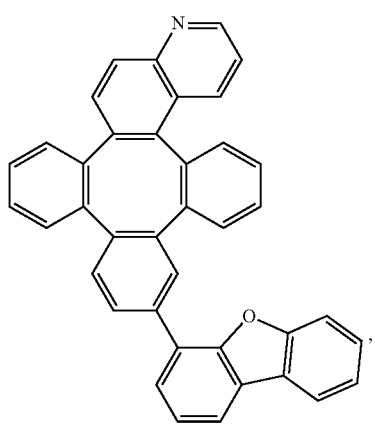
Compound N21
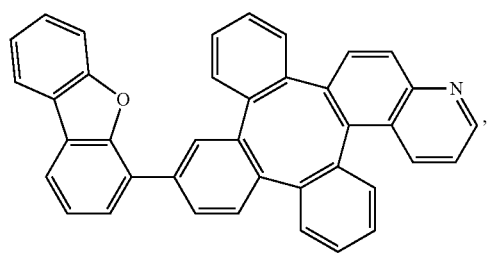
Compound N22
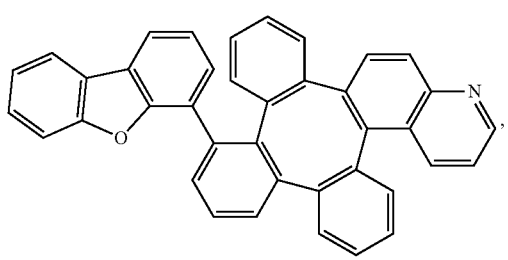
Compound N23
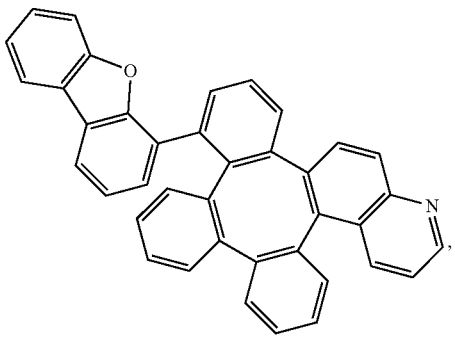
Compound N24
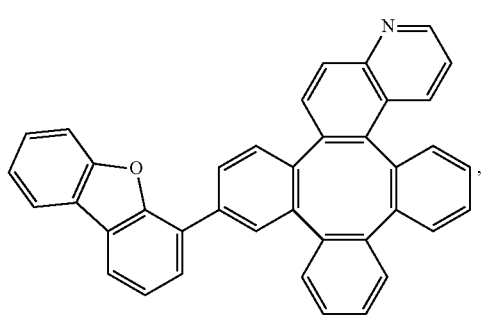
Compound N25
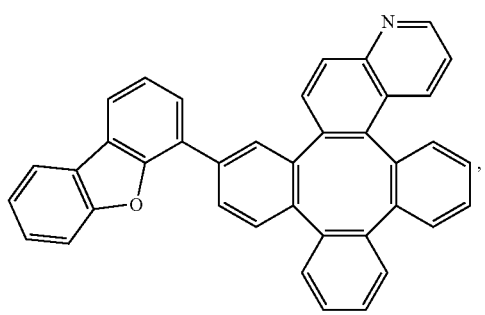
Compound N26
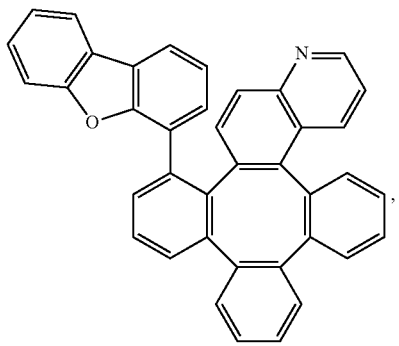

Compound N27
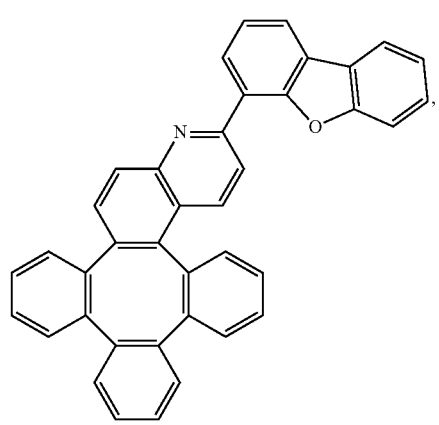
Compound N28
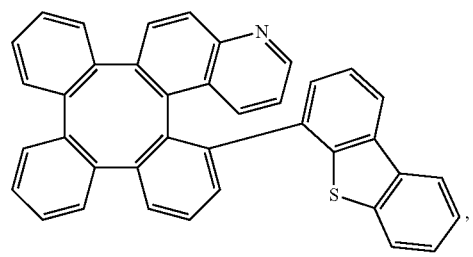
Compound N29
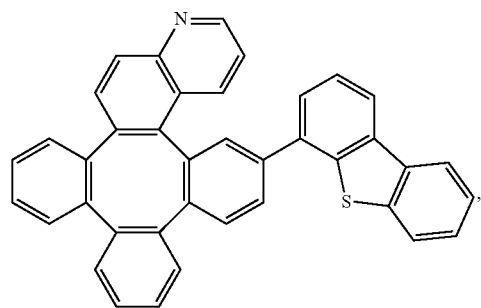
Compound N30
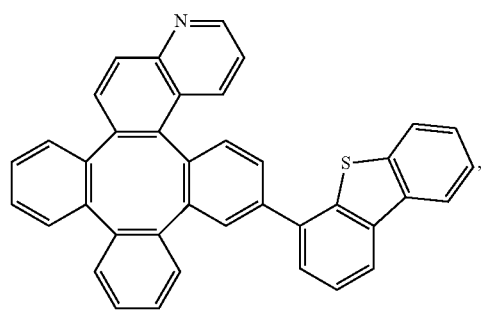
Compound N31
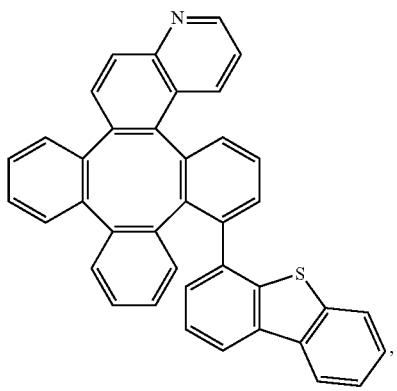
Compound N32
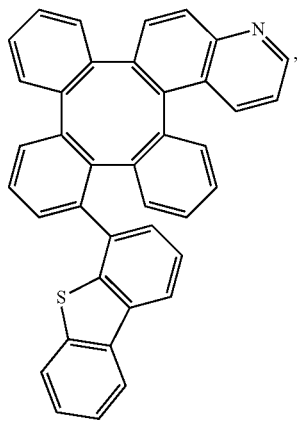
Compound N33
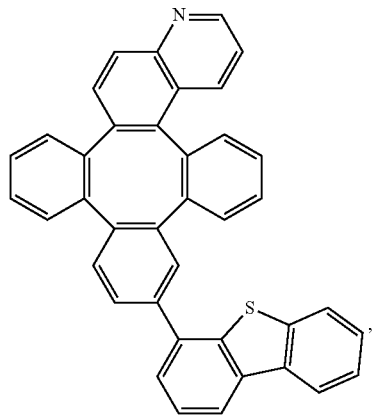
Compound N34
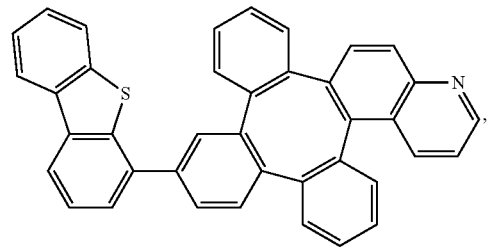

-continued
Compound N35
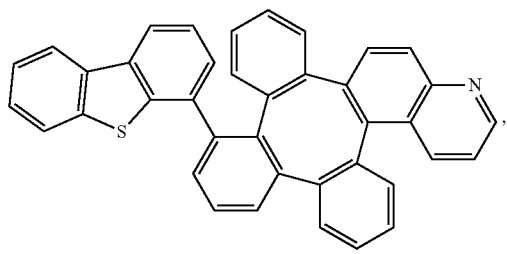
Compound N36
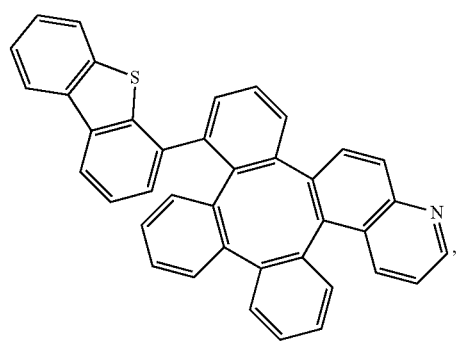
Compound N37
Compound N38
-continued
Compound N39
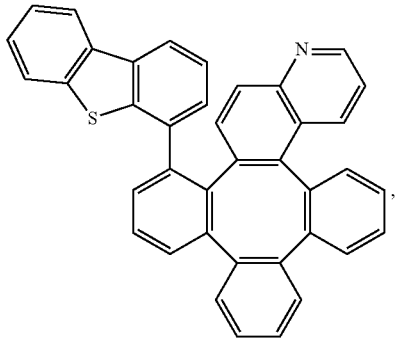
Compound N40
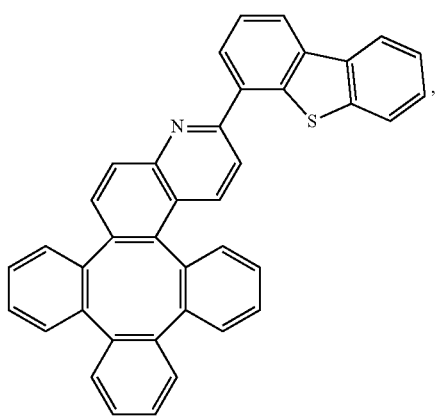
Compound P1
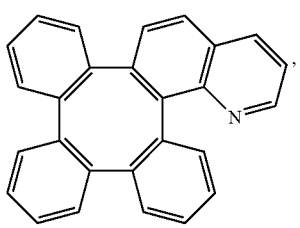
Compound P2
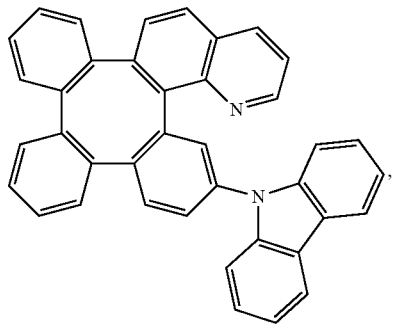

Compound P3
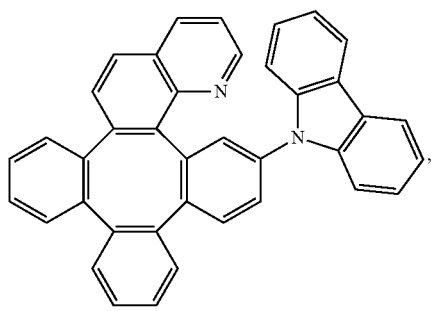
Compound P4
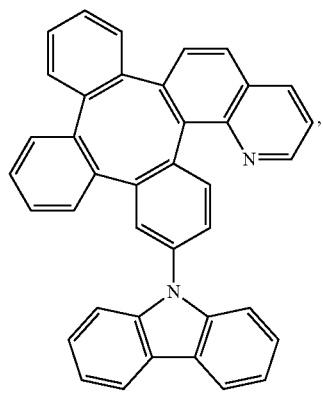
Compound P5
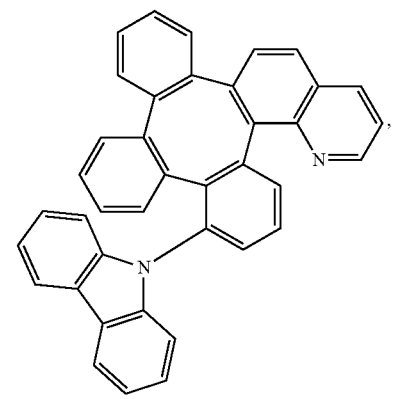
Compound P6
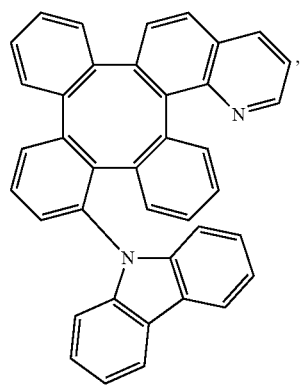
Compound P7
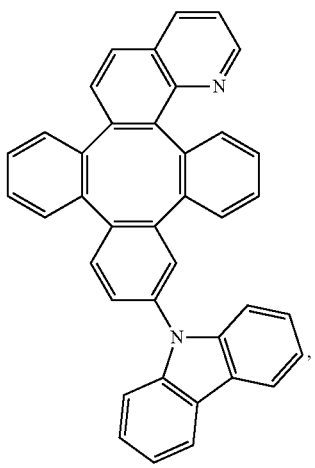
Compound P8
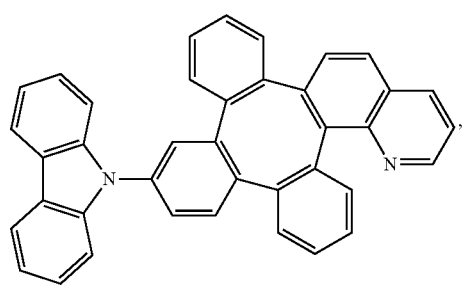
Compound P9
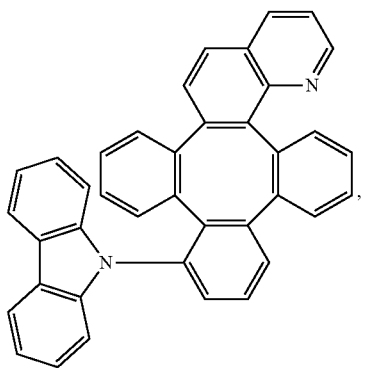
Compound P10
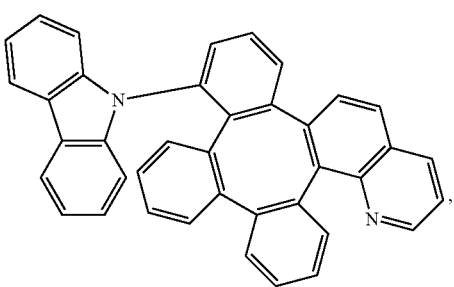

Compound P11
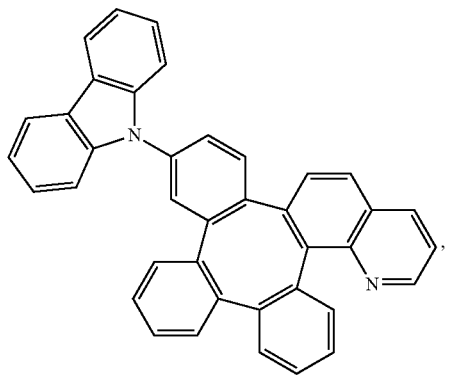
Compound P12
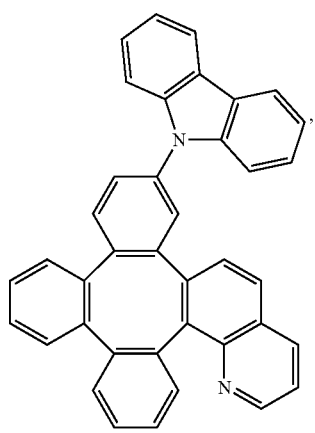
Compound P13
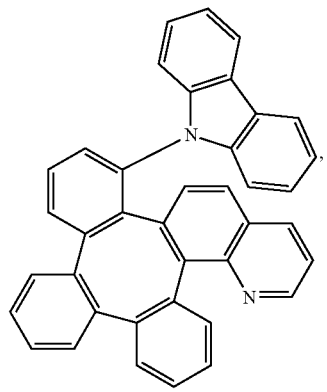
Compound P14
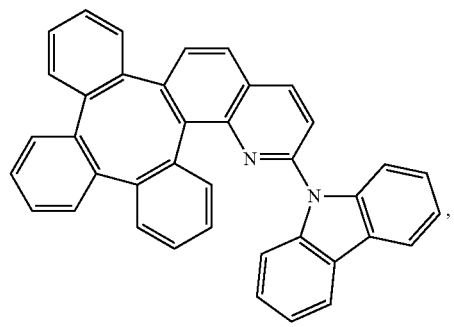
Compound P15
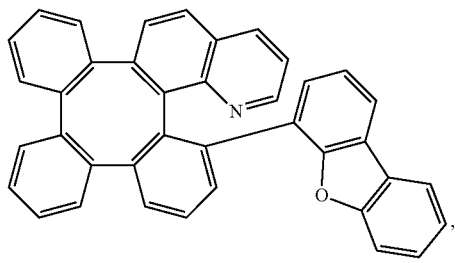
Compound P16
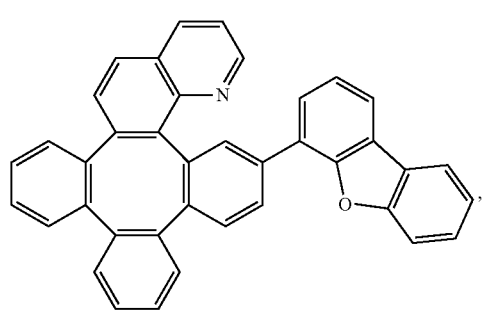
Compound P17
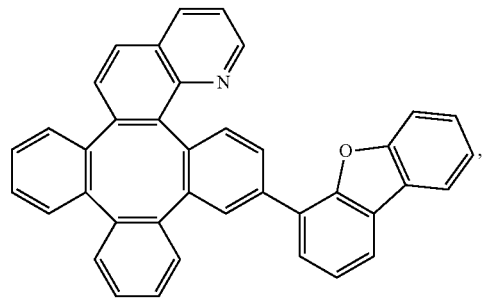
Compound P18
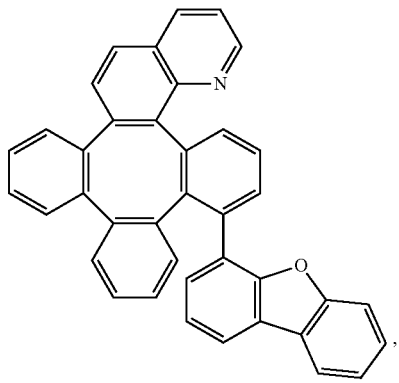

-continued
Compound P19
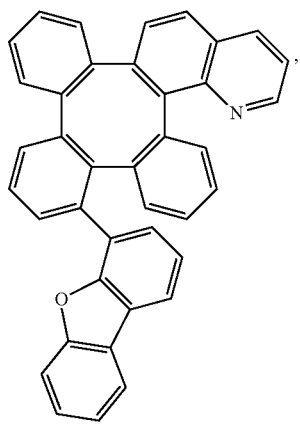
Compound P20
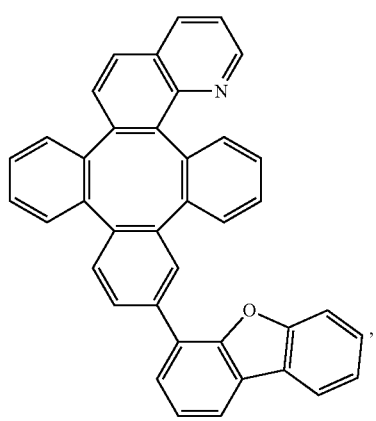
Compound P21
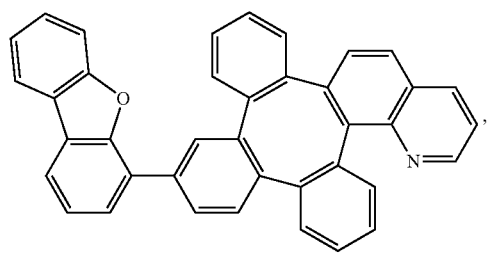
Compound P22
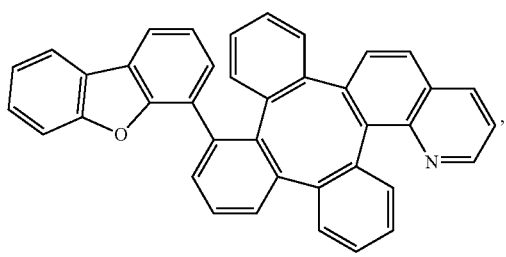
-continued
Compound P23
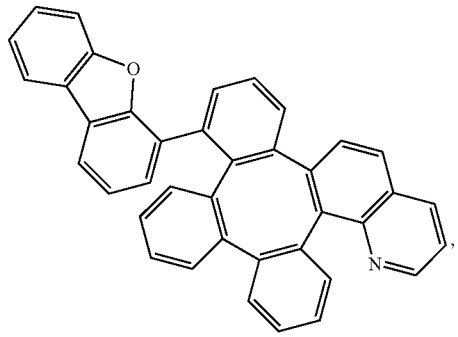
Compound P24
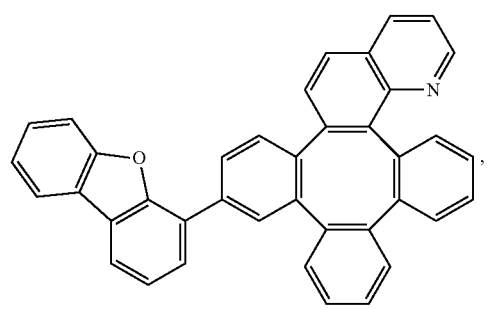
Compound P25
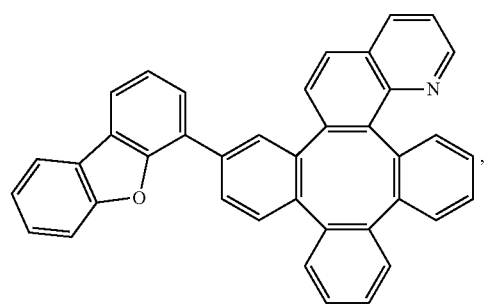
Compound P26
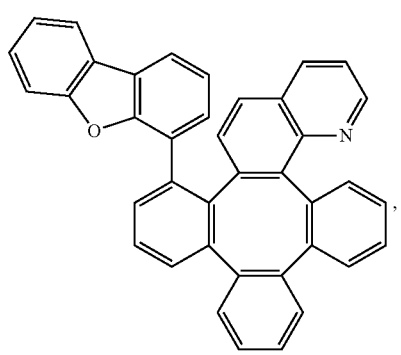

Compound P27
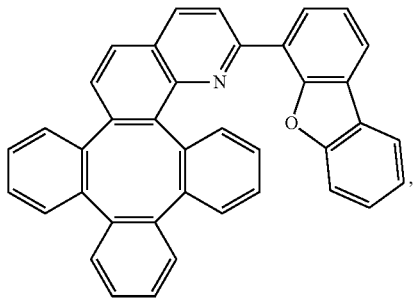
Compound P28
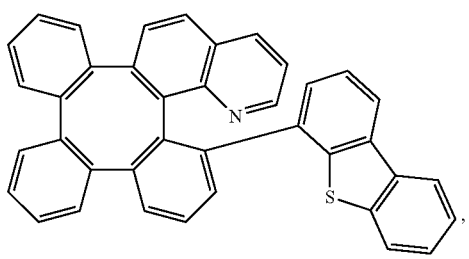
Compound P29
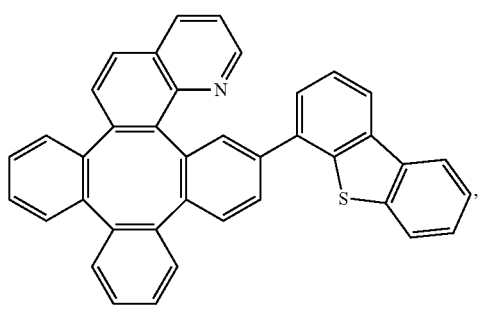
Compound P30
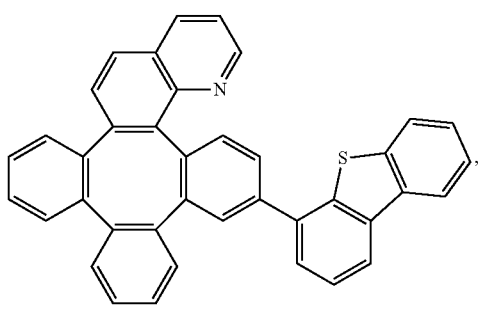
Compound P31
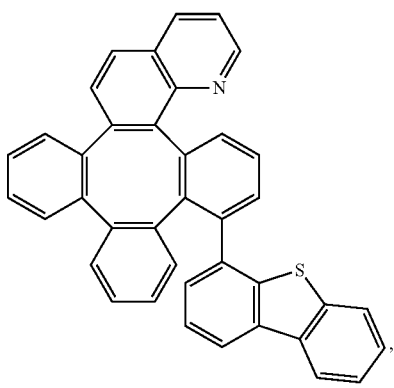
Compound P32
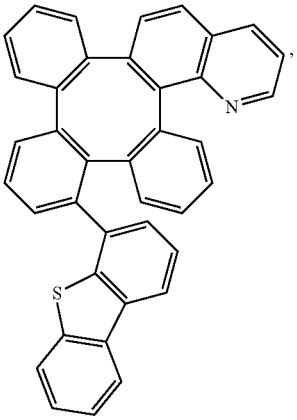
Compound P33
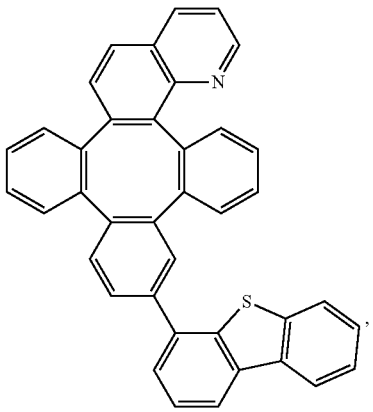
Compound P34
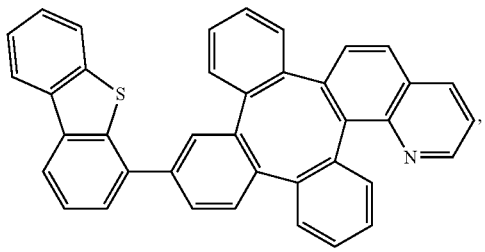
Compound P35
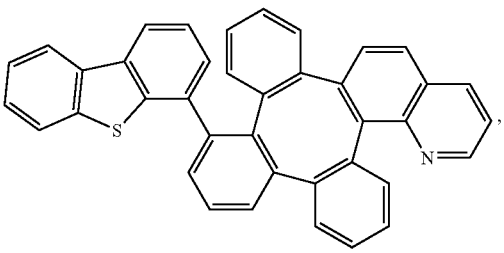

-continued
Compound P36
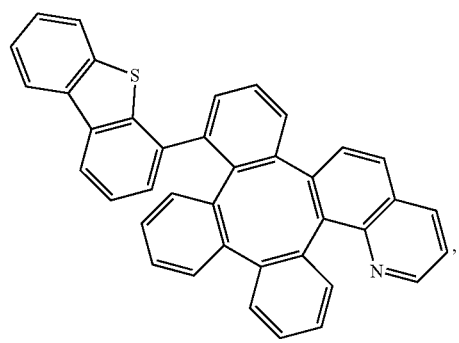
Compound P37
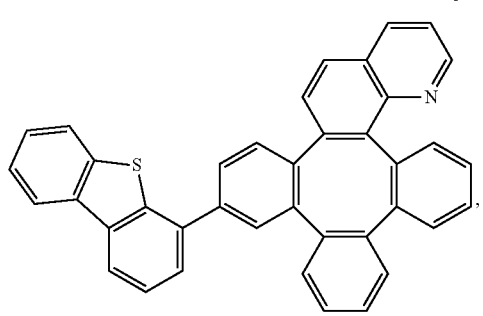
Compound P38
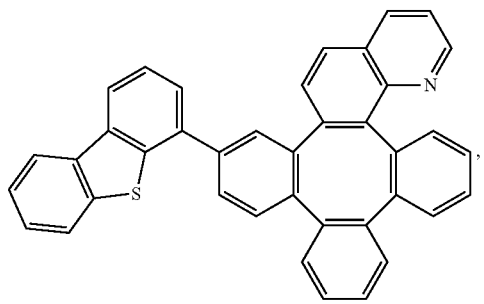
Compound P39
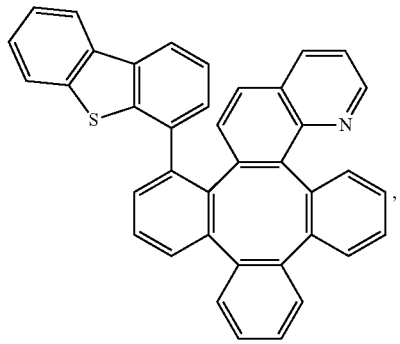
-continued
Compound P40
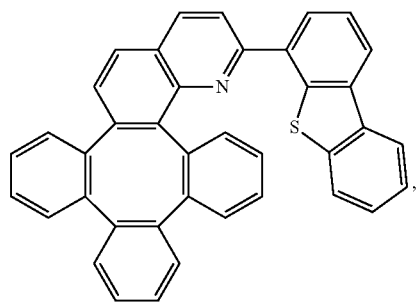
Compound MA1
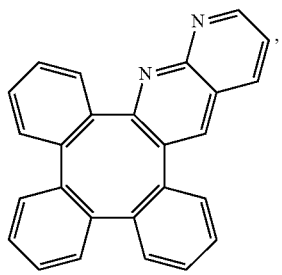
Compound MA2
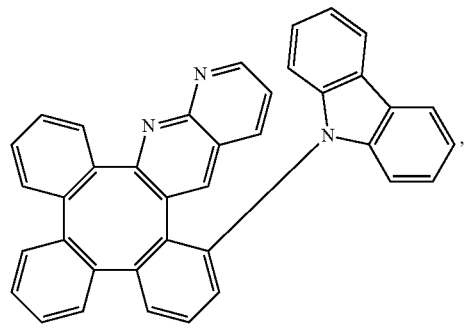
Compound MA3
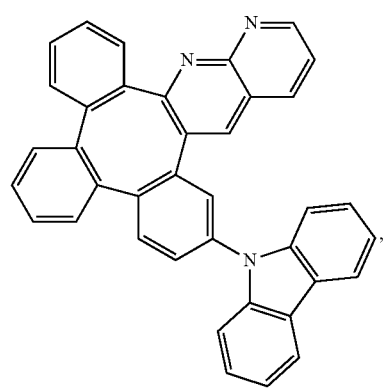

Compound MA4
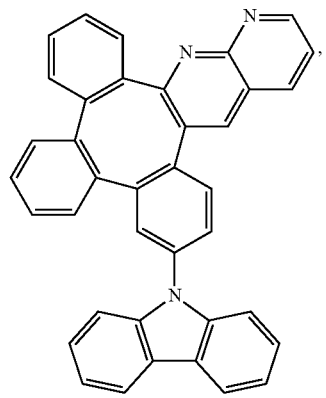
Compound MA5
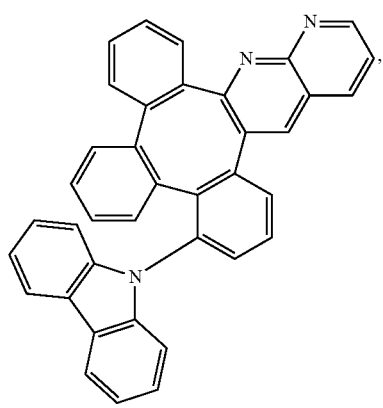
Compound MA6
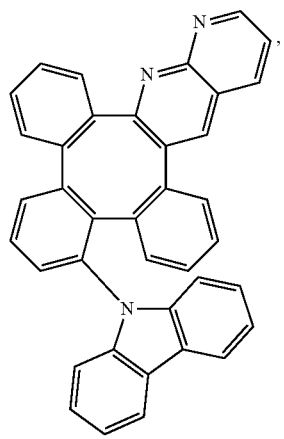
Compound MA7
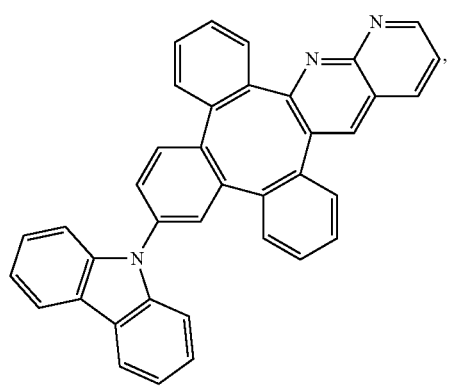
Compound MA8
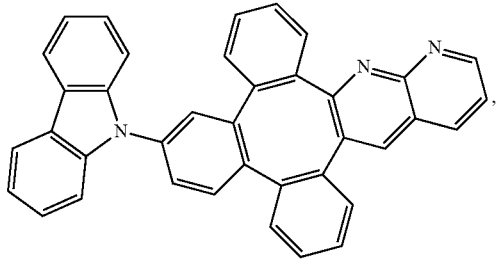
Compound MA9
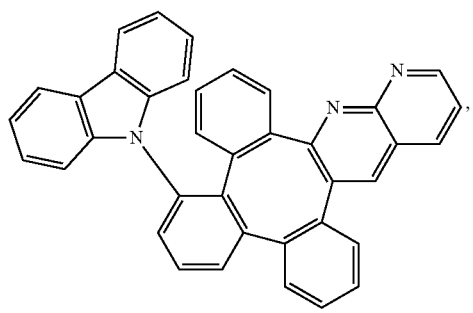
Compound MA10
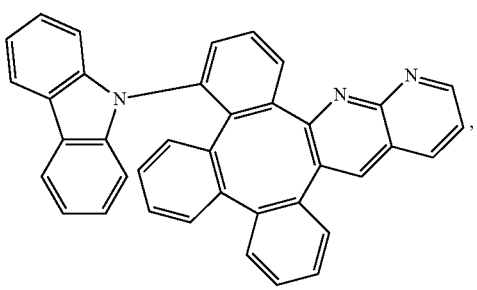
Compound MA11
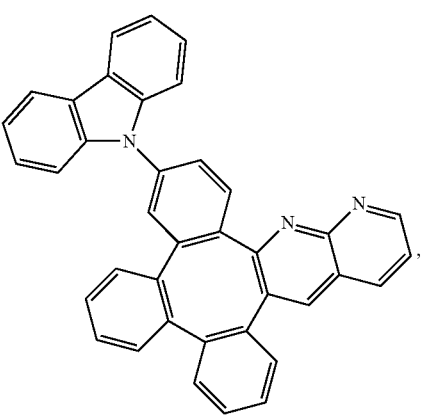

-continued
Compound MA12
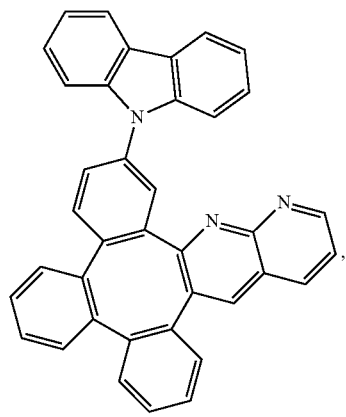
Compound MA13
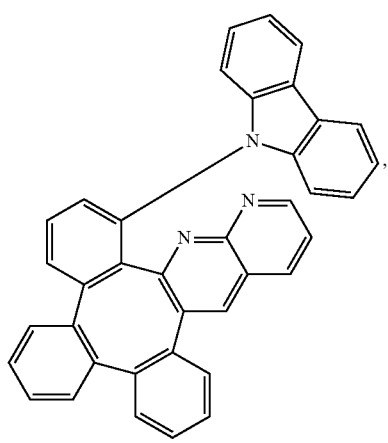
Compound MA14
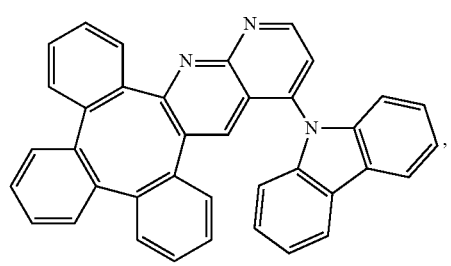
Compound MA15
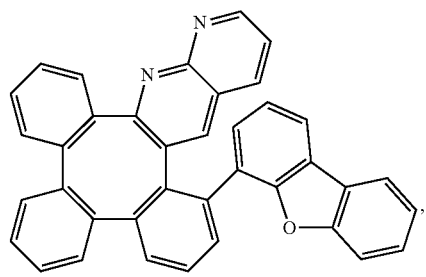
Compound MA16
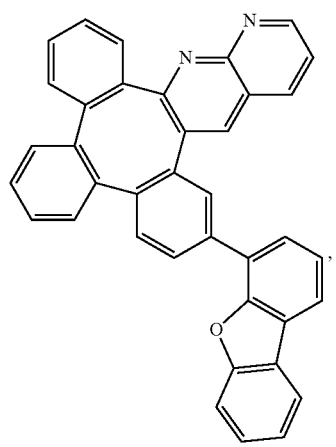
Compound MA17
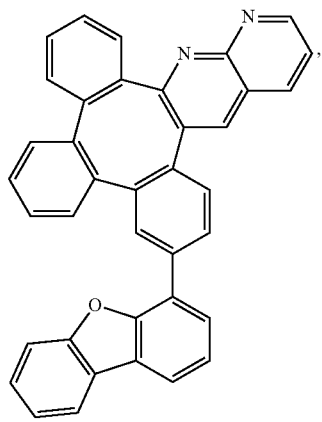
Compound MA18
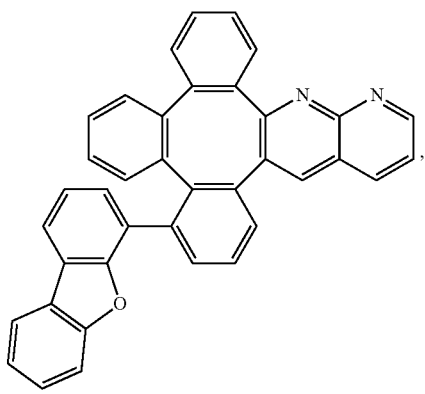

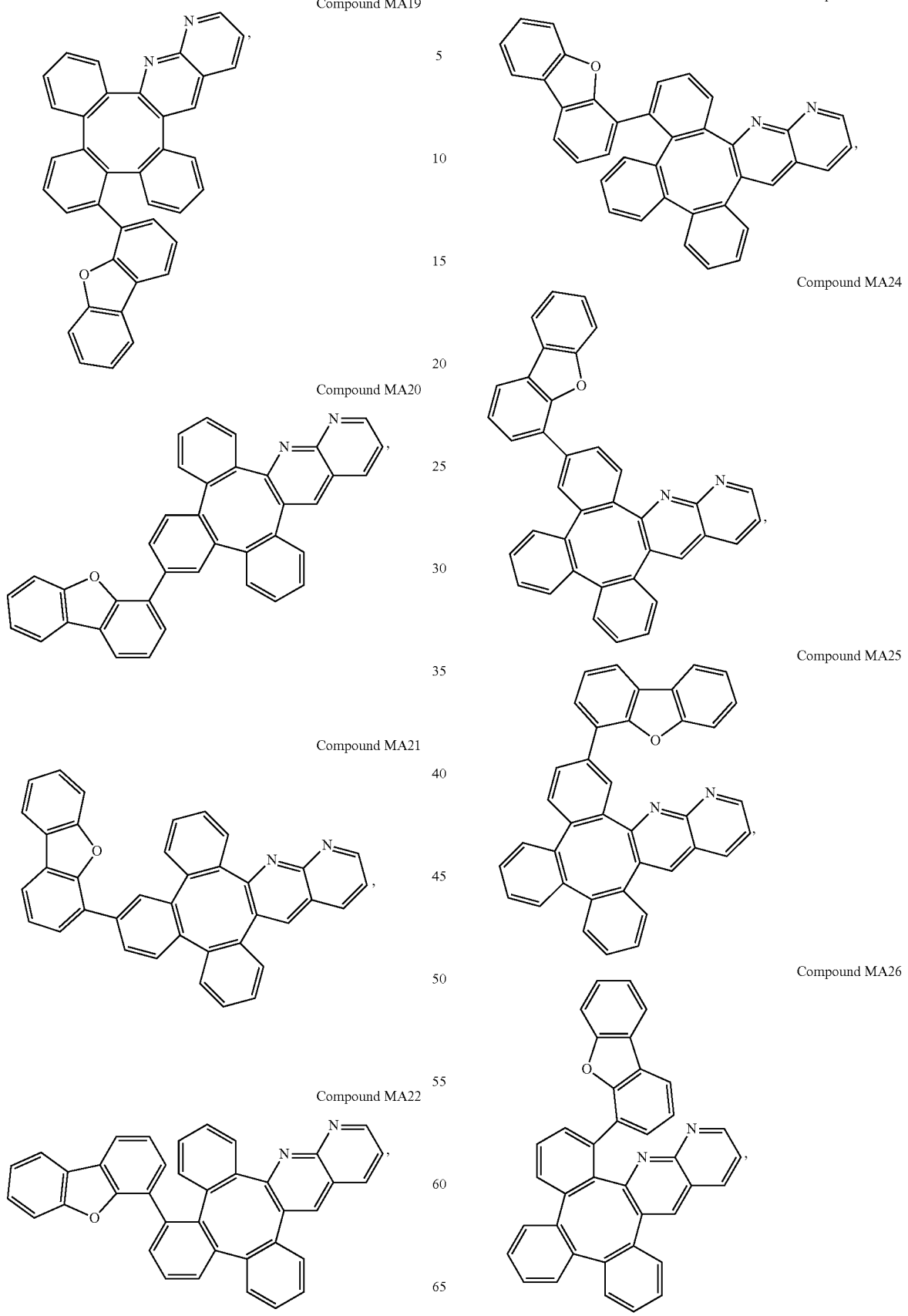

-continued
Compound MA27
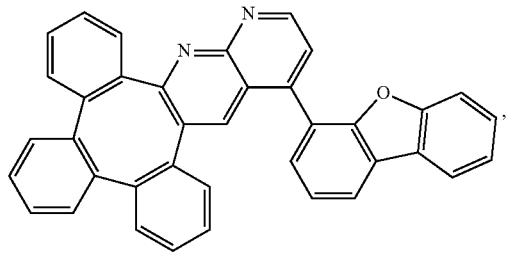
Compound MA28
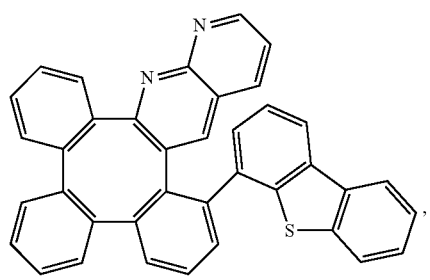
Compound MA29
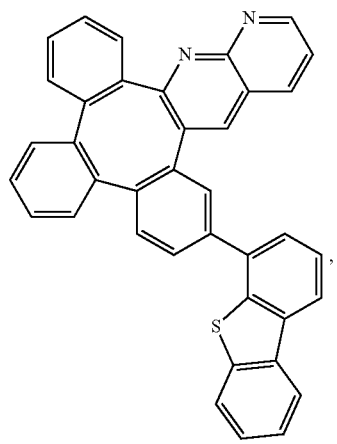
Compound MA30
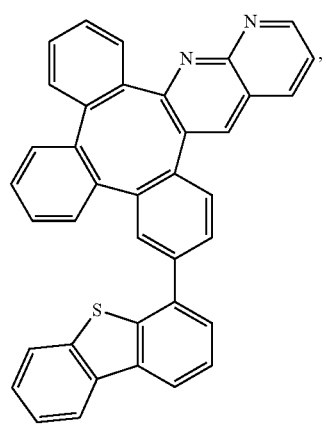
-continued
Compound MA31
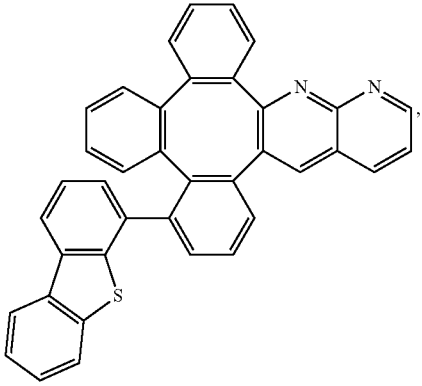
Compound MA32
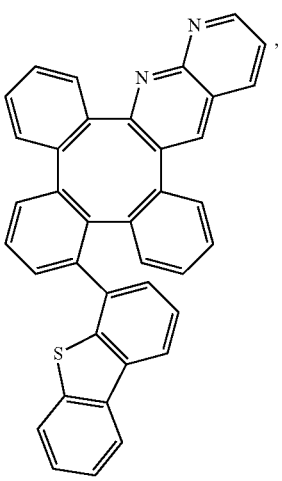
Compound MA33
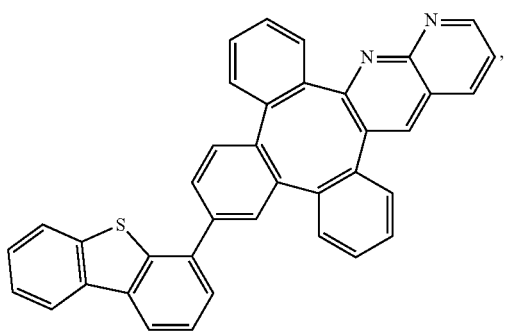
Compound MA34
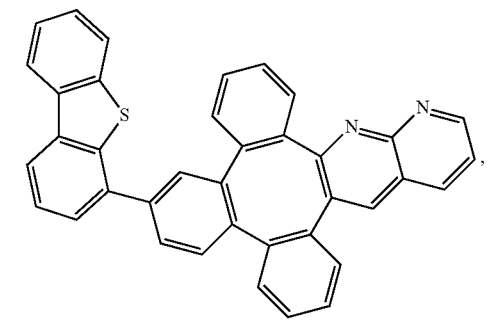

-continued
Compound MA35
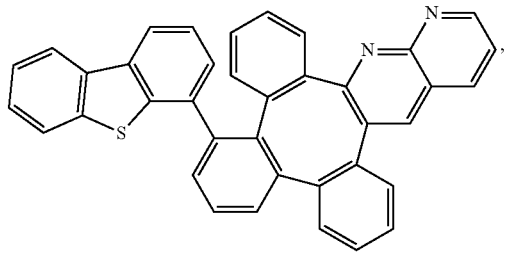
Compound MA36
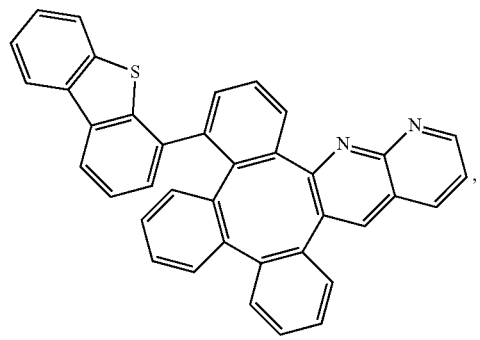
Compound MA37
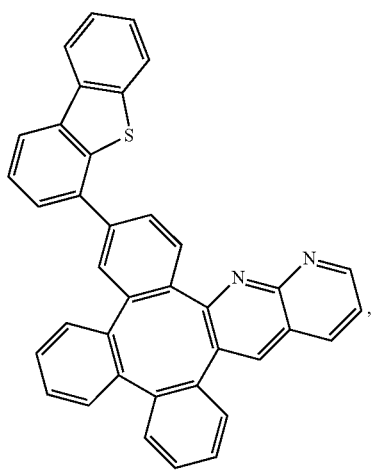
Compound MA38
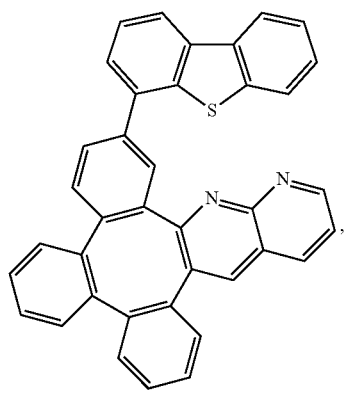
Compound MA39
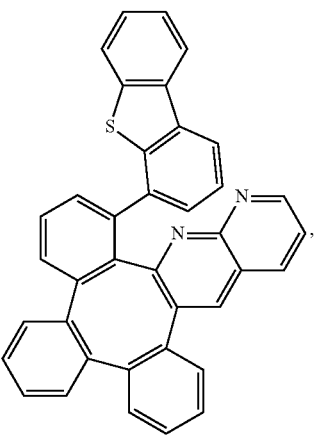
Compound MA40
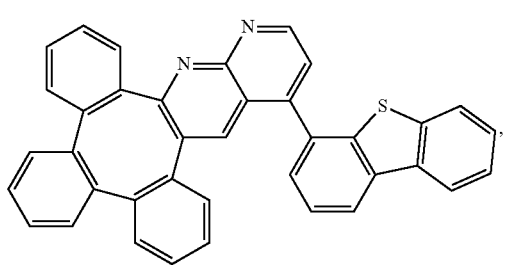
Compound MB1
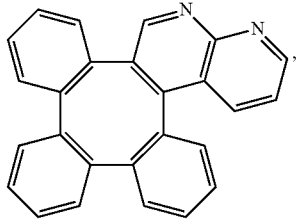
Compound MB2
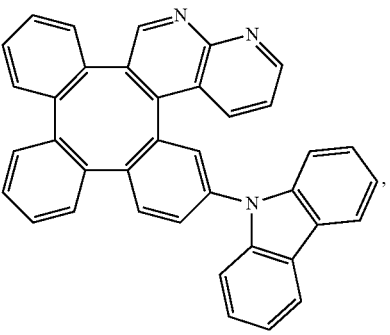
Compound MB3
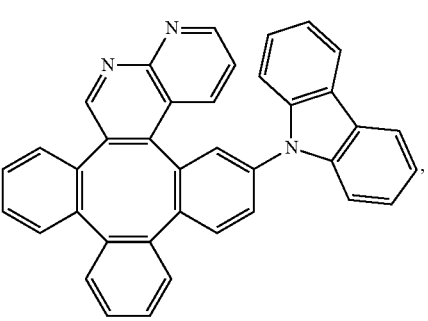

Compound MB4
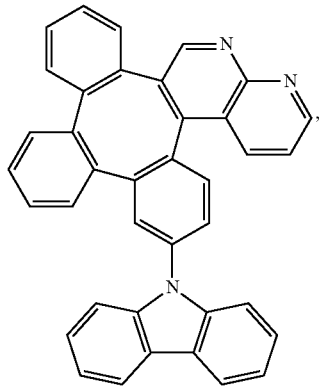
Compound MB5
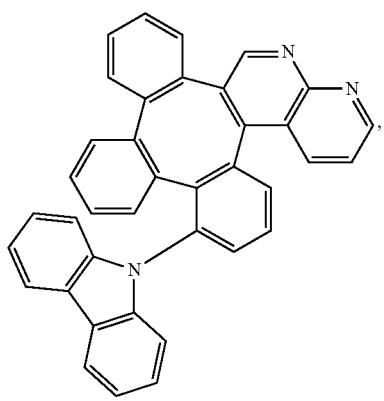
Compound MB6
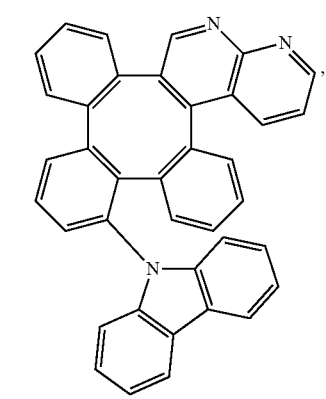
Compound MB7
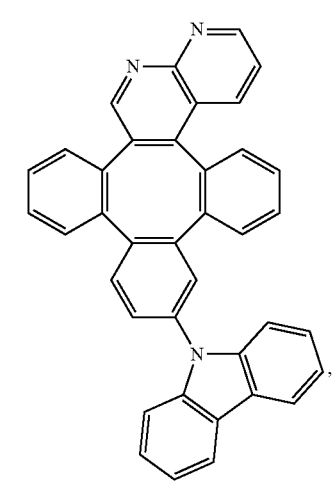
Compound MB8
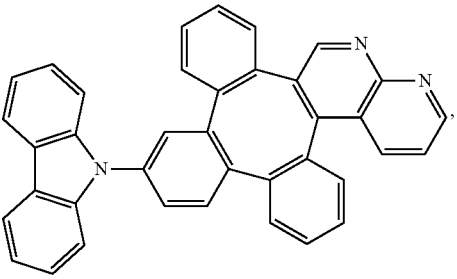
Compound MB9
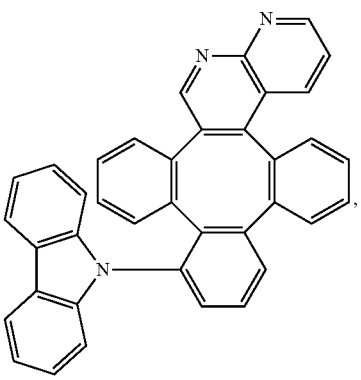
Compound MB10
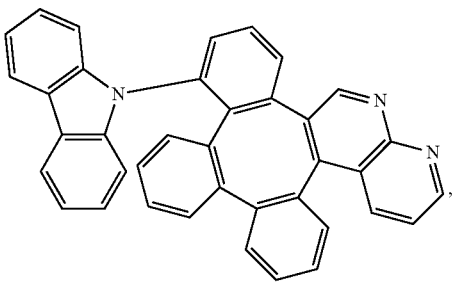
Compound MB11
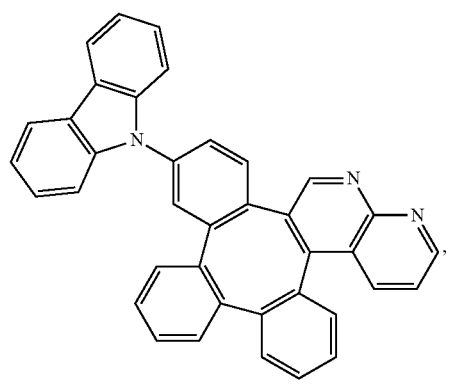

Compound MB12
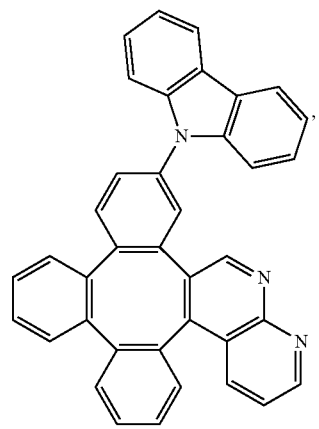
Compound MB13
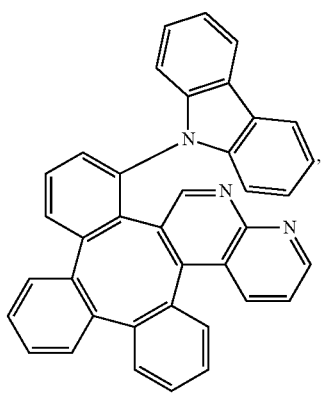
Compound MB14
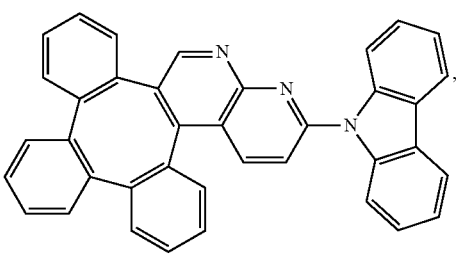
Compound MB15
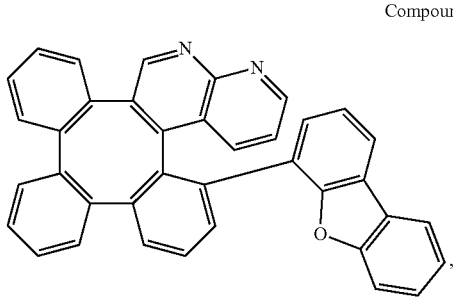
Compound MB16
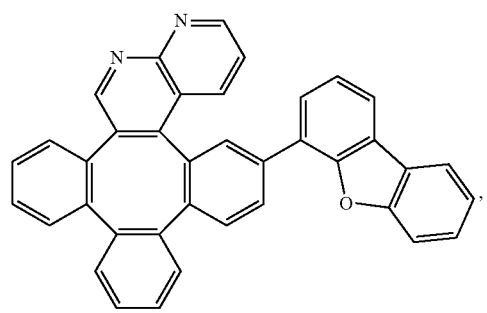
Compound MB17
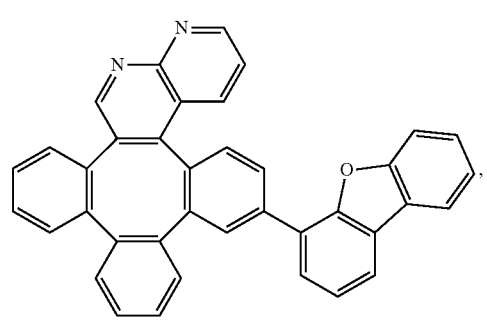
Compound MB18
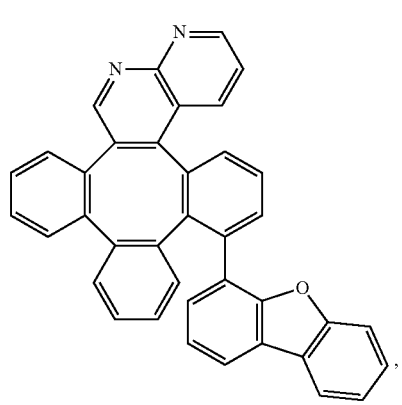
Compound MB19

Compound MB20
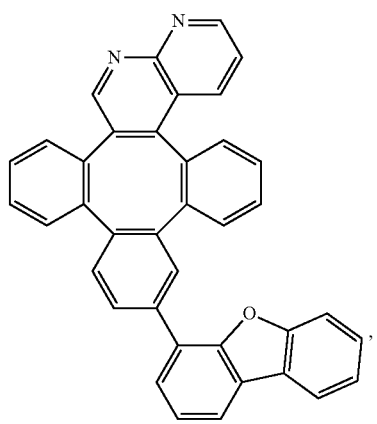
Compound MB21
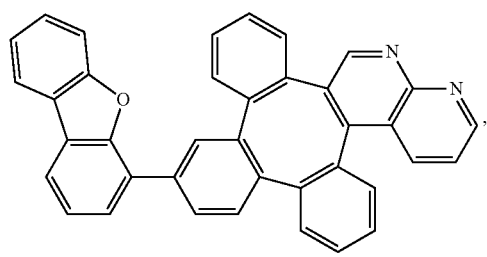
Compound MB22
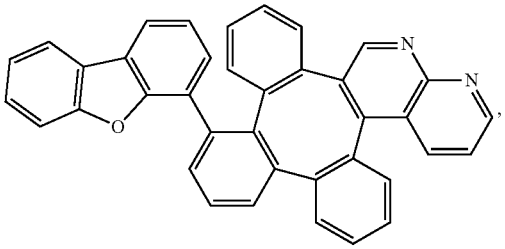
Compound MB23
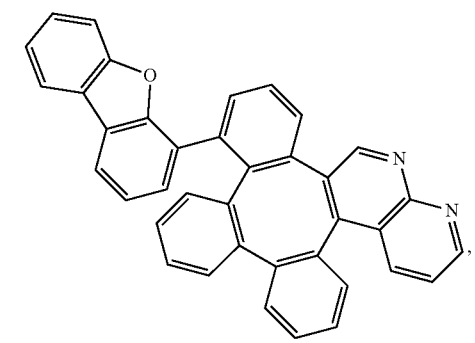
Compound MB24
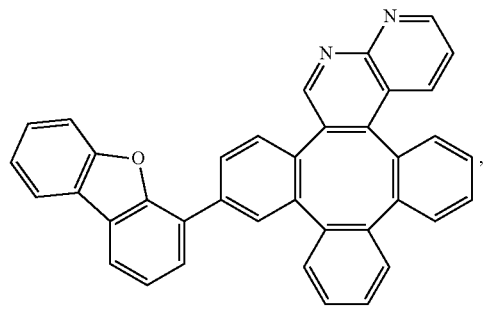
Compound MB25
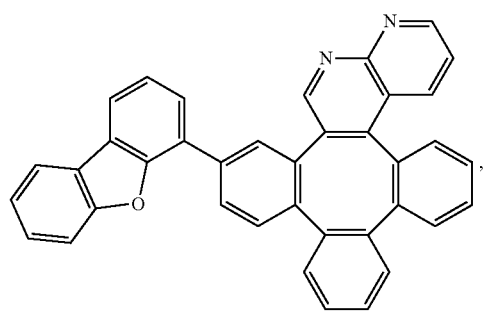
Compound MB26
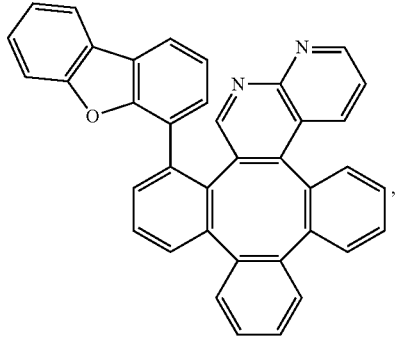
Compound MB27
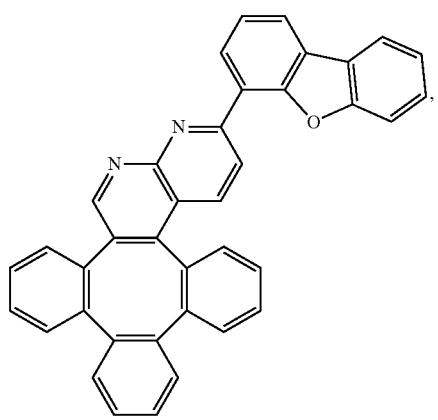

Compound MB28
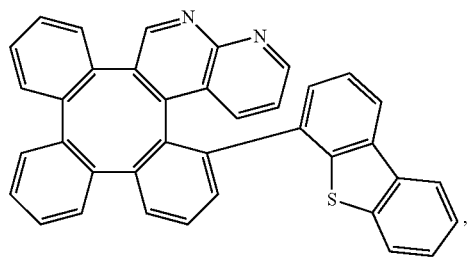
Compound MB29
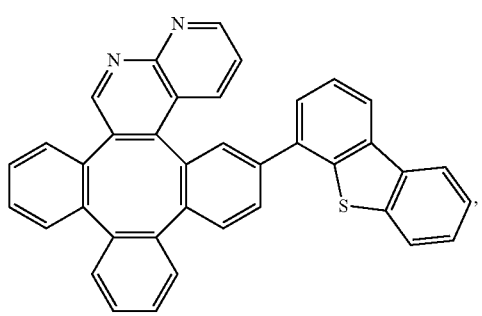
Compound MB30
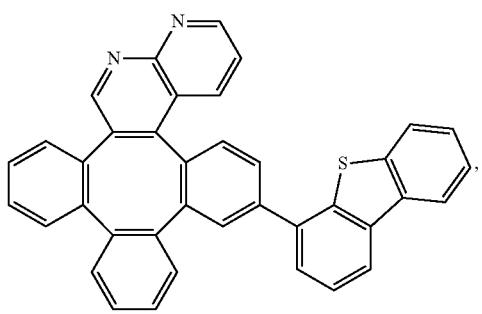
Compound MB31
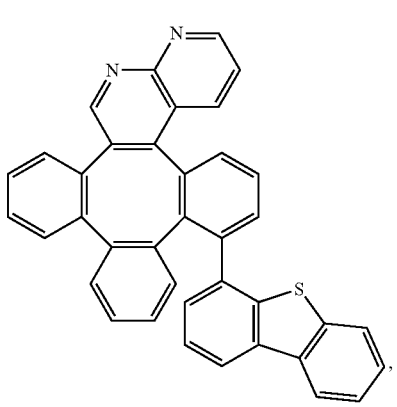
Compound MB32
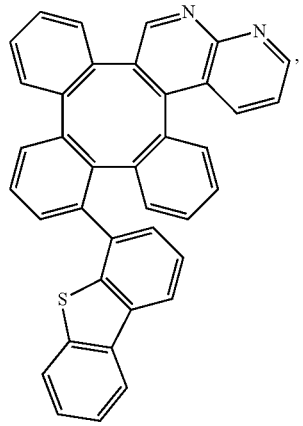
Compound MB33
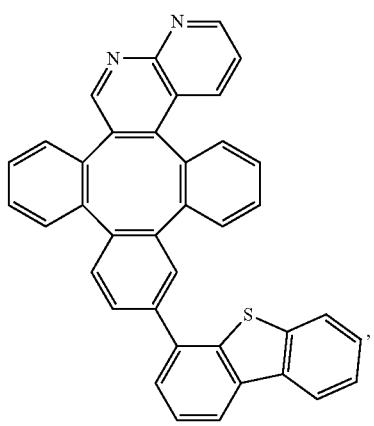
Compound MB34
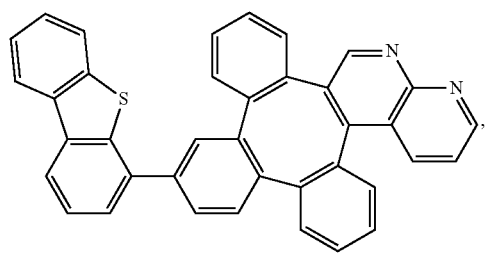
Compound MB35
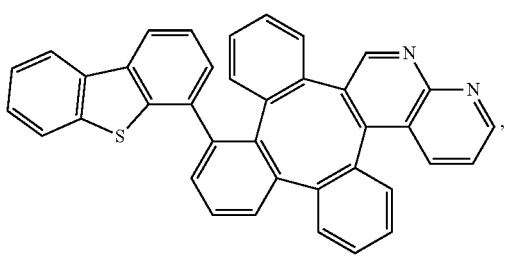

Compound MB36
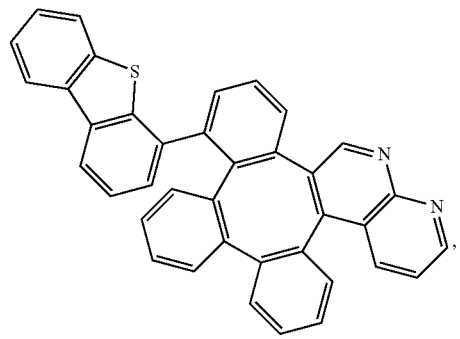
Compound MB37
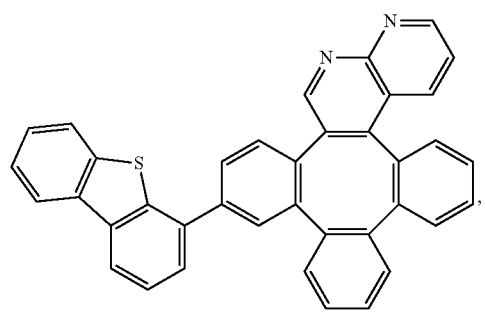
Compound MB38
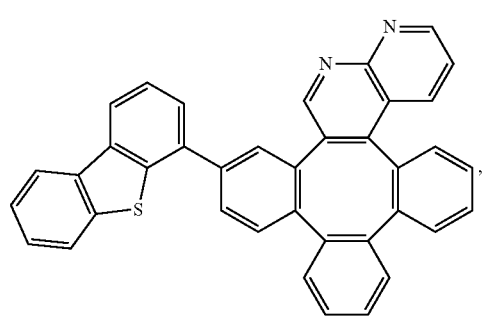
Compound MB39
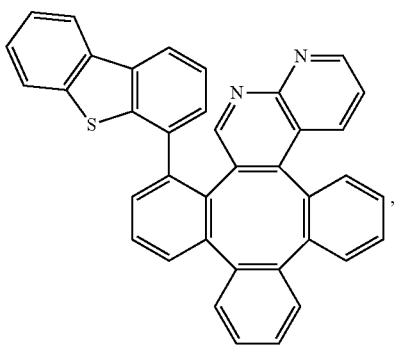
Compound MB40
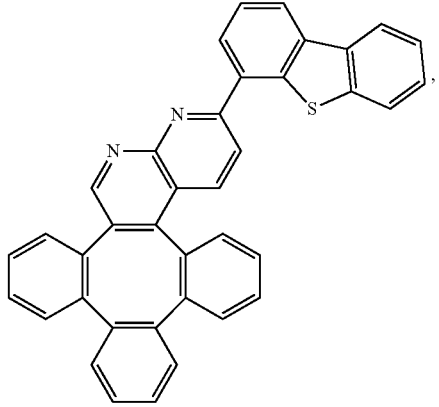
Compound MC1
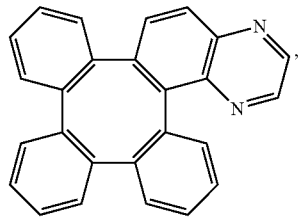
Compound MC2
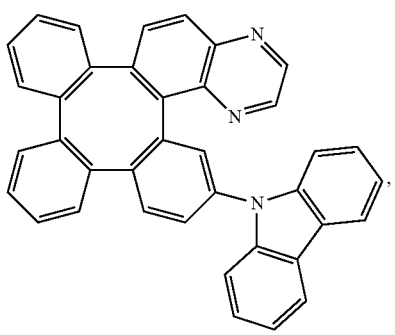
Compound MC3
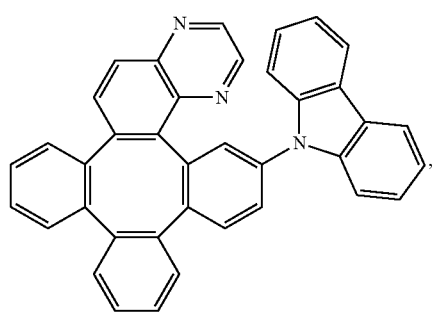

Compound MC4
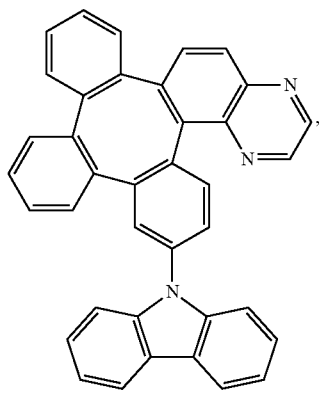
Compound MC5
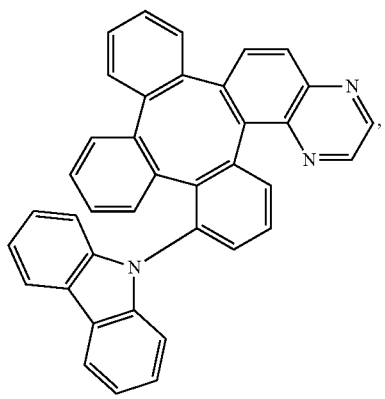
Compound MC6
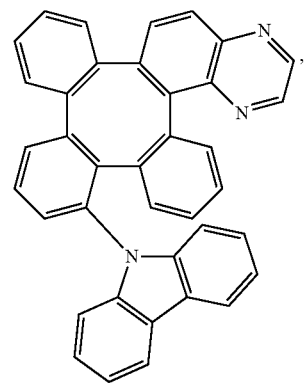
Compound MC7
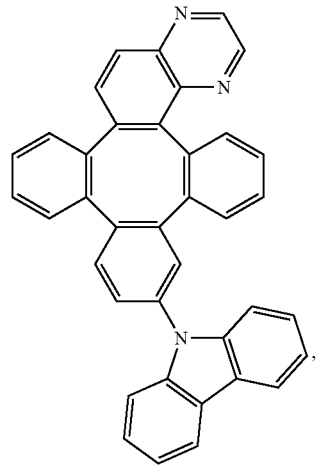
Compound MC8
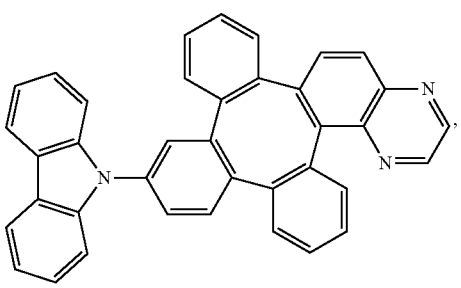
Compound MC9
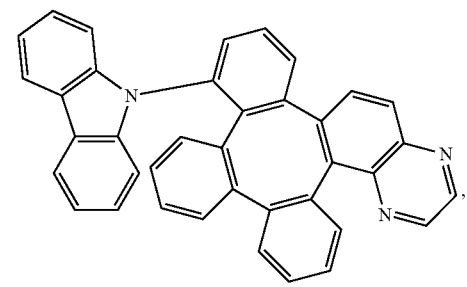
Compound MC10
Compound MC11
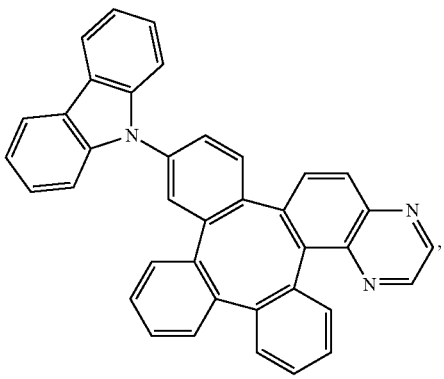

Compound MC12
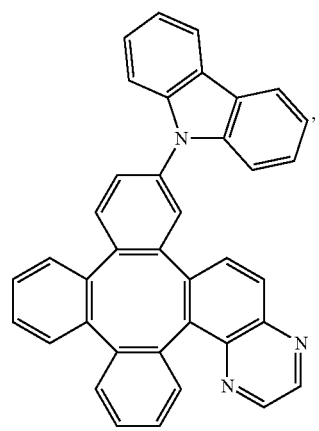
Compound MC13
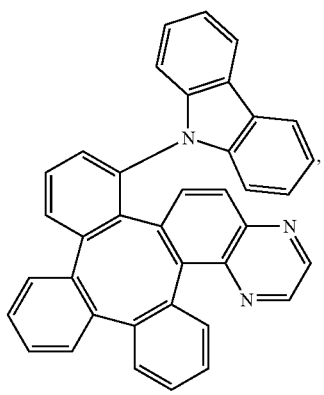
Compound MC14
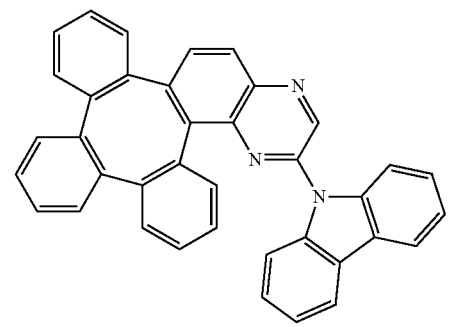
Compound MC15
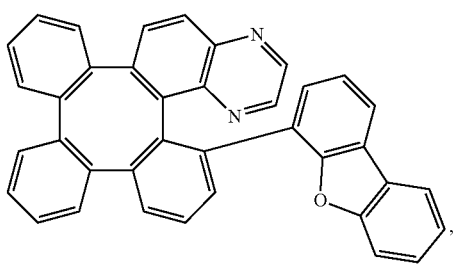
Compound MC16
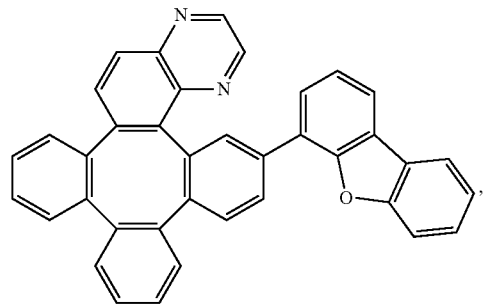
Compound MC17
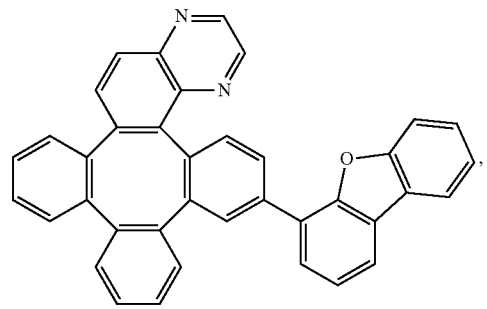
Compound MC18
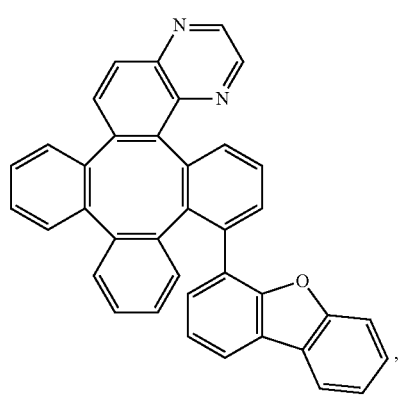
Compound MC19
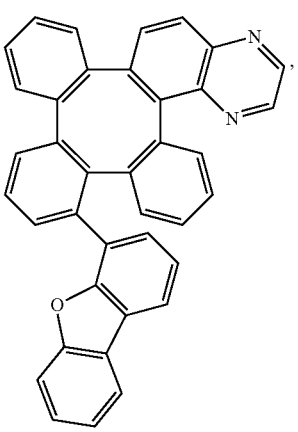

-continued
Compound MC20
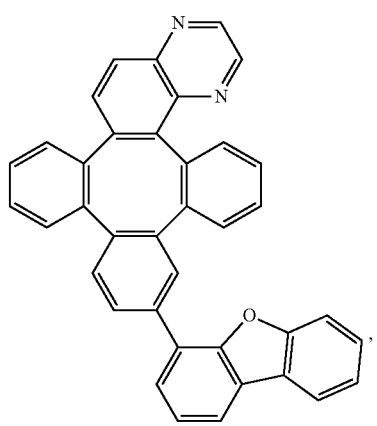
Compound MC21
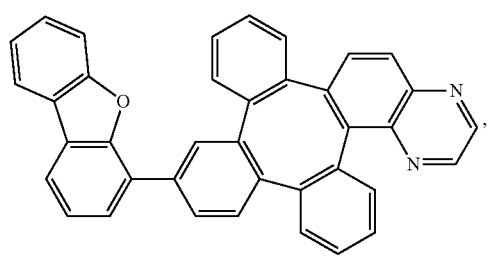
Compound MC22
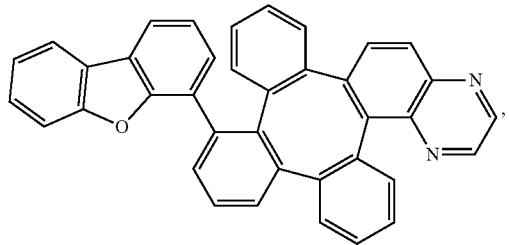
Compound MC23
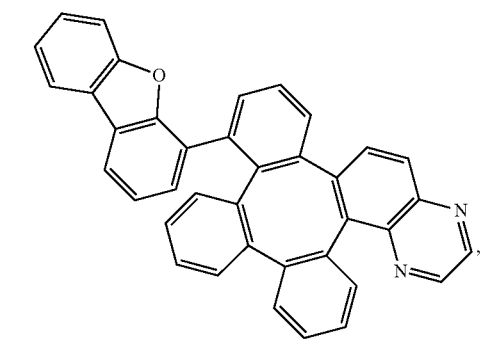
Compound MC24
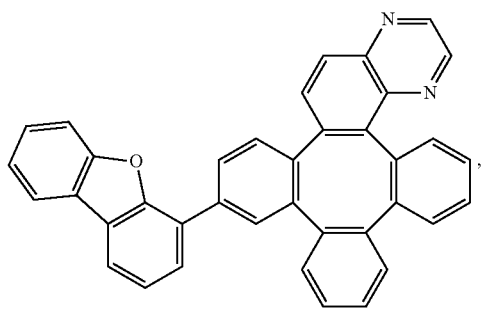
Compound MC25
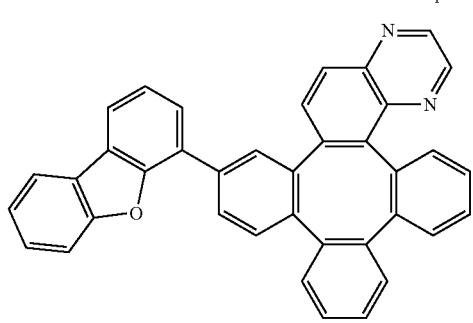
Compound MC26
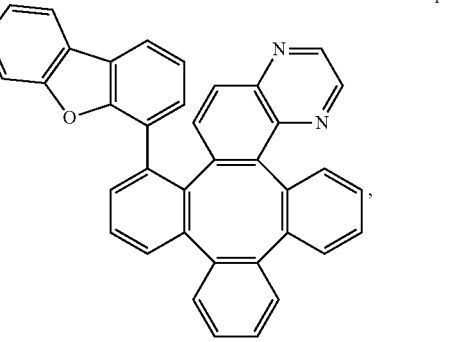
Compound MC27
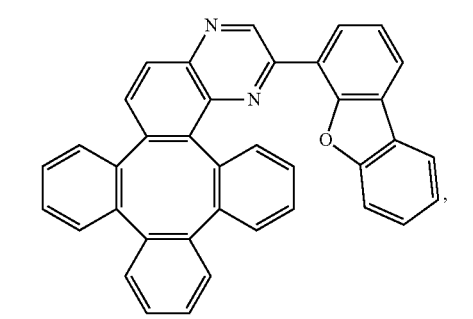
Compound MC28
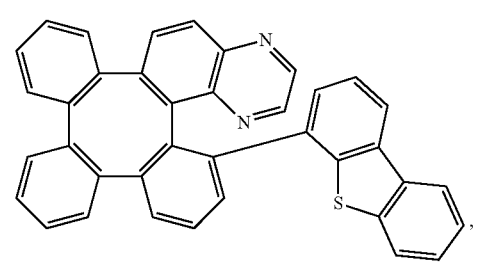

-continued
Compound MC29
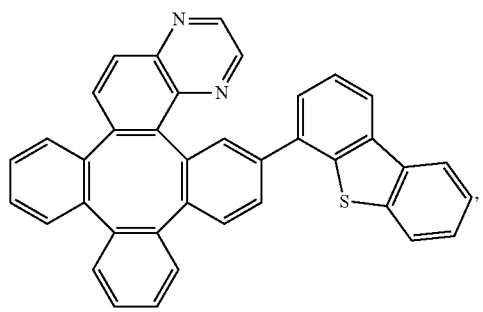
Compound MC30
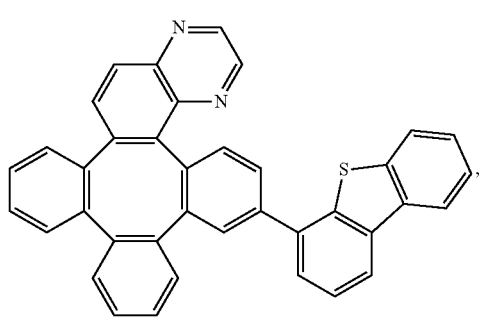
Compound MC31
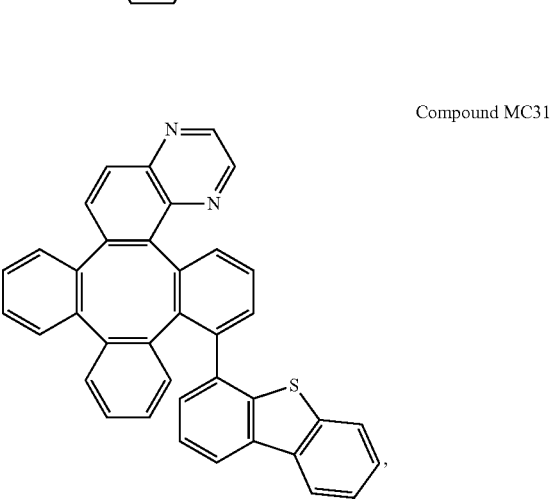
Compound MC32
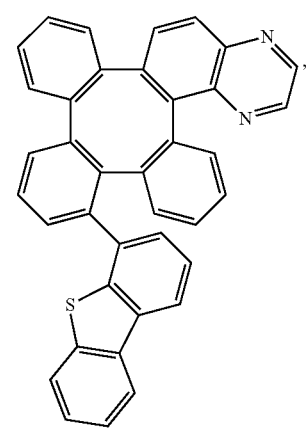
-continued
Compound MC33
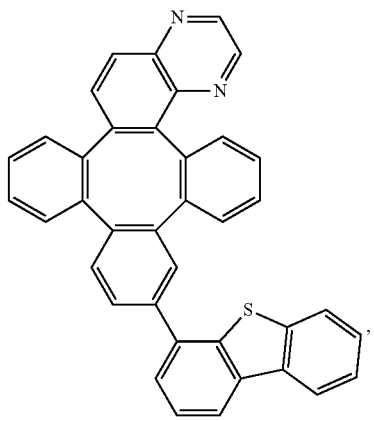
Compound MC34
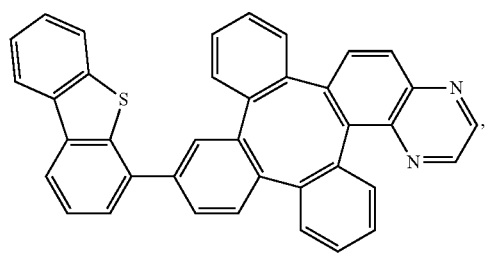
Compound MC35
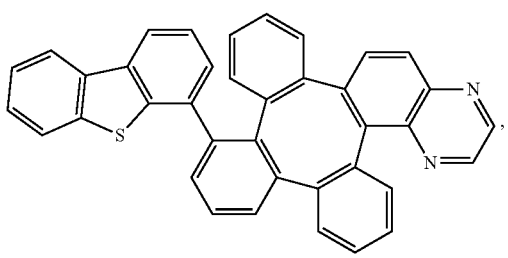
Compound MC36
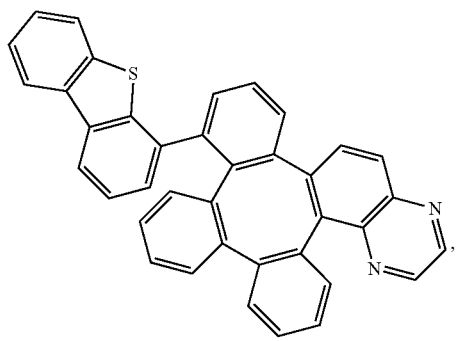

Compound MC37
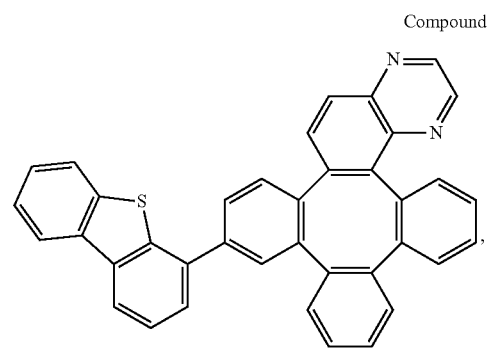
Compound MC38
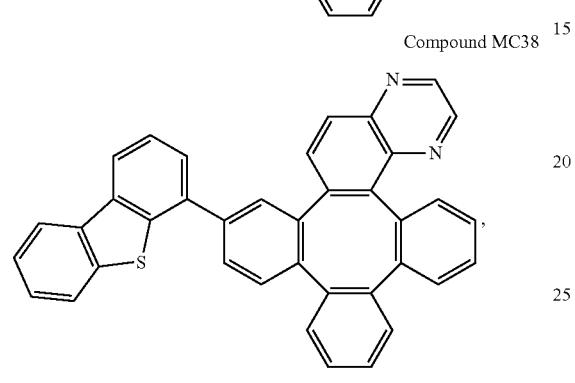
Compound MC39
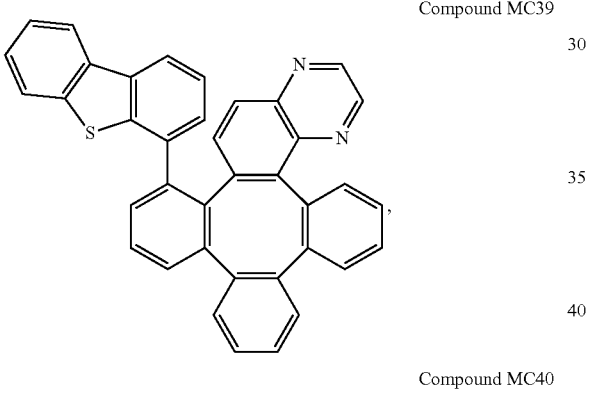
Compound MC40
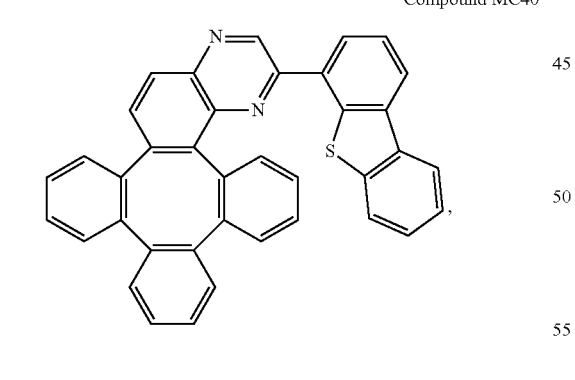
Compound NA1
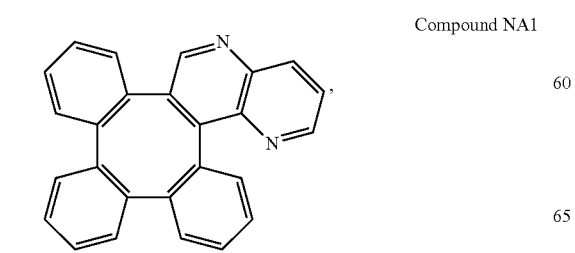
Compound NA2
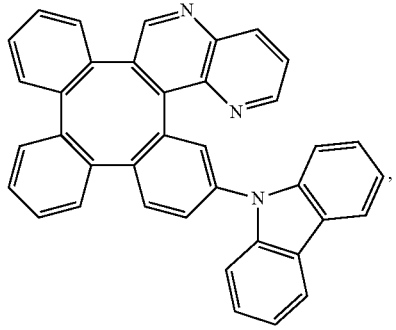
Compound NA3
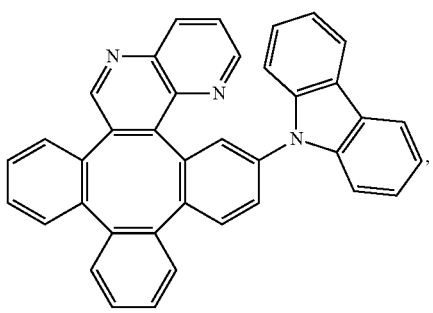
Compound NA4
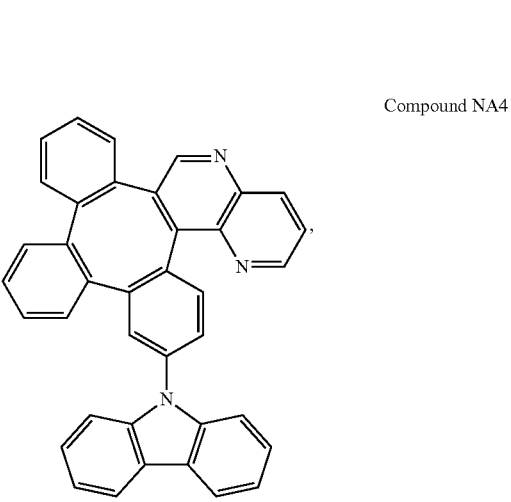
Compound NA5
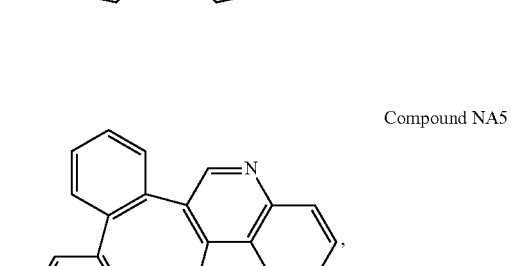

Compound NA6
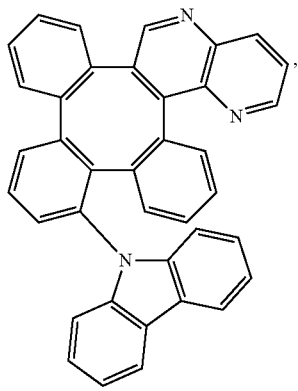
Compound NA7
Compound NA8
Compound NA9
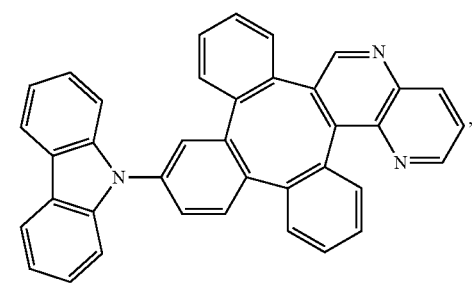
Compound NA10
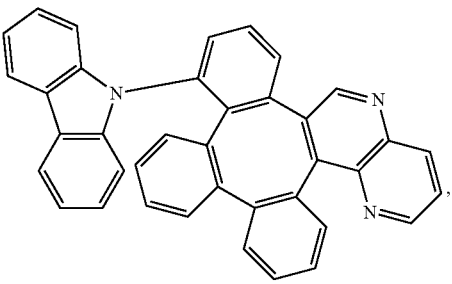
Compound NA11
Compound NA12
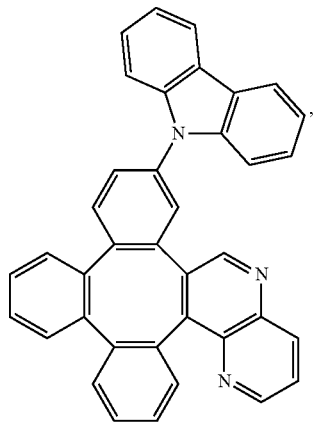
Compound NA13
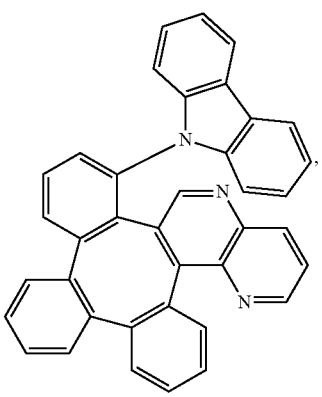

-continued
Compound NA14
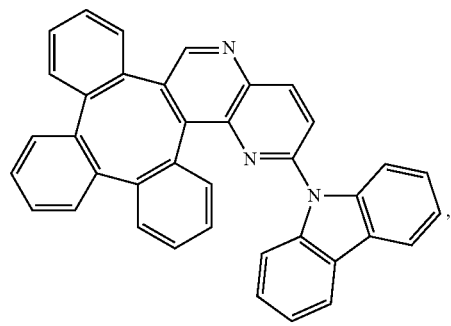
Compound NA15
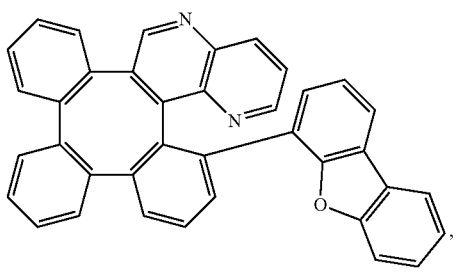
Compound NA16
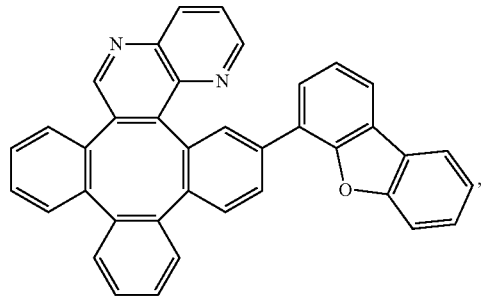
Compound NA17
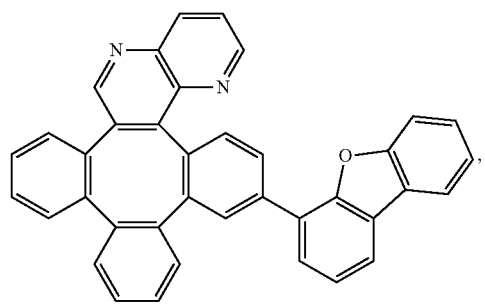
-continued
Compound NA18
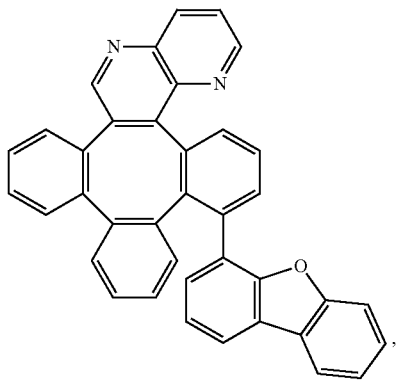
Compound NA19
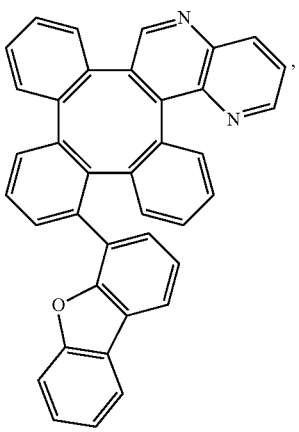
Compound NA20
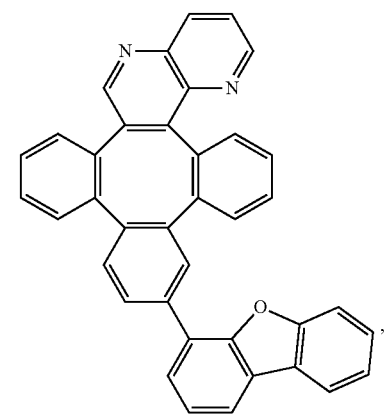
Compound NA21
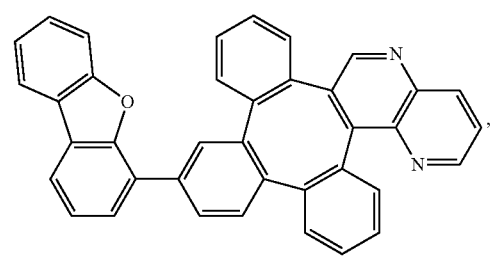

Compound NA22
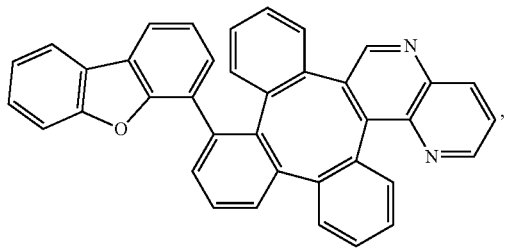
Compound NA23
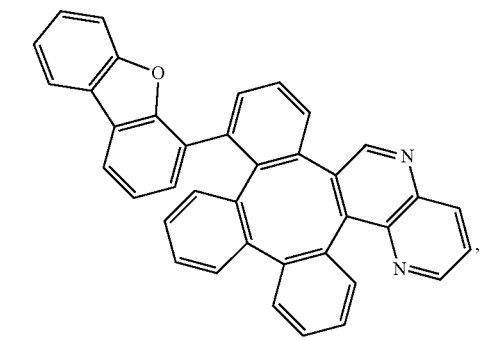
Compound NA24
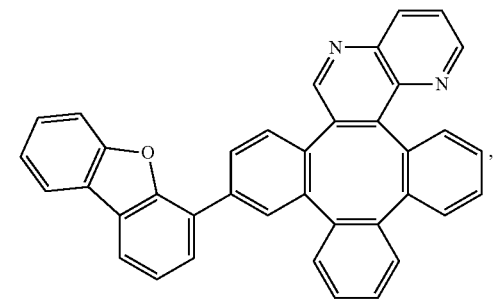
Compound NA25
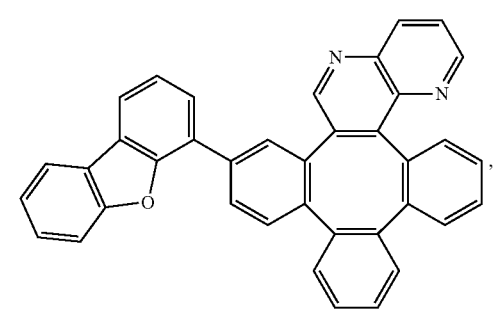
Compound NA26
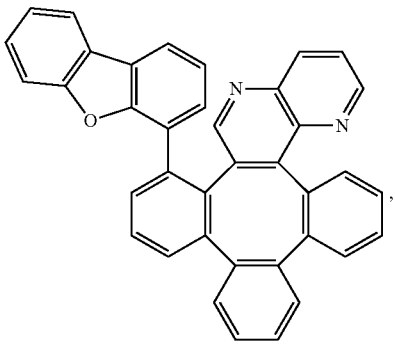
Compound NA27
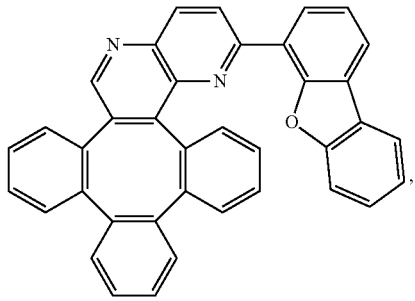
Compound NA28
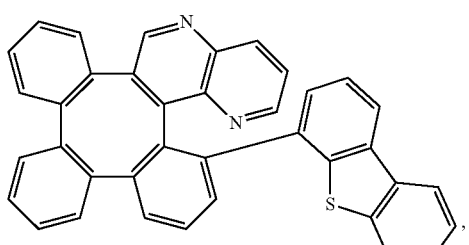
Compound NA29
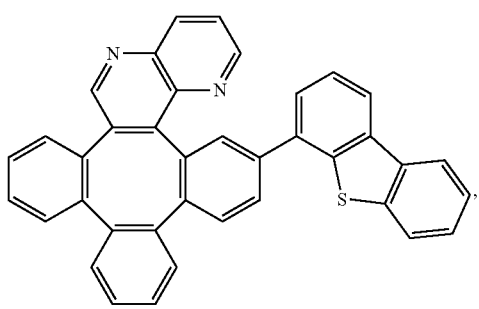
Compound NA30
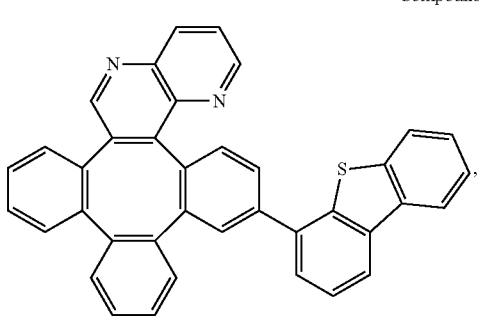
Compound NA31
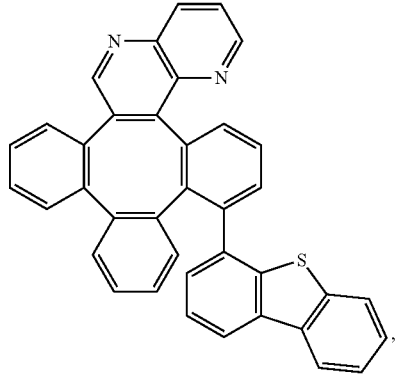

-continued
Compound NA32
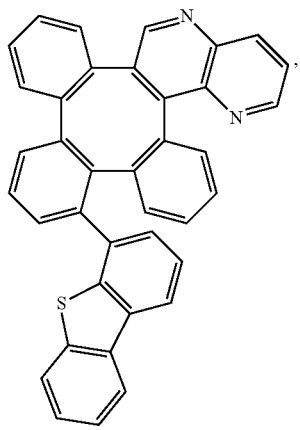
Compound NA33
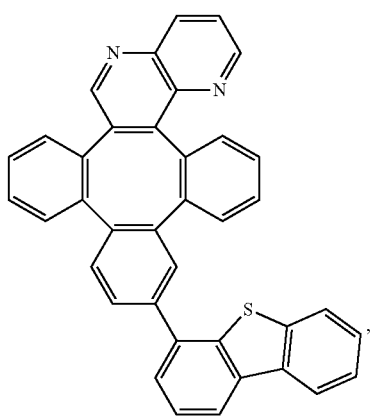
Compound NA34
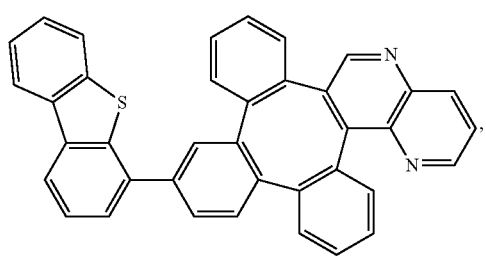
Compound NA35
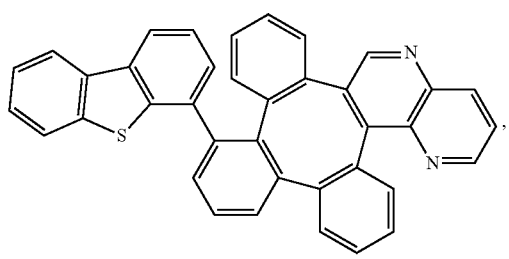
-continued
Compound NA36
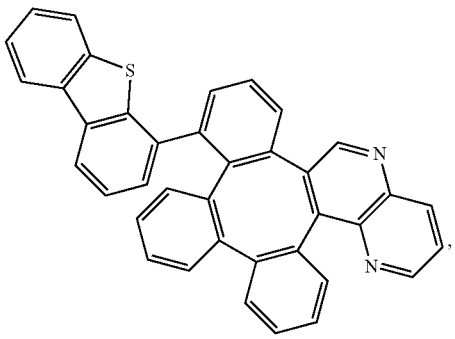
Compound NA37
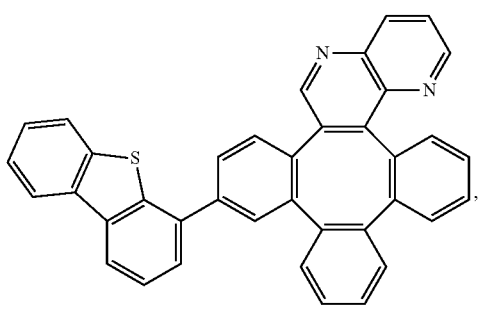
Compound NA38
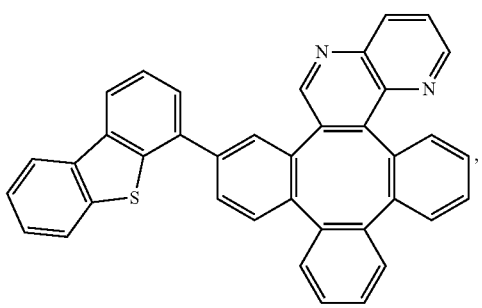
Compound NA39
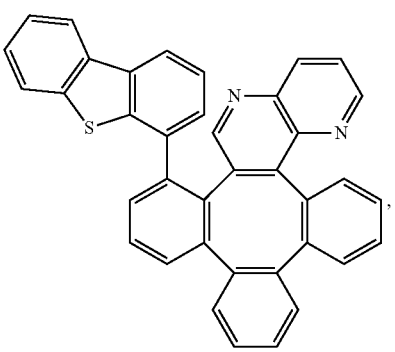

Compound NA40
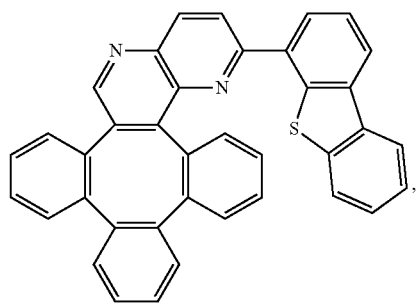
Compound R1
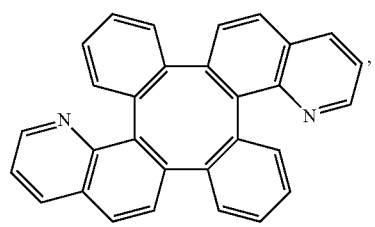
Compound R2
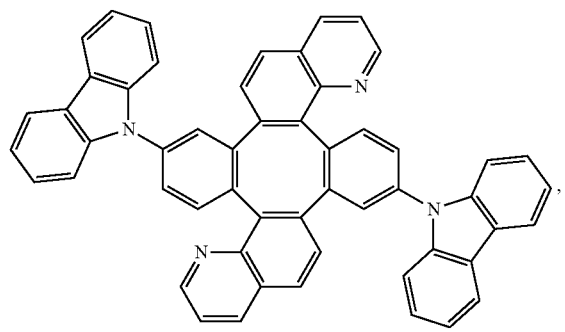
Compound R3
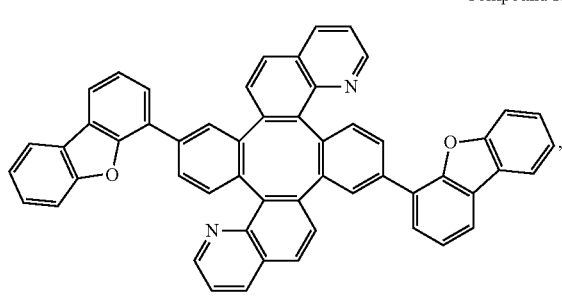
Compound R4
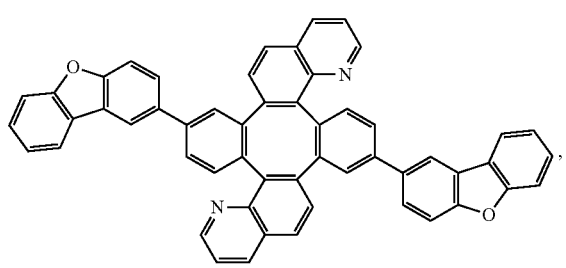
Compound R5
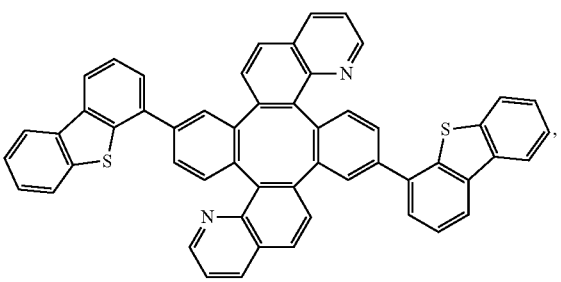
Compound R6
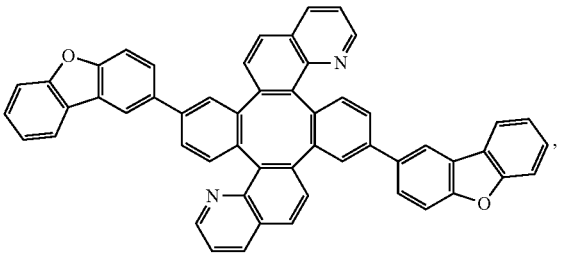
Compound R7
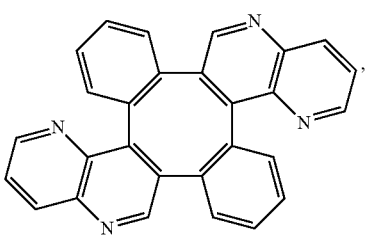
Compound R8
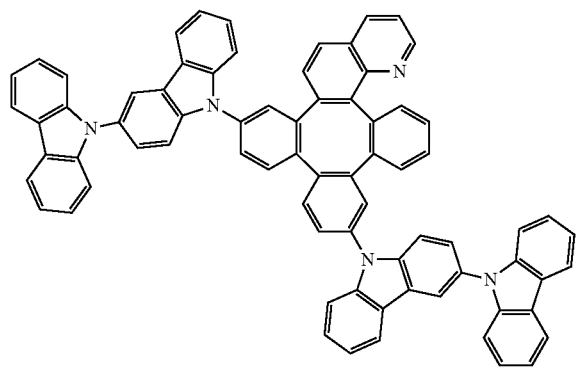
Compound R9
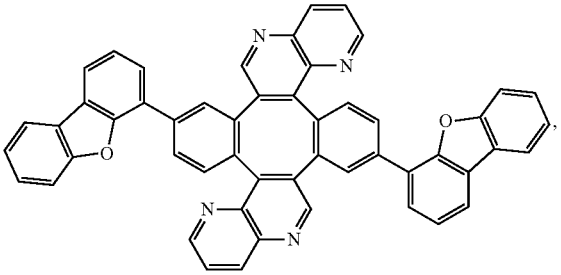

Compound R10
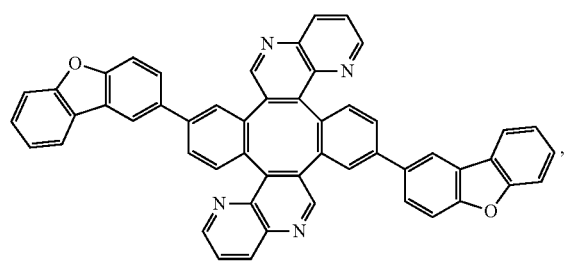
Compound R11
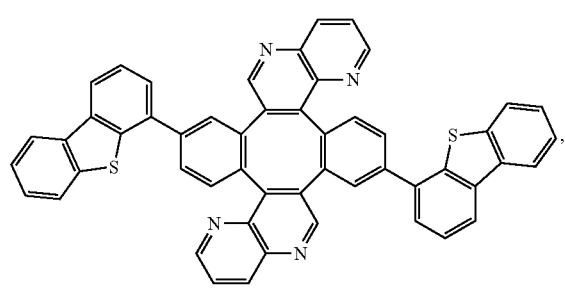
Compound R12
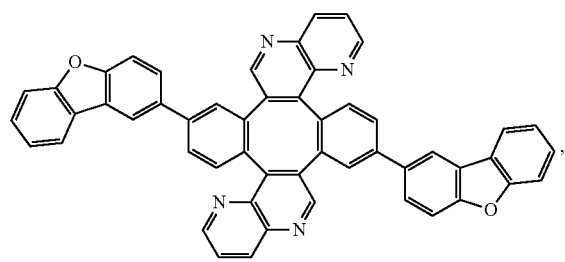
Compound R13
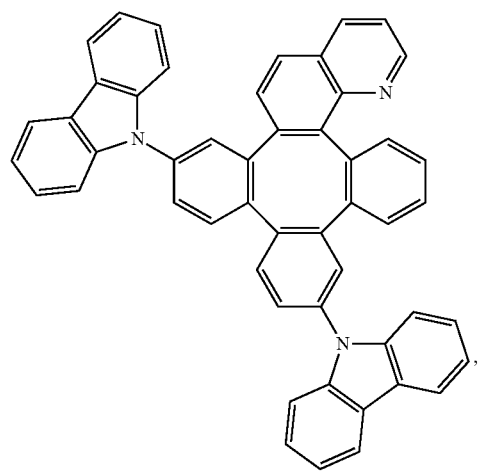
Compound R14
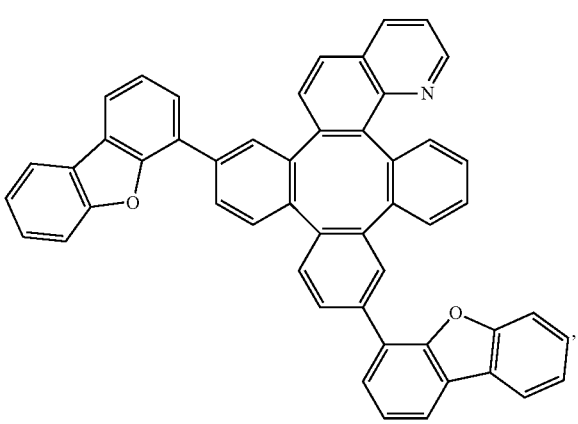
Compound R15
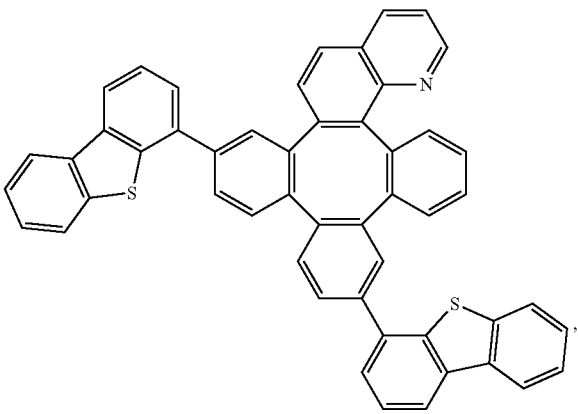
Compound R16
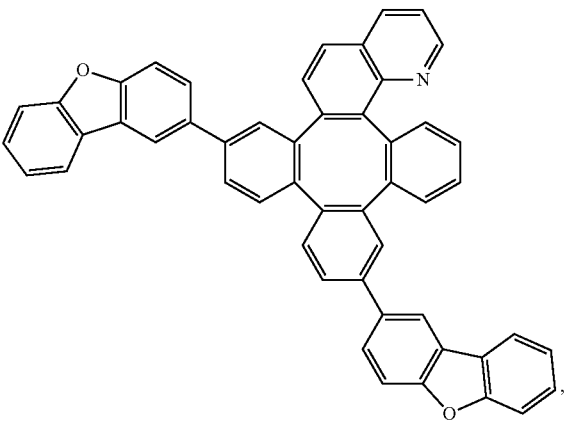

Compound R17
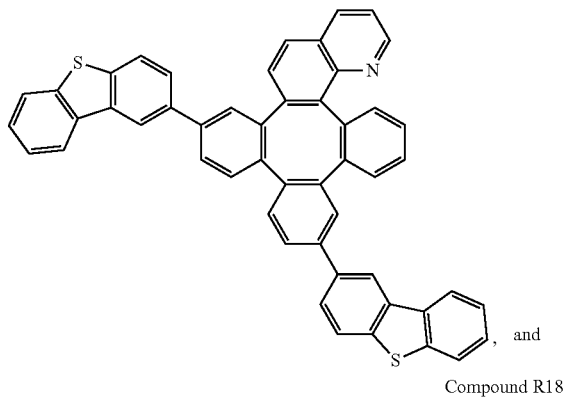
, and
Compound R18
10. The compound of claim 1, wherein the compound is selected from the group consisting of:
Compound 1t
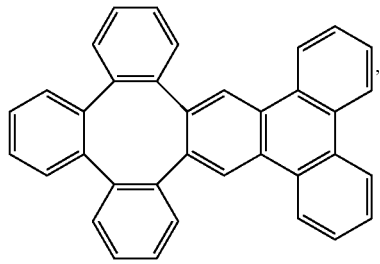
Compound 1
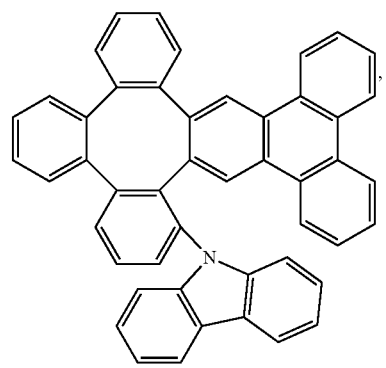
Compound 2
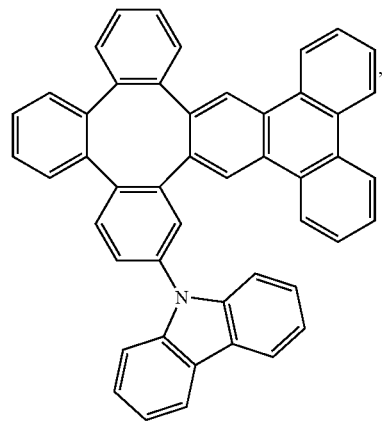
Compound 3
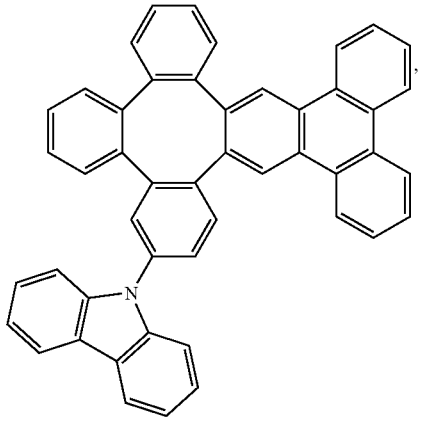
Compound 4
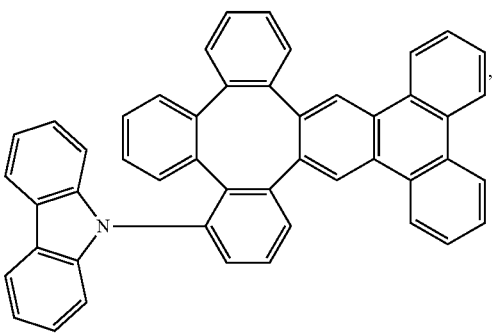
Compound 5
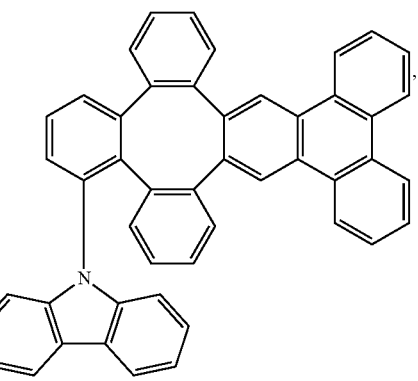

Compound 6
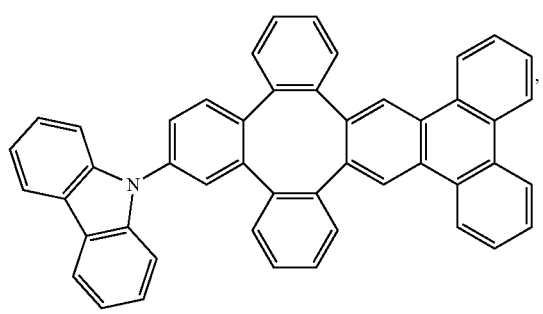
Compound 9
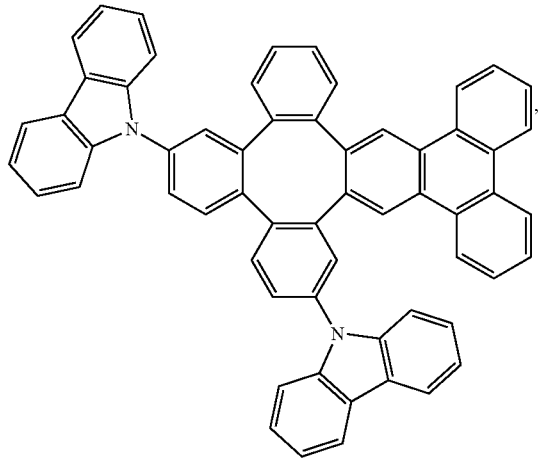
Compound 7
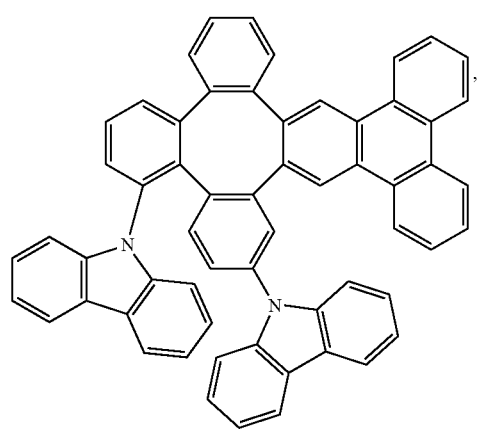
Compound 10
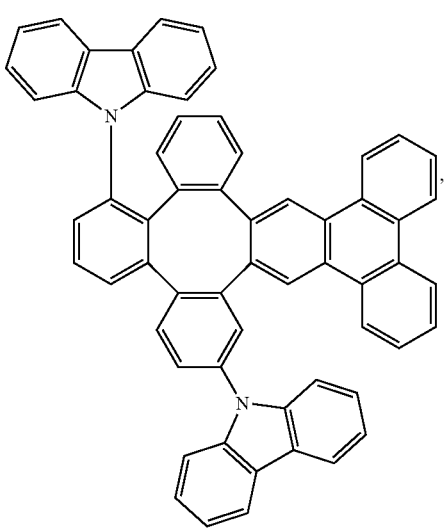
Compound 8
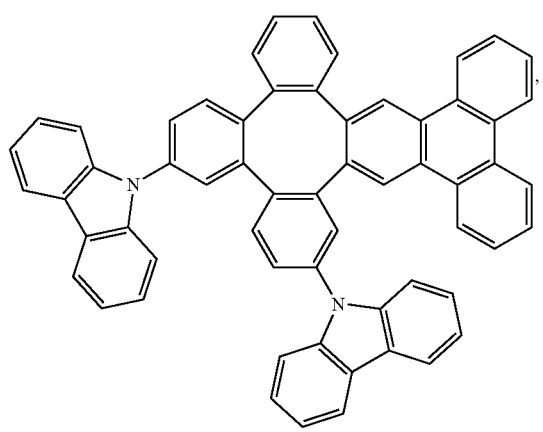
Compound 11
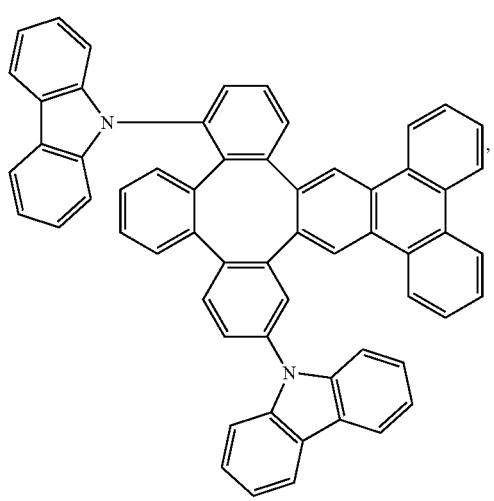

Compound 12
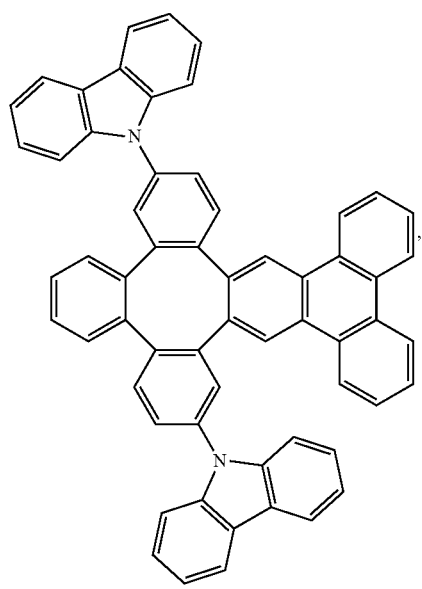
Compound 13
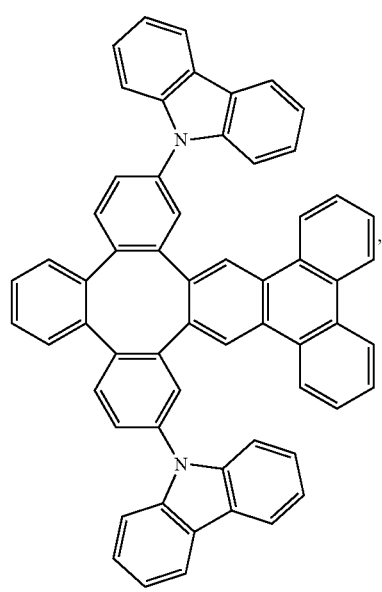
Compound 14
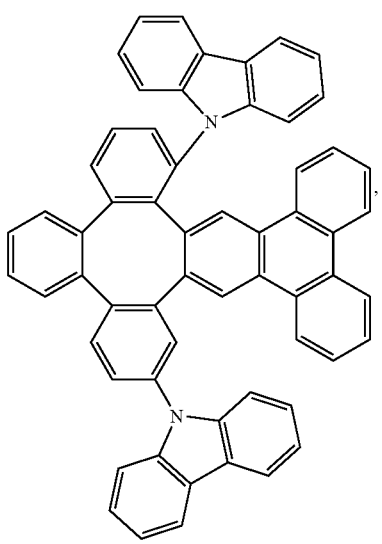
Compound 15
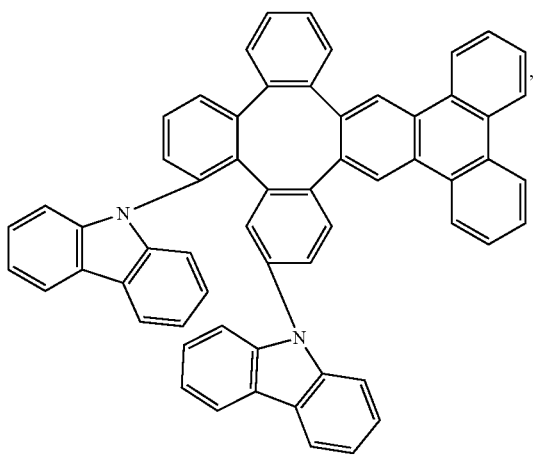
Compound 16
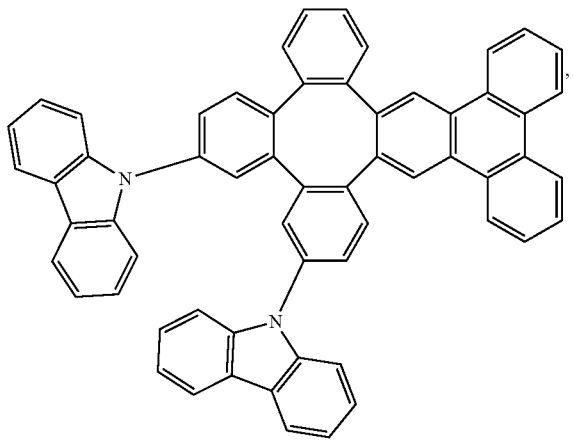

Compound 17
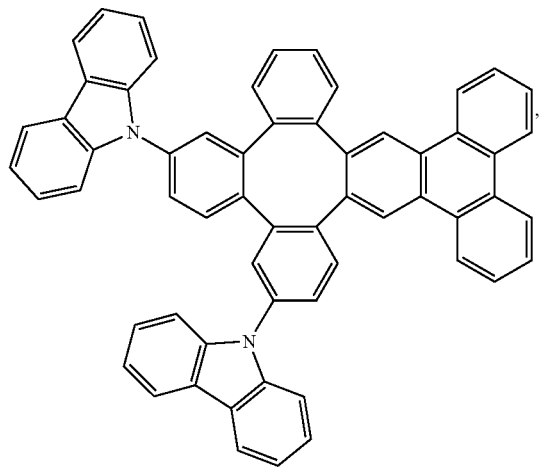
Compound 18
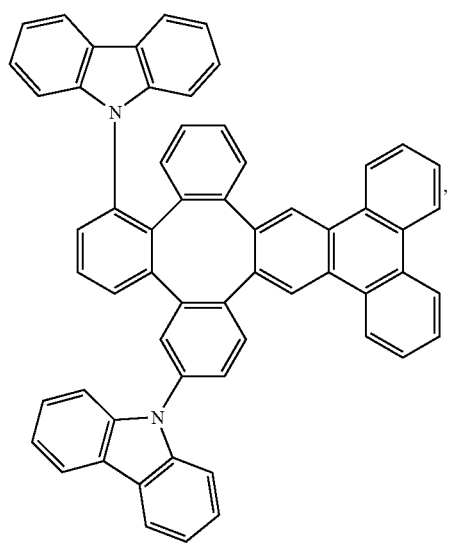
Compound 19
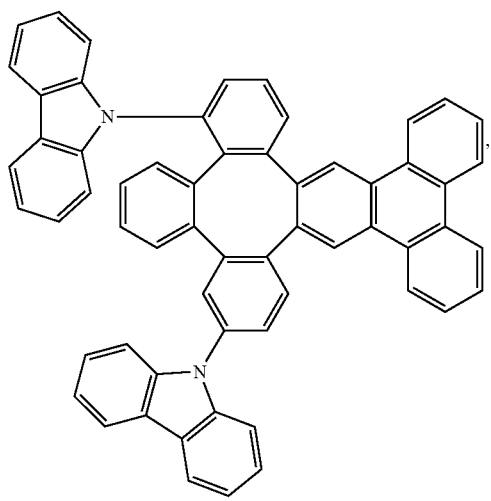
Compound 20
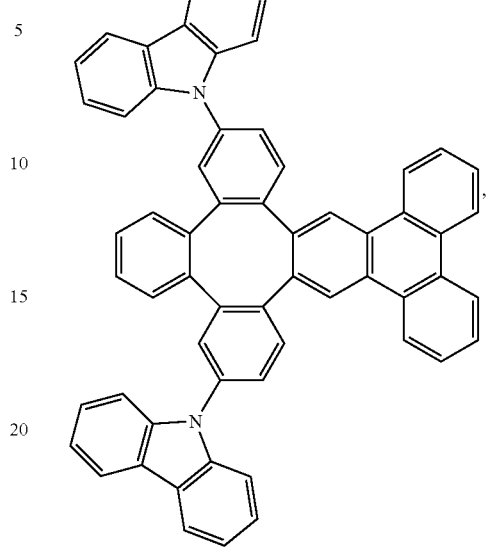
Compound 21
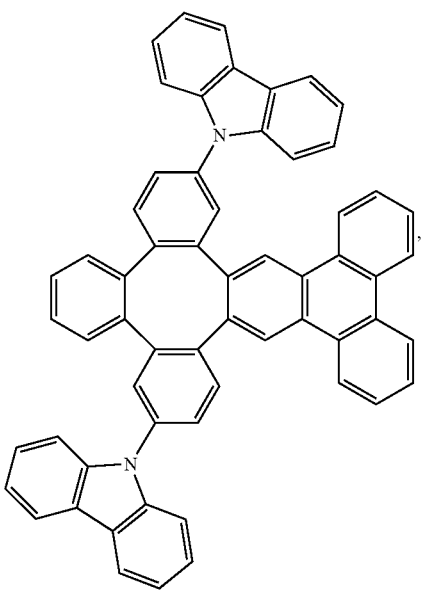

Compound 22
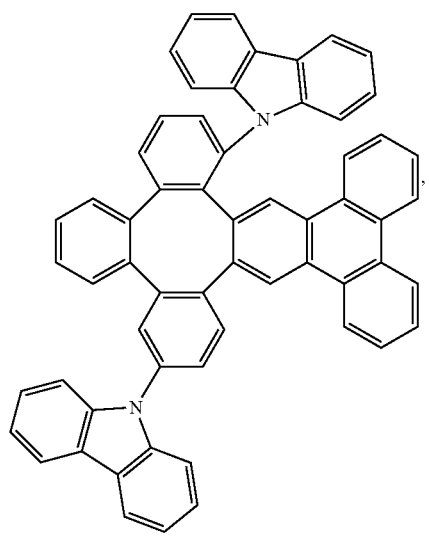
Compound 25
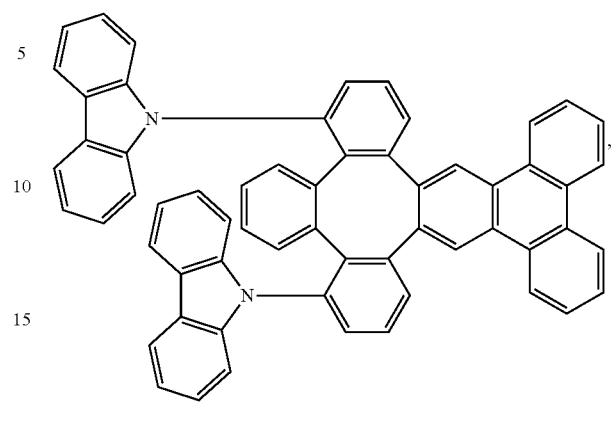
Compound 23
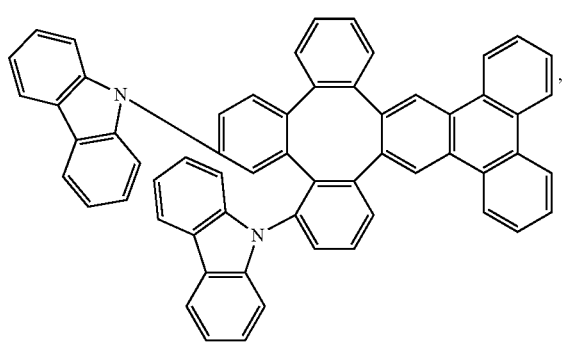
Compound 26
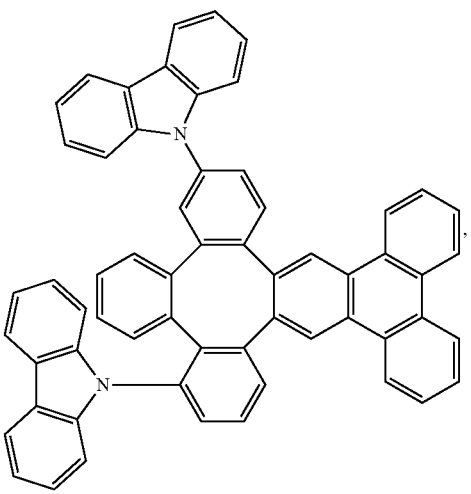
Compound 24
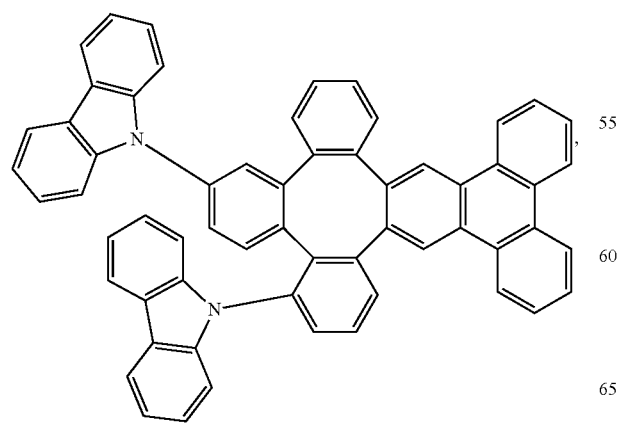
Compound 27
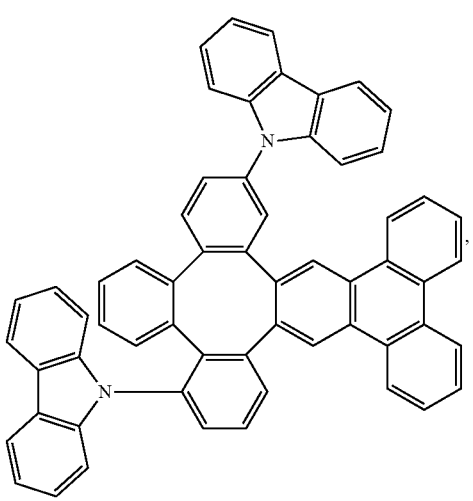

Compound 28
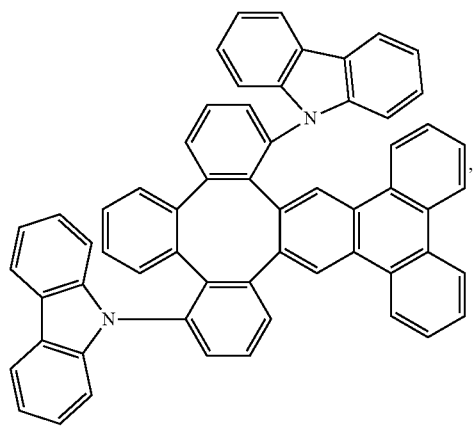
Compound 29
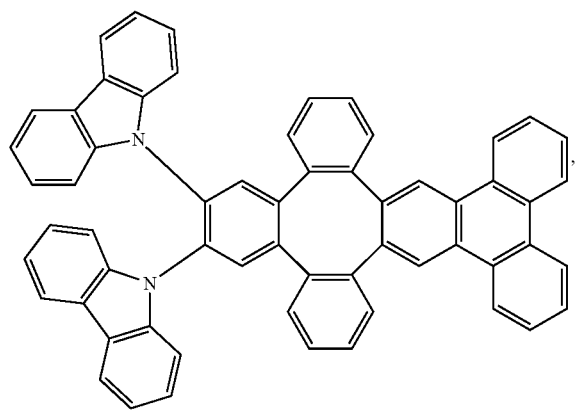
Compound 30
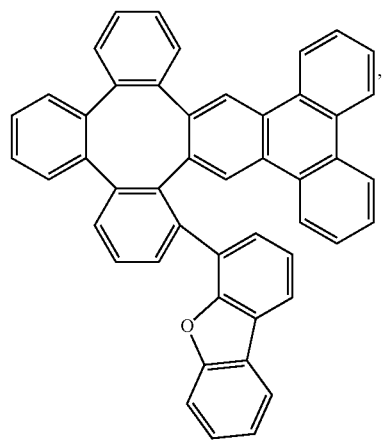
Compound 31
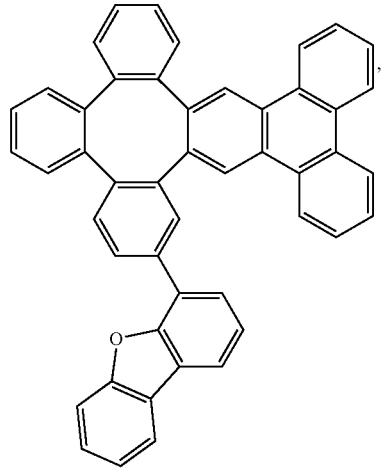
Compound 32
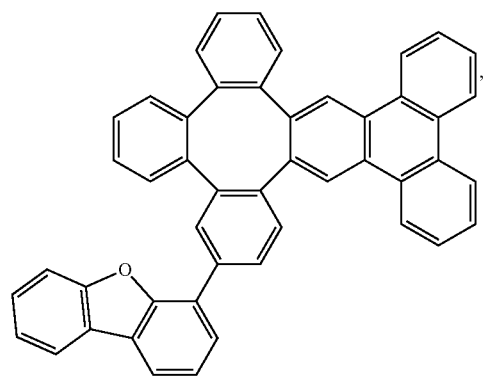
Compound 33
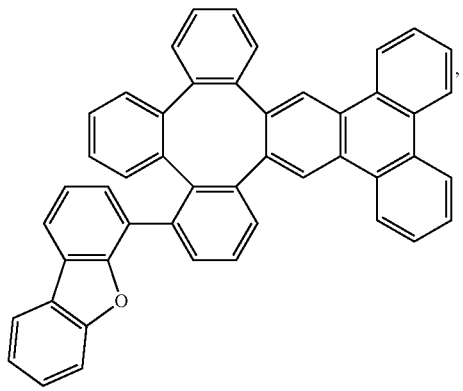

Compound 34
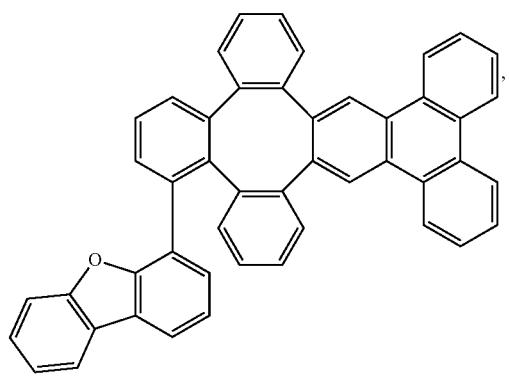
Compound 35
Compound 36
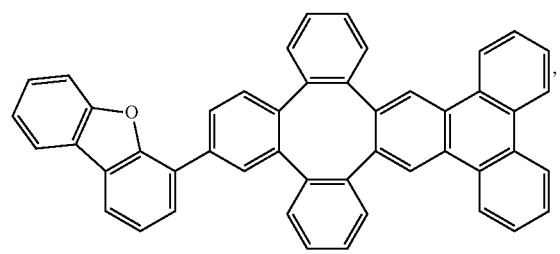
Compound 37
Compound 38
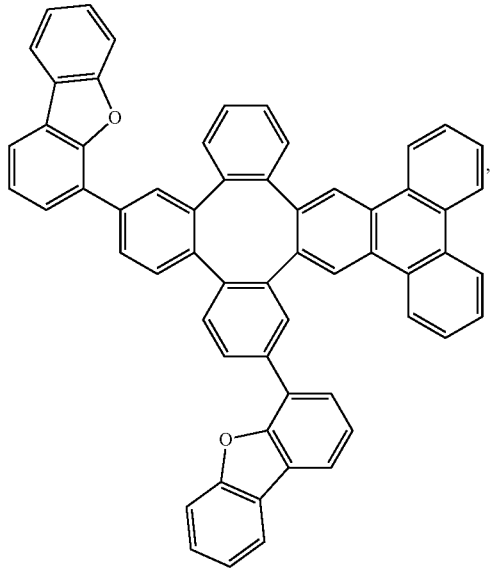
Compound 39
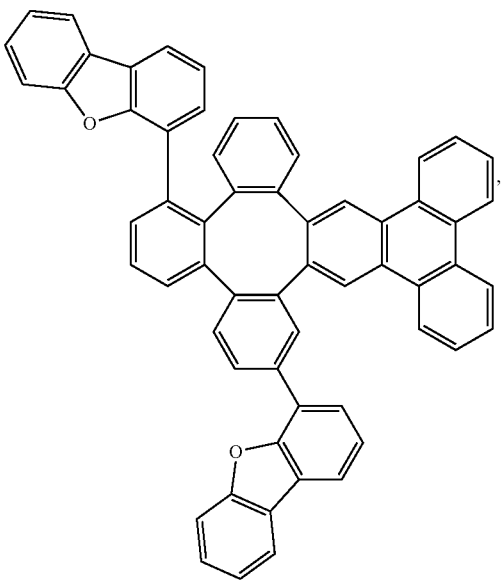

Compound 40
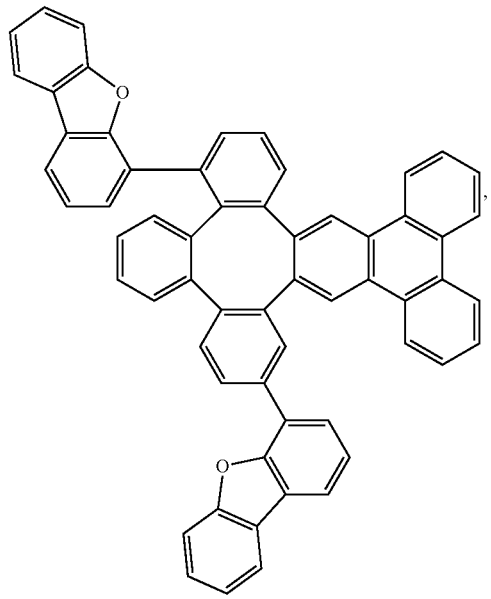
Compound 41
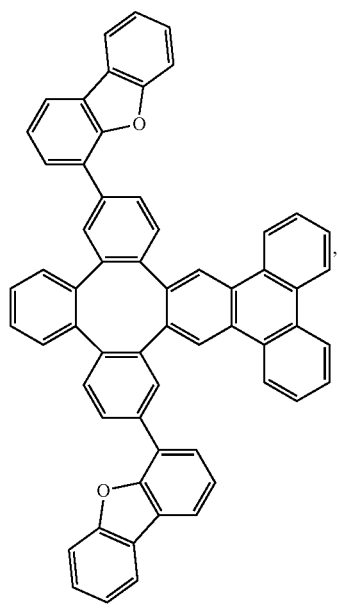
Compound 42
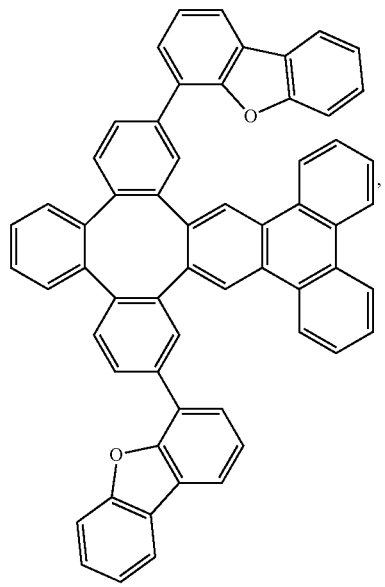
Compound 43
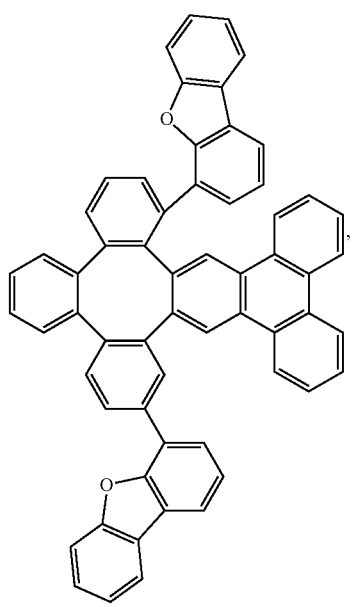

Compound 44
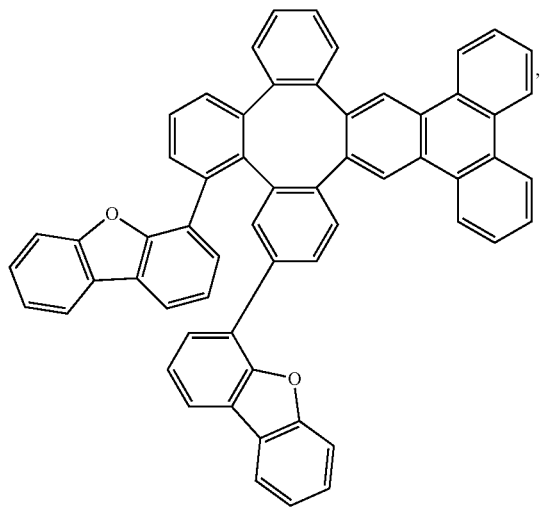
Compound 45
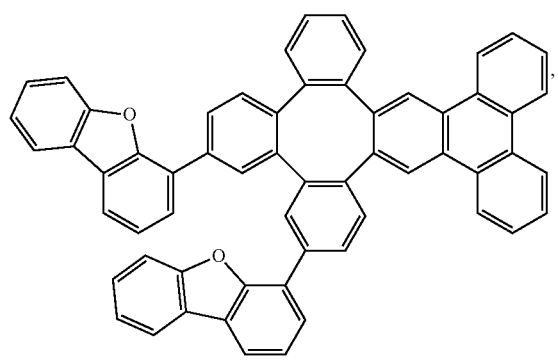
Compound 46
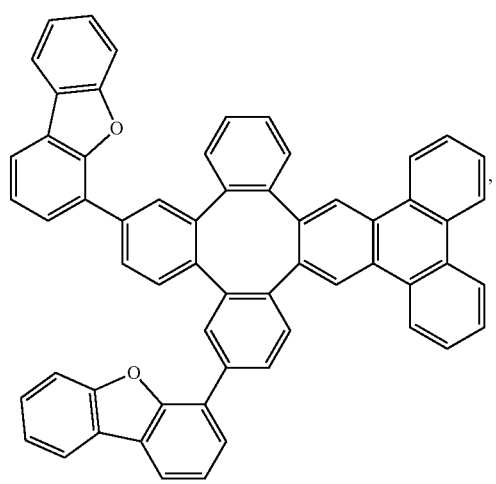
Compound 47
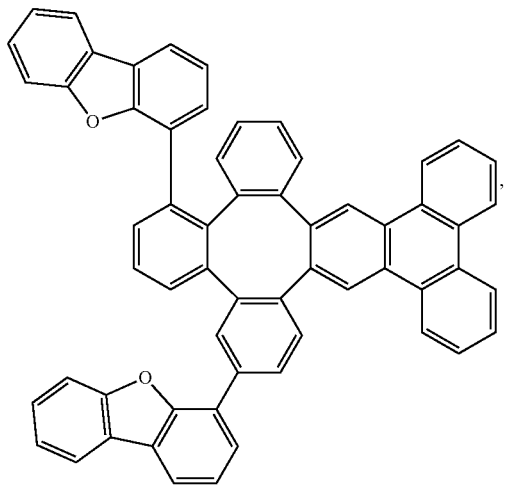
Compound 48
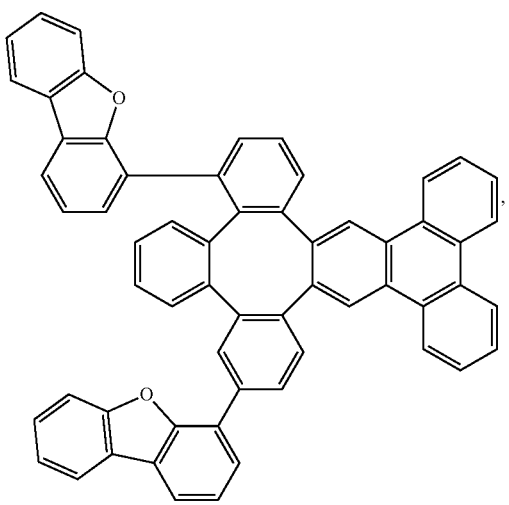
Compound 49
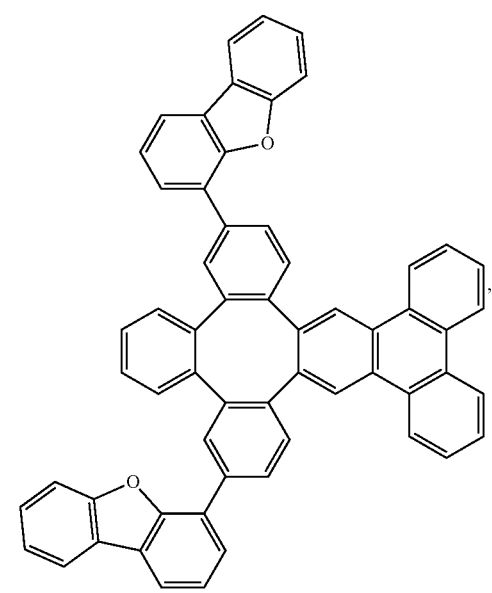

Compound 50
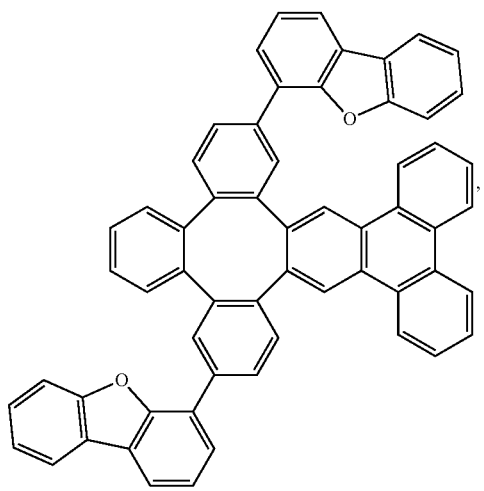
Compound 51
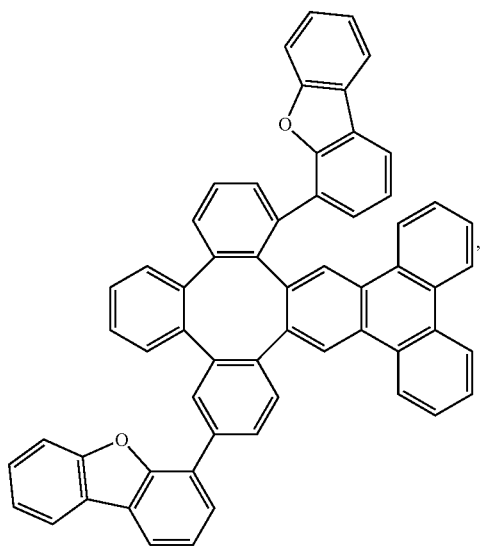
Compound 52
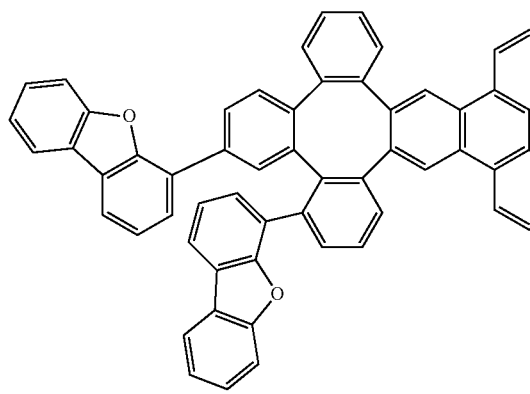
Compound 53
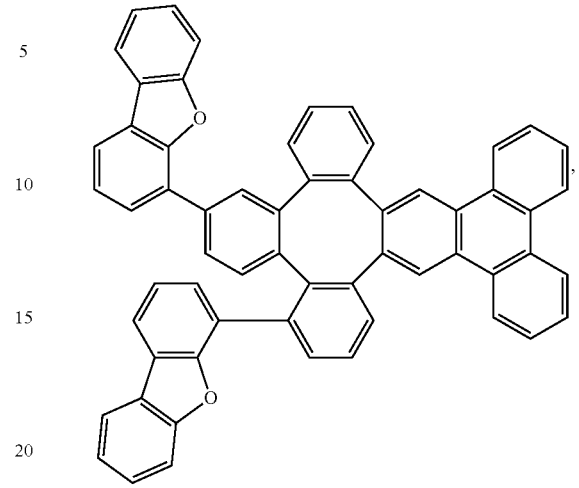
Compound 54
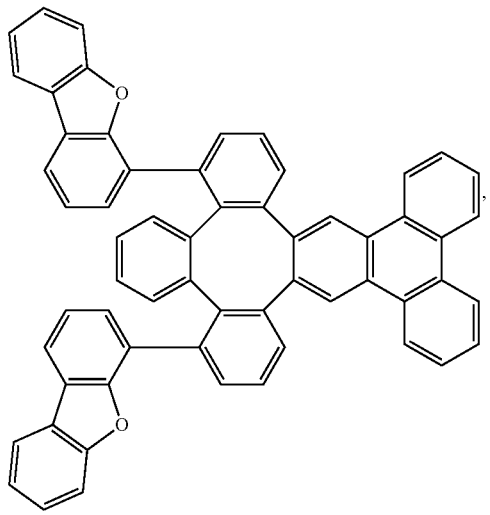
Compound 55
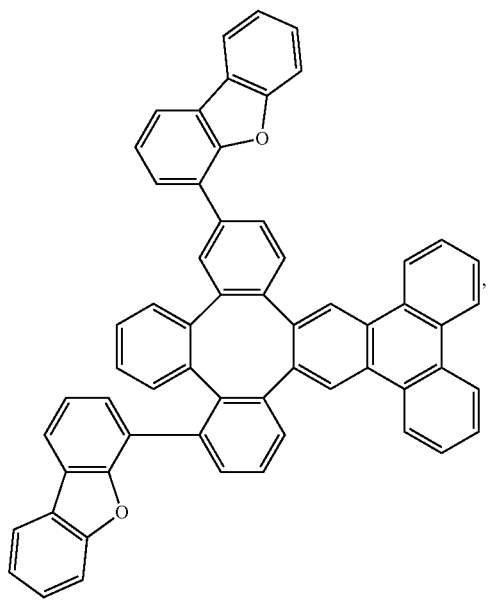

Compound 56
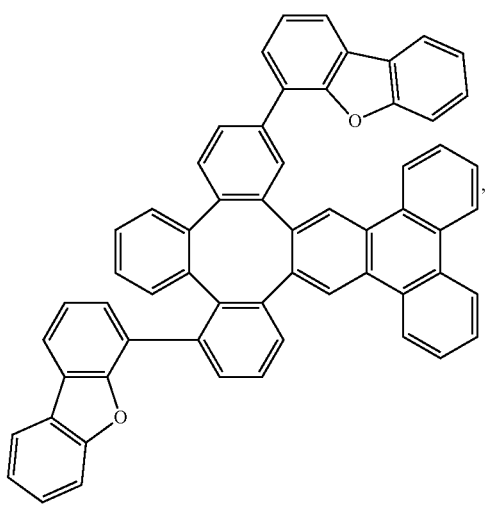
Compound 57
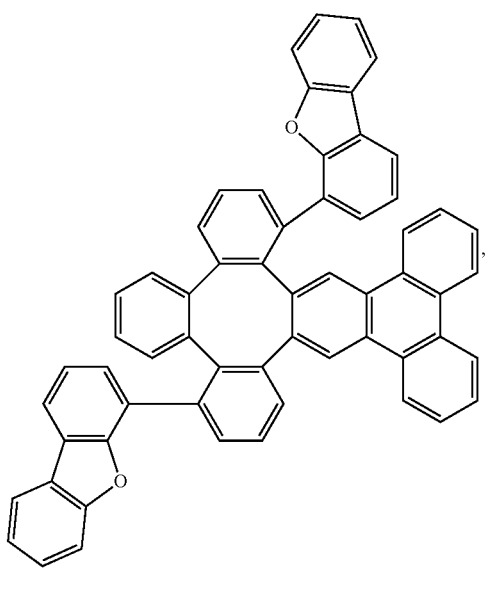
Compound 58
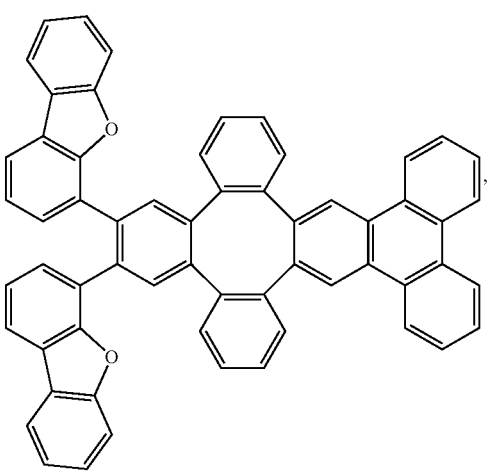
Compound 59
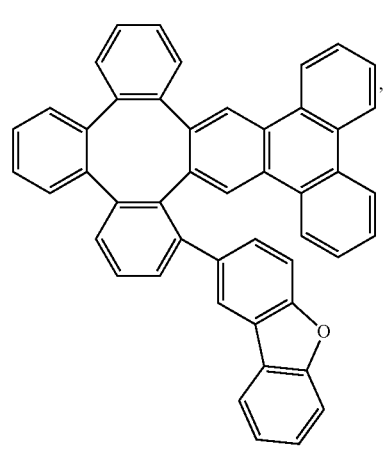
Compound 60
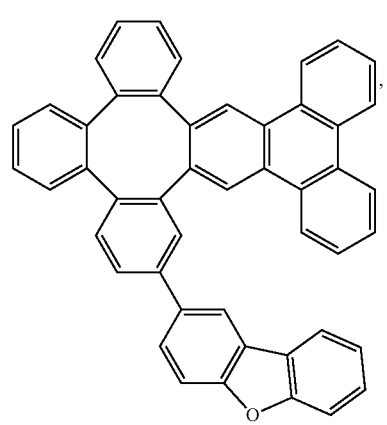
Compound 61
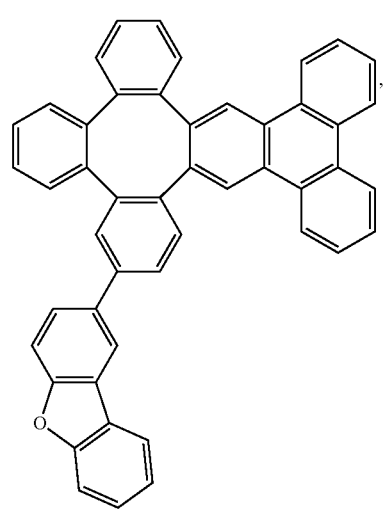

Compound 62
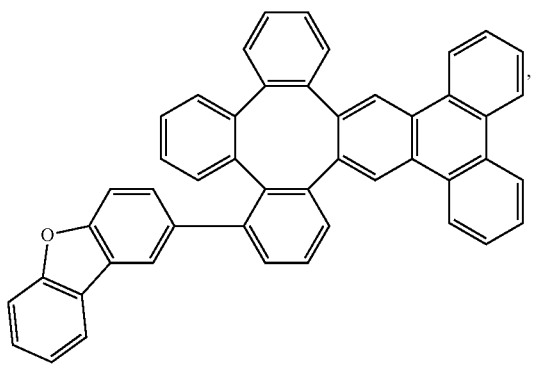
Compound 63
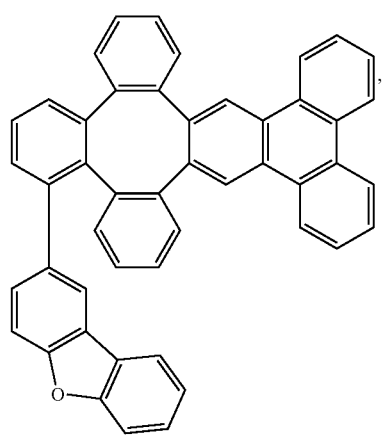
Compound 64
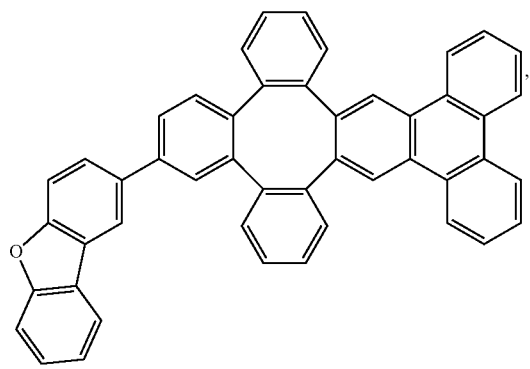
Compound 65
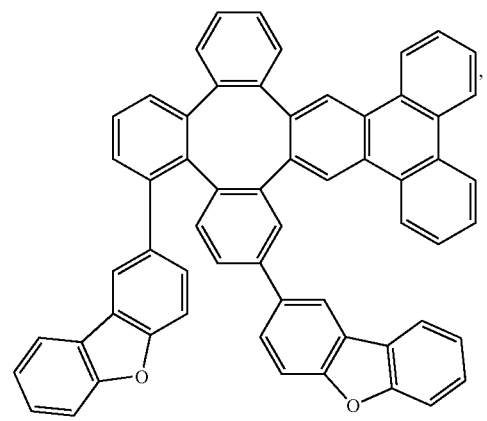
Compound 66
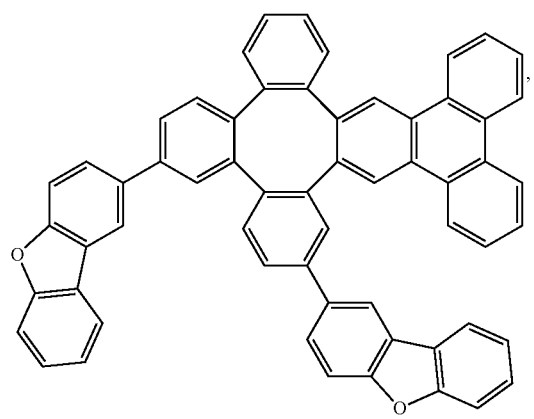
Compound 67
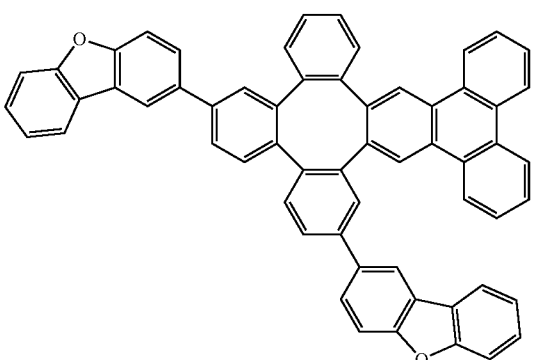
Compound 68

-continued
Compound 69
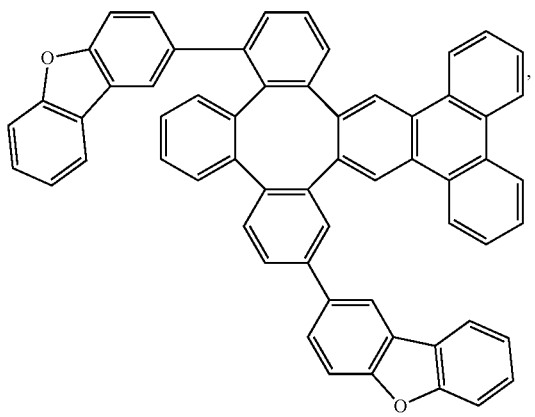
Compound 70
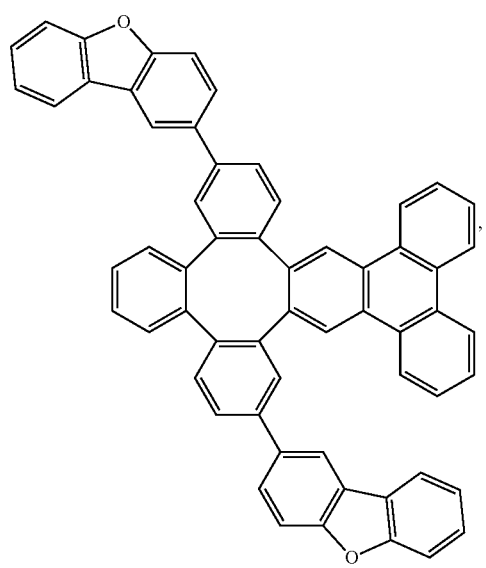
Compound 71
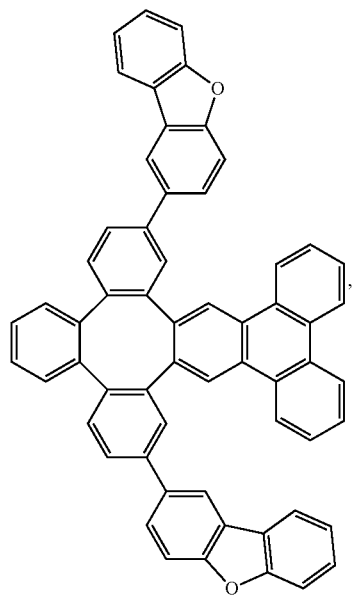
-continued
Compound 72
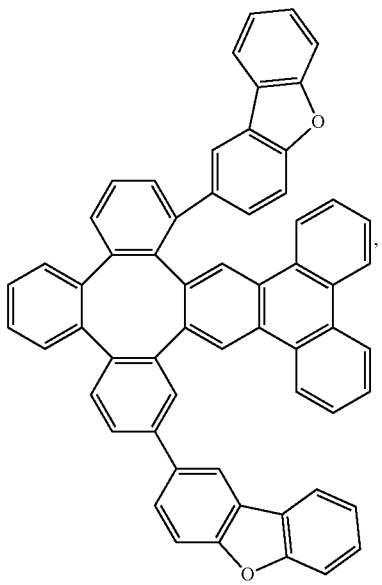
Compound 73
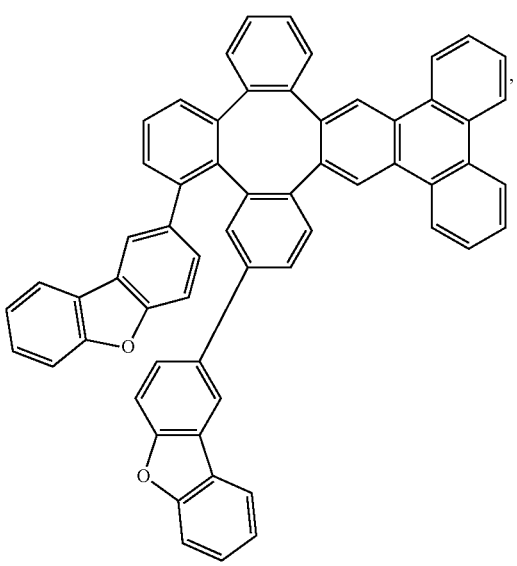

Compound 74
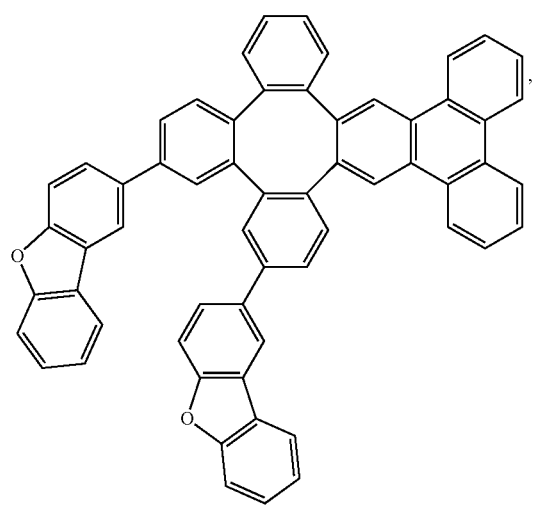
Compound 75
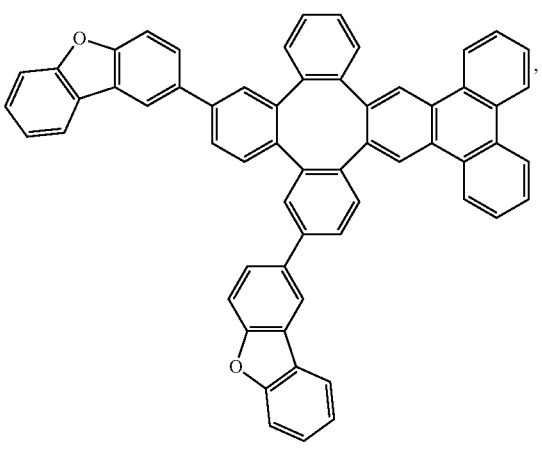
Compound 76
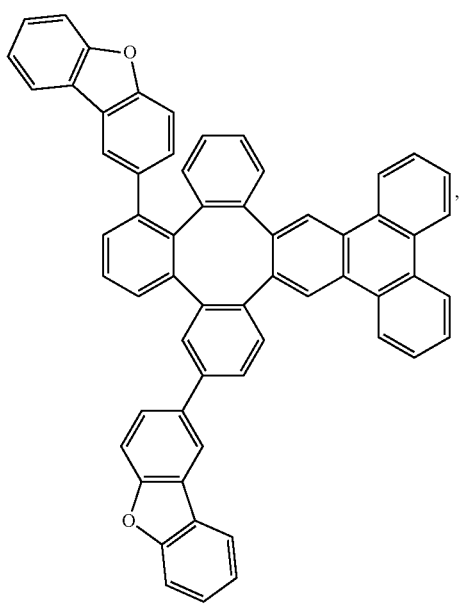
Compound 77
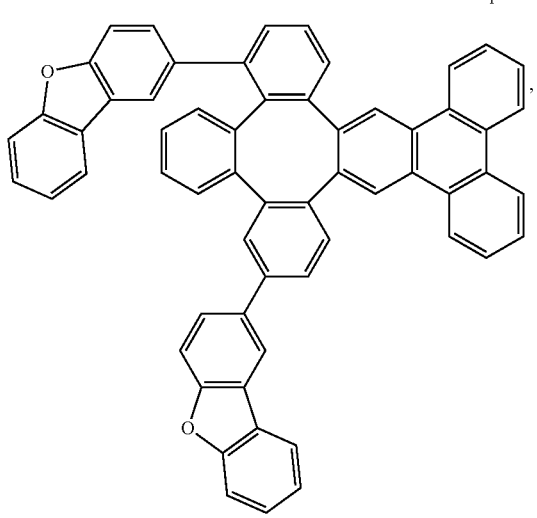
Compound 78
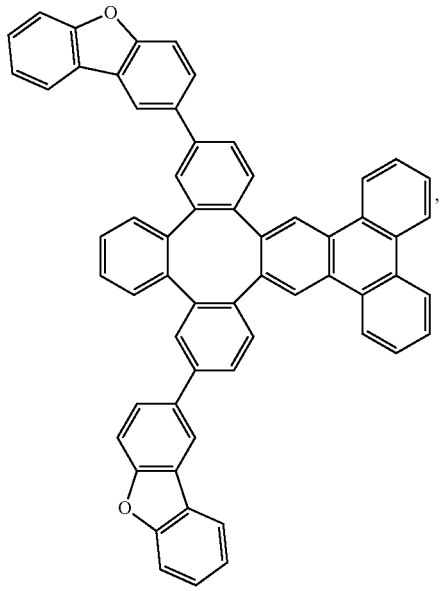

-continued
Compound 79
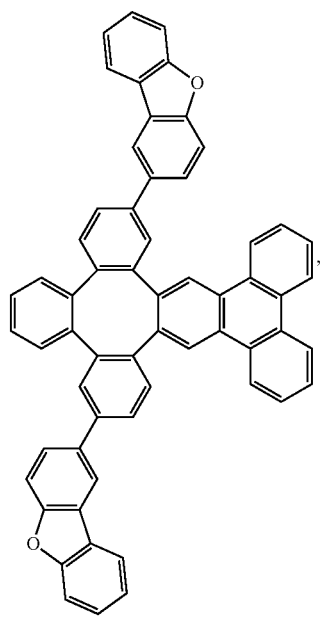
Compound 80
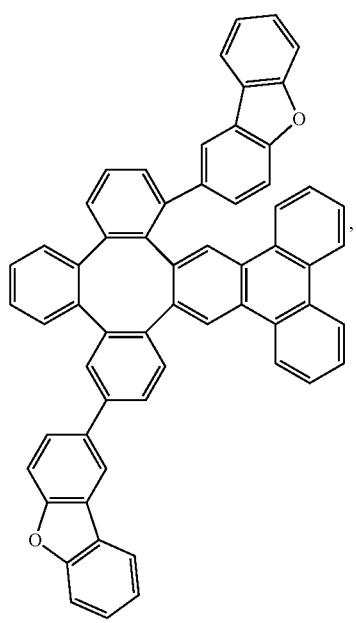
Compound 81
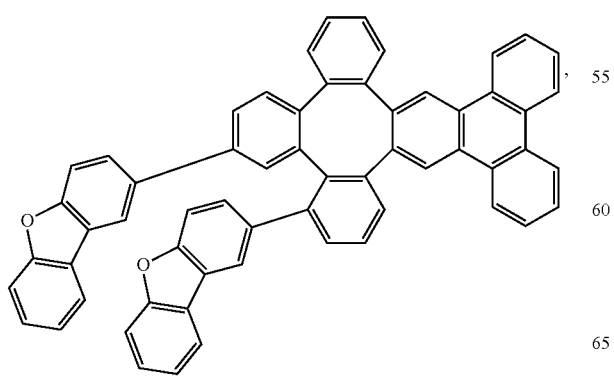
-continued
Compound 82
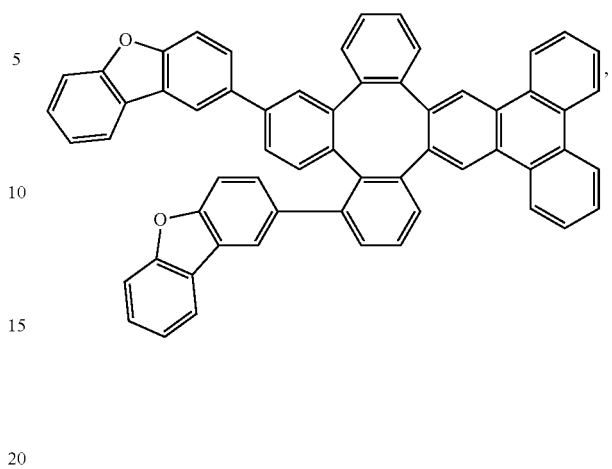
Compound 83
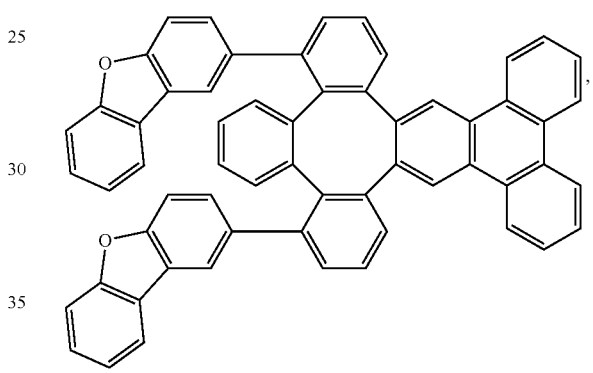
Compound 84
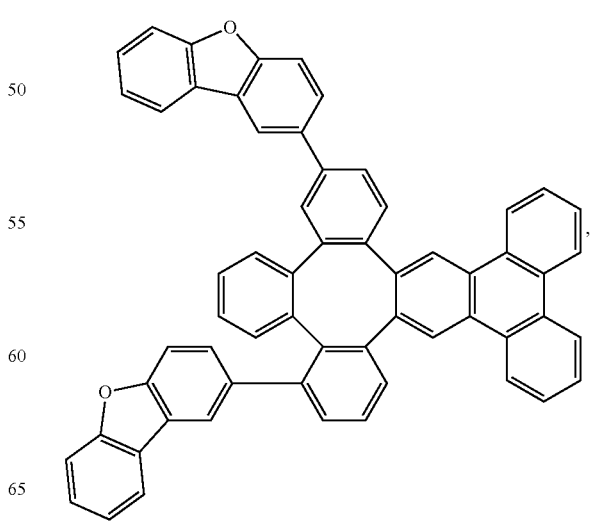

Compound 85
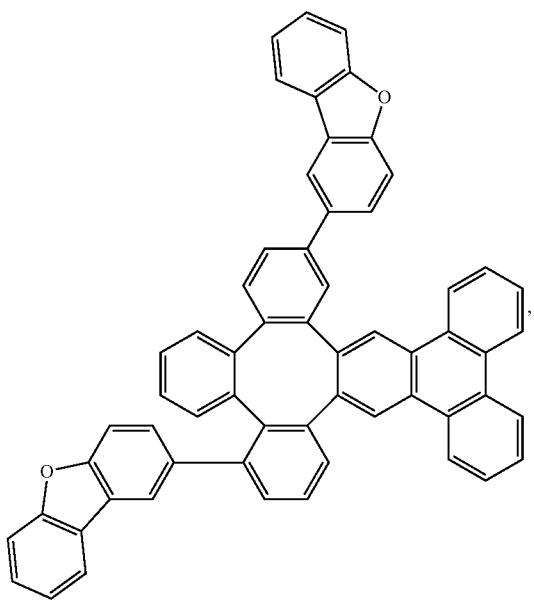
Compound 86
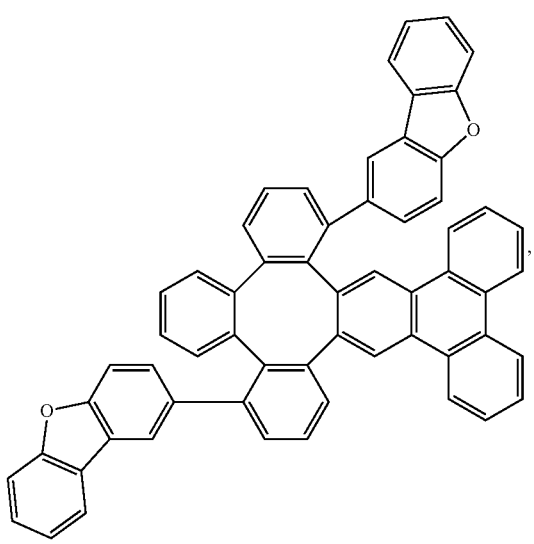
Compound 87
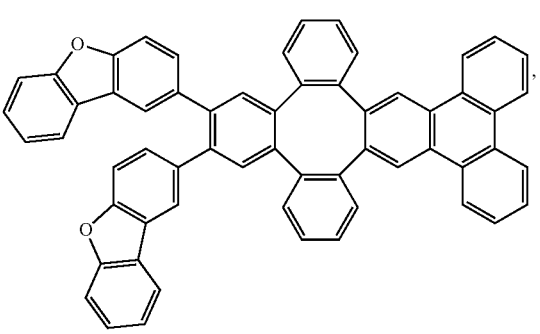
Compound 88
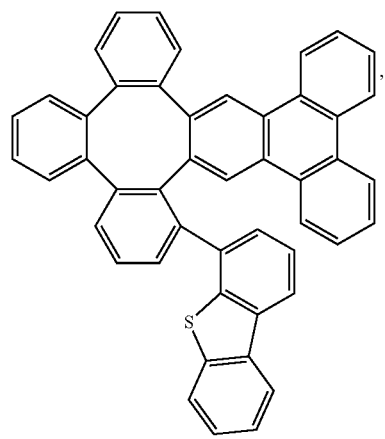
Compound 89
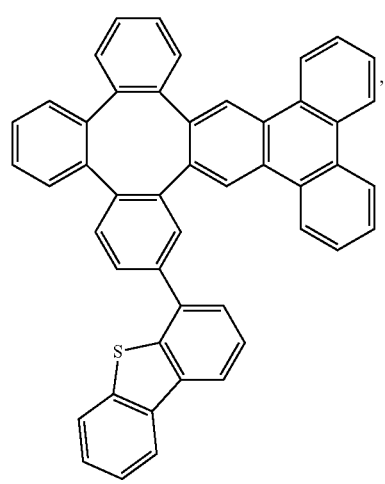
Compound 90
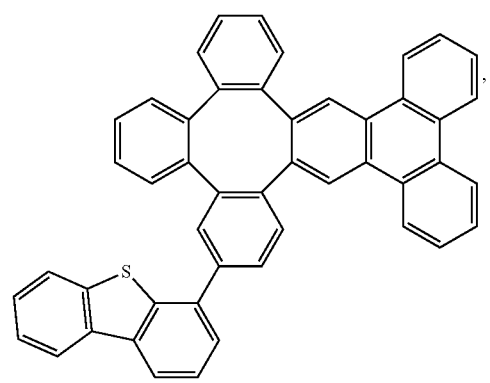

Compound 91
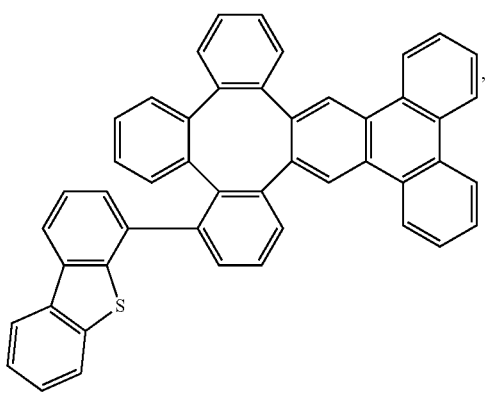
Compound 92
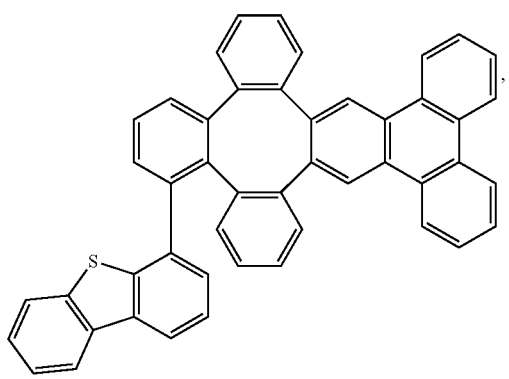
Compound 93
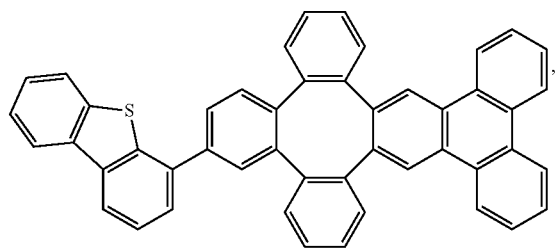
Compound 94
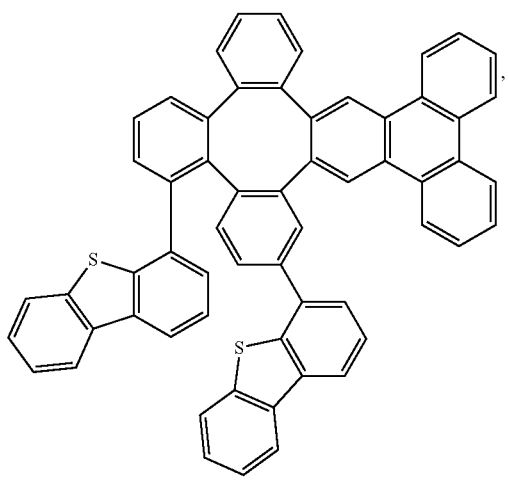
Compound 95
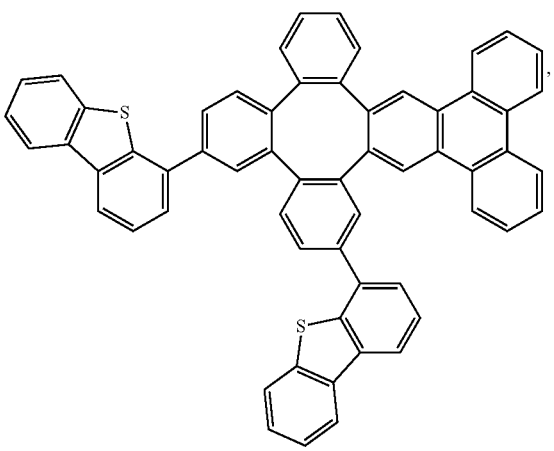
Compound 96
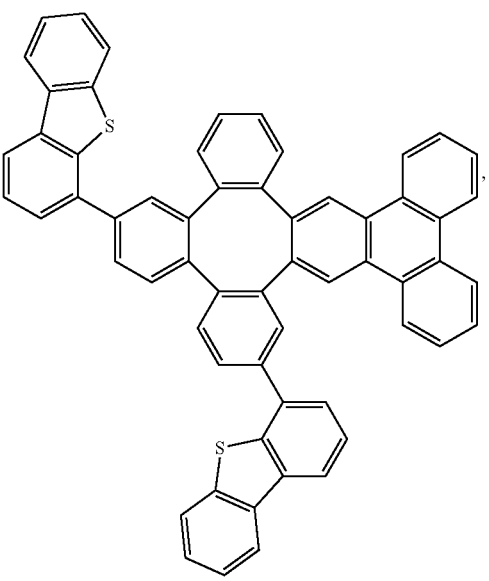
Compound 97
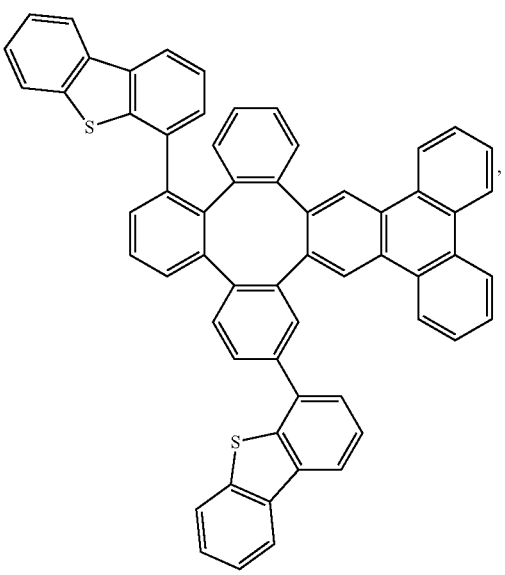

Compound 98
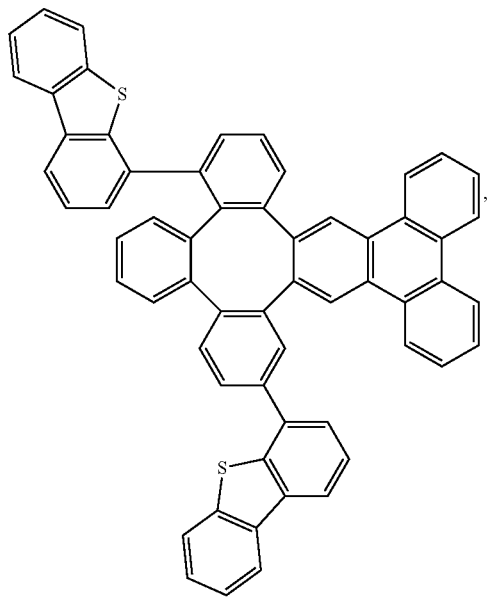
Compound 99
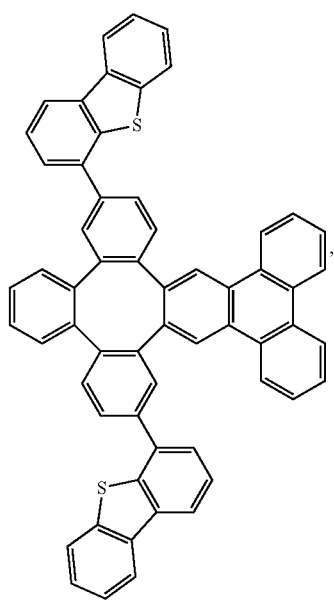
Compound 100
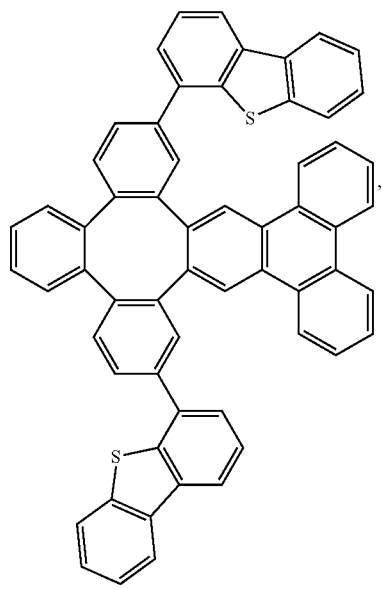
Compound 101
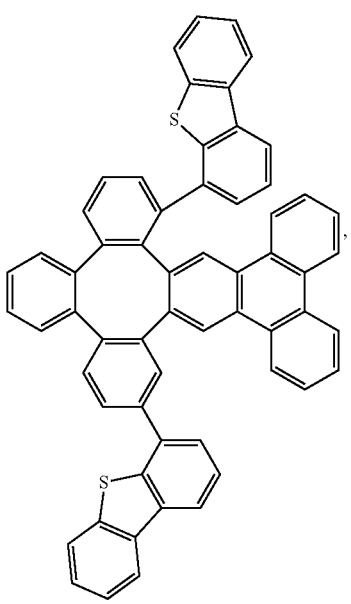

-continued
Compound 102
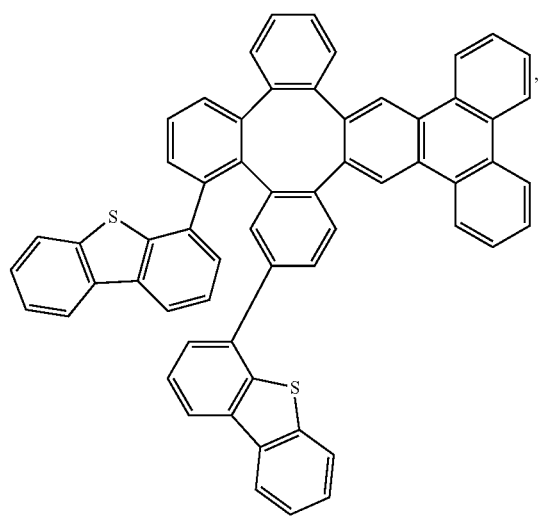
Compound 103
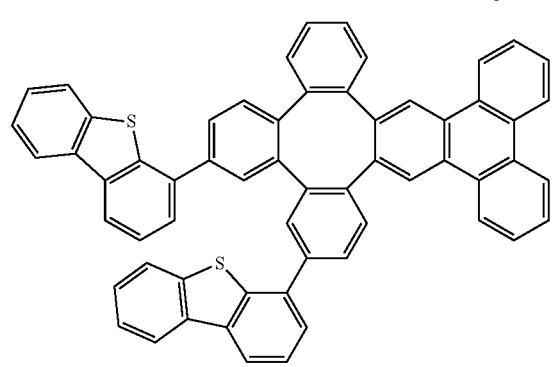
Compound 104
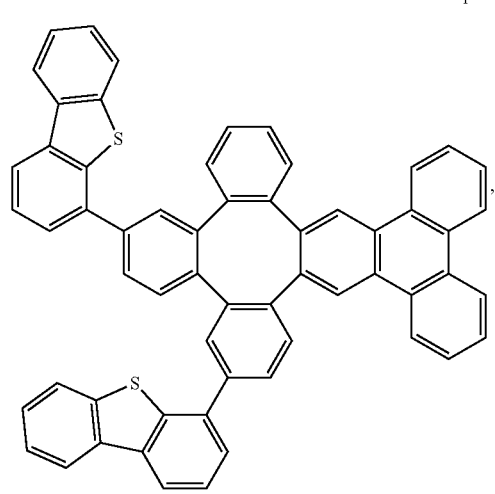
-continued
Compound 105
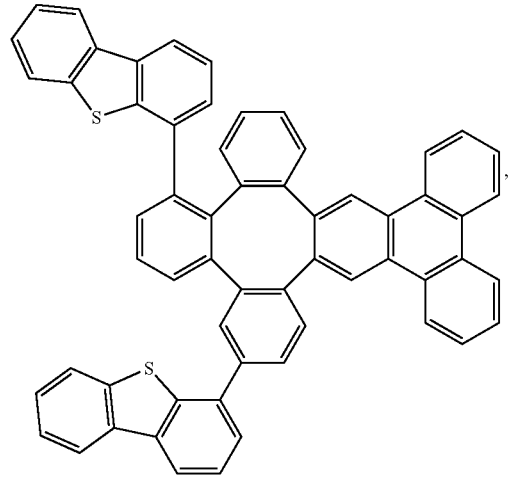
Compound 106
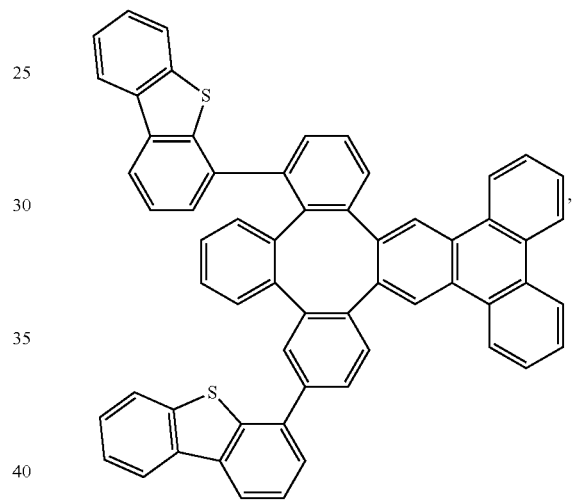
Compound 107
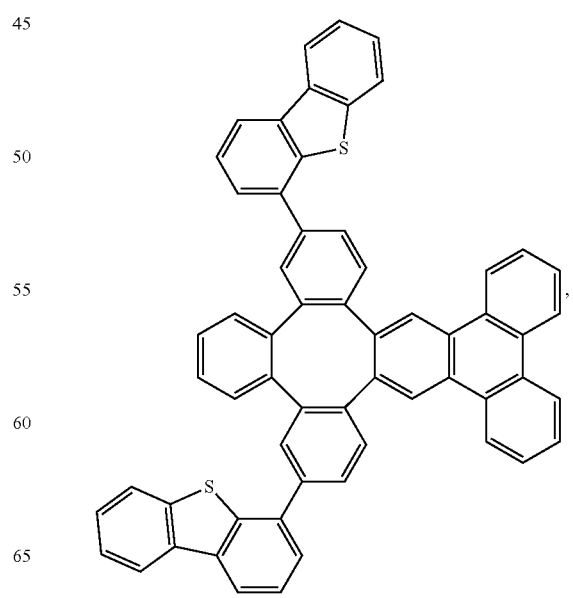

Compound 108
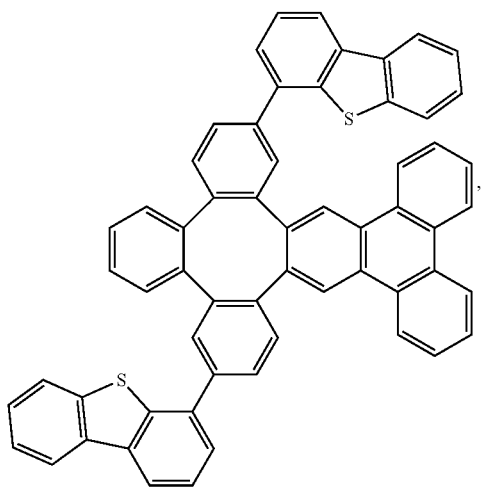
Compound 109
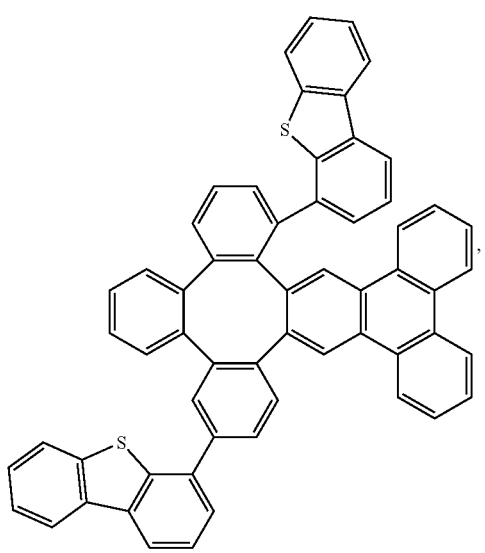
Compound 110
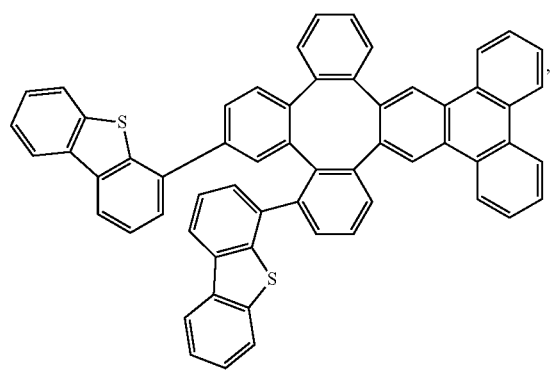
Compound 111
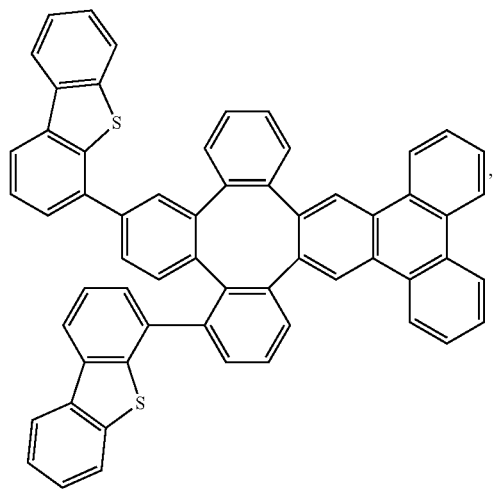
Compound 112
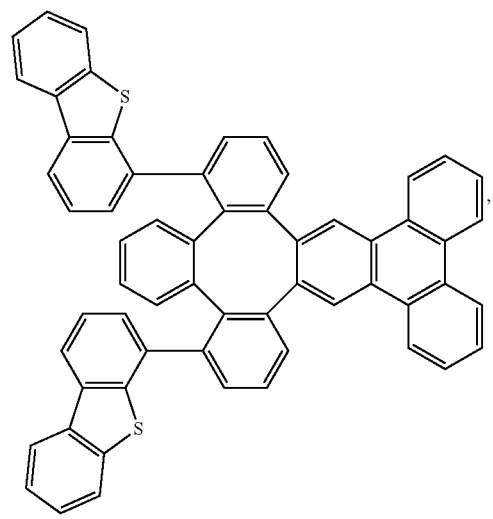
Compound 113
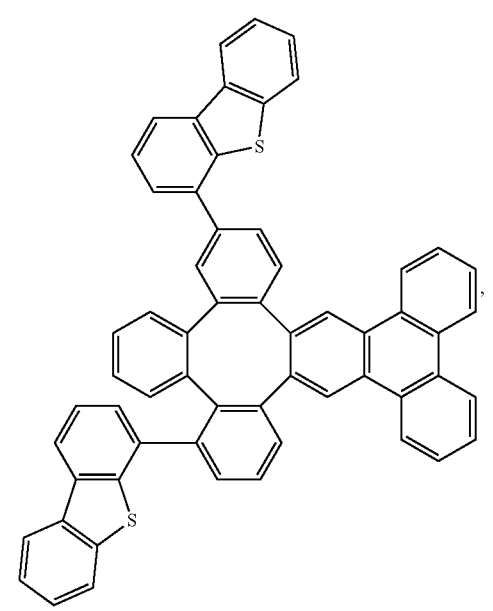

-continued
Compound 114
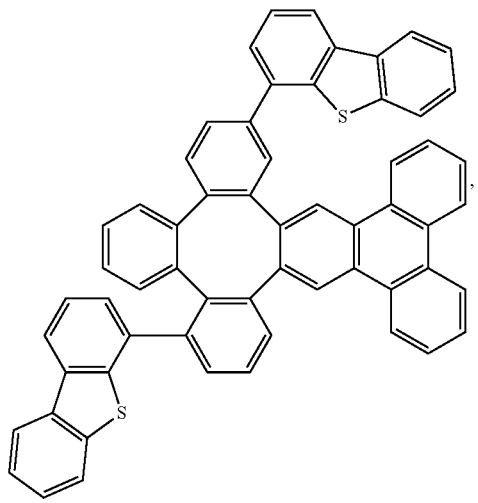
Compound 115
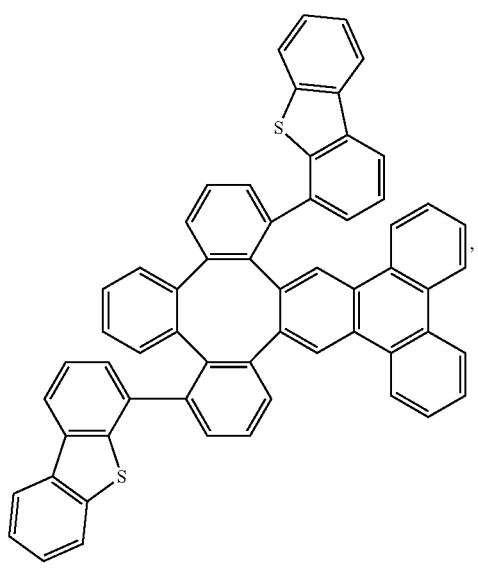
Compound 116
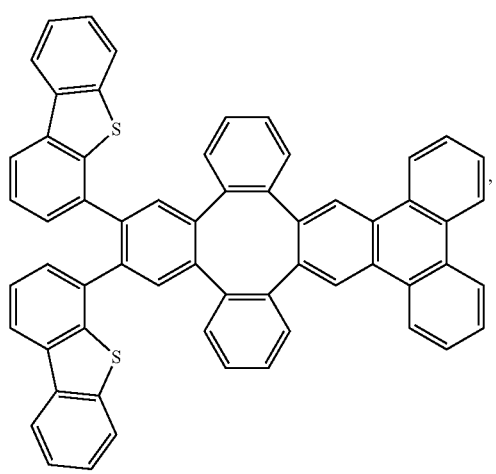
-continued
Compound 117
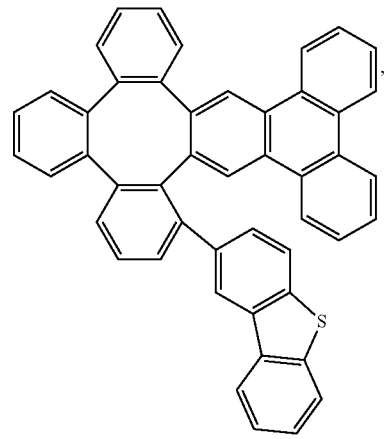
Compound 118
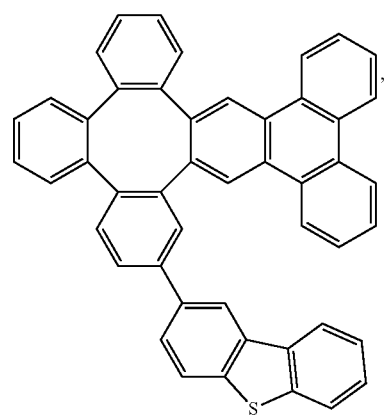
Compound 119
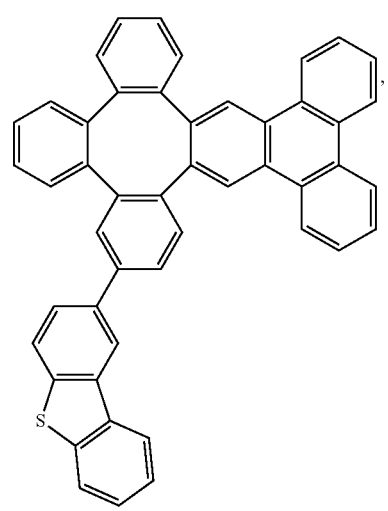

Compound 120
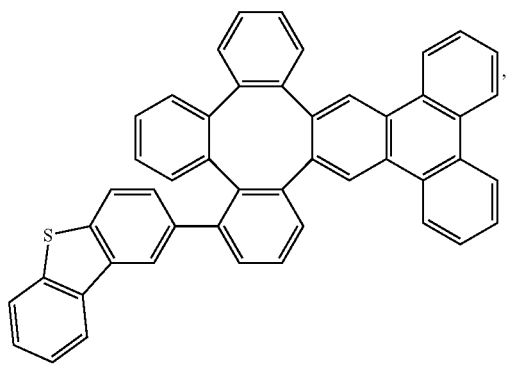
Compound 121
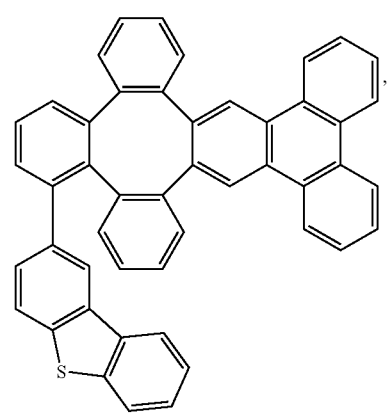
Compound 122
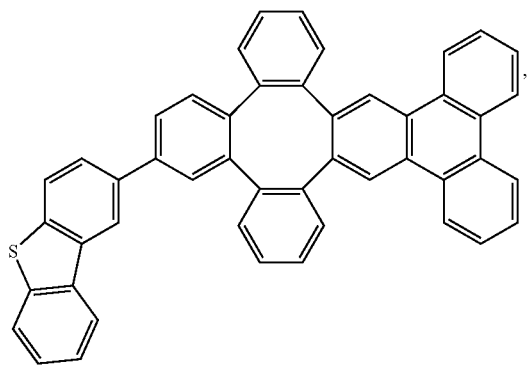
Compound 123
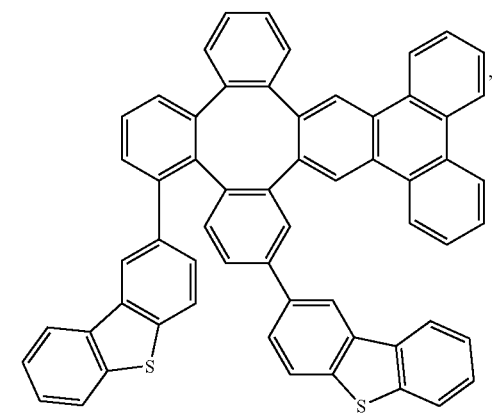
Compound 124
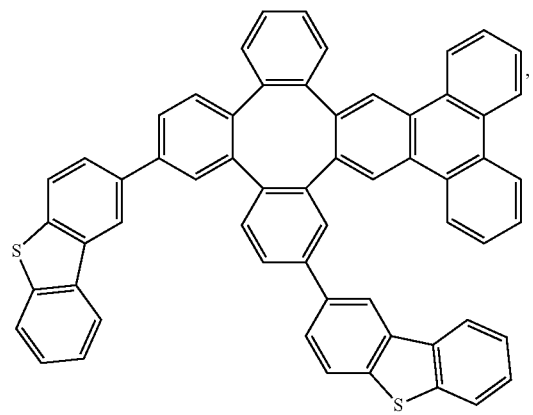
Compound 125
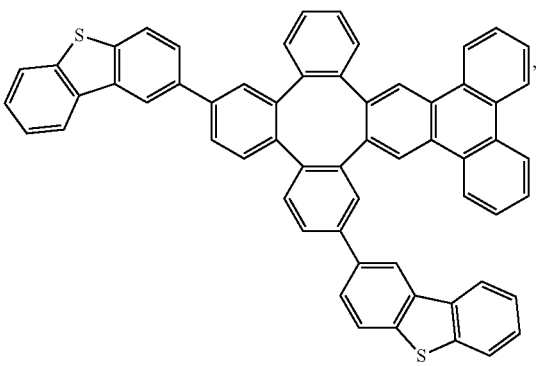
Compound 126
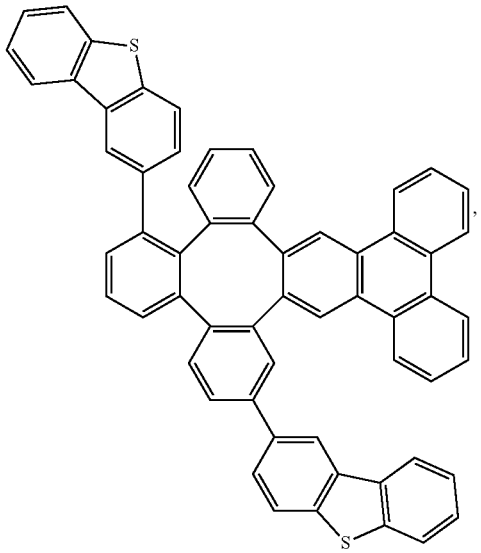

Compound 127
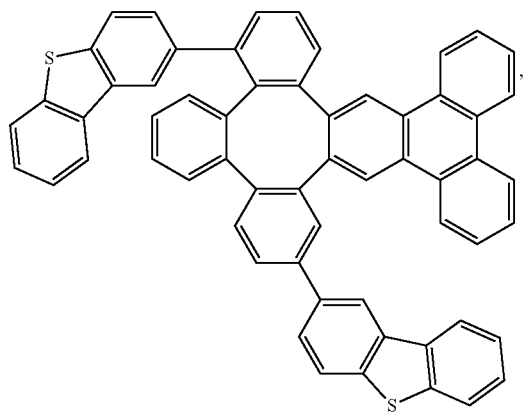
Compound 128
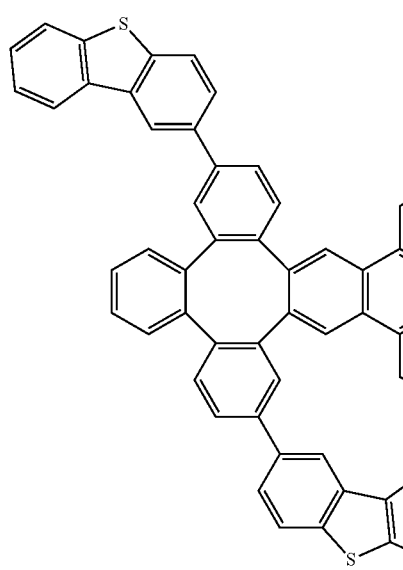
Compound 129
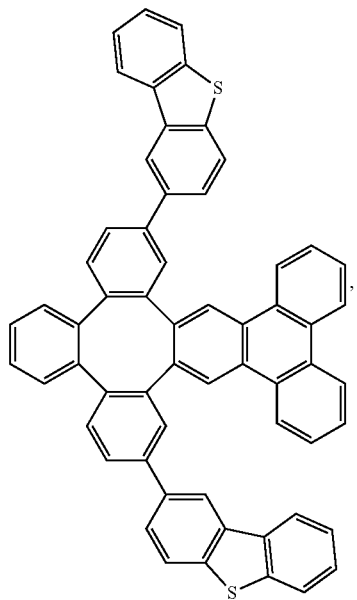
Compound 130
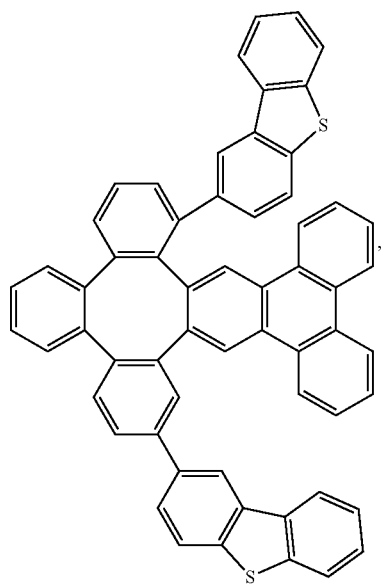
Compound 131
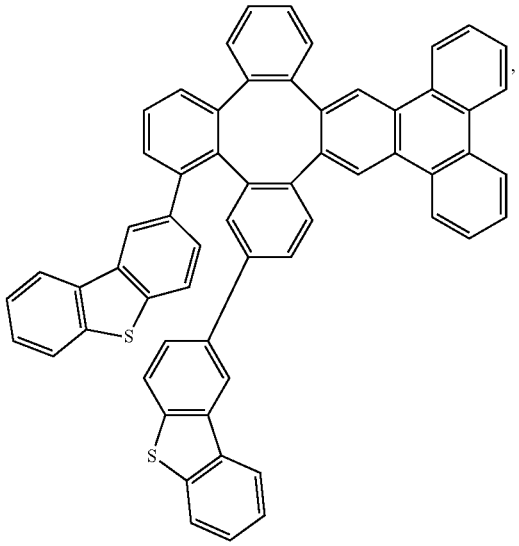

-continued
Compound 132
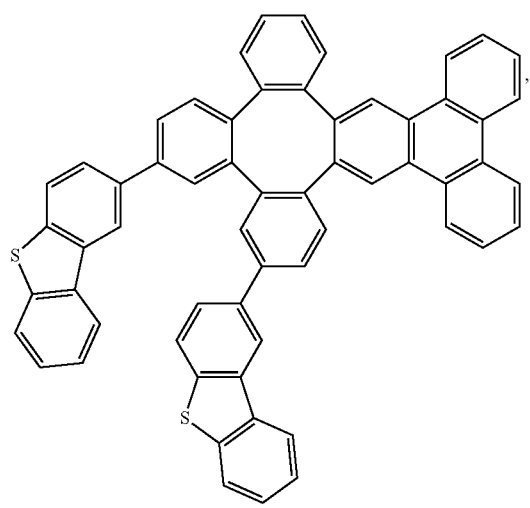
Compound 133
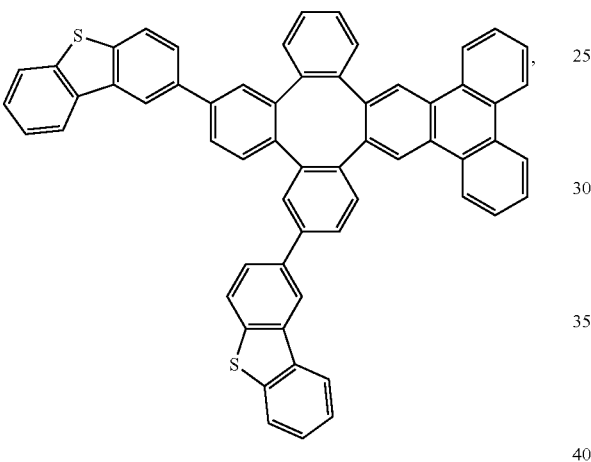
Compound 134
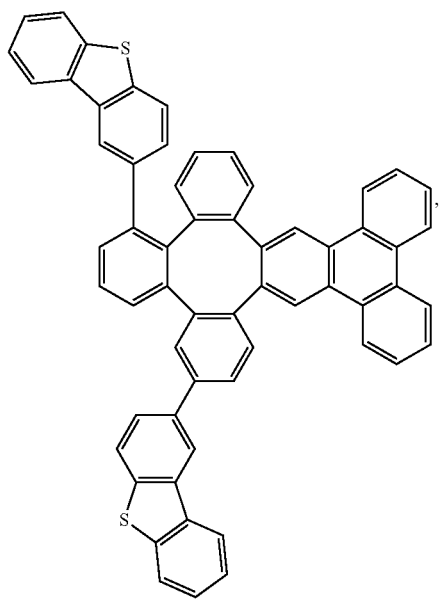
-continued
Compound 135
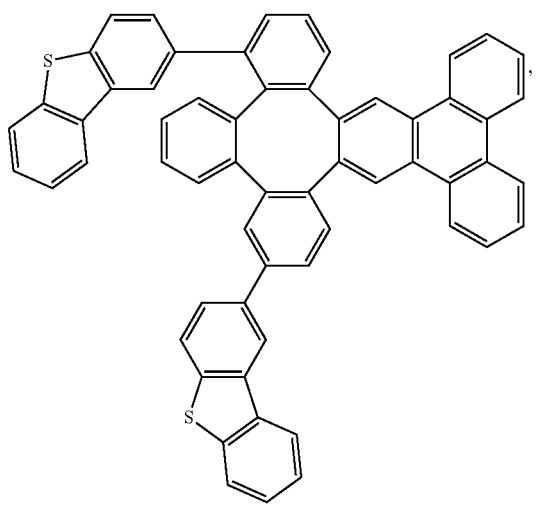
Compound 136
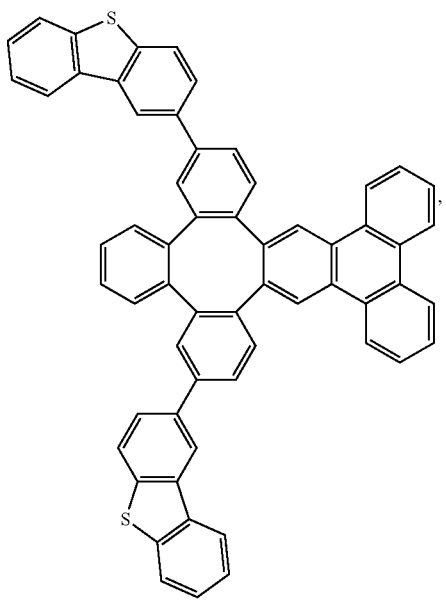

Compound 137
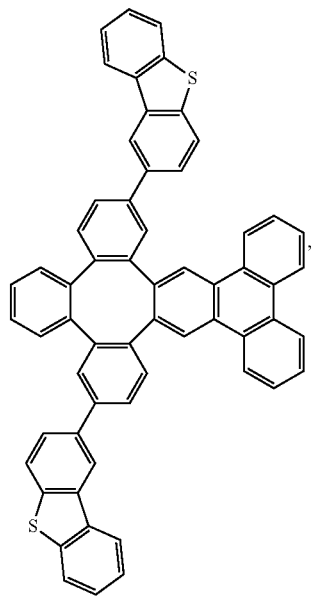
Compound 140
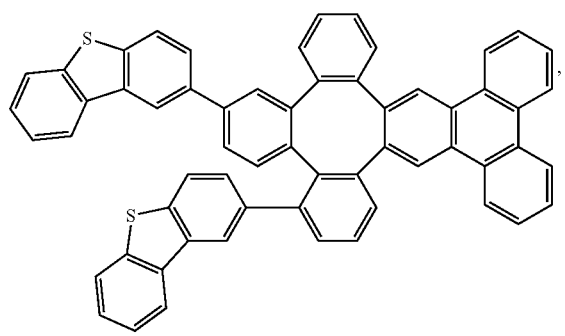
Compound 138
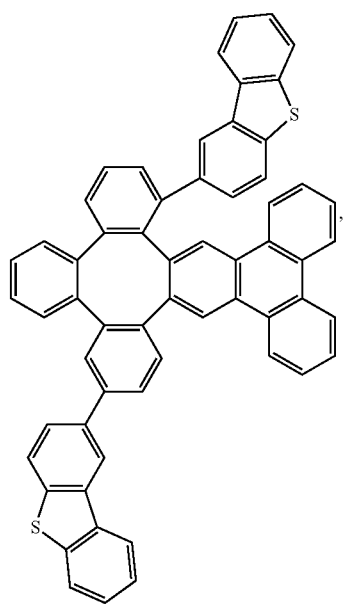
Compound 141
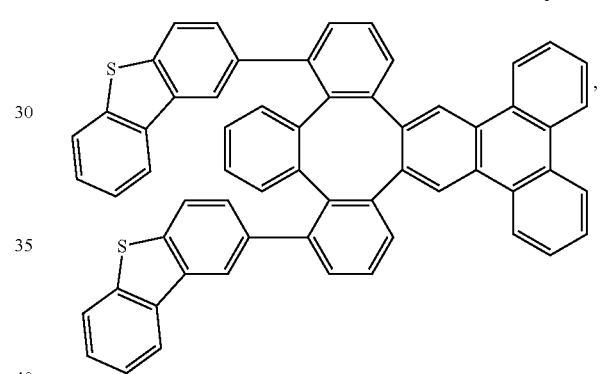
Compound 139
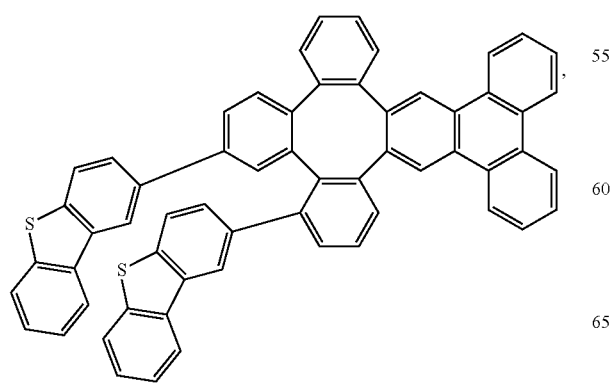
Compound 142
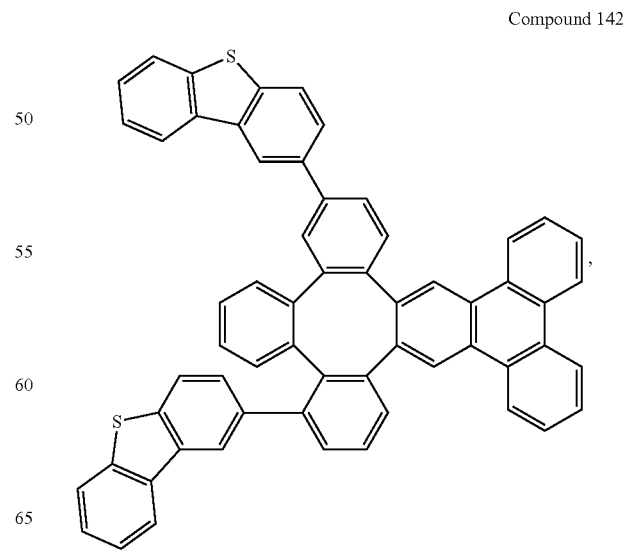

Compound 143
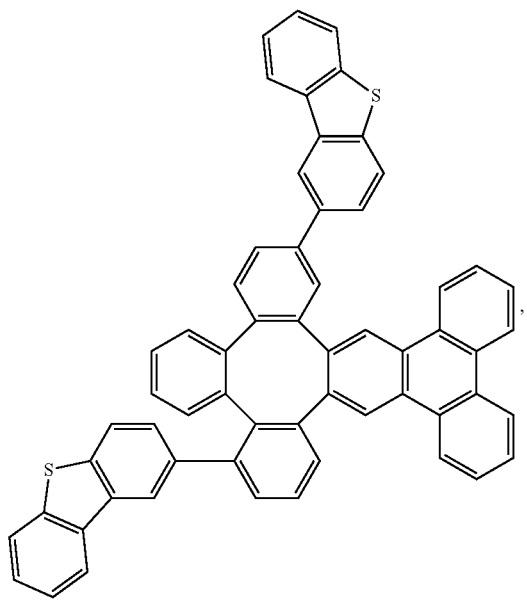
Compound 144
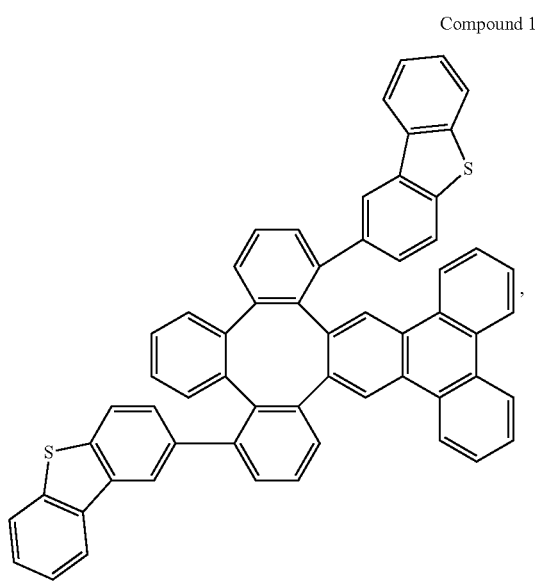
Compound 145
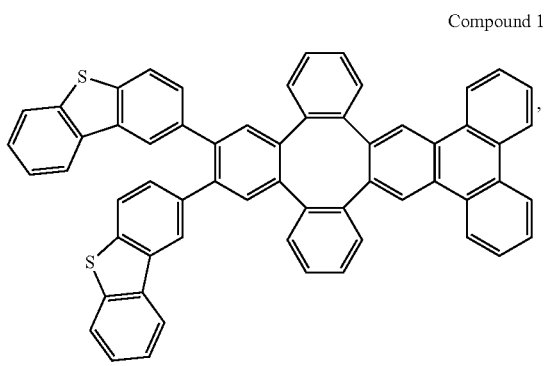
Compound 146
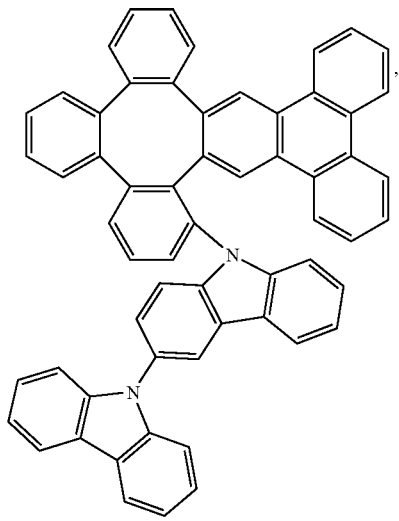
Compound 147
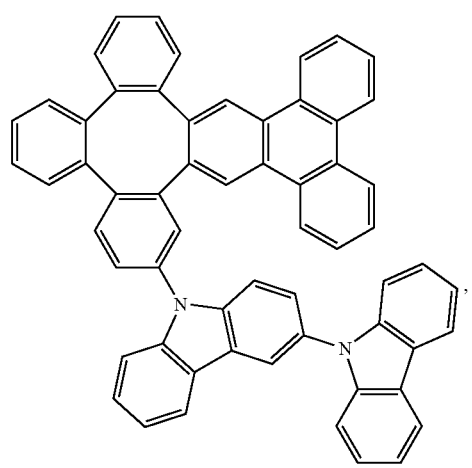
Compound 148
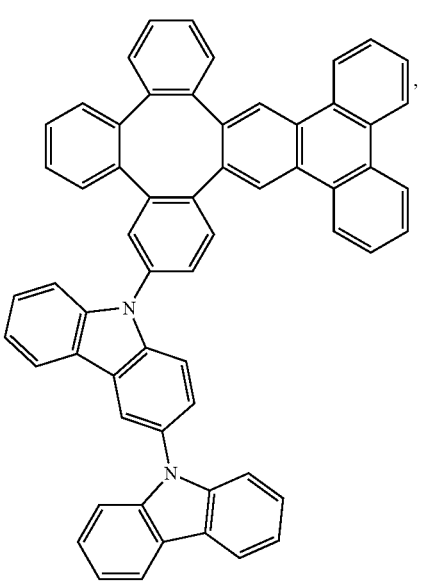

767
-continued
Compound 149
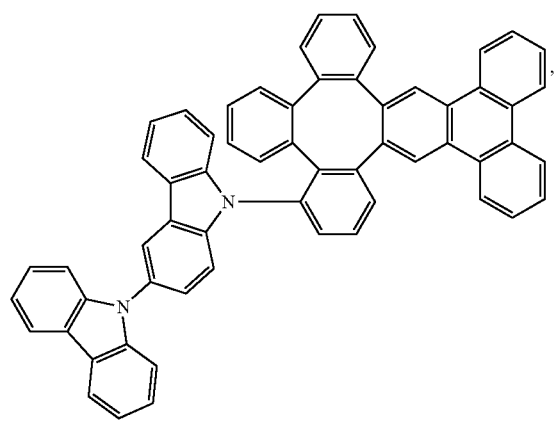
Compound 150
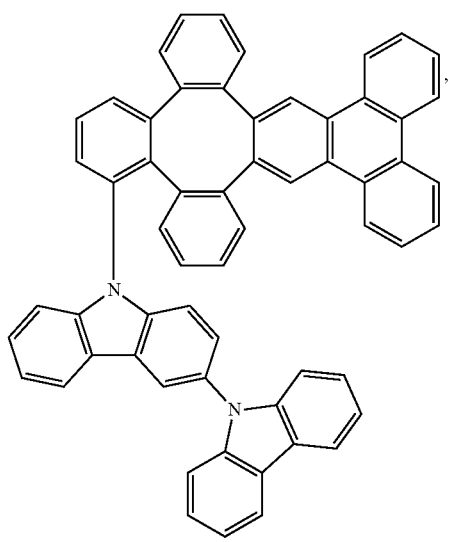
Compound 151
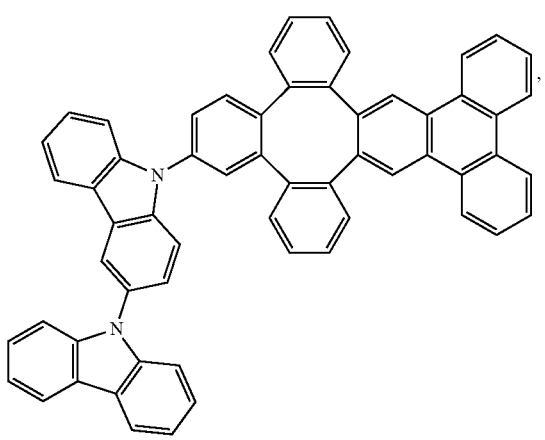
768
-continued
Compound 152
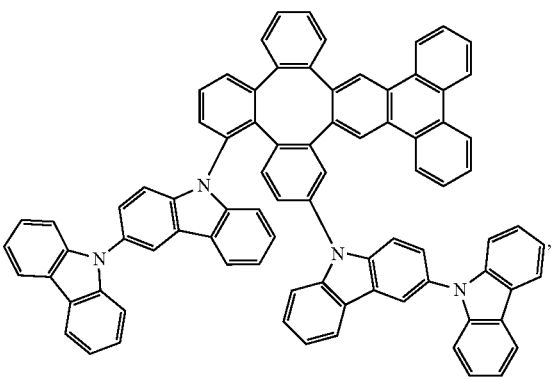
Compound 153
Compound 154

Compound 155
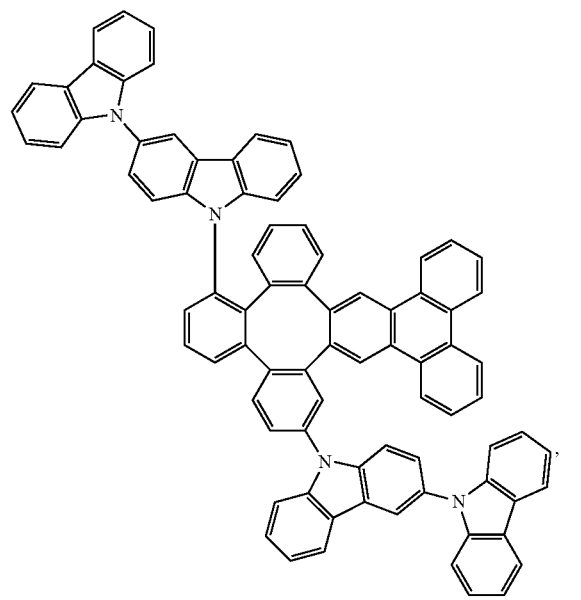
Compound 156
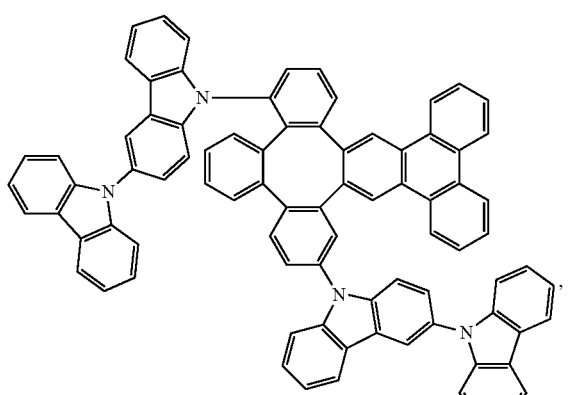
Compound 157
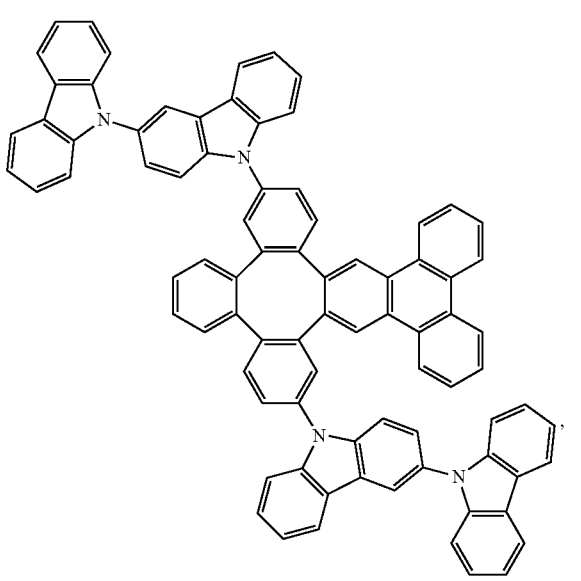
Compound 158
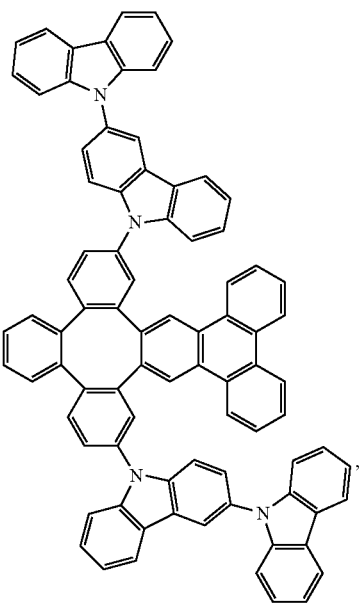
Compound 159
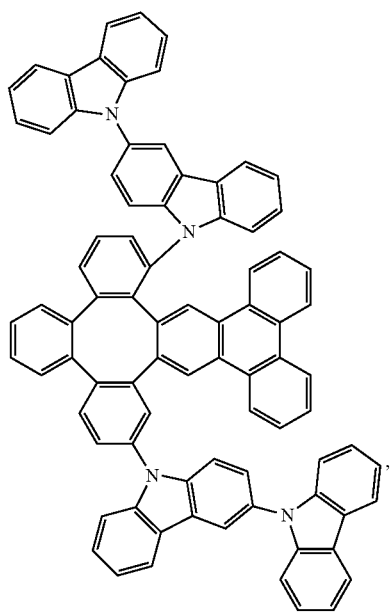

-continued
Compound 160
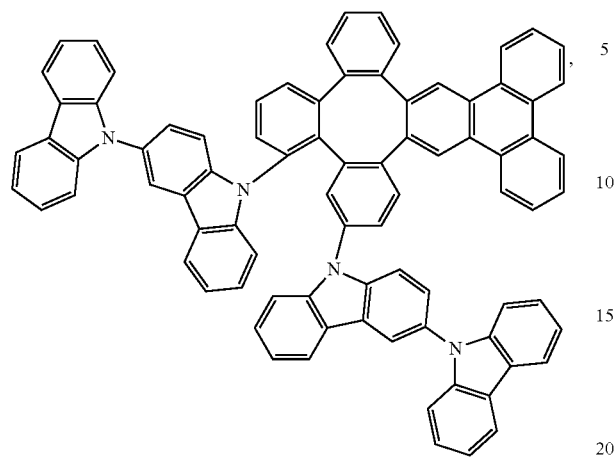
Compound 161
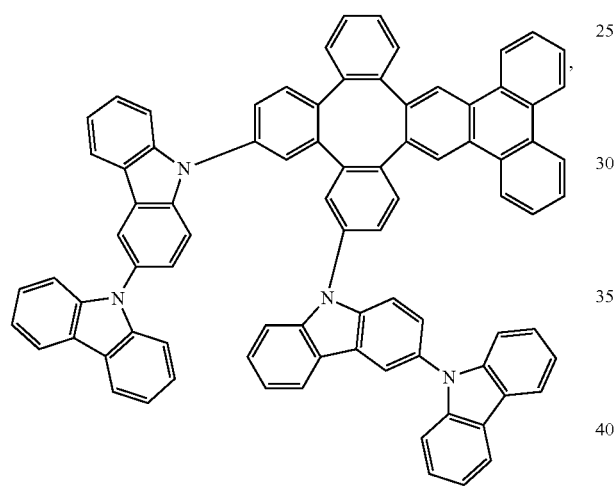
Compound 162
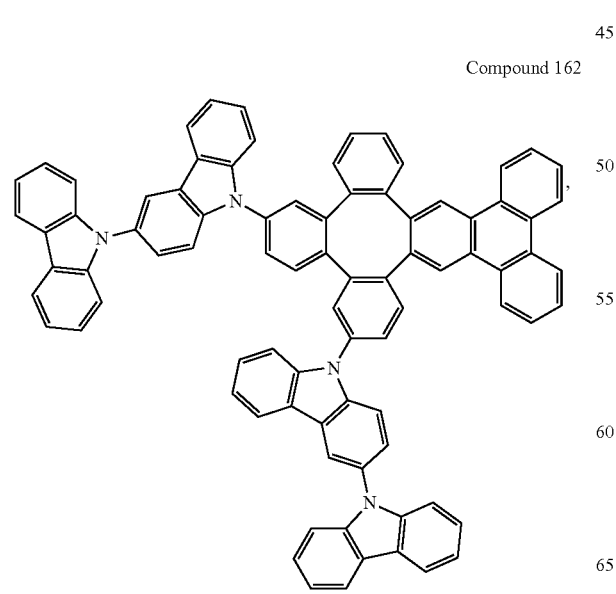
-continued
Compound 163
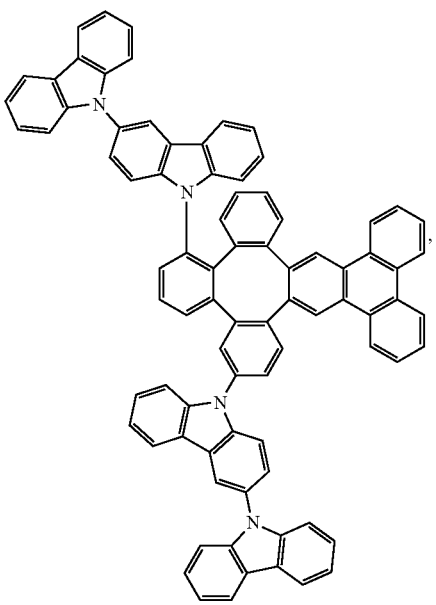
Compound 164
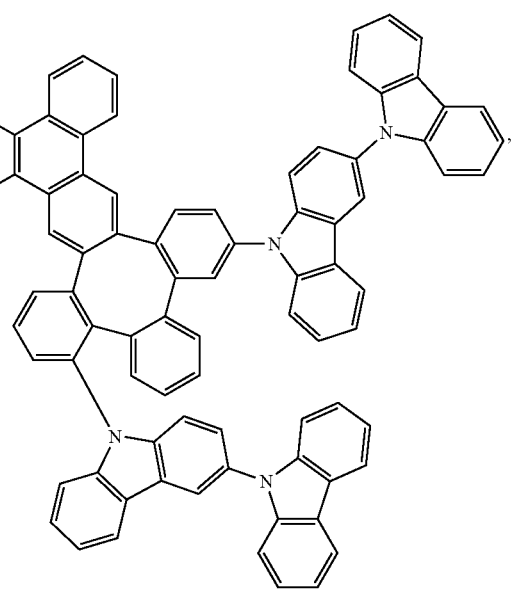

Compound 165
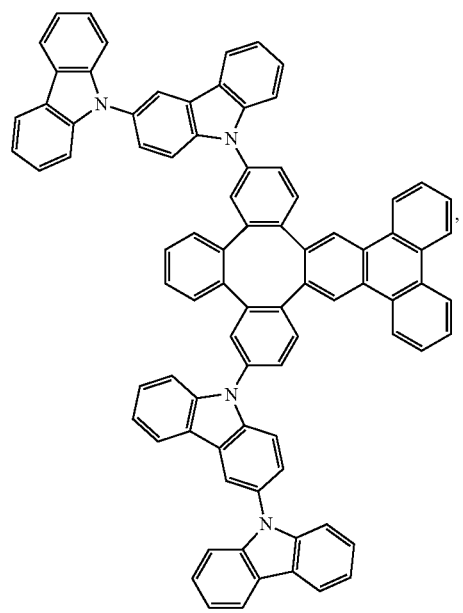
Compound 167
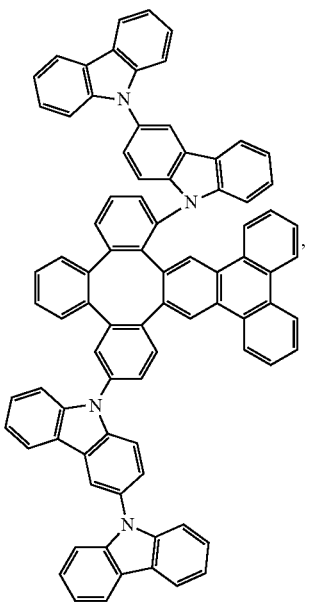
Compound 168
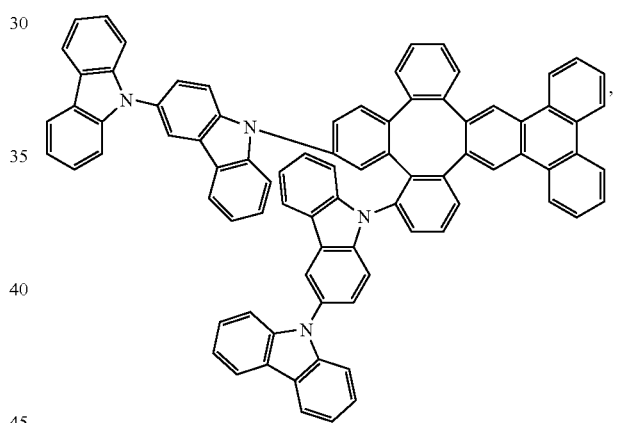
Compound 166
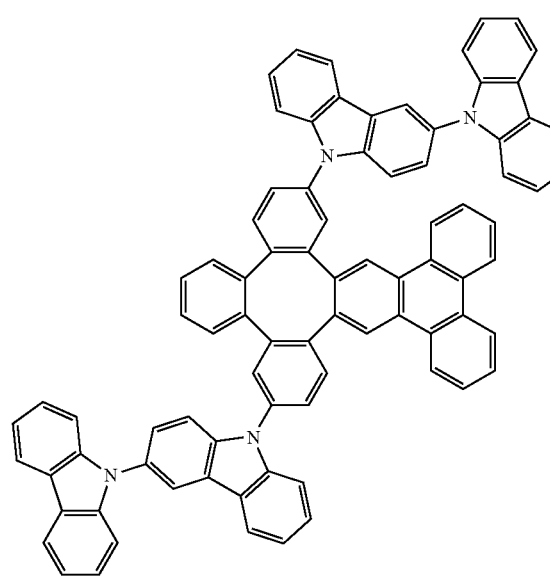
Compound 169
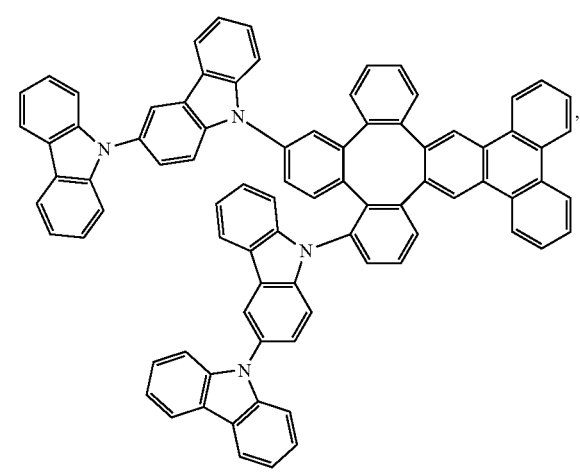

-continued
Compound 170
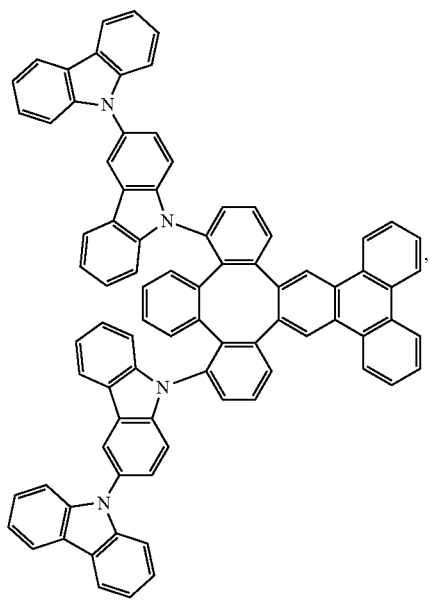
Compound 171
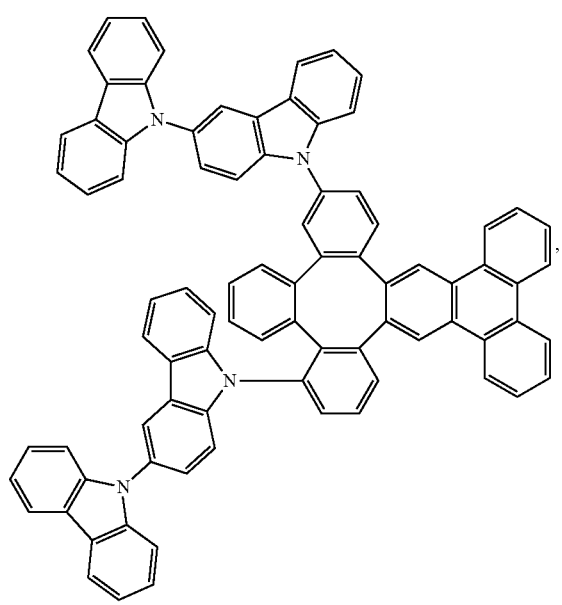
Compound 172
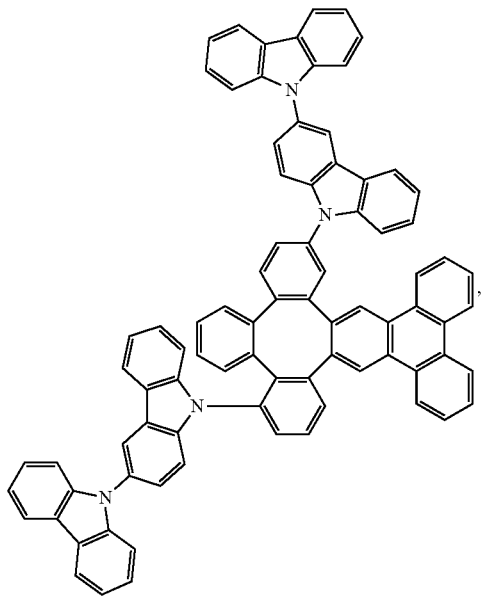
Compound 173
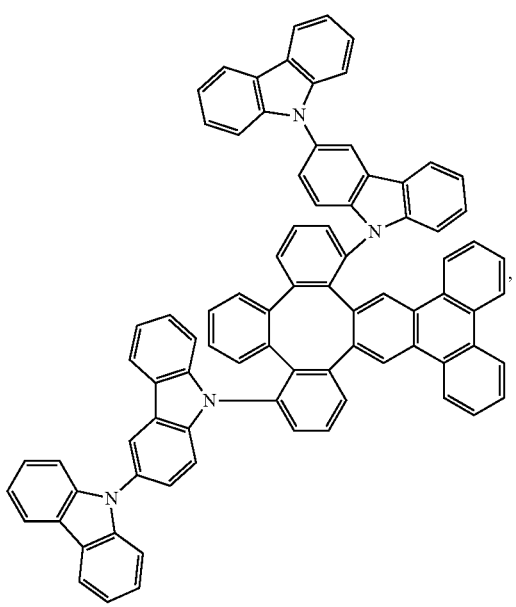

Compound 174
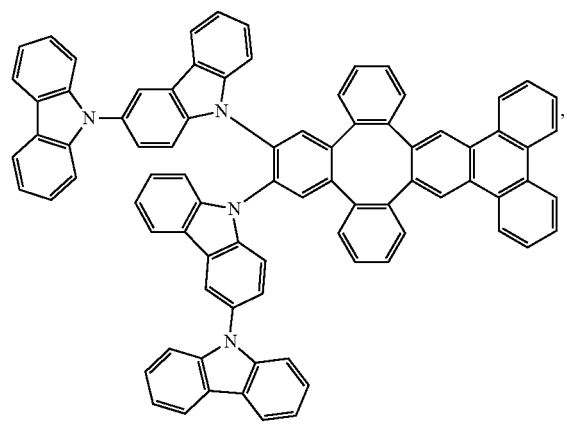
Compound 175
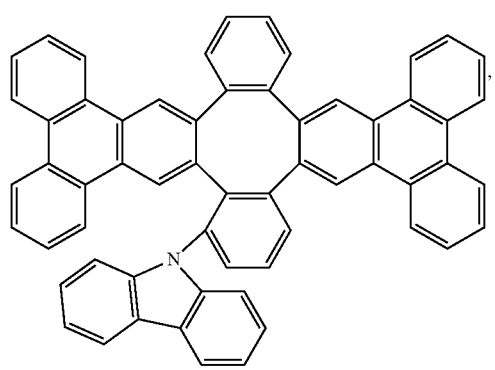
Compound 176
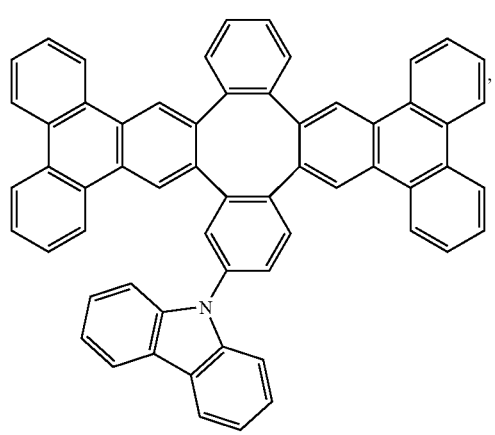
Compound 177
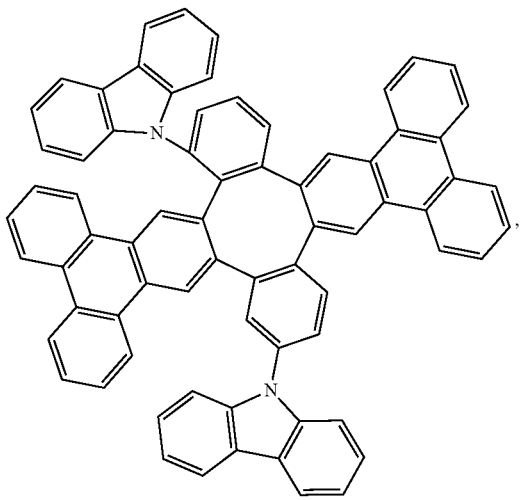
Compound 178
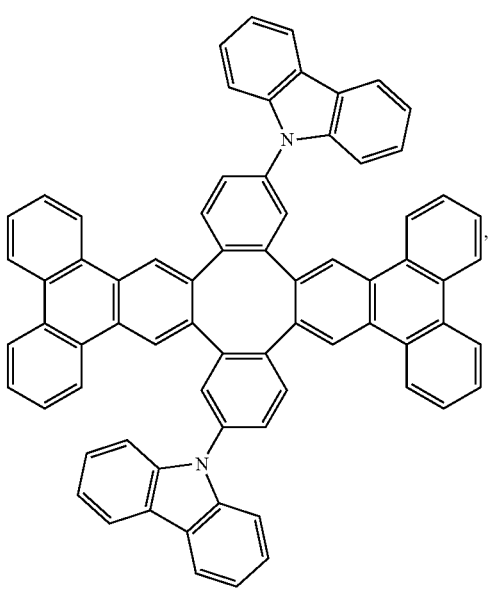

Compound 179
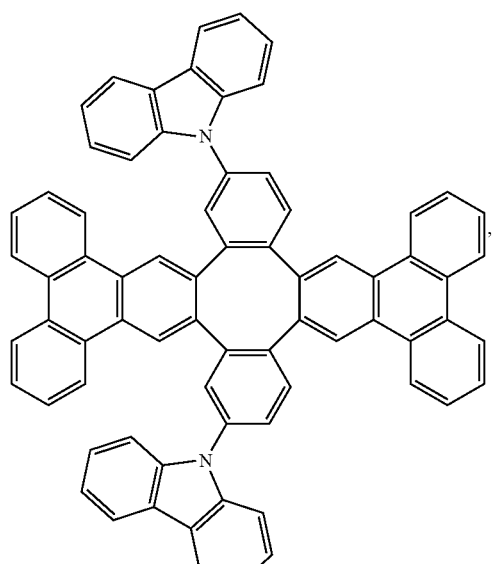
Compound 180
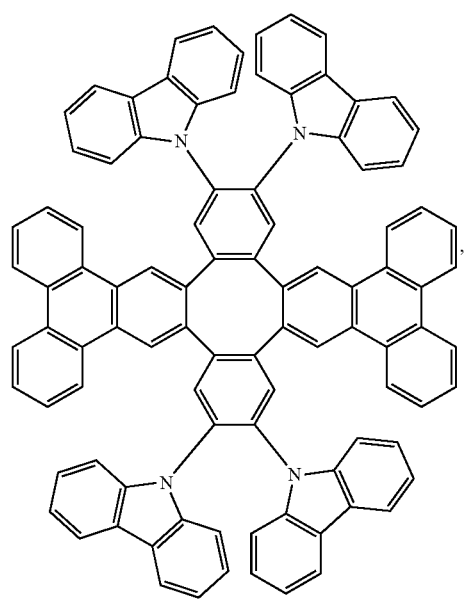
Compound 181
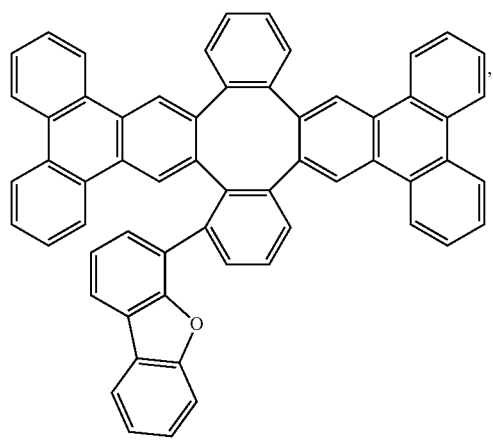
Compound 182
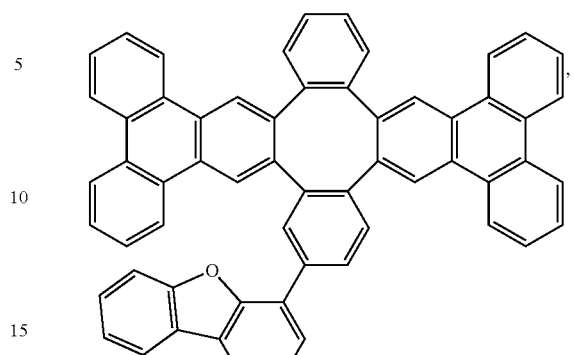
Compound 183
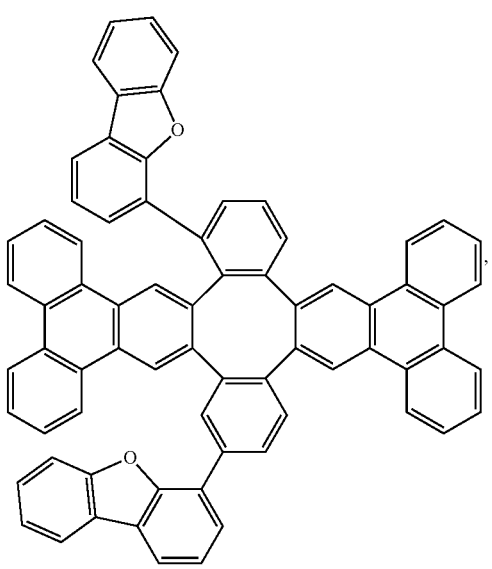
Compound 184
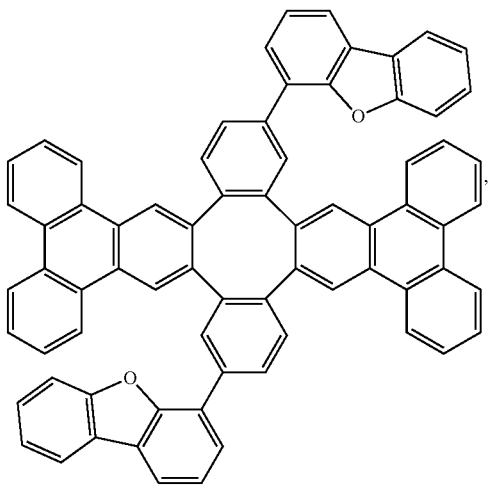

Compound 185
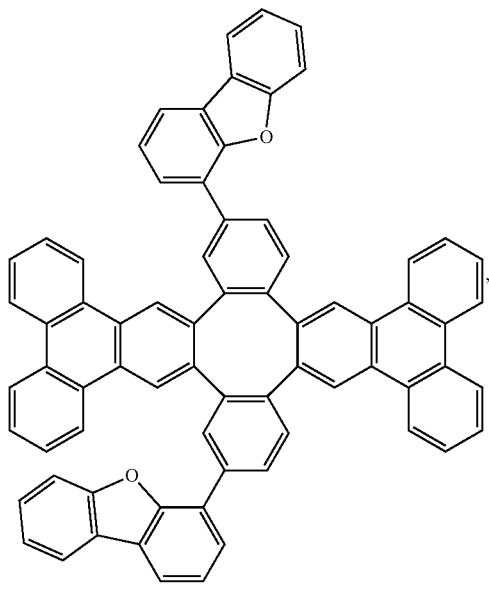
Compound 186
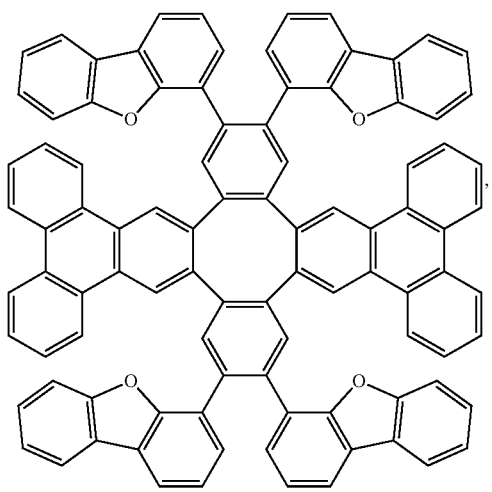
Compound 187
Compound 188
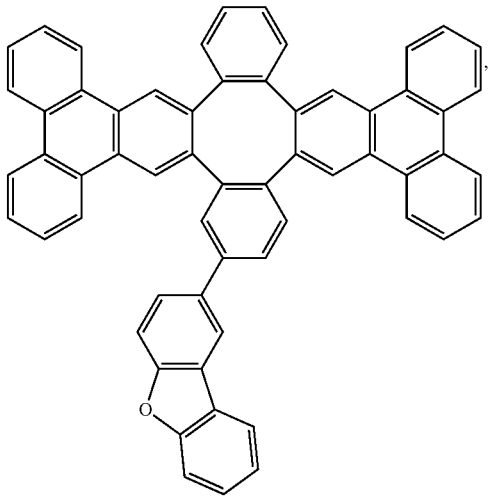
Compound 189
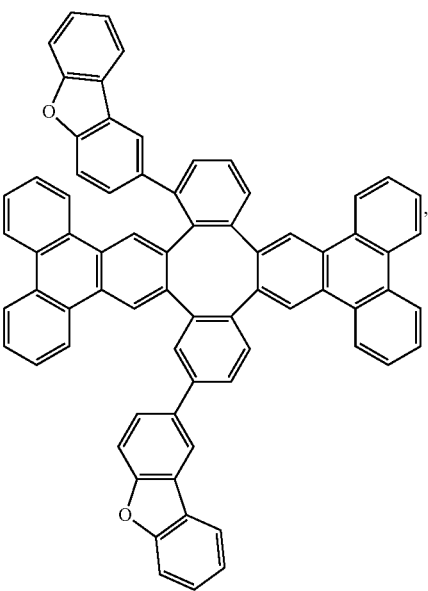

Compound 190
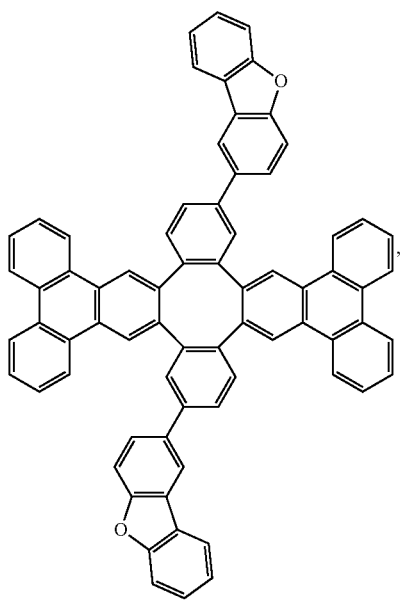
Compound 191
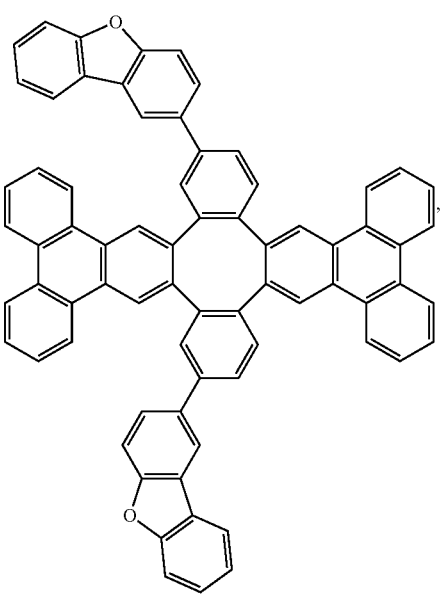
Compound 192
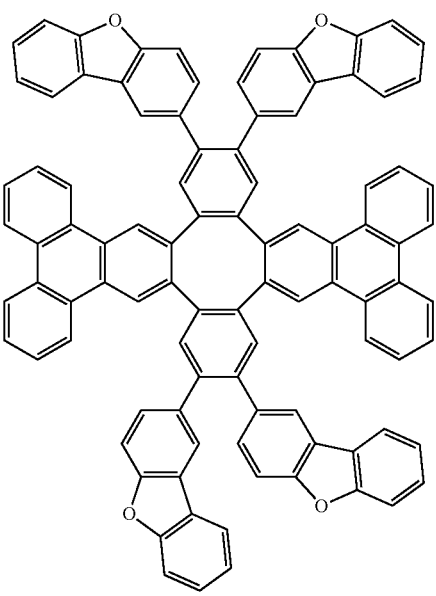
Compound 193
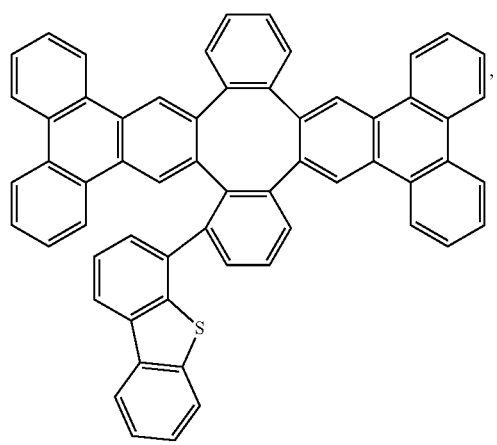
Compound 194
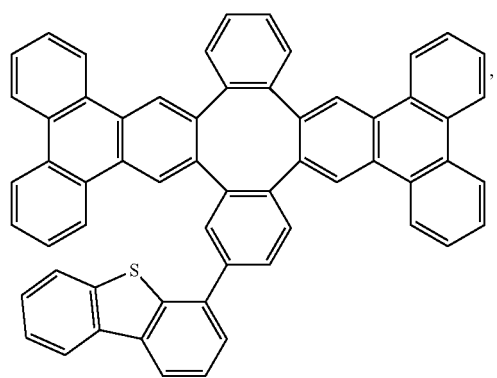

Compound 195
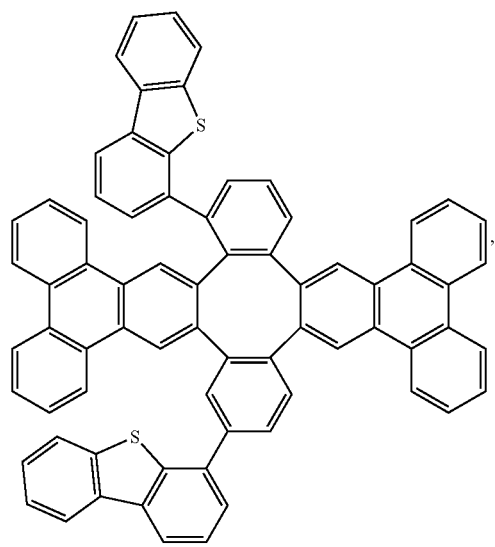
Compound 196
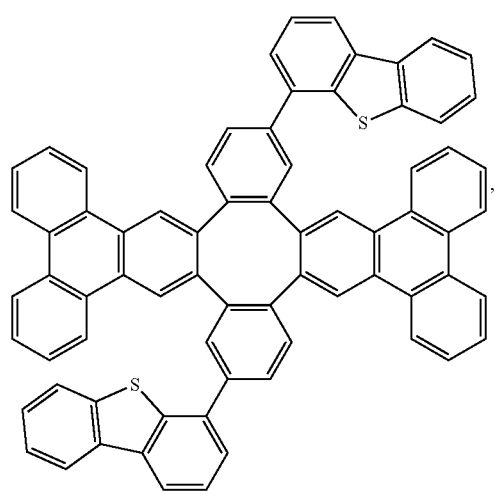
Compound 197
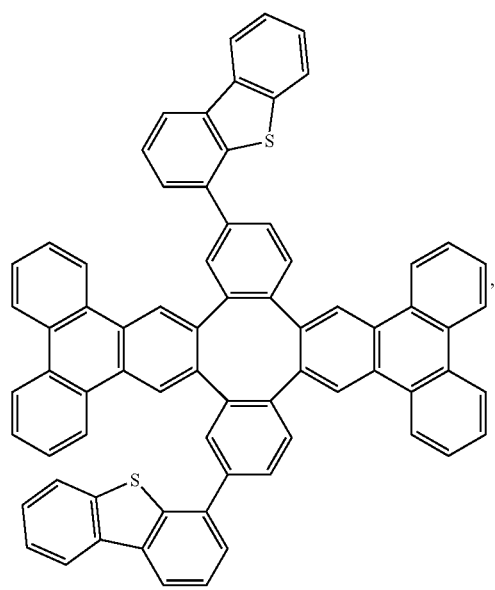
Compound 198
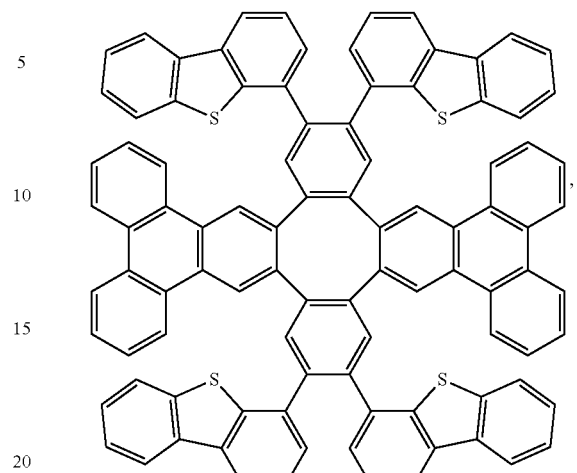
Compound 199
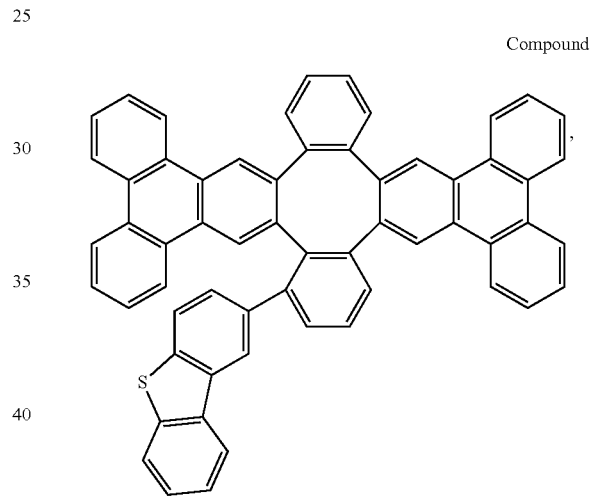
Compound 200
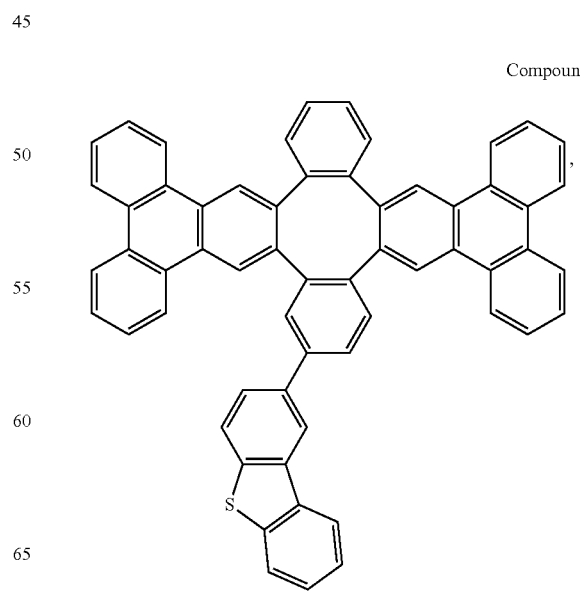

Compound 201
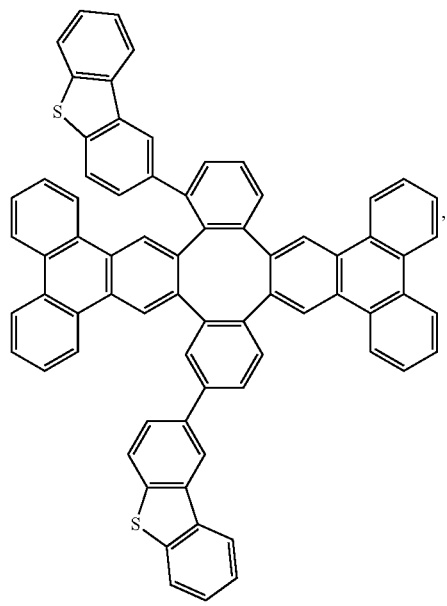
Compound 203
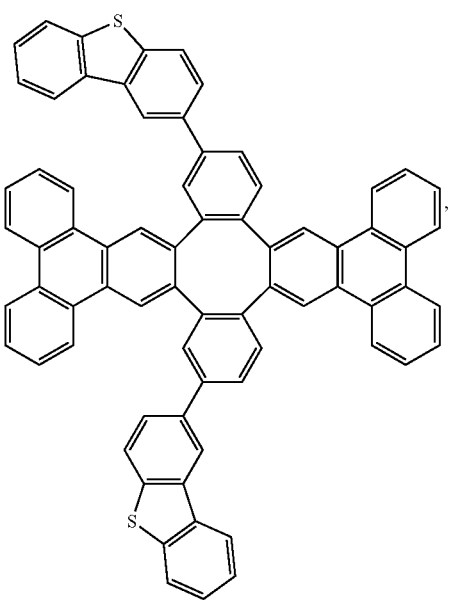
Compound 202
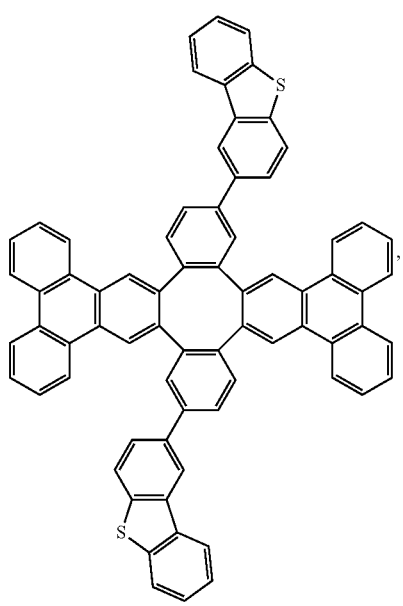
Compound 204
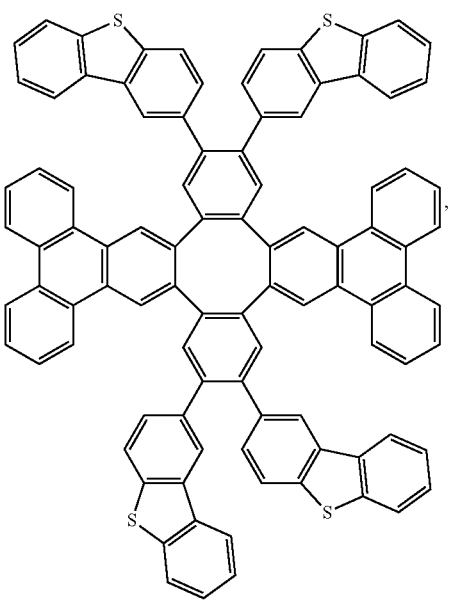

-continued
Compound 205
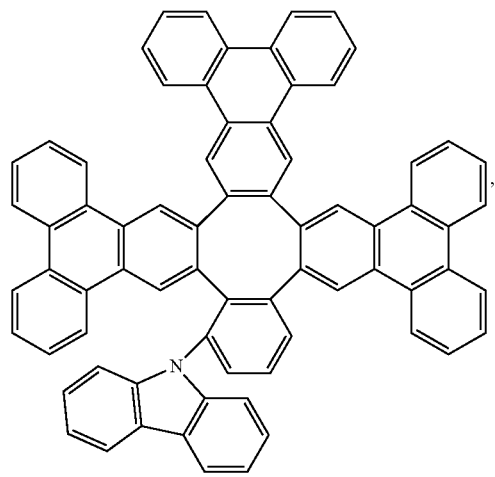
Compound 206
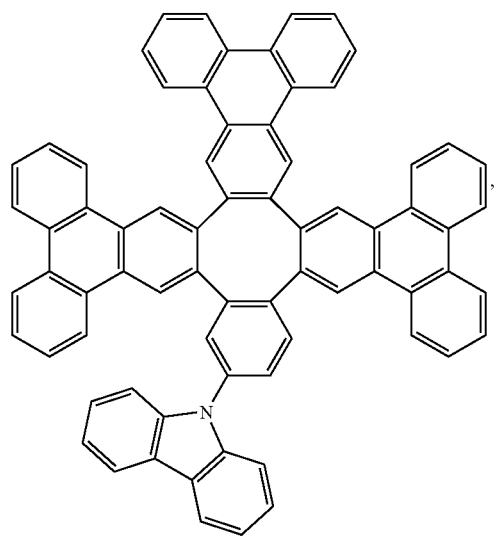
Compound 207
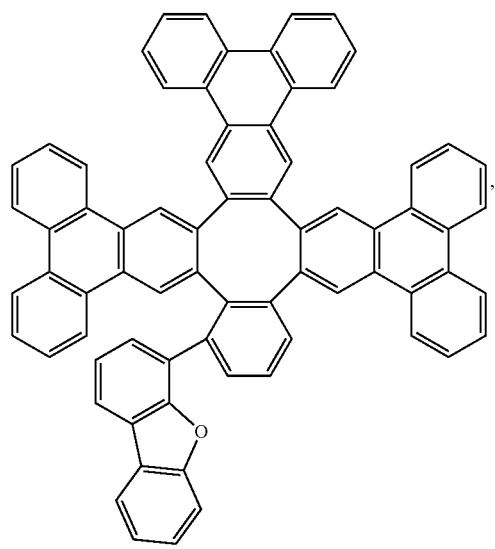
-continued
Compound 208
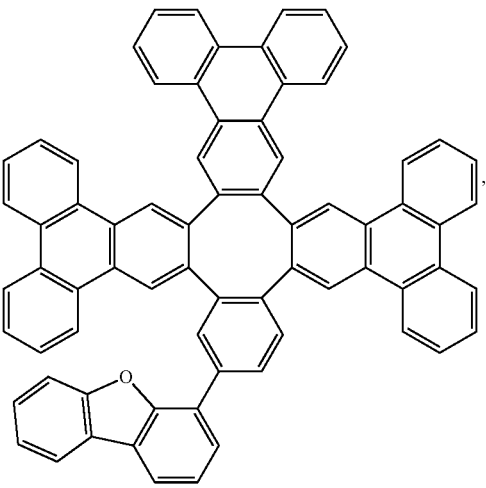
Compound 209
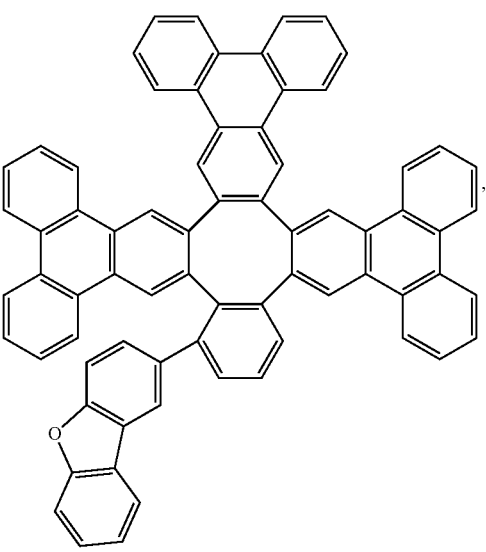

Compound 210
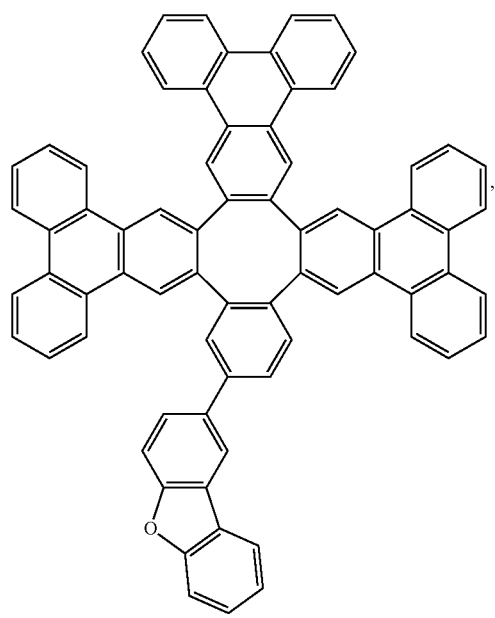
Compound 211
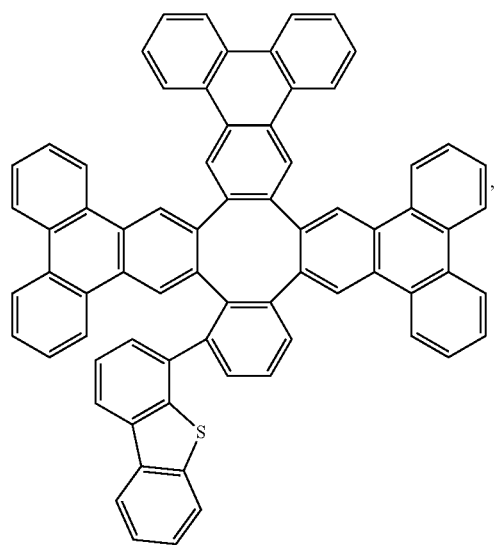
Compound 212
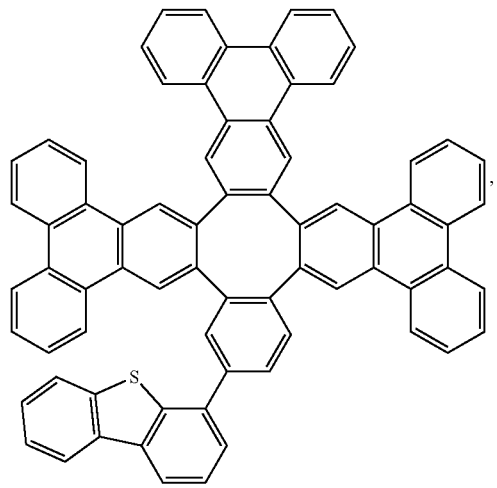
Compound 213
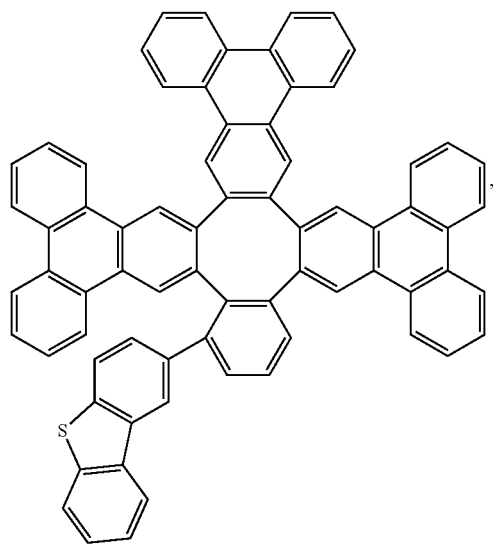
Compound 214
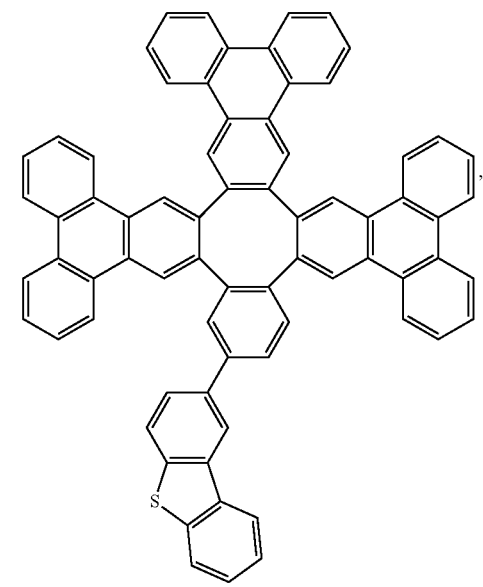

Compound 215
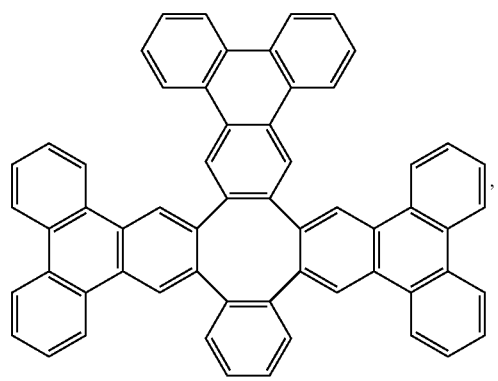, and
Compound 216
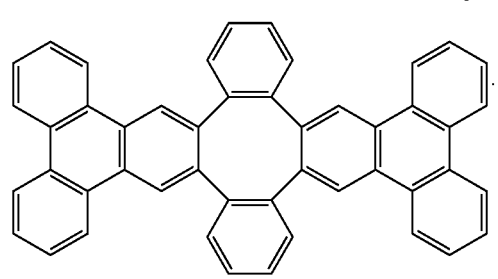.
11. The compound of claim 1, wherein the compound is selected from the group consisting of:
Compound T1
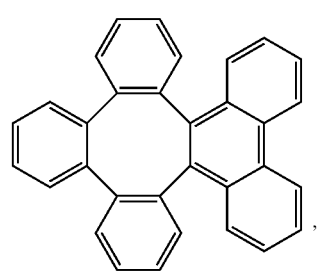,
Compound T2
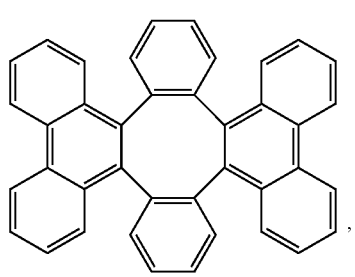,
Compound T3
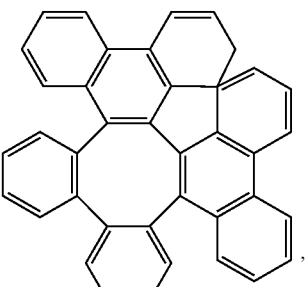,
Compound T4
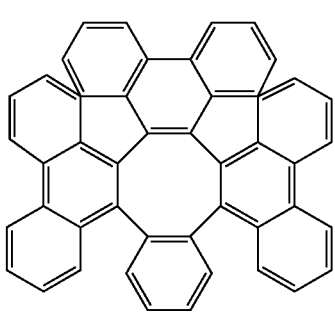,
Compound T5
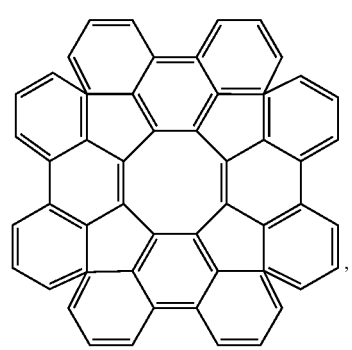,
Compound T6
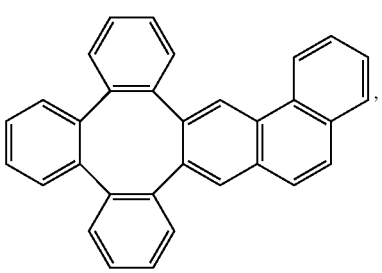,
Compound T7
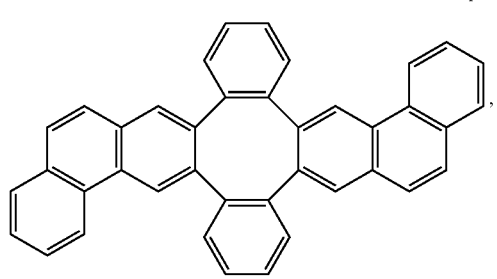, -continued
Compound T8
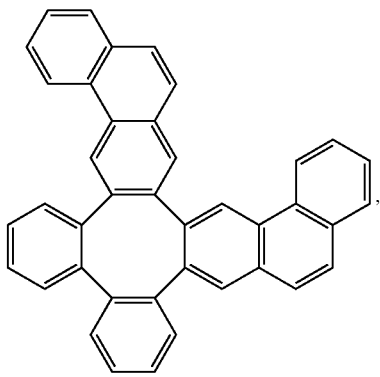
Compound T9
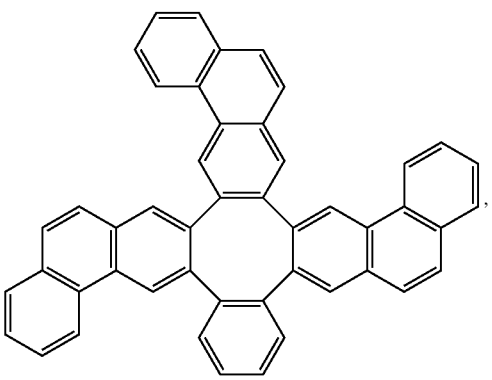
Compound T10
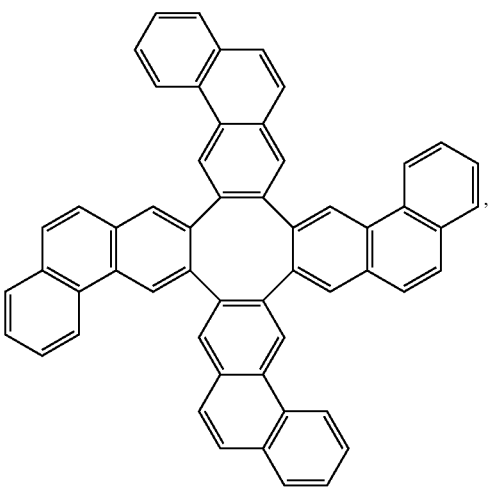
Compound T11
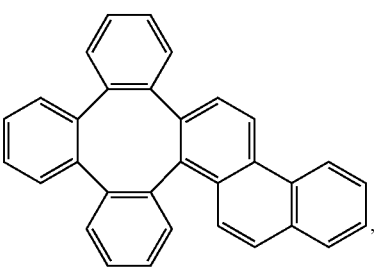
-continued
Compound T12
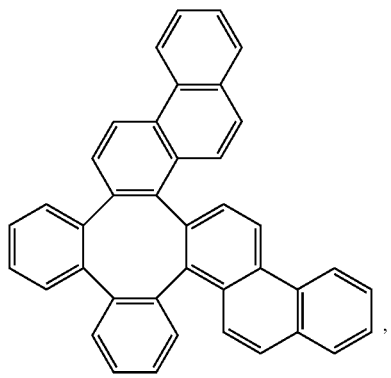
Compound T13
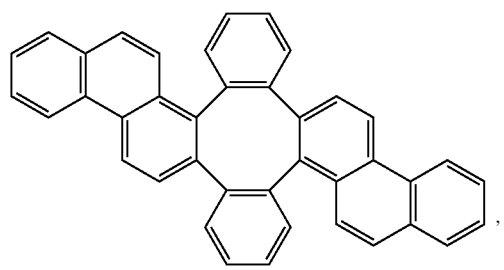
Compound T14
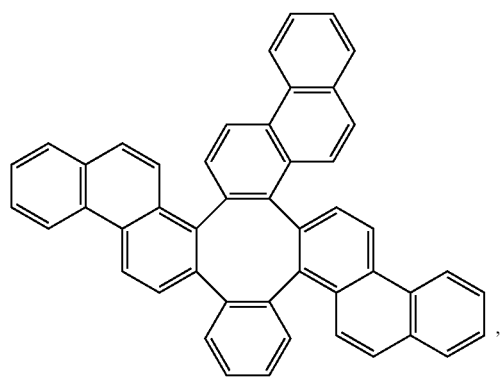
Compound T15
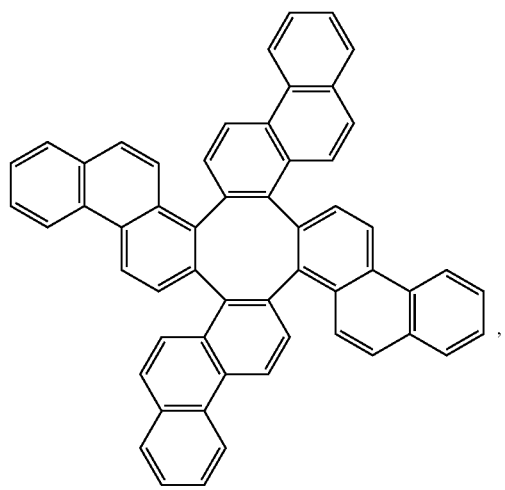

797
-continued
Compound T16
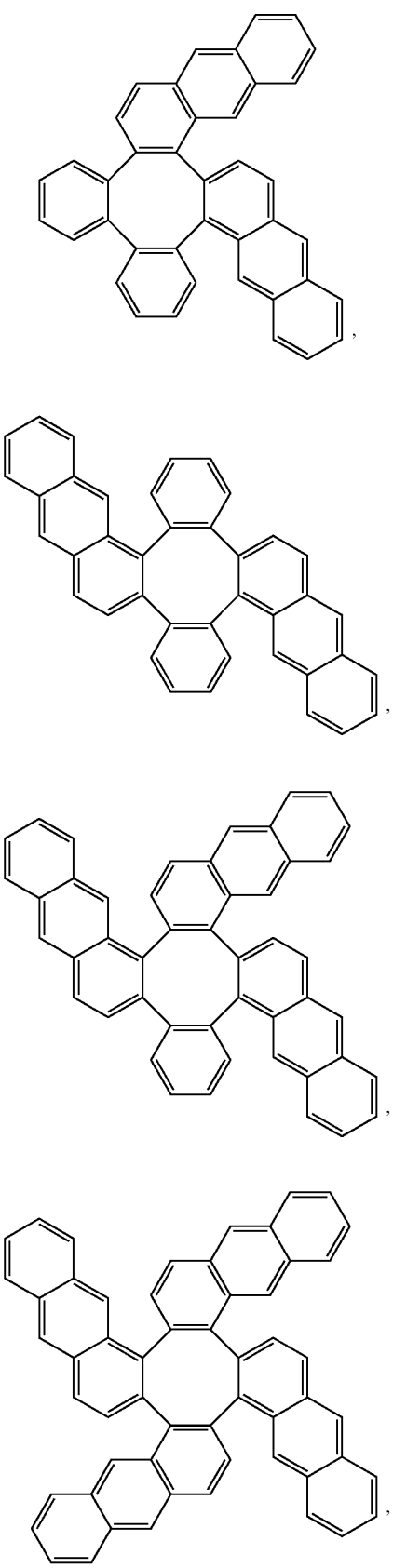
Compound T17
Compound T18
Compound T19
798
-continued
Compound T20
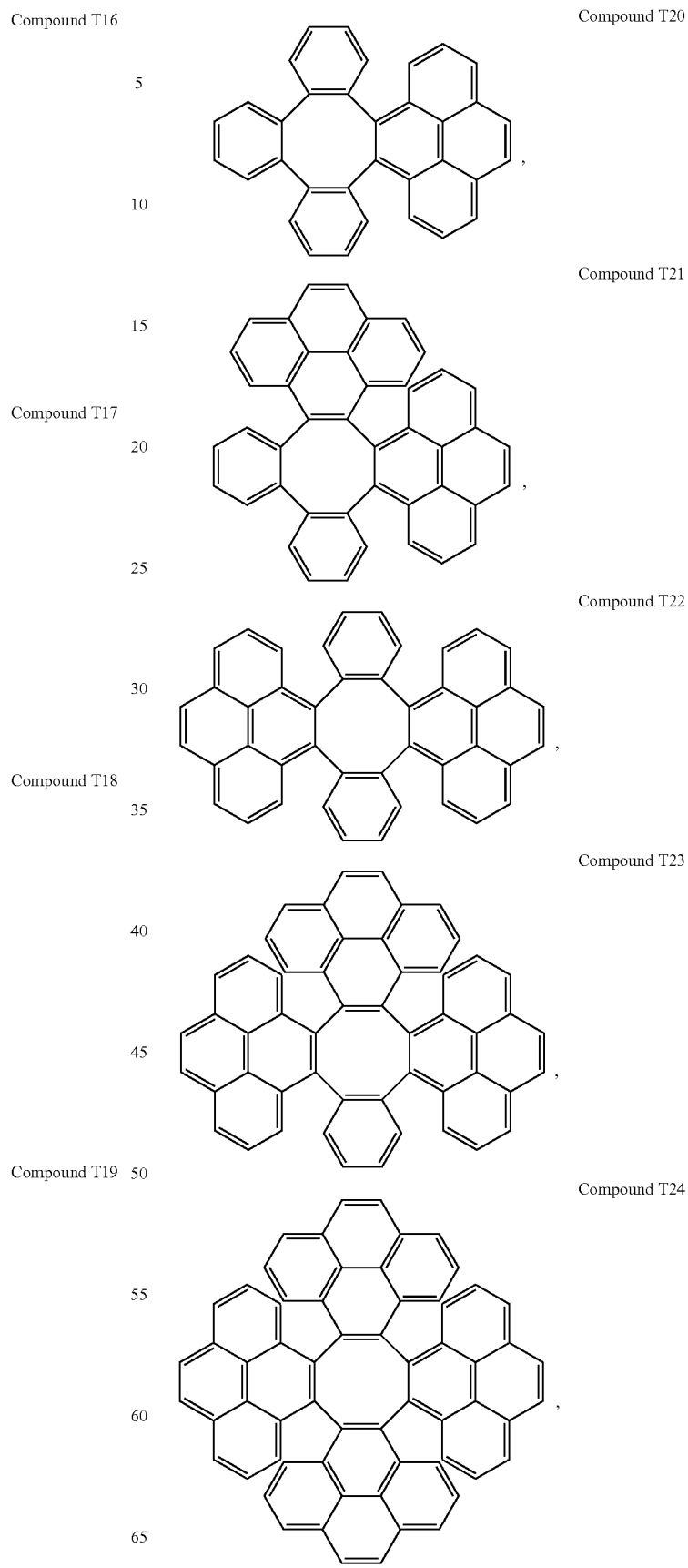
Compound T21
Compound T22
Compound T23
Compound T24

-continued
Compound T25
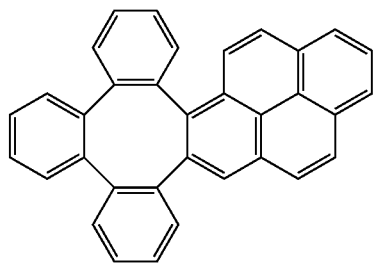
Compound T26
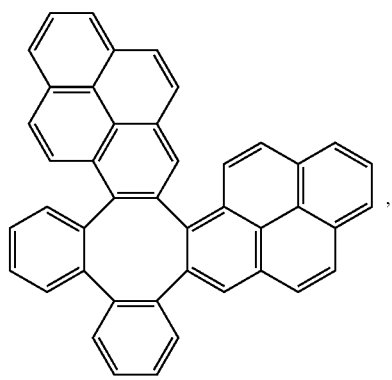
Compound T27
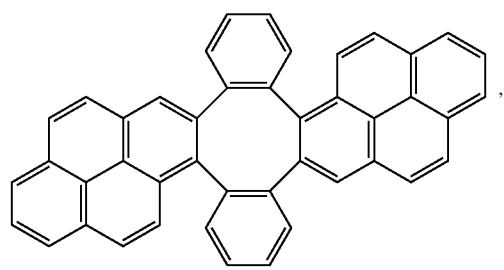
Compound T28
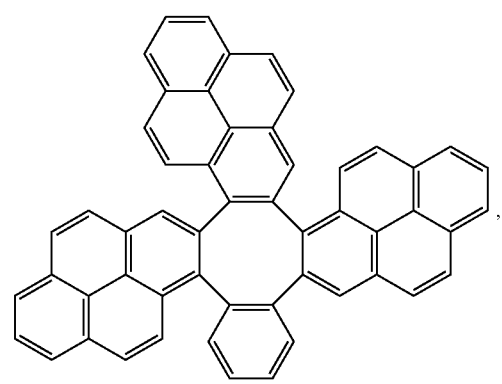
-continued
Compound T29
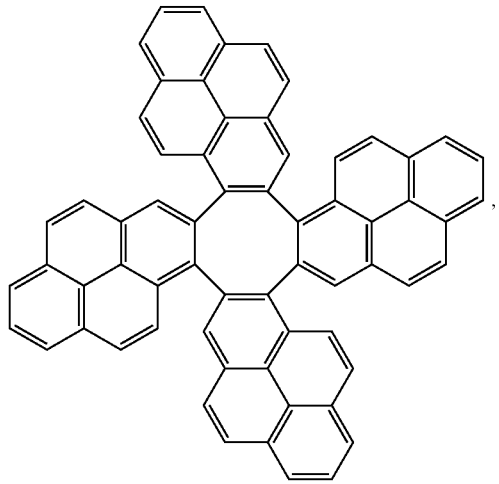
Compound T30
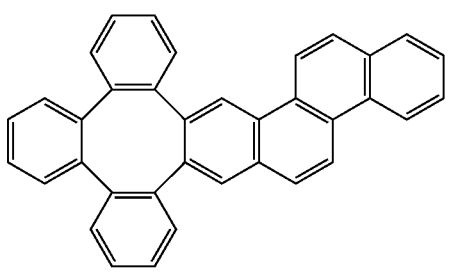
Compound T31
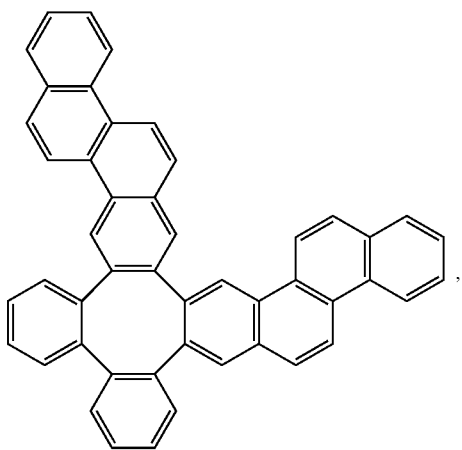
Compound T32
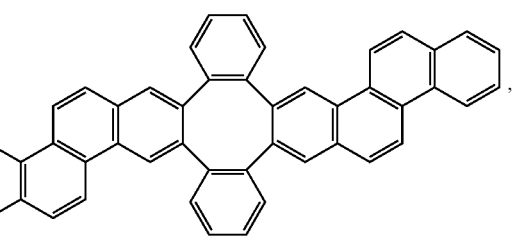

801
-continued
Compound T33
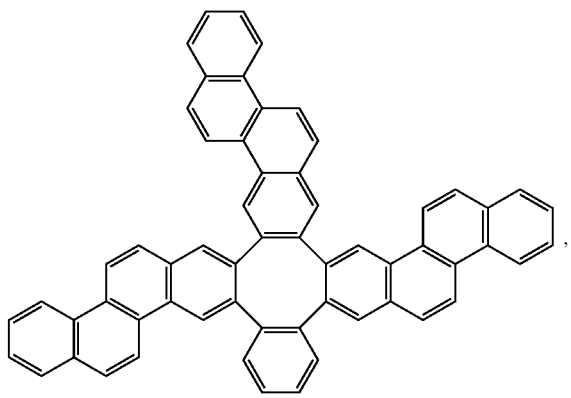
Compound T34
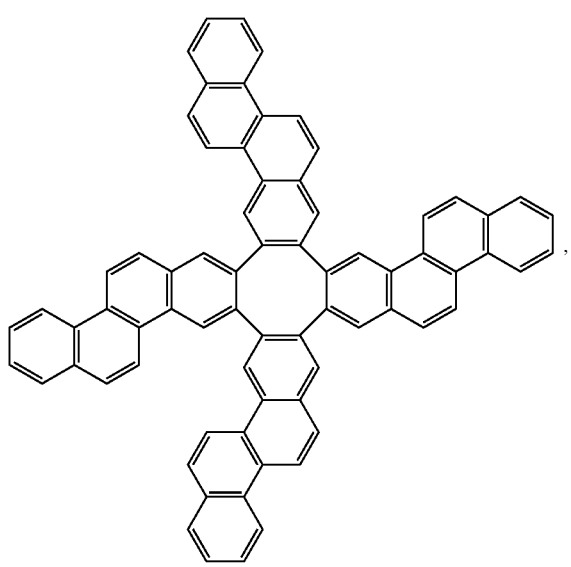
Compound T35
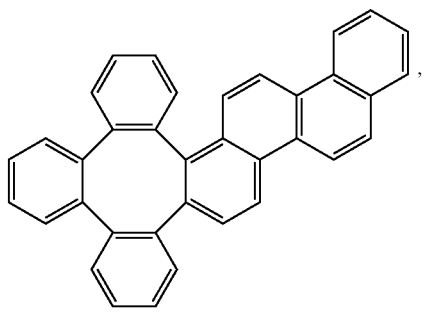
802
-continued
Compound T36
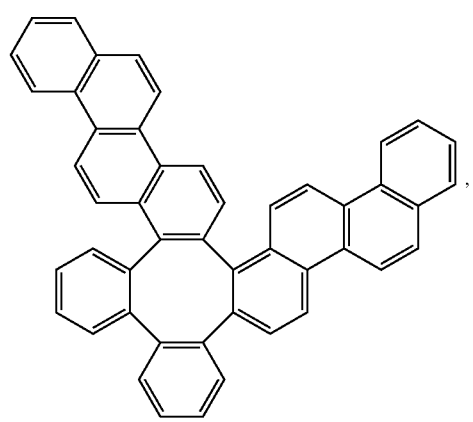
Compound T37
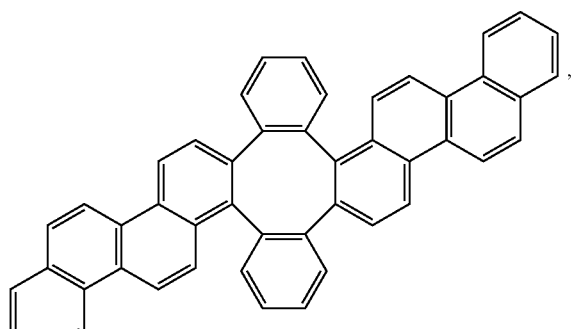
Compound T38
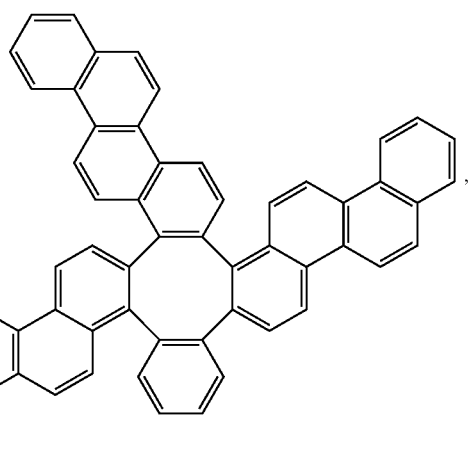

803
-continued
Compound T39
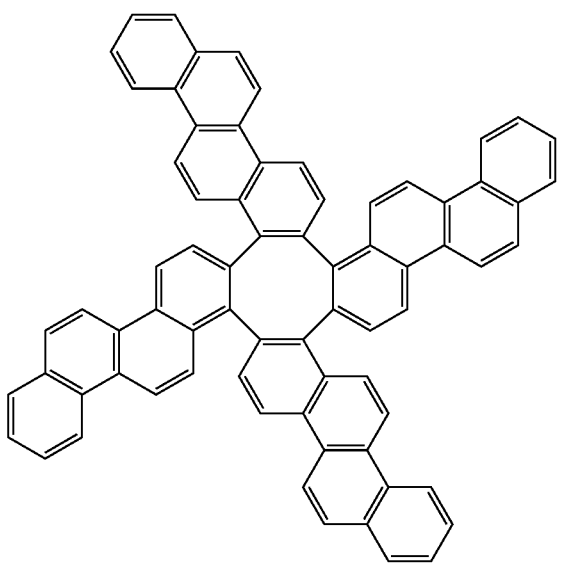
Compound T40
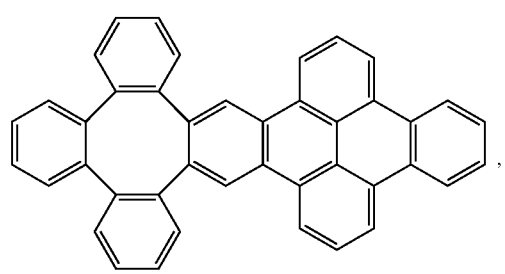
Compound T41
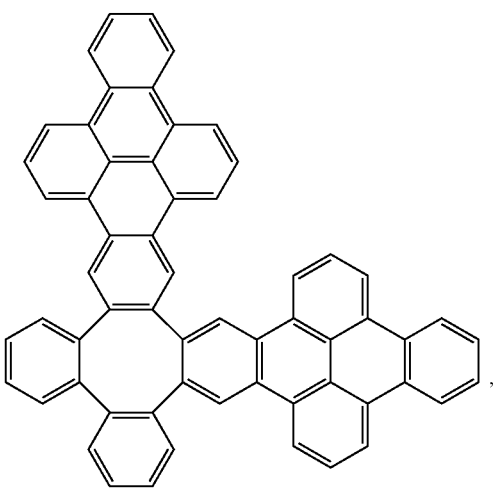
Compound T42
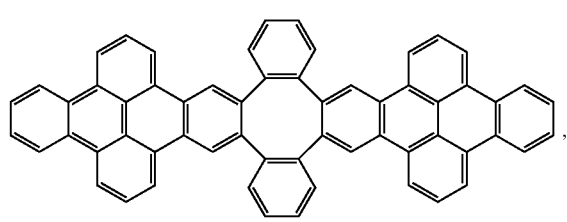
804
-continued
Compound T43
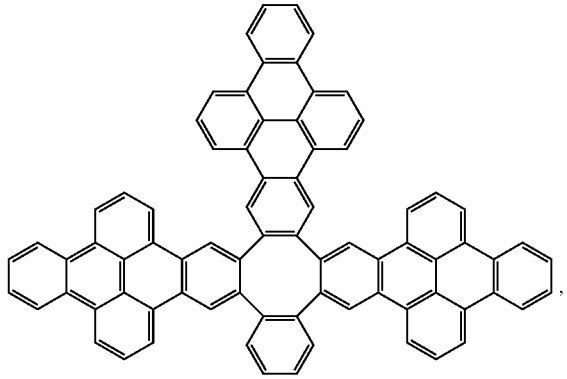
Compound T44
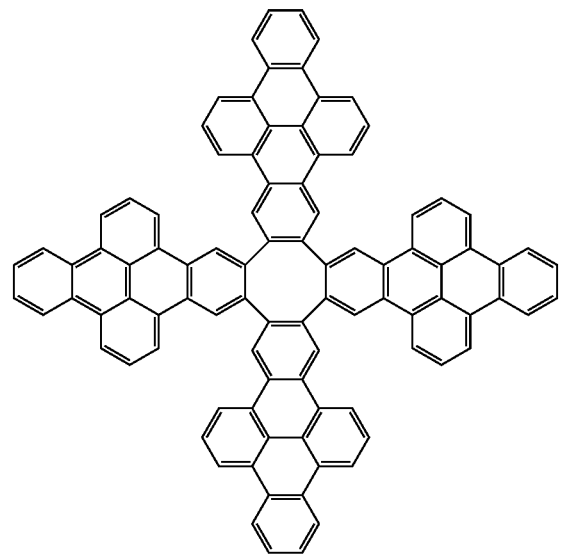
Compound U1
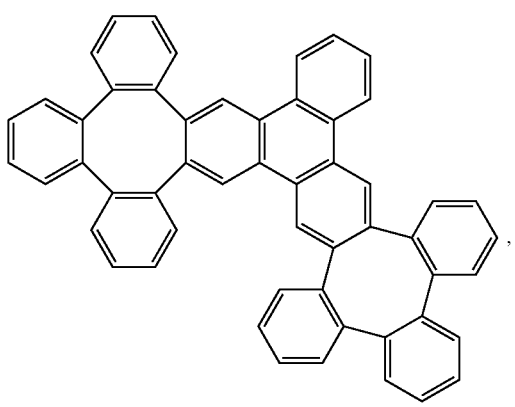

Compound U2
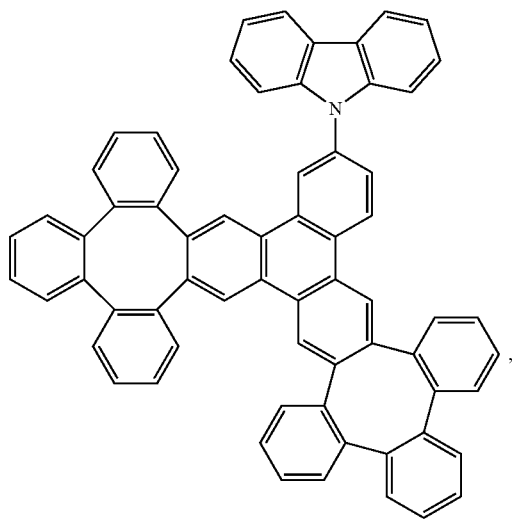
Compound U4
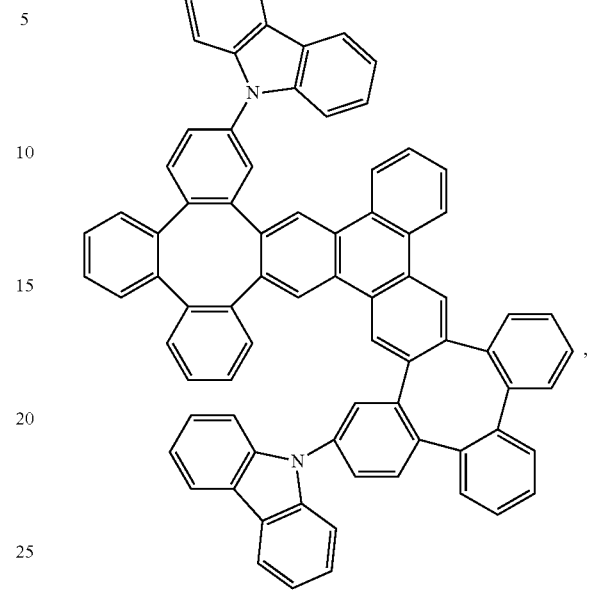
Compound U5
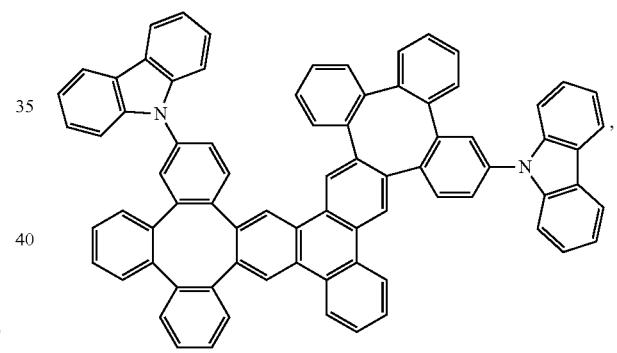
Compound U3
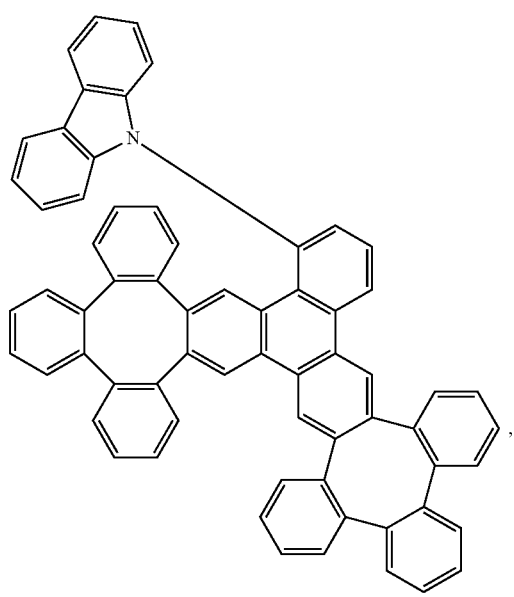
Compound U6
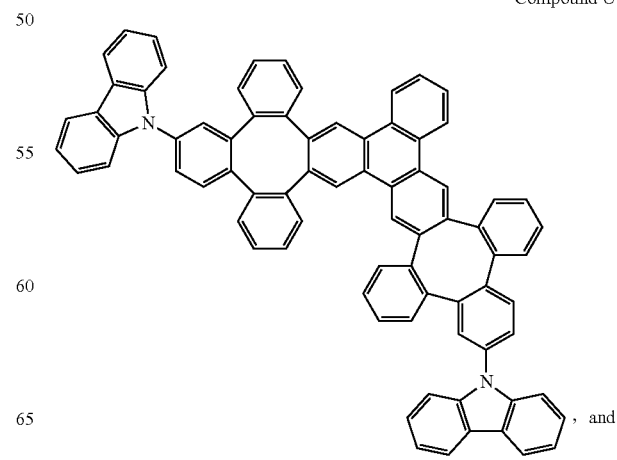
, and Compound U7

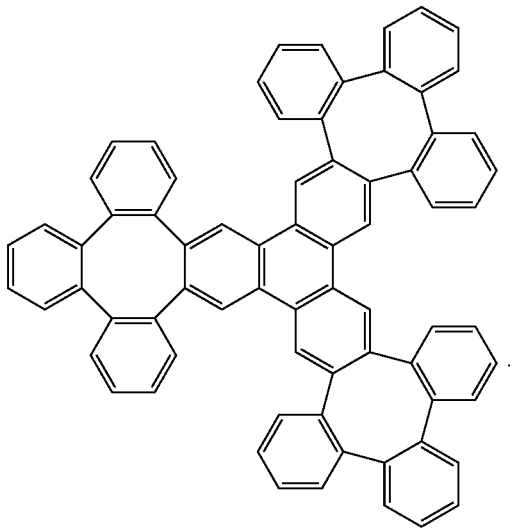

12. An organic light emitting device (OLED) comprising:
an anode;
a cathode; and
an organic layer, disposed between the anode and the cathode, comprising a compound having Formula I:

Formula I

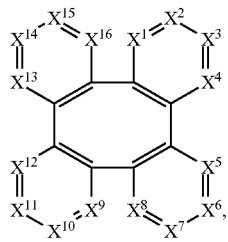

wherein $X^1$-$X^{16}$ are each independently selected from the group consisting of CR and N;
wherein at least two adjacent $X^1$-$X^{16}$ are CR;
wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosily, alkenyl, cycloalkenyl, heteroalkenyl, alkynyl, aryl, heteroaryl, acyl, carbonyl, carboxylic acids, ester, nitrile, isonitrile, sulfanyl sulfinyl, sulfonyl, phosphino, and combinations thereof;
wherein at least one pair of adjacent R is Attachment A

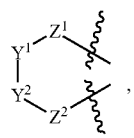

Attachment B

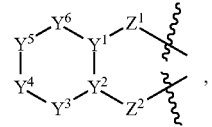

Attachment C

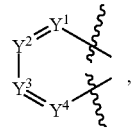

or fused with two or move aromatic rings such that no acetic unit of more than 3 fused rings is formed;
wherein in Attachments A and B, $Y^1$-$Y^2$, $Y^2$-$Y^3$, $Y^3$-$Y^4$, $Y^4$-$Y^5$ and $Y^5$-$Y^6$ are connected by single or double bonds;
wherein $Y^1$-$Y^6$ are each independently selected from the group consisting of C and N;
wherein any unsaturated C in $Y^1$-$Y^6$ are substituted by $R^1$;
wherein in Attachment A, $Z^1$ and $Z^2$ are each independently selected from the group consisting Of $C=CR^2R^3$, $C=NR^2$, $NR^2$, O, SO, $SO_2$, $BR^2$, $PR^2$, $SiR^2R^3$, and Se;
wherein in Attachment B, $Z^1$ and $Z^2$ are each independently selected from the group consisting of $CR^2R^3$, $C=CR^2R^3$, $C=O$, $C=NR^2$, $NR^2$, O, S, SO, $SO_2$, $BR^2$, P, $SiR^2R^3$, and Se;
wherein in Attachment C, at least one of $Y^1$-$Y^4$ is an N;
wherein $R^1$-$R^3$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein

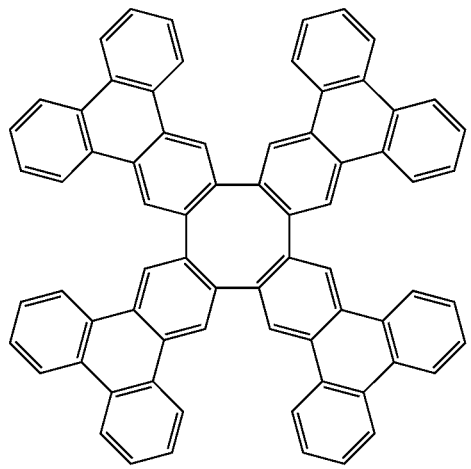 [SMILES: c1ccc2c(c1)c1ccccc1c1cc3c(cc21)-c1cc2c4ccccc4c4ccccc4c2cc1-c1cc2c4ccccc4c4ccccc4c2cc1-c1cc2c4ccccc4c4ccccc4c2cc1-3]

is excluded.
13. The OLED of claim 12, wherein the organic layer is an emissive layer and the compound of Formula I is a host.
14. The OLED of claim 12, wherein the organic layer further comprises a phosphorescent emissive dopant;

wherein the emissive dopant is a transition metal complex having at least one ligand or part of the ligand if the ligand is more than bidentate selected from the group consisting of:
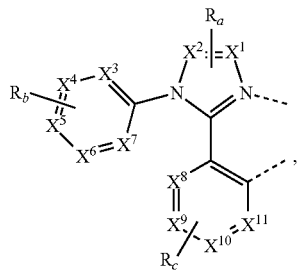
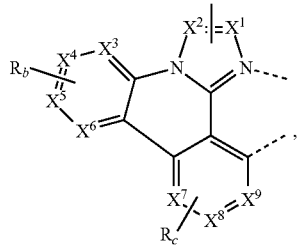
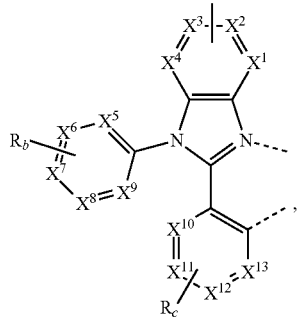
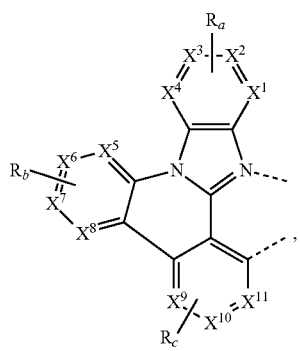
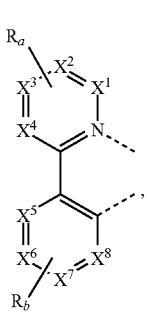
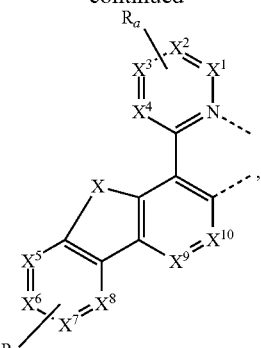
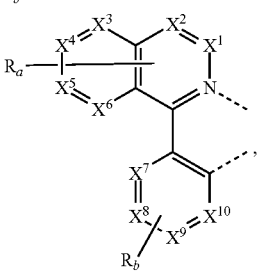
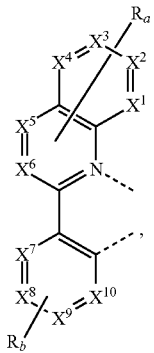
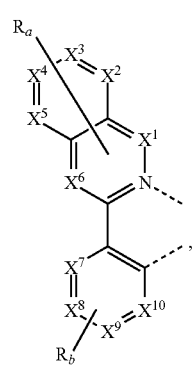
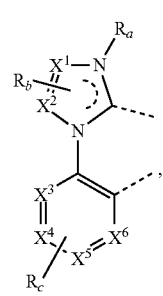

811
-continued

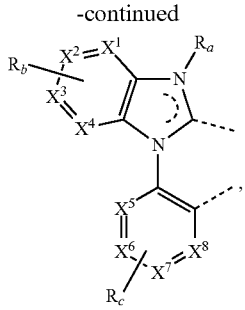

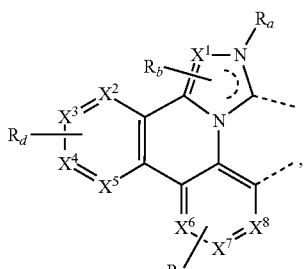

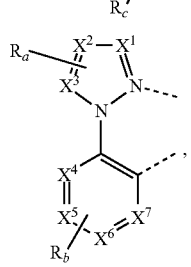

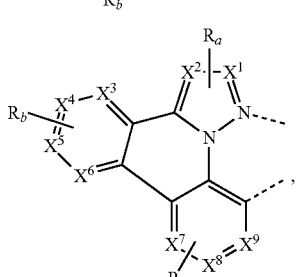

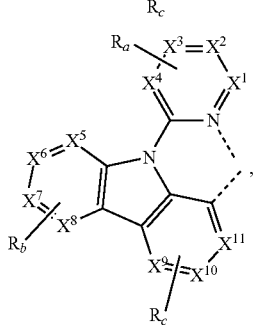

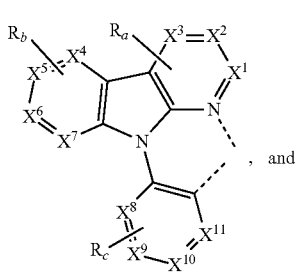
, and

812
-continued

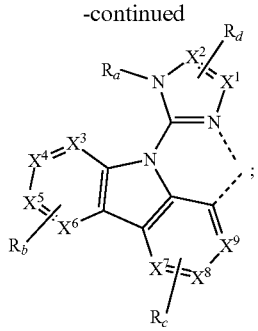

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

15. The OLED of claim 12, wherein the organic layer is a blocking layer and the compound of Formula I is a blocking material in the organic layer.

16. The OLED of claim 12, wherein the organic layer is a transporting layer and the compound of Formula I is a transporting material in the organic layer.

17. The OLED of claim 12, wherein the organic layer is an emissive layer and the compound of Formula I is an emitter.

18. The OLED of claim 17, wherein the OLED emits a luminescent radiation at room temperature when a voltage is applied across the organic light emitting device, and wherein the luminescent radiation comprises a delayed fluorescence process.

19. A consumer product comprising an organic light-emitting device (OLED) comprising:
an anode;
a cathode; and
an organic layer, disposed between the anode and the cathode, comprising a compound having Formula I:

Formula I

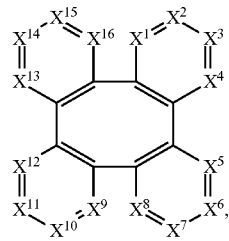

wherein $X^1$-$X^{16}$ are each independently selected from the group consisting of CR and N;
wherein at least two adjacent $X^1$-$X^{16}$ are CR;
wherein each R is independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroarkenyl, alkynyl, aryl, heteroaryl, acyl, carbonyl, carboxylic acids, ester, nitrile, isonitrile, sulfanyl sulfinyl sulfonyl, phosphino, and combinations thereof;
wherein at least one pair of adjacent R is Attachment A

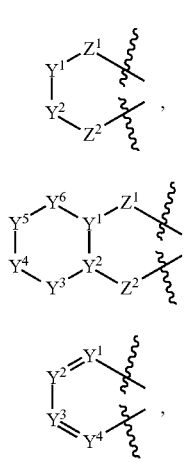

Attachment B

Attachment C or fused with two or more aromatic rings such that no acene unit of more than 3 fused rings is formed;
wherein in Attachments A and B, $Y^1$-$Y^2$, $Y^2$-$Y^3$, $Y^3$-$Y^4$, $Y^4$-$Y^5$ and $Y^5$-$Y^6$ are connected by single or double bonds;
wherein $Y^1$-$Y^6$ are each independently selected from the group consisting of C and N;
wherein an unsaturated C in $Y^1$-$Y^6$ are substituted by $R^1$;
wherein in Attachment A, $Z^1$ and $Z^2$ are each independently selected from the group consisting Of $C=CR^2R^3$, $C=NR^2$, $NR^2$, O, SO, $SO_2$, $BR^2$, $PR^2$, $SiR^2R^3$, and Se;
wherein in Attachment B, $Z^1$ and $Z^2$ are each independently selected from the group consisting of $CR^2R^3$, $C=CR^2R^3$, C=O, $C=NR^2$, $NR^2$, O, S, SO, $SO_2$, $BR^2$, P, $SiR^2R^3$, and Se;

wherein in Attachment C, at least one of $Y^1$-$Y^4$ is an N;
wherein $R^1$-$R^3$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl sulfonyl, phosphino, and combinations thereof; and
wherein

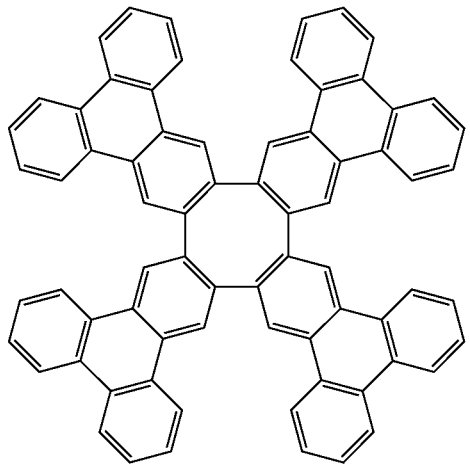 [SMILES: c1ccc2c(c1)c1ccccc1c1cc3c(cc21)-c1cc2c4ccccc4c4ccccc4c2cc1-c1cc2c4ccccc4c4ccccc4c2cc1-c1cc2c4ccccc4c4ccccc4c2cc1-3]

is excluded.

20. The consumer product of claim 19, wherein the consumer product is selected from the group consisting of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a microdisplay that is less than 2 inches diagonal, a 3-D display, a virtual reality or augmented reality display, a vehicle, a video walls comprising multiple displays tiled together, a theater or stadium screen, and a sign.

* * * * *